US011013798B2

(12) United States Patent
Diel et al.

(10) Patent No.: US 11,013,798 B2
(45) Date of Patent: May 25, 2021

(54) ORF VIRUS-BASED PLATFORM FOR VACCINE DELIVERY

(71) Applicants: SOUTH DAKOTA BOARD OF REGENTS, Pierre, SD (US); FEDERAL UNIVERSITY OF SANTA MARIA, Santa Maria (BR)

(72) Inventors: Diego G. Diel, Pierre, SD (US); Eduardo F. Flores, Santa Maria (BR)

(73) Assignees: South Dakota Board of Regents, Pierre, SD (US); Federal University of Santa Maria, Santa Maria (BR)

(*) Notice: Subject to any disclaimer, the term of this patent is extended or adjusted under 35 U.S.C. 154(b) by 265 days.

(21) Appl. No.: 16/086,894

(22) PCT Filed: Mar. 21, 2017

(86) PCT No.: PCT/US2017/023337
§ 371 (c)(1),
(2) Date: Sep. 20, 2018

(87) PCT Pub. No.: WO2017/165366
PCT Pub. Date: Sep. 28, 2017

(65) Prior Publication Data
US 2020/0188509 A1 Jun. 18, 2020

Related U.S. Application Data

(60) Provisional application No. 62/311,013, filed on Mar. 21, 2016.

(51) Int. Cl.
*A61K 39/275* (2006.01)
*C12N 15/86* (2006.01)
*A61K 48/00* (2006.01)
*A61K 39/00* (2006.01)

(52) U.S. Cl.
CPC ............ *A61K 39/275* (2013.01); *C12N 15/86* (2013.01); *A61K 48/00* (2013.01); *A61K 2039/5256* (2013.01); *C12N 2710/24221* (2013.01); *C12N 2710/24234* (2013.01); *C12N 2710/24243* (2013.01)

(58) Field of Classification Search
None
See application file for complete search history.

(56) References Cited

U.S. PATENT DOCUMENTS

| | | | | |
|---|---|---|---|---|
| 6,106,841 | A | 8/2000 | Osorio et al. | |
| 6,365,393 | B1 | 4/2002 | Schmeer et al. | |
| 8,741,653 | B2 | 6/2014 | Leyrer et al. | |
| 8,795,681 | B2 | 8/2014 | Wu et al. | |
| 2003/0013076 | A1 | 1/2003 | Robinson et al. | |
| 2006/0008471 | A1 | 1/2006 | Weber et al. | |
| 2011/0287051 | A1* | 11/2011 | Martinon | A61K 39/12 424/199.1 |
| 2020/0188509 | A1* | 6/2020 | Diel | A61K 39/205 |

FOREIGN PATENT DOCUMENTS

| | | | |
|---|---|---|---|
| WO | 9957295 | A1 | 11/1999 |
| WO | 2016074942 | A1 | 5/2016 |

OTHER PUBLICATIONS

Peralta et al. (Frontiers in veterinary science. Jun. 19, 2018; 5:134).*
Diel et al. (Journal of Virology. Mar. 2011; 85 (5): 2037-2049).*
Diel et al., "Orf Virus ORFV121 Encodes a Novel Inhibitor of NF-KB That Contributes to Virus Virulence", Journal of Virology, vol. 85, No. 5, pp. 2037-2049, Mar. 2011.
Hain et al., "Immunogenicity of a recombinant parapoxvirus expressing the spike protein of Porcine epidemic diarrhea virus", Journal of General Virology, vol. 97, pp. 2719-2731, Aug. 22, 2016.
Rziha et al., "Generation of recombinant parapoxviruses: non-essential genes suitable for insertion and expression of foreign genes", Journal of Biotechnology, vol. 83, pp. 137-145, 2000.
South Dakota Board of Regents, PCT/US2017/023337 filed Mar. 21, 2017, "The International Search Report and the Written Opinion of the International Searching Authority, or the Declaration", 15 pages, dated Jun. 12, 2017.

* cited by examiner

*Primary Examiner* — Shanon A. Foley
(74) *Attorney, Agent, or Firm* — McKee, Voorhees & Sease, PLC

(57) ABSTRACT

The present invention is directed to novel vaccine delivery platform based on the Orf virus (ORFV) genome, which carry heterologous antigens, methods of making and methods of using the same for prevention of infections, diseases, and other conditions in animals.

14 Claims, 95 Drawing Sheets

Specification includes a Sequence Listing.

Experiment I

Pox-A/RabV-G
(n=5; SC: 3; IM: 2)

Boost

Group 1
ORFV-024-RabV G

| Animal # | Group | Dose | Ab Titers against CVS-PV (200TCID$_{50}$) Day 0 | Day 23 p.i. | Day 44 p.i. |
|---|---|---|---|---|---|
| 117 | SC | 2x10^7,9 | neg | 40 | 640 |
| 118 | SC | 2x10^7,9 | neg | 320 | 640 |
| 127 | SC | 2x10^7,9 | neg | 320 | ≥1280 |
| 132 | IM | 2x10^7,9 | neg | 640 | ≥1280 |
| 135 | IM | 2x10^7,9 | neg | 160 | 640 |

Pox-B/RabV-G
(n=6; SC: 3; IM: 3)

Boost

Group 2
ORFV-121-RabV G

| Animal # | Group | Dose | Ab Titer against CVS-PV (200TCID$_{50}$) Day 0 | Day 21 p.i. | Day 42 p.i. |
|---|---|---|---|---|---|
| 1 | SC | 2x10^7,6 | neg | 20 | 20 |
| 2 | SC | 2x10^7,6 | neg | 20 | 1280 |
| 3 | SC | 2x10^7,6 | neg | 10 | 640 |
| 4 | IM | 2x10^7,6 | neg | 20 | 640 |
| 5 | IM | 2x10^7,6 | neg | 20 | 640 |
| 6 | IM | 2x10^7,6 | neg | 10 | 640 |

Immunogenicity of candidate vectors in cattle

Experiment II

| | Animal # | Group | Dose IM | Day zero | day 30 p.i. | Day 60 p.i. |
|---|---|---|---|---|---|---|
| IM n = 15 | 32 | ORFV-024Rabv-G | 10^7,9 | Neg | <20 | 1280 |
| | 29 | ORFV-024Rabv-G | 10^7,9 | Neg | <20 | 80 |
| | 33 | ORFV-024Rabv-G | 10^7,9 | Neg | <20 | 320 |
| | 48 | ORFV-024Rabv-G | 10^7,9 | Neg | <20 | 160 |
| | 57 | ORFV-024Rabv-G | 10^7,9 | Neg | nt | 320 |
| | 75 | ORFV-024Rabv-G | 10^7,9 | Neg | <20 | 80 |
| | 83 | ORFV-024Rabv-G | 10^7,9 | Neg | <20 | 640 |
| | 90 | ORFV-024Rabv-G | 10^7,9 | Neg | <20 | 320 |
| | 162 | ORFV-024Rabv-G | 10^7,9 | Neg | <20 | 80 |
| | 163 | ORFV-024Rabv-G | 10^7,9 | Neg | <20 | 160 |
| | 164 | ORFV-024Rabv-G | 10^7,9 | Neg | <20 | 80 |
| | 165 | ORFV-024Rabv-G | 10^7,9 | Neg | <20 | 80 |
| | 167 | ORFV-024Rabv-G | 10^7,9 | Neg | <20 | 160 |
| | 168 | ORFV-024Rabv-G | 10^7,9 | Neg | <20 | 640 |
| | 169 | ORFV-024Rabv-G | 10^7,9 | Neg | <20 | 320 |
| IM n = 15 | 38 | ORFV-121Rabv-G | 10^7,9 | Neg | 40 | 640 |
| | 42 | ORFV-121Rabv-G | 10^7,9 | Neg | <20 | 320 |
| | 43 | ORFV-121Rabv-G | 10^7,9 | Neg | 160 | 2560 |
| | 49 | ORFV-121Rabv-G | 10^7,9 | Neg | 20 | 640 |
| | 56 | ORFV-121Rabv-G | 10^7,9 | Neg | 40 | 320 |
| | 65 | ORFV-121Rabv-G | 10^7,9 | Neg | 80 | 640 |
| | 77 | ORFV-121Rabv-G | 10^7,9 | Neg | <20 | 640 |
| | 79 | ORFV-121Rabv-G | 10^7,9 | Neg | <20 | 640 |
| | 123 | ORFV-121Rabv-G | 10^7,9 | Neg | 80 | 320 |
| | 159 | ORFV-121Rabv-G | 10^7,9 | Neg | 20 | 1280 |
| | 160 | ORFV-121Rabv-G | 10^7,9 | Neg | <20 | 320 |
| | 161 | ORFV-121Rabv-G | 10^7,9 | Neg | <20 | 640 |
| | 170 | ORFV-121Rabv-G | 10^7,9 | Neg | 80 | 1280 |
| | 171 | ORFV-121Rabv-G | 10^7,9 | Neg | 80 | 1280 |
| | 172 | ORFV-121Rabv-G | 10^7,9 | Neg | 320 | 2560 |

Neutralizing Antibody Titers Against RabV

FIG. 8

ORFV-024-RabV-G (n=3)

Boost ⇓

| Animal # | Group | Dose | NAb Titer against CVS-PV (200TCID$_{50}$) Day 0 | Day 21 p.i. | Day 42 p.i. |
|---|---|---|---|---|---|
| 1 | SC | 10^7,8 | neg | 10 | 80 |
| 2 | SC | 10^7,8 | neg | 10 | 80 |
| 3 | SC | 10^7,8 | neg | 10 | 80 |

ORFV-121-RabV-G (n=3)

Boost ⇓

| Animal # | Group | Dose | NAb titer against CVS-PV (200TCID$_{50}$) Day 0 | Day 21 p.i. | Day 42 p.i. |
|---|---|---|---|---|---|
| 1 | SC | 10^7,8 | neg | 10 | 80 |
| 2 | SC | 10^7,8 | neg | 10 | 160 |
| 3 | SC | 10^7,8 | neg | 10 | 80 |

Neutralizing Ab Titers against RabV

ORFV-024-RabV-G
(n=5; IM: 5)

Boost ⇓

| Animal # | Group | Dose | Day 0 | Day 21 p.i. | Day 42 p.i. |
|---|---|---|---|---|---|
| | | | Ab Titers against CVS-PV ($200TCID_{50}$) | | |
| 34 | IM | 10^7,8 | neg | ≥10 | 160 |
| 61 | IM | 10^7,8 | neg | ≥10 | 160 |
| 69 | IM | 10^7,8 | neg | ≥10 | 640 |
| 74 | IM | 10^7,8 | neg | <10 | 80 |
| 97 | IM | 10^7,8 | neg | ≥10 | 80 |

ORFV-121-RabV-G
(n=4; IM: 4)

Boost ⇓

| Animal # | Group | Dose | Day 0 | Day 21 p.i. | Day 42 p.i. |
|---|---|---|---|---|---|
| | | | Ab Titer against CVS-PV ($200TCID_{50}$) | | |
| 25 | IM | 10^7,8 | neg | ≥10 | ≥1280 |
| 33 | IM | 10^7,8 | neg | ≥10 | ≥1280 |
| 67 | IM | 10^7,8 | neg | ≥10 | 640 |
| 72 | IM | 10^7,8 | neg | <10 | 640 |

| Group | Animal ID | Virus shedding (day post-challenge)* | | | | | | |
|---|---|---|---|---|---|---|---|---|
| | | 0 | 3 | 5 | 7 | 9 | 11 | 14† |
| 1 | 1 | − | − | − | − | − | − | − |
| | 2 | − | − | − | − | − | − | − |
| | 3 | − | − | − | − | − | − | − |
| | 4 | − | − | − | − | − | − | − |
| 2 | 5 | − | + | + | + | + | + | + |
| | 6 | − | + | + | + | + | + | − |
| | 7 | − | − | + | + | + | + | − |
| | 8 | − | + | + | + | + | + | − |
| 3 | 9 | − | + | + | + | + | + | − |
| | 10 | − | − | − | + | + | − | − |
| | 11 | − | − | − | + | + | − | − |
| | 12 | − | − | + | + | + | − | − |
| 4 | 13 | − | + | + | + | + | + | − |
| | 14 | − | + | + | + | + | + | − |
| | 15 | − | + | + | + | + | + | + |
| | 16 | − | + | + | + | + | + | − |

*Virus shedding was assessed by real-time PCR in faecal swabs.
†Experiment was terminated on day 14 p.c.

>pZ024-RabV-G (recombination plasmid used to generate ORFV-024-RabV-G virus) (SEQ ID NO:1)
GAACTCGAGACTAGTAGGCCTGCGCGCAAGCTTAACCAGCAGACCTTCTTCACCAAGGGGCTCAGTCCGCTGATGCG
CCACACCTACATCTACAACAACTACGCCTACGGCTGGATTCCCGAGACCGCGCTCTGGAGCAGCCGTCTGGGCGACT
ACCGCGTCACGGACTTCTACCCGATATCGCTGGGCATGCTCAAGAAGTTCGAGTTCATGTTCTCGCTGCTGGCGGAC
CCCGGCGGCGCCTGCCCCGCGTACGAGCCCAAGCTCAACACCGAGTTCCTGAACCGCGGCTCCTTCTCGGGCCGGTA
CGTGAACCCCTTCCACCGCTTCGCGGCGCTGCCCGAGCGCGAGTACATCTCCTTCCTGCTGCTGAGCTCGGTGCCCA
TCTTCAACATCCTCTTCTGGTTTAAGGGCGAGACCTT CGACACTGCCAAGCACAGCCTGCTCGGCGCCGTGTACACC
ACGCCCGAGAGGCACATCGAGCTCGCGCGGTACCTGCGGCGCACGGGCGACTACAAGCCGCTGTTCAGCCGCCTGGG
CAACGACGACACCTACTCGAAGCCCTTCTCGGGGTTCACGCGCATCAGCAACCCCACGCCCATCGGGCGGCTGCCGC
CCTCGGACTTCGAGACGCTGGCCAACCTGAGCACCATTCTCTACTACACGCGCTACGACCCG GTGCTCTGTTTCCTG
GTCTTCTACGTGCCGGGGCTCTCCGCGACCACGAAGATCACGCCCGGCGTGGAGTTCCTCATGGAGAAGCTCTCGCT
CGCGCCCGAGAACGTGGTGCTGCTGTAGCCTCAAACATAAAATATAGGCGCCTCTGATCGCACTGCTTCAGTTCAGA
CAGAGCTAAGGTCGACCTGCAGATATACTATATAGTAATACCAATACTCAAGACTACGAAACTGATACAATCTCTTA
TCATGTGGGTAATGTTCTCGATGTCGAATAGCCATATGCCGGTAGTTGCGATATACATAAACTGATCACTAATTCCA
AACCCACCCGCTTTTTATAGTAAGTTTTTCACCCATAAATAATAAATACAATAATTAATTTCTCGTAAAAGTAGAAA
ATATATTCTAATTTATTGCACGGTAAGGAAGTAGAATCATAAAGAACAGTGACGCCTCGAGGAATTCATGATCCTTC
AGGCCCTTCTGTTTGTGCCTCTCCTAATCTCTTCG TTGTGTCTCGGGAAATTCCCCATCTACACAATACCAGACAAA
CTTGGTCCTTGGAGCCCCATCGATATACATCACCTCAGCTGTCCAAATAATTTAGTTGTGGAGGATGAAGGGTGCAC
CAATCTATCAGGATTCTCTTACATGGAACTAAAGGTGGGATACATCTCTGCCATAAAAGTAAATGGGTTCACTTGTA
CCGGTGTTGTGACAGAGGCTGAAACCTATACCAACTTTGTTGGTTATGTCACCACCACAT TCAAGAGGAAACATTTC
CGCCCTATACCGGATGCATGCAGGGCTGCATACAACTGGAAGATGGCTGGTGATCCTAGATATGAGGAATCTCTTCA
AAATCCTTATCCTGATTACCACTGGCTACGGACCGTAAAAACCACTAAGGAGTCTCTTATCATCATATCTCCGAGTG
TGGCTGATTTAGACCCATACGACAAATCCCTTCATTCTAGGGTGTTCCCTGGTGGGAAATGTTTGGGAATAACGGTT
TCTTCCACCTACTGCTCAACCAACCATGATTACACCATCTGGATGCCCGAGGAACCAAGACTCGGGACATCTTGCGA
CATTTTTACCAGCAGCAAAGGGAAAAAGGCATCTAAAGGAGGCAAGACTTGCGGATTTGTGGATGAAAGGGGCTTGT
ACAAGTCTCTAAAAGGAGCGTGTAAACTCAAGCTGTGCGGAGTTCTCGGACTTAGACTTATGGATGGAACCTGGGTT
TCCATTCCAACATCAGACGATACCAAATGGTGC CCTCCGGATCAATTGGTGAATCTACATGACTTTCACTCAGACGA
AATAGAGCATCTCGTCGTGGAGGAGTTGGTCAAGAAGAGGGAAGAGTGTTTGGACGCATTAGAGTCCATCATGACCA
CCAAATCTGTAAGTTTTAGACGTCTCAGCTATTTGAGAAAACTTGTCCCTGGGTTTGGAAAGGCATACACTATATTC
AACAAGACTTTGATGGAGGCTGACGCCCACTACAAGTCAGTTCGGACTTGGAACGAGA TCATCCCCTCCAAAGGGTG
TTTGAAAGTCAGAGAGAGGTGTCATCCTCCTGTGGACGGAGTGTTCTTCAATGGCATAATTCTGGGTCCAGACGGGA
ATGTCCTGATACCAGAGATGCAATCATCTCTACTTCAACAACATATGGAGCTGTTGGAATCTTCTGTAATCCCCTTA

FIG. 25A

ATGCATCCCTTGGCGGACCCGTCAACAGTCTTCAAGGAAGGGGATGAAGCGGAGGATTTTGTTGAAGTTCACCTCCC
TGATGTTCACAAACAAATCTCAGGGGTTGACCTTGGTCTCCCGAGTTGGGGGAAATATCTCCTGATGATTGCAGGTG
GTCTGGCGACTCTAGTTCTGATAATCTGCTCGATGGCATGCTGTAGAAGAACCAAGCGAACAGAGTCAAGAAGACGA
GGCTCTCGAGAGTCAGAGAAAAAGGTAACGGCAACCCCCCAGACTAGGAAAGTCGTATCTTCATGGGAGTTATACAA
GAGTGAAGGCGATGCCAGGCTGGATTACAAGGATGACGACGATAAGTGAGCGGCCGCGCCGGCTTCATCCGCCGCAG
CATAAGAAAAACCTGCAACTTCGCACACGCGCGCACGCACACGGTCTACGTGTAGTTACCCTGTAAAGACGGGCTTG
CTCCCGAACAAGCGCTCGAAGAAGAGCGTGCACATAGCCTTATTGTCCAGCAAGTTGACTATCTCTGTACACAGCCT
CTTGAAGTACACCTCGTACATGATCCGCTCGTTTTTATCCAGTCTGAAGGTCTTGT CGACCACGCGCTCGTAGGACT
TCACGTTCGCGATCCGGCGCCGCCAGGGGCCCTCCTCGCACACGTACGCGAAGAAGTAGCGCTCGCCGATCTCGATG
GCCTCCGCGTTCGCCGCGTTGTACCGCGTCACCAGCGCCACGTTGGGGTTGTCGGGGGACTTGAAGTTCTTGTGGTG
CGTTCGGCTCAGCAGGAACCAGTCCAGCGGCATGCTGCGCGCCTCGAACTCGAAGGTGAGCTCGTCCTCCAGCGAGC
GCAGGATCTCCACGCCCACGTTCCCGGAGCCCTCCTCCGCCAGCGCGCGGCAGAGCATGTCCTTGTACTTGCGGATC
ATGAGCTTGTGGAAGGGCGCCACGTCGCGGCGCGTCTCGCTGGTGCCCTTGCTCACGCGCTCGCTGCCGCCGCCGTC
GCTCACCGCAAACTTGATCGTGGTGTACTTCTTCTTGGACTGCATGATCAGGTTGCAGTACACCGCTTCGAACTCCA
CCTTGAAGTTCGCGAAGAGCACGTGCTCGTTGATCACGCGCTCCAGACAGCGCCCCACGCGCCGCGAGAACGCGATG
TCGGAGGCGCCCACCTCCAGGAACACGGAGTCGGTGTCGCCGTAAGATCTGCCGGTCTCCCTATAGTGAGTCGTATT
AATTTCGATAAGCCAGGTTAACCTGCATTAATGAATCGGCCAACGCGCGGGGAGAGGCGGTTTGCGTATTGGGCGCT
CTTCCGCTTCCTCGCTCACTGACTCGCTGCGCTCGGTCGTTCGGCTGCGGCGAG CGGTATCAGCTCACTCAAAGGCG
GTAATACGGTTATCCACAGAATCAGGGGATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCCTGACGAGCATCACAAAAATCGACGCTCAA
GTCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAATGCTCACG
CTGTAGGTATCTCAGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACTGGCAGCAGCCACT
GGTAACAGGATTAGCAGAGCGAGGTAT GTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACT CACGTTAAGGGATTTTGGTCATGAG
ATTATCAAAAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGATACC
GCGAGACCCACGCTCACCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAGCTCCTTCGGTCCTCCGATCG
TTGTCAGAAGTAAGTTGGCCGCAGTGTTATCACTCATGGTTATGGCAGCACTGCATAATTCTCTTACTGTCATGCCA
TCCGTAAGATGCTTTTCTGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTT TAAAAGTGCTCATCATTGGAAAACGTT
CTTCGGGGCGAAAACTCTCAAGGATCTTACCGCTGTTGAGATCCAGTTCGATGTAACCCACTCGTGCACCCAACTGA
TCTTCAGCATCTTTTACTTTCACCAGCGTTTCTGGGTGAGCAAAAACAGGAAGGCAAAATGCCGCAAAAAAGGGAAT
AAGGGCGACACGGAAATGTTGAATACTCATACTCTTCCTTTTTCAATATTATTGAAGCATTTATCAGGGTTATTG TC
TCATGAGCGGATACATATTTGAATGTATTTAGAAAAATAAACAAATAGGGGTTCCGCGCACATTTCCCCGAAAAGTG
CCACCTGACGTCTAAGAAACCATTATTATCATGACATTAACCTATAAAAATAGGCGTATCACGAGGCCCTTTCGTCT
CGCGCGTTTCGGTGATGACGGTGAAAACCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGGTGTCGGGGCTGGCTTAACTATGCGGCA
TCAGAGCAGATTGTACTGAGAGTGCAC

FIG. 25B pZ121-RabV-G (recombination plasmid used to generate ORFV-121-RabV-G virus) (SEQ ID NO:2)

GAACTCGAGACTAGTCTGCGACCGACATCGCACACATGAAGGACACAATTGGTTTGTTAATCCGGACAATGAAGGAC
AAATTGTTTTTGTTAATCAGGACAATTGGACACAATCAGATTAATTTTTGTACGATCATAAAATCGATATTTGATGC
ACATATATTAGTAAGTATATTAGACTAAATTCTCCGGGGAGGCAAGCAGTTGGATACGGCGGGGCGGGGCACGACGT
GCACGGAGAATTCGGGCGGGTCCCCCTTCCCCCCACCCCCACGCACCACGATGCGTCTAATCTTAGCGCTCGTGGCC
TGCTTGTTGGCGGCGCCGATGCCGTTATCGGGTCGTTCGACAAGCACCCCAAACACACAGTCCGTACTCGGCTCGAC
GAGTTCGGAACCAAGCTCGGAAGACGCTGTGGCTTCGAGCACAACGACAAGCACACTCACAAGCACTACAAGCACAC
TCACTATGTCCACAAGTGTGGACACCACTACTACCTCGGGCGCTACGACG TCCACAAACAGCACTCCTGCAGCGAGT
GTGAGTTCTTCCACACCCGCAGCCACTGAGGCATCGACGGCACCAACGACGCCGTCGACGCAGACGACAGTGAAGGT
AACGAAAGACAAAGACACGAAGGCGTCTGCCTACCTCGTTTTACTAATCACGTTCATGGTCATGACAACGCTAGTGA
TGGTTGTGGTCGTGGTCGTGATCGTGTACAAACAGGGACTTTGTGACTGCTGCTGTAAGATGTTTCCCTGCTGCA AA
GAGCTCAAGGACTACCTCGACGAGGAGGAGAGCGCCGGGCTGTACGACGCCTTGACGTGGAGCCGCTCAGACCCCGG
CCTCCGGCTCGTCGTGCGCGCGGACCCCAGATGATGAGGATCGGATAAGATCGGCGTGTTTTTCCCGCCCGTCGCGA
ACATTATGCCTCTAAATGCCGAGAATTAACTGAAATTCAAACACGCTTTGGGACTCAACTCTGTGGCCCACACAACC
AAGCTTGCATGCCTGCAGGTCGACCTGCAGATATACTATATAGTAATACCAATACTCAAGACTACGAAACTGATACA
ATCTCTTATCATGTGGGTAATGTTCTCGATGTCGAATAGCCATATGCCGGTAGTTGCGATATACATAAACTGATCAC
TAATTCCAAACCCACCCGCTTTTTATAGTAAGTTTTTCACCCATAAATAATAAATACAATAATTAATTTCTCGTAAA
AGTAGAAAATATATTCTAATTTATTGCACGGTAAGGAAGTAGAATCAT AAAGAACAGTGACGCCTCGAGGAATTCAT
GATCCTTCAGGCCCTTCTGTTTGTGCCTCTCCTAATCTCTTCGTTGTGTCTCGGGAAATTCCCCATCTACACAATAC
CAGACAAACTTGGTCCTTGGAGCCCCATCGATATACATCACCTCAGCTGTCCAAATAATTTAGTTGTGGAGGATGAA
GGGTGCACCAATCTATCAGGATTCTCTTACATGGAACTAAAGGTGGGATACATCTCTGCCATAAAAGTAAATG GGTT
CACTTGTACCGGTGTTGTGACAGAGGCTGAAACCTATACCAACTTTGTTGGTTATGTCACCACCACATTCAAGAGGA
AACATTTCCGCCCTATACCGGATGCATGCAGGGCTGCATACAACTGGAAGATGGCTGGTGATCCTAGATATGAGGAA
TCTCTTCAAAATCCTTATCCTGATTACCACTGGCTACGGACCGTAAAAACCACTAAGGAGTCTCTTATCATCATATC
TCCGAGTGTGGCTGATTTAGACCCATACGACAAATCCCTTCATTCTAGGGTGTTCCCTGGTGGGAAATGTTTGGGAA
TAACGGTTTCTTCCACCTACTGCTCAACCAACCATGATTACACCATCTGGATGCCCGAGGAACCAAGACTCGGGACA
TCTTGCGACATTTTTACCAGCAGCAAAGGGAAAAAGGCATCTAAAGGAGGCAAGACTTGCGGATTTGTGGATGAAAG
GGGCTTGTACAAGTCTCTAAAAGGAGCGTGTAAACTCAAGCTGTGC GGAGTTCTCGGACTTAGACTTATGGATGGAA
CCTGGGTTTCCATTCCAACATCAGACGATACCAAATGGTGCCCTCCGGATCAATTGGTGAATCTACATGACTTTCAC
TCAGACGAAATAGAGCATCTCGTCGTGGAGGAGTTGGTCAAGAAGAGGGAAGAGTGTTTGGACGCATTAGAGTCCAT
CATGACCACCAAATCTGTAAGTTTTAGACGTCTCAGCTATTTGAGAAAACTTGTCCCTGGGTTTGGAAAGG CATACA
CTATATTCAACAAGACTTTGATGGAGGCTGACGCCCACTACAAGTCAGTTCGGACTTGGAACGAGATCATCCCCTCC
AAAGGGTGTTTGAAAGTCAGAGAGAGGTGTCATCCTCCTGTGGACGGAGTGTTCTTCAATGGCATAATTCTGGGTCC
AGACGGGAATGTCCTGATACCAGAGATGCAATCATCTCTACTTCAACAACATATGGAGCTGTTGGAATCTTCTGTAA
TCCCCTTAATGCATCCCTTGGCGGACCCGTCAACAGTCTTCAAGGAAGGGGATGAAGCGGAGGATTTTGTTGAAGTT
CACCTCCCTGATGTTCACAAACAAATCTCAGGGGTTGACCTTGGTCTCCCGAGTTGGGGGAAATATCTCCTGATGAT
TGCAGGTGGTCTGGCGACTCTAGTTCTGATAATCTGCTCGATGGCATGCTGTAGAAGAACCAAGCGAACAGAGTCAA
GAAGACGAGGCTCTCGAGAGTCAGAGAAAAAGGTAACGGCAACC CCCCAGACTAGGAAAGTCGTATCTTCATGGGAG
TTATACAAGAGTGAAGGCGATGCCAGGCTGGATTACAAGGATGACGACGATAAGTGAGCGGCCGCGGAGCACTGCTC
GGAGGAGTGCTGCAAAGTGGAGGAAGTTCTGTGAGAAAGTGCGTTTTTCTGTAATGTGAAATAAGATAGCCTTATGT
GTGCACAGACATGGCGAACAGGCTTGTGTTTCTCGACCCCGAGACCCTAGCCGAGGCCGACGGCATCCC CGGCTATG
GGGTGTTCGAGCCCGGCAAGAAGAAATGCATCTTCACAAAGATCCGCACCAGCGTCGCACTCGCGTGCCGGTACGCC
GTCTCGGACGGCGGCCTCATCGACGAGTTCGTCATGGCGACATACGGGACCAGACGCGCGTGCCGGCTCGTCCGGCA
CCTGACGATAAGCGCGGAGGGCGTGATGACCCGGCCCGCCAGCAACTGCGCGCCGCACATGGTGCTCATCTGCCTCA
GAGGCGTGGCCGCCGTGTCCAGCGAGGACATGGGCTTCGGTCGCTGCATCATGGAGCGCGGCACCATGTTCATGGTC
AAGTCCGCGCACAGCGCCGTCGTCTGCGGCAACCCCGCCTGCGAGCTGCTCGTCCTCTTCTACGACTACTTCACCCC
CATCCCCCGGCCGCTCTCCGGAGACGAGGTGCTGTTCACCCGCGACCTCGCGCACGTGGACTACGCCCCCGAGTCGG
CGGTCGTCTTCAAGATGGATTACAACCTCGAGACCGACGTGG CCACGCTGTTTGTCGGGGGGTACATATTCCGCGCC
AAGGGCCTGATGATGGAGACGCGCGAACAAGTGGGCGACGAGTGCGACTGCTGCCGCCACAGCTCGCCGGTGCTCGT
CATGGATCGCGAGAAGATGATGTCGTCGCTGCGCATGATAGATCTGCCGGTCTCCCTATAGTGAGTCGTATTAATTT
CGATAAGCCAGGTTAACCTGCATTAATGAATCGGCCAACGCGCGGGGAGAGGCGGTTTGCGTATTGG GCGCTCTTCC

FIG. 26A

GCTTCCTCGCTCACTGACTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCGTGGCGCTTTCTCAATGCTCACGCTGTA
GGTATCTCAGTTCGGTGTAGGTCGTTCGCTCCAAGCTGGGCTGTGTGCACGAACCCCCCGTTCAGCCCGACCGCTGC
GCCTTATCCGGTAACTATCGTCTTGAGTCCAACCCGGTAAGACACGACTTATCGCCACTGGCAGCAGCCACTGGTAA
CAGGATTAGCAGAGCGAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGCTCTTGATCCGGCAAA
CAAACCACCGCTGGTAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTAAGGGATTTTGGTCATGAGATTAT
CAAAAAGGATCTTCACCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCGTTCATCCATAGTTGC
CTGACTCCCCGTCGTGTAGATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAGCGCAGAAGTGGTCCTGCA
ACTTTATCCGCCTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCATAATTCTCTTACTGTCATGCCATCCGT
AAGATGCTTTTCTGTGACTGGTGAGTACTCAACCAAGTCATTCTGAGAATAGTGTATGCGGCGACCGAGTTGCTCTT
GCCCGGCGTCAATACGGGATAATACCGCGCCACATAGCAGAACTTTAAAAGTGCTCATCATTGGAAAACGTTCTTCG
GGGCGAAAACTCTCAAGGATCTTACCGCTGTTGAGATCCAGTTCGATGTAACCCACTCGTGCACCCAACTGATCTTC
AGCATCTTTTACTTTCACCAGCGTTTCTGGGTGAGCAAAAACAGGAAGGCAAAATGCCGCAAAAAAGGGAATAAGGG
CGACACGGAAATGTTGAATACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTTCCCCGAAAAGTGCCACC
TGACGTCTAAGAAACCATTATTATCATGACATTAACCTATAAAAATAGGCGTATCACGAGGCCCTTTCGTCTCGCGC
GTTTCGGTGATGACGGTGAAAACCTCTGACACATGCAGCTCCCGGAGACGGTCACAGCTTGTCTGTAAGCGGATGCC
GGGAGCAGACAAGCCCGTCAGGGCGCGTCAGCGGGTGTTGGCGGGTGTCGGGGCTGGCTTAACTATGCGGCATCAGA
GCAGATTGTACTGAGAGTGCAC

FIG. 26B pZ121-PEDV-S (Sequence of recombination plasmid used to construct ORFV-PEDV-S) (SEQ ID NO:3)

GAACTCGAGACTAGTCTGCGACCGACATCGCACACATGAAGGACACAATTGGTTTGTTAATCCGGACAATGAAGGAC
AAATTGTTTTTGTTAATCAGGACAATTGGACACAATCAGATTAATTTTTGTACGATCATAAAATCGATATTTGATGC
ACATATATTAGTAAGTATATTAGACTAAATTCTCCGGGGAGGCAAGCAGTTGGATACGGCGGGGCGGGGCACGACGT
GCACGGAGAATTCGGGCGGGTCCCCCTTCCCCCCACCCCCACGCACCACGATGCGTCTAATCTTAGCGCTCGTGGCC
TGCTTGTTGGCGGCGCCGATGCCGTTATCGGGTCGTTCGACAAGCACCCCAAACACACAGTCCGTACTCGGCTCGAC
GAGTTCGGAACCAAGCTCGGAAGACGCTGTGGCTTCGAGCACAACGACAAGCACACTCACAAGCACTACAAGCACAC
TCACTATGTCCACAAGTGTGGACACCACTACTACCTCGGGCGCTACGACGTCCACA AACAGCACTCCTGCAGCGAGT
GTGAGTTCTTCCACACCCGCAGCCACTGAGGCATCGACGGCACCAACGACGCCGTCGACGCAGACGACAGTGAAGGT
AACGAAAGACAAAGACACGAAGGCGTCTGCCTACCTCGTTTTACTAATCACGTTCATGGTCATGACAACGCTAGTGA
TGGTTGTGGTCGTGGTCGTGATCGTGTACAAACAGGGACTTTGTGACTGCTGCTGTAAGATGTTTCCCTGCTGCAAA
GAGCTCAAGGACTACCTCGACGAGGAGGAGAGCGCCGGGCTGTACGACGCCTTGACGTGGAGCCGCTCAGACCCCGG
CCTCCGGCTCGTCGTGCGCGCGGACCCCAGATGATGAGGATCGGATAAGATCGGCGTGTTTTTCCCGCCCGTCGCGA
ACATTATGCCTCTAAATGCCGAGAATTAACTGAAATTCAAACACGCTTTGGGACTCAACTCTGTGGCCCACACAACC
AAGCTTATATACTATATAGTAATACCAATACTCAAGACTACGAAACTGATACAATCTCTTATCATGTGGGTAATGTT
CTCGATGTCGAATAGCCATATGCCGGTAGTTGCGATATACATAAACTGATCACTAATTCCAAACCCACCCGCTTTTT
ATAGTAAGTTTTTCACCCATAAATAATAAATACAATAATTAATTTCTCGTAAAAGTAGAAAATATATTCTAATTTAT
TGCACGGTAAGGAAGTAGAATCATAAAGAACAGTGACGCCTCGAGGATGCATCA TCACCATCACCACAAGTCTTTAA
CCTACTTCTGGTTGTTCTTACCAGTACTTTCAACACTTAGCCTACCACAAGATGTCACCAGGTGCTCAGCTAACACT
AATTTTAGGCGGTTCTTTTCAAAATTTAATGTTCAGGCGCCTGCAGTTGTTGTACTGGGCGGTTATCTACCTATTGG
TGAAAACCAGGGTGTCAATTCAACTTGGTACTGTGCTGGCCAACATCCAACTGCTAGTGGCGTTCATGGTATCTTTG
TTAGCCATATTAGAGGTGGTCATGGCTTTGAGATTGGCATTTCGCAAGAGCCTTTTGACCCTAGTGGTTACCAGCTT
TATTTACATAAGGCTACTAACGGTAACACTAATGCTACTGCGCGACTGCGCATTTGCCAGTTTCCTAGCATTAAAAC
ATTGGGCCCCACTGCTAATAATGATGTTACAACAGGTCGTAATTGCCTATTTAACAAAGCCATCCCAGCTCATATGA
GTGAACATAGTGTTGTCGGCATAACATGGGATAATGATCGTGTCACTGTCTTTTCTGACAAAATCTATTACTTCTAT
TTTAAAAATGATTGGTCCCGTGTTGCGACAAAGTGTTACAACAGTGGAGGTTGTGCTATGCAATATGTTTACGAACC
CACCTATTACATGCTTAATGTTACAAGTGCTGGTGAGGATGGTATTTCTTATCAACCCTGTACAGCTAATTGCATTG
GTTATGCTGCCAATGTATTTGCTACTGAGCCCAATGGCCACATACCAGAAGGTTTTAGTTTTAATAATTGGTTTCTT
TTGTCCAATGATTCCACTTTGGTGCATGGTAAGGTGGTTTCCAACCAACCATTGTTGGTCAATTGTCTTTTGGCCAT
TCCTAAGATTTATGGACTAGGCCAATTTTTCTCCTTTAATCAAACGATCGATGGTGTTTGTAATGGAGCTGCTGTGC
AGCGTGCACCAGAGGCTCTGAGGTTTAATATTAATGACATCTCTGTCATTCTTGCTGAAGGCTCAATTGTACTTCAT
ACTGCTTTAGGAACAAACTTCTCTTTTGTTTGCAGTAATTCCTCAAATCCTCACTTAGCCACCTTCGCCATACCTCT
GGGTGCTACCCAAGTACCTTATTATTGTTTTCTTAAAGTGGATACTTACAACTCCACTGTTTATAAATTTTTGGCTG
TTTTACCTCCTACCGTCAGGGAAATTGTCATCACCAAGTATGGTGATGTTTATGTCAATGGGTTTGGATACTTGCAT
CTCGGTTTGTTGGATGCTGTCACAATTAATTTCACTGGTCATGGCACTGACGATGATGTTTCTGGTTTTTGGACCAT
AGCATCGACTAATTTTGTTGATGCACTCATCGAAGTTCAAGGAACCGCCATTCAGCGTATTCTTTATTGTGATGATC
CTGTTAGCCAACTCAAGTGTTCTCAGGTTGCTTTTGACCTTGACGATGGTTTTTACACTATTTCTTCTAGAAACCTT
CTGAGTCATGAACAGCCAATTTCTTTTGTTACTCTGCCATCATTTAATGA TCATTCTTTTGTTAACATTACTGTATC
TGCTTCCTTTGGTGGTCATAGTGGTGCCAACCTTATTGCATCTGACACTACTATCAATGGGTTTAGTTCTTTCTGTG
TTGACACTAGACAATTTACCATTTCACTGTTTTATAACGTTACAAACAGTTATGGTTATGTGTCTAAATCACAGGAC
AGTAATTGCCCTTTCACCTTGCAATCTGTTAATGATTACCTGTCTTTTAGCAAATTTTGTGTTTCCACCAGCCTT TT
GGCTAGTGCCTGTACCATTGATCTTTTTGGTTACCCTGAGTTTGGTAGTGGTGTTAAGTTTACGTCCCTTTACTTTC
AATTCACAAAGGGTGAGTTGATTACTGGCACGCCTAAACCATTTGAAGGTGTCACGGACGTTTCTTTTATGACTCTG
GATGTGTGTACCAAGTATACTATCTATGGCTTTAAAGGTGAGGGTATCATTACCCTTACAAATTCTAGCTTTTTGGC
AGGTGTTTATTACACATCTGATTCTGGACAGTTGTTAGCCTTTAAGAATGTCACAAGTGGTGCTGTTTATTCTGTTA
CGCCATGTTCTTTTTCAGAGCAGGCTGCATATGTTGATGATGATATAGTGGGTGTTATTTCTAGTTTGTCTAGCTCC
ACTTTTAACAGTACTAGGGAGTTGCCTGGTTTCTTCTACCATTCTAATGATGGCTCTAATTGTACAGAGCCTGTGTT
GGTGTATAGTAACATAGGTGTTTGTAAATCTGGCAGTATTGGCTACGT CCCATCTCAGTCTGGCCAAGTCAAGATTG
CACCCACGGTTACTGGGAATATTAGTATTCCCACCAACTTTAGTATGAGTATTAGGACAGAATATTTACAGCTTTAC
AACACGCCTGTTAGTGTTGATTGTGCCACATATGTTTGTAATGGTAACTCTCGTTGTAAACAATTACTCACCCAGTA
CACTGCAGCATGTAAGACCATAGAGTCAGCATTACAACTCAGCGCTAGGCTTGAGTCTGTTGAAGTTAACTCT ATGC

FIG. 27A

TTACTATTTCTGATGAGGCTCTACAGTTAGCTACCATTAGTTCGTTTAATGGTGATGGATATAATTTTACTAATGTG
CTGGGTGTTTCTGTGTATGATCCTGCAAGTGGCAGGGTGGTACAAAAAAGGTCTTTTATTGAAGACCTGCTTTTTAA
TAAAGTGGTTACTAATGGCCTTGGTACTGTTGATGAAGACTATAAGCGCTGTTCTAATGGTCGCTCTGTGGCTGATC
TAGTCTGTGCACAGTATTACTCTGGTGTCATGGTACTACCTGGTGTTGTTGACGCTGAGAAACTTCACATGTATAGT
GCGTCTCTCATCGGTGGTATGGTGCTAGGAGGTTTTACTTCTGCAGCGGCATTGCCTTTTAGCTATGCTGTTCAAGC
TAGACTCAATTATCTTGCTCTACAGACGGATGTTCTACAGCGGAACCAGCAATTGCTTGCTGAGTCTTTTAACTCTG
CTATTGGTAATATAACTTCAGCCTTTGAGAGTGTTAAAGAGGCTAT TAGTCAAACTTCCAAGGGTTTGAACACTGTG
GCTCATGCGCTTACTAAGGTTCAAGAGGTTGTTAACTCGCAGGGTGCAGCTTTGACTCAACTTACCGTACAGCTGCA
ACACAACTTCCAAGCCATTTCTAGTTCTATTGATGACATTTACTCTCGACTGGACATTCTTTCAGCCGATGCTCAGG
TTGACCGTCTCATCACCGGCAGATTATCAGCACTTAATGCTTTTGTTGCTCAAACCCTCACTAAGTATACT GAGGTT
CAGGCTAGCAGGAAGTTAGCACAGCAAAAGGTTAATGAGTGCGTTAAATCGCAATCTCAGCGTTATGGTTTTTGTGG
TGGTGATGGCGAGCACATTTTCTCTCTGGTACAGGCAGCACCTCAGGGCCTGCTGTTTTTACATACAGTACTTGTAC
CGAGTGATTTTGTAGATGTTATTGCCATCGCTGGCTTATGCGTTAACGATGAAATTGCCTTGACTCTACGTGAGCCT
GGCTTAGTCTTGTTTACGCATGAACTTCAAAATCATACTGCGACGGAATATTTTGTTTCATCGCGACGTATGTTTGA
ACCTAGAAAACCTACCGTTAGTGATTTTGTTCAAATTGAGAGTTGTGTGGTCACCTATGTCAATTTGACTAGAGACC
AACTACCAGATGTAATCCCAGATTACATCGATGTTAACAAAACACTTGATGAGATTTTAGCTTCTCTGCCCAATAGA
ACTGGTCCAAGTCTTCCTTTAGATGTTTTTAATGCCACTTATCT TAATCTCACTGGTGAAATTGCAGATTTAGAGCA
GCGTTCAGAGTCTCTCCGTAATACTACAGAGGAGCTCCAAAGTCTTATATATAATATCAACAACACACTTGTTGACC
TTGAGTGGCTCAACCGAGTTGAGACATATATCAAGTGGCCGTGGTGGGTTTGGTTGATTATTTTCATTGTTCTCATC
TTTGTTGTGTCATTACTTGTGTTCTGCTGCATTTCCACGGGTTGTTGTGGATGCTGCGGCTGCTGCTGT GCTTGTTT
CTCAGGTTGTTGTAGGGGTCCTAGACTTCAACCTTACGAAGTTTTTGAAAAGGTCCACGTGCAGCATCATCACCATC
ACCACTGAGTCGACCTGCAGATATACTATATAGTAATACCAATACTCAAGACTACGAAACTGATACAATCTCTTATC
ATGTGGGTAATGTTCTCGATGTCGAATAGCCATATGCCGGTAGTTGCGATATACATAAACTGATCACTAATTCCAAA
CCCACCCGCTTTTTATAGTAAGTTTTTCACCCATAAATAATAAATACAATAATTAATTTCTCGTAAAAGTAGAAAAT
ATATTCTAATTTATTGCACGGTAAGGAAGTAGAATCATAAAGAACAGTGACGCCTCGAGGAATTCGCCACCATGGTG
AGCAAGGGCGAGGAGCTGTTCACCGGGGTGGTGCCCATCCTGGTCGAGCTGGACGGCGACGTAAACGGCCACAAGTT
CAGCGTGTCCGGCGAGGGCGAGGGCGATGCCACCTACGGCAA GCTGACCCTGAAGTTCATCTGCACCACCGGCAAGC
TGCCCGTGCCCTGGCCCACCCTCGTGACCACCCTGACCTACGGCGTGCAGTGCTTCAGCCGCTACCCCGACCACATG
AAGCAGCACGACTTCTTCAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCGAGCTGAAG GGCATCGACT
TCAAGGAGGACGGCAACATCCTGGGGCACAAGCTGGAGTACAACTACAACAGCCACAACGTCTATATCATGGCCGAC
AAGCAGAAGAACGGCATCAAGGTGAACTTCAAGATCCGCCACAACATCGAGGACGGCAGCGTGCAGCTCGCCGACCA
CTACCAGCAGAACACCCCCATCGGCGACGGCCCCGTGCTGCTGCCCGACAACCACTACCTGAGCACCCAGTCCGCCC
TGAGCAAAGACCCCAACGAGAAGCGCGATCACATGGTCCTGCTGGAGTTCGTGACCGCCGCCGGGATCACTCTCGGC
ATGGACGAGCTGTACAAGTAAGCGGCCGCGGAGCACTGCTCGGAGGAGTGCTGCAAAGTGGAGGAAGTTCTGTGAGA
AAGTGCGTTTTTCTGTAATGTGAAATAAGATAGCCTTATGTGTGCACAGACATGGCGAACAGGCTTGTGTTTCTCGA
CCCCGAGACCCTAGCCGAGGCCGACGGCATCCCCGGCTAT GGGGTGTTCGAGCCCGGCAAGAAGAAATGCATCTTCA
CAAAGATCCGCACCAGCGTCGCACTCGCGTGCCGGTACGCCGTCTCGGACGGCGGCCTCATCGACGAGTTCGTCATG
GCGACATACGGGACCAGACGCGCGTGCCGGCTCGTCCGGCACCTGACGATAAGCGCGGAGGGCGTGATGACCCGGCC
CGCCAGCAACTGCGCGCCGCACATGGTGCTCATCTGCCTCAGAGGCGTGGCCGCCGTGTCCAGCG AGGACATGGGCT
TCGGTCGCTGCATCATGGAGCGCGGCACCATGTTCATGGTCAAGTCCGCGCACAGCGCCGTCGTCTGCGGCAACCCC
GCCTGCGAGCTGCTCGTCCTCTTCTACGACTACTTCACCCCCATCCCCCGGCCGCTCTCCGGAGACGAGGTGCTGTT
CACCCGCGACCTCGCGCACGTGGACTACGCCCCCGAGTCGGCGGTCGTCTTCAAGATGGATTACAACCTCGAGACCG
ACGTGGCCACGCTGTTTGTCGGGGGGTACATATTCCGCGCCAAGGGCCTGATGATGGAGACGCGCGAACAAGTGGGC
GACGAGTGCGACTGCTGCCGCCACAGCTCGCCGGTGCTCGTCATGGATCGCGAGAAGATGATGTCGTCGCTGCGCAT
GATAGATCTGCCGGTCTCCCTATAGTGAGTCGTATTAATTTCGATAAGCCAGGTTAACCTGCATTAATGAATCGGCC
AACGCGCGGGGAGAGGCGGTTTGCGTATTGGGCGCTCT TCCGCTTCCTCGCTCACTGACTCGCTGCGCTCGGTCGTT
CGGCTGCGGCGAGCGGTATCAGCTCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGAC TATAAAGATACCAG
GCGTTTCCCCCTGGAAGCTCCCTCGTGCGCTCTCCTGTTCCGACCCTGCCGCTTACCGGATACCTGTCCGCCTTTCT
CCCTTCGGGAAGCGTGGCGCTTTCTCAATGCTCACGCTGTAGGTATCTCAGTTCGGTGTAGGTCGTTCGCTCCAAGC
TGGGCTGTGTGCACGAACCCCCCGTTCAGCCCGACCGCTGCGCCTTATCCGGTAACTATCGTCTTGAGTCCAACCCG

FIG. 27B

GTAAGACACGACTTATCGCCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGATCCTTTTAAATTAAA
AATGAAGTTTTAAATCAATCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTAGA TAACTACGATACGGGA
GGGCTTACCATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTTGCCATTGCTACAGGCATCGTGGTGTC
ACGCTCGTCGTTTGGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTTATCACTCATGGTT
ATGGCAGCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAATACGGGATAATACCGCGCCACATA
GCAGAACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAA TACTCATACTCTTCCTTT
TTCAATATTATTGAAGCATTTATCAGGGTTATTGTCTCATGAGCGGATACATATTTGAATGTATTTAGAAAAATAAA
CAAATAGGGGTTCCGCGCACATTTCCCCGAAAAGTGCCACCTGACGTCTAAGAAACCATTATTATCATGACATTAAC
CTATAAAAATAGGCGTATCACGAGGCCCTTTCGTCTCGCGCGTTTCGGTGATGACGGTGAAAACCTCTGACACATGC
AGCTCCCGGAGACGGTCACAGCTTGTCTGTAAGCGGATGCCGGGAGCAGACAAGCCCGTCAGGGCGCGTCAGCGGGT
GTTGGCGGGTGTCGGGGCTGGCTTAACTATGCGGCATCAGAGCAGATTGTACTGAGAGTGCAC

FIG. 27C

OVRF -024-RabV-G Complete Genome (SEQ ID NO:4)

CGAGAACGCGGACCAGGAGTTCCTGCGGGAGGAGCTACGGCAGAGGCTGGAACTGCTGAATGCTTTCGAGGACGGGC
GTCCGCGGGAACGCGACTCCGCGGAGGCGGCACCCCGCAGCCGCGAGACCTCGCTCTAGAGTCAGGGAGTCCGGGAG
TCAGGGAGTCAGGAGCCCGGGAGACAGAAGTCAAGTAGTCGGGTAGACAGGAGTCAGGTGGTCGGGTGACCCGCCGT
CCGAGTCCCGCAAAAAGTTTTTATAAAGTTTTCGGGAGAGGCCGACCGCCTTCCACGGTTCCGCGGAAAAGTTTTTA
TAAAAAGTTTTCGGGAGAGGCCGACTCCTTCCAACGTTTCCTCCTCTCGCGTGCCGCGGGCGGCCGCTCTCCCGCGA
CGGTCCCGCCAACGCGTTTACAAAGTTTTAAAAGTTTTCGAGAGAGGCCGACCTGTCTTCCAACGGTTGCGCGAAAA
GGTTCTGCGGAGGTTTGGAAGAGCCGCCCGCCCTCCGACATCCTCCGAAAAGTTTTCGCAAAAGTTTTTAAAGGTTT
CGCGAGGAGTTTTCGAGGGAGGCGACCTGCCTTCGAGGTTCCGCGTAAACGTTTTTACAAAGCGTCGGAGAGGTGGG
GGCGACCTGCCCCTCCTCCGAAAAGCTCTTGAGAGTGTTCGGGAGAGGCGGCCGGCCTTCGCGGTCGCGCGAAAAGG
TTCTGCGGGAGTTCGCGGGAGCCGCCCGCCCTCCGCGCCCCTCCGAAAAGTTTTTGCACGAAGTCTTTTGGCGTT CT
CGAGAGGACGCCTACCCCGACGGTAACGCGGAACGTCTCGGGAGGTCGGCCTCTCCGCTCCCGCGGTCGCGGGCGGC
GGCCCGTCTCCAGAGGCTCCGCGAAAAAGTTTTATAAAAGTTTTGGAGAGGTACCTGACCTCCTAAAGTTTTCAGAG
AGTTCTCGCAAAAGTTTTGGGAGGTCGACCTGACCTCCTAAAGTTATCGAAGAGTTCTCGCAAAGAGTTTGAGAGGC
CGACCTGCCTCCAACGGTTCCGCTAAAAAGTTTTATAAAAGTTTTGAGGGAGGTCGACCTGCCTCCAACGGTTCCGC
TAAAAAGTTTTATAAAAGTTTTGAGGGAGGTCGACCTACTCTCGAGGTTCCGCGAAAAGTTTTATAAAAAGTTTTTA
CAAAGTTTTTGAGGGAGGTCGACTACCCCCGGATCCTCCGCCTCGCGTGCCGCGGGCGGCCGTCCAAGAGTTTACGG
AACGTTTTGGAGAGGAGAGGCCGACCTCCCAAAGATTTTGCGGAACGT TTTGGAGAGGAGGACTGGCCTCCGAAAAG
ATCTTACAAAGAGTTTGGAGGGAGGACTGGCCTCCAGAGGCTCCGCGAAAAAGTTTTGCAAAGTTTGGAGAGAGGTC
GACCACCCCCGAGGTTCCGCGAAAGTGTTTGCGGAGAGTCCGAGAGAGGCAGACACTGCCTGCGAAAAGTTTTCGCG
GACGGGTTGAGCGGGTCACCGACCTCCGAACAGTTTACAAACGTTTTACGGAGAGTTGAGAGGCAGGCCGACC CGAC
AGTTTAGTTTTGGAAGGACGAACCTGTCACGGGAAAAGTTTACGAAGAGTTTTGGGAGAGGCCGACTGTTAGCCGAG
CGCGCGCGAGCGAGTTCACGTTCTCTCGCTCGTGTGCGGGTTAACTCGCTCACTGGTTCTCCTCTCTAACTCGGAGG
GGCGAGCGAGTGGTTGACTCGCCCTCCTCTCACTCTGAGTGAGTGATAACTAACCGTTAACTATTAACTCGTCCTCC
ACTCTCTCGCTCTGAGTGAGGATTGACTTGTTAACTCGTCCTCACTCTCTCGCTCTCTCACTCTGAGTGGTGAGAGA

FIG. 28A

TTAACTGTTCAACTCGTTAGCTCGTCCTCTGCCTCTCACTCCAAGACTGAGTGGGTGCGTTGACTGCTCTTGTTCCC
TTACTCCGAGGGGCGATTGAGTGAGCAACAGCTACTCGTTCTCTCGTTCTCTCACACCGAGTGAGCGAGTGAGTAAG
TTAACTCGTTCTCTCGTTCTCTCGTTCTATTTTCCGAGGAGTGAGC GAGTGATGTAACGGTTACTTGTTACTTGTTA
TCTGTTCCCTTACCTCGGCGAGTGGTGCGTCAACTTGTTCTCGTGAGCGAGTACGGTCACTTGTTTTCTCGTCTCTG
CCTCGAGAGTGGTCAACTTGTTCTCGTGAGTGAGTTGACGTTAACTGTTGTTCCCTTACCTCGTGAGTGAGCGGTTG
CTTGTTCTCGTGGGTGAGTTAACCGCGTTCCCTTACCGGAGTGAGCGGGCGGCGATAAAAATAATTAATTG ACTGAT
TCGCTCGTTCACGAGCGAAGGGCGGCGCAAGGGGCGCGGGATGCTGGTCTAATCTACTAAGGCCGAATACAAAAACG
GATGGGAGACCGGGGAGAGGGTCACAGCTCCGAGCGGTGCATCTGCGCCAGCTGGCGGCGCCACTCGGCCGCGGGCC
GCGTGGCCGCCCAGGCCGCGTTGTAGCCGCCCGCCACCGCGACGCAGGTCAGCTCGAACTCCGGCGCGAGCTCGCGC
ACGTCGTAGATGTGCACGGTCGCGACGTTCAGCAGCAGCGCGCCCTTGCGCAGCGAGGCGAAGGTCGCGTGCATGCC
GGCGGCGAGCGGGTACACCGGCGAGAGCGTCCCGCCGCCGTGCGCGACCACCGCCATGTGCCGCCCGTCGCCGCCGA
CGGTCAGGCAGGTCACCGAGGCGGAGCCGTTCGCGCGGACGGGGCCCGCCTCCACGAGGGCGGCCGGCAGCGGCGGC
GCCGCGGGGCGGAAGAGCCCGCCGAGGAGGAAGCCCAGCGCCAC CAGCGCGAGCGCGCCGAGCAGCCTGCGCGGCGA
GGGGTGCATGCTTGCTGGCTGTGGTGTGGAGGGCGGGTGTGGGTGTCCGCGGCTGTGGCGGGAGGGTCTCGACTGCT
AGGCGGTCCTTTTTCACTTTGCGCCGTGGCGCCTCCTCCGCAGGCGAAGGGCTGCGGCGGGCCCGGGCCGGGCCGCT
ACCCCGCCGCGCGGCCCGCGGCCGCCAGCGCCGCGGCCAGCCGCCGCCACCGCGCGCCCGCCGCGAGCA GCAGCCCC
GCCGCCGAGCGCCCCGCGCCGCCGCGGGCGCGCGCCGAGGCCGCGGCCCCGCGCCGCGCCAGCAGCAGCGGCAGCCG
CGCGTCCAGCGGGCCGCCGCGGCGCAGCGCCGCGCGCAGCAGCGCCGCCAGCGGCAGCCGCCCCGCCGCGTCCGGGC
CCGCCGCGCGCGCGCCCGCCGCCAGCAGCGCGCGCACCAGCGCCGGCGAGGGGCGCCGCGCGCGGACCAGGTGCTCC
ACGAGCAGGGTGGTGAGCAAGGATTCTCGAGAAGTAGGAGTCATGTGTGACGACAAGGAGAGACGTTATATTAGGCG
CGTCCTACTTCACTTTGAAGATGGTGTAAAGTGTTAAAACTTGAACACCGTTCACTCTACCACTGCCGTTACCGTGT
CCTGCCCCAAAAGCGACCACAGTGCTTTTTCCACCACCTGTTCCAAATCCGTTCCAAAAGCTCCCATCCATTGTTGT
TAGAACTTTCAGATGTTTCTCTAGGTTGTTTAGTTCCACTGC AAGTTTTGACCATTATCGTTACTGGACATGCTGTT
GGTAATGAGTTTAATAACCAATCATAAAAATAGTTATAATTTGTTATAATTTATAATTTGTTATAAAGCTATAAAGT
AGCAAACACTTTAATGTTATATTTTGCCTAACCCTCCGTTAACACCACCATTAACACCACCACTTAAGCTTTTACTA
CCACCACTACCACCTCCAACACACATTCTTTTCTCTAAAGGTCCCCAAATTCCACCTCCTGAACTTG GACGTTTTAC
AGCACCTCCGGGTGTACTTGCGTACCCTTTAGAAGTTCCACTGTGACTGTAGATATGATACTGTCCTTCTCCAGGCA
TGATTAAAGTGTGTTGTAATTAGTGTTATCTACACAACTGTGTGAGACGCTCAAATAAAAAGAAGCTACATTTTACA
ATTTTGATTAGCTGATGTACCACGCTGTATCGCGGCCACCACAAGAACCCAATCCAGTAGAACCAAATCCAGAGTCG
CCGCGGTCGGTGTTGTCCAAGCAGTTAACCTCTTGAACTGCTGGGCACGATATGCGTTCGCATATTAGCTGAGCTAT
CCTGTCTCCCTTCTTAACCTCAAAGTCGCTGTTTCCGAAGTTAAACAGCACCACTCCGACGTTGCCTCGGTAGTCTT
CGTCGATCACGCCAGCGCCCACGTCGATAAAGTGTTTGACTGCAAGGCCAGAACGTGGTGCTATGCGTCCGTAGCAA
CCAGAAGGGGGCTTTATCAGAAGGTCAGTAAATACTACGC GACTGCAATGCGAAGGGATGACACAGTCGTGTGCACT
ACATAGGTCTAATCCTGCGGCACCAGGAGATCCTCTGGCTGGTATAGTGGCGTTTTGGCTGAGGCGAACAACCTGAA
GAGTTTCCGTGTGGCAGAACTCCATGGCTAGGGTGGCGAGCGGCCGATCGACTACGGGGTGTACAATTTACACTTTC
TCCAGAAAAATCAGGGGCGGGTCAGCATGGCGCGGCGCAGGTCCAGCAGCGAGTCGTACGACAGG AAGCACAGGATG
GAGGTCACGATCTCCGGCGGCAGGGCGCACGGGCACATGAGGCCGGCGATCTGCTCGGCCAGCGAGACGCGCAGCCG
CATCATGCAGATCTTGCCGAAGAGCGCCGTCCCGTAGATGGGGAACTCGGCCGCGCGCTCCAAAAAGGCGTTCTGCA
CGAAGAGCGCCTTCGCGTCGTCCGCCGCGCGCAGCACGTCCAGCAGCGTCGCGTCCGTGTGGCAGCGCACCGCGCGC
ATGCTCGCGATCTCCTGCTCGCACGCGCGGATTACGGTCGCGTAGTCCGCCAGCGCGCGCTCCGCCAGCATGCGCGC
GCCCTCGCCGCGCAGCGCCAGCTCCTGCACGCACAGCAGCGCGGCCTCCGAGCGTCGGAACACGTGGCCCCATTGCT
CGGATGTGATCAGCGCGCGCGCGAGCAGCTCCGTCGGCGGGCGGCGCGCGAGCACGGCCGCCGTCGCGCGCACGTTG
TTGCGGCGCAGCATCTCGGAGACCGCGCATAGGCCCGA GGCCGACATGTGCTCGAGCTCCGCGCCCATGCGCACCAG
CCGGCAGCAGGCGCCGTGGCTGAACACCGCCGCGCGGTGCAGCGCGGTCTGCAGGTTGTTGTTGCGCAGGTTCAGGT
CCAGCCCGCGCTCGAGCACGAAGTCCACGACGCCGCCTCGCAGCTCCCGTAGGTCGCCATGTAGTGCAGCATGGTGT
TCCCGCACGCGTCTACGGCGGCCGGGTCCACGCCCGTGAGCGTGCGCACCATGCCCTCGGAGA TCTTGGCCGTGCGC
GCGAGGTGGTGCAGCGTTGTGCGCCCGTACGCGTCCACGACGCACGCGTCCGCGCCCGCGCGCAGCATCATGTCCAC
GAGCGCGGCGGAGACGCCGCCGGAGCACAGCAGCGCCGCCAGCGGCGTCAAGCCGTTGCAGTCGCAGGCGTTTGGGT
TCGCGCCGCGCTCGAGCAGCAGCCGCAGCACGTCCTCGCGGATCCACTGGTTCTTGGCGTACACGTGCAGCGGCGTT
ACGCCGTAGGTGTTGCCCTCGTTCACGCGCGCGCCCGCGTCCAGCAGCAGCCGCGCGACCTCGAGCTCGGCGCCGTC
GGGGCCGCAGAAAGCCAGGAAGGAGGAGAGCACGCTGTCGCAGACGACGACGCTGGCGTCGCAGACCACGTCCGCGC
CCGCCTCCAGCATGAGCGCGACCACCTCCGGCCGCACGCCGTCGTACTGCACGTAGGCGTGCAGCGGCGTGCGGCCG
CAGGAGTCCTTGGCTTTCACGTCCGCACCGGCCTCC AGCAGCACGCGCACGATCTCCGCGCACTGCTCGTGCCGCGC

FIG. 28B

GAAGTGCACGCAGAGGTGCAGCGGCGTGCGCCCGTGCTCGCCGCGGAAGTTCACGTCCGCGTCGGTGGCCACGAGCG
CGCGGACCGTTTCGAGGTCCACCTGCCCGGACTCCAGGTAGCGGAAGAGCAGGTCCGCGTGCGGGACCACGACGGAC
TCCCGCGAGAGCATGGCGGCGTTTACAAATATTGAAATCTTTTTTCACTCATCTTTATGGG CGCTGGATGCGCAATA
AGGGTGGGAGTAAAAAACTTCTACAAAAAGCGTACAAAAGGTACAAAAGGCGGGGCGGGGACGGGCTGGCAGTGGGT
GCTGCGGGCCGAATTGGTCTCTACACGGGGACGCCCTCGCCGGAGCCGGTGAGCCGGTAGCCGGCGCCGGCGATCAT
GGTCAAGCGCTGCACGAGCTCGTTGCGCTTGACGCCGGCCTCTGAAACGCACACCATGTGGTGGATGTACCGCTCGA
TGCACTCGCAGCGCGGGAGAGTGGAGTCAAGATCGGATGCGAGTTGCAGAATGTCATCCCAGAGCTCGGAGAACTTG
CTGTACAGTTCTCGGAGGTCTCTCTCCATGCGAGCCATAAGAGAGTCAGGATGCGGCGTTCCTTCGGGGGTCTGAGC
GAACACCGCGAACAGGCTGGTTATGCCGTGTTCCAGAATAGAGTGGTTCCGTGTCAATGCCGCAGACAAGGGTCGTC
GTCCGCGCAACGACTGGCGGCAGAGCGCTGTTTGTGCCGCACCGCCCATTCCTCTGGCGATCGCGTCCACCGACGCA
GTGATCATCTGCGCGCCGACGTCATTGTAGCGCGCGTTAAACTCAGTAATCATGATTACGAGATTGCAGATTTCATA
GTAGCACTTTTCCAAGTCGACGCGCAGTTTCACGATCTGGTTGACAATCTTGCACGCCTTTCGCCGCGTCTCCGCCA
CGTTGGCGACTCGGACTTGCGCTTCCTGGTCGATGGACGGCGGAAACACTTCAAACCCA AGGTCGCACAGTTCAGCG
GTGGGGACTAGCGTCACGATGATGTACTCCGCGTCGCCACCCACTTGCGGCAGGAAGAACACCGACCGCGCGGCGGG
AACGACCAGAACGTCGCCTTCCTGCATGTTAGTTTTTAGAAACTTAGTGTTGTTCACGGAGATGCCGGCCATGCCCT
CGTTTTTTACACATATTATGGTGACGTACGCGGCGACCGTGGGGGCCATGTGGTGGCGCATGTACCACTCGTCGTGC
TTGAGTTTCAGACCGTGAGATTCGCCGACCTCGAAGTGCATGTTGGCGTCTCTGACGTAGCGCGAGAACTCGCTGCG
ACAGATTCGGGCGGGCGCCCGGTGGAACGTCGACTCGAAGAGACTGATGTCTGTCCATTCGCCCACATGAGTGACCA
CCGAAGAAGTGTTTTCGATCCGAGTCTCGAACACCGAGTCCACGAGCACCGGACAGTTGGTTCCGGGCACCGTCAGC
ACCAAGGGCCGCGCCTCCACGGGGGCGACGGA CGAGGCCACGGAGTCGGTGTCCCCGTACCCGTAGTCGTCGTCGGA
GTCGCCGCCTCCGTCGGCCCCGTCGCGCGGCCTCCGCAGCGGCATGCAGCCGGCGGTGGGAACGCACTGGTTTCGGC
CACGGCCGAAGCGGCCAAACAGTCTCGCCAGGGCTGACATCCTTGGACGGCCACACCAAAACCAAAAAAACATATTT
TATCAGTTATTTGTCGATTTTCACCGGCTCACCGAGGGCAGGACCTCCTGGATCCCG GACACCCCCGCCAGGCAGCG
GGCCGCGCGCTCGCGCACCCAGAAGCGGTCGTAGCCGTGCCGGAGCACGAAGGCCGCCGTGGCGTGGCAGTCCACGC
GCTCGATGAAGCCGTGGACGGCGCGGCGCGCGTAGCTCGCCGCGAAGGCGCGGACCACCGCCGAGCAGCGCCCCGAG
GGCGAGTCGTCCGTCTCCAGCGCCAGCGGCATGCTCGCGATGCGCGACATCAGGTTGGAGGTCTGCGGGATGTTGAG
CTCGCGCGTGGCGGTCATCTGCGCCTCGAGCCCGGCCTTGAGCACCTCGTCGCAGCGGCCCCACTCCAGCGCGCAGA
CCACGCGGATCTCGTACCCCTTGAGCCGCAGCGCGGTCTCGATGTCCACGGAGGTGAGCACCGCGCTGAAGCGCAGG
CTCTCCTCGTCCGCGGGGTCGAAGAGCACGGGGATCTTAACCTCCGCGCTGCGCGTGACCTCGCAGAGCGCGATCGC
GAGCAGCCCGCGCGTGAGCTTGCTCACCAC GCGCGGCTTGCCCACGGGGTACACTGGCTCGCGACCTCGCGCAGCGG
GTACGCCAGTCTGAAGCAGCGCGCGTCCGCGGGCACCGGGCTCGCGCCCCATGTTCAGCGCGGAGAAGTGCACCGGG
CAGGCGGCGCAGCCGCGCGCGGCGTTCGCGAGCACCATCTCGCGCAGCCCGCGGAAGGCCGCCATGTCGCAGGAGGG
GAAGATGCGCGCGAGCGCGGCCTGGTGCGCGAGCGCCGCGTCCGAGAGCGCCTGC GCGGCCGCGGCGGCGGCCTCCT
CGGCGGCGGCCGCGCTCTCGTCCGCGGAGACCACGTCTTCGGGCACGTCCACGCAGACGCCGCCCCAGAACTCGCAG
TACTCGGAGAAGAGCGTCGCGGGCGCAAAGCGCGCGAGGTCCACGAAGGCGACGCGGTTGCCGAGCCTGGAGAGCAG
CGTGTTCTCCGAGATGCGCGTCCAGCCCTTGCCGGCGAGCTCCATGACCTGCCGCGTGTCGAAGAAGGAGCTGTAGA
AGCCGTACACGGTGATGTTTTCCTTGCACGTCGTCAGCCACATGAGGAAGTCGCGCACCACCAGCTTCGCGCAGTCG
CCGGAGAACACGGGGCCGGCGTTCGTCGCGATGGAGTTCAGGCGCACGGTGCCGTCGCTGCCGAAGCGGTACACGAA
CCAGGCGGCCACGCTGTTGCCGGAGGGCGCGTGAACGTGTGGCTGCGCCCAGGAGTCGGCGCTCGCGGCGGTGCGCA
CGTCGTGCGAGAGCACCTCGGTGTCGGGGCGCGAGTAGGTGCTGGGGTCTTTGATCCAGATGGCGTAGCTGCCCACG
CAGCACACGTTCATGAGGTCGAGCAGCGTCTGCCGGCGCAGCGGCGTGCCGAGCCGGCGCACGGCGTCGTGCGAGAC
CATGCGCAGGTCGTAGAGGCCCACGTCCGAGAGCCACTGGTTGAGCTCGTCCATGGACAGGGCGTCGCGGGGGGGCG
GGCTGTCTTCGAAGGCGGCGCGGAGCTCGGGCTCCGTCTCCGCGCGCTGCCGC AGGATGTCCAGGAAGGGGCTGGAG
GAGTCGGGGATGTAGCAGTCGGGGTCGTGCCTGGACACTATAGCGAACCGCTGCGTCGCGGGCGCGGGCGGCGGGGC
TAGCGCGTCGGCGCGTGCGTCGATGAAGGTGCACGATATACGCACGGACTTGAGCGAGGGGAGGACGACCGCGGCGG
CGCGCGCGCCCTCCGCGTCGAAGATCATCGTCTTTCCGTCCCTCGCCTTCGCGAGCGCGTATTCTCCAGGCACGAGG
TCCGTCGGCGGCGGCTCGTCCCAGGCCTGCCGGTCAGGGACGCCGCCGCACACCTTTCCCCAGAACCCCAGCATCCT
CCAAAATACCTAATAAGGACGGCCAATAGCGGGGCTTGCGGGCGTTCGGACCTTCCGCGCTTTAATTTTAATTTATT
GGCTTGCAGAACTCCGAGCGCCAGTCCCGCTCGAAGACCGCGGACAGGTCCTTGACGATGTCGCCCTTCTCGGCGTT
CACGCTCACGAAGGCGTGGTAGCGGTAGTGCGTGCCGTCGAGGTTGGCGACCGTGAGGTGCGCGAAGGTGTCGTCCA
CGATGAGCAGCTTAGTGTTGTTCGCGGCGTCGTCCCGGCCGGGTACCACGAACTTGCGCACGGACATGTCCACGCTG
CCGACGCCAAAGTCGTCGAGGCTGCGCGCGGCCGAGACCGACAGCGGGTCCGCGTTCTTCCACTCGGTAATGATCAC
GCGCACGCGCACGCCGCGGTCGATGGCCGCGCGCAGCAGCGCGTCTATGAT CCGCGGCCAGTACTCCACGGCGCTGG

FIG. 28C

CGTGCTTGATCACCGGCACCATAGAGAGCAGCGAGAGGTCGATGCTGTTCTTGGCGTTCTCGATGCGGTGCAGCACG
AGGTCCTCGTCGAGCGTGCGGTAGAAGCCTAGGAAGCGCTCCGGCGAGTCCGAGAAGAATACGCCGCCCCCGGAGTG
GTCGAGGTGGAAGTTCGTGGCCGTGGGCGTGACGACGGCGCAGCAGAGCCGCGTGAACGGCACCTTCGGCTCCACG A
TCATGGAGTAGAAGGTGTTGTAGCGGTTCATGAGGTCCCAGGCCAGGTGCTTGTTGGTGGAGTAGAGCCCGAGGTTC
TTGATGGTGGACACGGACCCGCCCGTGAGCGAGGCGCTGCCCACGTACCAGTGCCCGGCGTCCGAGAGCCAGAAGCT
GCCGAGCAGGTTGCCGACGCCTTCCCGCGTGGACACCTTGACCTTGTAGTAGTTGACGCCCGCCTCGCGCAGCTCGT
CCGCGTCCTTGTCCTTGCTCTGCACGTCCACGAGCAGCGTGACGTTCACGCCCTCCTTGGCGAGCGTGCAGAGCTTG
TCCTTGACGTCGACGCCCTCCTTGGTGGAGCTCAGGTTGCAGCAGAAGCTGCAGATGTACAAAAACTTCTTCGCGGA
CTCGGTGATGGCGGTGAAGCAGTCGAGGGTGCTCATGTTGCCCTGCGCCAGGGACGCCACCTCTGCGGGCAGCGTCT
CCACGACGCGGCAGTCGGCGCCCAGGGGGATGGAGGAGAACGGCCACAT TTATTTATCTCACAAAAATAATAGGGCT
TCAGGGAAAGTCTTTTAGCAGGCGGGCGAGTTCTTCGAGTTCCCTTAGGAGTTCTTCCATTTCTTCGGAAGTCAGCA
ACTGGAGCTCGGACTTTAGTTGAATATCTTCGAGGAAACCGTCTAGCATGTTCGCCATGTCTTCCGGGGAGCACTGC
GCCACATCTTCGGGGACAGGATCGGGTGTGGGCATTAGGTCTCCGCTTACTTGAACGTCGTCCATCATCCTGTC GAT
GAGGTCTTCGACTTCTAGACGGGGTCCGTAGATCAGCATATTTGGTGATGGAGGTAGTTTAAGGTGCGAGAGTTAGT
GTTATACGACGGCCAACGTGTGTTTATCGCGCGTACATTTTCAATAATAACAAACTCCCCTTCCTGCGCCTGCTCGA
GAAGCAGCTCGTCCAGCTCCTCCTGTCGGCGCGCGGCCACGCACTCCGCACAGACCCAGGACGCCGAACACCACCGC
CGCCGAGATCGACAGACCCAGCAGCACCGACATCCTCACGCGGGCATCCGGCTATTTAATCGTTCTGGAAACGTATT
AATATGGGCGTCGTCATGTGCGGGTGTCTGTTTGTGTGGGCGGGCTGGATCGCGCGCCGCGTGCGCGGCTTCTGCGT
GGCGCTGCGCCAGAGGGTGTCGCGCGACAAGGGCTACGTGGCCGTCATCCAGACCTGCGACGACGACTACTTCACAG
AGGAGGAGTTCGACGACGGCAAGCAGGTGGTCGCGCTCCTGCGCGAC GTCTCGCGCGTGGTCGCCGCGCCCGCGGGC
GTGACGGAATAAGTTAGGATAAGGAGTCGAGGGGAGAAAAACAGCGGTCACACTATAAACTCGCGCGAGGCCGATTT
TGACGTGCTCATGTCCGGAAGCTCCGCTTTCTGCAGCGCGGAGCGGCACACGAAGCACACTTCCGTGTTGGTGGGAG
TTATGCAGTGGACGTGGTAGCCGTGCCCGCACACCATGACTTGGAACGGACACGCGCCGGGACAGGCCGCGT TTATG
CATCCTTCCGGCGAGCGCTTGTTGCAGATGTAGCACACGTCTGAGCACGCCAGCGTGCAGGACACGGCCAGCCTCCA
CTGCTTAACCTTAACGGGCATGGCTAGTTGAACACGACCATGGGCGAGTCGCGAGCCTCGAGTCGGGGGTTCAGGGC
AAACCGTTTCACGCCGTCAACGGTTCTTCTCTTTGCAATTTTCTCTCGGCACAGGCTCGTCAGCGTCATCTCGGCCA
GGCGCGCGTCGTTGCCTAGGTGCCGCGCGGCGTCCTCGACCGTCACGCCCGTCTTGCCGGCCTCGTCCATGAGCACA
ATGCAGACCAGGTGCGCGCTAGAGCATATGACCTCCTGCTCGCGTCCGCCGGCAGCGGGGATGGTTAGCTCCGCGCG
CCCGAAGGCCGCCAGCGGCGCCACGTCGTAGGCAGTGTCTGCTCGGGCGAGCGCCGACTCCACGGCACCGCGGAGCG
ACTCCGGCGGCGTCATCGCGGCCAGCGGCACCGGCGTGGGCACGG TGTACACGTTCACGGGCATGAGCACCATCTCC
GGGTCGTGGTGGCCGCTCTCTTCGCCGTCGTGCTCCATGGGCTGCGGCGGCGGCAGCAGCGGGAGCAGCAGCCGTCC
GGACATGAGCCGGCGCACAAGGTCGTTGAGCGCGGACGAGGCCATCGGCGGGTACAGCTCCATGGCCAGCTTCAGCG
ATAGGTGCTTCTCGAGGTTGACGCCGGTGTAGACGCTCTTCACGATTCGCGCGAAGGCCACGCGCGCGAA GGCCGCC
AGCTCCTCGCGCGGCAGGCGCTCGATGTAGGAGAGCAGCATGTCGGTGTCGCACGGCGGCGCCGCGACCACCGCGCC
GTAGAGCGCCTTGCCCGAGAGCCTTTCCAGCGCCCTTGCGTGCAGGCCGTGGGTCTTGAGCACGTCCACGTAGTTCA
CGTACAGGCAGAGCGCGCGATCGAGGTTGCTCTCCGCGACGTGCGTCTCGATGCACTCCACGATGAGCGGGCCCATG
CGGTCCTTGATGAGGTCTATGAGCCCGCCGGAGGCGACTCGCGCGCTCATGAGGCACGTGCGGCAGTACGCCATCAG
GCCCTCGAGGTCCGCGGCGATCACGTCCTCGACCACGTTCGCCACGACGCGCGGCCAGAGCCGCACCTTGCTCACGT
TCTGGTGCCGCACCATGTCCACGAGCTCGTCGTACGAGCCGCCGGGCTCGTGCGCGCGATCGACGATGCACCTCGCC
ATGGTGCGGCTCTGGCGCATGAGCTCGTTCGTGAAGCGCACGC ACGCGTCCTCGGAGAAGAGCGCGCTCAGGCAGGA
GTAGCAGCGGTCCGCGACGAGGTGCGGGAAGCGGCACTCCACGACGCCGCGGCCGATCCGCAGCACGCACTCGCCGT
ACATCTCGTCCATGGCCTCGCGCAGACAGTCGTCCAGCACGTCCGCGTTGTGCGCCCACTGGATCACGCAGAGGTAG
GGCTCGATGTTCTCGCGCGCGTTTTCCACCTCCTGCACCATGTACTCGAGCACGGTCATGTCCTCGTG GATGTCGGT
GCCCAGCATGCGCCCGGGCGGCAGCCAGCTCTTGCGCGCGATCGCCTCTCGCAGGCACGCCACCGCCGTGAAGGTGT
TGACGCGGAGCTTGGTCAGTAGCCGCCGCAGTCGGGAGATGTGTGCCACGGAGAGGTCCATCTCCATGGCCTGGGCG
ATGAGGCGCGTGAGTTCCTCCTCCATGGCGGCGGCTCCGCGGGCAGATATACGCGAACAACGGTAAGCCGTGCTATT
TCATTTTTGGACAAAAAGCTAGTCGTCGACGCGCATGTTGTCGAGGTTCCGGCACAGCGAGAGCACGTCGTCGCGCG
CGCGCCTCCGGCGCAGTTGATTGTTCGCGCGCCGCGCGTCCGCGAGCGCCTGTCTGTACATCGCGGAGTCCGCGTAC
CCGTGCAGCGGCGAGCGCCGAGTGCCGGGCCTCGGGCTCGCGCGGCGCGGGAGCGGCGTTGGCGCGCGCCTCGAGCG
CCGCGCGAAGTGCGCCTGCATGGCCAGCAGGCAACCGAACGGCATCATGTATCGGTCCATGAGGCACTGGCTGGCCG
CGGACGGCTCGCGCGGGTGCAGCAAGCCGCCGCCCACGTCCTCCATGACGTCGCGCAGCACGCAGCGCAGCATGGTC
TCCATGCCGTCCACGGGCTTGAACCTCATTGGGGAGGCGTCGACGTAGAAGCCGTCGGCCACGAAGTAGAGCGCGTC
CAGCCCGCCGAGTTTCTCGCCGAGACCGACGAAGACTCGTCCACGTGCCAGTCCACCACCGAGGCC TTGAAGAGCAC

FIG. 28D

CACGTGCCGGACGTCGTGCGAGCGCGCGAGTGGCGTCGATGCGGCCTGTCATGCGCACGCTCACGCACGGCGTCATC
CCGTTCTTGTAGCAGAACTGGCGCGCGAGCTCCTCCTGGCGTACGATGTCGACCATGCTCTCCATGAAGGAGGTGGA
GAGCAGCATCGCGCCGCGCGCGGCGCGGGTCGCGTTTTCGTCCACCTCCACTTCCATCCCGCCGTCGATCCTAATCA
TCTATCGTATTTAAATTTTCGGCGGAGCAGACACGCGGCTGCTCGCTGCGCGATCGCTTCAGCCGCGGCGGCGTCAC
GCACGCGTTGCGGCGGCCGGCACGCACGAACGACCGCCGGGGCTCTTCGCTGAGCGAGCGCCGCGGCCGCGTGACGC
GACAGTCGCGGGTGGGTTGCCGGGAGTCGCTCGCGCGCCTTCTGCGCATTTCGCCGGAACGCCGTGTTTACGTAGGG
TATTATATTTTCAACGTAACTAAATGGACGGGGGCGTGCACAAACGGCCTTTCATCGTGAACGTGGATGGCATGGGC
AAGGTGCTCGTGCTCCGGTACTTGCGGATGTGCGAGGTGCCCGAGGCTAAGTGCGAGGGCTCGCGCGCGTCCTGCGT
GCTCAAGATGGACCCTCCCCGCTCACCCAGTTGCGAGCGCAGGCCGTCTCTCCCGCCGTCCCCCCCATGCCCCATGC
GCACGCCCCCCGGGTCGCCGCTCCAGGCTCCCTTGATGCGCACGCAGATGCTACAGGGGCTGTT CGACGCCGCCAAA
AACAACGGCGAGCAGATGTGCCGCCGCCAGTAACCTAGGCGTGCGCAGTACGAAAGTTAGTGCGTGATCACGTTTTT
TGCAATGTCGATCACGCCGTGCGTGCCCGTCTTGCGCTCGCGCTCCACCACGCCAGTCACGGGCCGCGCGTCCGAGA
CTAGCGACCCCAGCATCGAGCGCACGGCGCCCTCCGCGGCGGGGTGGCGCGTCAGCAGCAGGAACATCACGATGTGC
GCGGAGACGCCGCGGCGGCTCAGATCGTGCACGGCGTCGCCGTCCATGAGCACGGTGTTTGAGAAGTACGTGAACAG
AGTGTTGTCTCGCACCAGGAAGGCTGAGTTCGAGACGCTCTCGAAGTCCACGATCTCGTCGTCCTGCACGCCCATGT
CCAACAGCGTCTGCACGAGCGCGGGCTCGTCCAGGAACACCACGGCGCGCGCGAACCCGCAGTCCAGCGCGCGCGCG
TCCGCCTCCAACACGCGCGAGGCGCCGCCCTCCGGCGGCAGGAAGGCGCAAGGCAGCGGCGTGCGTCCGTCCGCCGG
CGCCTCCCCGAGCTCCTCGAGCGCGAAGGCCAGCAGCGTCTCCATGCGCGCGCGCGCCTTGTCGAAGTTGTCCGCGA
GGTCGCGGATGCGGTCTGTCTGCGAGAACATCTTCAGCATCGCCATGAGCTGCACGAAGGGGTGCAGCACGTATATG
TTGTCCACGAGCAGCGTGGGCAGCGCGCGCAGCGTGGCCTGCCGCACGTTGAAGCTGTCCAG GATGTGCCCGCCCTC
CTCGTCCTGCAGCACCACGTAGTTCTTCAGGTAGGGCACGCGCAGCAGCACGGTCTGCCGCCCCGTGACGAAGTAGA
TCAGGAAGGCGAGGTTGATCAGGAACGGGCGCGCGTTCGTCTGCACCATGTCGATGTCGCCGTACTCTATCTCGGGG
TTCAGCAGGTGCAGGGCGTACGAGCCGTAGCACACGCACCGCTTGTTGTGTCGGCGCAGGTGCTCCTTCACGAGCCG
CTTGACCACCTCCACCAGGTCCGAGTGCTTGTGCCGCGCCATCGGCGCGGCCTCCTCGGACGGCGGCAGCACCGCGT
ACGAGTTGAGCGCGCGGCTGGCGAGCGCGCGCGCGCGGGGCGCGTCCACGCGCCGCACCGCCGCGTTGATTGCAGGC
GTCGGCGTCGTGAGAGAGCCCAGCGTGCGCGTGAACTCGCTCACGATCACGCTCTGCAGCTCCAGCACCGTCAGGAT
CTGGCCCAGCTTCTCCAGGCGCCGCTGCCTCGAGAAGTACTCCTCGATGCGCGCGGCGATTTCCTTCTCGGAGCCGC
CTAGCTTCTTGAAGAAGCGACGACGACTCTTTACAACAAGAGAGAGAAAAAGCTTCCTATCGAAGTTGAGGACGCGG
GTCATGTTGCGGCGCTGCGCGCGCAAGAGCACGCAGCGCTCCATGGAGGGGCGCGAGCCGAGGTACTCTTCGATCAC
GGGTGGAGCCATGACAGCTCTATTTTCTGAACCCGCGATTATTGTACAGCGCAAGCCGCG CGCAGACCTGCTGGCAC
AGCAGCGTCGTGTTTCGCATGCACACGCGCGAGGACTCGATCGTGCGCGCGTCCGGTGCCCAGGCGCGCAGCTCCAT
CAGTTCCTGCTCGACGAAGTCCACGGGCTCCACGAAGCGCTCTGCGCAGAGTCCGTCCGTGAACGCGTTGACGATCT
GCCGCACGAGCACTACCACGTCCACCTGCTCCACGAGGCGCACGCCCATGGCGATGTGCACGAAGAGGCAGCGGAAG
AGCGCGTCCATGGCCATCTGGTGGTCCGAGCAGGGCCCGACCGCGGTCTCGCAGCCCAGCGCGAAGCGCCCGATGCC
GCGGTACTGCACCATCTCCGAGGGCGAGAAGGAGAGCCGCTCCATCTTGAGCACGGGCGGCGGGCCCGCCGGCAGTC
CGCGCGCGAGGTCCAGCACCGGCGTCCACCCGGGCGTGAACATGTCCGGGATCAGGAAGAGCCCGTAGCTGGCCATG
CGCGCGATGTCGAAGGCGTGGTCCACGACCTTGTTCACGGCGCTGTCCGCGCGGTTTACGCGCAGCGCCTGCAGGAT
CACGTTTCCGGAGGCGTGTCGCGTGATCGCGAGTCCGCGGTCGCGTACCCGCGCAGGCCCGGCACCGCGTACGCGGT
CAGACACACGGCCAGGCGCGCGCTGTGGCACGTCCTCGACCGAGCGCAGCCGCATCTCTCCCTCCGACACCAGACAG
CCAAGCGACTCCCTCACCGCCGGCGCGAGCACCTCCGTGGCGCAGAGCGCGTCGTGCA CGCGCTTGAGCGCGTTCGG
CTTCAGCGCGTAGCCGAAGAGCAGCCGCGTCATCCGCGAGCCCGAGAACGCGAAGCGGCGCACGTACTCCTCCGCGA
GCTCGGGCCGGTCGTTGATCCACGAGGTAGAGAAGACGTGGTCGGAGGCGAAGAGGTCCGCGCCAACCGCGAGCAGT
GTGGATAGAGACACGGTGTCGAGGAAGTCCACGACGTCGGGGAAGTTCTGGCGCACGCAGGCCTCGGCGACGCGTCT
GGTGTGCACGCACATGTCGGTGACGGGCACCCGGTGGCCGGACTCCACGACGGACACGCAGACGTCCTCGGTGACGG
CGTCCACGGGCATGGTACGCAGCAGCTTGCCGAGCACGTCGCCGAACCCGCCATCGAGCGCCTTGCGCCACACGAAC
CCCGCGTCGAACTTGCCGGGGAAGTCCGCGATCACCGAAAGCTCCGCGTGCGAGAGGTTGTCCACGTTGAGGTAGGT
GGCGGCGTCCACGAAGATGGGCCCGAAGGCGCCGGTGTCGGAGACGCGGTCTCTGAGGTAGTCCCTGGCGTAGTGGA
GGTACTCCCGCACCTGGCCGGCGCGGATGCGCTCGAGCGCGAAGGCCTTCATGGTTTCGGAGCAGAGCACGGAGTGC
CGCAGCCCGTCCAGTGTGCGCCGCACGTCGTAGACGCCGCGCATCTGCGCGAGCATCTCGACGGCGTCCGCCGGCGT
CGCCGCCGCGAGCCCTGAGTTCACTGGAGGTATCCTGTGTTCTGCGAGCATGCGCT TGAGGAAACAGAGGTCCAGCG
GCCGCGTGGTGTACAGCGCGGAGGCCATCTCGGGGCGCGCCTCGACGATGTCCTCGATCATCTCGTCCGTGAAGGCC
GCGTTGATGTTGTGCACGCTGCGCGCGTTCACGTGCAGGAGGATGTCGCCCACGTTGTCGGGGAATCGCTCCTCGAT
GAGCCGGACGTCGTCCTCCGTGATGTTCATGTAGGGAATGCAGCGGCAGAGCAGCGCGTAGTCCGCGAACTGCGCGA

FIG. 28E

TGTAGGGCGTGTGGAACTCGATGTGTCTGGCGAAGAGCGCGCCGCAGCGCCGCCGCGAGAGCTCTTCGAGCAGGTCC
TCGGGCGTGACGTGCTGCGGGCGGAAGAGGTGCAGGTGCGTGGGGTGATCGGCGGCCACGCGCGCGTACAGCCGCCG
CGGGAGGTGCCTGGGGTGCACGCCGGCGAGCACGAGCTCCATGGCCTCTGAGGTAGACAGTGCGGCGAACGCGCGCT
CGGTGCCGCCCGCGGCGACGGCGGCGCCGACAAATCTCTTGAGCAGCTGCAGCATCGCGTGTTTGGGCTTTCGCGGA
AGGCGCTTATTTTAATGTTATTGGCGGTGGCCGGTGCGAGATAAAAATTAGAACTGATGCCGCAGTTGTTGATGATG
ATATTAATTGCGCTGGCCGGCGAGAGATAAAAATTAGAAGGTGATGCCGCAGTTGTTGATGAGGATGGTGAGTGCGC
TGGAGCAGGCGGTGTGGCGCGCCAGCTTCTTGCTGGCCCCGTCGGCCACGGAAA CGACCTTTCCGGATATCGTGATG
GTGCAGGTGAAGCGCGGACAGTGATCCTCTCCGCCAGAACGCGTCTCGCAGAACTCCAGAGATCTGCGCGTCATCAT
GCAGAACTCGTTGACCGCGCTGACCGGGTTAAGACTTTTGAGGCGCATCACGGCAGACTGAGTCATGATGTCGATGT
CGCCGCCGAAGAGCGTATCGCACCCAGCCTCGGTCTCCATGGGCTCGGTGTCGGAGTTTTCGTCCTCCTCGGTGGGC
GCGGAGGGCGCGCACTCTACGAACCAGCGGGGCGGGTTTCCGTCCTCGCAGCAAACCTCGTCCGAGTCCAGCAGGCG
GTACAGCTGGCGGTTCGCCTCGTGTTTGGATATGCCGAGTTCCTTCGCGATCTGCTTGGCCGGCAGCTTGTCGTCGG
ATTTTCTGAGAAGCTCGAGGATCAGAGATGCGCACTCGCAGGCCATTGTGGCGTATTTACGGGGCGTGCGTTTTTTT
AGGATTTTGGCTTGCCTTTCTTTTCGCAGAACTTGGGAGGATTGAAACTCTTTTGGCAATTTTTGCAGGCGTACTTG
ATCAAGGGCGGCTCGTCCGCCGAGCGCGTCTGGATCATCATCGGCATGGTGTTCTTGCTCTGGCACGAGGGGCAGGG
CAGGTTGAACTTCTCGTCAAGCACGTTGAAGTACCCGCTGTAGTCGTGGTCCGGCACCTCCTCGATGTCGTAGGGCA
CCCGCGCGGCCGCGCACTTGACCGCGAAGAGCAGGTACCGCAGCGCGTCGTG CTCTGCGCCGCTGGTCGCGCGGATC
TGCGCGCGCAGGTCCGCGTAGTCCTCGTTCGCGTCCACCTCCAGGCTGCGCTTGTTCTTGTACGAGAGCCGGTTCTT
GGCGTCCTTCGAGTACTCGATGCCGATGTTGTGCGCGGGGTCAAAGTTGGTCTCGTCGGTGTTCGAGGTCTTGGTGT
TCACGATGTTCTTCAGCGCGAAGCGCTGCGCGCAGTCCAGCGCCCATCGCGCGATGCGCGCGGCCTCTGCCGCGTCG
GTGTGCTTCGCCGCGAGGTCGCGCAGCCGGTCTTCGTCCATCGCCCGATTTTAGGTTGGGTATATTATCTCAATTCC
GCTCTTCCGCGGGCCGCGGGCGCGCGCCCGCGGCAAATTAGGCGTTACAAATGGACTTCGTGCGGCGGAATACATGA
TACACGCCATCGACCGCAACCTCGACTTCATGAAGGCCGAGGTCCAGCAGAAGGTCTCCATCTTCCGGTCATCACCA
AGGACGTGCTCGCGAGCACAAACTTCTTCGTGTTCGTGCACATGTCGCAGCGGCACGAGGTCTTCGACGCCGTGCTC
AAGGCGGCCTTCGACGCGCCGCAGCTCTTTGTGCGGGCGCTCTCGCGGCACTTCGAGGCCTTCGTTGCCGCCATCCG
GGCCTACCGCGCGACCTGCGCGGAACTGCTGGCCGACGCGCGCTTCATGGAGGTGGCCGCGCGCGCGGCCGAGCTCG
CGGAGGTCATTGGCGTGAACCACGACATCGCCGCGAACCCGCTCTTCGCG GACGGCGAGCCCGTGCGCGACGCGGAG
CTCATCTTCGCAAAGACCTTCCGCAAGACCGAGTTCCGCGCCGTCAAGCGCCTCGCCGTGCTGCGGCTGCTGGTCTG
GGCCTTCCTCGTGAAGAAGGACCTTGGCGGCGAGTACGCGGACAACGACCGCCAGGACCTGTTTACGCTGCTGCAGA
AGGCCGCGGGGCCCGTGCGCCACAGCGCGCTCACGGAGAGCATCCGCGAGTACCTCTTCCCCGGAGACAGGCCCA GC
CACTGGGTCTGGCTGAACGCGCGCGTGGCCGACGACGCGGAGGTGTACCGCGACCGGCCCGCGCGCACGCTCTACGA
GCGCGTGCTCAGCTACGCGTACTCAGAGGTCAAGCAGGGGCGCGTGAACGCCAACACGCTCAAGCTCGTGTACCGGC
TCGAGGACGACCCCGACATCAAGGGTCTGCTGCTGCAGCTCATCTACGACGTGCCCGCGGACATCGTCGGCGTCGTG
GACTCCGCGAACGAGGAGTGGCGGAGCTACTTCGTGAGTCTGTACCGCGAGAACTTCGTCGACGGACGCACCTTCAC
CTCGGACGCGCGCTTCCGCGACGACCTCTTCCGCGTGGTCGCCGCCGTCGAGCCCGACTTCTTCGAGCCCGAGCGCA
TCCGCGAGGCCTTCAGTGCAGACGCGCGGCTGCGAGAGCGCTTCACGGACATGGACCTCAACAACGCCTTCATGTCG
CACCTCATCTACGACTCCGTGGACCCCGACGTCGCCGCCGCCGAGCGC GGGCTCGCGCTGCGCGTGCACAACGAGGA
CTCCGACTACTTCATCCGGGAGTACAACACCTACCTCTTCCTCAGCGAGAAGGACCCGCTGGTGCTGGACCGCGGGG
CGCTCACGCGGCTCTCTGACGTCCCTACCGAGCGCTTCCGCGACCTCTTCAGCGACAGCGTGCTGCGCTACTTCCTG
GACGCGAAGCTGGGCACGCTCGGGCTGGTGCTCGAGGACTACCGCGAGGACGTGGTCGCCGCCATGCTTCGGC ACCT
GCGCCGCGTCGAGGACGTGTCTTCCTTCGTGACGTACGCCGCGCGCAAGAACCCCGCCTGCGTTCCCGGCGTCGTGC
GCGCGGTCGTGAGCAACTTCAACCCCGCGGTGGTCGCGGCCATGCGCCCCTTCCTGCGCGAGCACATGACGCGCGTG
GACGCGCTGCTGGACGGAATGCCGCACCTCTCGGAGGCCGACCGTCGGTACATCCGCCGCGTGGTGCTGCAGGGCCG
CGCCTGATTCGCCGTCAATAAATCGCGATGGTGGACAGCGGCACGCACGACGTGGACTCAGCCGCGCAGGAGCGCAC
GCCCAACCAGCAGACCTTCTTCACCAAGGGGCTCAGTCCGCTGATGCGCCACACCTACATCTACAACAACTACGCCT
ACGGCTGGATTCCCGAGACCGCGCTCTGGAGCAGCCGTCTGGGCGACTACCGCGTCACGGACTTCTACCCGATATCG
CTGGGCATGCTCAAGAAGTTCGAGTTCATGTTCTCGCTGCTGGCGGACCCCGGCGGCGCCTGCCCCGCGTACGAGCC
CAAGCTCAACACCGAGTTCCTGAACCGCGGCTCCTTCTCGGGCCGGTACGTGAACCCCTTCCACCGCTTCGCGGCGC
TGCCCGAGCGCGAGTACATCTCCTTCCTGCTGCTGAGCTCGGTGCCCATCTTCAACATCCTCTTCTGGTTTAAGGGC
GAGACCTTCGACACTGCCAAGCACAGCCTGCTCGGCGCCGTGTACACCACGCCCGAGAGGCACATCGAGCT CGCGCG
GTACCTGCGGCGCACGGGCGACTACAAGCCGCTGTTCAGCCGCCTGGGCAACGACGACACCTACTCGAAGCCCTTCT
CGGGGTTCACGCGCATCAGCAACCCCACGCCCATCGGGCGGCTGCCGCCCTCGGACTTCGAGACGCTGGCCAACCTG
AGCACCATTCTCTACTACACGCGCTACGACCCGGTGCTCTGTTTCCTGGTCTTCTACGTGCCGGGGCTCTCCGCGAC

FIG. 28F

CACGAAGATCACGCCCGGCGTGGAGTTCCTCATGGAGAAGCTCTCGCTCGCGCCCGAGAACGTGGTGCTGCTGTAGC
CTCAAACATAAAATATAGGCGCCTCTGATCGCACTGCTTCAGTTCAGACAGAGCTAAGGTCGACATCTATATACTAT
ATAGTAATACCAATACTCAAGACTACGAAACTGATACAATCTCTTATCATGTGGGTAATGTTCTCGATGTCGATAGC
CATATGCCCGGTAGTTGCGATATACATAAACTGATCACTAATTC CAAACCCACCCGCTTTTTATAGTAAGTTTTTCA
CCCATAAATAATAAATACAATAATTAATTTCTCGTAAAAGTAGAAAATATATTCTAATTTATTGCACGGTAAGGAAG
TAGAATCATAAAGAACAGTGACGCCTCGAGGAATTCATGATCCTTCAGGCCCTTCTGTTTGTGCCTCTCCTAATCTC
TTCGTTGTGTCTCGGGAAATTCCCCATCTACACAATACCAGCAAACTTGGTCCTTGGAGCCCCATCGAT ATACATCA
CCTCAGCTGTCCAAATAATTTAGTTGTGGAGGATGACAGGATTCTCTTACATGGAACTAAAGGTGGGATACATCTCT
GCCATAAAAGTAAATGGGTTCACTTGTACCGGTGTTGTGACAGAGGCTGAAACCTATACCAACTTTGTTGGTTATGT
CACCACCACATTCAAGAGGAAACATTTCCGCCCTATACCGGATGCATGCAGGGCTGCATACAACTGGAAGATGGCTG
GTGATCCTAGATATGAGGAATCTCTTCAAAATCCTTATCCTGATTACCACTGGCTACGGACCGTAAAAACCACTAAG
GAGTCTCTTATCATCATATCTCCGAGTGTGGCTGATTTAGACCCATACGACAAATCCCTTCATTCTAGGGTGTTCCC
TGGTGGGAAATGTTTGGGAATAACGGTTTCTTCCACCTACTGCTCAACCAACCATGATTACACCATCTGGATGCCCG
AGGAACCAAGACTCGGGACATCTTGCGACATTTTTACCAGCA GCAAAGGGAAAAAGGCATCTAAAGGAGGCAAGACT
TGCGGATTTGTGGATGAAAGGGGCTTGTACAAGTCTCTAAAAGGAGCGTGTAAACTCAAGCTGTGCGGAGTTCTCGG
ACTTAGACTTATGGATGGAACCTGGGTTTCCATTCCAACATCAGACGATACCAAATGGTGCCCTCCGGATCAATTGG
TGAATCTACATGACTTTCACTCAGACGAAATAGAGCATCTCGTCGTGGAGGAGTTGGTCAAGAAGAG GGAAGAGTGT
TTGGACGCATTAGAGTCCATCATGACCACCAAATCTGTAAGTTTTAGACGTCTCAGCTATTTGAGAAAACTTGTCCC
TGGGTTTGGAAAGGCATACACTATATTCAACAAGACTTTGATGGAGGCTGACGCCCACTACAAGTCAGTTCGGACTT
GGAACGAGATCATCCCCTCCAAAGGGTGTTTGAAAGTCAGAGAGAGGTGTCATCCTCCTGTGGACGGAGTGTTCTTC
AATGGCATAATTCTGGGTCCAGACGGGAATGTCCTGATACCAGAGATGCAATCATCTCTACTTCAACAACATATGGA
GCTGTTGGAATCTTCTGTAATCCCCTTAATGCATCCCTTGGCGGACCCGTCAACAGTCTTCAAGGAAGGGGATGAAG
CGGAGGATTTTGTTGAAGTTCACCTCCCTGATGTTCACAAACAAATCTCAGGGGTTGACCTTGGTCTCCCGAGTTGG
GGGAAATATCTCCTGATGATTGCAGGTGGTCTGGCGACTC TAGTTCTGATAATCTGCTCGATGGCATGCTGTAGAAG
AACCAAGCGAACAGAGTCAAGAAGACGAGGCTCTCGAGAGTCAGAGAAAAAGGTAACGGCAACCCCCCAGACTAGGA
AAGTCGTATCTTCATGGGAGTTATACAAGAGTGAAGGCGATGCCAGGCTGGATTACAAGGATGACGACGATAAGTGA
GCGGCCGCGCCGGCTTCATCCGCCGCAGCATAAGAAAAACCTGCAACTTCGCACACGCGCGCACG CACACGGTCTAC
GTGTAGTTACCCTGTAAAGACGGGCTTGCTCCCGAACAAGCGCTCGAAGAAGAGCGTGCACATAGCCTTATTGTCCA
GCAAGTTGACTATCTCTGTACACAGCCTCTTGAAGTACACCTCGTACATGATCCGCTCGTTTTTATCCAGTCTGAAG
GTCTTGTCGACCACGCGCTCGTAGGACTTCACGTTCGCGATCCGGCGCCGCCAGGGGCCCTCCTCGCACACGTACGC
GAAGAAGTAGCGCTCGCCGATCTCGATGGCCTCCGCGTTCGCCGCGTTGTACCGCGTCACCAGCGCCACGTTGGGGT
TGTCGGGGGACTTGAAGTTCTTGTGGTGCGTTCGGCTCAGCAGGAACCAGTCCAGCGGCATGCTGCGCGCCTCGAAC
TCGAAGGTGAGCTCGTCCTCCAGCGAGCGCAGGATCTCCACGCCCACGTTCCCGGAGCCCTCCTCCGCCAGCGCGCG
GCAGAGCATGTCCTTGTACTTGCGGATCATGAGCTTGT GGAAGGGCGCCACGTCGCGGCGCGTCTCGCTGGTGCCCT
TGCTCACGCGCTCGCTGCCGCCGCCGTCGCTCACCGCAAACTTGATCGTGGTGTACTTCTTCTTGGACTGCATGATC
AGGTTGCAGTACACCGCTTCGAACTCCACCTTGAAGTTCGCGAAGAGCACGTGCTCGTTGATCACGCGCTCCAGACA
GCGCCCCACGCGCCGCGAGAACGCGATGTCGGAGGCGCCCACCTCCAGGAACACGGAGTCGGT GTCGCCGTACACGC
TGCGGAAGCCCACGCGCTCCGTGCGCTCGCCGGCCACCGCCGCGTCGATCTCCAGCTCCGCGGCGCGGCCCGCGAAG
GCCTCGTCGCGCAGCAGCGGGTTGTCCGGCGCCGCCGCCAGCGACAGCCGCGTGCCGCACACCGACGCGCCGTCTAG
CGTGCGCTCCAGGTACGCGATCATGGTGCGCCCGATGGCCGTGCAGCTCTTGGCCGAGGCGTACGAGAAGAGCGCGC
TGTTGCGGAAGCCCATGAGCCCGTACACGGAGTTGGCCGTGATCTTGTACGTGTACTGCATCGAGTTGTAGATCTCG
CGGTCCACCGCGGTCTCCGCGGCCTTCATCAGCTTCTTGTACTTGGCGCGCGCGTCCAGGAAGGAGCGCAGCAGCAT
CGGGATGATGCCCTTGGCCTCGCGGTCGAAGATGGCCACCTCGGCGACGAGCTCCGGCGAGCGCGGCTCGCAGGGCA
CCGCGATGTACCGCGGCGCCGGGAACATCCGCCGGA CGTCCACGGCCGCGACCTCCGCGTCGAGCCGGTTGTCCGAG
ACGACCACGCCGACCAGCGTCTCCGGCGACAGGTTCGCGTAGATGCAACGTTCGGGTACAGGCTGTTGTAGTCGAAG
ATGAGCACGTGCTTGTTGTGCATCTTCTGCTTGGGCGCCATCTTGGACTTCGTGTCCGCGCGCACCATCACCGTGCG
GTTCTCCAGCAGCAGCTTCATCAGCGGGCCCTTGATGCAGGTGCTCGCGCGGTACTCGAAG ACCACGCTCTGCGGCA
GCAGGTACGTGGACGCGGCGGCCGCGATCTTGGTCTCCACGCCGTAGTGCGACCAGAGGTAGAGGCAGAGGCAGGCG
TCGTGCAGGCAGTACCGCGCCATGTCCAGACACACGTCCAGCGAGTAGTTCGCGTACATGTCCGCGAGGCTGACGTC
GTCCTTGCCGAAGGCCAGCGTGACGCGGTCGCCGGGCGCGCGCGCCGCGGGGTCCGCGAGGTCCACGGTGAAGCCGT
CCTCGCCGACGCGTTTGTGCAGCACGCGGCACACGCGCTCGTCGACGGTCACGTAGTTGCCGGTGCTGAGCACGCGC
GCGAACACGGCCGCGTTCCCGTCGGCGTCGGTGCTGCGGTCGCCGCGAAAGCGGACCGCGTCCGGCCGCGCGTCCTC
CACGACCGCGGTGCAGTGGAAGGCGTTCTTGGATATGGCGTCCAGCTTGTAGGAGTCCAGCTTCTCGGTGCGCTGGA

FIG. 28G

TGAAGGCGTACAGGTCGAAGTAGATGGTCCCGTTGTTGTTGTTGATGTGGAAGGTGGTGCTCGAGACGCCGCCGACG
CCCTTGTGGCTGGACTTCGTGCGCTCGTACACGCAGAAGTTGACTGTCTCGGTCCCGTCCGGCAGCCGGAAGCGGAT
GTGCTCGCCCGTGAGCAGCGACAGCCGCGAGTCCAGGTACCGCAGGTCGAAGTTGTGCCCGTTGAAGGTGACCACGA
AGTCCAGCGGCATCTCGAGCAGGCGCTTGGCCACGCGCAGCAGCGTCACCTCGGGACAC AGCGTGACCTCCGCGTCG
AACTTCACGTCCGCCGGGTCCAGGCAGACCGGGATCTCGCGCCGTGCCGCCTCCTCGAGGTCCGCGTCGGAGAGCAT
GTCAGAGTTCGTCAGCGTGAATCGCTTCTCCGCGCCGTCCTTGTCCACCACGCAGAAGCTGATGTGCGAGACGGCGT
TCTTGAAGACGGAAGGAAACTTTTTCTCGAAGTGGCACTCTATGTCGAGGAAGAGCCCCGAGCGCGTCACGTTGAAG
CGCGGGATCTTCTCCGCGAAGCACGCGCCGGGGTCGTCGCAGTGGAAGCAGTTGCTCCCCAGGTCGCGCAGCAGCGC
GGGGTCCACGCGGTAGCACCCGTCCGGGTCGATGTCGTGCGCCACGAAGAACCAGGACACGTTCAGAAAGTCGGACA
TGAAGACCTCTGGCGGCGCGAGCTTGCGCTCGCTGGCCACCAGACACAGCTCTATCTCCGAGCGCTGGCGCTCCGGA
ATCTTCGCCGAGCGCGCCACGATCTCGTCGAT GCTGACCACGGACATGGGCCCGAGCGCGCGCGTCCACGCCAGCGG
CTGGGCGATGTCGGCCACCGCGTCCGCGCGCACCACGTAGTAAAAGTGCTGCACGAAGCGCAGGTACACGACGGCGT
TGTCGGCGCGGCGCGCCTTGAGGAAGAGGAACCGGCTGTCATTGCTGCGGTTCTCGAACCAGTTCAAACATTTCAGC
TCCATTTCAAAGAGCATAATAACATTTCATTTAAATGGAGCCTCGCTTCTGGGGCCG CGCCATGTGGGCGGTGATCT
TCATCGTGCTGCGGCGCTTCGAGGAGCACCGCGACCTCGAGCGCTGCAAGCGGCAGCTGTACGTGATCTGCTCCACG
CTGCCCTGCATCGCGTGCCGGCGACACGCCACCGCCGCCATCGAGAAAAACAACGTCCTCTCCAGCGAGGACCCCAA
CTACGTGCTCTTCTTCTTCATCAAGCTCTTCAACAACCTCGCCTTCGACGACAGATACAAGATCGACCCCGCGAAGG
TGCGCCCGCTCGTCTAGAGCATGCCCTCGTACGCGCGCGAGTTGTCCGAGTACACGGTCACCGCGATGCCCTCGCGC
GGCGTCACGTGCACGTGCATGGAGTCCGTGATCACGAAGCCCACGCCCGTGACCGGCTCCTCGCCCGCGTCGTCCGT
GAAGAGCAGCCCGTGGTTGAAGAGGTAGAACTCGTTCTCTGCGAGCGAAAGCCGCCCGCGGTCGCAGAGGTAGTAGA
AGATGTCGTCGTCGCGCACGGCCAGCGTGAACGTGGACTCGCTCACCACGATGTACTTGTCCAGCTCCTCCAGCACG
GACGCGGCCGCGCGGCGCGCGGTGGCGCGGCACTGCGTCGGGCACTCGCACGTGTCTGCAGAGTACAGGATGCGCGT
TCGCCCCGAGGCGGTCTCGAGAAAAACGTTAATCGCCTCCATCGCCCAGAAGCGACTCGAGGATCGCGAGCACCGTG
CGCAGCACGAGCCCGATGGTGCAGAAGGGAACCTCTCCCGACTCCGAGCACTCGC GGATCTCCGTCTCCACGCGGTC
GTGCACTTTTATGGAGGGAGCCGTCGTTCCAGTGGCCTCCATCGCGACGGACACCACCTTGGCCACGAACTCGCGGA
TCTTGCTCATGCGCCGGAGCACGGTCACGCGGAAGAAGACGGCCGCGAGCAGGTACTCGGCCACGCAGCTCGCGGCG
ATGAGCGCCTGCGCGTGCCTGGTGTTGAGCACGTGCGCGTCGGGCACGAAGTCCGAGATCTTCAGGTGCGAGAGCCG
CACGAGCGCGTTGGTGTCCTTGACGCCGTCGCAGGAGATGTTCGCGAAGATGAGCTTCTCGTAGTCGAGCGCCTCGA
CCACGCGCTGCGCGTCCATGTGCCGCTCGCCCGAGAGCGCGCGGCTCAAAGGGCCCCAGCACACCGAGCCCGCGAAG
CAGGGGTCCACCACGCCGTGCATCGCCAGCAGCGTCACGTCGGCCACGCCGCGAGGATGGCCGCGTCGTCGAGCTCG
TTCGCGGGCGTCGCGCCCGTCAGGGACGCGCTGCGCAGCGCCGGCGCCGCGTGCCGCGCGCAGAACTCGCACCCGCA
GCCCGGCGGCAGCGGCGGCTTCGAGAGCAGACTCATGAGCCCGCCCACGTGCCCGTGCTCGGTGATCAGAAGCGCCA
GGATGCTGTCGGTGCTGCCCTCTATGGCGGCTGTGGCCGCGCTCGAGGGCTCTCCCGTGACCTGCCATCCGCAGACA
ACCTTGAGCATCTTGCGCTTGAGCTCGTTGGGCGCCTCCGAGGCCAGCATCGT GCGCGGGAACGTCGCGTTGAGGCG
GAAGTCCTGCAGCAGCTTTTCGAGCGTCGCGGTCTTGGCGTGCCGCCCTTTGCGCCACTCCTCCCCCAGGTGCCACA
TGAGCTCCTCGGCCGTGTCCAGCGTCGGCGAGACGCGGGCCTTGGGCACGCGCGCCGCGCTGCGCATCAGCGGCTCC
GAGGCGCGGAAGCTGCCGCGCGCGTGCAGGCGCATGGACGCAGACGAGGACCGCATCGAGGGTCGCTGGCAGAAGCT
CGTCATCGTGAAGCGCCGCGTGAGCGGACCTACCTCGTCGCGCGACTCGTCGAAGTCCGGGTCAGGGTCCGTCGTGT
CGGTCTCGGCGCTGTGCGTGCTGGGCGCGCTGCTGCGGGCGCTGCGCGTGCTCTGCGTGCTGAAGCTGCGCGTGCTG
CGCGTGCTCTGCGTGCTGAAGCTGCGCGAGCAGGAGTCCGCCGTGTCCGCTTCCTCGTAGTGGAAGTCCACGTGCTC
CTCCGGCAGCCGGCGCGAGCGCGACT TGGAGATGCCGACCATCCCGTCCGCGCCGACCGGGCGCACGCAGAGCGCCA
TCGCGCCCTCGCGCACCGCCTGCGCGAACTCGCGGCTGGCAACCATGCGGGGGTCGAGGAACTTGATGATGTTGAAG
TATGGCCACTCGCAGACGAGCCGCGCGCAGGTCGCGACGTCGTCGACGCTTCTGAGGGCCCTGTTCAGCGGGGGGAT
GTTGCTGCCGTCGGCCAGTGCGACGAGGTCCTCGGGGGAGATCTCGAGCTT GGGAATCATCTCGTTCACGAGCGCGG
GGTCGATGGCGTGGCAGACGGTCTCTACCTCAGTGCGCGAGAGCTTGAGCTGCGCGCAGGCCGTCCACGGCGCGCAC
GTGAGCGCGAACACCGCGGAGACTCGGCCCTTGCCGACCATCGCCACAACCTCGGGCTCGTAGACCAGGCCGGCCTT
GAGCAGAGCCTCGAGCACCTCTATGTCGTCGGCGGCGAGCAGCGCGCGCCTGTGGAAGCACACCGCGGGCATCATC T
TCTTGCAGATGCCGCGGGTGCTCTTGAGGGCCGTGATAAGGTCGGGGAGCCTGACGTGCTGCGGCTGGAAGAACATG
ACGTTGGCGGGGCTCGCGGCCACCGCCTCGTCGTACACCGACATCGGCAGGTCGCCGTGGAGCCCGCACGGCAGCAG
GCTCAGCAGCTGCGCGCGCGAGAGCTTCTCGGCGCAGAAGTTCTTCTTGGCCAGGGCGGCCGCCGCGTCGCGGGCCT
TCTTGGGGTATAACAACATGGCGGGCTTTAAACACGAAACAAAAATCCAGGTTGTAACATTTCAATTTTGCATGTTC
TGGGCCTCCTCGCAGAGTTTCTCCAGGCCGCCGGCCACGATGGCGTCGACGAAGAGGTCGGCCTCGGTGAAGCGGTG
GTTGCCGCGCACCGCCACCAGCGCGTTCTCGGTGACCACCACCGACAGCTGCTGCGCAGCCGTGCGCAGGTCGAAGT

FIG. 28H

GTCGGCACGCGAGCCCGTGGCCCAGAGTCTGGTCCAGCGCCGCGAGCACCTCCTCCAGGCTCTCCTCGCGGTGGTTG
TAGAACCACATCAGTACGAAGTAAGCCACGTAGGTGTAGAGGTAGTGCGCGACCGCGCGGGCGCGCACCAGCGGCTG
GTTGCAGCGCGCGAAGGCCATTCCGCTGGCGATGAGGTCGTCGTCCAGCGTGGCGTAGTCGCCCCAGTTGAGCGCGC
TGAACTGCACGCTGTAGACCGCGCGCACGAACCCGGACTCGAGGATGTCGATCTGCGACGGCGCGCCCCAGGTC ACC
AGCCGGTACACGATGCCGCGCTGCATCAGCCGCATGAGGTCGCCGCCGACCTCGCGCAGGCGGTGCGTCAGCGAGGC
GAAGGCCAGCTTCCGCTGCGTGTACTGCAGGCCCACGGCCACGCACCCGTCCGACTCCACCAGCACGAGCTTGTGGT
CCGTGCAGCCGTCGCTGCGCAGGCCGCCCTCGCGCGCCATCATGTCGGTGACGAACATGTACTTGCGCGCGCGCGGC
CCGACCAGGATGCGCGTCTTGCCTTCCATGCGCAGCACCACGTCCTCTAGCAGCCGCGTGCTGTCCACGCGCTCCAC
CTGCGGGTGGATGGTGGGCTGGTAGTTGTACAGCAGCCGCGGGGACCAGTTGTAGGCGAACGCGAAGAGGTGCGTGT
CCAGGAGCGAGATGGGGAAGACGCCGCCTTCGGTGGCGCGCCGGAGGATGGCGAGCTTGGTCTCCGCGGGCAGCAGG
CTCCCGGTCACCGCGCCGAAGAACATGGGGTGGTTGCGGAACTTGAG CGCGTACGCGCTCAGCACCTCCTCTCGCGA
GAATATTGAGTCCGCGGGGTTGGAGCTCGCGGGCAGGAGCACGTCCTCCACGCTCAGCACCTCGTCGATGAAGGGCA
GCACCATGTCCACGTTGGAGGCGGTGAACCACTCCATGTCCACGGCGTTGCGCTCCACGATCACCCGGATCGTCTCC
TCGGATATGTTCTCGGCGAAGGCGCTCTGCAGCTCGATCAGGTTCTCGGTGGCGTCGATGCTGAGCCCGAGG CGCAT
GCCCTGTTGCAGCACGTCGTTGATGGGGTTCACGTACATGGCCACCGCCATGCACCCGGCGGCTGCACGCGCCAGAG
GTTGGAGTACGCGGACACGTCCGTGATGCGCAGCGTCTCCAGCACGTTGTACATCCATTTCCAGCGTGTCCACGTAC
ACCTCCGCGTGCTCGAAGATGATGTCGAGCTCGAACGCGGACAGCGGCAGACTCACGTAGATCTGGCAGGCGTCGAA
GAGTTCCTGCGCGTACTCGGAGAAGCACGCGTACGCGATCACGCCCGCGCGGTTGACGATGTAGTCGGCCTTGAACA
TCTTCGTGAGGTAGGCGTACAGCGACCGGCAGGCCACGTGCGGCCTTAGCTCGTCGAGCACGGCGTCCAGCACCTCG
CGGTGCTGCAGCACGGAGGGGTGCAGGAACTGCGTGAAGTCCACCGCGGTCTCCTCCATGAAGTCGGGGATGGTCTC
GACGACCAAGCGGTGGTTCCGCACCGCGCGGAAGCCGGTGTTCAT CGGCGCGATGCTGTGCTGGTCGTGAACCTCCA
GCAGGATCTCGTAGCCGATCTCTCGGCAGCTCAGCGCCGCGCGCGCCTCCGTCACGCTCGCGTTCCGGAAGAACTGC
CGCAGGTGCTCGTCCGTGCGGCAGAGCGTGACGGATTGGGGGATGCGGGAAAGGTCGCAAAGAGGGCTGTGGACGGA
GATGCGCCGCAGCGCGTGGTCTACGAACTCAAAACCGCGCCTCGACATCGTGAAGTCGCGGAGGGCGTAC ATGTTGT
AGGAACAGAGGCGGAAGAGGCAGTCTATGTCTAGCATGTTGGAAACGCAGTACGCGTGTCTGTGGAGGTGCGGGAGC
ATGGCGGGCACGACCTCGGTCGTGTTCTGGAGCATGGTGCATACGAGGTCGGGCGCGGTGAGGTCAGGAGTGACGAT
GAGGATGCAGGAGCTGGAGAACTTGCTGAGCTCGGAGGCCAGCCGGTGAAGGTTGTAGTCGTGGCGCTGGCTGAAGT
TGCTGTTTATCGTGCCCGTGAAGCCCATGAGCGCCGCCAGCGTCAGGTCCTCGCGCTCGATGGCCCAGATGTCCAGG
CCGGAGGCTATCATGCAGCGCACCAGCGCGGCGGCGCGGTCGCTCGTGGGGTAGCTCATGGTGCTGTCGGTCGTGCG
AATCAGCATGGGATAATGCTTCATTTTTACGGTCGGGGGGTGCGGACTGTGGGGCGCACAGGGCCCGCGGGCGGCTC
GTGCCGGTCCGCGGCGTTCGCCGAACGCAGGAACGGGCCCATGCGCGCCCAGGCCATCCACAGCCCCGCCGTCAGCG
CCAGCAGCCAGACGAATACCACGATCATCTTTTATGTAGCGGGAACTCGCGCTCACTCCCCGCCGCACGGCGACGGG
GAGAGCCCAGAGCCGAGCTCCATGCGCGTGCTCTGCACGGTGAGCGACTCCACGAGCTTGGACACGTTCATGCGCGT
GTTGTCGGGCACCAGGTGCGCGAGGCGCGCGTACACGTCCTCGTGCATGCGCTTGCTGCAGCGGTCCA GGCTCGCGG
AGAGCGCGGAGACTAGCGCGGTGTGCTTCGCGTACACGAAGTCGCCGAGACACACGGTCTCGAGCCCGAGCACGTCG
GCGCTCTCCGCGTCCTTGAGCGCCACGAATATCTTCTGCTCCTCGCGCGTCATCGAGCGCATGAGGTAGTCGTGCAG
CCGCGAGCGCGAGATGAGCCCCTGAGAGATCTGCGGGCTGCGCATGAAGCGCCGGCGCATCGCGCACAGCAGCTCCT
CGTCGACGACGTACATGCTGTCCTTGATGGAGCTCTTCTCGTCGAGCACGAGCAGACCGTCGTTGGCGACCACGTTG
ATGAAATCGTCCACGTGCCGCGCGTCTATGTCGTAGCGCGTGCCGCCGCACTCGATGTGCGAGGGCGGCGACTTGAG
CCGGTTCGCGAGCGCCTTCACGTCGGAGACGTCGATGTACAGCGAGGACTCGCGCGGGACGCAGCCGAGGATGCGCG
TCTCGAGCGGCGTGAGGATGAGCACGCGCTCGGCGCCGTCGACGAGCTTGCCGTCGTCGGGGGAAAAGAAGTTGTTC
TCCACGATGCTCGAGACGAGGCTGGCGAGCACGCCGTCGCGGTAGGCGCCGAGCGCGAACTCCTGCACAAAGGGCGC
GTGCAGCAAGTCCACGGGAATGCGCATCTCCACGCGGCGCGCGACCGACTTCTTCTTCTGCAGGTGCCGCCGGTCCA
CCATCTCGTCCACGATGTCCGATATGCGGGAGCAGAGGTACGCCTTGAGGACGTTGGCGTTTACCT TGTTGAAGATG
AGCCGTTCGTCCTCCATTTAAGCTGCTCAAACGAGCTTTAAATAGTGGAAACACAGCAGCACGCCGATCGCCGCCGC
TATCAGGCCGATTAGAAAAACGGTGGTCCAGGGGACGCCCTTGGGCCTATCGCACGCCGGCTTTTCGGTCATTACGG
TGCGCACGATGTTTAGGAACTCCTCGAAGTCCTCGTCCGAGTTGGAGAGGAAGGAGCCGAAGACGCCGGTGTACAGT
TTGTCCATTTACTACTAGATATTAAACGGCGCTTCCAACTCCTCGTCCTCGAAGCCCGCGCCAGGCTCGACGACGCC
CAGGCCGCGCACGTCCTGCTCCTCGGTGAACGTGGTCTGAGTCTCGCTCATGCGCACACACGTCTGCTCGCCCTCGA
GACCGAGCACGGTCAGCGAGCACTCGCGCGGCATGGTGATCTTCTTAACCGCGAAGGTGACTTTGCCCTCGCCGCCC
GAGCGGTAGAACACCACCGGCGCTAGGATGAGCGTCGCCATCTGCGCGTCGCGGGTTGCGAGGTTTTCTATCTCTCG
CGTCAGCGGACATATCTGCGGCTGGGTGTCGTCGTCGCCGGTGAACTCCAGGAGAGCGCCGGTCAGGCGGTTGAGAT
ACAGACATCCGGACTTAAAGGTGTTGTCGATGGCCGTGTCGGTGTTGAAGTTGCGCAGCGACGGCGGAACGCGAAGC

FIG. 28I

CGGTTTTGATGTTGTCGTATATGTTCTCCAGCAGCTGGTAGAGCAGCGGACTGGCGCTCACGGGCTTGAGTACCCGC
TGTCGTTCTGCCGCTGCATGTCGGTCTTCTTGCTCGGGTAGATCTTAAACTCGCCCTTCACGACGATGAGCGGCGAG
ACGAGCTTGGATGCTAGACTTTCGACGAGACACACGTTGATGTTGGAGCAGCTCGGGTACTGCGACGGAGTTAGAGT
CACCGCCTCGATGACCTTGGTCTGGCTCGACGAGAGCGACTTGGCGAAGTTGATCGCGTCGGTGCACGACATCGCCT
GGTTCTCGCCGAACCGCCTGGCGGACGCTGCATCCTCCTGCTGAGGAGCGCGGTTAGACGCGACGGTGGTTTTGGAT
ACAGCGCGTTTCATTATGCAGCGATTTTAAAGTACGTGTATACTTTCAGTTTTGTCGCCGAGCGTTCAGCGCCTGCA
TGCAGAGGAAGTACAGGATGATGGTGCACGGGATCGTGGTCAGCAGCGATACGAAGTCCATCACTGTGAGGACGCGC
AGCGCCCCGCGCGAGCGGATGCCCAGCGAGGGCGCGC CGCGGCGCGCGATGGTGGCCCCGTTCGTCACCACTACCAG
CAGCATTAGGATGGTCGCGCCCACGGCGACGCCCAGGTCCCGCGACTCCATTTATAGTACAGTATAGAGCGACCGCG
TCACGAACTCTCGGCTGGCCAACACGCGTCCGTCGGGCGGGTGTCCGCCGGCCTTCCCGCGGAACTCCGGGACCTCG
AAGCTGGACTTCGTCACGCGGTACGTGTACTTGCCGCGCCAGACCAGGTTTTCCTTCTGGAA GACGCCGTCCATGGT
CACGCCCGCCATGAAGGCGTCCTTGACGATGACCAGCACCGCGTCTAGCTTGCGCCCGTTGATGTGCGTGACGAAGT
CCGTGCCGCTGCGGCTCGCGCAGCGGATGTCCACGCCCGAGGGCAGGTCCACCACGAACACGAAGCGCTTCGGCGCG
TAGAGCACCAGGTCCGAGGACGGCGACGCCGAAGGCGCCGAGGGGAACTGCCGGTGGTCAAAAGGGTGCACCACGCC
CACGATGGACGTGACGCGGTCGTCCGGGAACTGCGTCGCGGCGCCGCCGCCGCGGTGCCGCGTGACCGTGCTTCTGC
CCACGTCGTCGCAGACCACGTGCAGCTCCGACACGATCGGCAGCAGCGTGGCCAGCATGCGGTCGGTCTCTGTGCGC
GTCGCGCAGCGGTACGCGATCCCGCAGTGCGCGTCCTGCGTGCGCCCGAAGAAGAGCACCAGCACGCTCGCGTCCTG
GTCGAAGGGACACACGGCCATCACGCCCACCGGCGGCGGCCCGTGGCCTGCGTACGCGGAGGAGAACTCCTGCACCT
CGACCACGGCGTCCTCGCGCGCCTCGCCGGGCACCATCGCCGCCGCCGGCCGCAGCGCCCGCACGGTCTGCTTAACC
GCACGCGCGGCGGCGGCCGCGCTCGGCGCGACTACGCGCACGGCCGCGTGCGCGCCCGGCGGCGGCGCGGTTCCGGC
CATCCAGCCCACCGGCGAGAAGAACACGTCGCAGACGTGCACGCCCGCGGCCTGCAGCGC GCGCGCGAGCGCGCGCA
CGGCCTCCCACTCCTCGCGAAAGGCGCTCGCGACCGCGAGCGCCTTCAGCACCGTGTCCACGGAGTTGACGGGCTTC
TGGAAGAGGTTCTCGTTGTTGTAGATGAACTCGGGGAGCTCCACGGGCACTGTGAACAGCCGAATCTCGTGCGCGCC
GCTGGGCGTGAGCCGCGTCGCGGGCTTGCGCACGCCGGCGCCGATCTGCTTGAAGAAGTGGTTCATGGCGCCGCCGG
CTTCTCGGGCTCCGGCGGGAGCAGACTATTTATTCGGGAGGTTATCCTTTCCGAAAGCACCTGCACGGACTTCCGCG
TCCAGCGCTCCATCTTCATGTACTCCTTCATGCCGTCGCTGAGCACCTCGACGGCCTCCAGCTTGGGCGCTGTCGGG
TCGAAGAGGATGCTCTTGAGCAGCGTCATCTTCTTGTCCGCGAGGAAGCGGAAGTAAGTGTAGATGCAGCGCAGCGC
GCGGAAGTTCTCCGGGTGCTTGATGGTGCACAGGATCATGAAGATGCAGGTGAACATGCCGCACTCGGACTCCATGA
GCTGGTTGACCTCGAGGTTGATGCAGCCGCGCCGCGCCTTGAAGTTGTCCACGAAGAAGCGCATGAGCACGTCCACG
TCGCAGTTGCGGTTGTCCAGGTCCGCGGTCTCGGCGTTCACGTTGAAGCCGTCCGAGAAGGAGTAGAAGTAGAAGTA
CTTGCAGGGGTGGAACTCCGAGGGGCTGTTGCCGCCGGAGTCGTAGAAGGACACGAGC CGCGAGACGGTGTCGAAGA
TGCAGCACTTCCAGTGGAACATGTAGCAGAAGCCGAACATCACGTAGCGCCGCCCGGCGCGCTCGATCTTGTCCTTG
AGCGTGAGGCTGACCATGTTGCAGCGGAAGCGGTCCGCCTTTTCGTGGATGGCCGCGCCGTTGAGGAAGTTCAGGTT
GAACTGGCCCAGGTACGCGACCTCGGTGCCGAACGCGAAGGGCGCCACCAGACTCTGGATGCTCACGTTGCTCATCC
AGGCGCCGCGGTCGGGCTTTATGGCGATGGGCACCACCTTGGTGTTCACGCCCGTGCTGACGCCCGCGCGCGCGAGG
TCGTCCACGTTCAGCGGCATCTGCGAGAAGTCCACGGCCTCGGACACCTTCTCGCGCAACGAGGGCTTGAAGAAGAA
GCCCAGCGGGACCTTCCACTCCAGCGCGATCGCCTCGCGGAAGCCGTAGCGACCCTTGAGGCTGGCCAGCAACGCGG
TCTTCTGCGCGACCTCGTCCTTCTCGGTGTC CGGCGGCGCGGCGTCGATGAGCCCGCGCTTCGCGAAGTCCAGCAGC
GCCGCCAGCGGATGCACGAGACGCGACCGGCCGTCGCGGATTCGTCGAAGCGCCGCACCACGTACCCGTTGCAGTTG
GTCTTGCCAGGTGCGCGCTGAGCCCCACCACCGAGTAGATGTGGCACAGAAGGTTGGTGAACCCCAGCTCCGGGATT
TTGCTCACCACTAAATCCGTGTACTTGTCCATTTATCATGGAGAATCATCTGCCGG ACATGCTGATGTTTCCCAACT
GCGTTTCTGTGTTTCCCTTTGAGTACTCGCTGGAGGACGTGTTCCGCCTCCCCGAGGAGCGACGGCGCGCGTTCGCC
ATGGCCGTGTTCCCGCTCTCCAAGCACCGCTGGAGGGGCGCGCGGCTCCAGCGCGACGAGCGAAGCGTGTGGCTCAG
CGTCGAGGAGGACCGCGGGCGCGCGCTGGACGAGCGGAACTGCTCTTGGCTCTCGGACGTGGCCGCGCGCATGGTCG
ACGACGAGGGCCGCGCGGTCACGCCCGAGGCGTACGCCTTCATGCGCGCCGCGCCCGGCGCGCGCGTCGCCGAGCTC
GCCGCGGACGCGGGCGTGCTAGCGGGCCTCGTCGCCGGCGGCAACGCGCTGCGCGTCTTCTCCTCGGAGTCCACGCA
GGCGCGCGAGGGCTGGAAGGCGCGCAGCGTGGGCGTGCTCGGCAACGCGGCGCCGCTGGCGCCCGTGCCGCTGGCAT
CGCTGCGTCCGGAAGTGCAGCGCGAGATC TTCGCCGCCTGGATCGGCCGCCGCCCCGTGGTGCTCACGGGCGGCACG
GGCGTGGGGAAGACCTCGCAGGTTCCCAAGCTGCTGATGTGGTTCAACTACCTCTTCGGCGGCTTCGAGCGCCTGGA
CGCCGTCCGCGAGTTCGCGGAGCGCCCGCTCGTGCTCTCGCTGCCGCGCGTCACGCTGGTGCGCGCGCACACCGCGA
CCTACCTCGCCTCGCTGGGCTTCGGCTCGGCCGACGGCTCCCCGGTCTCGCCGC GGTACGGCGCCATCCCGGACGCC
GAGCGGAACACGGCCCCGCGCGCCTACGGGCTCGTGGTGGCCACTCACCGGCTCACACTGACCGCCATCCGCCGCTA
CGACACGGTCGTAGTGGACGAGATCCACGAGCACGACCAGATGGGCGACATCGTGGTCGCGGTCGCGCGGAAACTGG

FIG. 28J

GCTCGAACATGCGATCGCTGGTGCTTATGACGGCCACGCTCGAGGACGACCGCGCGCCTGGAGGAGTTCCTAGTC
CGGCCCGCCTTTGTGCACATAGAGGGCGACACGCTCTTCCCCATCCGCGAGGTCTACGTGAAGAACACGCAACAGCC
GCCGCTCTCGCGCAAGTACGCGGAGGCGGAGCTGCAGAACGTGGCGCAGGCGCTCGGCACCTTCGTCCCCGAGCAGG
GAAAGTGCGGCATCCTCTTCGTAGCCACGGTGGCGCAGTGCGCGCTCTTCGCGGAGACCATCGAGGCCAAGCACCCC
GGGCTGCTGGTGCGCGTGGTGCACGGGAAGGTGCCCTCCGTGGCCGCGGTGCTCGAGGAGGTCTACGCCGCGGACCG
GCCCGCGGTGCTGGTTTCCACGCCGTACCTGGAGTCCAGCGTGACCGTGCGCACCGCCACGCACGTCTACGACACTG
GGCGCGTGTACGTGCCCGAGCCCTTCGGCGGCCGCGAGACCTTCGTCTCCAAGTCCATGTACACGCAGCGCAAGGGC
CGCGTGGGCCGCGTGGCGCCCGGCACCTACGTGCGCTTCTTCGACACGCGGC TCGCGCTGCCGCTGAAGCGCATCGA
CTCCGAGTTCCTGCACCCGTACGTGCTTTACGCGCGCATCTTCGGGCTAACGCTGCCCGATGACCTGCTCGTGCATC
CCAGCGACCTCGCGCTGCTGCGCCGCACCGAGGAGTACGTCGACGGCTTCGGCATCAGCCTCTCGCGCTGGACGCAG
CTGCTGGACCGGCACTACATGCACATGGTCGAGTACGCGAAGGTGTATGTGCGCGGCGGGCGCCTCGCCGCCGCGCT
GGACGCCTTCGAGCGCACCGGCGTGATGACGCACGAGGCCACCGAGGCCATCCGCGCCGTGGACATGCTCGCGGCCG
TCCTAAACGTGCGCAAGTCCAAGGACCGCTACCGCGCGGAGTGCAAGGTGCTCTTCGGGCCCTTCGCGGGCAAGAAG
TTCGTGGTCGCCGGGCGGCGTCCGCCCGGCTCGCACGTGCTCATGGTCACAGACCGCGTCTTCATCGAGGCCGAGCC
CCCATTCTGAGGACCACCTTCTTGGAGACGCCCGAGAAGTCGTCGGCGACGCCGCGGCGCGCCACCACAAGGCAGTA
CGAGGTTACGTGCGGGCAGCGCGCGATGCAGCGGAAGGCTTCCTCCTGCGACAGCGAGAAGGCGAACACGTAGAAGG
TGTGCGGGGACTTCAGCGGCGTGTGGTCCATCGAGTAGATGACACCGAGCTTCTTCATGCGCCACATAAGCGCGTTG
ATGTGGTCGGCGCGCAGCGCGCGGCCCTTGAGCACGCCGCAGACGAAGCT CGAGCAGGCCACGACGTCGTAGCGCGT
GTTCCTGCTGAAGACCAGGTGCGGTGCGCCGCCGGCGCGCCGCGCGGCCGCGCGATTCTCCACGATGTCCTCTATGG
AGCGCTCGCTCGCAAAGAAGTCCAGGAACATGTACTGGTAGGCCACGGCCGGGCGCGACTTGCTGAACTTCATGAAG
GCGTCCGAGTCCATGATGGCGTCCATGTCCTCGGCGGCGAGCCGGTGCTGCAGCCGGATGCCCTCGAAGGTGTGG AA
GAGCCGCGCGTCCGCGTGCATGGACAGCGCGAGAGTGACGAAGTCGAGAAGGTCCGCGTCGCCGAAGCGCACGAGCA
CGTTACCGGGCGTGCGCGTCTTGCGCATGAGCCGCGCGGGCGCGCCGTCGTTGTGGCTGCGGCGGCGCATTTTGTCG
CCGGGGGACTCGGGCGGCAGGCGATCATGACCAGCCGGTGCCGCTGCGCGTCCTCGGCGTTGAAGATCGAGGACGTG
AAGCCCGGGTACAGCATCGCGCTCCGAGATGGCGTGCAGCACGTCGCGCTTGAGCCCGGCCACCAGCCGCTCCGCGT
TCTCAACGAAGTAGTTCTCGTAGTCCAGGATGTCGTGCGCCATCCAGGGGAAGTTCAGGTACGCGTTCATGGCGTAG
TCCTCGGCGTCGAAGCAGATGCGCGTGTCTGGCGTCGCCGCGATCGGAAGGTCCTTGATGCCGCGGAGCAGCCCGTC
GTAGTCGGACTCGTCTACGAAGGAAAGCACCACAAAGAGGTCCTCGCC CACGGTCTCGTAGTCGAAGAGGTGGTAGA
GCTCTCTTAGCGCCAGCACGGCGAGCGCGTTGTCCAGCGAGGCGTGCACGCGCGCCAGGATGCTGTAGAAGGGCGTG
GCCATCATCACGGCCTTGCCGCCCTCGCAGGCGACGGCGCGCGGGAAAATGACCTCCGGCGTGCGCGGCAGCCGCCC
GAACGTCGCGTTCAGCAGCGCGACCGTGGCCGCGTCGCTCTGGCGCAGGAACACTACCACCGAGGGGCCCGAG ATGC
TGAGCATGCGCTCGCGCATGCGCGCTGGCAGGTCCGGCGTGGTCACGAGGTCCGCGAAGCGGCCGCCGTTGTAGAGG
TCGCCGCCGCCGAGGAAGGTGAGCACGTCGAAGCAGTGCAGCACCTCGTTGCGGAAGTAGTACTCGTTCTCGAGCTC
CTTGGCGTACGCGCGTATGTCCACGTTCTCGAAGTTTGTTCGCAGACCGCCGCCGTCGAAGAACCAGGACGCAAGCT
CGCGGACGGCGTCCGCGGGCCTGTTGCGGCGGCTCTTGCACCAGAAGCTCATGTAGTTGCGCGAGGTGGAGGCGTTC
GCCAGGAAGAAGCGGTGGTCGAAGGAGATGAGCACATGCTCGAGCAGGTGCGCGAGCCCCAGGACCGCGCCCACGTC
GCGCCCAAAACCGAAGTTTGATATCCCCAGGTAGACGTCCCGTTTCATAGACGGCCTCAGGAACACCCTGACGCCGT
TTTCCAACACTATCATTCTCCGGTATTTACTTACCCAAAAGTAGTA TTGGGAGAAGTGTTTGAACGTCCCCTCGCCT
TTTTAAATCAAAAGTAGACTTCTCGCGCCCGTGCGCCACCGTCACGCGCGCGCGGCGCGAGTCCATACCGGCGATCA
CCGCGCTGCTCTGCGGTGCGTCCGGCCGCGGGAAGAGCACGGACTCGGAGATCCCGTCCAGCTGCGCGTCGGTGCGC
TGTCGCCACGCGTGCGCGTCCGCGAGCTCGCGCACGGCCAGCTGCATCTTGTTCGTCGGCAGGAACGTGAA CACGTA
CGCCGCCGCCAGGAAGACTGCGAAGAGCACGAACTCAACCGCCCATGACATTTAGGGAGCTGATTTTGTTCCACGCG
GCGACGCACGTCGTGACGGGCGACCCCGAGGCGCCGCGGCGCGCGGCCTCGCTGTGCCGCGGCTTCGGCGTGGACTT
CCGCGCGATTCACGCGGAGTTCGCGCGGCGGTACCCGCGCACCGCGGCCGCCGTGGAGCGCGCGCAGCCGCTGCCCG
AAGTCGACGCCGCCTTTCCGCCGGACGCGCGCCGGCAAGTCGTGCGGCTGCGCCTCGAGGCTGCGGCGCTGGTCGTC
AAGGAGTCGCGTGCGCTCTCGGCCTCCATGCGCGGCGTGGCGGTGGTCGACGGCTGCTGCGTGCGCGTGTGCCGCGC
TAACGACGAGCTGCTGGGGTTCCTCGCGCGGCGCTACGACCCCGCGGTCTACCGCTACGCGGAGGTGCCCTCGCCGA
GCGTGCGCCCGGGCTCGAAAGTCTTCGCGTGTGCGGGCCGCAGC GTCACCTTTGCGGCCGCGCACCGGAGCCGCATC
ACGGCCAACCGCCCGCTGCGCGTGGTCGTGACCGAGGCCTGTGTGGACGGCGTGCTCGCGCGCGGCGCCGCGGAGGT
ATTCGACCGCGGCTCCGGCGTGCTGCCCCGCGCGCTGCGCGAGATCTTCTACCGCCTCGACGAGGACGGCTGTCCCA
CGGGCCAGACGCCAGGCTTCGCGGACAGTATGGCGTCGCGCAGCTGATCTATGTCCACCTTTTTCTCGT CGATCTGC
GCCACGACCACGAAACTGCGAATGTCCACAGCGGCCATGGTCTTGGCCACCGGGTCGTACTTGAGGAGCAGCACGTA
CTCGTTGCCGAAGTGCTCGGTGACCTCGGTGATGAGCCGGTACACGCCCATGCCGAGCACGTTCACCGCACCGTCCT

FIG. 28K

TGGCGAAGAGCGAGAGGATGTTCACGCACTTCAGCTCCATCTCGCCCTCGAGGCGCGCGAGCATGCGCCGGGTGACC
TCGCATACTGAACAAAGAGGCTTACCTAGTAAGATAAGCGTTAGCTTAGCCGCGGTCGGTGACGCGTCGGAGGCCAT
TTATGGGGATCAAAAACTTAAAGGCGTTGCTGCTCAGCCACGGCGCGCTGACCCCGCACGAGCCGGGCGGCGACGAG
CGCTTCCCTGCCGTGTTCGTGGACGGCTTCAGCGTCATGATGACCATGGCGTACTCGTGCGCGGACGAAGACGAGTT
CCGCGCGGCCGTCGAGGAGCGCGTGCAGCACTGGATGAGCGT GTCCGAGAGCGGGCGGATCGTGGTCTTCCTCGACC
GCGGCGAGATTCCGATCAAGCAGCCGCTGCGCGACCAGCGCCGCAAAGCCACGCGCGACCGCGCCGCGCGCCACCGC
GAGTTCATCGCCGCCGCGGAGGCAGAGGCGGCGGCAGAGGCCGTTGGCGCCCGCGAGGACAAGCAGGAGGACGAGCA
CGCGGAGTTCGCCGAGGAGATCCGCGCCGAGAAGCAGCTAAAGCTGCAGCGCATCCGCTTCCAGCTC AGCATCGCCA
ACCACGAGGTCGTTAAGTCGCTGATAGAGTCCACGCCGCGCGCGCTGGCGATGCCGTGGAGATCGTCTTCTGCGACG
GCGTCGACGCGGAGATGGTCATGTGCGCGCGGCGCCGAGGCCGAGCGTCGCGGGCGCTGGCCGCTGCTCGTGACCAC
GGACCAGGACGCGCTTTTGTTCACGTCCACCGATCGCGACGAGAAGATAGTGAGCACCGTCTCCGCCTGCTACGCGT
TCAGGCCCACCGAGACGACCGAGTACCTGTGCAAACTTGCGGCGCTGGCCAACGGCTGCGACTTCTTCCCCGGGCTC
GGCGGCATATGCGTGAGTGTGGAGTCGCTGCGCCGCGCCACGCTTTTCCCGGAATTCTCCGTGCGCAACGCCGCCGT
GAGTCTGTGCACGCGGCCCATGCGGCTGTCCACGCAGGACGCGCTGGAGCCAGAGGCCGCCGCCGAGGTCGTGGAAT
TCATCAGGCGGTACGCCGCCGGCGACGAGCGCATCTACCGCGAGGTGCCGCCCGGCGCGTGCTGCGGACGCGCGTTT
GTGCGCGGAGCGCTCGCGGCCGAGTGGGCCGAAGCGCTGCCGGCGGCCACGGGTCTGAGCGTGGTCGCGGACATGAT
CGCGTGTCTGCCCGCGCGGCGGGACCCCGCGCCCGAGGAGGTAGAGCGGCTGCTGGCGCTGGAGGCGCGCGCGCGAG
GCGCGCGCGTCACGGATGCGATGCTCGCGCAGACTGCGCAGCTGCTGGGTTACGGCGCGAGTGCG GGCGCCGACGGC
GCCTCCGCCTTCGCGGTCTCGGGCGCCAAGGGCCTGATGTGTCGCCTGCGCGGCACGGCCATGTTCTTCAACGCGGA
GTACGTGGAAATTGAAAGCGAACCCAGACTGTTAAAGCTGCGGTAGCATGGTGTTCCCGATCGTGTGCTCAACGTGC
GGCCGCGACCTGTCGCACGAGCGGTTTCTGCTCATCGTGCGACAGCGGCCGCTAAAGGTTGTTTTGCGGACGGTGCG
CAACGTCTGCTGCCGTATAAAGTTGTCTACACAAATAGAGCCGCACCGGAACCTGACGGTGCTGCCCATGCTCGACA
TAAGCTGATTTTTCTTTTCCGCTCTGTATGCGCGAGTTCGGACTCGCGGCGCGCATGGCCCGCGCCATCGAGGACGT
GTGTCCGCGCGGCGCGGTGATATTCGTATCCAGCGCCGCGTCCATGACCGACTGCCTTAACCCGTCGGTGTTCAAGC
ACGCGGCGATATACGCGGGGCGCGTGGACCGCGCGCCG CTGCCGCCGCCCTCGCCGGTCCCGGCGGAGGCCGTGACG
GAGCCCTGCGCGATAGACGCCATAGCGCCTTACGGCGCGCGCGTGGTCCTGCTCTCGGAGCTGCTGCGGAGCTGCGT
GGCCGTTCAGGCCTACCGCCTGGCAGTCCCCGGCGCCCTCGCGCTCATGAACCTCGCGGCCGACGCGGCCTTCGAGC
TCGTGGGCACGCCCTACGGCTTTAACAGCGACCGAACGTACTGCTTCAAGCTCGTTGCCGACT GCTTTGCTAGCGTG
GGCGTGACAACGAAGACCAGGCGCATCATGGGTCGCGACGTCGTGCTCAGCCAGGACTTCCTGGAGAGCGGCATGTG
GACCAAGGTGCTGGACTCCGCCGCGGAGCCGCCGTGGCTGGTCTAGAACAGCGGCGGCGCGCGGGTCCCGAGAACGG
GCCGCGCCACCTGCAGCCGCTGCTGCAGCGCGCGGCACTGCGCCTCGGCGTCGGCAGTCTCGGCAGGGTCGACGGGC
GTCGGAGTCGCGGAGGTGGTCCTGAACGGCTGCGTGTTCACCGAGACGCGGATGCGCTCCTTGCAGGAGCGCTGCTC
GATGCAGTTGGCCAGCATCTTCATCACGTGCAGGTACTCCAGCAACACGAACTTTTCGAGGGTGATGCCGTCGAAGG
GCGACGACCCCACCACGCCCAGCGGGCTGGACACCGCGCCGTCGAGCACCTCGCCGCGGGACTCCTTGCGCGCGCGC
TCGAGCAGGTCCTCTGTCCGAGCCACCACGCTGCCG AAGTCGGCGGCCGCGGGGGCGGGAACAGGCGCAGCAGCTGC
GCCGTCCGCGTCCGCCGGCATCTCCTCGATCTTGAGACCGGCCGCGAACTCCGAGGCCGCGTGCACGGGCGAGGCGC
CGCGCCGCACCATGAAGTCGCACAGACGCGATAGCGCGGAGGAGCGCACCGGCATGTCGAGCAGGCGCTCGGCCTCC
ATCTCGGCGACCGAGTCGGCGCACGCGTCCGGCGCGCCCGCCCGCACGAGCTCGTCGCAGC ACCCCGCCTCCTCCAT
GAGCGCGGGCATGAGCTTGTACTGCGCCATGTTCACCAGCCCGTACTTGAGCTCGAGCAGGTCCGCGAGCTCGGAGG
CCATGGGTCGGTTTTTGGTGTAGATGACGCGCTCCACGGCCTCCGCCATGTCCACGGCCTGCATGAGCTCGCCGACG
AGCACGCTGGCCACGAGCGTGGCCAGCGTGACGCGCACGGTGGGCACACAGACCGCGAAGAAGGAGGTGGAGTGGGT
GAAGCGCATGAGCGCGCCGTGCAGACGCGCGAGGTCCGCGCTGTTGCCCGCGTGCACGAAGCGCCGGCGCAGCCGCG
CCAGCGCCTCCACGAGGTCCTCGCGCGTGGTCACGCGCACGTTCGCGATGCACAGGTCGTGGTCGCGTTGGCGATCT
GCGCGCGGCGCTGCGGCGAGCTGCCGGGCAGCAGCCGCGCCTTGGCCTCGACGTCGAGACAGCCGCAGGCGGCGCCG
CGGACGACGAACTTCAACAACGACTCGAACACGC GCGCGCCCGCGCGGGGCGCTTGCTTGGACGACTCCATTTACTT
TAAATAATTTACGAGATCAAAATAAAATGACTCTGCGCATCAAACTCGAGAAGCTCAAGCAGATCGTAACCTACTTC
TCGGAGTTCAGCGAGGAGGTCTCGGTGAACGTGGACGTCGGCGATGGCCTCATGTACATATTCGCGGCGCTGGGCGG
GTCCGTGAACATCTGGACCATCGTGCCGCTCAGCGCGAGCGTGGTATACGACGGCGATG TCAGCCGCGTGTTCAACC
TGCCCGTGCTCAAGGTGAAGGCCTGTCTGTGCAGCTTCCACCCCGACTCGGTGGTGAGCCTGGAGCCCGACCTCGAG
GACAACGTGGTGCGGCTCTCGAGCCACCACGTGGTCAGCGTGGACTGCGACAACGAGCCCGTGGCGCACCGCACGAA
CACCGCCATCTGCTTGGGCATTAACCAGCGCAAGTCCTACGTGTTCAACTTCCGGCGCTACGAGGAGAAGTGCTGCG
GCCGCACCATCGTCAACCTGGACCTGCTGCTGGGGTTCATCAAGTGCATCCACCAGTACCAGTACATCACGGTCTGC
TTCCGCGACAAGAAGATGGTGCTGCACACGCCCGGGAAGGTGGACAACTTCTTCCGCGAGTACTCCATGACCGAGTG

FIG. 28L

GGCGCCCGACCTCGAGCGCTTCTCGTTCAAGATCCCCATCTCCTCCGTGAACAAACTCCGCGGCTTCAAGAAGCGCG
TGGTCATGTTCGAGTCGCGCGTGGTCATGGAC GCCGACGACAACATCATCGGCATGCTCTTCACCGACCGCGTGGGC
ATGTACCGCGTTAACGTGTTCATGTCCTTTCAGGACCGGTCTCTTTCATGCGACTAAATACCCTCATGGGCGGGTCG
GTGAGCCTGCCCTCGCGGGACCTGCCGCCGCCGGTGCGCACGCCGGAGATGAACATCGTGCCCGAGCGCGACCTCGC
GGACACGATGGCGCGCCTCTCCACCGCAGACCCGCCGCAGCCGCTGGGCGTCGGCGA CGACGCGCGCATGGCCGTGC
TGAAGACGACCTTCCCCGAGTTCGCGATATCGCGGCCCGCGACGGGCATGCTCGCCGCGCAGCGAATCAGGTACGAC
GGCGACCCGCGCGTCTGCTGCGGCGGGTTCGGGATCTCACATTACTGGGAGAGGGGGGCGCGCCGATCGAACGTCGC
GTTCGAGGGCGCGGCGCTGCGCACCTGCGACCCCACGCGCTTCGACGCGGGCGCGTGCGACGCGCTGCTCTTCCGCG
AGTGCGCCGCCGGCGGCGTCGACGCGGACTTCTGCGCGCACTGGATCAACGCGGCCGTGACGCGGCGCACGGACCGA
CAGTCGCGCGCGCGGCTGAACGACATGTTCGTGCGCGATTGCCAAAACGACGCCGCCCGGCCTCACTGCGTGGCCTG
GATCCGCGCGATGCGAAGCGCGCGCGCGACGGCGGACGACGGTCTAATAGACGCCGTGCTCTCGGTGCAGAGTCCCG
AGTTCAAGGGCAAACACATGCGCTGCAGCTACCCCTCGCCGGCCACACTCGCCATGGCCGCGAACGTAGACGAGCCG
CGCGAGTGTTGGGACCCCGAGTGCGTGGCCGGGAACGTGGACTTCATGCTGAGCGATAACTACACGAACCTGGGCCT
GTGTCGGCTCTCGCGCTGCTCCATCGGCGTCACACACCTGCGGATAGACGCGCGTTCGCGGCTGCGCATGCGGTGCG
CCGGCGCGCTTGCCGGGCTCACGAAGGCGCCCGTGAACCAGACTGTCGTCGTCGG CGACAACCTCGCGCGCGCCTTC
GAGCCGCGCGTGGAAACGCTCGGCGTGTTGGCGCTGTGCGTGGTGTATCTGCTAATTGTCTGGCTCTAAATGGGGGC
CGCCGCCAGCATTCAGACCACCGTGACCACCGTCAGCGAGCGCATCCGCAACGAGCTCGAGCAGAGCGCGAGCGCTA
GCGCGACCGCCGACTGCGACGTCACCATCGGGAGTCTGATTATCCGCAAGAACCTGGGATGCAGCGTTTCCGTCCGG
AACATGTGCTCGGCCAACGCCGGCGCGCAGCTGGACGCCGTCATGAAGGCCGTGAGCAGCACCTTCAACGACCTCTC
GTCGGACCAGAAGGCCTACGTGCCCGGGCTGCTCACGGCCGCGCTCAACATCCAGACCACGGTGAACACCGCCGTCA
AGGACTTCGAGACGTACATGAAGCAGACCTGCACGGCGGACGCGGTCATTCACAACAAAATCAAGATCCAAAACATC
GTCATGGAAGAGTGCGCCTCTCTGCCAGGGAGTCCGGCCACGCACCTGGAGTTCGTGAACACCGGCACGGCCGTGGG
CAACTGCGGCGTGAAGGCCGTGATGGACGTGCTCGCGAAGGCCAGCACCACCGTGCGCAACGACCAGGAGGCCGGCA
AGGGCTACCAGACCATCATCATCGCGATCGTGGTCGCCATCCTGGCGGCCATCTTCGCCTGGTACGCGCGGCACATG
CTATTCATGTCCACCTCCGACAAAATCAAGCTCGAGCTCGCCAAGAAGCCCGT GGTGCACTGGACCACCTACCTGGA
CACCTTCTTTACGGAATTTCCGCCGTCCGTCTAGATACGCGCAACATTGAAACATTATATCCACCTCTCAAACGGCG
GTATGGTCCGACGCGTCCTCCTCGAGCGCGTGGACGGCATCGTCGAGCACTCGCGCGCAGACCGACGCTACTTGGAG
GCCATTCAGCGACACCTCGAGGGGTCTACGCCCGGGCTGCGGCAGATGTGGCGCTTCCTCTACGACCTGCTGCGACG
GTGTTCGTCGTCATGTACATCGTCTTCCGCCTAATCGTGCGCAACCCCGGCATCTGCGCCATCCTCGCGCCGCGGTG
TACTACCTGTTTTTGTGTCTCTTTAGCATGGACTGATGGCGATCACAGACAGACCATCGCCCGCGCGCGCGTGACCA
GCTCCGGCGCCGCGAAGACGTCCTGCACCGGGAAGTCGTCGATCTCGAACACGGAGCCGTCCGCGGACCAGATCACG
CGCACGTTGTCGCTCACCGAGACCTC GGTCAGCGTCACGCCCAGCACAACCGCGTCGTTGGTGCTCACCAGCACCAG
CGCGCCGGGCTCCGCGCGCCGGTGCAGCGGCGGCCCCGAGACTGAGCGCCGCTGCACGCGGAACATGTCCGCGAACT
GCTTCGAGAGCAAGTCCAGGTGGTTGCGGATGATCCACTCGAAGAAGTACGCGCAACCTCCGCCGCCGCACAGGAAG
CGCGAACCCGCGGGCATCAGCAGCCGCACAACGTCCATGTAGCAGGCCTGC GGCAGGCTCGCGCGGTACAGCCGCGT
CTTCGGCGAGAGCACCACCAGGCTGGAGGTGCTCATCTGGAAGACCAGCTGGCTAACGGAGACGGTGAGCGTGCACG
CGGGCACGGAAACCACGTCCAGGCAGATGTCGTCCAGAAAGATGCTCCGCTGGTAGAGGTGGTACAGGATGGCCACG
ATCTGAAAGGCCGTGGCGTCGCTGATGGCGCAGGGGCGGTCGGCGCAGCGCATCTGCGCGCAGGACCAGCCCCCGA A
GGACTCGAAGCAGACGGTGATCATGCCCGTGCTCGGACAGTGTGGCGAGCGCCGACACACCGGAAAGCCCACGGCCT
TGCGGCAGCGCACCATGGTCGAGAGCTCTATCCAGCAGCCTGCCTCCTCCTCGCCCATGCCCATGGCTACCGGCGTG
AAGGCCGTGACGTCGTCGCAGATGCGCCGCTCCAGAAACCCCACGCCCGAGGAGGGGTGCGCGGCCGGTGGCGAGGT
GATGCGCGCCGGGACGCGGCTCGGAGCGGGCTCGGGAGGCGAGCTGCGCTCGACCCGGGCAGCCGCCGCCGGCCGCG
ATGCCCTGCGCGCGGGCGCGCGTTCGCGCGACTTGTTTGACTTGCTGGCCTCGTCGCTAGCGTCATCGAAGCGGTCG
TTCCTGTCGCCGCGGACGTCCGCCTCGTCGCCCGCCGGCCGCGCGGCGGGCGACGTGCCGTCCCGCGTACGGCCCGC
GTTCGGCGCGAATGTCACGCGCCGGTGCACGTACGGCTCCGTAGAGCCC GTGGGGGCGCCGCGCCCGCGCCCTCGGC
GGAAGGCCTGCCGGGACGCGCCGAAGCGGGCGAACTCCCCCTTCGCCCGGCCCCTTTTTTCTTCCATGATATTTATC
ACAAAAAAAACTTCTCTAAATGACCAATCTGCTTTCGTTGGTCGACCCGGAGGACCTGGCCTTCTGCGCCGGGTTCC
CGTCCTTCGACGAGACCATGCTCGTGATCGCGGGGGCGCGAGTGCGCTTCCCACGCTCGCTGCTCTCGCTCTTC AAC
GTGGTGCCGCGCACCATGACGCGCTACGAAACCGAGCTCGTGGGCACCGAGATGGTGGTGGGCGCCGTGTTCACCAC
CGCGTACAACGTCCGCCGCAACCTAGGCCTCGGCGAGGAGCCCGTGACCATGCGCGACATCGAGAAGTACTTCCTGG
ACTCCGAGAACGAGGTGCTCACGCTCATCGTGCACAACACCGACTTTTCCGCCATGAGCGGCGTGCGCCGGCGCGGC
GGCCGGCGCATCGCCAACCCCGTCATCTTCCGCAGCGGGTCCACGCCGCTGCTCATCGTGATGGAGTCGCGCAAGAA
GACCAACATCTACCGCGAGCGCACCGCGGAGCAGGCCAACGCCTCCTACAGGGAGGTCGGCTCCTCGCTCGCGCTGG

FIG. 28M

TCACTCGGTACGCGGGTCTGCAGCTGGTCGACGTGCACACGCCCAGCTCCGTGCTAACGGTCTCCGCCGTCTACGGC
TTCACCGAGGACAAGGGGCTCAAGAAGCTGGGCTCCGACAAGGAGCTCGCGGACTACCAGTCCACGCCGCTCACCGA
CCCCATCCGGCTCAGCGACTTCTCCAATATATTCGACGGCGTCAAGAAGAGCATCCAGCTCACGAACGTGCCCGTGC
CCTCCGCCGGCGCCGAGGCCGCGCCGTAGGCTTTCATGCGCGATAAATCGGATGGCGGCGCCGACGACGCCCGTGGT
GCACCTCACGCCGGTGTTCGTGGAGCCTACGATCGCGCACTCGCTGCTGCGCGCAGAGTCCTACCTCGCGATCGCGG
TCCTTGAGCTCGTGCTCGCGCTCGTGCTCGCGCTCGTCTTCTTCCGCGACGAGCTGGGCGCGCTATTCCGCCGCGCG
CCGCGAGCGCCTTCGCCGCTGGACGCGTACCTGCAGGCGAGCCTCGTCTGCGACGGCGACGCGCTGCTGATCGAGCT
GCCCGAAGGCCGGGTGCCGGCGCTCGCGCTGGACGGGCGACCCGTCGCGTTCCCGGGGTGCGAGAGCCTTTTGTACC
GCATAAATGGACCACGAAAAGTACGTCTTGTCGATGTTCTTGGAGGAAGATAACTCCTTCTTCTCGTTCGTCGCCGC
GCTGTCCGATGACGAGGCGCTCGGCGCCGTGCAGTCCGCTGCCGCCCTCCTGGACTTCCTGCTCTCCGTGGTGGTCC
GCGGCAAGGAGAAGCTCGCCGCCGCGGGGCACCACTACGACTCCATCGCGGACGGACGCGCGCGCGCCGCGTTCGAG
TTCCGAGACCTGCGCGAGCTGGCGCAGCTCTTCGACCGGCGGCCCTGCGGCGTCCAGGACCGCGTGCGTGTGCGCGA
CGGGCCCGCGCGCGCCTTCGTGGACGCGGCACTGGGGCTCATGCGCGAGCGAGGCTTCGACGGCACGCAGGCCGCGG
AGCGCGCGCGCTCATCGCGCCGAACGATCTGCCCGCGCTGGGGGCAATATCGGCCACGCTCTCGCCGGGTCTATAAC
GTAAAAAGAAGGTCCGTGTGTTTCGCGGGCGGCCAACAAACCAGTCGCTTAAATGGAGGGGGTGGAAATGGACAAGC
CGCTCCTCTACTTCGACGAGATCGCGGGCGCGCGCGACTACGACGCGGCCTTCGCGGAGAAGCACGAGCCGCCCAAG
ATCCCCGGCCGCGGACAGATGAAGCTGCTGGTCTGCGAGCTCGTGTTTCTCAACCGGCTGCACCTGCACGGCATGCT
CGACGGCAGCGTCATCGTGTACGTGGGCTCCGCGCCCGGACGGCACATCTGCTGCCTGCACTCGCACTTCCAGGAGC
TCGGCGTCTCGCTTAAGTGGGTGCTCATTGACGGGCGCAAGCACGACCCCTGTCTCTCGGGGCTGCGGAACGTGACC
ACGGTGACGCGATTCGCGGACGAGGCCTACCTCCGCGAGCTGCGCGGCGAGCTGCGGCGCGCCAAGATCGTGCTCAT
TTCGGACATCCGCTCCAACCGCGTGGACACAGAGCCCACCACCGCGGACCTGCTGCGCGACTACGCGCTCCAGAACA
CCATGGTGAGCGTGCTCAAGCCCGTGGCCTCCAGCCTGAAGTGGCGCTGCCCCTTCCCGGACTCCTGGGAGAAGGAC
TTCTACGTGCCCTGCGGCAAGGAGATGCTGCAGCCGTTCGCGCCGCCGTTCTCCGCGGAGATGCGGCTGCTCACCGT
GCACTCGGAGACGCGCCCGAAGCTGCGTCTGATCACGCTCAGCGACGCGGTCAACTATGAAAAGAGGATGTTCTACC
TCAATAGCGTGGTCCGCCAGCGCGTAATTCTGAACTTTGACTATCCCAACCAGGAGTACGACTTCTTTCACATGTTC
TGTCTGCTCTCGTCGGTGGTGTGCTCGTGCGAATTTAAATCGCCCAAAGAGAAGGTGCTGAGCCTGCAGAACCGCTT
CTTCCGCTTCCTGCGCATCCCGCCCTCCATCACGCTCGGGCTGCGCCGGCACGATGAACCGCCACAACACGCGGTAC
CTGGCCAAGATCCTCTGCCTAAAGGCCGCGGTAAGAAGCGACCCCTTCGCGGTGGTAAGTAGGGACACCGTGCGCAT
GTACGACATCGAGGTCGAGTACGGCGACCTCGTGACGGTGGTCACCGTCACGCACAAACTCGAGACCAGCCGCACCG
TCTTCCAGGTCTTCAACGAGACCTCGGTCGCGTACTCGCCGCTGCCGGACGACTACGGCGAGCCCATCGTGCTCACC
ACGTACATGCAGCGCGAGCACACCAAGTTCCCGCTCTCCATGCTCTACATCGACGTGGTCGCCTCGGACATGTTCCC
CACGTTCAAGCGCCCCACCGAGGAGGAGGCCGCGGTGGTCGCGGCCATGCAGCGCGTGGGCGGGCGCCGCGATCCCG
TGCTCAAGCTCCCGCGCATGCTGGACACCGAGCTCGTGTGCAAGATACTGCACCTGCCCGAGCACCCGCTGCGCGTG
GTGCGCTTCCTGCGCCGAAACATGTTCACGGGCGTGGAGGTCGCCGACCGCTCGGTGTCCGTGGTCCTCGACTGACG
AAGGGCAGCACGGCCAGCGAGGCCGCCGCCACCAAGCACAGCGGCAGCCACGCGCGCGGGTCCGCCACGGGCACGAA
GACGTGCTGGTTCAGGTATTTCGCCTGGAAGCGCTCCGCGGTGGAGTCCACCTTGGACCCGCAGGCGTTGGTGAGGC
GCACGACCGCGTCCGCGACGCGCACGTCCCCGAGCGATATCACGCAGTCCGAGACGTTGCACCCGGCGATGTTTTTC
TTCAGCGCGCGCGGTAGCAGCGCGTCCGCGCGCTTGCAGGGCGCGTACCAGCAGTAGTAGGGCAGGCGCGTGTCGCG
GCCGGTGTCGACCACGGCCTGGCTGGGCTTGAGGCACGCGCAGCGCTCGTCGTCCGGGTGCGCGTCGCAGAAGGCGT
AAATCTCCTCGTCGGGCGCGTCCGGCCCGGGCGCGGTCGGCGGCGCCGCGCGACGGCGGAAGAACATCTCTGAAAAA
ATACTTCGACCAGAAAACGACCACCGATCTTATTTCAAAGATAAAAATACTATTAATACGCACTCGGAGAATCATGT
CGGTGGTGGCGCGCGTATCGTACAGCCTGTACTCGCAGAGCGAGATAAGCGCCACGGACGTGGTCATCAGCCAGTTG
AAGAACGACGAGGACCTGGGCACGGTGAAGGACCCGCGCCTGGGCGCCTCGGACGGGTCCATATGCCGCACCTGCGG
GCTCACGGAGATGGAGTGTTTCGGGCACTGGGGCAAGGTGCGCATCTACGAGTCCTACATCGTGCGCCCCGAGTACA
TCCCCGAGGTGGTGCGGCTGCTCAACCACCTCTGCGTGCGCTGCGGGCTGCTGCGCTCGCGCGACCCGTACACGACG
GACGTGGCCGCGCTCAGCGTGCACGAGATGCGCAAGATGAAGGACCGCATGATGTCCAAGAAGAAGGCCTGCTGGAA
CAGCAAGTGTCTGCAGCCGTACCAGAAGATCGTCTTCTCCAAGAAGAAGATCTGCTTCGTGAACAAGGTGGACGAGA
TACCCGTCCCCAACGCGCTCATCTACCAGAAGCTGACCTCCATCCACCGCAAGTTCTGGCCGCTGCTGGAGGTGTTC
CAGGACCCCGCGAACCTGTTCTACAAGGAGTACATGCCCGTCCCGCCGCTGCTCATCCGGCCGGCGATCAGCTTCTG
GATAGACAACATCCCCAAGGAGACCAACGAGCTCACCTACCTGCTGGGCATGATCGTGAAGTACTGCTCCATGAACG
CCGAGGAGCAGGTCATCCAGCGCGCCGTGATCGAGTACGACAACATCAAGATCATCTCCTCGAACTCGAGCAGCATC
AACCTCTCCTACATCATCGGGGCAAGAGCAACATGCTGCGCAGCTTCGTGGTCGCGCGGCGCAAGGACCAGACCGCG
CGCTCGGTCATCGGGACTCCGCGCTCTCGGTGTGCGAGGTCGGCATCCCCGACTACATCCGGAACACGCTCACGCAG

FIG. 28N

AAGGTGTTCGTGAACTACCTCACCAGCAAGCGCGTGCGCGCTGTTCGAGGACCGCGCGGTCAAGTTCTACTTCAA
CAAGCGGCTGCGCCAGCTCACGCGCATCAAGGAGGGCAAGTTCATCAAGGACAAGATCCACC TGCTGCCCGGCGACT
GGGTGGAGATCCCCATGTCCGAGGGCACGAACGTGATATTCGGCCGCCAGCCCTCGCTGCACCGACACAACGTCATA
TCCTCGACCGCGCGCGCCTCGCCCGGCTACACCATCAAGATCCCGCCCGGGATCGCGAACTCGCAGAACGCGGACTT
CGACGGCGACGAGGAGTGGGCCGTGCTCGAGCAGAACCCCAAGTCCGTGATCGAGCAGAGCGTGCTCATGTACCCGG
TGACTATCTTCAAGCACGACGCGCACGGCGCGCCGGTGTACGGGTCCATCCAGGACGAGATCGTGGCCGCGTTCTCG
CTGTTCCGGCACCAGAACCTCTCGCTGGACGAGGTGCTGAACCTGCTCGGGCGCTACGGGCGAGACTTCGCGCCGGA
GCCTGGCCAGAAGACCTTCTCGGGCGCCGACGTCTTCCGATTCATGATAGGCGCGGACATAAACTTCAAGGGCGTGC
TCGAGAACGGGCGCGTGGTGGCGCCGAACGTCGAC AGCGACCTCGTGGTGGCCATGCGCGCAACCTCGCTAGCGGGG
CTGATCGCGGACTACGCCACGAACGTGGAGGGCGTGCGCTTCGTGGACATGGCCTCCTACGTGTACAAGCGGTACCT
GGCCATCTACGGCTTCGGCGTGACCTTCCGCGACCTGCGCCCGGACCCGAGTCTGGTTCGCCGGCTGCACGCGCTGA
ACACCGAGAAGATAGAGCAGATCAAGGACGCGTACTCGCGGTACCTGCAGGACGTCGCGG ACGGGAAGCTGGTGCCG
ATGGCGCCCGCGGACGAAGCCGACGCGCTGGACTCGCTGCTGGCCAACCTGACCAACCTCAACGTGCGCGAGATCAA
CGAGTACATGCGCGAGACGCTGGAGCGCAACCCCGATAACAGCCTGCTCAAGATGGCGCGCGCCGGGTACAAGGTCA
ACCCCACAGAGCTCATGTACCTGCTGGGCACCTACGGGCAGCAGCGCGTGAACGGCGCCGTCGCCGAGACCAAGATA
TACGGGCGCGTGCTCCCGTACGCGTTCCCCGACTCCGCGGACCCGGAGGCGCGCGGCTACATCATCAACTCGCTCAT
GAACGGTCTCTCCGGCTCGCAGTTCTACTTCGCGATGCTGGTGGCGCGCTCGCAGTCCACGGACATAGTCTGCGAGA
CCTCGCGCACGGGCACGCTCGCGCGCAAGGTCATCAAGAAGATGGAGGACACGGTCGTGGACGGGTACGGACAGATC
GTGAGCGGCTCGGTACTGCTCAAGTACGCGGCCAACTACGCGAAGATCCCGGGGTCCACCACCAAGCCCGTGGAGCT
GCTCTTCCCGCACGAGAGCATGACCTGGTTCCTGGAGATCAGCGCGCTCTGGACGAAGATCCGGCACGGGTTCGTGC
GCATGCACCGGCAGCGCCTGGCCACCAAGATCCTGGCGCCGTTCAACTTCCTGGTCTTCGTGAAACCGGCGCCCTCG
GAGGCGGAGGCGCTCTCCGCGCGGGACCTGTACCACATGATCCAGCGCGTGATGAACG ACGTGCGCGAGAAGTACTT
CTTCTCGCTGGCGAACGTGGACTTCATGGAGTACGTCTTCCTCACGCACCTGAACCCCTCGCGCGTGCGCATCACGC
GCGCGACCGCCGAGCTCATCTTCCGCAAGCTGTACCAGAAGCTGAACGCGCTGCTCGGCGGCGGCACGCCCGTGGGC
ATCATGTCCGCGCAGGTGCTCTGCGAGAAGTTCACGCAGCAGGCGCTCTCGAGCTTCCACACCACCGAGAAGAGCGG
CGCCGCGAAGGTGAAGCTGGGCTTCAACGAGTTCAGCAACCTCATCAGCATGAGCCGCAACCACACCGAGATAGTGG
CGCTGACCGCGCCGAGCCCGGATAAGCTGATGCCGCTGAAGGTAAACTTCGAGTTCGTGTGTCTGGGCGAGCTCGTG
CCCGAGATCGAGACCCGGCCCTCGGGACGGCCCTCCGTGCACCGCGTGGACATCACGGTGCACCGCCTGCGCATCAA
GCGCGCGCACCTGACCGAGGTCCTGGTGGACACCATCATCGAGCGCTTCGTGTCCTTCAACGTGCTCGTGAAGGAGT
GGGGCAGCGACATGACCGTGGAGGGCGACCGCGTCACGTACACGCTGCTGCTGCGCTTCGTGGAGCCGGAGCAGCTC
AACTTCCACAAGTTCATGCTGGTGCTGCCCGGCGCCGCGAACAAGGGCAAGGTGAGCAGGTTCAAGATCCCGATCAC
CGAGACCACGGTCTACGACGACTTCGACGCCGCGCGCAAGGCCTACCGCATGAACA TCGAGCTCATGAGTCTGAAGG
AGCTGGGGATATTCGACCTCGAGGACGTGAACGTGGTCCCCGGCATGTGGAACACCTTCGACATATTCGGCATCGAG
GCCGCGCGCGGGCACCTCTGCGAGAGCATGCTGGACACCTACGGCACGGGCTTCGACTACCTGTTTCCCTCCTGCGA
CCTGCTCGCGAGCCTGCTCTGCTCCGGGTACGAGCCCGAGTCCGTGAACAAGTTCAAGTTCTGGAACGCGAGCGCGC
TGAAGAAGGCCACCTTCGGCGACGGCCGCGCGCTGCTGAACGCGGCGCTGCACAACCGCACCGACGCGGTCGCGGAC
AACAGCAGCTGCCACTTCTTCAGCAAGACGCCCTGCGTGGCACGGGCTACTACAAGTACTTCGTGAACGTGGAGATG
TTCATGCGCATGGAGCGCGAGATCCAGGCGCGCCGCGCAAGATGGAGGAGATCGAGGAGGCCGCCGAGGAGGAGTTC
TAGGCGCGACAGCGCCTTACTTTGCGACC GTGTTACGACGACACGACACGGTTAGGACGGCGAGTCGCAGACGAACA
TTTTTATGAGCTGGTAGCGGAAGTTGGCGTTTTCCAGGAAGGCGCCGCGGAGGTCCCGGATCTCGTAGTAGGTTTTG
AGGAAGTACACGAAGCGCGCGGGCTGCGTCATAGTCGGGTTCTCCGCAAGCCGCTTGTGCATCACGTACCCCATGGC
GGCGGCGCCGCTGCGGTTGACGCCGGCCACGCAGTGCACGAGCGTGGGCTTCTG CTCGGCCTCGAGGCGCGCCAGCA
GCTTCACGAGCGCGGGCATGATGGAAGCGATGTTCGTCGTGTCGTCGTCTCTCAGCGGAATGTGGTACGCCGTTATC
CCCGCGGGCGTCGAGTACTTGGACATGGTCATGTTAACCAGGCACTTGAAGTCGACGCCGGAGTCCCCCCGCAGCAC
GGCGCGCGCGTCCTCGGCGCTGCCCAAGTACACGTGGTCCGTGAGCCGCGTCATGCCCGAGGGCAGGGCCAGCGGCG
GCCCCGCGCGCGTGCACCGCAGCAGGAGCCTGGCGTACCACTCGCTCTTATCGCCCATATTTATTTATATGATACAA
ATGGCAGACGTCACAACACTGACGGCCAACGGTCTGACCCTGGAGTTCGCGCGCGAGCGCGCTCTGCGCAGCCTGCG
CGCCGCGCGCACCTCCACGCTGGTGTTCTTCACGCTCACGCTCGCGGCCTCGCTGTTCGTGCTCTGGCTGCAGCTAA
CCGAGTTTCCCGTCTTCGAGGAGCTCGGCAAGTACGCGCGCATCAAGAGCGCGGTGCGGTCCTGGCGCCCGCTGGTG
GAGGCTAAGACCGAGATCGAGTCCGACCTCGGCCGGCAGAAGACCGCCGACCGGCCCGAGCTCTTCGAGTTCAGGTG
CGTGGACTTCGGCAAGTTCTACCTGCCGGTGAGGTACAGCCCCACGACCTTCCTGCCGCAAGCCGTGCGCCGCGGCG
CGGGCGATGGCTGGATGGTGCACAAGGCGGCGGCCGTGGACCTCGCCGCGCA GCAGTTCTGCGAGTCCGTGCTGCGG
CACCGCGCCAACAACGTCATCACATGCGGGTCAGAGATGATGCGGCTGGTGGGCTACAGCGGCTACTTCGAGGACGA

FIG. 28O

CCACTGGTGCGCCGCGACGTCCGGCGTGCTGACGTGAACGATCACACGATGGCCGTGACCAGCAGCCCGGCGATGAA
CCACAGCAGCCGCGAGTTCGGCAGCAGCAGCACGAGCACCAGCAGGTATGCCAGGATGAAGATGTCGACCACGTCCA
CGTCGAAGAGCCCCATGAAGGAGAAGAGCGGCGTGGTGAGGAAGTAGATGGCGCCGGGCCAGAAGCGCGCTAGCCAC
GTGGCGAGCAGCGACCACAGGGAGGGCGCGCCGCTGAGCCGCGTCTTCACCTGTATGTAGTACTCGGGGTAGACCAC
CTGCTCGGCGCCGGAGAGCACCACGCGCGCCAGAGAGAGCCGCTTCTCCAGCGTGAACACCTCGGTGAGCAGGCCGC
TGCGCAGCCCTCCCTCCTTGATGATCGCGTCGTAGAGCTTCTTCATGCCGCCGACGCTGATGATGTAGGCGTCTAGC
GAGACGTCGTATCCGCCGGGGTAGACCATGAGCTCGGGGTCGCCGGTGCCGGGGACGTTGGTGGCCAGCGCGCCGGT
CATGTAGGTCTCCTTGAGCTGCGTCATGTACCAGCCGTTCGCCTTCATCGCCTCGATGAGCGGCTTTACCATCTCGG
GCTTGCGGAAGGTCATGTCGTTGTCGACCACCAGGATGAAGTCATCGTCG GAGTACTTGGTGGGGACAGTGCCGGCC
GATATGCTCTCCCAGAGGTTGAGGTGGTGCGCCGCGCGGCGCTGCATCTCCTTCGGACACGTGGACTTGCACATGTC
CGTGAAGAAGTGCGGGTAGTCTTTGGAGTCCACGTCTTTCCATTCCACCGCCTTGAGCACGTGGTCGCCCTTGGGGT
GCGGCGCGGGAGGAGATGGCTTGGGTGCCGGCGCGGGGGCCGGCGCGGGGGCAGGTGCAGGGGCCGGTGCAGGAG AG
GGAGCAGGCGCGGGTTGAGGCTTGGGCGGGTCGTCGGCGAGGCCCACCAGGTACGGCAGCGTGGGGAACACCTCCTT
GGTCCCGCGGCCTTCGGCAACCCCGATTATGTAGGCCGTGATTTCGGGTGGATCCATTTAGTTATTAAAATTAATCA
TATACAACTCTTTTATGGCGGCTATGGATTCGGCTATCCAGTCCTTGACCGAGCCCACGATGCCCGCCAGGAACAGG
AAGAAGGCGAACTCCAGGTCCACGCGGTTCAGAGAGTCGCTGAAGTACACGAAGACGTCGCTGTCCGGGAAGAAGCT
GCGCCGGAACATGTTGTACCCGTTGACCTTGTGCGCGACGTGCTCCGCGCTCAGCAGCGTCTCGTCGAAGGGGTACG
GGTCGCTGAAGCGGAACACGTACATGGCCGGGTTCGCGTAGTAGTACTTCATGGTGTTTGTGACGAAGAGGCTCGCC
AGCGAGATGATGATCTTTTTCTTCTCGATCTCGATCTTGATGTGGTCC TCGAAGCGCTTCATGTTGTAGGCGTTGGT
GTCGTGCACGCGGATGAGCACGCGCGAGTCCGACATGATGTCCTGGAACTCCGCGCGCGCGTCGGGGCTCTCGGCGG
GCGTCTCCGCGGGCCGCGCCACCTCCGCGCACACCGTCGGCCTAGCGCGCGGCGGCGTGCGCATGGGCCGCGCCCCC
ACGCGCTGCGAAGCGAAAAACTCCACGGCGCGAGCCTCGCCCGCGTCCGCGTACACTCCACCAGGTAGTTGCG GCTG
CGCGTGGTGCGGCCGATGGTGTTCAGCCGGTGCAGCTCCGCGACCAGCCCGGGCATGATGGAGGTGTACACCTCGGT
GAGCAGCATCACGGTGTCGAAGTCCTCCTTGCCGCAGACGCGCGTCTTCACGAGGAAGTGGTGCACAGCCGTCGCGA
TAGAGAGCCGCAGCGTGGACTCGGTGACCTCAACGCTGGCGTCCTTGGTCTTCTTCGCGCTCCGCGAGGCCATGAAC
GAGACGAGGAAGTCCGCGCTGCTGTTGAGCACGATGACCAGCGCGACGATGAAGTTGAGGTTCAGCGTCTTCGCGGA
CTGGAACAGCTCGGTGGCCGACGCGTGCACGTCGAGCAGGTTCGCGGAGAGCCGCAGGAAGAACACGCCGCGCTTGA
TCTCGGCCGCGAAGCGACGTTCGTACTCCTGCCGGCGCGCGTTGATCGCGATGAGGAAGTTCAGGATGAGCCGGTTG
ATGTTGTACTTCACGGCCCAGGTCTGCGTCTTCATGATGGTGTCGAAGGACATCACGATGTTGAAGATGAAGCGCTG
GCTGTGCGAGAAGTAGCTGTAGGGCTCGCTGAGGAAGATGGACTTGTTGGTCGCGGGCACTACCACGCCCGCGCGCG
CGCCGGACGCGTCGGTGTTCAGGTCCGGGATGTTCATGCCGCAGATGCGGCAGTAGGCCATGCCGTCCTCAAAGTAC
ACGAACTCCTCCACGAACTCGTTGATCTTGGCAAAGTAGTCCACGTCCACGCGCATCGCGACCGCGAGCCG GATCTG
GTGCTCGCAGGGCGGCGACTCGAAGCGCACACCCTCGCCCCAGCCCGGCGGCTCGCGCACGACCAGCGCGGTGCGCG
AAGCCGGGCGGAACTTGGCGTCGCGCGCGTTGAGCAGCGCCGGGAAGAGGTCGCAGAGGTGCCGGCTCGAGAGGAAC
ACGTACTTGTACAGCAGCCGGCGCGCGTCCGCGGCCATGGCGTCCACGAAGGCGCGGCCCCACTCCGCGACCGCGGG
CTGCTCCTCCGCAAAGTTGTTCGGGTAGACCTTGTCCGTGGCCGCGAGGAACACCTTCTTCACGTCGAGGAAGTCGC
GGATCACGATGGGGACGCGCGCGCCGTCGAGCTCGTACATGAACACGTAGCGCAGGTTGAGCTTGCGCCGCGAGACC
GGGATGCCGATGTGCCGACACAGGTACGCGAACTCGAGGTACTTCTTCGAGAAGCGGATGCGGTCCAGGTTCTTGGA
GACGTACTGCAGCATGTTGCGCATGTTGAAGGGGATCTCGCGCA CGGCGGGCTCCGCGGCGTCGTCGAAGGCGGTGC
GCAGATCGCTGGTGCGCTGCACGACCACGGCTTCGCCGGTGGCGTCGTCGTGCACCAGCACGTTAACGCGCCGCTGC
CGGATGACCATGTCGAAGGTGTTGAAGAACATCTCGTACATGCTGTGCCGAGTGTCGTCCGCGATGCGCTCGCCCAC
CGAGAGGCTCGCGGTGGCGTCGTCGCGCACCTGCTTCTCGAACTTGTACCCGATGTAGGAGAATATCGA GATCAGCG
TGGCGTCGTCGGCGTCGGGGTTCTGCTCCATGGTCGCGAAGAGCAGGCGGATGTCGTCCTCCGTGATCGCGTCCACG
TTGTACAGGTTGACCACGAAGATGGACTTGTTCTCGGCGATGAAGTCAGTGTAGGACTTGGTGGCCGTGTTCGGGTC
GCGCATGTACGCGCGGATCTTCGGCACGATGCTCGCGAGGATGGACTCCCTGGAATCCATTTAAGGACGGCAAGGGC
GCGCGAGACCGTCTCAAAACTGAAATCGTATAAACTCTTAAAAAATTGGTATTGAAAGTACGCACCACCAAATAAAG
CGTCGAGGTCGGGCATGTCTTCGTGGCGACTCAAAATGAGCAAGTGTTCAGGTTCCAGCAGCGTCCAGACTCTCGAG
GATCTGCGTAATCGTCTTCGCTCCGAGGCCTTGGGCAACGATTTCCAAGAGCCCCGCGACGACCTCTTCCCCAGCGG
CGAGGAGTGTCTGGACATCGACGGGCCCTGCCCTTGCGATGA GGCGGAGCAGGAGATCGACCAGGAGCAGTTGCCTG
TGCCCGAAACCGTGCCCGAACCGCCGGCCAAGACTCCTAAGCGCCGACCAGTGAAGAAGGATAAGGCAGATAAGGCA
GATAAAGACAAGTCGACCAGAGGCGCAAAGAAACCGTGCCCTTCGGACGACAAGGATGACGAGCTCAAGAGCAACGA
CGTCGACAACAACGAAGAGTCCGGCGACACAGATGGCGGCGCGAGCGCCCGAAGCCCCAGCGACATC GACAACGTGG
ACGAGATGGACGACTCCGACCTCATGGTGGCGTTCTCCACCATCCTCGCAGACTTCAAGGACATCACCCAACGAGTG

FIG. 28P

AAAGCTCTTTCGTCCGTACTCACGGACGTACAGGCGGCCGGCATACGCAGGTGCTTCTCGACGCTCGGCAAGGCTCT
GACGGAGGCGGCCCACATCGCCAACACCGGAGCTAAGCCAGTCACCGCGCCTCGCAAGAAGAAGGCCGCCACCTGCA
AGAAGTAGGCGCACTAAATAGCGAGGCTCGGTATGCGGGCGCTGCACCTGTCAGACGGCAGACTTTTTTTTGACAAG
GAGCTGACGCAGCCGGTCCCCGACGACAACCCCGCGTACGCTGTCCTCGCGAAGATCCGGATCCCACCGCACCTCTC
GGATGTGGTCGTGTACGAGCAGGACCTCGAGTCCGCGCAGCAGGGCCTCATCTTCGTCGGCCGCGACGCCAAGGGCC
GAAAGCAGTACTTCTACGGGCGCGGACACGTGGAGCGGCGCACGGCCGTCCGCAACGCCGTGTTCGTGCGCGTGCAC
CGCGTCATGAACAAGATAAACGCCTTCATCGACGACCACCTCGCCTCCGGCAGGAGGCCGAGGCGCAGATGGCCGCC
TTCCTGCTCATGGAGACGAGCTTCTTCATCCGCGTCGGCAAGACGCGCAGCGCGAGAGCGGCACCGTGGGCATGCTC
ACGCTGCGCAACAAGCACCTCGCCGAGGCCGAGGGCGGTGAGGAGATCCGCGTCGCCTTCGTGGGCAAGGACCGAGT
CGCGCACGAGTTTGCCGTGCGCGAGGGGCAGCGGCTCTTCGCGGCGCTGCGTCGGCTCTGGGACCCGGGCGCGCCCG
ACAGGCTGCTGTTCGACCGGCTGAGCGAGCGCCGCGTGTACACCTTCATGCGACGCTTCGGCATCCGCGTCAAGGAC
CTGCGCACCTACGGCGTGAACTACACCTTCCTGTACAACTTCTGGTCCAACGTGCGCTCGCTGGAGCCGCGTCCCTC
CGTGAAGTCGCTCATCTGCACCTCCGTGCGGCAGACCGCCGAGACGGTGGGGCACACGCCCTCGATCTCGCGCAGCG
CCTACATGGCCACCGCGGTGCTCGAGCTCGTCAGGGACGGCGCGTTCCTGGACAGAGTCGCCGCCACCGACACGCTC
GACGACTTCGTGGACATCGTCGTGGACTATGTAAATAACTCTGAGCAGGTAAATGGATGAGGCGCTGCGCGTGGCGG
CGCGCGTCGTGGACGGGCTCCGGCCGCTGGACGTGGCCGTGTGTCTCACGCAGCTGCGCGGAGCCGCGCCCGAGCGC
CGCTTCCCGGCGCTCGACGAGTGCTCCGGCGAGGCCTTCCTGGACTTCGAGTTCGCCGGCGGGGACGTGGCGTCGCG
GTACCTCTCCGCGCACACGCGCGAGCTCCGTGCGGCGGAGCGGCGCGAGCACATGGCCGCGATCGCGCGCTGCGTCA
CCGAGGCCGACCTGGCGCTCGCAGACCGCCCCCGGGGCAAGGCGCGCGCGGCGCTGCGCGTGTGCCGCAACCGCGAG
AAAGTCGCGCGCTTGGCGAGGCTGCTGCGCGACGCCGAGAGCAGCGGCGCGGACTTCGCCTTCATACGCGCGGCCGT
GGCGTAGCAAAACGTAAAAACAACACATTCCCTAAATCGCCATGGACGCGCCAAGTCTCGACTGCATGCTCGCCGCA
CTCGCGGCGAAGGCGTCTTCGGTGGACCGAGGCGCCCCCGAGGACGAGGTGCACCACGAAGTGGAGCTCGTGCTCGT
AGACCCGCCGCTGTCCACCCTGGCCGCCACGCTGCGCCTGGCCTCGGAGACGGAGTCCTTCATCCTCTTCACGGTGA
CCGCGCTCGCCAAGGAGGAGGGCAAGCTGCGCGCGCGCGTGCCCATGTCGCGCGTCGTCGGCCTGGACGTGAAGAAC
GTGCAGCTGGTAAACGCCATCGACAGCATCGTCTGGGAGCGCAAGGCGCTCGTGGAGGAGACCGCGCTGCAGGAAGG
CTGTCTGCTGCGCCACTCCACCGAGCGGCGGCACCTCTTCGTGGACTACAAGAAGTACCTCTCGGCCATCCGCGTGG
AGCTGGTAAACCGCGTGCGCGTGCGCTCCAAAGAAGTCGTCGCGGACTTCAAGTTCAAGTACTTTCTGGGGTCCGGC
GCGCAGGCCAAGAGCTCGCTGCTGCACGCGCTCAACCACCCCAAGGTGCGGCCCTCGCCCACGCTGGAGTTCGAGGT
CGTCCCCGCGGGCGAGGCCGTGGACGAGGCCGCCGTGCTCGCGGAGCTGCGCGCCGTGGCGAAGGCGCTCTTCATGG
CGCCCACCGACGCCGTCTTCCTGGCGCCGCCGGCCGAGATGCCGGTGCGCACGCTCATGCTGCAGAAGCAGGAGATC
CCCGCGCTAGACCTCGACGGCCTCTTCGCGGTCTCCAAGACGGACGGCGTCTCTGCGAGCGTGCGCGTGGACGAGGA
CGGCGTCTTCTGCGCGTTCTCGCACCTCGCGTACACCATCCGGTACCCGCTCGCGCGCAAAGTGCAGGGCCGGTACC
GGCTCTGGTGCGAGGCCGTGCGGCCCGTGGGCGAGCGCGTGTGGTCCATGTTCGTGCTGGTCGTGGAGGAGCCTGCG
GGCGATGACCGCGTCGCGGCCGTGGCCGGCGCCGTGGAGGCGCTGCGCGGCGTGTGTGCGCGCGTCGAGTTCAAACC
CAAGCGCGTGGACGGGCCCTTCTCGGCGACCTCCGAGCTGGTGGAGCACATCAAGAGCGCGCTGCAGACGGAGCCAG
AGGGCGTGGTGCTCTTCTACGCGCGCGGAGAGAAGTCCAAGCGCGACCTCAAGGTCAAGCGCGACAACACGGTGGAC
CAGACCACGAACGTGATGTTCCGGTACATGTCCAGCGAGCCCATCGTCTTCGGCGAGGGCTCCACCTTCCTGGAGTT
CAAGCGGTACAGCAACGACCGCGGGTTCCCCAAGGAGTACGGCGCGGGGCGCATCTTCCTGCGCGAGGACGTGGTCT
ACCACAACAACATCTACTGCATCGAGTTCACGAAGACGCACCTGGAGGTGGGCCTCCGCAGCGTGGTCGTGCCCGTG
AAGTTCATCGGCGAGTTCTCGCAGGAGGGGTACCTGCTGCGGCCGCGGCTGGCCAAAACGGAGTGCTACTTCCGCAA
CCCCTCATTCTACGGGAACCAGCACTCGGTGGTGCTCGAGCACACTCGCGACCAGCTGCTCTCGGTGGGGGACGTGT
TCGACGAGAGCCGCATGGCCGCCGTCGGGCAGACGCTGGCCAACGACGCCTTCCGCCTGAACCCGGACACGCCCTAC
TTCACCAACCGACGCACGCGCGGGCCGCTGGGCGTGCTCTCCAACTACGTGAAGACGCTCATGATATCGCTGTACTG
CTCGAAGACCTTCCTGAACAACGCCGAGCGACGCAAGGTGCTGGCCGTGGACTTCGGCAACGGCGCGGACCTGGAGA
AGTACTTCTTCGGCGAGATCGCGTCCATGGTGGCCACGGACCCGGACGCGCGCGCGATCGAGCGCGCCATGGGCGCT
ACAACCGCCTCAACGCGGGGCTGAAGTCGCGCTACTACAAGTTTAACTACATCCAGGAGACCATCCGGACCTACGTG
GAGAGCATCCGCCAGGTCATGTACTTCGGGCGCTTCAACATCGTGGACTGGCAGATGGCCATCCACTACTCCTTCCA
CCCGCGGCACTTCGCCACGGTGATGCGCAACCTGCGCGAGCTCACCGCGCCCGGCTGCAAGGTGCTCATCACCACCA
TGGACGGGGACTTCCTGTCGACGCTCTCCGAGAAGACCAGCTTCGTGATCAACCGCAACCTGCAGGAGAGCGAAAAC
TTCATGTCGATCGAGCGCGTGGCCGATGACCAGGTCATGGTCTACGCGCCCTCGACCATGGCGCAGCCCATGACGGA
GTACATCGTGCGCCGCGCGGACATCGTCAAGCTCTTCGCGGACAACGGCTTCGACCTCGTGGACCACGCGAACTTCG
AGACCGTGATCCGGCGCAGCCGCCGCTTCGTCGAGGGCGTCTCGCGGCTGGAGACGCGGCCCTCCACCAAGAACTTC
TTCGAGCTCAACCGCAACGCGCTCACGGAGATGGACAGCACCGACGTGGCCGCGCTGCTAAAGATCTACGTGCTGTA

FIG. 28Q

CGTCTTCAGCAAGCGGTAGGCAGAACCAGGGCGTCGATTCCGCGCCCGCGCCGGCGCGGAAGGCGTTGAACAGCTCC
GCCAGCCAGGCTGCGGTCTCGCGCGCGTCGATCGGGCCGCCGTCGTCCGGCGGCGGCTCGCGCGCCGCGCGCAACAC
CAGCGTCTCCGCGGGCGGCAGAGGCTCCAGAGCCTCGAAGACCGCGCGGCTCGGGAACAGCGCGCGCATCATGCGCG
AGCGGTGGCCGAACACCGCCTTGACCGCGCGCAGTGCCGAGCGGTTGTCCAGCCGCAGCGCTCGGTCAAAACGATGC
ACGCGCGCGGGCGCGCCGCGGTGGTCGCGCTCCACGAGCACGTGCCGCCACGCCAGCGCCGCGCCGACGCGGTCCAG
GCTGGGCGCGAGCGCCACCAGGCTTTTCAGCTCATGTAAATCTCCGCGCATGGCC GACGGCTCCATTTACTACTGCG
GAGGAACGCACGTGGTCGCGGCCGCGCCGGGCGCCGCGCTTGTGGTGCTGGACGCGCCCGGAGCGGTAGCGGCGGCC
GCGCCCGCGGGGCAGCGCGTCTTCTTCGCCGAGTACGGCCTCGAAAAGCGGGCCAACGGCCCGATCACGGCGCGGCT
GCGACGCTCCGGGTTCCGCGGCGCCGCGAACGCCTGGGCCTCCGTGGCGGACTTCGAGGCCGGCGGCCGTCCCTCCG
CGTGGACGCTGCGCGCGGAGGAGGCTTCGCGCGTACCGCTGCCGACGGACGCGGCGCTGGTCCTGGCCTGGGGCGCG
CGCGAGGAGCCGCTGCGGGCGTGCGTGCTGGCGCGCGCGGCAGACGCAGAGGCGCCGGTGGGCGCCGCGCTCAAGGA
AGCCGCCTTCGACGCGCGGGCGCCGGCGGCCGCGCTGTTCGCGGCGCTGGGCGCGCCCGCGCTCGCGCCCCCGCTGC
GGGCGCGGCTAGTGGCGCCGCCGGGCGCGCCGCCGCGGACGCGGCTCTGCGAGAACCCGGCCATGCTGCGCGCGTTC
GCAGTGGGCTGGTTCGGCGCGCAGCTGGGCGAGGCTTCCGAAAATGAAAAGGTATTTGCCGCCTTTGATAAGGCGAG
GTCGTGTTTGGACGACCGCTGATGGCGACGCCCGCGAACGCACCCGCGCTGCTCGTCGCGGTGCTGCGACACCGCCC
GTACCGCGTGGAGTACCACCCGGACTGGGAGCCGGTCATCGAGACGCTGGTGG ACGAGTACGACGCGGTCGCGCCCT
GGCTGCTGCGCGACGCGACGAGCCCCGAGCCCGAGCGCTTCTTCGCGCAGCTGGCGAAGCCGCTGGCGGACAAGCGA
GTGTGCGTGTGCGGCATCGACCCGTACCCGCGCGGCGGCACCGGCGTGCCCTTCCAGTCCCCGGACTTCAGCAAGAA
GACCATCCGCGCGATCGCGAGCTCGGTCGCGCGCACGACCGGCACGCAGGGCTACGCGAACTACGACCTGGACGCGG
TTCCGGGCGTGCTGCCCTGGAACTACTACCTCTCCTGCCGCGAGGGCGAGACCAAGAGCCACGCGATGTACTGGGAG
CGCATCTCGCGGCTGCTGCTGCAGCACGTGGCCAAGCACGTGAGCGTGCTCTACTGCATGGGGCGCACGGACTTCCA
GAACGTGCGCGCGCGCCTGGACGTGCCGGTGACGCTGGTGGTGGGCTTCCACCCCGCGGCGCGCGACGGGCAGTTCG
CGCGCGAGCGGGCCTTCGAGGTCATCAACGCCTTATTGGAGCTCAACGGGAAGTCTCAAGTGGACTGGGCGCGAGGA
TTTTCTTTTTATAGTGAAAATTAATCCGTGGTCCTAAATGGCGGCGCCCATATGCGATAACTCTCACGTGTTCCTCC
TCAAGCGCCTGGGCGTGCCGTCTTCCTGCCGGCGCTCGGAGGACCCGCGCTTCGTGGAGATCCTGACTCCCTTCGAG
CTCGCAAACTACATCGAGCGGCACCCGGGATGCTGCCTCTTCGAGACGCTG CGCGACGAGGAGGACTGCTCCGTCGT
GCGCGTCTTCGCGGACGTGGACATGGACAGCGTGCTCGAGGAGGAGGACTTCGTCGCGGCGCTGGAGGACCTCATCG
TAGAGCTCGCGGCCTTCTTCGACCGCTTCGCGAGCGGCTCCTGCGGCACCGTGCCCGGCGAGGTCAAGCGCGCCATG
CTCGCGAACTTCTCGGTCACGCGATCCACGGCCGAGCACAAGACCAGCTTCCACCTGATCTTCACGGAGACGTACA C
CACGCTGGACACGCTGGTGGCGGCGAAGCGCCCGCTGCTGGACCTGTGCCGGCGCTCGGACAACGTGCTGCTGCGCG
CGCTGGACACGGCGTGTACCGCCGCGGCGCGACGCTGCGCGTGGTGGGCACGCGCAAGACGCCGGAGTCGAGCGCGG
TCCACTGCGACGACATCAAGGACTACCTGTTCACGTTCGTGGAGCTCTCGGACGCGAGCGTGTACTTCGAGCTCGCG
GAGCGCGAGCAGCACACGCTGAGCACCGTTTGCTGGGAGACCTCCTACATCCCCTTCGGCGACGCGATGCGGCGCGT
GTGCCAGGCGGTGGTCAACGACATCGTGAACCTCCGCGACATCACCGAGGACAACTTCCTCGACACGCCGCTGGTCA
TCGACTACGCGACGCGCTGCGCGCTGTGCAAGAAGCCCAAGCACAAGCACGCGCACCACATCACCATGGGCAACGGC
TGTCTGCGCCTGGTCAAGGGCGGGAACGCGCACAGCTGCAAGGTCAAGA TCATCCAGCTCGAGGGCAACCGGCTCTT
CACGGCCGCGCAGATCATCATCGCGTCCGAGGTCGTGAAGCTCACCGAGCGCAACGACTACATCGTGTGGCTGAACA
ACTCCTGGCGCTTCAGCGCGGAGGAGTCGCTCATCACCAAGCTCATCCTGGACGTGCGGCACTCGCTGCCCGCGGAC
TACGCCAACGACATGCTGTGTCCGCGCAAGCGCAAGGTCGTGGAAACCAACATCCGCGACATGCTCGTGGACAT CTC
CGAGACGGACACGCAGTACGACAAGCTGCCCTTCACGAACGGCGTGCTGGACCTGGCCACGGGCGAGTTCCTCACCG
GCGACCGCGCGAAGGCCTGCGTGTGCACGGTCTCCACCGGGTACGCCTTCTCGCGCGAGGAGTTCGCGGCCGCGGCG
GACTCGGAGGCCATGCGCCGGCTGGTTGGCGTCATCGACGACATCCAGCCGGACACGCCCGAGAACGCCGATAACCG
CGCGCTGTACGAGCGCGCCATGTCCAGCGCGCTCTGCGGCGCCACGAAGACGGTCATCGTCTTCTTCTACGGCGACA
CCATGACCGGCAAGTCCACGAGCAAGCGTCTGCTCATGTCCGCGCTCGGCGGACTCTTCATCGAGACCGGGCAGACC
GTGCTCACGGACGTGCTCGACAAGGGCCCGAACCCCTTCGTGGCCAACATGCACCTGCGGCGCGCGGTCTTCTGCAG
CGAGCTCCCGGACTTCGCCTGCAACAACGCGCGCAAGCTGCGCTCCGACAACTTCAAGAAGCTGACCGAGCCCTGCA
TCGTGGGCCGGCCCTGCTTCTCCAACAAGATCCACAACCGCAACCACGCCACCTTCATCATCGACACCAACTACCGC
CCGGTCTTCGACCGCGTGGACAACGCGCTCATGCGCCGCGTGGCGCTGGTGCGCTTCCGCACGCACTTCTCCTCGTC
GGCCACTCGCGCGGCCGCCGCGCACAACGTCGAGTACAGCGCGGTCAAGGAGATGGACGAGAGCCTGGACAC CAAGA
TCCAGCGCAACTACTTCCGCTACGCCTTCCTGCGCCTGCTCGTGCAGTGGTTCGGCAAGTACCACGTCCCGCAGGTC
TCGCTGGCGCCCACGCCCGACGCGGTACCCGACTTCGCCTTCCACCGCCGCGTGGCCGAGCTGGTGGTGGCCAGCAA
CGACGCGCACCGCCGCGCGATGGAGTCGCTGTCCAAGCTGGGGTACGTGCTCGTGGGCGGCAACGTGGCCATGCCCG
CGGACGCCTTCCGGCAGCGGCTGGCCGCGCACTTCAACGCGCGCGTGCACGGCGGCGACATAGACGCCTTCATGTTC

FIG. 28R

AAGCACAAGAAGGTCGTCAACGTAACGGAGGAGTACGTGGAGTACGTATTCATCGAAGATGTCGAGAATAAATAGGC
GGGCATGAACTCGGACGTGATCAAGCTCTTCGCCGGGCACGACGAGTCCGTGCCCGGCATCCTGCCGCACCAGCTCG
CGACCGTGGACTTCCTGATACGCCGCGTTCTAGACGACAACGTCA GCGTGCTTCTCTTCCACATCATGGGCTCTGGG
AAGACCGTCATCGCGCTGCTGTTCGCGATGGTGGCCTCGCGCACCAAGAAGGTGTACATCCTGGTGCCCAACGTGAA
CGTCATGAACATATTCAACTACAGCATGGTCATGGTCGCTAACCTGTTCAACGCGCCCTTCGTGGCCGAGAACATAT
TCGTGTACTCGACGACTAGTTTTTATTCGCTAAACTGCAACGACGGCGTCATAAACTACAACGGCCTCGG CAAGTAC
GAGAACTCGGTCTTCGTGGTCGACGAGGCGCACAACATCTTCGGGAACAACACCGGCGAGCTCATGATGGTGATCAA
GAACAAGACGCGCGTGCCCTTCCTGCTGCTCTCGGCCTCGCCGATCACGAACACGCCGCTCACGCTCAGCAGCATCA
TCAGCCTCATGTCCGATAAGGACGTGGACGTCGGCGACATCGTGGTGCAGGGCAAGAAGGTGTTCCAGATCCTGCTG
AACGAGCACGGCGTGCGCGTGATCCGCGAGGTGCTCAAGGGGCGCATCTCCTACTACGAGATGCCGGACACGGACAT
GCCCGAGGTGCTCTACCACGGGCGCCGCTTCCTGGACACGCGCGTGGTCTACTGCCGCATGTCGCGCCGGCAGGAGG
ACGACTACCTCACTGTGCGCCGGCTTTGCAACAACGAGATGTTCGAGAAGAACATGAACAACGTGTCCATGGCGGTG
CTGGGCCCGCTGAACCTGGTGAACAACCTGGACGTGCTCTTCCAGGCGCAGGACAAGGACCTGTACCCGAACCTGCG
CATCAGCAACGGCGTGCTCTACGGGAACGAGCTCACCAAGCTGGACATCAGCTGCAAGTTCAAGTTCTTCATCTCGA
AGGTGGGCGCCATGCGCGGGAAGCACTTCATCTACTTCTCCAACTCGACCTACGGCAGCCTGGTCATCCGCAACGTG
ATGCTCAGCAACGGGTACTCGAGTTCGGCGGCTCGCAGAGCAACAACCCGCACACCACGCCCGACGGG CGCGCCAAG
ACCTTCGCGATCGTGAGCAAGATGAAGGCCTCGCTGGAGGAGCTGCTCGAGGTGTACAACTCCGCGGAGAACAACGA
CGGCGGCGAGCTCATGTTCCTCTTCTCCTCGAACATCATGTCCGAGTCCTACACGCTCAAGGAGGTGCGGCACATCT
GGTTCATGACCATCCCCGACACCTTCTCGCAGTTCAACCAGATCCTGGGCCGCGCCGTGCGCAAGTTCTCCTACGCG
GACGTGGCCGCGCCCGTGAACGTGTACCTCATGGCGGCGGTGTACTCGGACTTCGACGAGGACATCGTCTCGCTGGA
GGACTACAGCGTGGAGGACATCAACGCGCTGCCCTTCGACGTGAAGAAGCTCTTCTACCTCAAGTTCAAGGCCAAGG
AAACCAACCGCGTGTACGCCATCCTGCAGGAGCTCTCGGACGCGTACTCCGCGCGCCCGCACCCGCAGCTCGTGGAC
GTGGTGCTGGGGGAGATCGTGCGCCAGTTCTTCGCGCGGCA CTGCCGCGTGCCCGCCGAGGACGCCGCGCTCGTGGC
CGCCGTCGAGGCCGTTCTCGGCACGCGCGAGGCAGCGGCCGAGTACATCCGCGCGATAGTGGACGGACACTTCTTCG
TGACCAACAAGACCTTCGGGAAGTGCCTGCTCTTCCGGCACGAGCGCGACATCGTGACCGTGCCCTTCGAGCTCGAG
CACGACCCCTTCGCGTGGGCGATCAACTTCCGCAAGGAGGTCAGTGTGGTGAATATATAACGGCAA ACATAAATAGA
AAGACCGTCCTCGCGCGCGATGTCGACCTTCCGGCAGACGGTGTACCTGGCGGTGACGCTGCAGCCGCACGAGCTCA
CGCTCGACTTCCGCGGCAACGTCGCGGAGGCGGTCATGCGCGAGTACCTCTACAAGGAGAAGGGCGGGCTCATGGCC
ACCGACATCGAGGTCTGCCTCGGAAACGAGATGCCGCTGGGGCGCATAGTGAACAACGCGGTTGTGGTCTCGGTGCC
CTGCAACGTGACCTTCAAGTACTACCGCGTCGGCGACACCGTGAGCGGCACGCTCAACGTCGAGGACGAGACCAACG
TCTTCGTGGACTGCGGCGACCTCATCTGCCAGCTCGGCAAGAGCTCGGGCGGCGTGACCTTCAACGAGTCCAAGTAC
TGCCTCGTGCGCAACGGAGTCGTCTACGAGCACGGCAGCCGGGTCTCGGCTGTGCTGCGCGAGGCGCGCTCCGGACG
CGAGTCCGCGTTCGTGTTCTCCGCAGTGCTGCTGGACGG CGTCCCCGCCGAGGAGAAGGACGAGAAGAAGGACGAGG
GCGAGAAGCCCGCGGAGAAGGAGACGCTTGCGAGCCCCGCCGCCAAAAACTAGCATTATTGGGCCGCGCGAACCTTC
GATAAATGCGCACGTACACGTCGCTGCTCTCGAAGCTGCTCAAGAGCAACCGGCGGCTCGGGAGCACGCGCGTCTTC
CGCGACCCGCTGCAGCACATCAGCGCGACCGCCTTTGTGCACCGGCGCATCGACCGGCACCGGC GCGTCTCCATCTG
CGCCGTGCTCACCACCACCGACGGGCTCGTGGTCGCGTGCCGGCGCCGGTACTCCTTTTTGTCCTCCGAGCTCGCGG
AGACGCGCTCGCCCGCGCGGCGCGTGCTGCTCGCAACCAAGCACGCGGACGCTCTCGCGCGCCTCGGCGCCGCGCGC
CCGCGCGACGACGTCATGTTTCCGGGCGGCGCGCCGCTGTCCGGGGAGTCGCCGCTGGCGTGCGTGCTGCGCGAGGT
CGAGGAGGAGACCGGGCTGCGCGGCGACCAGGTCAGCGTGGACGAGCGGCTGTTCGTGCACGCCTTCATCGACGACC
TGGTCTCGGGCCGCGACTTCGACGCGATCATCTTCACGGGCGCAGTCGCGCTTTCGAGCGCGGAGGTGGCGAAGCAG
TTCCGGCCCAACGACGAGGTCAAGGGGCTGGTTTTCCTGCACCCCGAGGACGCGGAGGGCGTGGGCGTGATGGCGCG
GCTGGCGGCGTTCGCGCGCTGCGCGGCGCGCCTGCGC TGCTGGGGCGCGGCCGTCACGCGATAGAGGCGGGGTCCAC
CACGTACACGAGGCGCCCGCCGCTCACGCGCACGGTGGGCGGGTCGCCCAGCGCGGTCAGGAAGTTCCCGTCGTCGT
CGAAGAGGCGCCCGCCGCGCTCGAGGAAGCCCTTGCGCACCGTGACCAGCGCCGTGGAGGTGGAGTACCACACGCTC
TGCCCGTCCGCGAGCCGCGCCGCGCGCGCGGGCCCGCGCGCGTCCGCCGGGCGCGCCACCAG CGCGGACCAGCCGGA
GTCGTCCTCCAGCGGCGCGAAGTCCGTGAAGGCCTCGCGCACCCACTCCAGCGAGCAGCGCTTGAGCACGCGGAAGA
GCTGCGTGAACTGCCGGGACTTGTCGCGGATGAGGGCCAGCAGGTCCTCGTCCACGGTGGCGGCGCCGGAGTCCTGG
CGCGCGACCACGAAGTGCACGTTCACGTAGCGGCGGTCGGGCGGCGTCATCTCGTGGCTGTTCAGGCGCACCGCGCG
GCCCACGATCTGGCGCAGCGAGGCCTCGTTCCAGGTCATGTCCAGGATGAAGATGTCGTTGATGGAGAGGAAGCTGA
GGCCCTCGGAGCCGCTCAGCGAGAACACGCAGACCTTGATCTTCTCGCCGTCGGTGTTGTCGCAGGCGTTGAAGGCG
TCCACGAGCTTGGCGCGCGTGTCGCGCGTGCGCGAGGAGAACTCCACGCTGGAGACGCCGAAGGCGCGGAAGTAGAG
CAGCAGCATCTCGATGCCGGTCACGTTGACGAAGG GCTCGAAGACCAGACACTTGCCCGGCGAGGCCAGGATGCGCA

FIG. 28S

GGCAGACCTCGGTGTACTTGCAGCTGCGCTCGCGCAGCTCGCGAGCAGCGAGACGTCCGCGGAGGTCATGCGGTCGC
CGCTGACGGGCGCGCCGCTGCGGAAGAGCCGCATGTCCGAGAAGACGCGGTCCTTGACGGCGCGCGCGAAGTCCAGG
AAGAGCGCGGCCACGGCCTCGTCGTACTCCTGCTTGGAGAGCACGGACTTGTCGGGCGCGTCCTCGAAGGCGAAGGT
GGCCGCGATGCGCCGGTACACGCGGAATACCGCGGCGCCGGACTTGCGCTCCATGGCGGCCGCGCGGCGGTAGGCCT
CGGTCTGCTTCGCGGTCATGTCCACGTACATCATGCGCACGCGCTTGCGCGCGAAGGCGGCGGAGCCGTCGACGTCG
TCGAAGATGGAGGCCTCGTTGGTGACTAAGTACGAGCACAGGCCGCCGAGCTTGTCCACGAGGTCCTCGGGGTTCGC
GAGCGCGCCGCCGTTGAAGAGCGGCGTCTGCCCGACCACGCCGGGGCGCAGCAGGTTCACGGCCATGGAGAACTCCT
TGACGCTGTTCACCACCGGCGTGGCCGTGAGGCAGAGCAGCTTCCCGCGGCCCATGGGGATGTTCTTCGCGAGGTAG
TTGTACACCGTGCGCGCGGGCCGCTGGCGCCCGTCCTCCTTGGTCAGCGACATCGAGATGAAGTTGTGGAACTCGTC
GATGACCACGCAGACGCGGCTGCTCGACGAGGCGGTCTTCATCAGCGTGAAGAAGCGGTGGTGGAAGCGCGGGTCGT
CGTAGTTGATGAAGGTGCACCCGGGCACGGCCTCGGGCGCGAAGCGCATCATCGTCGAGGTCCAGGGCTGCTCCACG
AGCGCCTTCTTCACGAGCACGACCACCGTCCAGTCCGTGAAGACGTCGCGCAGGTGCTTGAGCACGTACACCGCGGT
CACGGTCTTGCCCACGCCCGTCTCGTGGAAGAGCAGCAGCGAGTGCATGCTGTCCAGGCCCAGGAACACGCGCGCCA
CGAAGAGCTGGTAGTCCTTGAGGCGCACGGACTCCTCCACGCCCTGCATCTCGGAGGGCATGTGCGCGGTGCGCCGC
AGCGCGTAGTCGATGTAGGCCGCGTGCGCGCTGGTCATGGCGACGGTCGGCGCTCCTTTTACGGGGTCTGTCGTCTA
TCTATTGTCGGCGCGGGTCTGATTTAGGGGCAGTAGTTACAAAAACGTTTCCGCTGCTCGGCGCGGCGTTTGGAGGA
GCGGTTGCGGCCGCGGCGGCGCAGCCGCGCGCGGCGCGTCTTCGTGGTGCGGTGGCCGAACCAGCGCCGGTGCATGA
CCGGGTGCGCGACCGCGGCCGCGCGATCCGCGCTCATGCAGGTTGCGTAGGTGCGGCACATGCTGCGCAGCACGCGC
CGCGTGCGCCGCTCCACGGCGTCGAGCCGCCTCGCGACGATGGGAAAGAGCCGGCGCCAGCCGCGCACGGCGAAGAG
CGGGCGCTCGCAGACCGGGCGCGCGAGCGCGTGGTAGGCGCCCAGCAGCCGCGGGTCCAGCGAGCGCACGTAGGTCT
CCACGAAGCCGTTGCCGAAGACGATGGCCTGCGCGCAGAGCGGGTTCGTCATCTCCCTCTTGGAGGCGATGGCGTCG
CCCACGAAGGCGCGCACGCCGCAGTGCCGCAGCACCAGGCGCCGCCGCGGGAAGTGCAGGTGCGGGCCGAGCGCCGC
GCGGGCGGCGGGGATGTGCAGCCGCGGAGAAAAACGCGCGCGTCCCGCCATGGCATCGAAGCGCTCCGTCTGTTTTC
AGTTATAGCGCCGCGGGCGGCTACTGCAGCAGCAGCTTGAGCTTGCGCTGACTCTCGTTCTCGATGCTCTTGGACTC
GGAGGTCATGCTCTCGTAGAGCAGCGAGTGCGTGACGTAGAGCGCCTCGTACACGCGGCTGGCGAAGGCCACGAAGC
GGTCCACGAACTCGCTCTCTACGGGGTCCTTGAGCACGCGGAAGGGCACGGCCAGCGCGTCGCGCCAGGCGGCGGCC
TTGGTGCGCTCGCGCACGTGCGCCACGAAGGCGGCGATGGCCGCGCGCCGCGGCTCGCTGGCGACCATGACGGCGCT
GTCCTTGAGCCAGCTGTCGCTCACGCACTTGAAGAGGCGCACGGTGCCGAAGAGGCTGCAGTACACGCGCAGCGCGT
GCACCACGTCGGTGCCGAAGAGCGTGGGCAGCTTGAGCACCACGAAGCGCTCCTGCGTGATCTCGAGCAGCGGGCGC
ATCACCTCGAAGGTGATCGCGTGGTAGTCGGCCACGTAGAGGTTGTTCTCGGTGAGGTGGTTGTTGGAGCGGATGGC
GCCGCGCTCCTTGCGGTAGAGCCGGTTGCGCGCGCTGAGGTCGAGCACGACCGCGTCGGCCTTGCCGCGCGCTCTGG
AGCGCACGCTGGTGATGCCGTGCGCCTCGAGCACCTTCTCGACGTCGCGCTCGTCGATCATGAGGTCGTGCGTGTAC
AGACTCAGCATCTCCGTGGGCATGCGGTTGATGTCGTTCACCCGCGAGCACTGCAGGAAGTAGTTGGTCCCGTAGGC
CAGGCTGGGCAGGTGCCCGACGCCGAGCTGCAGGTCCAGCGCGGGCGTCGAGTCGAAGGTGGGCAGCGTCACGCTGA
GCCCCTCGCGGATGCTGCGGCGCACGGCCTCCACCGCGTCCATGGCCGATTTATTGGACGCACAGTCTGTTTTCATT
TCGCGGCTACTGCGCAGTCACCTTCTCGGCCACGATCCCCGCGTCGTAGCTGAGCCGGTACACCTCGTTGCACACCA
CGACCATCTGCCGCGGCACGTACATGAGCGGGTTGTGCGCCTCCATGTGCGCGGTGGTCACGCGCACCGCCAGCTTG
TCCTTGCCCCTGGAGACGTTGGAGTTCAGCGCGGTGGGCGAGAAGAAGGTGCTGGGCGTAAAGTTGAACTGCAGCGT
GCGCACGCCGGGCGTCTTGCCGAGGATCTCGCCGAAGACGCGCGAGACTGCGCTGTTTCCGAGTACAGCACCTCGTT
GCCGAAGCGCACGTCCATGCGCGCGATGACGTCGATCTTGTTCTTGAAGTCCCCCTTGAGGAAGGGGTCGGCCACGA
AGAGGTCCTTGGCGCGCGCCTCCGGCGAGCGGTTGTCGCCGTTGTACACGTTGCGCTGGCAGGTCCACACGCCCACG
GGCACGGAGGCGTCGCCGATGTTCACGGAGTGGATGGCGGTCGTGAAGCGGATGCGGGAGGTCGCGCGGCTGTAGGC
CCCCGTGATGGCGGAGAACTTCTTGGACATGTTGTACACGACGGAGTTCTTCCTGGTGGCGAACACTAGGATGTTCG
TGTGCAGGAACACGCGCATGCCCACGGGCACGTCGTCGATGCGCACGAAGACGTCGGTGTCCTGGATGGACACGACG
CCCGACGGGGGCACCTCGACTATCTCCGCGGTCTCGGGGAAGCCCTCGGGGTAGCAGTTCGAGACGATCACCATGTC
CTCCAGCAGGCGCTCCACGAAGGCCATCACGAAGTCGCCCTCGGACTGCTGGAAGCCGGGGTACGATATGAAGCGGT
TGTTGGCGTCGCTGAGCACGGGCTTCATGTACACGGACAGGGAGGTGCACGCGTGCACGTCCGTGATCACCGCGGTG
GTGTGGTTGATCTGCTCCACGCGCCGCCGCGGCATCTCGATGAAGGCCGGGCGCGGGCACAGGTTCTTGACCATGTA
GCCGATGAAGCTCAGCTCCATGGAGTAGGGGAACTCCTTGGCGAGCTTGGCGGCGTCGAAGGTCTCGTCGTAGACCA
TGACGCAGGCGACGGGGTTCAGCGTGACCGTGACCGTGACCTTGCTGTCGCTGAGCTTGAGCGTGCTGAAGGTCTTG
TCCGCGTCAAAGGGCGTCTTGATGTAGGCGTGCACGCAGGCGGCCTCCTTGATGACGTCGTTGGGCGAGCTCCCGGT
GGAGAGGTCGTTGAGCTCGCGCGAGAAGCCCGAGAGCTCCATCACGCGCTCGTTGTCCAGGCAGGAGTCGAACAGCT
CCTCGCCGGAGGTCTCCCAGATGGTGTCCGCGGCGGAGTTCACGGCCACGTGGCGGATGAGCTTGTACGCGATGTAG

FIG. 28T

GGCACGTAGCACATCTTGCCCACGCCCTTTATCTCGGGCAGGTCCACGCTCAGCACGAAGTTGTTCATGGCCGAGAT
GTACTTGTCGCGGATCTCGAAGGTCACGGTGACCGCGTCGCTGGTGGTGTCCACCACGCCCTGCGTGGTGATGTACT
GCGGCATGTACACCGTGGGCGCGCGGTGGTCCGTGGCGAACACGCTGGCGCGCCGCACGGCGTCGTCGCCGCCCA CC
AGGCTCACCACGGAGTTATTCATTTATTCCCTGGGAAAACCAGTTAAATAAGGCTCTTCAGAGCCATGCGCACCGTC
CGGCCGTCGGGCTCCAGGTAGCAGCGCCCGTAGACGCCCTCCGTGGCGCGCGTCTCGTTGATGAGCGCGCGCACGCG
GTCGGGGTCCGCGTACATCTCCAGCGGCAGCAGCTCGATCTTGGGCTCCTCGCGCAGCGCGACGAGGTGCCGGATGG
AGCCCGCGAAGGAGTCGCGGCACAGCCGCGAGCAGAACTCGCCCACGGCGCCGCCGTCGAGCGTCTCCACGGCCAGC
GCGGCCGTGCCCACGCGCTGACGGCAGAACCAGCACGTGCCGTCCGCGGCGCGCAGCGCCAGCCGCTCCGCGGACAC
CGTGTTGAAGTACTTCGGCAGCACGTACTCGATGCGGCACGCCGCCGGCGGCGCGCAGGCCGACGCCCGCGGCGCGG
ATATGTCCACCCGCGAGAGCGCGATGCGCTTCATGGGCGGCGGTGGAT GCTATTTATGTCGCCCGCGGCTTTTCAAA
GGTCGAGCGAGCACGCCGCGAAGCGCGCGGGCGAGAACACGTACTCGTGGCCGAACTCCGGGATCTGCGCGGCGCGC
TTGCGCGCGCGCATGTGCGCGAGGAAGTTCTCCCAGGTGAGCTGGTTGCTGTTGTTCTTCGCGTAGTTCTTCACGGT
CTGCGGACGCAGGTTGCGCGTCACGCCCGTGACCTCGAAGATCTTGTCCAGGAAGAAGGAGTAGTTGATGGTT TTGG
TGGGCGTGATCTCCTGGCAGAAGAAGACCAGCTGCTTGAATATCTCGATGACCTCGTTGATCTTCTCGGTGCTGAGG
TCCAGCTTCTCGTTTTTGACCTGGTTGATGATCTCGAAGACCAGCTTGTAGTCCTTCTTGTTGATCATCTCGCTGTC
CTTGAGGAAGCTGGAGACGTAGTTGGCGTCCACGTCCTCGGGCCGGATCTGGTGCCGGTCCATCATCGCGCGCAGGT
CGCGGATGACCTCCTCCGAGCACTGCTTGGAGAGCAGCCGCCGGAGCACGTTCCGCAGGTGGATGAGCTTGTTCGAC
ACGTGGAAGTTGGACCTCTTCTGCACGCGGATGCCCATGGGAAACACGGTCTCGCAGAACAGGCAGAACTCGTAGTC
CGCGTCGGACACGAGCCCGTTGCGGCGGCAGCCGCCGCACATGCGCAGGTTCATGCTTGCTCCAGCCCCAGCACGCG
CAGGATCTCGCGGTCCAGCACTTTAGTGTCCAGCGTGCGGGTTCTA CAGAACTGGAGGAAGCCCGCGAGCGCGCGCG
CGCGCCCTGGCTGCGAGAGCAGCAGCATGCGCGCGTTCCCGGGGTCCTCGTTGATGAAGCGCGTGAGGTTCAGCGAG
CACCGCGTGCAGCGCCGCGGCGGGTCGAGCTCGACCGAGTACGCCGCGAACCAGACGTTGTCGCCCATGTATTATTT
ATTAACACAGAACGTCGCACATGTTGCGCGAGGACATGTACGGGTCGTACTCCTGCCCGTAGATGAGGATG GTGCAG
TACCGCGAGATCATGAGCATGGCCTCCTCCATGGTGAGCAGGTCGTCCTCGAACATGGCCTTGTGCTGCATGTGCTG
GCTCTGCTTGGCGGCCATCGCGGCCGCGCCGTCGCCGCGCAGCCACTCGTTCAGACACTGGCCGTCGCCGGCGTCCT
GCGCGAAGGTGTTGCGCATGGCGCGCATGAGCCTGGCTTCCCTGGCCGAGCGGCTGAGCACGGTCATGGGGTCGTAG
AGCCAGGGGCCTGCGTCCGTGAACAGGATGGTGCAGTACCCGTTGGCGAAGGCGTCCGCGCCGCTGCAGTTGTCGAT
GCCGTCGCCGACCCTGTAGCACACCGCGGAGACCAGCCGGTACATGATGCCGTTGAGCATCATGTCCTGCGACACCT
CGATGGGAATGTCGCTGATCACGGGCCGCATGTTCGTGAAGCAGTCGCCCGTGCTGGCCATGCCCCCGCGCCGGTTC
ACCAGGAACACCAGCACGCCGTTCGTGATCACGGGCGCGCGGTC GCGCTCGTAGAGGTAGCCGCTCGCCGCGCACAC
GGCGGACGCCACGTCCGTGCGAGAGACCGCGCCCATGTTCTGGGCGGGCATGTACAGCACTCGCCCGGCCTCCGCGG
TGCACGAGAAGGGCTGCTCCCCGCCCACGTGGATGGGCGCCGTCGATGTCGTGATCATCTTGCTGGAGTCCACCACC
AGGTAGGGCACCGTGTGCATGGCCATGTCGCCCATGCCCCCGATCCCCGTTCCGAACGACGGCCGCGAC ACGCTCAC
GAGCGTCGGCTTGAACGAGACTATGGAGAAGATGGAGGCCAAAATCTGCTCCTCGTCGGTCATGATGGAGGCGCACG
AGGGGTGGATGATCTTCATTAGGGCGTTGTCGATGGACTCGTCGCTCTCGCAGTAGAAGACGCCCATGCGGAGGTTC
AGGATGCACCGCCGCAGGTTGGTGTGCAGCACCGCGCGCTGGATCTCCATGGACACGGAGTCGCCGACGCCGGGCAT
CACGATGGGCGTTTCCTCGGTGAGCTTGTTCACCAGCAGCTGGTAGTTGTTGGGTCGCACGCGGCTGTTGTGGTGGA
GCTGCGCCAGGAGCGAGAGGCTGTCCCCGTTGACGAACGCGGACTCGATGGCCGGCAGCTTTACGCCGAACAGCGCC
ATGGCGATGGGGTGCACGAAGCCCACGGAGTCGGACGACTTGAACGAGAAGAGCAGGTCGCCCGAGGAGCTCATGTC
TTTGAAGTGCACGGACTGGAACTGCGTGGCGGAGAGCAAGTT CTGGTAGCTGGACATGCTCTGCAGGTCGTCGATCT
CCTTCATCTGCTTGTTTACGCGGGTCGAGTTCCTCCCGTAGATGATCACCAGCGGGTGCGTCTGGCTCACGGATAGC
CCCGAGTCCGTCATGGCGGCGCGCACGCTGTTCAGCAGATCGAACAGCTCCGACCGGTCTCTGTTCTGGATCCCGAC
CTTTGCCATCACAGACATGAGCTCCTGGATGGTCATGTTCTTGTGGTCTCGGCGCGTGGACCGCAGG TAGTCGGCGA
TCATCTCGCCTTCCTTACGGATCTTCATCTGCCAGTCGTGCATGGAGGTCATGCGGTCCACAGGCATGAGCACGCTG
TCGGAGGACGACTGCGCGGCGCTGCCGGACTGGCGCGAGCCAGGGCGCGCGGACGACGGGCGCGCGGAGCTGCCGCG
GCTGGAGGAGGACCTGGACCTCCGCGAGGATCTTCGCTGCGAAGAGCTGCGCACGGGCCGCTGGGCGCGCGCCCCGG
CGGAAACCATGTCCTCGCGGTTTATGCTTAGGAGCGAGCTGCAGACCGCGCACGACAGCGACTGTTTTGGAATGTGG
ATGTGGTCGCACTCCAGTGACATGCCCGCATTGTCGTAGCCCGGGACCAAGTCGAACTTTGCGTTAAAAAAATCTGA
TGCGCACGCGGGCGATTCCATTTATACCGGGAGTTTTTATGAGGTGCCGGTATTATCCACGCGATCTCGCAGTGTGC
TGGGAGTATCTCGCGTAGCCGCCCCCGTGAGCAAACGACG CAAGTCGTTGATGGCCGACTGTGTTACGGACTTCGCC
GTCTCGATGTCGCGCGTAAGGCTGAGCGACTCGGCGTTGAGGTCGCGCACGCTGTCCGCGATGTCGGCCAGCTCCTT
TTTGATGAAATCCTTATCATTATCGGCGTTGATGACTTTGTCCGGCACTCTAGACTCTAGAACCGGTGACGCGGCGG
GCGCCTTGATCGTCGGGCAGCTGGACGCCGGGTACTGGGGCGGCGGCAATGATTGCTGTAGGAAG ACGGGCTTAGCG

FIG. 28U

GCAGGCGCCGGTTTTGTCGGCAAGGGCGGCGCCGGCGGGCACTGTCGTGTAGACGGCGGGCACGCCGGCGCGGGGCA
CGCCGCCGGTGGCGGACATGTCGGCGCAGTTGCGGGTGGACACGCGGGCGCGGGCGCCGGCGCGGGGCACGGCGCGG
CAGGCGCAGGGCACGCGGGAGCCGGAGCTGGAGCCGGGCACGGCGCGGCAGGCGCAGGGCACGCGGGAGCCGGGCAC
GCCGGCGCGGGAGGACATGCCGGCGCAGCGGCAGGACAGACCACCGCTGTCGCGGAGCACGCGGCAACCGGCGTGGA
GCACGCGGCGGGCATTACGTTCAGAGGCGTCGACTGGACCTTGGCACCACGGGGCAGTAGCGATGGCGCTAGGGGCG
ACTGTCCGGTGGTTGGACGCTGCATGCAAGCAATCGCAGATTTCAGACGGGACTGGTAATACCTGCCCGCTTCCTTC
ACCGTGTACTTGTCGACGGAGTCTACCTCCTCATCGGGAGGACATGGCTGCTCCGGTGCGGGAATGACTGCTTGAGG
ACACTTGGTGAACAGACTGGAGCTGGTCTCCGCTAGCACCAGTTTAGACTTGGCCAAGTCGGAGGCAAACTTTCTTC
TGAGATCCATTTAAGCCTTCAAAATTGAACGTGTACGCCGACCGCTAAATGGAAGAATCGGTGGCCGTCGAGTACGC
GGACGAGGACGAGGATGAATTGAGGAGTACGAGGAGGAGGACGAGGACGAGGAGGAAGAGTCT GCCGAGGGCGCCGC
CGCCTCCTCGGTCCGACGTAGCGCTCTCTGCCGCCGAGAAGCTGGTGGCCTCGGAGGTCCCGGACGACGCGGCTGCC
GCGGACACCAACGTGCGTCAACGCGTCACCGCGCGCGTGGAGGAGCTTAAGGCGCGCTACACACGGCGGATGAGTCT
ATTTGAGCTCACCGGAATTGTAGCAGAGAGTTTCAATCTTCTGTGTCGCGGGCGGCTGCCGCTCGTGGCGGACGCCG
CAGACCCGGCGCTCGACAACGAGCTCAAAGTGGTGGTTCGGGAGCTCGAGGAGGGCGTCTGCCCCATCGTCATCGAG
AAAAACGGCGAGTTCCTCTCGCCGGGCGACTTCGACCCCGAGTGCCTGCGCTACCACCTGACGTACATGACCGACCT
CTGGAAGTCCCAGGGGCGCATGTAGCCGCGGCTACTCCGACTCGGCGGCCTCCGCGATTTTTCTTTTATCATGTCC
AGCAGCTCGCGCACCACGATGGGGCGGCCGCAGTAC GTGATGCCGTTTTCGGATATCACGCTCTGCGCGATGTCCAC
CAGCGAGCCCTCGCGCTCCCAGTACTCGCGCGCGAGCACCTCCTTGTACAACGCGCGGTGGTTGGCCACGTACCGCA
CCAGCGTCTGGATGTTCTTCACGCCCACGCTCTTGAGGTCCTGCGGCGAGAACTTCTCGCGCAGCGACACGAAGACG
TCCCGGACGAGCTTGCCGATCTCCACGTTGGTCTTGAACTCGTTGTACAGCACCACGTAGA GCTTGCACACGACCGT
GGCGAACTTCGCGGGCTTGAGATCCTTGTTCTGGAAGACCAGCATGCTGCTCATCACCTTCTTCATGAAGGCCAGGT
ACTTCGCGCGGTCGCCCTCGACGCTCACGCTCCCGACCTCGAGATCGGACACGCAGCGGATTCCGTGCTCCGCGCTC
TCCGCGGAGACGCGCAGCAGCTCCTGGTACTCCTTGAGCTTCTGCTTGTCCGTCATCAGCGAGTTGTCGAATACCGC
CACCAGCTTGAGCACGTAGTTCTCGTCCGAGAAGACCTTGTTCAGACACTTCACCAGGAAGCTGTAGTGGCTCTGCA
GGATCTTCATGACCGCGTTGGCTCCGCTGGCTCCGCGGACGTGCGATATCATCTCCATGATCTTCTTGGAGTCGTCG
ATGATCTCCTCGGTGTCGTTTCGCATGTTGCGGTACATCGCGTTCAGCGAGACCAGCGTCTGCGCGGCCAGGAGCAC
GTCGCGGAACACGCGCGCGAACTCGCGCTTCTCCTCCGCGTCGGCGATGCTGTTGTACACGGACTTCGCCACCGCGT
TCGACTTCAGGAACCAGAAGGAGAGCGCCTGGTAATTGAAGTGCTTCATTAGCGCCAGCACGTCCGCCTCGCTCATT
TCCGGCGCAATGGGGCACACCGAGCTTTCGAGCACGGGCACCATGCTGACGAGCGTGTCCACGTCCGTGTCGAAGTC
CAGGCAGTCCACGCAGAGCCCGGTGCCGCGGCTCAGGTGATCGCGGCTGATGTTGTAGA AGCGCTCGTAGCAGGTGC
GGAGGCGGTCCATGTCGGCTGCGTTTTAGGGAGACACACACTCTTGAATTATGGCTGCGGGTAGAACTCCTGCAGCA
GCGCCGGCGCACGCGCGGAGTCCGGCTCCACTCCCAGCTTCAGCGCGCAGTTCACGGACCAGGTCTTCATGAAGCGG
TCGGGCGCGTCCGTGACCACGTGCCGGAAGAGCTTCGCGAAGTGGCGGCTCACGGCGTTGGGCACGGTCGCGTTGCG
CACGAAGGCCGTGAAGCGCGAGGTCAGCTTCGGCGCGAAGCGCTTGCCGTCCACGAAGAAGCCAGAGGTGGTGAGCG
AGAGCCCGTTCTCCTCGCGCACCACGCGTCGCGCGGCCTTGTGCGGAAACATGCTCGCGAGGCGCCCGCTCGCGTCC
TGGTCTAGGTGGATGGCGTCCGTGGCCGCGTCCTTGCGGATGCGCACCACGTCGTGCACGATCTCCTGGATGAGGAT
GCGCGTGGCTGCGGTCTCCGTCAGCCGCATGGGGAAGTAGACCATGTCCCCGGAGATGAGCACGTTCCCGCTAGCGT
TTACGTAGCTCACTATCTCGGACACGGTGCGCAGACGCACGATCGCGCCTTCGCAGCAGTGCACCACGTAGTACCCG
GCGGTGGCGCGCAGGCGCTTGTTGTCCGCCTCGAAGTCCGCCTCCAACCCCTCGTTGAAGTACTTGTCGAATATGAT
GGGCAGGAAGGATAGTTTTGACTCGGTGACCACCTTCCCGAAGTTGAGGATGTACGG GTTCAGCGCGCTGCGGTCGA
CCTCTTCGTCGTACACGCAGGACTTGAAGGTGTCGGTGTGCGCCTGGCTGCGCAGGAAGCAGCACGGAATGCAGATG
CGCTGCAGGCGGTGGAAGATGGAGAGGAAGCCCACGCTGTTGTAGCGCCCGTCGGGGTCCATGCACGAAAACATGAC
GCCGTTTCCGTTCACGAAGACCTCGCGCGTCTCGGACTTGAAGAAGTTGTTGCTGACCTTGGCCATGTCCGCGTCCA
GCGACTGCACGATCACGGGCTTGCGGTTCTTGGTCTTGGTGTTCTGGCAGATGCGCGACCAGTACACGGTCTCCACC
TTGGTGAAGTCCGAGGACTGCTTCACGTTGTTGAACATCACGCTGATGGCCACGATCAAGAACGTGAAGTACTTCTC
GATGTTCGGGATGTAGTTCTTGACCTTCACGGACACGTGCGACTTCGCGAGGATGATCGAGATGCGCTTGTCCGTGG
AGAGCAGGATGTTGTTGGTCGCCGTCTCCACGAAGATGAAGCTCGTTTCCATGTCCAGCTTCATCTTAGACGTGATG
GTCGTGTTCAGCGACACCTTGTAGGTGATGTCGCCCTTGCGCGGTCCATCTTTACGTCCATGCTCTCGATGAGCTTC
GTGAACAGACTCACGTCGTTCACCGTGAGCGTCTCCGTCGCTCGAGATGACCAGGTCGCCTTCCGGGCCCCACACCG
AGAGGTTCAGCGGCTCGTCCACCAGCAGGAAGCGCGTCCCCGTCATCGACACGAA GAAGTCGTCCGTCTTCGAGAGC
AGGATGTCGAAGTCGCCCACCTCCGCTCGCTTGTCCGGCGACTGCTGCGCGATCGCGCGGAGCCCGGACTCGCGCAG
GTTCGTGCGGAAGATGTTGTTGAACTTGGTCTCCACGTTCATGTTTAGGTCGAGGTTCGCGAACTCGCGGATGAGCC
GCTCCTCGAACTTGAGGATGGAGTCGTTGGGCTCCTCGAAGGAGCCGAACTCCGGCGCGGAGGTGTCCGCCGCGCGC

FIG. 28V

GCCACCCAGACCACCAGGAAGTTGCACGCGTCCGCGTACGCGTTGTAGAGGATGCCGTCCGTGCGGATGAGCGTTTT
CTTTTGCGTGGGCGAGAACGGGTTGAAGATGGTGTTGTCCACGTAGCTGTACTCCAGGTTGTTCTTGTGCGAGTACA
CGATGATCTCGTCCTGCAGGCCCAGCAGGCTCCCCAAGTACCCCTTGAGCTGCCGCACGCGCATGGTCAGCAAGATG
TGTCTGCGCACGTGCTCGGGGTCCTTCT GGATGTACTGCTTCGCGAAGAAGTAGATCGGCGAGGCCTCGTCCACGGA
GTCGTACAGCGACAGGTACAGCACGCGCTCGATCTCCTGGTGGCGCCCCACCAGCACCACCAGCTGCGGCGCGACGG
TGTAGAGCATGGTCGCGCGGGCGTATTTATAGCCGGCGTTAAACTGAAATAAAATACGCGGGTCGCGAGGCAGCGCC
ATGTTCCAGCCGGTGCCCGACATGGCCGCCGAGGCCGACATCGACCTCGGCGA CGTCAGCGTGGACGCGACGCGCGC
GGGCGCGCGCGAGAAGACCGTCTTCTTCGCGCGCAACAAGCGCATGTACCCGCACCGCAGCAAGGACGAGGAGCGCA
AGCTGTCGCTGGGCTTCTTCTTGCAGCGGCTGGACTTCCTCACGTCGCGCGAGGTCAACCTGCAGTTCCGGTCGCTG
GACGCGCTGCGCACCGAGAACGTCATGAAGAAGAACAACGTGCTCGTGGCGCCGTACATCCTCATCGCGACGCTCGC
GGGGCGCGGCTTCCGCATGACGGAGACCATGGTCGAGCTCTACTTCCCCGAGCTGTACCGCGAGACCAGCAAGCGCT
TCCGCTTCTGCGCGCAGATAAAGGTCATCCAGGACTTCCTGGGGTTCGCCCACGACAGCTACCACACTTACGACTTC
GAGACGTACTTCGCGTTCGTGGCGCTGGTGCTGCGCGGCGCGGACTCCGCGGCCGAGGCCTTCGACGTCCGCGCCGA
GAGCGGGCTTGTGCGCAGCCTCACCGAGATCACGTACCGGCTCTACGTGATGCAGCTGCGCTCCGACGCCGCGCAGT
GGAGCGTGAGCACCGGCGCCGTAGTCTCGCAGGCGGTGAACACCGTGCTGTCGGTCGTCGGCGACCTTGCCGCGCGC
GCGGAGGCCGAGCGGCTCACGCCCGTGTGCGACCTCGCGCGCGAGAACCCGCTCTCGCTCGAAGACCTGCGCAAGTA
CGGCCCGCGGCTGCGCTCGCTGCTCACGACCATGGCGCGCGCGCGATCCTT CAAGACGAACCGGCGGGACAAGGACG
CGCTGTCCCGGTTCTGCCGACTGACGGCGGGCCCTAGCCCGTCTGCGTGCCGCGCGTCGCCATAGGCGTCGGCGCGC
GCTCGCCGCCGGAACACTCGGGGTCGCTGAACATGTAGATGAGCGCGACGCCTAGCAGCAGGTACATGATCATGCTG
ATCACGGTTTTGAACACGACGGCGGCGAACGTGTTGGACCGCAGTCGGTGCTCGCAGAAGTGCATGAACAGGTGCC G
CATGAGGTCGATGGCCCCGTTGGCCACCTGGAAAAGGGCGAGGCCGCCGATGGACTTGATCACCGTCACGTAGCACG
GCCGCATTCCGACGACGCTATTTACTCACTGTCAAAAGAAACGGCGCCATCCGACCGGAGGTTGAGGTTGCGCTTCA
TGTTGTTCCAGTACATCTCGCCGATGCTCGAGTAGTACGCCGTCAGCCGCGATATTTTTTCTCGGACCAGCTCGTAG
GCCTTCTGCATCTCCGCAACGCCGATCTCCGCGTCGCCCACGTACCGGCCGCTGCGGCGCACGATCAGCAGCAGCGC
CTTCAGGTTCTCCAGCGCGATCATGTCCATGTACAGCGACTTCGAGAGCTGCACGAAGAGGTTGTACCGCTCCAGGA
TGCTGTTCTTCACCTCGTCCGCGATCGGGACTCCGAAGATGCGCTCCGTGGTGTACACGGACTGCGTGAGCTGCTTG
AAGAGCGCGGAGATGCAGCAGGTCGCGCGCTTGACGGCGTCGAGCTGCT TCTCGGAGCGCGCGCTCGCGATGCTCAG
CGCGCTGTTCACGACGTTGCTCGTGTCGCGCACGTAGCGCGTCTTCAGCGCGGCGTTGATGGCATCCGCGATCTCGT
TGCTGCTCACGCTCGAGTCGTCCGAGCTGCCCGAGACCTCGTCCAGCAGCCCCGAGATCGTGATGTCGGGCGAGCCG
CCGACGGTCACCAGACGGTCGAGCAGGTTGCAGGGCATGGACATGAGGATGCCCTCGCTCGAGAGGCAGCCCTC GTC
GATCATGCTCTGCAGGTTGCGCTTGAAGGCCGTGTTTTCGGGCATGAACCCGTCCACGCTCATGAGCTCGTCGACCG
TGCTCGCGGAAAAGATGCCCCTCACGTTGATGCGGTCCAGCATGCCCATGTCCTGCGAGCACAGCACCACCGACTGG
TCGGCCGTCTCGGCGGCGTCCTTGGCGCCGCCGTAGATGATGCGCGGAAACCGCCAGCTCCCGGAAAGGAGAAGGAG
GGAAACCGGCACTGCGCGCTCGGGCCTCGGTAGCCCTGCGCGTCGCGCACGTTGGCGTGACCATGAACTGCAGCAGG
TCGTGCGCGGACGCCATGATCTTCTCCACCTCCTCCTTGCTGCAGCAGACCTTGCCCAGGCTGCGCGCGATGTTCGT
TTTGCTCACCGAGGGCGAGACCGTGACGGCGGTGTGCCGGCGGCTGCCGAGCGTGTACGCGCTCACGCTAACGCGGT
ACCCCATGGCGCCGAAGAGCAGCTTCACGAAGTCCAGGTAGCTCTCC TTATTGATGTAGTGCGGCGCGCCCTTGTCT
TCCATCCTCAGCCCGGCGTAGGCCATGAGCACTTCCTTCATCGCCGTCTCGGGGTCCGAGTTGCACACCAGCCGCAG
CATCTGGAAGAACTGCGTGAAGGCGCGCTGCGAGAGCCCGATGTGGTGGTTGGGCTGCGTCGACCGGCGCGGGAACT
CCCTGGGCGTCATGGCGTTGATGCCCGAGAGCGTCTCCATCACGAGCGCGCCCACGGTCTTCTGGCCCATGA CGCGC
GGGTAAAAGCACACGCGGAGGGGCTCCTTGCCGGCCGCGAGCGCGTCCGAGAGCAGCGAGCAGTACGTGACGTTGTC
GTGGTCGAAGAGCGCGAAGGTGTAGCAGACGGAGCTCATGAAGAGCGAGTCGGCGGTGCTCATGGACTTGAACTCCG
TGTACGCGATTCCGTCCCAGAACAGGCTCTTTCCGGGCGCGATCAGCGGGGACGCGCGGTCGGCGCGCATCAGCATG
GAGAGCAGCGTCACGTAGTAACGGATGTTGGCGGAAACGTCTACGAACTGCATGCCGGGCGAGGCCACGCGCAGGGT
CGCGCCCGAGGTAGTGAGCACCTCCAGGCTGTCCATGAGCGTCACGCTGGGGTGCAGCTGCGCAAGGCGCGCCAGCT
GGCTCTGGTAGAAGATGGACACGGCGAGGCTGGCCACGCTGCCGCGCGCCATGCGCAGGTTTTGTCCGTTGAAGGTG
AGCTGGCGCAGCGAGAACACGGAGTCGAAGTACTGGAAGAAGGTG AGCAGGTACTTGAGCGGCATGGTCGTCAGCTC
GGTATCCACCTGCGGCGTCTGCGTGAGCACGATTCCGTTCTTGGCCGCGGCGTCGGGGATGTCGTACATGGCGTCCA
TTCTGGCGCGGGAGGCGTCGGTGAGCAGCGCGCGCACGTTGAGCAGCATGAGCAGGTCTCGCGCGAGCATGGTCCCG
TCGACCAGCCGGGCGCGAAAGCCGATCTCGGCGGGGCCGGCGATGTTGGGGTAGATCAGGTTCAGCAGGT ACGTGTT
GTCGAAGCTCAGCGAGGGGAAGGAGATGGGCGACTTCGCCGGGAGGCCTGTGGGGTAGCGCACGTAGCCGCCGCAGA
TGCGCGCGTGCGCCTCAAAGCTGGTCACGCGAGTCTTCAGCAGGTTGCGGGTGAAGGGCGGCACGTCCTTGAAGGAC
TGCGTGCAGATCACGGGGTTGGCGGTGTCGGTCAGCTTGAGGTTGGTGGGCTTGAGCTCCGCGAAGTTGGGGCCCAG

FIG. 28W

CAGCACGGGGACGAGGTGCGAGTTGGCGGCGCTGTCGAGCAGGAAGTTGATGCCGAACTGCTTCACGGCGACCTCGG
TTTCCTCGTCGCTGGCGAGCTTCTCCGCGTCCTCGAGGAAGAGCGCGTCCAGCGGGTGCACGTACGTGCGGTTGACG
TCGTAGCTGGGCTTGAAGTCCGAACACAGCGTGGGGAGCACGGTGGAGACGAGCTGGAACATGTATTCCGCGCCCTC
CACATGGTGCAAGGCCATGTGCACGTTTGGGGCCGTCATTTAT TTAGTATTAAATGACGGCCGTACCGGTAACCGAT
ATTCCTGGAGACTACGGGCCGACGTCCTTTTCGGAGGACAACTACCCGCTGAACAAGCACTACGAGCTCACCAAAGG
CCAGCTCTCGATCCTGCGCACGGTCAACGACAAGCTGCTCGCGCGCACCGTGCAGCACTCGGACGGGGAGAGCGATG
AGAGCGAGAGCGAGGAGGACGACATCTCCAGTCCGCTGCCGCCGGACGAGGAGGAGCCGGACTCGTGC GTGGCCCGA
GTCATGCCGCGGGACGCGGACCTGGCGGCGCCAAAAAAGGCCGACGGCTACATCATTGCCGCCGAGCAGCAGCGCCA
GCAGCGCATAAACATTCTGGTATCCGATCGAGAGGCCGTCGTGGAGCGGGAGCCGGTTCAGACGTCGTTCGCGCGCG
TCTCGGCTATCCCGATCCACGGGGACGGCGCGCGCCGCACCACCGCCTCCTTCTCCGCGACCACGCCGTCGCTGGGC
GCCGTGTTCGACGACGCCAAGCGCGTGCGGCTGCTGGAGGAGGAGGTCAAGGAGCTCCGCAGAAAGTGCGCGACCTC
TCAGGATAACGGAAACCTGGAGAACTTCACCAAGGTGCTGTTCGGCAAGGCGCCGCGCGCGAGCGAGCTGAACAAGC
GCGTGGTCATCGTGAACTACGCCACGCTGAACAACGTGACGCTGTCCATGGATGACCTCGAGAAGTGCTCCGACGAG
GAGGTGGACCGCATGTACTCGGTCATCCGGCGCTACAACGA GACGCGGAAGAAGAAGATCCTGGTCACGAACGTGGT
CATCATCGGGATCACCGTGCTCGAGCACGTGCTGGTGAAGCTTGGCTTCTCGGAGGTGCGCGGGCTCAGCGCCGACC
TCTCGTCGGAGCTCATCGACGTGGAGATCGGCGAGGACTGCGAGCACATCGCGGAGCGCCTGGGGTTCGGGAACAGC
CCGGTGCTAAACGTGGCGCTCTTCGTGGTAAAGCTGTTCGTGCGGAAGCTGAACCTGATCTGATCA ACACATGCCGC
CGTCGAGGTCCATGGCGTTCATGAGGTTGGAGGCGCGGCGGCGCGCGCCGGTGGAAGCGGTGGAGGCGCTCGAGGTC
GTGAGCAGGGAGTGTTGCCGGAGGAGGCGCGGCGGCGGGAGCTAGAAGCAGAACTCGAGGTTCCGCTGGTGGTGGCG
GCGACTCGTGCCGCTCGTGCCGCTCCTGCCAGTGCCAGTGCCGCTGCGGCGTGAAGTACCGGTGCCGGACCTGCCGC
TGGAGCTTTTCTTGCGGCCGCCGTTAACGCTGTCGATGCCGAGCAGGTCCTCGCACACCTCGCCGACGGTTCCCTGC
ACGTCCAACTTGCCGTTCTTGACAACCCCGTACACGATCTTGCCGCAGTTGGACACAGCCTGGATGGTGGTCTCGTC
GCTGTCAAAGGCGTTCATTCCGCCGCACGCGCCGTCGTTGTTTCTTCGAGAAGGCGCGCCGCTGCGGCGACTCCGGG
TGCTGGCGCTGGACCGAGTTCCGGAGGACCTGGAGCCCGTGGACCGGCTGCCGGTCGACCTGGTGCCGGTAGTGCGC
CTTCTGGACGAAGAGGAGGAGGCGCTTCCGCGGCGGGTGGACGAACTAGCCTCCAGCGCGCCGGCGCCGCCCACACA
ATCCACGTCGGCGGCGGCAGCGCCTCCGCGAATGACCTGCTCGTTGTTGAGCTGCGTCAGGAGAGATCGCAGCTGCG
GCGCGATCTTCTGCAAGGTGCTCACGTAGTCGTCGTAGCTGCTCTGCGGGCGCTGCGCCATTTT TTCGGACGCCATT
TATTACGCGGAATATCTACGACGACGCAGCACTGAATCGGTTTCTCGCGACGGGAGATTCCGCGGTCGGCGCCGGTG
CGGTGTTGTCGCCGGGCGACGAGGTAACCAGCGCGTGGAAGGCGCGCACCTGGTCGTCCGTCATCTTGTCCTCGAAC
GAGGACGCGCCCGGGGGAAGCAGGTCCTTGTTGCGCGGAACGGCGGGCGCCGAGACGCACGACCGGCGGTACATCAT
GATGACGATGTAGCACACGATCGAGATGACGATCACGGTCAGCAGCGCGTCGAGGAGCCCCATTTATTACCTGTATA
TGCCCGCGTTTACCGGGCGGTGAGCTCAATGTCGGTGTTGTTTAGCCGGGCGTACGGGACGCTGCCGGAGCACTTCC
TGTACATGCTGAACACGAACAGCCCGAGCAGCAGCACGGCGCCCACTATGAAGCAGGTTACGCACAGCGCGCGCCAC
ACGTAGTCGGTGACGTTGGTGTTCTTGCTGAAATCCACGAAGGCGAAGACGCAGGCGGCCGTCAGCAGCAGCACGCC
GCATATCAGCACTCCGGAGTAGTAAGAGCTCAAGGTCTCGAATATGTCCATTTATCTGAGGAGAAATTTAAATTACT
GAATGGACGAAGTGGAATAGAAACCACGAGAACACGACGGACTGCAGCACGAAGATGGTGCTCAGCTTCGTCTTCAT
GGGCATGCAGAAGTTCGCGGCCAGCGCCATACAGAAGATGAACACGAGCACCGCCGGGTCGT AGTCGGACACCATTT
ACACTACGCTAAAAGGCATATCTCGGCGCGCGACGTCCACGAGCACCAGCACGCGGACGCCCGCGGGCGCGCCGGCG
GCGACCGCGGCGAGCTGCCCGGCCGTGGGGTTCACCAGCAGCAGTGCGCGCGCGGTTCGCGGGACAGGGTCCTCGTA
GGACATGGTCGGTGTGGACCCGGGACGCAGCGGCCGCCCCTGTCTGTCGAAGAGGCCCTCGGGAAACGAGGTGCCCG
GAACGGCCACGACGACGGTGTCGCTATCTAGAAACATTTATGGTCTTGGTTTCCACGGATCGCCTCGAGTAGACCGC
CACGAAGTAGAAGATGACGCCCGCCGCGAGCGCCGCCACCAGGAAGGGCGGCACGGCGGGCAGGTTCGCGGACGCGT
TGTCGCGCACGCCGGGGTCCGGGTCTGCGTAGCCCGCGCCCACGGCCTTGCCGCAGTCGGCGATCATGTGCGCGCGC
GAGTTCTGCATGACCAGGCTGTCCACGTCGATGCGGCACCCCACGTAGCGGCACCGCGAGCGCTGCTCGTCCTGGCT
GAAGAAGAGCCACTTGCGGTCGCGCGACTGGTCCGTGCACTCGTGCGCGCGGCAGACGCGCGGGCCCAGGTACTTCC
CGAGCGTGGTGCCCGCGACGCACGCGCACTCCGGCGCGGCGCGGTGCGCGTCGCAGTAGCGCCGCAGCGCGGAGTCG
CCGAAGGCGAAGGAGGCGGGCCGCGCCACGCGCACGAATTCCGAGCAGAAGCGCGCGTCC ATGTGCTTGGCGCAGAG
CGCCGCGTAGGTGTCCAGCGCCGCGTAGCGGCCCGTGCGCAGCCAGGCCATGCACTCGGGCGCGTCAGGCTCCACCG
CGCAGCGGCTGGCCATGACGCCGTCGCAGTGCGCGGTCTTGTACCCGTTCGCGAACACGGACGGGCACCCGGGCCCC
GGATTTGTGCAGCAGCGCGCCATGGCGGCGTCCGTGGGCGGCGCCGAGGCGCCGATCTCGAACGCGCACATGGTGCC
CTGGCGCAGGTACGGCTTCGCGATCTCGGGAACGTAGTCTGCGCGCAGCAGCGAGCCCGGGCGGAAGAAGAGCGAGT
CGCAGGGCGGGCCTCGCACGAGCCGCGCGCGGCTCGCCAGCTCTGGCGAGAGGAAGCGCCCGCACTGCCCGGGGTCC
ATGGTCGGCAGCAGACAGAACCGCGGCCGTACGGTCTTCAGCTTCGGGTCGGAGAAGGTTTCTGATTCTTCCGCGAA

FIG. 28X

GGCGAAGGTGTCCGTGGCGCTCGTGTGGGTGACGCGCAGCGCGTACTCGCCGGGCGTCGGCGTGTCGAGCACCTCCA
CCTTGGATACGGTGTCCCCCATTTGAAGACGCTATTTACGCCGCTGCCTACTCGGCGAAGAATAGGTCCTCCGACTT
GGCGCCCGCGTACACCGGGCAGGCGGGCGCGGCGGAGCGAGTGCGCACGATACCGCGGCCAGTGAGGCGGAAGGCGT
AGATGGCGAACAGCAGGCCGAGCACGATGTACATGAAGGTGGTGGCGCCCACGGACCC GGTCACGTGCGTCACGATG
ATGGTGACGATGGACATGATCGTGCACACGATGGCCATGCCGGTGTTGTTGGCCGCGTAGGGGTGCATGATCTGCAT
GGCCGCGCAGTATCCGATGACCAGGCACGGCAGCGGGAGGATAAGTGAGGCAATACCTATCATTACTAGAGCGAGCA
CGGGGGTGGACGTCAAGGCCAATACAAAAATCACAATACCTGTTAGTATGCGGATATCCTCGTACTGGAGGACGCTG
TAAGGCGCGATATTCCCTCCAGGCACTGGCCGGGGGGTAGCCGGGACTAGGGGGGAGTCGGCAGTGCCGGGGTCTTT
GGGGAGAAAGGCATTCTGCTCCTCCGGGCTGAAGAGCTCGGCGTCCTGAACGCCGCCGGCGGTGAACTCGTCGTTAT
AGTAACTAAAGTAGCTTTCCATTTATATGTTGAAAAATGTTTGGAGGCGTACAGGTGGACGACAAACTCTACGCGTA
CCTAAAAAAACTCGCCGGACGCGGGCGGCCGCTGTGTCTGTTCCGCGACAACGGCGAGTTCGTCGAAGTCTTCGCGG
GGTCCGCGTTCCGCTTTGTGCTGCCCGTGGGCCTCTTCGCGGACCTGCGCGTGCGCACGCGCGGCGTGGCCTTCCCA
AAACTGCGCGACTCCGCGCGCATGCGCGGCGTGCGGGTGGACGCGCACACGCTGCCCTCGCTGTACCCCAACCAGCG
CATCGTGGTGGACGAGGTGCTCGCGGCCCGCGACCAGTTGCTGGCCGCGGGCCGCG CCGTGTACGTGACGCTGCATC
TGGCTTGCGGCTTCGGGAAGACGCTGACCGCGTGCCACCTCATCGCCACGCACGGCCGCCGCGCGGTGGTGTGCGTG
CCCAACCGCATGCTGGTGCCGCAGTGGCGCGCGGCCGTGGCGGAGCTGCGGGTGCCCTTCGCGGTCTCCTGCGACGG
CGCGGCCTCGCTGCTGCGCTCGGGCGAGCTCGACCGCGCCATGGTGGCCATCGTGGTCAGCCGGCACTTCGCCAACG
ACGACTTCTGCCGCGCGGTGAGCCGGCAGTTTGACGTGCTCGTGCTCGACGAGTCGCACACATACAACCTCATGAAC
AACACCGCGGTCTCGCGCTTCTTAACCAAGTACCCGCCGCCCATGTGCTTCTTCCTGACCGCGACGCCGCGCACGGC
CAACCGCATCTACTGCAACCGCGTGGTGAACGTGTCCGTGGTCAGCCGCCTCACCAAGGTGGTGCGCGTGGTGGACG
CCTTCTTCGAGCCGTACACCACGCCCAAGATCCGCACGCTCGAGCGCAGCCTCGATGGACCTCAGAACAAGTACCAC
GTCTTCACCGAGAAGATCCTCGGCGAGGACGTGCACCGCAACAAGCTCATCGTGGACACCGTGGTCGCGGCCATGGC
CGCGGGCGAGGCGCGGCGCGTGCTCGTGCTCACCAAGCTGCGCGAACACATGGTCGGGCTGCACGCCGCGCTCTGCG
AGCGCCTCGGTGCGGAGACGGTCTTTCTCGGCGACGCCAAGAACAGGAAGACGC CCGAGGTCACGCGCGCACTGCGC
GACAAGGACCGCTTCGTGCTCGTGTCCACGGTCTTCTTCTCAGGCACGGGCCTGGACCTGCCCAACCTGGACGCGCT
CGCGGTGGCCGCGGCCGTGCTCAACCGCATGGTCATGGAGCAGATGATCGGACGCGTGTGTCGCGAGTCGCACGCCA
ACACGCGCACGCTGTTCGTGTTCCCGGACTCCTCCGTGCGCGCGATCCGCGACACCGTGTCTGCGTTTGCGCAGCGG
CTCGTGGCGCTGGCGGTGGACGGGCTGGGCTTCGTCCGCGAGCGCGCCGCCGCCGGCGCGAAGAACGAGCCGGCGCT
GTACAGCGCCATCAGCGGGCGAGATCTCGCAGCGGTGTAAGCGCGGACCCGCACGCCGCGCACGAGAGCGTGCTGGA
GCAGGCGAGTCCCAGCGACAGTGTGGACAGCCTGTCCACGTCCTTGATGCTCACCAGCCGCGAGTTGCACGACGAGC
ACACGGGGTCGCTACTATCATCGACCACTGTGGTGACGCGGCGGCGTCTGCGCTTTTTGTTTCCAGCGGCGACATCG
ACCACGCCTCCCTTAGAGCCCCCCTTCGCCCCCGCCTTAGCTTTCACCGCGCTCATCTTTTATTTATCATAAAAACA
CGTCTGCGTACGCGTTCGCGCACACGTCCCGCAAATCCGCGCGCGCGCCGCAGCGCGTGAAGCGCGCGGCGTCCGCC
TCCGCGATCCGCGCGCACGGCAGCGGCGCGCCCTTCTCGTCCGCCATCACGC GCGCAGAGATCCCGGTGGCCCCCAG
CGCGTACGACACCACCACGTCGCCGACGCAGCGGTACACGTTGCCGGAGCCGGCGAGGCGGTCGAACGCGGCGCCCT
CCTGGCGCAGCTTGTCGAATATGCGAGGAACGAGGATGTTAAAAATGAGAACGAAATAGCAGATCAGCAAAAACAGC
GAGATCATGACCTCCGAGAGCGATTTATATACCTTGAAAGAGCTAATACGACTTCGGGACTCGCTGCACCTCGCCAC
CGGCGCCGCCGTCGAGCGCTACAACGCGCTCGTGGAGTGGGCCGCGCGCACGTACTGGACGGTCGCGGTGCTGCCCT
CCGCACCGTGCGCCTCCATCGAGAAGTACTACTGCGTGTGCAAACCCGACTGCGCGCTCGAGCCCGGCGAGTACTCC
GTGAGCCGGCTGCACTTCGGACTCACGCACGCCTGGGTGCGCGGCGCCGCCTTCAACTCGGCCAGCGGCGCCGAGGT
CGAGCCGCCAGAGGAGGTGCGTAGGGCCTGCGAGGCGCTCGACGCCGCCTTCGCGGACCTCACCTTCGTGCGCTTCT
CGGTCTTCGGCCGCGAGTGGACGGTCGACGACGCCGTCACAGACCACCCTCGCGCGACGAGGTGTTCGCCGCGTGCG
CCGCCTCCGGCGTGCGCGTCGCGCGCACGCTGCGTGTGCGCGGCGGGCGGGAGAGTCCTTCGCGCGCGCGGACTTCG
ACGCGGTGCACGCCGCGCTGCGCGCGGAGGGCGACGTCGCTCGCGGCACC GCGGTCTGTCTCGCGCTGCGCGGGTCA
TCGCGCCGCTGGATAGCGGACCGAGCGCCTCGATGCTTCATGCGCGTGCGCCGCGTGGAGCTCGAGCCCGTGGACGC
TCGGCACCACTGCCCGGTGCTGATCTCAGCGCGCGGCGACCGGGTGCTCTGCCGCGGCGTGGGGCACCTCGCGGACG
CGCGCGCGCGCGAGGGCGTCTTCGTGGCCGTGCGCAGGTACCCGGAGTGTCTGGTGCTCTGCGACGAGGCGGCCG CC
GGCGCGGCGGAGTGCTCGCGCGAGGAGGCGCTGCGGCTGCTGGTGCGCCGCTTCGGGCGCGACTTCGCCGTCAGCGA
GGAGGGCTACGTCTTCCGCGTGCAGGACATGGACCTGCGCGGCGTGTCCGCGCGACTGGGGCTCGCGCCCTGCGCGA
GCCTGGAGGATCTGCGCCGAGCGGTGGAGCGCGACCGCGCGCTGATGCGGCGGCTGCGCGCGGAGGGCGCCGTGCGC
CTCGCGTGCGAGTGCGTGGGATACCCGCGCCAGAACGCGGTGGAGCTCATAAATAATATGCGCTTTCAAATAACGGA
AGAAGGCGCGGTGGCGAACTTTGAGCTGGCGAACGCGAGCTGTCTCGGCAACCCGACCGCGGAGTCCATCTTCGCGA
GCTTCGCGCAGTTCGTGCCGATCTTCAACGTGCTATCGGCGATCGCGCGCGCGCAGCCATGATCGTGGCGGCCTTCG

FIG. 28Y

ACCTGGGCACGCGCAACCCCGCGCGCACCGTGCTGGAGGTGCTCGACGGCACGGTGCGCGTGGTGGACGTGGCCAAG
CTGGACTGGAGCCGCGACTGGGAGAAGCGCGTGCACCGCGACGTGACCGCCTTCCCCGCTAACGTGGTGCTCGTGGA
GCGCCAGTGCAAGATGTCGCCTTTTTCTAAGTTCATATACTTCATACGCGGGCTGCTCTACGACGGGCGGCGCCGCA
CGCGCGTGCTCGCGGTGCCGCCGGCCATGACCGGCAGCACCTACCGGCAGCGCAAGCGCCGCTCGGTGCGCAC CTTC
CTCGCGCTCGCGGAGAGCTTCGGCATCCTGGACGCCGTGCCCGCGCGGAAGAAGCTCGACGACGTCGCGGACAGCTT
CAACATGGCCATCAATTACGTGCTCCGAACAAACTGAAATACGACTGAACGAATAAGTCATGCTGGCGCTGTTCGAG
TTCCTGCGGTCCGTGGAGGACTGCTACCGGCGCACCATCTTCAACTTCCACATCGCGCACAGCGCCGAGGCGGGCGA
TGTCTACGGCGTGCTGCGCGACCGCATTTTGGCGGCCACGCGCTTCGAGGAGGTAGCGCCGCCGGGGCTCGCGGACG
CGCTGGCCAAGGTGGTCTACTGCGACATAAGCACCACCAAGCACCTGGTCAACCACGCGGCCTTCGCGGCGCGCGCG
CGGCCGGCGCGGCGCGGAGGCAGCCTCGCGCAGTTCTTCGACGTGCACGTGGGCGAGGACGCGGAGAGCCGCCGCAC
CGCAGAGATCTTCGACCGCGAGCGCTCCTCGCTGGTCTCGTACGTG AAGACCACGGCCAAGCGCTGCAAGATCGACT
ACGGCGAGATCAAGCGCACCATCCACGGCGGGCGGCAGACCTACTTCTCGGGGCGGCGCTCGGACGACTTCTTGAGC
ACCACCGTGCGCGCGGACCCGAGCAAGCCCTGGATCAAGTCCATCTCCAAGCAGCTGCGCGTGGACATCCTGCACCA
CGCGATCTGCACGCGCGGCAAGAGCTCCATCCTGCAGACCATCGAGATCGTGCTCACGAACCGCACCTGCG TGAAGA
TATTCAAGGACTCGACCATGCACATAATCCTCTCCAAGGACGACCGCGAGCGCGGGCTCGCGGACCTCGCGGACAAG
CTCTTCGGGACCTACGCGACCACCTTCCGCGTCATCGCGGCCATCACCGGCAACGCCTGCTTCGCGGCGGTGGCAGA
CGCGGCCGCGCGCGTGGTCGCGCTCCCGGACGCGGACGCGAAGCTGGCGGCGGTGCGCGGGCTCGCGGAGTGCTACG
GCGTGCGCAACTTCAAAATCGGCATGTTCAACCTCACCTTCACGGGCGCCATCGAGCACACGGTCTTCCCCTCGCTG
ATCCCCGCGGAGAGCAAGATCAAGTTCTTCAAGGGCAAGAAGCTTAACATCGTCGCGGTGCGCTCCACCGAGGAGGG
CCGCGAGTGCGTGGAGCAGGCGCAGGCGCTGCTCGCGGCCATGCGCGAGCGCTCCGCGCGGCTCGCGGCCGCGGACG
TGGCCACCGCGAGCGTGGACTTCCTCAAGGAGCTGCTGGGGCCA TAGTGAAATAATACTGATTTCTTAAATATGGAG
CAGGCGCTCGGATACAAGTTTTTGTTGCCCGACCCCAAGGACGACGTCTACTACCGCCCGCTCCACTTCCAGTATGA
GTCCTACGCCAACTTCATCAAGCACCGGCTTAAGGACATCCTCACGGTGCGGCGCACGCTGCTCACCTTCAAGAACG
GCACCGAGTCCATCGTGCTCGAGATCGACGACGTGAAGATCTCGGCGCCGGAGTTCTCGCCCATCGTGG CCAGCATC
AAGGGCCACAGCTACGAGGCGCTGGTCACCTTCACGGTGAACATCTACCGGCACGTGATGACCAAGGACGGCCTCAC
CGTGACCAAGATCAACAGCTACGAGGGCACCGACTCGCACCTCGTCAAGCTCCCGCTGCTCATCGGCTACGGGAACA
AGAACGCGCTGGACCCCTCCAAGTTCGTGGTCCCGAACGCCATCGGCGGCGTCTTCATCAACAAGCAGTCATCGAGA
AGCTCGGCATCAACATGATCGAGAAGATCACCACCTGGCCCAAGTTCCGCGCCGTGAAGGCCAATCCTTCACGCTCT
CCTTCTCCTCGATCTCGCCCGTGCACGTGATGCCCGCGCGGTACCGACACTACAAGATCCTGCTCGACGTGAACCAG
CCCGACAACTTCGTGATCTCCTCCGCGAAGACCTTCATCACCGTGAACGTGATCGTGATGGTGCAGTTCCTCGCGGA
CGTCACGCTCGAGTTCGTTGCGCGCAACCTCTGCTTCGACAT GCCGCCCGAGGCCGCGCACCTGGCCACCGCGCTCG
TGGAGAGCGCGAAGACCGTGCCCGCGGGCGCGGACGTGGCCGAGTACGTGAACGCGCTCATCGCGGCCGAGCACGCG
AAGCAGAAGTCGACGCTGTCCAAGGAGGAGTTCCGCTACGAGATGCTCAGCAACTTCCTCCCGCACATGCAGGACAG
CGCCAACCAGCTCAAGGGCCTGTACCTGCTCTCGCTGGTGCGCAAGATGGTCTTCTGCGTGTTCTTC CCGAACCGGT
ACCCGGACCGCGACTCGCTGGTCTGCCACCGCGTGTACACCTACGGGCGCTACTTCGAGGCGCTGGCCATGGACGAG
CTCGAGACCTACATCGGGAACATCCGCAACGACATCCTCGCGAACCACAAGAACCGCGGCACCTGCACCGTGAACAT
CCACGTGCTGACCACGCCCGGCTTCAACCACGCCTTCGCGGCGCTGCTCAGCGGCAAGTTCCGCAAGTCCGACGGCA
GCTTCCGCACGCACCCGCACTACTCCTGGATGCAGAGCATCTCCATCCCGCGCAGCGTGGGCTTCTACCCCGAGCAA
GTCAAGATCTCGAAGATGTTCAAGGTGCGCATGTACCACCCCAGCCAGTACGGCTTCTTCTGCGCCTCGGACGTGCC
CGAGCGCGGGCCGCAGGTCGGGCTCATCTCGCAGCTCTCCGTGCTCGCCTCCATCTCGAACATCCGCACCGCGGACT
TCGTCGAGCTCACCAAGCGCGTCTGCGACTACGTGCGCTC CTACCCCGCGCGCGACATCAGCTACTTCGAGACCGGG
TTCGCGGTCACCGTCGAGAACGCGCTCGTGGCCTCGCTGAACCCCGCGATCGTGGACGCGTTCGTGCTCGACCTGCG
CCGGCGCAAGCGGCTCGGCTTCTTCGGGAACCGCGAGATCGGCGTCGCGCTCGTGCGCGACCGCATGAACGAGGTGC
GCATCAACTTCGGCGCGGGCCGGCTCATCCGCCCGCTGCTCGTGGTCGAGAACGGCGTGCTCGTC ATGGACGCGGAG
GCGGAGCGGCTCGAGCGCGACCTCTCCGCGATGACCTTCTCGGACGTGCTGCGCGAGTTCCCGCACGTGATCGAGAT
CGTGGACGTGGAGCAGTTCAGCTTCAGCAACGTCTGCGACTCCGTGCAGCGCTTCCGCACGCTGCCGCCCGAGGAGC
GCGCGCTCTTCGACTTCTGCGACTTCCCGGCCGAGTTCCGCGACGGGTACGTGGCCTCCTCGCTCGTGGGCATCAAC
CACAACTCCGCGCCGCGCGCCATCCTCGGCTGCGCGCAGGCCAAGCAGGCCATCTCCTGCCTGAGCGCGGACCTGCG
CAACAAGGTCGACAACGGCATCCACCTCATGTTCGCGGAGCGGCCCATCGTGGTCAGCAAGGCGCTGGAGACCTCCA
AGATCGCGGACAACTGCTTCGGGCACCACGTCACCATCGCGCTCATGTCCTTCCGCGGCATGAACCAGGAGGACGGC
ATCATCCTGAAGCGGCAGTTCGCGGAGCGCGGCGGGCT CGACATCCTCACCTGCAAGAAGTACCAGGTCGAGATCCC
GCTCGAGAACTTCAACAACCGCGAGCGCGTGCGCTCCGCGGCGTACTCCAAGATCGACGTCAACGGCGTGGTGCGCC
TGAACGCCTTCCTCGAGCAGGGCGACGCCATCGCGCGGAACGTGTCCTCGCGCACGCTCGACGACGACTTCGTCGCT

FIG. 28Z

GACAACCAGATCAGCTTCGACATCGCGGAGCGGTACTCGGACATCTACGCCGCGCGCGTGGAGCGCGTGCAGGCCGA
CCTCACCGACAAGGTCAAGGTGCGCGCGCTGACCGTGCGCGAGCGCCGCGCCATCCTCGGGGACAAGTTCACCACGC
GCACCAGCCAGAAGGGCACGGTCGCGTACGTGGCCGACGAGACCGAGCTGCCCTACGACGAGAACGGGATCGCGCCG
GACGTGATCATCAACTCGACCTCCATCTTCTCGCGGAAGACGCTCTCCATGCTCATGGAGGTCATCCTCACCACGGC
CTACGGACACAAGCCCTTCGCCGAGGACGGCTCCAACCGCCCGATCTGCTTCCCCAGCACCAACGAGACCGACTTCG
AGACCTACATCGAGTTCGCGCGGCGCTGCTACGCGCTCTCGCACCCCGAGGCCGCCGCGGACGACCCCGAGTTCGAG
CACCGCGTCTTCTGCGAGCGCGTGCTCTTCGACCCCGAGACCGACGAGCCCTTCGCGGCGCGCGTCTTCTTCGGGCC
GCTGTACTACCTGCGTCTGCGGCACCTCACGCTGGACAAGGCCACGGTGCGCTGCCGCGGGCGCAAGACCAAGCTCA
TCCGGCAGGCCAACGAGGGCCGCCGCCGCGGCGGCGGCATCAAGATCGGCGAGATGGAGCGCGACTGCATGATCTCG
CACGGCGCGGCCTTCACCGTCGCCGAGATCCTGCGCGACTCCGAGGAGGACGCGCAGGAGGTGCTCGTCTGCGAGAA
CTGCGGCGACATCGCGGCGCGGCTCAACGGCACGCACGTCTGCATCCGCTGCTCCAAGATGAGCCTCTCGCCGGTGC
TCACGCGCATGGACTCCACGCACGTGAGCAAGGTCTTCACCACGCAGATGAACGCGCGCGGCATAAAGATCCGCGTG
GAGTTCGAGAAGCAGGACCCCTGCTTCTACGGGACTCCGAAACGGTTCAGCCTCGCGCCCGACGAGTCGCTGTTCTC
GCCGGAGGACTGAACCCGCCGTCGCGACCGCGTCGCTACGACTAGCTTATCGTTCGACTGATGCGAAACGCGCGGCG
GCGCCGCGACTTAGCTTATATCGACTGATGCGAACGCGCGACCTCTCGCGACTTTCTAGCTTCTCAGACTGATGCTA
CCATATCGCGGCGTGCTGGCCCCACCACCAGGGCTTCTCGCCGTGGCTGACGCGGGGCTGGCTGCGACGCGCGCCGC
AGTAGCTGCGCGCGCCCCAGTCGCCGCGCACGTGCGCCGGGGGCAGGCTCCCGTCCAGCGCATGCCGCGTCACCTCG
GCGCCGGGCCGGCGGCACGTGTGCACGTCCGTCTTGTTGGAGACGAGCACTGCGTACTGCCGCATGGTCTCTATGTG
ATGCTCCAAGTGCTTGCCCGCCTTCCGGTTGGACTCACAGCACGTTTTTGCTTCGGCTAAGGTTTTTTCTAGAGGGG
CTAGTAGCTTATCCACGCGCTCGGGCAGGACGCACGCGGAGCCGTCGAGCCCCACGCGGAACGGGGTCACCGGGATG
TTCCCGTCGTAGCGGTCCCACAGCATCCTGAGGTAGGTTGTGCCGTCGTCGTCGGCGTGCGTCCACACTCGACGATG
TTCGTGGCAACGACCGTCGTATGTAAGTCTGTCTCGACGCTCGTAATAGTTTCTGCTTATATTGTACGCGTCTCCGT
ACTCGAAGTAGTATATATCTCCGGGTCCTGGACTTGCTATATTGTTTTCGTCGTTTCTACGATGTATACCGTCTGGA
TAATACGATATTCTAACTGCACTGCAATCCACCGTAGAAGGTTTAGGTAACTTTTCTAATTCTCCTTGTTGGTCATG
GTCAACTGACTTGTACACAGCTCCGTCGTGTTCTGAGGGAGTTATAAATATATCCATGGTGAAAGAAGTTCCTCGTT
TTGAGAATTTGTCCCATGCGGTAAAACAAAGGCCGTCCATCATAAACTCCGGTACACTCATAACAAACCTGCACTTG
TGATCATCAAATGATATTTTAACATGGTCTTTGTCTTTTACGTCCGTACCGTTAACTTCTTTCATAAACTGTATAAT
TGCAAGAACTCCTCTTGCGTATTCTATAGTTCTGGTATCAGACACCAACTTTTCTGTTTTAATATAAACGTCGTTTA
CATCTACACCGTACCACCAGTAAATAGGAAGTCCTATGTAGATGGCTGTGTTTCTAAAATGGGATGCAAGCGTACTT
ATGTCACGGAAAAAGGCCACACAAAAAAAATCCTGTTTTTGAATCTATAATTTTTCTGGTGCTGTCCTCTGTAACTCC
TAAAATGTCCATAATTCTTTCGTTGTGAAGAGTAAGGTGACCTGTCATTATGCTGTATACGACCATTAAGTAAAACT
TTCCAAGCGTGTCTACGTTTATAATATTTATCTTAGCATGCTCGCATAGCATAGTTACGTGGACCTTCATCCATTCG
TCGTCAACAAACATATTTTTGTACATAGTGTTTTGGTTTACGTATTTGCTAAAATACAGGTTTACAGGTCTACGAGA
TACTTTCGTTCCATCTACTTTTGGTGCGCTTCGTATGTACTCGCGCAAAACGTCTCTTATAATTTTTCTATGAGTAC
GTGGTATACATATTACCGTCCCAAGTGGATGATGCCACTGACGCTGAACGATATCTTTAAATTCAGATACCAACGAA
CTGTGGTTCTCCATTTATAATTAAATAATTAGACCATATCTACCACAGACCTTACCAAATGGCGCCGTGTCTTTGAC
GACGCCACCAAGCATCTAAATTATAAGTATTGTATGGATTATGTCTATTAAAGATGGATGTGCGAGGAGTTCTTGTC
CATGTTGGTCTGTAAGTCTCTCTCACTATGGGGTAATTGCTGCTCGTTGTATTGGAAGACCCTAGCCCGACTGGAAT
TTTTGAACAGCAAGGTTTGTCTTTAACGTAATTTTCTAGAGGAGATATAAGTTTGTCTAGTTTATCTATGTCCATAC
ACAAAGGATTATCGTTATTATCTTCATCGTCTATGACTTCTACTTCCGATAGAGGAGGCTTCACGCTCAATAATCCA
ATGAACCTGTCTCTTAAAATTCTGTGATATGATGTCTTATCATCATCTATGTCTCCATCAAAACGATGTTTTAAACA
CACAACGTTATCGTATGTTAATTTATCCCGGCGCTCAAATTCATTGTTCGCAGAGTCTTCTGTGTGGCTATAGTAGT
GGTAGTCTAAGTAGTACCCGTTGTTTTCATAGTTTCTAGTAAAAATGGTAGGCGTTTGGTTATTATCAACATCATGT
TGTTTAACATAAGTATCTTCTTTGTAGTTAGGGTGTCTGGCAGTAACACCATCTTTAGGTACGTAAGAAATACGCCT
GCTAAAACTAGGATGAAATTTAAATCGTATAGCGCCTCTATTTCCTACGTCATCTTTTGTTATACCATCAACAACAC
CTTGTTTGGAATGATCTAGTGTTTTATACGTAAATCCGTTATATCTAGTTGGATTCATAAAAACATCTAGATAAAAT
GTAGTTCCGTATTTAGTTATTTTATCATATACTGTATAACAAAGGCCGTCTAAAATGAACTCTGGTACTGACGATAT
AAAGTTTGTGCTAAAACCACCAAATGATATATTTATATGCGGTGTGCGAGTAGAATAATCTCCGACTTTGTCATAAG
TTATATACATATATCTAGCAAAAGTCACTGCACCGTTAGAATTCTTTTTAGGATCCTCTTTATTAAAATAATCATCG
AGTAACGTATGTACGTTTGTACTAAGCCCATCACCTCTCCACCAATACATAGGTATTCCAAAAACTAATGACTTGTT
ATTGTAATAAAACGCTACAGAACCCATATACCACAAAAAGAGATAACAAAAGTAATCCATTTGTGTATCTACATCTC
TGGGGTCGTTTAAATTCATATTATCCATAATAAACCCATTGTCCGTAGCTCCTGTCATTATCCTGTATACTACCATT
AGCAAAAGCCTACCCACTGTACTCACGTCTGTAAAAGTTTTTATAGCCACAGCACTTTCGTACATCCATACATTGTT

FIG. 28AA

TCTAAAAAGCTCAACATAAACAGGATTTTTGTCAACATATTGTTTCATAATCAAATTTAGTGGCTTTCCAGTTTTTT
TATGAGTGTCGCTTAAAGAAGGAGCATTCTTAATGTACTCTCGAAGCAAATCTCTCACAAGCTTTCTTATCTCTATA
GGAATGCATGTTTGGCTGTTTAATTCTTTATACCAGTTAGCGCTAACAAACGTTCTAAACTCGTCCACGAGCTTCTC
CATTTATAATTAAATAATTACAGACGGCAACACAGCGGTTATCTAATATCTACCGTATCCTGTCTGTACATCTATTT
TTTTGTTGAGATCAAGAAGAGCTCTACGTAGACTCTCCAAGTGTCTTTCAGTCTGTCTAACCGGTTACCTGTTTCTC
TGCAGCAATCAGTTATAGTTTTGTAACTGTCTAACAAGCTTACGCGCTCTTCCACACTTTCTTTAGTTGGAGCTCCA
GCCGCGTACACTCCGTTGGTTGAATTGCCTGTATCATCATCAGGCGGAGCCAATAGGTTTTCTCCGTCACCTTCCTC
CATATTGAATCCAACGAACACAAACGCGTAAGTGTTCCTCTATTTAAAGTA TTGATTTTAGAAAAAGGCAGGCCTCG
CTGCCCTGATTCGGTGGCAAACACGGGTTGAACACGCGGAAGTCGCTCGCGGCCGTGAAGATCTCGTCCGCGCACGC
CTCCACGCTCGCGAAGCGCGCGGGCGAGACGCCGTCGTGCGAGCGGAACCCGAACTCCGAGGCCGCCACCGCCGCGC
CCTTGAAGAGCACGCAGCGCCACTTCTTGCGGACGTCGAAGGCCTCGTCGTTGGGGTCGAACACGCGCCGGTCCAC G
CGCGGGCCGCCCGCCGTGCGCGCGAACTCCAGCGCCGCGTTCGCCGCGTTGAACTCGCGGATGTTGTCGTAGTTCTC
GTAGACGGCCCAGAGCTGCAGCGCCACGAACATCGCGGCCGCCGCCGCGAGGGCCACGCAGAGCGCGGACACCGCGT
CCATCTTTTATGTGCAGAATTATTCGTCGGCGCGGAGCTCGCGCAGCTCCGCGGCGCGCAGCCGCGCGAAGGCCGCC
TTGAGCGCGCGCAGCAGCTCCTCGGTGTCCGCGCGCAGCATGTCGAAGCGGTGGTAGCTGTCCAGGCGCGCGCGGCA
GCCGAAGAAGCGCGCGACGCACGCGGTGACGATGTCGTTCACGTAGAGCACGCCCGAGGCCGTGCAGTACACGGAGC
GCGGCTCGCGCGGGTCCGGCGGCACGTCCACGGCGACCGCGTGCGCGGCCACGTCCTCGAGCACCTTGCGCTCGAGC
ACGGCGAGGAAGTCGCGCAGCTGGCGGCGGTTGTCCAGCCAGGCGTAGG TGGTCGCGAAGAGCGTGAGCCGCCCGCG
CGGCGCGATCGCGGTGTAGGGCGCGTACCCGCGGAACTCCCGGGGGTGCACGACCTTGACGTTCTCGTGCTCGCGGC
GGAAGGCCTCAGTGTCGAGCAGCGCCGCGAGCGCGTCCACGAGCTTGTCGGAGACCTCCACGCCCGCGCCGAAGGCG
ATGAGCTCGATCTTCTGCTCGCTCTTGGGGCGGAAGTCGTGGAAGGTGTGCAGCAGCATCTCGCGGAGCTGCGG CGG
CTTCTCGACGGCCTCGAGCGCGTCGCCGCGGACGAGGAAGTAGTCGAGGTCGTGCAGCGAGACGTGCTGCCCGGCGG
CGCTCTGCGCGAACTTGAGGAAGACGCAGAGGCCCGCGCGGCGCTCGAGCACGTCCTCGACGTGCGCGTGGAACACG
TGCCGCGAGGGCATGGCCTCGATCGCGGAGAGCCACTCCTCGTTGACGCAGGTGGTGGTGTTCTCCAGCACCACGCC
CTGCGTGAGCGAGGGCCACTGCAGGTGGAAGGCGAACTCGTGCTTGATGAGCGAGGCCACGGCCGGGTCCAGGTCCA
CGGCCAGCGCGGCCTCGCCGACGAGGGGAGCGTCCGCCATCACGCGGAGGACGCCTGGCCCATCTCCTTTTTCGCCT
TTTTATTCAGGATCATTATTCTTTCGTTGACCAGGTCCATGAGCATCTTGATGGCGGCGGCCGCGGCCGCCGCGTCG
CCGCCGCACATCTGCGCGATGCGCGTGAGCATGTGCAGCAGCGCGGC CTCGTTCAGGTCCTCCTCCATTTAGAGGCC
GTAAGGGCGCGCGTCGTCGCGACGAGGGGACGCCTCCCGCTGCAGCGTGGCGCGCACGGCGAAGGCGAGCAGCGCGC
CGGCGCACTGCGTGAGCACGCACTCCGCGAGCGCGACGAGGAGCTCGGAGAGCACGAGCACCATTTAGAGGCGCGCA
CGGGTTTAATTGCCGCCGTCAGAGTCGGCATCTCCCTTGTCGCCGCCGTCCTTGCAGTCGCCCTTGGCGTCG CCGGC
GTCGACGATGTCGGCGAGCCGCGTCTTCATGTGCGAGAACTGCGCGAGCAGGATGCCGGGGTCGAGACAGCGCTTGA
CGACGCTCTCGTCGGCGAAGTCGTAGCAGATGCGCTCCTGGTTCTGGCAGAACACCGAGTCTTCGATGATCAACACC
CTCCTGGTCCCGGCCGACCGCATGATGGCCATGGCCCGGATGAGCCTCTTCTTCGATCCGCGTATGGACATGGACCG
GAGCACGTTCTCCACGTCGGAGTCGGAGACGTTGCAGCAGCAGAGGTGCGTGATGCTGGCGCGCCCGTTGACGGGGA
TGTGCTTGTAGGTCTGGCAGAGCAGCACCAGCGACACGTTGATGTGCCGCCCGTAGTTCATGAGGCCCAAGAGTGTG
GGCGACCGCGTCTGCGTGTCGCCCATATCGTCGAGAATGATGAGGAACTTCTGCTTCTTCGTCTGCGCGTGCCGCTC
GATCTTGCGCTTGGCAACCGAGAGGTTGTACTCGAGCTCCTCGTG CGTGGTGACCTTGTGGATGTGGTCCGGCCACA
CGAAGCCGTCGTAGGCGGCGTTGTAGACGGGCGTGAAGAGCAGGATGTGCTTGAAGCGGCGCACGAGCGTGCGGAAG
AGCGAGAGCAGGTAGGCGGTCTTGCCGGAGCCGGAGCCGCCGACGAGCGCCATCCTGAAGGGCGCCTCAATGAGACT
CTCCCGCTTGAAGCGCACCTCCTGCACGACATCCATCGTATATTTACTGTCACTAAATTACCGGCTCCGA GAAATAT
AGAAATTAGAGCCTCCTAGAGCACACCGAGGCTCATCGGCAAGATGGCACATAACACGTTCGAAAACGATAGCGAGA
CGGCTAACAACCAGTACGTGGCGTCAGTCAAGCGCCAGAAAATGATTCGGCGATACATTAAGATGTTCTTCCGGTTC
GTTACGGCGATAGCTATCATTGTCCTGGCTATTCTAGTTGTGATCCTGTCGCTATCTCTAGACGAATGTCTGCACAG
AGAACACCCTCATGACTATTCGCATGTACAAAATTCAACATGTCCCGGAATTCCATTGGGTGATAAGTGTTTAACAC
TTAACACACCGTCTACATGGGAAGATGCTAATCAAATGTGTAGCAATCTAGGTTTCAGTTTACCATCAAAAGGACTA
CTTAAAACGCCGTGGCTCACAGATTACCTTGATGGAACTTGGGGAAATAAACTGGGAAATGTCTTTGGACCAACTGG
CGAACTCGAGCAGGTCATGGGACAGCACGAAACCCGCAAATAT TTTTGTGTGTCTGGTTAGATGATTAAATCTAATA
AATGGGTTGCTGTAAGGTCCCTAACCGCCAGTCTATAAGGACTTTGAAAAAGGTGTCCTGCCCGGTCGCCAGCCTCG
TTACCATTCTCTCCCTAGCTACCAGCCTCTGTGCGATAGTCAGATACACTAATTTTTTTCTAAAAGAGGCGTGTGAC
GAAGGATGGATGCCAATAAAAGACATATGCATTTTAAACACGCACTTTAAAGCCACCAAGGACGACGC CCACAGAAT
ATGCGAAAGCCTAGACGGAAATCCGCCGGCCATCCCCAATCCCACTCTGCTAAAGGGTGTAATGGTTCTCACCGGAG
AAAGACAGTTTTGGATGACTCACCACCCGGACTACACATCTGTATACGAGCATAATGAAAAGTTGCAAATTCCAAAA

FIG. 28BB

AACACTAAGTACGACAAAGATAGACACATTTGTTTGATGAGCGAGGACGGATTGATACACCATAACTGCATGATGAA
CGTAACCGTGGTATGCATGAAGGAGATGCACGGATAACTGAAAATATACTGTTTGAACGCAAAGACGCCATGTCGCG
ACTTCAAATACTGACCTCATTTGGACAAATCTACGCACCCGACGAAGCTCGGCTGCGCGAGATCGCGCGTGATTTGG
GAATATGCACCATAAAACGCGCATTCGGCGACATGCTGTACGGCTTTATAGACTTCAACCCGGTGCCCCTGACCCAA
GTAAACATGCTCATGTCCAACTGCTACTTCGCGGTCAACGG CAACCTGCTTCCGTGCACGGAGGACTTCCGGCTCAG
ACTCCCGGCAACGGAGATCTCTGCGGCCTACCTGACGAGAACGGGACGGACGATCCTGTGCGGCAAAGACTTCAACA
TAGTGGCGCCGTCAGGGTTCAAGCCGTCCATGCGGCTGCGCGACCTTAGTCACGTGTCTGCGCTTGTAGAGATCCTG
GAGCTCTACGACGAGTCCGGGGATTACCAATTCGTGCTCGGCCCCAGCGCGCAGTTCATGCTGCGG CTGATGGAGAA
GGAGAATGTCTGTCTGTTCGGCAACGGTTGGTGCATAGTGGACCTGCGCAAGCTAGACGTAACCATATAATTGCTGC
TGCTATGTCGTGCCCGACTCTGTGCGACAAAGACAGCGGCTAACCAGACTCTTCGTCCCTGTTCTCCAAGCAAAAAA
CTGGAGTGAGTTGCCATTTCCGTCTCCAACCATATAATTAGCATCCTTGTTTTTATCCTGTATTTTTATCAGTTTTT
ATGCTAGTTAAAACATAAATAGTAAGGCTAAAAAGAAGAGTTCTAGAATCTTGCAACAACCAAGATGAAGGCGGCGG
CGGTGTTGTTGCTAGCGCTACTGGGAGCGTTCACCAACGCAGCGCCCGTCAGCAACCAGCGTCTTGGCAGTGAGGAG
AAAGAAAAATTCTGCTCGACTCATCATGACGAAGTGTACGCCAGGTTCCGGCTTCAGATGCGCGTGGGTGTACGACA
CAGTCCGCTCTACGTTCCCAGCAACATGTGCATGATGGA CATAGAAGACTCTACGGATGACATAGAAGAGTCCACGG
AGAAAGAATACACGTCTACGGCTACGGGTGAGGCGGCCGGAGTGAACGTGTCCGTGGCACTAGTGGGAGAAGGCGTG
AAAATACCGTTTAGTTACATAGGCCTTGGATTCAACCCATCTACAGATGGCTACCTGTACGTCAACGTCTCGTCACG
AGCTCCTTGGGTTCAACAGACTCCAGACCTATCCGCGAACAGCGGCTGGGGTATTAAACAGGTT CTAGAAAAAGAGT
TACTGGCCATCCAGATAGGGTGCGACAACCAAAAATTTCCCGAAGAACCCACAACTACCCCCTCACTTGTCACGACA
ACGCTTTCCCCAACAACGACTTTAAATCCGAATAACGAAAACACAGACACTACGCCGACGCCCACCGGCGCCAGTGT
AGACGGAAAGCGCAATCCAGATGACATTGACTTCTCGCTGATCGTGGACCCCCGATGCGTGACCTCTGTAAACCTGC
ACTTCGAGCTCAAGGACGCGTGCATGGACTACAAAAAAGAGTCGCCGTTGTCGCTGAAGGGGAAATATGGAGACAGT
GAACTAGTAAAACAGGAGATTAAAGACGTGGGAAAGAATCACAATATGTGCAGTCTTAACCTCAGCCCTGGCCATTG
AGCTGTTTTTATTCGGCAATATAATAAGGTGATTATTGAACATTAAACAAAACTTATCCCACAACGCCGCAACAATG
GAAGTGTTGGTGATCGTCTCCATTATCGTCGCCGTAA TATGCTTAACCGGAGCGGCGATGTACATCCTTATTGAACT
CGGCTTAGCCGCCGAGCGCGCTAACAAACGCGCGCGCGTGAAGAAAAATATGCGCAAATTAGCCACTCAATTGGGAA
ATGGATCTGTCGACTCCGGCATAGGCATAGGCCCGTGCATAATGTCGCGCACCATGGACTCTGGACCCAGTCGCTGG
GACAGCGACAGTGAGGGTGACGGAGACAGCCTGTCCACGACGTCCACCAGCGAAGGGGGGAC TCTCACCCGAGTGTG
GGTTGGGAGCGGGTCCGGGCCCATGTACGAAAACTTCTGCGGGAACGGCACCCACCGCCACTCTCCCACCAACGACC
CTGGCTACCACTCGCGGGAGACTCTCTGCAGCGGACCTCCCCGTCAGGCGCCGGCGCTACCGCCCACCCCGAAGCCC
GACGAGGTAACGGTGGACGTGGGGCCCAGACCCAACGACCAACACGGTCCGTACGAGGAACCTGATCCCATTCCCCT
GCAGGAACCCGAGCCGCCGATGCAGATCGAGGTAACCATCAACGGGCCCGGTGAAGAAGGCGAGGTGGAGGGAGAGT
TTTTCTACGACGAGTAGCCGCCAAAACTGAATAACTATCGGGCTTCGTAAACGCGCAGACATGCCGCTGTTCCGGAA
GCTCATGGTTTCGCGCTCCCTGGTCAAGGAATGTCTGACTCTGGACTTCCGGCAGGGCGAGCGTCTCCCCACCCGAT
GCTTCCTCCCGGTGCCCGCGGGGACGACATTCCAC AGAGTCTGCGACACCTCGCCGCTGACGGACGAAGTATCCCGG
CACGTGCAGGAGCCCGTCATGGGCACCGGACGGGTCCAGTACTACTACTTCGAGAGCGGGCAGGGCATGATCGGCGA
CAACGCGGGCATGTCGCGCATGCTCGTGTGCACGCGCTCGGCGTACAACGGCGGCGACGTCGTCGTGCGGTCCACGC
GGAGCAGAGCAGACAAGACCGTGGTCGCGCCCTGCCAGGGCATGGCGCTGCTGCTGAGCC CCTTCTGCGCCTTCGAC
ATCACGCCGGTGGAGAGCGGCTCCGCGATATTCGCGGAGGTCATCGTCACTTCGCCCAGCATGGACCACGTCGAGGC
GGTCACCGGCACGGGCGAGGCGGCCGTGCGGATATTCAACTCGCACCACCCGCTCTGGCCGCGACACGGCTCGAACG
TCTGCTTCGCGCTGCGGTTGCTGCGAGACGTGCGCACGGGCGAGCGCGTGGTCGAGCAGATGTTCATGGACGGGCGC
TGGCACACCGTGCTGAGGACGTCCTGCGGCAACAAGGTCTGCGTGCCCGCCGACCTCGTGGGCCAGACGAACCTCGA
GGAGGTGCCCTTCTGCGACGTGACGCCCGAGATCATGCGCCGCGCACTGGCGATCGACCCGCCGTACGAGGCCGTGG
CGCACCCGCGCCGCTGCGTGTACGGCGCCATGGACGTCCGGTGCGCGAACGAGTACCTCGTGTACTGCACCTTCAAG
ACGGAGCCGGCGCGGCGCAGCACGTCCTCGCCGGGCCCGGACGGCCCCCTGTCGCCCGCGACTCCGTCGACCTCGCG
GGCCGCGGCTGCGCGCGCCCCCACGACGCCGCAGGAAGTGGCCTCGCCGACCACGAGGCTCGTGGAGACCTGCCTGC
GCGACGCCCTCGACGGACTCTGACCCGAAGGACCCACCGTCCACTCACATTCCACTGCCAGACAACTCAAGCTTTTT
CTGCATCTACCTCGCTAATAATTGAATTGTTATAGTACAAACAGGCGCACTCGAGCAC AATGGCGTGTTTTATCGAA
TTGTTAGACTCCATCTTCAACCGACACCACCGTAATTTCGGGCCGGAGGACATGTACAGGCCCTCTGACGCCCCGCC
CCCCAAATCTCACACGCCTCGCACTCCCCGCACCCCGCGGACCCAGTGTCCCGGACACCCGCGGCGACAAAGCTCCT
CTCCCATCTACGGTGCTTATGTGGACTCCCTGCCGAGGAACAGAAAGCGGTTCCAGAATCAACACAGTTGTCCCGGA
GATTACGAGCGGTGTCAACTCCAGGACACTATCAGCCTGGAGGCGACGCTACTCACGGTTACCTCGACTTCCATCTC
CAGCATATCCAGCTCTAGTAGCTCAGACTCTAGCTCATTGGGGCAGTGCAGACTGTCCATTGTGTCCGCGACATCGA

FIG. 28CC

CCTCCACGACCTTCTCCTACTCGTCCTGAGCGCCACACTTATTTTTGTATAATAGTTTGTATTGAACCTTAGAGACA
TCCACAAATAGTTAGGAAGCATGAGTAGTTCAAGTAGCGAGACCACCCCTAAGCCCAAGCCCATCCCTGCTCCTCCC
ATGACTCAGGAGGAGTTTAACAAAGAAGTGAAGAAACGAAAAGAACAGAAAAAGGAAAAATCTAGAACCGTTGAACG
TGAGTCAGAAACCGTAACTGTATCTTCCGACGGATCAGAGATAAAAAAGACTTACGAGCGCGAGTCTGAGAGAACAA
CCGAAACAGAAAAGAACAACACGTCAACCGATGATGATAATAAGCAGAACACCCCT GTAGAGAAACCAGAGGAAACT
AAGCCTGCTTCTACTCCTGAAGGTGAGAAGCCAGCTGAAACTCCTGCCCCGACTACTGACCCCCAACCCACTACACA
ACCACCCGCAGAATCAGGCCCTGGAAGTCAACCCACACCTGTTCCAGAACCAACCCCCGCACCTGAGCCTGCACCGG
AACCCACTCCTGCCACTCAGCCTGCATCAGTAACTCAACCCGCTCCAACACCAGAGCCAAGTCCAGCCCCTGAAACT
ACTCCGGCTTCCGAACCAACCCCTGCACCAGAACCCACTCCCGCTCCAAAACCTACACCAGCCACAGAACCGACTCC
TCAACCAACCGTAGAAACAACACCATCTGCTCCAGCACCAACTCCCGAGGCCCAACCACCCGCCAACAATCCCACTA
CTGAAACTACCACTGGTACCAGCACCTCCTAAGTGAGTACGTAAGCATTTCGGAGTAACGTCGTAGCAAGCGCTAGT
CCGCCGCGAGCGGTTCTTGCAAGTTTTTT CGGGTAAAAAGCGTACACCGTCGCCTTGTAGCGGCGGTGTACGCTTTT
TTCACGCCCTTTTTGCAAAATTTAAATTGTACCCGCGCCGGCTCTAGGAAAGATGGCGTGCCTCAGGGTGTTCTTGG
CGGTGCTCGCGCTGTGCGGGAGCGTGCACTCGGCGCAATGGATCGGCGAGCGCGACTTCTGCACGGCCCACGCACAG
GACGTCTTCGCGCGGCTGCAGGTGTGGATGCGCATCGACCGGAACGTGACCGCC GCGGACAACAGCTCGGCCTGCGC
GCTGGCGATAGAGACGCCGCCGAGCAACTTCGACGCGGACGTCTACGTCGCCGCGGCCGGCATAAACGTCAGCGTGT
CCGCGATCAACTGCGGCTTCTTCAACATGCGCCAAGTAGAGACAACGTACAACACGGCACGCCGGCAGATGTACGTG
TACATGGACTCTTGGGACCCCTGGATGCTCGACGACCCCCAGCCGCTCTTCAGCCAGGAGTACGAAAACGAAACGCT
GCCGTACCTGCTGGAGGTTCTGGAGCTAGCGAGGCTGTACATTCGCGTGGGCTGCACGGTGCCCGGAGAGCAGCCCT
TTGAGGTGATCCCGGGGATCGACTACCCCCACACCGGCATGGAGTTTCTCCAGCACGTTCTACGGCCGAACCGCCGG
TTCGCTCCGGCGAAGCTGCACATGGACCTCGAGGTGGACCACCGGTGCGTGAGCGCCGTCCACGTGAAGGCGTTCCT
GCAGGACGCCTGTAGCGCCCGCAAGGCGCGGACGCCACTCTACTTCGCGGGGCATGGCTGCAACCATCCAGATCGCC
GGCCAAAAAACCCAGTACCGCGCCCTCAGCACGTGTCGTCACCGATCTCCAGGAAGTGCAGCATGCAGACGGCGCGC
TGAGGGCGCTCACCGCGCTGACGGCGGCCGTGGTGTGCGCGATCGCCGTTGCGCTCGAGCGCGGGGCGGAGGCCGAC
GCCGTGGACCTTATCCTTATAAAATTTTCAATGATATGCTAGTTTTTTATGCGACCTTCCTTAGAAAATTCGGAATTC
AAAAATGAAATAAAACGGCGTTTAGCACGCATATTATTAATACCGACCACCATGGCAGGCGTCCGCAGCTGCCAGAA
GAAAGTCCCTTCTACTGCGGGCTCCATGTCATTTCAACGGGGCAACCGGAGCATCCAGCCTGCGATGTCCGAGGCGT
TGCAGAATGATTTCAGCTACAACCCGCGACCGCCTCCGCCGAGCGCAGAAGAGATTGACTTCTTCTGCGTGGACATG
CGCAAAGTACTGATGGAAATTGAGGCCAAGCCCAACAGCTCCAAGTACCCCAATTTCATCCACCCGGTTGACAGCAG
CCCGCCGTGCACGCCGGCGCGCAAGCGCAACGGCTTCGGCCGCAAGGCACTGAACAAGACCCCGGTGCCGCAGCAGG
CCAAGCGTGACGGCTACTCCCGCTAATGCAGTCCACACACTTCACACACTACATCAGCACTCAAGCTTATAATCACC
ACACAATGAATTAGCCCAGCCCACACACGTGCCAAGCACACATAAAATCACCCACCTGTCCTGATCGTTCCCAATTA
CTCCCAATCACCCGTGCTTTACACGCACGTAAATCACCCTCTCCTTCGTTCCTGATCGCTCCTCCTCCTTAATCACA
CATACACCCCGTAATTTTGTACTTTTGTACTTTAATTTGTACACTTTACACACTGACTTTGTACTGCCTTTGTACTT
TATTTTTGTACTGAAATTGGACGATACTTATCTTTGTATTCACATCCAAGTTTTGCAAATTCCACAGCCGGTCGCGA
AAAGTGAAATCGTACCGTTTTAGGCTTCGATCCCCCTCCCGCGCGAAGACTCGCCAGCATGGACTCTCGTAGGCTCG
CTCTTGCCGTCGCCTTCGGAGGCGTCCTCGCCAGCATGACACAGCGCCGCCGCCTGGCTTCTCTCATCGCCAGCATC
GGCCAACGGCTGATGGGCGGCGACGGCATGCGTCGCGTCGCCGTTCGGTTGATCGACCAGCTCATGGCCGGACCC CC
GGACATCAACGACGAGGCCTTCCAGCGCGAGATCCGCGTGGGCGAGCTCTTCCAGGCGCTCCACCGCGTGGTCGAGC
AGGCACGCCGAGAGAAGTACTTCGAGGTCTGCGGCGCCGGCAACGACGCCGACGCGCCCGTCGTCGAGATGGACACC
GCGGCCGCACCCCCGCAGCCCCAGCCCGCGCCCTTCGTGGTCACGCCGCAGAACGCGTTCATGTTCGTGCCGCAAGG
CAGCCACGTGCACGTGGACGAGAGCGTGGACCCGTTCTTCGGCATGAGCCCCTCCATCTTCGGGCGCGACCTCCCCC
TTCAGCCGCCCGAGGAGCTGCTGAGCGACCACGACCCGCTCATGAGCCAGGCCGGCGAGCCGCCGAGCCCGCGGTCG
CCCTGCGAGGCCGACCTCTGGTGCTTCGAGACGCTCGGCGACAGCGACAGCGATTGAGCCCGCACCACACCCCACCT
CACCCACCCCACACTCCACCTCACCTCACCCTAACACCAACACCCTAA CACCCAACACCTCAACCGGACAATGAAGG
AGTCCCACATTTCACTGAAGGACGCGGATGAAGCCGCACATCCCCACATGAAGGATTGGCAACGGTCAAACATTTCA
CCTGCAATGAAGGACGATGCGCGGTCGCATTGGCCTGCGACCGACATCGCACACATGAAGGACACAATTGGTTTGTT
AATCCGGACAATGAAGGACAAATTGTTTTTGTTAATCAGGACAATTGGACACAATCAGATTAATTTTTGTACG ATCA
TAAAATCGATATTTGATGCACATATATTAGTAAGTATATTAGACTAAATTCTCCGGGGAGGCAAGCAGTTGGATACG
GCGGGGCGGGGCACGACGTGCACGGAGAATTCGGGCGGGTCCCCCTTCCCCCCACCCCCACGCACCACGATGCGTCT
AATCTTAGCGCTCGTGGCCTGCTTGTTGGCGGCGCCGATGCCGTTATCGGGTCGTTCGACAAGCACCCCAAACACAC
AGTCCGTACTCGGCTCGACGAGTTCGGAACCAAGCTCGGAAGACGCTGTGGCTTCGAGCACAACGACAAGCACACTC
ACAAGCACTACAAGCACACTCACTATGTCCACAAGTGTGGACACCACTACTACCTCGGGCGCTACGACGTCCACAAA

FIG. 28DD

CAGCACTCCTGCAGCGAGTGTGAGTTCTTCCACACCCGCAGCCACTGAGGCATCGACGGCACCAACGACGCCGTCGA
CGCAGACGACAGTGAAGGTAACGAAAGACAAAGACACGAAGGCGTC TGCCTACCTCGTTTTACTAATCACGTTCATG
GTCATGACAACGCTAGTGATGGTTGTGGTCGTGGTCGTGATCGTGTACAAACAGGGACTTTGTGACTGCTGCTGTAA
GATGTTTCCCTGCTGCAAAGAGCTCAAGGACTACCTCGACGAGGAGGAGAGCGCCGGGCTGTACGACGCCTTGACGT
GGAGCCGCTCAGACCCCGGCCTCCGGCTCGTCGTGCGCGCGGACCCCAGATGATGAGGATCGGATAAGATC GGCGTG
TTTTTCCCGCCCGTCGCGAACATTATGCCTCTAAATGCCGAGAATTAACTGAAATTCAAACACGCTTTGGGACTCAA
CTCTGTGGCCCACACAACCATGGCTGGCTTCCTAGGCGCGTTCAGAGGCGTGTGCTCCGACTTATGGCAGTCGCTCC
GTGGACACGGACACCACTCTTCCAGCTGCCCGCGACGACGCGCCAACAGCATGGACGACCGCGACCGGCGCCGGCAC
CGCCACCGCGAGATCCCCAACAGCTCGGCGTCGCTGAACAGCGACCCGATGCCGCCACGCAGTGCGGGTGCGCGCCG
GCACTACGACTGCCGCCCCTCGGAAAAGAGCAGACACTCCTCCGACAGGCACCACTCGGCGGACCGACACCAATCGG
CGGACAGGGACAGACACCGTCGCAGTCGCAAGAACTACGACTCGCACCCGTCGCGCAGGAACCGCAACTACGAGCGG
GCGGACTACCAGAGACATCCCTCACAGACCCACCCAGAAGCCCC CGCGCAGACCTCGACGCTCAAGGTGACCTCCCT
CAGCACCAGCTGCAGCACCCTGTCCCAACATCACTACGAGACCCCCGACCACATCTACGACATCCCGGAAGACGGTC
GCGGGGCGTCGGCTCCCCCTCGCGCGGACCTCGCGCTCCCCCCGCTCGCCATGCCCAAATCCAAGCCGCGCCGCACG
CGCCCGGCGTCCATGAACGACTGCCTGATGAAGCACTGCGGCGCCGGCAGACCCAACCTCCAAGACGAC ATATGCAC
ACTATGTACTGATATAGAGACACAGCTGAGCGCACTAGAGAAGTCTCTGGAGTCAGAGCTCAACTTCTATCGTCGCT
ACATACAAGACACTAAGACCTTGCTCGCCACGCGAGCAGCAAACATCGGCAGCAAAGCTCTGATCTACACCGACGAC
TACAACGGCAGTGGCAACGTCGGCGAAGGGGAGCACTGCTCGGAGGAGTGCTGCAAAGTGGAGGAAGTTCTGTGAGA
AAGTGCGTTTTTCTGTAATGTGAAATAAGATAGCCTTATGTGTGCACAGACATGGCGAACAGGCTTGTGTTTCTCGA
CCCCGAGACCCTAGCCGAGGCCGACGGCATCCCCGGCTATGGGGTGTTCGAGCCCGGCAAGAAGAAATGCATCTTCA
CAAAGATCCGCACCAGCGTCGCACTCGCGTGCCGGTACGCCGTCTCGGACGGCGGCCTCATCGACGAGTTCGTCATG
GCGACATACGGGACCAGACGCGCGTGCCGGCTCGTCCGGCAC CTGACGATAAGCGCGGAGGGCGTGATGACCCGGCC
CGCCAGCAACTGCGCGCCGCACATGGTGCTCATCTGCCTCAGAGGCGTGGCCGCCGTGTCCAGCGAGGACATGGGCT
TCGGTCGCTGCATCATGGAGCGCGGCACCATGTTCATGGTCAAGTCCGCGCACAGCGCCGTCGTCTGCGGCAACCCC
GCCTGCGAGCTGCTCGTCCTCTTCTACGACTACTTCACCCCCATCCCCCGGCCGCTCTCCGGAGACG AGGTGCTGTT
CACCCGCGACCTCGCGCACGTGGACTACGCCCCCGAGTCGGCGGTCGTCTTCAAGATGGATTACAACCTCGAGACCG
ACGTGGCCACGCTGTTTGTCGGGGGGTACATATTCCGCGCCAAGGGCCTGATGATGGAGACGCGCGAACAAGTGGGC
GACGAGTGCGACTGCTGCCGCCACAGCTCGCCGGTGCTCGTCATGGATCGCGAGAAGATGATGTCGTCGCTGCGCAT
GATCCCCAGCATCGTGCCCGGCCAGCGGGAGATCTGCCTTCGCGAGCGCGGCTGGGCCGTCCTCGAGACGGACGCCC
GCGGACACTGCGAGCCCGGCGTCCTGAGGCTGGCGCTCGCCGGCCTGCGGCTGTTCGCAGGATGCCTGCGCTCCGTC
GTGGGGCGGCGCGAGCTGTCGCTGTTCTGCTACGGCATCGCTCCCAAGTTCGGCGGAGAGTTCGAGGACGCGCCGCG
CCCCATGGAGATCGACGGTTAGTTGTTTTTATCCCTGTAC ATACGCCGCAAACTGAAACTTTAGGGCACCGCGTAAT
AGTGCACGAACGCCCAGTGGACCGCTTCCGCAGCCATGGAAAACAACGAAGGCAACGAACGCAACAACGAACACCCG
CACGTTCGAGAATTCAAGGAGGCGTCCCTGTACGGGTTTCTGGTGTCGGCCGCGGACGTGACCGTCGAGGACGTGCG
CCGGTACCTTCAGTTCGGCGCGGACGTGAACTACAGGGGCGCGTACCTGTGCACGCCGCTGCACG CGTACCTGCAGT
CCGGCTGCGAAAAGCGCCTAGACGTCGTGGACGCGCTGCTGGACGCCGGCGCAGACATCAACGCCAAGGAGATCTGC
GGGCTCACGCCCGTGCACCTGTACGCGAGCTACGCGGATGTGGACGTAGAGTTCATGCGCGGGCTCATCGAGCGCGG
CGCGAGCGTGTGCGGCGAGAGCTCGGTCACGGGCTGCCTGTACTCGTACCTGTACACACACAGCGTGGACGGCGGCG
CGCGCCTGGACGTGGTCGAGCTGCTCGTGCAGGCGGGCGCGGACGTGAACGTCCGCGGCGAGGCGCGCAAGACGCCG
CTGCACGTGCACTGCGCGGGCTTCGAGGTGGATTCGGACATCGTGGAGCTGCTGCTGCGCGCGGGCGCGGACCCCGA
GGCGCTCGACGAACACGGGCTCACGCCCGCGGACGTGCTCGTGAAGTCCGTGGGCGCCAACGTGGCGACGCTGCGGC
TCTTCCTCGACGCGGGCGTGAGCGTGGCCACGTCGCGC GACGCGCGCGGACGCACGCCGCTGCACCACCACGCGGAC
TCCTTCCGGGCGAGTGCGGTCATCGTGCGCGAACTGCTCGCCGCCGGCTGCGACGCGGCGGCCACCGACGACCTCGG
AAACACGCCCCTGCACAGCCTCGCCACCTTCTGCTCGTGCCGGCGCTCGGTGCTCGACCAGCTCATCGCCGGCGGCG
CGGACATCAACGCCCGCAACCACTACGGCCACACCTGTCTGTACTACGCGTCCATCTACAACC CCTCCGTCTGCTCG
AGGCTCATCGCCGCGGGTGCGGACGTGACCGCGCGCACGCCGGACGGACGCACGCCGCTCTCGGGCATGATCATGCG
CAAGCACACGCGCGCCGTGCGCGCCGCCCTGGCGACGCGGCCTCCCGCGGACGCCGTCGCCGCGTCGCTAGACGTCG
CGGTACAGCCCGAGCCCACGGACGCCACTCGCGCGTGCGTGCGGTACGTGGTGCTCTGCGGCGGCACGCTCTCGGCG
CGCGTGCGGTCGCGACACGCGGACTTCGTGCGAGAGTGCGAAAGCGAGGTGGTCGTGCTCAGAACCACCGTGGTGGG
GCTGCCCGGCACCTCGCTGCTGGACATCGTGCGTGCGGCGCAGCCGCCGCCGGTACTGCTCTCCCCGCGCGTGCACC
ACGTGCTGCAGAAGCTGTGTGTGTACGCGGAGTTGGTAGACGCGCGGCTGCGCGAGATGCGGCACAAGACCAACCTC
GTGGACGCGGTGTCGCGGCTCGTGTGTCCGTGCGCG CTGCCGCCGGAGGTGGTGCGCGGCATCCTCGTGCACGTGCC
GATAGACAGCCTGCGGCACACGTTGACCCTCGGCGTGGCGCAGGCCTTGCGTTTCCTTCCCTCGCATAAATGAAATA

FIG. 28EE

TTATTTTTTGTGGTAGACCGGATCTCCCCGATGGACCCCGCCGGACAACGACTGCGCGCGCCAGGGCCGTGGCGCCT
GAACCCGCCGACCGCGGCCGCGCTGGAAAGCGCGCTGCTGCGGCCCGCGGCGTCGGCGGGC GCCGACCGCTGCGCGA
ACGCGCACGTGGACAGCCGCAACATGGGCGTCGGCGAGGGCCGAGAGGTGCCCGCGGACGTCGAGGGGCTCATGACC
GAGATCCACCTGCGGTACGGAATGACGCGCGTCCACCGGAACGTTCACTTCGTGCAGTTCTGGCACGGCGAGCACGT
GCGCCGGCGCCCCGCGCGACACGTGTTCACGGTCTGGATCTGCCTCAGCGGCGAGGTGCGCATCTACGCAGAGTGCT
GCCAGGCGGGGCACGGCTTCGTGCTCTGCCGCCAGATGGCGGCCGGGTACATGTTCGTGACCGAGCCCACGGACTCG
GTCACGGTCTCGGTGCCGCACCGGCTGCGCAACTCGCGGTCGCCGGTGTGGCTGGCGGCGGTCTTCGCCACGCGGCA
CTTCGAGCCGCTGCCGCCGCCCATGTACGCCGTGCCCGGGCACGTGGTGCTCGCGCGCAGCGCCTCCATGCTCTGCG
ACTGCTGGCCGTCGGACCCGCGGCGCCGCAACGTGATCTTCTACATGCGGCTGTCGGGCGCGATGGTGCGCGTGGTC
GTGCCGGGCGCGGAGCTTGAGATCGAGTGCACCTCGGGGTTCCGGCCGGACCACTTCTCCATCGACGACGAGTGCGT
GTGCTGCGAGCGGCCGCACGTCGCGCGAACCGCGGTGTGGACGCTGGCGGAGATTTGCCGCGGCGCCACGGTGGTGC
TCGCGCCGCCACTGCCCCGCGACCGCGCCGCGGGGCTGCTCGCGGAGATCCGCCTGGCC TCGCTGCGATGGGTGCGC
GTGCGTGCGGTCCGCAGCGGCAGAGAAAGCGTGGGCCCGTTCCCCTCGGTGGTGTGGGCGGCGGTCTTCTCCGCCGT
TCGGCTCTTCCTGGACGGAACCGTGCCTGCCTTCCCGGCGTGTGTGGAGAATGGACGCGCGGCGTACGGCATGGTGT
ACGTGCCCTCGGAGGAGCCGCGGATGGACGGGCTCTGTGTGTTCCCGACGCCCGCCGAGCCGGCGGCGCTCTTCGTC
CGCGGAGACCAGGTGCTCGAGGCCGGCGCGGCCGCCGCCATAATCGCGGCCGCTGAGAAGCGCGTCCAGGCCGCCAA
TGGGTCTCCTGCTGCCGCGGAGGAGGACATAGGTGCGGCGGCCGATGCCGCCGCAGAGAGCGTGGAGCAGGACCAGC
GCGTCGAGTTTGACCTTGGGCCTGGGCCTGACCCCAGCCAAGAAGCGCCCGCGGACGCGCAGCGTGCCGATTCGGAC
GACGACACCGGCTCCGAGACTGAGACCGGCGACGAGAGTGTGGGCGGCGAGGATGACAGCGACTCCTCCTCCTCTTA
CTCGGTGATGTCGGACGACGAAAACGACAGCGGCGACGAGGGCTGGGGCGACTCTAGCGACTCCGGCATCGAGGACG
ACGACGGCGGTGTCGGCCAGGCCGCCGAGGAAGAAGAGGAGGAAGAGCGCGACGTCCTCGGCGCAGCGGCCCAGATG
CTCGGAGACTGACCGGTGGTGAAAACATAAAAATAAACTGTTCAACACTTGTACTCC GGGCACCAACACTACTATCC
ATACCCACCCTCCCTCCACACACTACAATGGCAAACAGAGAAGAGATTGACGCCTCCGCCGTCATGGCTGCCTACCT
CGCGAGAGAGTACGCGGCGGCTGTAGAAGAACAGCTGACGCCGCGCGAGCGCGATGCGCTCGAAGCCCTTCGCGTTT
CCGGCGAGGAGGTCCGGTCGCCGCTGCTGCAAGAACTCTCGAACGCGGGCGAGCACCGCGCCAACCCCGAAAACTCG
CACATCCCCGCCGCCCTCGTCTCCGCGCTTCTCGAAGCCCCCACTTCCCCCGGCCGCATGGTCACTGCGATTGAGCT
CTGCGCGCAGATGGGCCGGGTATGGACGCGCGGCCGCCGGCTCGTCGACTTCATGCGGCTCGTGTACGTGCTCCTAG
ACCGTCTGCCGCCCACGGCCGACGAGGACCTCAGCGCCTGGCTGCAGGCCGTCGCGCGCGTGCACGGCACGCGGCGC
CGCCTGCACCGCGTTCTCGGCGTCGGGGCC GTCATGGCAGGCGTCGGTATGCTGCTGCTCGGCGTGCGCGTGTTGCG
GCGCACATAACTTTTTATCTCGGCTCAAACTGAAATACGACATTGGACTACGAAACCTATAATTTTGCCCACGGCCG
CGCGAGATAGGATAATAAATAACCTCTGAGCAACTAACATGGCCGATGAGAGAGAGGCCGACGGCGCGCTGTTCCGG
TACCTGGAGAGCGAGGACCGTCCGGACGTGGAGCACATGCGCCGGCTGCTGGACG AGGGCGCGGACGTGAACTACGC
GGGCCCGCGCGGGTACGCGCCGCTGCACATGCTCATGCGCGGCAACCCGCTAGACCCCGACGCGGTGCGACTGCTGC
TCGCCGCGGGCGCGGACGTGAACGCGACATCGCTCTGCGGGTTCACGCCGCTGCACTCCTACATGTGCTTCGGGACC
GTGACGCCAGACACGCTGCGTGCGCTCATGCGCCACGGCGCGAGCGTCAGCGACCTCGAGCGCAACATCAACGCGCT
GATCGAGTACTTCAACCGCGACGGCTGCATGGGCGGCGCGGAGGCGACCGTGATCGCACTGCTGGCGGAGCACGGCG
CGCACGTGAACGCCAAAGACGACCTTGGACGAACGCCGCTGCACATCTACCTGTCCGGCTTCTTCGTGTCGGCACCG
GTGGCGCTCGCGCTGATCGCGCTCGGCGCGAACCCGAACGCCACGGACGCGTACGGGCGCACGCCACTGCACGCCTT
CCTGCGCTCCCGCGACGTGGACCCCGCT GTGCTGAAGACGCTCATAGCCGCGGGCGCAGACCCGCTCGCGCGCGACA
TCATCCGGCGCACGGCGCTGCACTACCACTGCGAGTCCTTCAAGACGCGCGCTAGTGTTATCGAGACGCTGGTGGCC
GCCGGCTGCGACCCCGCGAGCACAGACCTGCTCGACAACACGGCGCTGCACAGCATGGCCATGGGCAGCTCCTGCCG
CGCCTCGCTGATCCGCCCGCTGCTGGCCGCGGGCGTGTCCGTGAACGCGCGCA ACGCGCGGCTGCAGACGCCGCTGC
ACCTCGCGGCCGTGTTCAACCCGCCGGCCTGCGCGCGGCTGCTGGCCGCGGGCGCGGACCCCGCGCTCGCGGACCTA
GACGAGACAACGCCGCTGCTGAGCATGGTGCGACACAACTGCGCACGCGCGCTGCGCACGGCGCTGCCCTTGGCGCC
GGACGCGCTAGTGGCCGGCGCGGTTAACCGCGTGAACGCGCGCACGCCGAGCGCGGCCACGCGCGAGTGCGTGATGG
CGCTGGCGCTGCGCGGCGCGCTGGACCTGCTGAGCGCGGAGAGCGTTGCCACCCACGCGGCCGCGATCCGCGCCTGC
GAGGCGGAGGTCGCGCTGCTGCGGCGCACGCGCCTGGGCGCGCCGCCGACGACGCTCTTCGCGCTGCTGACAGGACG
ACCGAACACGCTGGTTTCCGCAAAGGCGGCGCGACGCGCGATGGCGGACGTGTGTGTCTACCGCGCGGCGCTGGCCG
CGCGCGTGGAGCGCGTGCGCCGAAAGTCCTCGCTGGTCGAGCGCCTCACCGCCATGGTGTGTCCGTGCGCTCTGCCG
CCAGAGCTAGTGACGCGCATCCTCGCGCTCCTGACCGTGGAGGAACTCGCTTGCGCAATGCGCAAATAATAATGAAC
TATAACTAGGCTTATTAGAGGCACTATTTGTGCAGAGTCGTTAGTTATAGTTAGTGTACTTACAATTGGAATGTCGA
AGAACAAAATTCTGGTGTGTGTTGCGATTATTCTTACTTATACATTATACA CAGATGCGTATTGTGTTGAGTATTTA
GAAAGTAGGGAAGATGAACAACAGTGCAGCGGTAGTAATGGTGCGTCTGCGAGTTTACCGCACATGCTCAGAGAACT

FIG. 28FF

CAGGGCCGCGTTCGGAAAGGTAAAAACTTTCTTCCAGATGAAAGACCAACTGAACAGTATGCTACTCACACAGTCGC
TCCTCGACGACTTCAAAGGCTACCTCGGGTGTCAGGCACTTTCCGAGATGATACAGTTTTACTTGGAAGAGGTGAT G
CCGCAGGCGGAAAATCACGGGCCGGACATCAAAGAGCACGTTAACTCGCTGGGAGAAAAACTCAAAACGCTGCGTCT
TCGACTGCGTCGCTGCCACCGCTTCCTGCCGTGTGAGAACAAGAGTAAGGCCGTGGAGCAAGTCAAACGCGTGTTCA
ACATGCTGCAGGAACGAGGTGTTTACAAGGCCATGAGCGAGTTCGACATATTCATCAACTACATAGAATCATACATG
ACTACTAAAATGTAAAAATGTATATAACTTTTAGCTATCGTTCGGATTCTCGTATCGTTCTGCTACAATGTATATAA
AAATGTATATTCACATAGTTACAGTTACAGTTACAGTTACAGTTACAGCTATATTTTTATGCTCACAAGATGCTATA
TAATTGAAAGGAAATTGTTCACTCTCTGTCAGGGCGCCATGGACTTTCTAGGCGCCGCGCTTCACGACTACGTTGCC
GACGCGGAAAATGTCCGCGTTGACGAGGTGCGGCGGCTGCTGGCCGCAG GCGCCTCTGTGGAGTACGCGGGCGAGTT
CGGGAAGACCGCGCTGCACCAGTACATGGGCCGTTCCGGCGCGGACCCCGACGTCGTGCGCGCGCTGCTGGACGCCG
GCGCGCGCGTGGACCTCCCGGAGACCTGCTGCGGCTGCACGCCCGTGCACCTCTGTCTCATGGCCGCCAATATCGAC
GTGGAGGTTCTCCGCATGCTCGTCCACGAGGGCCGCGTCGAGGACTGCGGCCGCGCCGAGCTTGCCTCCGCGGT GCT
CAAGGAGTTCGTGGTGAACCGCGCCTTCGACGAGAACGTCACCGAGCGAGTGATGCGCGTTCTTGTGGCCGCGGGCG
CGGACGTTAACGCCACCAGCGTGGTCGACCGCACGCCGCTGCACGTCTGCCTCACGGGCATGTCCACGCACCCGGGC
ACCATCGCCGCGCTGCTGCGCTTCGGTGCGGACGTGAACGCCGTGGACCTCTGCGGCATGTCGCCGCTGGCGGTGCT
AGTGCGCTCGCGCGCGGCGACCGCAGAGCTGGTGCGCATGCTGCTCGACGCGGGCGCAGACGCACACGCGGTCGACA
GTCGCCTGGACTCGCTGCTGCACCAGCACTTTCAGTCCGCGCGCCCGCGGCCGGAGGTGGTGCGCGAGCTCATCCGC
CACGGCTGCTCGCCGCGGGCGCGGAACCGAATCGGCAACACGCCGCTGCACGAGGCCGCAAAACACTCCTCCTGCAA
ACACTCGCTGGTGGGGCCGCTGCTGGCTGCCGGCGCGAGCGTGGACG CGCGAAATAACACGGGCAAGACGCCGCTCC
ACTTGGCGGCGGCGTCCAACCCGCGCGCGTGCCGCCGGCTGATCGCGCTTGGGGCGGACGTGGTCGCGCGCAGTTAC
GCGGGCGTCACGCCGCTGGCGCAGCTGGTCGCGGACAATAACTCCGCGCTGGTGACCGCGGCGCTGGACACGCAGCC
CGAGCCGCGGGCCGTGGCAGAGTCGCTGCGAGCTACCACGCCCGTCGGCGAAACAGCGTGCTCGCGGCTCTG TGTGG
CGTACGTGGTGGCGCGCGTGCCGAGCGAGGTCCTCGGCGAGCCCGAGCGCGCCCTGCACGCGGCCTTCGTGGCGGAG
TGCTTAGCGGAGGTAGCGGCGATACGCCGTGCGCTGCGGCACACCTCCAGTCTCGCTGCTGGAGATCCTGGTGGCCG
CGCGCCCGCCGCGGAGCCTGCTCTCGCGCCGCGCGCGGCGGCTGGCCGAGAGCCGGACGACGGTCTACCGCGCGCCG
CTCCGTGCACGCATCGCGGCCATGCGCCATCGCTCGCGACTGGTGGAGCGCGCGCTGCGCACGCTGCGCGGCTGCGT
GCTCCCGCGCGAGGTGCTGGAGCGCGTGCTGCGGTGTCTGTCCACACAGGACCTGCGGACATCCGGACTGGCCGAGT
AGCTTTTTCTGAGATAAGTGAATAAACATGGTGGGATTCGATCGCGCCGCCAACGCCACGCCATGGACGCCGCCGAG
ATGGAGGAGCTCGACATCAACGCGGAGTCGGCGCTGTACGACTAC TTCATCCTGAACGCGGACAGAGCCCGCGTGGG
CGAGGTGGTCATGCTTCTCGCACAGGGCGCGGAAATAAACTACGCGGACAGCTTCGACAAGACGCCGCTGCACCTGT
ACTTGCACACGCGACACCCGCGCTCGGACGTGATTCTGGCGCTGATGGAGGCAGGCGCGGTCGTGGACACGCCGGAG
CGCTGCTGCGGCGCGACCGCGGCGCACCTGTACATCCTCAACGCGGCCGAGGTCGACCTGTCGGTGCTGG AGGCCAT
GCTGACCTGGGGCGTGCGCCAGAACGACCAGCACTCGGAGCGGCTGCTCTCGAGCTTGTTGCGCGAGTACGTGGTGA
CCCGCGCCTACTCGGATCAGACCGAGCCGATCATGGACTTGCTCATCGGCATGGGCGCCGACGTGGACATGCCGGTC
GGCGTGAGTCGCACGGCGCTGCACGCCTGCCTTACGGGCCTGAACACGAACCCGTGCATGATTCGCGCGCTGCTTCG
GCGCGGCGCCAGCGTGACCGCAAAAGACACCTACGAGATGACGCCGCTGGCGGTGCTGCTGAAGTCTGCGAGCGCGA
CGCCGGAGCTCGTGCGCATCCTCGTGGAAGCAGGCTCCGACGTGAGCGCCACCGACTTCCGCCTCAACGGCATGCTG
CACCAGCACGCGCAGTCCACGCGCCCGCGCGCGAGCGTCATGCGCGAGCTCATCCGGCTGGGGTGCAGCCCAGCGGC
CAAAAACATGTTTGGTAACACGCCGATGCACATGCTGGCCATG GAAAGCTCCTGCCGCCGCTCGCTGATCCTCCCGC
TGCTGGAGGCAGGGCTTTCCGTGAACGAGGAGAACCCGCACTACGGCACCGTGCCTCTGCACGTGGCCTCGGGGTAC
GACAACACGCAGGGCTGCCTCAAGCTCCTCCGGCAGGGAGGAGACCCCGCCGTCGTGTCGGCCGCCGGACGCACGCC
GATCTCGAACATGCTCGTCAAACGCAACCACGTGGCGGTCGCCGGCGCGCTGTCGACACACCCGAGCG CGGTAGTGG
TCGTGCAGGCTCTCGAGCAGGCTCTCGAGCACGTGCTGAACGCCGGGCCCAGCGAGGCCTCGCGGCTCGCCGTGGCC
TTTGTGGTGGCGCGCGCTGGCGCATCCGCGCTACCGGAGGCCGTGCGCCGTCTGCACGAGGGCTTTGTCGCCGACTG
CGAGCGCGAAGTCGCGCTGCTTTCTCAAACCATGCTCGGCACACCGGCCGTGAGCGCGCTGGCCGTGCTGGTCAGCA
AGGAGGTCTTTGGCACTGTTATCTCCTCGCGTGCGCTGCGTGTCGCGCGGGAGGTCCGCGTGTACGCAAGGCCGCTC
CGCGAGGCGCTCATAAATCTGCGCCACAAATGCCGCTTAGTTTCCAGCCTTAAAAGGCAGGTGGGACCTTGCTCGCT
GCCCGGCGAACTGGTGGAGCGCGTGCTCGCGACCGTGCCACTGACCGACTTGCGCCGCTCGTGCGGCCGCCGCGCGC
CCGAGTGACTGCCCATCCCGTTGCTACGCGACTCGGTGACT GCCCGCTGTTTTTCTTTCCCCGTTTCTTCTTATTAG
GAGTTGTTGCCCGCCTCCATGATCCTCGCGCGCGCCGGCGGGCGACCTCGCACGCCCGCGGCGGCCGCGGCCGCCGC
CGAGGACGGAGAGCACAGTGATCGCCGGAAGCGCAAGCGCAAGACGCCCAACTGCGAAGACGCCGACAACTCCGACG
ACGAGCTAGCGCAGACGCCGTGTGACCGCGAGTGGCCGGACTGTCGCGCGAGCTCGATCACGAGCT CCGACTCGGTC
TCTCTCGGCGACGAGATCTACCTGCGATACGTGGCCTCGCAGGTGGACTTCGCGCAGACCTGGGCCCCGCCGGTGCG

FIG. 28GG

GCTGCTGCGCTTCTTCGGGAACTTCTCGAAGGAAACGCTCAACCGCATGTCGCGGCGCGGGTACGTGAACCGCTCCT
ACTTCCAGATGGCGCACGCGCGCTTCTCGCCCACCAACGACGACATGTACCACATGGCCACGGGCGGGTACGGCATC
GTGTTCCGCTTCGACCGCTACGTGGTCAAGTACGTCTTCGAGCACCGCAACGGCATGTCCGAGATGGACGCCTCTAC
GGAGTACACAGTGCCGCGGTTCCTGCGCAATAACCTCAAGGGCGACGAGCGCGAGTTCGTGGTCTGCGCGCTGGCCA
TGGGGCTGAACTACCGGCTGGGCTTCCTGCACTCGCTGTACCGGCGCGTGCTGCACACGCTGCTGCTGCTCATGCGC
GTGGAGGAAGGCCAGCGGCCCTCGGTGGAGATGTCCAAGAAGCCGCTGCTGCGCTGGTTCGAGGCGCGCAAGGACAG
CGAGTCCTTCGTGCGCCTGATCTCGTACTTCTACCCCTCGGCCGTGCAGAGCAACGTGAACCTGATCAACAACTTCC
ACCACCTGGTGCACTTCTTCGAGCACGAGAAGCGCGCGCGGTACGTGTTCGACCGCGGGGCCGTGATCGTGTTCCCT
CTGGCGCGCGGGTCCGCGGACTCGATCTCGCCGGAGGCGGCGGCGGCGCTGGGCTTCGCGCCGC ACTCGGAGTTCCT
CAAGTTCGTGTTCCTGCAGATCGCGCTGCTGTACCTGAAGATCTACGAGCTCCCGGTCTGCACGAACTTCCTGCACG
TGGACCTGAAGCCCGACAACGTGCTCATCTTCGACAGCGCGCGCGCGCTCAGCGTGACCGCGGCCGGCGCGACTTTC
CGCTTCGAGGAGCCCGTGCGCGCGGCGCTGAACGACTTCGACTTCGCGCGCGTGGCCACCATCGAGAACCGCAAGAT
CTCGGGCAGCGTCCGCGTGCCGCAGAACTGGTACTACGACTTCCACTTCTTCGCGCACACGCTGCTGCGCGCGTACC
CGCACATCGCCGCGGAGGACCCGGGCTTCCACGCGCTGCTCTCGGAGCTCACGGTCTCGTGCTCGCGCGGGACCTGC
GACCGCTTCCGGCTGCGCGTGTCCTCGCCGCACCCCATCGAGCACCTCGCGCGGCTGGTGCGCCGCGACGTGTTCTC
CCGCTGGATAAATGCCGCTGCAGACGCCCCCGACGCC GCCGCACTCTCCTGAGCCCACGCCCGCGGCGCCGGGCTCG
CTGTACGACGTCTTCCTCGCGCGCTTCCTGCGCCGGCTGGCCGCTCGCGCGGCGCCGGCCTCGGCCGCCTGCGCCGT
GCGCGTGGGTGCGGTGCGCGGCCGCCTGCGGAACTGCGAGCTGGTGGTGCTGAACCGCTGCCACGCGGACGCGGCCG
GCGCGCTCGCGCTGGCCTCCGCGGCGCTCGCCGATACGCTGGCGGAGCTGCCGCGCGCGGAC AAGCTCGCCGTCGCG
CGCGAGCTGGGCGTGGACCCCGAGCACCCGGAGCTGATGCCGGACCCCGCCTGCGCGGGCGAGAGCGCGCTCGCGCA
GAACATCGACATCCAGACGCTGGACCTGGGCGACTGCGGAGACCCCAAAGGCCGCCGACTGCGCGTGGCGCTGGTGA
ACAGCGGCCACGCGGCCGCGAACTGCGCGCTCGCGCGCGTGGCGACCGCGCTGACGCGCCGCGTGCCCGCGAGCCGG
CACGGCCTCGCGGAGGGCGGCGTGCCGCCGTGGACGCTGCTGCTGGCGGTGGCCGCGGTGACAGTGCTCGGCGTGGT
GGCAATCTCGCTGCTGCGGCGCGCGCTGCGGGTGCGCTACCGCTTCGCGAGACCGGCCGCGCTGCGCGCGTAGCCGC
GCAAAATGTAAATTATAACGCCCAACTTTTAAGGGTGAGGAGCCATGAAGTTGCTCGTCGGCATACTGGTAGCCGTG
TGCTTGCACCAGTATCTGCTGAACGCGGACAGCAGCACGAAAAGATGGTCCGAAGTGCTGAAAGGTAGCGAGTGCAG
GCCTAGGCCGATTGTTGTTCCTGTAAGCGAGACGCACCCAGAGCTGACTTCTCAGCGGTTCAACCCGCCGTGTGTTA
CGTTGATGCGATGCGGCGGGTGCTGCAACGACGAGAGCTTGGAATGCGTCCCCACGGAAGAGGCAAACGTGACGATG
GAATTCATGGGTGTAGGTGTGTCCAGCACTGGATCTAGTGTGAGCACTCAACATCTGGAA TTCGTGGAGCATACAAA
GTGCGACTGTCAGCCGCGCGGCGGACAGCAGACGACACCGACGCCACCTAGACGGCGCCGAAGGGCTTATTAGCAGC
AGTTTTTGTAGCGGGACGTTTCTGGGTTTCCTTGCGCGCTCGGCGGCGGGGCTGCTGCTCGCGGCGGGCGCGCGGTG
GCGGCGGCTGGCCGCGGCGCTGGCGGCCGCGGGCCGCGCGGCGGGGTAGCGGCCCGGCCCGGGCCCGCCGCAGCCCT
TCGCCTGCGGAGGAGGCGCCACGGCGCAAAGTGAAAAAGGACCGCCTAGCAGTCGAGACCCTCCCGCCACAGCCGCG
GACACCCACACCCGCCCTCCACACCACAGCCAGCAAGCATGCACCCCTCGCCGCGCAGGCTGCTCGGCGCGCTCGCG
CTGGTGGCGCTGGGCTTCCTCCTCGGCGGGCTCTTCCGCCCCGCGGCGCCGCCGCTGCCGGCCGCCCTCGTGGAGGC
GGGCCCCGTCCGCGCGAACGGCTCCGCCTCGGT GACCTGCCTGACCGTCGGCGGCGACGGGCGGCACATGGCGGTGG
TCGCGCACGGCGGCGGGACGCTCTCGCCGGTGTACCCGCTCGCCGCCGGCATGCACGCGACCTTCGCCTCGCTGCGC
AAGGGCGCGCTGCTGCTGAACGTCGCGACCGTGCACATCTACGACGTGCGCGAGCTCGCGCCGGAGTTCGAGCTGAC
CTGCGTCGCGGTGGCGGGCGGCTACAACGCGGCCTGGGCGGCCACGCGGCCCGCGGCC GAGTGGCGCCGCCAGCTGG
CGCAGATGCACCGCTCGGAGCTGTGACCCTCTCCCCGGTCTCCCATCCGTTTTTGTATTCGGCCTTAGTAGATTAGA
CCAGCATCCCGCGCCCCTTGCGCCGCCCTTCGCTCGTGAACGAGCGAATCAGTCAATTAATTATTTTTATCGCCGCC
CGCTCACTCCGGTAAGGGAACGCGGTTAACTCACCCACGAGAACAAGCAACCGCTCACTCACGAGGTAAGGGAACAA
CAGTTAACGTCAACTCACTCACGAGAACAAGTTGACCACTCTCGAGGCAGAGACGAGAAAACAAGTGACCGTACTCG
CTCACGAGAACAAGTTGACGCACCACTCGCCGAGGTAAGGGAACAGATAACAAGTAACAAGTAACCGTTACATCACT
CGCTCACTCCTCGGAAAATAGAACGAGAGAACGAGAGAACGAGTTAACTTACTCACTCGCTCACTCGGTGTGAGAGA
ACGAGAGAACGAGTAGCTGTTGCTCACTCAATCGCCCCTCGGAGTAAGGGAACAAGAGCAGTCAACGCACCCACTCA
GTCTTGGAGTGAGAGGCAGAGGACGAGCTAACGAGTTGAACAGTTAATCTCTCACCACTCAGAGTGAGAGAGCGAGA
GAGTGAGGACGAGTTAACAAGTCAATCCTCACTCAGAGCGAGAGAGTGGAGGACGAGTTAATAGTTAACGGTTAGTT
ATCACTCACTCAGAGTGAGAGGAGGGCGAGTCAACCACTCGCTCGCCCCTCCGAGT TAGAGAGGAGAACCAGTGAGC
GAGTTAACCCGCACACGAGCGAGAGAACGTGAACTCGCTCGCGCGCGCTCGGCTAACAGTCGGCCTCTCCCAAAACT
CTTCGTAAACTTTTCCCGTGACAGGTTCGTCCTTCCAAAACTAAACTGTCGGGTCGGCCTGCCTCTCAACTCTCCGT
AAAACGTTTGTAAACTGTTCGGAGGTCGGTGACCCGCTCAACCCGTCCGCGAAAACTTTTCGCAGGCAGTGTCTGCC
TCTCTCGGACTCTCCGCAAACACTTTCGCGGAACCTCGGGGGTGGTCGACCTCTCTCCAAACTTTGCAAAACTTTTT

FIG. 28HH

CGCGGAGCCTCTGGAGGCCAGTCCTCCCTCCAAACTCTTTGTAAGATCTTTTCGGAGGCCAGTCCTCCTCTCCAAAA
CGTTCCGCAAAATCTTTGGGAGGTCGGCCTCTCCTCTCCAAAACGTTCCGTAAACTCTTGGACGGCCGCCCGCGGCA
CGCGAGGCGGAGGATCCGGGGGTAGTCGACCTCCCTCAAAAACTTTGTAAAAACTTTTTATAAAACTTTTCGCGGAA
CCTCGAGAGTAGGTCGACCTCCCTCAAAACTTTTATAAAACTTTTTAGCGGAACCGTTGGAGGCAGGTCGACCTCCC
TCAAAACTTTTATAAAACTTTTTAGCGGAACCGTTGGAGGCAGGTCGGCCTCTCAAACTCTTTGCGAGAACTCTTCG
ATAACTTTAGGAGGTCAGGTCGACCTCCCAAAACTTTTGCGAGAACTCTCTGAA AACTTTAGGAGGTCAGGTACCTC
TCCAAAACTTTTATAAAACTTTTTCGCGGAGCCTCTGGAGACGGGCCGCCGCCCGCGACCGCGGGAGCGGAGAGGCC
GACCTCCCGAGACGTTCCGCGTTACCGTCGGGGTAGGCGTCCTCTCGAGAACGCCAAAAGACTTCGTGCAAAAACTT
TTCGGAGGGGCGCGGAGGGCGGGCGGCTCCCGCGAACTCCCGCAGAACCTTTTCGCGCGACCGCGAAGGCCGGCCGC
CTCTCCCGAACACTCTCAAGAGCTTTTCGGAGGAGGGGCAGGTCGCCCCCACCTCTCCGACGCTTTGTAAAAACGTT
TACGCGGAACCTCGAAGGCAGGTCGCCTCCCTCGAAAACTCCTCGCGAAACCTTTAAAAACTTTTGCGAAAACTTTT
CGGAGGATGTCGGAGGGCGGGCGGCTCTTCCAAACCTCCGCAGAACCTTTTCGCGCAACCGTTGGAAGACAGGTCGG
CCTCTCTCGAAAACTTTTAAAACTTTGTAAACGCGTTGGCGGGACCGTCGCGGGAGAGCGGCCGCCCGCGGCACGCG
AGAGGAGGAAACGTTGGAAGGAGTCGGCCTCTCCCGAAAACTTTTTATAAAAACTTTTCCGCGGAACCGTGGAAGGC
GGTCGGCCTCTCCCGAAAACTTTATAAAAACTTTTTGCGGGACTCGGACGGCGGGTCACCCGACCACCTGACTCCTG
TCTACCCGACTACTTGACTTCTGTCTCCCGGGCTCCTGACTCCCTGACTCCC GGACTCCCTGACTCTAGAGCGAGGT
CTCGCGGCTGCGGGGTGCCGCCTCCGCGGAGTCGCGTTCCCGCGGACGCCCGTCCTCGAAAGCATTCAGCAGTTCCA
GCCTCTGCCGTAGCTCCTCCCGCAGGAACTCCTGGTCCGCGTTCTCG

FIG. 28II

OVRF-121 RabV –G Complete Genome (SEQ ID NO:5)
CGAGAACGCGGACCAGGAGTTCCTGCGGGAGGAGCTACGGCAGAGGCTGGAACTGCTGAATGCTTTCGAGGACGGGC
GTCCGCGGGAACGCGACTCCGCGGAGGCGGCACCCCGCAGCCGCGAGACCTCGCTCTAGAGTCAGGGAGTCCGGGAG
TCAGGGAGTCAGGAGCCCGGGAGACAGAAGTCAAGTAGTCGGGTAGACAGGAGTCAGGTGGTCGGGTGACCCGCCGT
CCGAGTCCCGCAAAAAGTTTTTATAAAGTTTTCGGGAGAGGCCGACCGCCTTCCACGGTTCCGCGGAAAAGTTTTTA
TAAAAAGTTTTCGGGAGAGGCCGACTCCTTCCAACGTTTCCTCCTCTCGCGTGCCGCGGGCGGCCGCTCTCCCGCGA
CGGTCCCGCCAACGCGTTTACAAAGTTTTAAAAGTTTTCGAGAGAGGCCGACCTGTCTTCCAACGGTTGCGCGAAAA
GGTTCTGCGGAGGTTTGGAAGAGCCGCCCGCCCTCCGACATCCTCCGAAAAGTTTTCGCAAAAGTTTTTAAAGGTTT
CGCGAGGAGTTTTCGAGGGAGGCGACCTGCCTTCGAGGTTCCGCGTAAACGTTTTTACAAAGCGTCGGAGAGGTGGG
GGCGACCTGCCCCTCCTCCGAAAAGCTCTTGAGAGTGTTCGGGAGAGGCGGCCGGCCTTCGCGGTCGCGCGAAAAGG
TTCTGCGGGAGTTCGCGGGAGCCGCCCGCCCTCCGCGCCCCTCCGAAAAGTTTTTGCACGAAGTCTTTTGGCGTT CT
CGAGAGGACGCCTACCCCGACGGTAACGCGGAACGTCTCGGGAGGTCGGCCTCTCCGCTCCCGCGGTCGCGGGCGGC
GGCCCGTCTCCAGAGGCTCCGCGAAAAAGTTTTATAAAAGTTTTGGAGAGGTACCTGACCTCCTAAAGTTTTCAGAG
AGTTCTCGCAAAAGTTTTGGGAGGTCGACCTGACCTCCTAAAGTTATCGAAGAGTTCTCGCAAAGAGTTTGAGAGGC
CGACCTGCCTCCAACGGTTCCGC TAAAAAGTTTTATAAAAGTTTTGAGGGAGGTCGACCTGCCTCCAACGGTTCCGC
TAAAAAGTTTTATAAAAGTTTTGAGGGAGGTCGACCTACTCTCGAGGTTCCGCGAAAAGTTTTATAAAAAGTTTTTA
CAAAGTTTTTGAGGGAGGTCGACTACCCCCGGATCCTCCGCCTCGCGTGCCGCGGGCGGCCGTCCAAGAGTTTACGG
AACGTTTTGGAGAGGAGAGGCCGACCTCCCAAAGATTTTGCGGAACGT TTTGGAGAGGAGGACTGGCCTCCGAAAAG
ATCTTACAAAGAGTTTGGAGGGAGGACTGGCCTCCAGAGGCTCCGCGAAAAAGTTTTGCAAAGTTTGGAGAGAGGTC
GACCACCCCCGAGGTTCCGCGAAAGTGTTTGCGGAGAGTCCGAGAGAGGCAGACACTGCCTGCGAAAAGTTTTCGCG
GACGGGTTGAGCGGGTCACCGACCTCCGAACAGTTTACAAACGTTTTACGGAGAGTTGAGAGGCAGGCCGACC CGAC
AGTTTAGTTTTGGAAGGACGAACCTGTCACGGGAAAAGTTTACGAAGAGTTTTGGGAGAGGCCGACTGTTAGCCGAG
CGCGCGCGAGCGAGTTCACGTTCTCTCGCTCGTGTGCGGGTTAACTCGCTCACTGGTTCTCCTCTCTAACTCGGAGG
GGCGAGCGAGTGGTTGACTCGCCCTCCTCTCACTCTGAGTGAGTGATAACTAACCGTTAACTATTAACTCGTCCTCC
ACTCTCTCGCTCTGAGTGAGGATTGACTTGTTAACTCGTCCTCACTCTCTCGCTCTCTCACTCTGAGTGGTGAGAGA
TTAACTGTTCAACTCGTTAGCTCGTCCTCTGCCTCTCACTCCAAGACTGAGTGGGTGCGTTGACTGCTCTTGTTCCC
TTACTCCGAGGGGCGATTGAGTGAGCAACAGCTACTCGTTCTCTCGTTCTCTCACACCGAGTGAGCGAGTGAGTAAG
TTAACTCGTTCTCTCGTTCTCTCGTTCTATTTTCCGAGGAGTGAGC GAGTGATGTAACGGTTACTTGTTACTTGTTA
TCTGTTCCCTTACCTCGGCGAGTGGTGCGTCAACTTGTTCTCGTGAGCGAGTACGGTCACTTGTTTTCTCGTCTCTG
CCTCGAGAGTGGTCAACTTGTTCTCGTGAGTGAGTTGACGTTAACTGTTGTTCCCTTACCTCGTGAGTGAGCGGTTG
CTTGTTCTCGTGGGTGAGTTAACCGCGTTCCCTTACCGGAGTGAGCGGGCGGCGATAAAAATAATTAATTG ACTGAT

FIG. 29A

TCGCTCGTTCACGAGCGAAGGGCGGCGCAAGGGGCGCGGGATGCTGGTCTAATCTACTAAGGCCGAATACAAAAACG
GATGGGAGACCGGGGAGAGGGTCACAGCTCCGAGCGGTGCATCTGCGCCAGCTGGCGGCGCCACTCGGCCGCGGGCC
GCGTGGCCGCCCAGGCCGCGTTGTAGCCGCCCGCCACCGCGACGCAGGTCAGCTCGAACTCCGGCGCGAGCTCGCGC
ACGTCGTAGATGTGCACGGTCGCGACGTTCAGCAGCAGCGCGCCCTTGCGCAGCGAGGCGAAGGTCGCGTGCATGCC
GGCGGCGAGCGGGTACACCGGCGAGAGCGTCCCGCCGCCGTGCGCGACCACCGCCATGTGCCGCCCGTCGCCGCCGA
CGGTCAGGCAGGTCACCGAGGCGGAGCCGTTCGCGCGGACGGGGCCCGCCTCCACGAGGGCGGCCGGCAGCGGCGGC
GCCGCGGGGCGGAAGAGCCCGCCGAGGAGGAAGCCCAGCGCCAC CAGCGCGAGCGCGCCGAGCAGCCTGCGCGGCGA
GGGGTGCATGCTTGCTGGCTGTGGTGTGGAGGGCGGGTGTGGGTGTCCGCGGCTGTGGCGGGAGGGTCTCGACTGCT
AGGCGGTCCTTTTTCACTTTGCGCCGTGGCGCCTCCTCCGCAGGCGAAGGGCTGCGGCGGGCCCGGGCCGGGCCGCT
ACCCCGCCGCGCGGCCCGCGGCCGCCAGCGCCGCGGCCAGCCGCCGCCACCGCGCGCCCGCCGCGAGCA GCAGCCCC
GCCGCCGAGCGCCCCGCGCCGCCGCGGGCGCGCGCCGAGGCCGCGGCCCCGCGCCGCGCCAGCAGCAGCGGCAGCCG
CGCGTCCAGCGGGCCGCCGCGGCGCAGCGCCGCGCGCAGCAGCGCCGCCAGCGGCAGCCGCCCCGCCGCGTCCGGGC
CCGCCGCGCGCGCGCCCGCCGCCAGCAGCGCGCGCACCAGCGCCGGCGAGGGGCGCCGCGCGCGGACCAGGTGCTCC
ACGAGCAGGGTGGTGAGCAAGGATTCTCGAGAAGTAGGAGTCATGTGTGACGACAAGGAGAGACGTTATATTAGGCG
CGTCCTACTTCACTTTGAAGATGGTGTAAAGTGTTAAAACTTGAACACCGTTCACTCTACCACTGCCGTTACCGTGT
CCTGCCCCAAAAGCGACCACAGTGCTTTTTCCACCACCTGTTCCAAATCCGTTCCAAAAGCTCCCATCCATTGTTGT
TAGAACTTTCAGATGTTTCTCTAGGTTGTTTAGTTCCACTGC AAGTTTTGACCATTATCGTTACTGGACATGCTGTT
GGTAATGAGTTTAATAACCAATCATAAAAATAGTTATAATTTGTTATAATTTATAATTTGTTATAAAGCTATAAAGT
AGCAAACACTTTAATGTTATATTTTGCCTAACCCTCCGTTAACACCACCATTAACACCACCACTTAAGCTTTTACTA
CCACCACTACCACCTCCAACACACATTCTTTTCTCTAAAGGTCCCCAAATTCCACCTCCTGAACTTG GACGTTTTAC
AGCACCTCCGGGTGTACTTGCGTACCCTTTAGAAGTTCCACTGTGACTGTAGATATGATACTGTCCTTCTCCAGGCA
TGATTAAAGTGTGTTGTAATTAGTGTTATCTACACAACTGTGTGAGACGCTCAAATAAAAAGAAGCTACATTTTACA
ATTTTGATTAGCTGATGTACCACGCTGTATCGCGGCCACCACAAGAACCCAATCCAGTAGAACCAAATCCAGAGTCG
CCGCGGTCGGTGTTGTCCAAGCAGTTAACCTCTTGAACTGCTGGGCACGATATGCGTTCGCATATTAGCTGAGCTAT
CCTGTCTCCCTTCTTAACCTCAAAGTCGCTGTTTCCGAAGTTAAACAGCACCACTCCGACGTTGCCTCGGTAGTCTT
CGTCGATCACGCCAGCGCCCACGTCGATAAAGTGTTTGACTGCAAGGCCAGAACGTGGTGCTATGCGTCCGTAGCAA
CCAGAAGGGGGCTTTATCAGAAGGTCAGTAAATACTACGC GACTGCAATGCGAAGGGATGACACAGTCGTGTGCACT
ACATAGGTCTAATCCTGCGGCACCAGGAGATCCTCTGGCTGGTATAGTGGCGTTTTGGCTGAGGCGAACAACCTGAA
GAGTTTCCGTGTGGCAGAACTCCATGGCTAGGGTGGCGAGCGGCCGATCGACTACGGGGTGTACAATTTACACTTTC
TCCAGAAAAATCAGGGGCGGGTCAGCATGGCGCGGCGCAGGTCCAGCAGCGAGTCGTACGACAGG AAGCACAGGATG
GAGGTCACGATCTCCGGCGGCAGGGCGCACGGGCACATGAGGCCGGCGATCTGCTCGGCCAGCGAGACGCGCAGCCG
CATCATGCAGATCTTGCCGAAGAGCGCCGTCCCGTAGATGGGGAACTCGGCCGCGCGCTCCAAAAAGGCGTTCTGCA
CGAAGAGCGCCTTCGCGTCGTCCGCCGCGCGCAGCACGTCCAGCAGCGTCGCGTCCGTGTGGCAGCGCACCGCGCGC
ATGCTCGCGATCTCCTGCTCGCACGCGCGGATTACGGTCGCGTAGTCCGCCAGCGCGCGCTCCGCCAGCATGCGCGC
GCCCTCGCCGCGCAGCGCCAGCTCCTGCACGCACAGCAGCGCGGCCTCCGAGCGTCGGAACACGTGGCCCCATTGCT
CGGATGTGATCAGCGCGCGCGCGAGCAGCTCCGTCGGCGGGCGGCGCGCGAGCACGGCCGCCGTCGCGCGCACGTTG
TTGCGGCGCAGCATCTCGGAGACCGCGCATAGGCCCGA GGCCGACATGTGCTCGAGCTCCGCGCCCATGCGCACCAG
CCGGCAGCAGGCGCCGTGGCTGAACACCGCCGCGCGGTGCAGCGCGGTCTGCAGGTTGTTGTTGCGCAGGTTCAGGT
CCAGCCCGCGCTCGAGCACGAAGTCCACGACGCCGCGCTCGCAGCTCCCGTAGGTCGCCATGTAGTGCAGCATGGTG
TTCCCGCACGCGTCTACGGCGGCCGGGTCCACGCCCAGGCCCGTGAGCGTGCGCACCATGCCC TCGGAGATCTTGGC
CGTGCGCGCGAGGTGGTGCAGCGTTGTGCGCCCGTACGCGTCCACGACGCACGCGTCCGCGCCCGCGCGCAGCATCA
TGTCCACGAGCGCGGCGGAGACGCCGCCGGAGCACAGCAGCGCCGCCAGCGGCGTCAAGCCGTTGCAGTCGCAGGCG
TTTGGGTTCGCGCCGCGCTCGAGCAGCAGCCGCAGCACGTCCTCGCGGATCCACTGGTTCTTGGCGTACACGTGCAG
CGGCGTTACGCCGTAGGTGTTGCCCTCGTTCACGCGCGCGCCCGCGTCCAGCAGCAGCCGCGCGACCTCGAGCTCGG
CGCCGTCGGGGCCGCAGAAAGCCAGGAAGGAGGAGAGCACGCTGTCGCAGACGACGACGCTGGCGTCGCAGACCACG
TCCGCGCCCGCCTCCAGCATGAGCGCGACCACCTCCGGCCGCACGCCGTCGTACTGCACGTAGGCGTGCAGCGGCGT
GCGGCCGCAGGAGTCCTTGGCTTTCACGTCCGCACC GGCCTCCAGCAGCACGCGCACGATCTCCGCGCACGCTCGTG
CCGCGCGAAGTGCACGCAGAGGTGCAGCGGCGTGCGCCCGTGCTCGCCGCGGAAGTTCACGTCCGACGAGCGCGCGG
ACCGTTTCGAGGTCCACCTGCCCGGACTCCAGGTAGCGGAAGAGCAGGTCCGCGTGCGGGACCACGACGGACTCCCG
CGAGAGCATGGCGGCGTTTACAAATATTGAAATCTTTTTTCACTCATCTTTATGGGCGCTG GATGCGCAATAAGGGT
GGGAGTAAAAAACTTCTACAAAAAGCGTACAAAAGGTACAAAAGGCGGGGCGGGGACGGGCTGGCAGTGGGTGCTGC
GGGCCGAATTGGTCTCTACACGGGGACGCCCTCGCCGGAGCCGGTGAGCCGGTAGCCGGCGCCGGCGATCATGGTCA
AGCGCTGCACGAGCTCGTTGCGCTTGACGCCGGCCTCTGAAACGCACACCATGTGGTGGATGTACCGCTCGATGCAC

FIG. 29B

TCGCAGCGCGGGAGAGTGGAGTCAAGATCGGATGCGAGTTGCAGAATGTCATCCCAGAGCTCGGAGAACTTGCTGTA
CAGTTCTCGGAGGTCTCTCTCCATGCGAGCCATAAGAGAGTCAGGATGCGGCGTTCCTTCGGGGGTCTGAGCGAACA
CCGCGAACAGGCTGGTTATGCCGTGTTCCAGAATAGAGTGGTTCCGTGTCAATGCCGCAGACAAGGGTCGTCGTCCG
CGCAACGACTGGCGGCAGAGCGCTGTTTGTGCCGCACCGCCCATTCCTCTGGCGATCGCGTCCACCGACGCAGTGAT
CATCTGCGCGCCGACGTCATTGTAGCGCGCGTTAAACTCAGTAATCATGATTACGAGATTGCAGATTTCATAGTAGC
ACTTTTCCAAGTCGACGCGCAGTTTCACGATCTGGTTGACAATCTTGCACGCCTTTCGCCGCGTCTCCGCCACGTTG
GCGACTCGGACTTGCGCTTCCTGGTCGATGGACGGCGGAAACACTTCAAACCCAAGGTC GCACAGTTCAGCGGTGGG
GACTAGCGTCACGATGATGTACTCCGCGTCGCCACCCACTTGCGGCAGGAAGAACACCGACCGCGCGGCGGGAACGA
CCAGAACGTCGCCTTCCTGCATGTTAGTTTTTAGAAACTTAGTGTTGTTCACGGAGATGCCGGCCATGCCCTCGTTT
TTTACACATATTATGGTGACGTACGCGGCGACCGTGGGGGCCATGTGGTGGCGCATGTACCACTCGTCGTGCTTGAG
TTTCAGACCGTGAGATTCGCCGACCTCGAAGTGCATGTTGGCGTCTCTGACGTAGCGCGAGAACTCGCTGCGACAGA
TTCGGGCGGGCGCCCGGTGGAACGTCGACTCGAAGAGACTGATGTCTGTCCATTCGCCCACATGAGTGACCACCGAA
GAAGTGTTTTCGATCCGAGTCTCGAACACCGAGTCCACGAGCACCGGACAGTTGGTTCCGGGCACCGTCAGCACCAA
GGGCCGCGCCTCCACGGGGGCGACGGACGAGGCCACGGAGTCGGTGTCCCCGTACCCGTAGTCGTCGTCGGAGTCGC
CGCCTCCGTCGGCCCCGTCGCGCGGCCTCCGCAGCGGCATGCAGCCGGCGGTGGGAACGCACTGGTTTCGGCCACGG
CCGAAGCGGCCAAACAGTCTCGCCAGGGCTGACATCCTTGGACGGCCACACCAAAACCAAAAAAACATATTTTATCA
GTTATTTGTCGATTTTCACCGGCTCACCGAGGGCAGGACCTCCTGGATCCCGGACAC CCCCGCCAGGCAGCGGGCCG
CGCGCTCGCGCACCCAGAAGCGGTCGTAGCCGTGCCGGAGCACGAAGGCCGCCGTGGCGTGGCAGTCCACGCGCTCG
ATGAAGCCGTGGACGGCGCGGCGCGCGTAGCTCGCCGCGAAGGCGCGGACCACCGCCGAGCAGCGCCCCGAGGGCGA
GTCGTCCGTCTCCAGCGCCAGCGGCATGCTCGCGATGCGCGACATCAGGTTGGAGGTCTGCGGGATGTTGAGCTCGC
GCGTGGCGGTCATCTGCGCCTCGAGCCCGGCCTTGAGCACCTCGTCGCAGCGGCCCCACTCCAGCGCGCAGACCACG
CGGATCTCGTACCCCTTGAGCCGCAGCGCGGTCTCGATGTCCACGGAGGTGAGCACCGCGCTGAAGCGCAGGCTCTC
CTCGTCCGCGGGGTCGAAGAGCACGGGGATCTTAACCTCCGCGCTGCGCGTGACCTCGCAGAGCGCGATCGCGAGCA
GCCCGCGCGTGAGCTTGCTCACCACGCGCGGCTTGCCCACGGGGTACAGCTGGCTCGCGACCTCGCGCAGCGGGTAC
GCCAGTCTGAAGCAGCGCGCGTCCGCGGGCACCGGGCTCGCGCCCGTCTCCTCGAGGAAGAGCGCGGCCTCAACCAT
GTTCAGCGCGGAGAAGTGCACCGGGCAGGCGGCGCAGCCGCGCGCGGCGTTCGCGAGCACCATCTCGCGCAGCCCGC
GGAAGGCCGCCATGTCGCAGGAGGGGAAGATGCGCGCGAGCGCGGCCTGGTGCGC GAGCGCCGCGTCCGAGAGCGCC
TGCGCGGCCGCGGCGGCGGCCTCCTCGGCGGCGGCCGCGCTCTCGTCCGCGGAGACCACGTCTTCGGGCACGTCCAC
GCAGACGCCGCCCCAGAACTCGCAGTACTCGGAGAAGAGCGTCGCGGGCGCAAAGCGCGCGAGGTCCACGAAGGCGA
CGCGGTTGCCGAGCCTGGAGAGCAGCGTGTTCTCCGAGATGCGCGTCCAGCCCTTGCCGGCGAGCTCCATGACCTGC
CGCGTGTCGAAGAAGGAGCTGTAGAAGCCGTACACGGTGATGTTTTCCTTGCACGTCGTCAGCCACATGAGGAAGTC
GCGCACCACCAGCTTCGCGCAGTCGCCGGAGAACACGGGGCCGGCGTTCGTCGCGATGGAGTTCAGGCGCACGGTGC
CGTCGTGCCGAAGCGGTACACGAACCAGGCGGCCACGCTGTTGCCGGAGGGCGCGTGAACGTGTGGCTGCGCCCAGG
CGTAGCTGCCCACGCAGCACACGTTCAT GAGGTCGAGCAGCGTCTGCCGGCGCAGCGGCGTGCCGAGCCGGCGCACG
GCGTCGTGCGAGACCATGCGCAGGTCGTAGAGGCCCACGTCCGAGAGCCACTGGTTGAGCTCGTCCATGGACAGGGC
GTCGCGGGGGGGCGGGCTGTCTTCGAAGGCGGCGCGGAGCTCGGGCTCCGTCTCCGCGCGCTGCCGCAGGATGTCCA
GGAAGGGGCTGGAGGAGTCGGGGATGTAGCAGTCGGGGTCGTGCCTGGACACT ATAGCGAACCGCTGCGTCGCGGGC
GCGGGCGGCGGGGCTAGCGCGTCGGCGCGTGCGTCGATGAAGGTGCACGATATACGCACGGACTTGAGCGAGGGGAG
GACGACCGCGGCGGCGCGCGCGCCCTCCGCGTCGAAGATCATCGTCTTTCCGTCCCTCGCCTTCGCGAGCGCGTATT
CTCCAGGCACGAGGTCCGTCGGCGGCGGCTCGTCCCAGGCCTGCCGGTCAGGGACGCCGCCGCACACCTTTCCCCAG
AACCCCAGCATCCTCCAAAATACCTAATAAGGACGGCCAATAGCGGGGCTTGCGGGCGTTCGGACCTTCCGCGCTTT
AATTTTAATTTATTGGCTTGCAGAACTCCGAGCGCCAGTCCCGCTCGAAGACCGCGGACAGGTCCTTGACGATGTCG
CCCTTCTCGGCGTTCACGCTCACGAAGGCGTGGTAGCGGTAGTGCGTGCCGTCGAGGTTGGCGACCGTGAGGTGCGC
GAAGGTGTCGTCCACGATGAGCAGCT TAGTGTTGTTCGCGGCGTCGTCCCGGCCGGGTACCACGAACTTGCGCACGG
ACATGTCCACGCTGCCGACGCCAAAGTCGTCGAGGCTGCGCGCGGCCGAGACCGACAGCGGGTCCGCGTTCTTCCAC
TCGGTAATGATCACGCGCACGCGCACGCCGCGGTCGATGGCCGCGCGCAGCAGCGCGTCTATGATCCGCGGCCAGTA
CTCCACGGCGCTGGCGTGCTTGATCACCGGCACCATAGAGAGCAGCGAGAG GTCGATGCTGTTCTTGGCGTTCTCGA
TGCGGTGCAGCACGAGGTCCTCGTCGAGCGTGCGGTAGAAGCCTAGGAAGCGCTCCGGCGAGTCCGAGAAGAATACG
CCGCCCCCGGAGTGGTCGAGGTGGAAGTTCGTGGCCGTGGGCGTGACGACGGCGCAGCAGAGCCGCGTGAACGGCAC
CTTCGGCTCCACGATCATGGAGTAGAAGGTGTTGTAGCGGTTCATGAGGTCCCAGGCCAGGTGCTTGTTGGTGGAG T
AGAGCCCGAGGTTCTTGATGGTGGACACGGACCCGCCCGTGAGCGAGGCGCTGCCCACGTACCAGTGCCCGGCGTCC
GAGAGCCAGAAGCTGCCGAGCAGGTTGCCGACGCCTTCCCGCGTGGACACCTTGACCTTGTAGTAGTTGACGCCCGC
CTCGCGCAGCTCGTCCGCGTCCTTGTCCTTGCTCTGCACGTCCACGAGCAGCGTGACGTTCACGCCCTCCTTGGCGA

FIG. 29C

GCGTGCAGAGCTTGTCCTTGACGTCGACGCCCTCCTTGGTGGAGCTCAGGTTGCAGCAGAAGCTGCAGATGTACAAA
AACTTCTTCGCGGACTCGGTGATGGCGGTGAAGCAGTCGAGGGTGCTCATGTTGCCCTGCGCCAGGGACGCCACCTC
TGCGGGCAGCGTCTCCACGACGCGGCAGTCGGCGCCCAGGGGGATGGAGGAGAACGGCCACATTTATTTATCTCACA
AAAATAATAGGGCTTCAGGGAAAGTCTTTTAGCAGGCGGGCGAGTTCTT CGAGTTCCCTTAGGAGTTCTTCCATTTC
TTCGGAAGTCAGCAACTGGAGCTCGGACTTTAGTTGAATATCTTCGAGGAAACCGTCTAGCATGTTCGCCATGTCTT
CCGGGGAGCACTGCGCCACATCTTCGGGGACAGGATCGGGTGTGGGCATTAGGTCTCCGCTTACTTGAACGTCGTCC
ATCATCCTGTCGATGAGGTCTTCGACTTCTAGACGGGGTCCGTAGATCAGCATATTTGGTGATGGAGGTAGTTT AAG
GTGCGAGAGTTAGTGTTATACGACGGCCAACGTGTGTTTATCGCGCGTACATTTTCAATAATTAACAAACTCCCCTT
CCTGCGCCTGCTCGAGAAGCAGCTCGTCCAGCTCCTCCTGTCGGCGCGCGGCCACGCGTCTTTCCGCGAAGAGTACC
ATCAGCTCCAGCCCCACTCCGCACAGACCCAGGACGCCGAACACCACCGCCGCCGAGATCGACAGACCCAGCAGCAC
CGACATCCTCACGCGGGCATCCGGCTATTTAATCGTTCTGGAAACGTATTAATATGGGCGTCGTCATGTGCGGGTGT
CTGTTTGTGTGGGCGGGCTGGATCGCGCGCCGCGTGCGCGGCTTCTGCGTGGCGCTGCGCCAGAGGGTGTCGCGCGA
CAAGGGCTACGTGGCCGTCATCCAGACCTGCGACGACGACTACTTCACAGAGGAGGAGTTCGACGACGGCAAGCAGG
TGGTCGCGCTCCTGCGCGACGTCTCGCGCGTGGTCGCCGCGCCCGCG GGCGTGACGGAATAAGTTAGGATAAGGAGT
CGAGGGGAGAAAAACAGCGGTCACACTATAAACTCGCGCGAGGCCGATTTTGACGTGCTCATGTCCGGAAGCTCCGC
TTTCTGCAGCGCGGAGCGGCACACGAAGCACACTTCCGTGTTGGTGGGAGTTATGCAGTGGACGTGGTAGCCGTGCC
CGCACACCATGACTTGGACGGACACGCGCCGGGACAGGCCGCGTTTATGCATCCTTCCGGCGAGCGCTTGTT GCAGA
TGTAGCACACGTCCCACTGCTTAACCTTAACGGGCATGGCTAGTTGAACACGACCATGGGCGAGTCGCGAGCCTCGA
GTCGGGGTTCAGGGCAAACCGTTTCACGCCGTCAACGGTTCTTCTCTTTGCAATTTTCTCTCGGCACAGGCTCGTCA
GCGTCATCTCGGCCAGGCGCGCGTCGTTGCCTAGGTGCCGCGCGGCGTCCTCGACCGTCACGCCCGTCTTGCCGGCC
TCGTCCATGAGCACAATGCAGACCAGGTGCGCGCTAGAGCATATGACCTCCTGCTCGCGTCCGCCGGCAGCGGGGAT
GGTTAGCTCCGCGCGCCCGAAGGCCGCCAGCGGCGCCACGTCGTAGGCAGTGTCTGCTCGGGCGAGCGCCGACTCCA
CGGCACCGCGGAGCGACTCCGGCGGCGTCATCGCGGCCAGCGGCACCGGCGTGGGCACGGTGTACACGTTCACGGGC
ATGAGCACCATCTCCGGGTCGTGGTGGCCGCTCTCTTCGCCGTCG TGCTCCATGGGCTGCGGCGGCGGCAGCAGCGG
GAGCAGCAGCCGTCCGGACATGAGCCGGCGCACAAGGTCGTTGAGCGCGGACGAGGCCATCGGCGGGTACAGCTCCA
TGGCCAGCTTCAGCGATAGGTGCTTCTCGAGGTTGACGCCGGTGTAGACGCTCTTCACGATTCGCGCGAAGGCCACG
CGCGCGAAGGCCGCCAGCTCCTCGCGCGGCAGGCGCTCGATGTAGGAGAGCAGCATGTCGGTGTCGCACG GCGGCGC
CGCGACCACCGCGCCGTAGAGCGCCTTGCCCGAGAGCCTTTCCAGCGCCCTTGCGTGCAGGCCGTGGGTCTTGAGCA
CGTCCACGTAGTTCACGTACAGGCAGAGCGCGCGATCGAGGTTGCTCTCCGCGACGTGCGTCTCGATGCACTCCACG
ATGAGCGGGCCCATGCGGTCCTTGATGAGGTCTATGAGCCCGCCGGAGGCGACTCGCGCGCTCATGAGGCACGTGCG
GCAGTACGCCATCAGGCCCTCGAGGTCCGCGGCGATCACGTCCTCGACCACGTTCGCCACGACGCGCGGCCAGAGCC
GCACCTTGCTCACGTTCTGGTGCCGCACCATGTCCACGAGCTCGTCGTACGAGCCGCCGGGCTCGTGCGCGCGATCG
ACGATGCACCTCGCCATGGTGCGGCTCTGGCGCATGAGCTCGTTCGTGAAGCGCACGCACGCGTCCTCGGAGAAGAG
CGCGCTCAGGCAGGAGTAGCAGCGGTCCGCGACGAGGTGCGGGAAGCGGCACTCCACGACGCCGCGGCCGATCCGCA
GCACGCACTCGCCGTACATCTCGTCCATGGCCTCGCGCAGACAGTCGTCCAGCACGTCCGCGTTGTGCGCCCACTGG
ATCACGCAGAGGTAGGGCTCGATGTTCTCGCGCGCGTTTTCCACCTCCTGCACCATGTACTCGAGCACGGTCATGTC
CTCGTGGATGTCGGTGCCCAGCATGCGCCCGGGCGGCAGCCAGCTCTTGCGCGCGATCGCCTCTCGCA GGCACGCCA
CCGCCGTGAAGGTGTTGACGCGGAGCTTGGTCAGTAGCCGCCGCAGTCGGGAGATGTGTGCCACGGAGAGGTCCATC
TCCATGGCCTGGGCGATGAGGCGCGTGAGTTCCTCCTCCATGGCGGCGGCTCCGCGGGCAGATATACGCGAACAACG
GTAAGCCGTGCTATTTCATTTTTGGACAAAAAGCTAGTCGTCGACGCGCATGTTGTCGAGGTTCCGGCACAGCGAGA
GCACGTCGTCGCGCGCGCGCCTCCGGCGCAGTTGATTGTTCGCGCGCCGCGCGTCCGCGAGCGCCTGTCTGTACATC
GCGGAGTCCGCGTACCCGTGCAGCGGCGAGCGCCGAGTGCCGGGCCTCGGGCTCGCGCGGCGCGGGAGCGGCGTTGG
CGCGCGCCTCGAGCGCCGCGCGAAGTGCGCCTGCATGGCCAGCAGGCAACCGAACGGCATCATGTATCGGTCCATGA
GGCACTGGCTGGCCGCGGACGGCTCGCGCGGGTGCAGCAAG CCGCCGCCCACGTCCTCCATGACGTCGCGCAGCACG
CAGCGCAGCATGGTCTCCATGCCGTCCACGGGCTTGAACCTCATTGGGGAGGCGTCGACGTAGAAGCCGTCGGCCAC
GAAGTAGAGCGCGTCCAGCCCGCCGAGTTTCTCGCCGAGACCGACGAAGAGCTCGTCCACGTGCCAGTCCACCACCG
AGGCCTTGAAGAGCACCACGTGCCGGACGTCGTGCGAGCGCGCGAGCTCCCAGGTGTCCTCGCCGA TGTTGCTGGCG
TCGATGCGGCCTGTCATGCGCACGCTCACGCACGGCGTCATCCCGTTCTTGTAGCAGAACTGGCGCGCGAGCTCCTC
CTGGCGTACGATGTCGACCATGCTCTCCATGAAGGAGGTGGAGAGCAGCATCGCGCCGCGCGCGGCGCGGGTCGCGT
TTTCGTCCACCTCCACTTCCATCCCGCCGTCGATCCTAATCATCTATCGTATTTAAATTTTCGGCGGAGCAGACACG
CGGCTGCTCGCTGCGCGATCGCTTCAGCCGCGGCGGCGTCACGCACGCGTTGCGGCGGCCGGCACGCACGAACGACC
GCCGGGGCTCTTCGCTGAGCGAGCGCCGCGGCCGCGTGACGCGACAGTCGCGGGTGGGTTGCCGGGAGTCGCTCGCG
CGCCTTCTGCGCATTTCGCCGGAACGCCGTGTTTACGTAGGGTATTATATTTTCAACGTAACTAAATGGACGGGGGC

FIG. 29D

GTGCACAAACGGCCTTTCATCGTGAACGTGGATGGCATGGGCAAGGTGCTCGTGCTCCGGTACTTGCGGATGTGCGA
GGTGCCCAGGCTAAGTGCGAGGGCTCGCGCGCGTCCTGCGTGCTCAAGATGGACCCTCCCCGCTCACCCAGTTGCGA
GTCCCCCCCATGCCCCATGCGCACGCCCCCCGGGTCGCCGCTCCAGGCTCCCTTAGGAGAAGCAAGGTTCAGCAAAA
ACAACGGCGAGCAGATGTGCCGCCGCCAGTAACCTAGGCGTGCGCAGTACGAAAGTTAGTGCGT GATCACGTTTTTT
GCAATGTCGATCACGCCGTGCGTGCCCGTCTTGCGCTCGCGCTCCACCACGCCAGTCACGGGCCGCGCGTCCGAGAC
TAGCGACCCCAGCATCGAGCGCACGGCGCCCTCCGCGGCGGGGTGGCGCGTCAGCAGCAGGAACATCACGATGTGCG
CGGAGACGCCGCGGCGGCTCAGATCGTGCACGGCGTCGCCGTCCATGAGCACGGTGTTTGAGAAGTACGTGAACAGA
GTGTTGTCTCGCACCAGGAAGGCTGAGTTCGAGACGCTCTCGAAGTCCACGATCTCGTCGTCCTGCACGCCCATGTC
CAACAGCGTCTGCACGAGCGCGGGCTCGTCCAGGAACACCACGGCGCGCGCGAACCCGCAGTCCAGCGCGCGCGCGT
CCGCCTCCAACACGCGCGAGGCGCCGCCCTCCGGCGGCAGGAAGGCGCAAGGCAGCGGCGTGCGTCCGTCCGCCGGC
GCCTCCCCGAGCTCCTCGAGCGCGAAGGCCAGCAGCGTCTCCATGCGCGCGCGCGCCTTGTCGAAGTTGTCCGCGAG
GTCGCGGATGCGGTCTGTCTGCGAGAACATCTTCAGCATCGCCATGAGCTGCACGAAGGGGTGCAGCACGTATATGT
TGTCCACGAGCAGCGTGGGCAGCGCGCGCAGCGTGGCCTGCCGCACGTTGAAGCTGTCCAGGATGTGCCCGCCCTCC
TCGTCCTGCAGCACCACGTAGTTCTTCAGGTAGGGCACGCGCAGCAGCACGGTCTGCCGCCC CGTGACGAAGTAGAT
CAGGAAGGCGAGGTTGATCAGGAACGGGCGCGCGTTCGTCTGCACCATGTCGATGTCGCCGTACTCTATCTCGGGGT
TCAGCAGGTGCAGGGCGTACGAGCCGTAGCACACGCACCGCTTGTTGTGTCGGCGCAGGTGCTCCTTCACGAGCCGC
TTGACCACCTCCACCAGGTCCGAGTGCTTGTGCCGCGCCATCGGCGCGGCCTCCTCGGACGGCGGCAGCACCGCGTA
CGAGTTGAGCGCGCGGCTGGCGAGCGCGCGCGCGCGGGGCGCGTCCACGCGCCGCACCGCCGCGTTGATTGCAGGCG
TCGGCGTCGTGAGAGAGCCCAGCGTGCGCGTGAACTCGCTCACGATCACGCTCTGCAGCTCCAGCACCGTCAGGATC
TGGCCCAGCTTCTCCAGGCGCCGCTGCCTCGAGAAGTACTCCTCGATGCGCGCGGCGATTTCCTTCTCGGAGCCGCC
TAGCTTCTTGAAGAAGCGACGACGACTCTTTACAA CAAGAGAGAGAAAAAGCTTCCTATCGAAGTTGAGGACGCGGG
TCATGTTGCGGCGCTGCGCGCGCAAGAGCACGCAGCGCTCCATGGAGGGGCGCGAGCCGAGGTACTCTTCGATCACG
GGTGGAGCCATGACAGCTCTATTTTCTGAACCCGCGATTATTGTACAGCGCAAGCCGCGCGCAGACCTGCTGGCACA
GCAGCGTCGTGTTTCGCATGCACACGCGCGAGGACTCGATCGTGCGCGCGTCCGGTGCCC AGGCGCGCAGCTCCATC
AGTTCCTGCTCGACGAAGTCCACGGGCTCCACGAAGCGCTCTGCGCAGAGTCCGTCCGTGAACGCGTTGACGATCTG
CCGCACGAGCACTACCACGTCCACCTGCTCCACGAGGCGCACGCCCATGGCGATGTGCACGAAGAGGCAGCGGAAGA
GCGCGTCCATGGCCATCTGGTGGTCCGAGCAGGGCCCGACCGCGGTCTCGCAGCCCAGCGCGAAGCGCCCGATGCCG
CGGTACTGCACCATCTCCGAGGGCGAGAAGGAGAGCCGCTCCATCTTGAGCACGGGCGGCGGGCCCGCCGGCAGTCC
GCGCGCGAGGTCCAGCACCGGCGTCCACCCGGGCGTGAACATGTCCGGGATCAGGAAGAGCCCGTAGCTGGCCATGC
GCGCGATGTCGAAGGCGTGGTCCACGACCTTGTTCACGGCGCTGTCCGCGCGGTTTACGCGCAGCGCCTGCAGGATC
ACGTTTCCGGAGGCGTGTCGCGTGATCGCGAGGTCCGCGGTCGCGTACCCGCGCAGGCCCGGCACCGCGTACGCGGT
CAGACACACGGCCAGGCGCGCGCTGTGCTCCGAGGAGAAGATCTCCTGCTCGTAGCCCTCCTCGGGCTCCTCGCACT
CGCGAGGGCGCCGCACGTCCTCGACCGAGCGCAGCCGCATCTCTCCCTCCGACACCAGACAGCCAAGCGACTCCCTC
ACCGCCGGCGCGAGCACCTCCGTGGCGCAGAGCGCGTCGTGCACGCGCTTGAGCGCGT TCGGCTTCAGCGCGTAGCC
GAAGAGCAGCCGCGTCATCCGCGAGCCCGAGAACGCGAAGCGGCGCACGTACTCCTCCGCGAGCTCGGGCCGGTCGT
TGATCCACGAGGTAGAGAAGACGTGGTCGGAGGCGAAGAGGTCCGCGCCAACCGCGAGCAGTGTGGATAGAGACACG
GTGTCGAGGAAGTCCACGACGTCGGGGAAGTTCTGGCGCACGCAGGCCTCGGCGACGCGTCTGGTGTGCACGCACAT
GTCGGTGACGGGCACCCGGTGGCCGGACTCCACGACGGACACGCAGACGTCCTCGGTGACGGCGTCCACGGGCATGG
TACGCAGCAGCTTGCCGAGCACGTCGCCGAACCCGCCATCGAGCGCCTTGCGCCACACGAACCCCCGTCGAACTTGC
CGGGGAAGTCCGCGATCACCGAAAGCTCCGCGTGCGAGAGGTTGTCCACGTTGAGGTAGGCGTAGTGGAGGTACTCC
CGCACCTGGCCGGCGCGGATGCGCTCGAGCGCGAAGGCCTTCATGGTTTCGGAGCAGAGCACGGAGTGCCGCAGCCC
GTCCAGTGTGCGCCGCACGTCGTAGACGCCGCGCATCTGCGCGAGCATCTCGACGGCGTCCGCCGGCGTCGCCGCCG
CGAGCCCTGAGTTCACTGGAGGTATCCTGTGTTCTGCGAGCATGCGCTTGAGGAAACAGAGGTCCAGCGGCCGCGTG
GTGTACAGCGCGGAGGCCATCTCGGGGCGCGCCTCGACGATGTCCTCGATCATCTC GTCCGTGAAGGCCGCGTTGAT
GTTGTGCACGCTGCGCGCGTTCACGTGCAGGAGGATGTCGCCCACGTTGTCGGGGAATCGCTCCTCGATGAGCCGGA
CGTCGTCCTCCGTGATGTTCATGTAGGGAATGCAGCGGCAGAGCAGCGCGTAGTCCGCGAACTGCGCGATGTAGGGC
GTGTGGAACTCGATGTGTCTGGCGAAGAGCGCGCCGCAGCGCCGCCGCGAGAGCTCTTCGAGCAGGTCCTCGGGCGT
GACGTGCTGCGGGCGGAAGAGGTGCAGGTGCGTGGGGTGATCGGCGGCCACGCGCGCGTACAGCCGCCGCGGGAGGT
GCCTGGGGTGCACGCCGGCGAGCACGAGCTCCATGGCCTCTGAGGTAGACAGTGCGGCGAACGCGCGCTCGGTGCCG
CCCGCGGCGACGGCGGCGCCGACAAATCTCTTGAGCAGCTGCAGCATCGCGTGTTTGGGCTTTCGCGGAAGGCGCTT
ATTTTAATGTTATTGGCGGTGGCCGGTGC GAGATAAAAATTAGAACTGATGCCGCAGTTGTTGATGATGATATTAAT
TGCGCTGGCCGGCGAGAGATAAAAATTAGAAGGTGATGCCGCAGTTGTTGATGAGGATGGTGAGTGCGCTGGAGCAG
GCGGTGTGGCGCGCCAGCTTCTTGCTGGCCCCGTCGGCCACGGAAACGACCTTTCCGGATATCGTGATGGTGCAGGT

FIG. 29E

GAAGCGCGGACAGTGATCCTCTCCGCCAGAACGCGTCTCGCAGAACTCCAGAGATCTGCGCGTCATCATGCAGAACT
CGTTGACCGCGCTGACCGGGTTAAGACTTTTGAGGCGCATCACGGCAGACTGAGTCATGATGTCGATGTCGCCGCCG
AAGAGCGTATCGCACCCAGCCTCGGTCTCCATGGGCTCGGTGTCGGAGTTTTCGTCCTCCTCGGTGGGCGCGGAGGG
CGCGCACTCTACGAACCAGCGGGGCGGGTTTCCGTCCTCGCAGCAAACCTCGTCCGAGTCCAGCAGGCGGTACAGCT
GGCGGTTCGCCTCGTGTTTGGATATGCCGAGTTCCTTCGCGATCTGCTTGGCCGGCAGCTTGTCGTCGGATTTTCTG
AGAAGCTCGAGGATCAGAGATGCGCACTCGCAGGCCATTGTGGCGTATTTACGGGGCGTGCGTTTTTTTAGGATTTT
GGCTTGCCTTTCTTTTCGCAGAACTTGGGAGGATTGAAACTCTTTTGGCAATTTTTGCAGGCGTACTTGATCAAGGG
CGGCTCGTCCGCCGAGCGCGTCTGGATCATCATCGGCATGGTGTTCTTGCTCTGGCACGAGGGGCAGGGCAGGTTGA
ACTTCTCGTCAAGCACGTTGAAGTACCCGCTGTAGTCGTGGTCCGGCACCTCCTCGATGTCGTAGGGCACCCGCGCG
GCCGCGCACTTGACCGCGAAGAGCAGGTACCGCAGCGCGTCGTGCTCTGCGCCGCTGGTCGCGCGGATCTGCGCGCG
CAGGTCCGCGTAGTCCTCGTTCGCGTCCACCTCCAGGCTGCGCTTGTTCTTGTACGAGAGCCGGTTCTTGGCGTCCT
TCGAGTACTCGATGCCGATGTTGTGCGCGGGGTCAAAGTTGGTCTCGTCGGTGTTCGAGGTCTTGGTGTTCACGATG
TTCTTCAGCGCGAAGCGCTGCGCGCAGTCCAGCGCCCATCGCGCGATGCGCGCGGCCTCTGCCGCGTCGGTGTGCTT
CGCCGCGAGGTCGCGCAGCCGGTCTTCGTCCATCGCCCGATTTTAGGTTGGGTATATTATCTCAATTCCGCTCTTCC
GCGGGCCGCGGGCGCGCGCCCGCGGCAAATTAGGCGTTACAAATGGACTTCGTGCGGCGGAAGTACATGATACACGC
CATCGACCGCAACCTCGACTTCATGAAGGCCGAGGTCCAGCAGAAGGTCTCCATCTTCTCCCCGGGCACGTGCTCGC
GCTCCACTACCTGGTCACCGCCTTTCCGCAGGCGGTCATCACCAAGGACGTGCTCGCGAGCACAAACTTCTTCGTGT
TCGTGCACATGTCGCAGCGGCACGAGGTCTTCGACGCCGTGCTCAAGGCGGCCTTCGACGCGCCGCAGCTCTTTGTG
CGGGCGCTCTCGCGGCACTTCGAGGCCTTCGTTGCCGCCATCCGGGCCTACCGCGCGACCTGCGCGGAACTGCTGGC
CGACGCGCGCTTCATGGAGGTGGCCGCGCGCGCGGCCGAGCTCGCGGAGGTCATTGGCGTGAACCACGACATCGCCG
CGAACCCGCTCTTCGCGGACGGCGAGCCCGTGCGCGACGCGGAGCTCATCTTCGCAAAGACCTTCCGCAAGACCGAG
TTCCGCGCCGTCAAGCGCCTCGCCGTGCTGCGGCTGCTGGTCTGGGCCTTCCTCGTGAAGAAGGACCTTGGCGGCGA
GTACGCGGACAACGACCGCCAGGACCTGTTTACGCTGCTGCAGAAGGCCGCGGGGCCCGTGCGCCACAGCGCGCTCA
CGGAGAGCATCCGCGAGTACCTCTTCCCCGGAGACAGGCCCAGCCACTGGGTCTGGCTGAACGCGCGCGTGGCCGAC
GACGCGGAGGTGTACCGCGACCGGCCCGCGCGCACGCTCTACGAGCGCGTGCTCAGCTACGCGTACTCAGAGGTCAA
GCAGGGGCGCGTGAACGCCAACACGCTCAAGCTCGTGTACCGGCTCGAGGACGACCCCGACATCAAGGGTCTGCTGC
TGCAGCTCATCTACGACGTGCCCGCGGACATCGTCGGCGTCGTGGACTCCGCGAACGAGGAGTGGCGGAGCTACTTC
GTGAGTCTGTACCGCGAGAACTTCGTCGACGGACGCACCTTCACCTCGGACGCGCGCTTCCGCGACGACCTCTTCCG
CGTGGTCGCCGCCGTCGAGCCCGACTTCTTCGAGCCCGAGCGCATCCGCGAGGCCTTCAGTGCAGACGCGCGGCTGC
GAGAGCGCTTCACGGACATGGACCTCAACAACGCCTTCATGTCGCACCTCATCTACGACTCCGTGGACCCCGACGTC
GCCGCCGCCGAGCGCGGGCTCGCGCTGCGCGTGCACAACGAGGACTCCGACTACTTATCCGGGAGTACAACACCTAC
CTCTTCCTCAGCGAGAAGGACCCGCTGGTGCTGGACCGCGGGGCGCTCACGCGGCTCTCTGACGTCCCTACCGAGCG
CTTCCGCGACCTCTTCAGCGACAGCGTGCTGCGCTACTTCCTGGACGCGAAGCTGGGCACGCTCGGGCTGGTGCTCG
AGGACTACCGCGAGGACGTGGTCGCCGCCATGCTTCGGCACCTGCGCCGCGTCGAGGACGTGTCTTCCTTCGTGACG
TACGCCGCGCGCAAGAACCCCGCCTGCGTTCCCGGCGTCGTGCGCGCGGTCGTGAGCAACTTCAACCCCGCGGTGGT
CGCGGCCATGCGCCCCTTCCTGCGCGAGCACATGACGCGCGTGGACGCGCTGCTGGACGGAATGCCGCACCTCTCGG
AGGCCGACCGTCGGTACATCCGCCGCGTGGTGCTGCAGGGCCGCGCCTGATTCGCCGTCAATAAATCGCGATGGTGG
ACAGCGGCACGCACGACGTGGACTCAGCCGCGCAGGAGCGCACGCCCAACCAGCAGACCTTCTTCACCAAGGGGCTC
AGTCCGCTGATGCGCCACACCTACATCTACAACAACTACGCCTACGGCTGGATTCCCGAGACCGCGCTCTGGAGCAG
CCGTCTGGGCGACTACCGCGTCACGGACTTCTACCCGATATCGCTGGGCATGCTCAAGAAGTTCGAGTTCATGTTCT
CGCTGCTGGCGGACCCCGGCGGCGCCTGCCCCGCGTACGAGCCCAAGCTCAACACCGAGTTCCTGAACCGCGGCTCC
TTCTCGGGCCGGTACGTGAACCCCTTCCACCGCTTCGCGGCGCTGCCCGAGCGCGAGTACATCTCCTTCCTGCTGCT
GAGCTCGGTGCCCATCTTCAACATCCTCTTCTGGTTTAAGGGCGAGACCTTCGACACTGCCAAGCACAGCCTGCTCG
GCGCCGTGTACACCACGCCCGAGAGGCACATCGAGCTCGCGCGGTACCTGCGGCGCACGGGCGACTACAAGCCGCTG
TTCAGCCGCCTGGGCAACGACGACACCTACTCGAAGCCCTTCTCGGGGTTCACGCGCATCAGCAACCCCACGCCCAT
GGGCGGCTGCCGCCCTCGGACTTCGAGACGCTGGCCAACCTGAGCACCATTCTCTACTACACGCGCTACGACCCGGT
GCTCTGTTTCCTGGTCTTCTACGTGCCGGGGCTCTCCGCGACCACGAAGATCACGCCCGGCGTGGAGTTCCTCATGG
AGAAGCTCTCGCTCGCGCCCGAGAACGTGGTGCTGCTGTAGCCTCAAACATAAAATATAGGCGCCTCTGATCGCACT
GCTTCAGTTCAGACAGAGCTAAGATGGCCTCCTACGTCAGCGGCGCTAGCGCCAGCGCGAACACCGCCCAGGGCGGC
GATTCTCAGTACCCACATTACTATTCCCACACACGCACCTCCAAGGCGACATCCGCGACGAAAGCGAAGGTTGCTTC
CACACCACGGACGACGAGCACTTGGATCTGTCCGACGACTACCTCGGCGATGGCGCACCACACTGCGGACACAGCCA
CAACCACAGTCGCAGAGATGGAGATCGGCACCGCCAGCGCGCACCGCGGCTCTACGAGGACCCGGTGCCCGCGAACA
TCATGGTGCCCACGCTCAGTCTAGAGCAGCTGCTGGAGGAAACCTCGGTCGCGGGGGGCCTTCTCGGCGGCAGGACG

FIG. 29F

GAGAGGGACGTGGAACAGCTCCTGGAGGAGTTCTCCGCGCTCTGTCCCGGGGACCAGATCACCGCGCTGCGCTGCAT
GGCGGCCTCCTTCTACCGCGACGCGCTGTTCGCGCCGTACGCCTGCATGCACCTCATCGCCAGTCGGATGCGCGTGC
ACTACGCGCGCGAGGTCGTGCACGTGGCCGAGGACCTCGCGGACGCGATGTCGGCGAACAGCGGCGTCTGCTTCCGG
CGGTACCGAAAGCGCGTGCTAGAGGACATGCTCGCGGAGGAGATGAGCGTGTACAATTACCTCGCGCGCGCCAACGC
GGACATCTGCGAGGACAACCTGCTCTCGGCCGTGGAGACGCTGCTGCGGCGCTTCCGTCGGATGGGCTGCTACCGCT
CTCTGTGCATGCTCAAGATCCTCGCGCTGCAGCACGAGGACCTGGCCGGCTTCATCCGCCGCAGCATAAGAAAAACC
TGCAACTTCGCACACGCGCGCACGCACACGGTCTACGTGTAGTTACCCTGTAAAGACGGGCTTGCTCCCGAACAAGC
GCTCGAAGAAGAGCGTGCACATAGCCTTATTGTCCAGCAAGT TGACTATCTCTGTACACAGCCTCTTGAAGTACACC
TCGTACATGATCCGCTCGTTTTTATCCAGTCTGAAGGTCTTGTCGACCACGCGCTCGTAGGACTTCACGTTCGCGAT
CCGGCGCCGCCAGGGGCCCTCCTCGCACACGTACGCGAAGAAGTAGCGCTCGCCGATCTCGATGGCCTCCGCGTTCG
CCGCGTTGTACCGCGTCACCAGCGCCACGTTGGGGTTGTCGGGGGACTTGAAGTTCTTGTGGTGCGT TCGGCTCAGC
AGGAACCAGTCCAGCGGCATGCTGCGCGCCTCGAACTCGAAGGTGAGCTCGTCCTCCAGCGAGCGCAGGATCTCCAC
GCCCACGTTCCCGGAGCCCTCCTCCGCCAGCGCGCGGCAGAGCATGTCCTTGTACTTGCGGATCATGAGCTTGTGGA
AGGGCGCCACGTCGCGGCGCGTCTCGCTGGTGCCCTTGCTCACGCGCTCGCTGCCGCCGCCGTCGCTCACCGCAAAC
TTGATCGTGGTGTACTTCTTCTTGGACTGCATGATCAGGTTGCAGTACACCGCTTCGAACTCCACCTTGAAGTTCGC
GAAGAGCACGTGCTCGTTGATCACGCGCTCCAGACAGCGCCCCACGCGCCGCGAGAACGCGATGTCGGAGGCGCCCA
CCTCCAGGAACACGGAGTCGGTGTCGCCGTACACGCTGCGGAAGCCCACGCGCTCCGTGCGCTCGCCGGCCACCGCC
GCGTCGATCTCCAGCTCCGCGGCGCGGCCCGCGAAGGCCT CGTCGCGCAGCAGCGGGTTGTCCGGCGCCGCCGCCAG
CGACAGCCGCGTGCCGCACACCGACGCGCCGTCTAGCGTGCGCTCCAGGTACGCGATCATGGTGCGCCCGATGGCCG
TGCAGCTCTTGGCCGAGGCGTACGAGAAGAGCGCGCTGTTGCGGAAGCCCATGAGCCCGTACACGGAGTTGGCCGTG
ATCTTGTACGTGTACTGCATCGAGTTGTAGATCTCGCGGTCCACCGCGGTCTCCGCGGCCTTCAT CAGCTTCTTGTA
CTTGGCGCGCGCGTCCAGGAAGGAGCGCAGCAGCATCGGGATGATGCCCTTGGCCTCGCGGTCGAAGATGGCCACCT
CGGCGACGAGCTCCGGCGAGCGCGGCTCGCAGGGCACCGCGATGTACCGCGGCGCCGGGAACATCCGCCGGACGTCC
ACGGCCGCGACTCCGCGTCGAGCCGGTTGTCCGAGACGACCACGCCGACCAGCGTCTCCGGCGACAGGTTCGCGTAG
ATGCACACGTTCGGGTACAGGCTGTTGTAGTCGAAGATGAGCACGTGCTTGTTGTGCATCTTCTGCTTGGGCGCCAT
CACGCGGCCGCCCTCGTAGAAGAACTTGGACTTCGTGTCCGCGCGCACCATCACCGTGCGGTTCTCCAGCAGCAGCT
TCATCAGCGGGCCCTTGATGCAGGTGCTCGCGCGGTACTCGAAGACCACGCTCTGCGGCAGCAGGTACGTGGACGCG
GCGGCCGCGATCTTGGTCTCCACGCCGTAGTGCGACCA GAGGTAGAGGCAGAGGCAGGCGTCGTGCAGGCAGTACCG
CGCCATGTCCAGACACACGTCCAGCGAGTAGTTCGCGTACATGTCCGCGAGGCTGACGTCGTCCTTGCCGAAGGCCA
GCGTGACGCGGTCGCCGGGCGCGCGCGCCGCGGGGTCCGCGAGGTCCACGGTGAAGCCGTCCTCGCCGACGCGTTTG
TGCAGCACGCGGCACACGCGCTCGTCGACGGTCACGTAGTTGCCGGTGCTGAGCACGCGCGCG AACACGGCCGCGTT
CCCGTCGGCGTCGGTGCTGCGGTCGCCGCGAAAGCGGACCGCGTCCGGCCGCGCGTCCTCCACGACCGCGGTGCAGT
GGAAGGCGTTCTTGGATATGGCGTCCAGCTTGTAGGAGTCCAGCTTCTCGGTGCGCTGGATGAAGGCGTACAGGTCG
AAGTAGATGGTCCCGTTGTTGTTGTTGATGTGGAAGGTGGTGCTCGAGACGCCGCCGACGCCCTTGTGGCTGGACTT
CGTGCGCTCGTACACGCAGAAGTTGACTGTCTCGGTCCCGTCCGGCAGCCGGAAGCGGATGTGCTCGCCCGTGAGCA
GCGACAGCCGCGAGTCCAGGTACCGCAGGTCGAAGTTGTGCCCGTTGAAGGTGACCACGAAGTCCAGCGGCATCTCG
AGCAGGCGCTTGGCCACGCGCAGCAGCGTCACCTCGGGACACAGCGTGACCTCCGCGTCGAACTTCACGTCCGCCGG
GTCCAGGCAGACCGGGATCTCGCGCCGTGCCGCCTC CTCGAGGTCCGCGTCGGAGAGCATGTCAGAGTTCGTCAGCG
TGAATCGCTTCTCCGCGCCGTCCTTGTCCACCACGCAGAAGCTGATGTGCGAGACGGCGTTCTTGAAGACGGAAGGA
AACTTTTTCTCGAAGTGGCACTCTATGTCGAGGAAGAGCCCCGAGCGCGTCACGTTGAAGCGCGGGATCTTCTCCGC
GAAGCACGCGCCGGGGTCGTCGCAGTGGAAGCAGTTGCTCCCCAGGTCGCGCAGCAGCGCG GGGTCCACGCGGTAGC
ACCCGTCCGGGTCGATGTCGTGCGCCACGAAGAACCAGGACACGTTCAGAAAGTCGGACATGAAGACCTCTGGCGGC
GCGAGCTTGCGCTCGCTGGCCACCAGACACAGCTCTATCTCCGAGCGCTGGCGCTCCGGAATCTTCGCCGAGCGCGC
CACGATCTCGTCGATGCTGACCACGGACATGGGCCCGAGCGCGCGCGTCCACGCCAGCGGCTGGGCGATGTCGGCCA
CCGCGTCCGCGCGCACCACGTAGTAAAAGTGCTGCACGAAGCGCAGGTACACGACGGCGTTGTCGGCGCGGCGCGCC
TTGAGGAAGAGGAACCGGCTGTCATTGCTGCGGTTCTCGAACCAGTTCAAACATTTCAGCTCCATTTCAAAGAGCAT
AATAACATTTCATTTAAATGGAGCCTCGCTTCTGGGGCCGCGCCATGTGGGCGGTGATCTTCTCGTGCTGCGGCGCT
TCGAGGAGCACCGCGACCTCGAGCGCTGCAAGCGGCAGCTGTACGTGATCTGCTCCGCTGCCCTGCATCGCGTGCCG
GCGACACGCCACCGCCGCCATCGAGAAAAACAACGTCCTCTCCAGCGAGGACCCCAACTACGTGCTCTTCTTCTTCA
TCAAGCTCTTCAACAACCTCGCCTTCGACGACAGATACAAGATCGACCCCGCGAAGGTGCGCCCGCTCGTCTAGAGC
ATGCCCTCGTACGCGCGCGAGTTGTCCGAGTACACGGTCACCGCGATGCCCTCGCGCGG CGTCACGTGCACGTGCAT
GGAGTCCGTGATCACGAAGCCCACGCCCGTGACCGGCTCCTCGCCCGCGTCGTCCGTGAAGAGCAGCCCGTGGTTGA
AGAGGTAGAACTCGTTCTCTGCGAGCGAAAGCCGCCCGCGGTCGCAGAGGTAGTAGAAGATGTCGTCGTCGCGCACG

FIG. 29G

GCCAGCGTGAACGTGGACTCGCTCACCACGATGTACTTGTCCAGCTCCTCCAGCACGGACGCGGCCGCGCGGCGCGC
GGTGGCGCGGCACTGCGTCGGGCACTCGCACGTGTCTGCAGAGTACAGGATGCGCGTTCGCCCCGAGGCGGTCTCGA
GAAAAACGTTAATCGCCTCCATCGCCCAGAAGCGACTCGAGGATCGCGAGCACCGTGCGCAGCACGAGCCCGATGGT
GCAGAAGGGAACCTCTCCCGACTCCGAGCACTCGCGGATCTCCGTCTCCACGCGGTCGTGCACTTTTATGGAGGGAG
CCGTCGTTCCAGTGGCCTCCATCGCGACGGAC ACCACCTTGGCCACGAACTCGCGGATCTTGCTCATGCGCCGGAGC
ACGGTCACGCGGAAGAAGACGGCCGCGAGCAGGTACTCGGCCACGCAGCTCGCGGCGATGAGCGCCTGCGCGTGCCT
GGTGTTGAGCACGTGCGCGTCGGGCACGAAGTCCGAGATCTTCAGGTGCGAGAGCCGCACGAGCGCGTTGGTGTCCT
TGACGCCGTCGCAGGAGATGTTCGCGAAGATGAGCTTCTCGTAGTCGAGCGCCTCGA CCACGCGCTGCGCGTCCATG
TGCCGCTCGCCCGAGAGCGCGCGGCTCAAAGGGCCCCAGCACACCGAGCCCGCGAAGCAGGGGTCCACCACGCCGTG
CATCGCCAGCAGCGTCACGTCGGCCACCGCCGCGAGGATGGCCGCGTCGTCGAGCTCGTTCGCGGGCGTCGCGCCCG
TCAGGGACGCGCTGCGCAGCGCGGACCCGCCCGGCGCCGCGTGCCGCGCGCAGAACTCGCACCCGCAGCCCGGCGGC
AGCGGCGGCTTCGAGAGCAGACTCATGAGCCCGCCCACGTGCCCGTGCTCGGTGATCAGAAGCGCCAGGATGCTGTC
GGTGCTGCCCTCTATGGCGGCTGTGGCCGCGCTCGAGGGCTCTCCCGTGACCTGCCATCCGCAGACAACCTTGAGCA
TCTTGCGCTTGAGCTCGTTGGGCGCCTCCGAGGCCAGCATCGTGCGCGGGAACGTCGCGTTGAGGCGGAAGTCCTGC
AGCAGCTTTTCGAGCGTCGCGGTCTTGGCGTGCCGCCCTTTGCGCCACTCCTCCCCCAGGTGCCACATGAGCTCCTC
GGCCGTGTCCAGCGTCGGCGAGACGCGGGCCTTGGGCACGCGCGCCGCGCTGCGCATCAGCGGCTCCGAGGCGCGGA
AGCTGCCGCGCGCGTGCAGGCGCATGGACGCAGACGAGGACCGCATCGAGGGTCGCTGGCAGAAGCTCGTCATCGTG
AAGCGCCGCGTGAGCGGACCTACCTCGTCGCGCGACTCGTCGAAGTCCGGGTCAG GGTCCGTCGTGTCGGTCTCGGC
GCTGTGCGTGCTGGGCGCGCTGCTGCGGGCGCTGCGCGTGCTCTGCGTGCTGAAGCTGCGCGTGCTGCGCGTGCTCT
GCGTGCTGAAGCTGCGCGAGCAGGAGTCCGCCGTGTCCGCTTCCTCGTAGTGGAAGTCCACGTGCTCCTCCGGCAGC
CGGCGCGAGCGCGACTTGGAGATGCCGACCATCCCGTCCGCGCCGACCGGGCGCACGCAGAGCGCCATCGCGCCCTC
GCGCACCGCCTGCGCGAACTCGCGGCTGGCAACCATGCGGGGGTCGAGGAACTTGATGATGTTGAAGTATGGCCACT
CGCAGACGAGCCGCGCGCAGGTCGCGACGTCGTCGACGCTTCTGAGGGCCCTGTTCAGCGGGGGGATGTTGCTGCCG
TCGGCCAGTGCGACGAGGTCCTCGGGGGAGATCTCGAGCTTGGGAATCATCTCGTTCACGAGCGCGGGGTCGATGGC
GTGGCAGACGGTCTCTACCTCAGTGCGC GAGAGCTTGAGCTGCGCGCAGGCCGTCCACGGCGCGCACGTGAGCGCGA
ACACCGCGGAGACTCGGCCCTTGCCGACCATCGCCACAACCTCGGGCTCGTAGACCAGGCCGGCCTTGAGCAGAGCC
TCGAGCACCTCTATGTCGTCGGCGGCGAGCAGCGCGCGCCTGTGGAAGCACACCGCGGGCATCATCTTCTTGCAGAT
GCCGCGGGTGCTCTTGAGGGCCGTGATAAGGTCGGGGAGCCTGACGTGCTGCG GCTGGAAGAACATGACGTTGGCGG
GGCTCGCGGCCACCGCCTCGTCGTACACCGACATCGGCAGGTCGCCGTGGAGCCCGCACGGCAGCAGGCTCAGCAGC
TGCGCGCGCGAGAGCTTCTCGGCGCAGAAGTTCTTCTTGGCCAGGGCGGCCGCCGCGTCGCGGGCCTTCTTGGGGTA
TAACAACATGGCGGGCTTTAAACACGAAACAAAAATCCAGGTTGTAACATTTCAATTTTGCATGTTCTGGGCCTCCT
CGCAGAGTTTCTCCAGGCCGCCGGCCACGATGGCGTCGACGAAGAGGTCGGCCTCGGTGAAGCGGTGGTTGCCGCGC
ACCGCCACCAGCGCGTTCTCGGTGACCACCACCGACAGCTGCTGCGCAGCCGTGCGCAGGTCGAAGTGTCGGCACGC
GAGCCCGTGGCCCAGAGTCTGGTCCAGCGCCGCGAGCACCTCCTCCAGGCTCTCCTCGCGGTGGTTGTAGAACCACA
TCAGTACGAAGTAAGCCACGTAGGTG TAGAGGTAGTGCGCGACCGCGCGGGCGCGCACCAGCGGCTGGTTGCAGCGC
GCGAAGGCCATTCCGCTGGCGATGAGGTCGTCGTCCAGCGTGGCGTAGTCGCCCCAGTTGAGCGCGCTGAACTGCAC
GCTGTAGACCGCGCGCACGAACCCGGACTCGAGGATGTCGATCTGCGACGGCGCGCCCCAGGTCACCAGCCGGTACA
CGATGCCGCGCTGCATCAGCCGCATGAGGTCGCCGCCGACCTCGCGCAGGC GGTGCGTCAGCGAGGCGAAGGCCAGC
TTCCGCTGCGTGTACTGCAGGCCCACGGCCACGCACCCGTCCGACTCCACCAGCACGAGCTTGTGGTCCGTGCAGCC
GTCGCTGCGCAGGCCGCCCTCGCGCGCCATCATGTCGGTGACGAACATGTACTTGCGCGCGCGCGGCCCGACCAGGA
TGCGCGTCTTGCCTTCCATGCGCAGCACCACGTCCTCTAGCAGCCGCGTGCTGTCCACGCGCTCCACCTGCGGGTG G
ATGGTGGGCTGGTAGTTGTACAGCAGCCGCGGGGACCAGTTGTAGGCGAACGCGAAGAGGTGCGTGTCCAGGAGCGA
GATGGGGAAGACGCCGCCTTCGGTGGCGCGCCGGAGGATGGCGAGCTTGGTCTCCGCGGGCAGCAGGCTCCCGGTCA
CCGCGCCGAAGAACATGGGGTGGTTGCGGAACTTGAGCGCGTACGCGCTCAGCACCTCCTCTCGCGAGAATATTGAG
TCCGCGGGGTTGGAGCTCGCGGGCAGGAGCACGTCCTCCACGCTCAGCACCTCGTCGATGAAGGGCAGCACCATGTC
CACGTTGGAGGCGGTGAACCACTCCATGTCCACGGCGTTGCGCTCCACGATCACCCGGATCGTCTCCTCGGATATGT
TCTCGGCGAAGGCGCTCTGCAGCTCGATCAGGTTCTCGGTGGCGTCGATGCTGAGCCCGAGGCGCATGCCCTGTTGC
AGCACGTCGTTGATGGGGTTCACGTACATGGCCACCGCCATGCACCCGG CCGGCTGCACGCGCCAGAGGTTGGAGTA
CGCGGACACGTCCGTGATGCGCAGCGTCTCCAGCACGTTGTACATCGCCGCGCGCATTTCCAGCGTGTCCACGTACA
CCTCCGCGTGCTCGAAGATGATGTCGAGCTCGAACGCGGACAGCGGCAGACTCACGTAGATCTGGCAGGCGTCGAAG
AGTTCCTGCGCGTACTCGGAGAAGCACGCGTACGCGATCACGCCCGCGCGGTTGACGATGTAGTCGGCCTTGAA CAT
CTTCGTGAGGTAGGCGTACAGCGACCGGCAGGCCACGTGCGGCCTTAGCTCGTCGAGCACGGCGTCCAGCACCTCGC
GGTGCTGCAGCACGGAGGGGTGCAGGAACTGCGTGAAGTCCACCGCGGTCTCCTCCATGAAGTCGGGGATGGTCTCG

FIG. 29H

ACGACCAAGCGGTGGTTCCGCACCGCGCGGAAGCCGGTGTTCATCGGCGCGATGCTGTGCTGGTCGTGAACCTCCAG
CAGGATCTCGTAGCCGATCTCTCGGCAGCTCAGCGCCGCGCGCGCCTCCGTCACGCTCGCGTTCCGGAAGAACTGCC
GCAGGTGCTCGTCCGTGCGGCAGAGCGTGACGGATTGGGGGATGCGGGAAAGGTCGCAAAGAGGGCTGTGGACGGAG
ATGCGCCGCAGCGCGTGGTCTACGAACTCAAAACCGCGCCTCGACATCGTGAAGTCGCGGAGGGCGTACATGTTGTA
GGAACAGAGGCGGAAGAGGCAGTCTATGTCTAGCATGTTGGAAACGC AGTACGCGTGTCTGTGGAGGTGCGGGAGCA
TGGCGGGCACGACCTCGGTCGTGTTCTGGAGCATGGTGCATACGAGGTCGGGCGCGGTGAGGTCAGGAGTGACGATG
AGGATGCAGGAGCTGGAGAACTTGCTGAGCTCGGAGGCCAGCCGGTGAAGGTTGTAGTCGTGGCGCTGGCTGAAGTT
GCTGTTTATCGTGCCCGTGAAGCCCATGAGCGCCGCCAGCGTCAGGTCCTCGCGCTCGATGGCCCAGATGTC CAGGC
CGGAGGCTATCATGCAGCGCACCAGCGCGGCGGCGCGGTCGCTCGTGGGGTAGCTCATGGTGCTGTCGGTCGTGCGA
ATCAGCATGGGATAATGCTTCATTTTTACGGTCGGGGGGTGCGGACTGTGGGGCGCACAGGGCCCGCGGGCGGCTCG
TGCCGGTCCGCGGCGTTCGCCGAACGCAGGAACGGGCCCATGCGCGCCCAGGCCATCCACAGCCCCGCCGTCAGCGC
CAGCAGCCAGACGAATACCACGATCATCTTTTATGTAGCGGGAACTCGCGCTCACTCCCCGCCGCACGGCGACGGGG
AGAGCCCAGAGCCGAGCTCCATGCGCGTGCTCTGCACGGTGAGCGACTCCACGAGCTTGGACACGTTCATGCGCGTG
TTGTCGGGCACCAGGTGCGCGAGGCGCGCGTACACGTCCTCGTGCATGCGCTTGCTGCAGCGGTCCAGGCTCGCGGA
GAGCGCGGAGACTAGCGCGGTGTGCTTCGCGTACACGAAGTCGCC GAGACACACGGTCTCGAGCCCGAGCACGTCGG
CGCTCTCCGCGTCCTTGAGCGCCACGAATATCTTCTGCTCCTCGCGCGTCATCGAGCGCATGAGGTAGTCGTGCAGC
CGCGAGCGCGAGATGAGCCCCTGAGAGATCTGCGGGCTGCGCATGAAGCGCCGGCGCATCGCGCACAGCAGCTCCTC
GTCGACGACGTACATGCTGTCCTTGATGGAGCTCTTCTCGTCGAGCACGAGCAGACCGTCGTTGGCGACC ACGTTGA
TGAAATCGTCCACGTGCCGCGCGTCTATGTCGTAGCGCGTGCCGCCGCACTCGATGTGCGAGGGCGGCGACTTGAGC
CGGTTCGCGAGCGCCTTCACGTCGGAGACGTCGATGTACAGCGAGGACTCGCGCGGGACGCAGCCGAGGATGCGCGT
CTCGAGCGGCGTGAGGATGAGCACGCGCTCGGCGCCGTCGACGAGCTTGCCGTCGTCGGGGGAAAAGAAGTTGTTCT
CCACGATGCTCGAGACGAGGCTGGCGAGCACGCCGTCGCGGTAGGCGCCGAGCGCGAACTCCTGCACAAAGGGCGCG
TGCAGCAAGTCCACGGGAATGCGCATCTCCACGCGGCGCGCGACCGACTTCTTCTTCTGCAGGTGCCGCCGGTCCAC
CATCTCGTCCACGATGTCCGATATGCGGGAGCAGAGGTACGCCTTGAGGACGTTGGCGTTTACCTTGTTGAAGATGA
GCCGTTCGTCCTCCATTTAAGCTGCTCAAACGAGCTTTAAATA GTGGAAACACAGCAGCACGCCGATCGCCGCCGCT
ATCAGGCCGATTAGAAAAACGGTGGTCCAGGGGACGCCCTTGGGCCTATCGCACGCCGGCTTTTCGGTCATTACGGT
GCGCACGATGTTTAGGAACTCCTCGAAGTCCTCGTCCGAGTTGGAGAGGAAGGAGCCGAAGACGCCGGTGTACAGTT
TGTCCATTTACTACTAGATATTAAACGGCGCTTCCAACTCCTCGTCCTCGAAGCCCGCGCCAGGCTCG ACGACGCCC
AGGCCGCGCACGTCCTGCTCCTCGGTGAACGTGGTCTGAGTCTCGCTCATGCGCACACACGTCTGCTCGCCCTCGAG
ACCGAGCACGGTCAGCGAGCACTCGCGCGGCATGGTGATCTTCTTAACCGCGAAGGTGACTTTGCCCTCGCCGCCCG
AGCGGTAGAACACCACCGGCGCTAGGATGAGCGTCGCCATCTGCGCGTCGCGGGTTGCGAGGTTTTCTATCTCTCGC
GTCAGCGGACATATCTGCGGCTGGGTGTCGTCGTCGCCGGTGAACTCCAGGAGAGCGCCGGTCAGGCGGTTGAGATA
CAGACATCCGGACTTAAAGGTGTTGTCGATGGCCGTGTCGGTGTTGAAGTTGCGCAGCGACGGCGGAACGCGAACGC
CGGTTTTGATGTTGTCGTATATGTTCTCCAGCAGCTGGTAGAGCAGCGGACTGGCGCTCACGGGCTTGAGGCGACCG
AAGTACCCGCTGTCGTTCTGCCGCTGCATGTCGGTCTTCTT GCTCGGGTAGATCTTAAACTCGCCCTTCACGACGAT
GAGCGGCGAGACGAGCTTGGATGCTAGACTTTCGACGAGACACACGTTGATGTTGGAGCAGCTCGGGTACTGCGACG
GAGTTAGAGTCACCGCCTCGATGACCTTGGTCTGGCTCGACGAGAGCGACTTGGCGAAGTTGATCGCGTCGGTGCAC
GACATCGCCTGGTTCTCGCCGAACCGCCTGGCGGACGCTGCATCCTCCTGCTGAGGAGCGCGGTTA GACGCGACGGT
GGTTTTGGATACAGCGCGTTTCATTATGCAGCGATTTTAAAGTACGTGTATACTTTCAGTTTTGTCGCCGAGCGTTC
AGCGCCTGCATGCAGAGGAAGTACAGGATGATGGTGCACGGGATCGTGGTCAGCAGCGATACGAAGTCCATCACTGT
GAGGACGCGCAGCGCCCCGCGCGAGCGGATGCCCAGCGAGGGCGCGCCGCGGCGCGCGATGGTGGCCCCGTTCGTCA
CCACTACCAGCAGCATTAGGATGGTCGCGCCCACGGCGACGCCCAGGTCCCGCGACTCCATTTATAGTACAGTATAG
AGCGACCGCGTCACGAACTCTCGGCTGGCCAACACGCGTCCGTCGGGCGGGTGTCCGCCGGCCTTCCCGCGGAACTC
CGGGACCTCGAAGCTGGACTTCGTCACGCGGTACGTGTACTTGCCGCGCCAGACCAGGTTTTCCTTCTGGAAGACGC
CGTCCATGGTCACGCCCGCCATGAAGGCGTCCTTGACGA TGACCAGCACCGCGTCTAGCTTGCGCCCGTTGATGTGC
GTGACGAAGTCCGTGCCGCTGCGGCTCGCGCAGCGGATGTCCACGCCCGAGGGCAGGTCCACCACGAACACGAAGCG
CTTCGGCGCGTAGAGCACCAGGTCCGAGGACGGCGACGCCGAAGGCGCCGAGGGGAACTGCCGGTGGTCAAAAGGGT
GCACCACGCCCACGATGGACGTGACGCGGTCGTCCGGGAACTGCGTCGCGGCGCCGCCGCCGCG GTGCCGCGTGACC
GTGCTTCTGCCCACGTCGTCGCAGACCACGTGCAGCTCCGACACGATCGGCAGCAGCGTGGCCAGCATGCGGTCGGT
CTCTGTGCGCGTCGCGCAGCGGTACGCGATCCCGCAGTGCGCGTCCTGCGTGCGCCCGAAGAAGAGCACCAGCACGC
TCGCGTCCTGGTCGAAGGGACACACGGCCATCACGCCCACCGGCGGCGGCCCGTGGCCTGCGTACGCGGAGGAGAAC
TCCTGCACCTCGACCACGGCGTCCTCGCGCGCCTCGCCGGGCACCATCGCCGCCGCCGGCCGCAGCGCCCGCACGGT
CTGCTTAACCGCACGCGCGGCGGCGGCCGCGCTCGGCGCGACTACGCGCACGGCCGCGTGCGCGCCCGGCGGCGGCG

FIG. 29I

CGGTTCCGGCCATCCAGCCCACCGGCGAGAAGAACACGTCGCAGACGTGCACGCCCGCGGCCTGCAGCGCGCGCG
AGCGCGCGCACGGCCTCCCACTCCTCGCGAAAGGCGC TCGCGACCGCGAGCGCCTTCAGCACCGTGTCCACGGAGTT
GACGGGCTTCTGGAAGAGGTTCTCGTTGTTGTAGATGAACTCGGGGAGCTCCACGGCACTGTGAACAGCCGAATCTC
GTGCGCGCCGCTGGGCGTGAGCCGCGTCGCGGGCTTGCGCACGCCGGCGCGATCTGCTTGAAGAAGTGGTTCATGGC
GCCGCCGGCTTCTCGGGCTCCGGCGGGAGCAGACTATTTATTCGGGAGGTTATCCTTTCCGA AAGCACCTGCACGGA
CTTCCGCGTCCAGCGCTCCATCTTCATGTACTCCTTCATGCCGTCGCTGAGCACCTCGACGGCCTCCAGCTTGGGCG
CTGTCGGGTCGAAGAGGATGCTCTTGAGCAGCGTCATCTTCTTGTCCGCGAGGAAGCGGAAGTAAGTGTAGATGCAG
CGCAGCGCGCGGAAGTTCTCCGGGTGCTTGATGGTGCACAGGATCATGAAGATGCAGGTGAACATGCCGCACTCGGA
CTCCATGAGCTGGTTGACCTCGAGGTTGATGCAGCCGCGCCGCGCCTTGAAGTTGTCCACGAAGAAGCGCATGAGCA
CGTCCACGTCGCAGTTGCGGTTGTCCAGGTCCGCGGTCTCGGCGTTCACGTTGAAGCCGTCCGAGAAGGAGTAGAAG
TAGAAGTACTTGCAGGGGTGGAACTCCGAGGGGCTGTTGCCGCCGGAGTCGTAGAAGGACACGAGCCGCGAGACGGT
GTCGAAGATGCAGCACTTCCAGTGGAACATGTAGC AGAAGCCGAACATCACGTAGCGCCGCCCGGCGCGCTCGATCT
TGTCCTTGAGCGTGAGGCTGACCATGTTGCAGCGGAAGCGGTCCGCCTTTTCGTGGATGGCCGCGCCGTTGAGGAAG
TTCAGGTTGAACTGGCCCAGGTACGCGACCTCGGTGCCGAACGCGAAGGGCGCCACCAGACTCTGGATGCTCACGTT
GCTCATCCAGGCGCCGCGGTCGGGCTTTATGGCGATGGGCACCACCTTGGTGTTCACGCC CGTGCTGACGCCCGCGC
GCGCGAGGTCGTCCACGTTCAGCGGCATCTGCGAGAAGTCCACGGCCTCGGACACCTTCTCGCGCAACGAGGGCTTG
AAGAAGAAGCCCAGCGGGACCTTCCACTCCAGCGCGATCGCCTCGCGGAAGCCGTAGCGACCCTTGAGGCTGGCCAG
CAACGCGGTCTTCTGCGCGACCTCGTCCTTCTCGGTGTCCGGCGGCGCGGCGTCGATGAGCCCGCGCTTCGCGAAGT
CCAGCAGCGCCGCCAGCGGGATGCACGAGACGCGACCGGCCGTCGCGGATTCGTCGAAGCGCCGCACCACGTACCCG
TTGCAGTTGGTCTTGAAGTTGGACACGTCCAGGTGCGCGCTGAGCCCCACCACCGAGTAGATGTGGCACAGAAGGTT
GGTGAACCCCAGCTCCGGGATTTTGCTCACCACTAAATCCGTGTACTTGTCCATTTATCATGGAGAATCATCTGCCG
GACATGCTGATGTTTCCCAACTGCGTTTCTGTGTTTCCCTTTGAGTACTCGCTGGAGGACGTGTTCCGCCTCCCCGA
GGAGCGACGGCGCGCGTTCGCCATGGCCGTGTTCCCGCTCTCCAAGCACCGCTGGAGGGGCGCGCGGCTCCAGCGCG
ACGAGCGAAGCGTGTGGCTCAGCGTCGAGGAGGACCGCGGGCGCGCGCTGGACGAGCGGAACTGCTCTTGGCTCTCG
GACGTGGCCGCGCGCATGGTCGACGACGAGGGCCGCGCGGTCACGCCCGAGGCGTACG CCTTCATGCGCGCCGCGCC
CGGCGCGCGCGTCGCCGAGCTCGCCCGCGGACGCGGGCGTGCTAGCGGGCCTCGTCGCCGGCGGCAACGCGCTGCGCG
TCTTCTCCTCGGAGTCCACGCAGGCGCGCGAGGGCTGGAAGGCGCGCAGCGTGGGCGTGCTCGGCAACGCGGCGCCG
CTGGCGCCCGTGCCGCTGGCATCGCTGCGTCCGGAAGTGCAGCGCGAGATCTTCGCCGCCTGGATCGGCCGCCGCCC
CGTGGTGCTCACGGGCGGCACGGGCGTGGGGAAGACCTCGCAGGTTCCCAAGCTGCTGATGTGGTTCAACTACCTCT
TCGGCGGCTTCGAGCGCCTGGACGCCGTCCGCGAGTTCGCGGAGCGCCCGCTCGTGCTCTCGCTGCCGCGCGTCACG
CTGGTGCGCGCGCACACCGCGACCTACCTCGCCTCGCTGGGCTTCGGCTCGGCCGACGGCTCCCCGGTCTCGCCGCG
GTACGGCGCCATCCCGGACGCCGAGCGGAACACGGCCCCGCGCGCCTACGGGCTCGTGGTGGCCACTCACCGGCTCA
CACTGACCGCCATCCGCCGCTACGACACGGTCGTAGTGGACGAGATCCACGAGCACGACCAGATGGGCGACATCGTG
GTCGCGGTCGCGCGGAAACTGGGCTCGAACATGCGATCGCTGGTGCTTATGACGGCCACGCTCGAGGACGACCGCGC
GCGCCTGGAGGAGTTCCTAGTCCGGCCCGCCTTTGTGCACATAGAGGGCGACACGC TCTTCCCCATCCGCGAGGTCT
ACGTGAAGAACACGCAACAGCCGCCGCTCTCGCGCAAGTACGCGGAGGCGGAGCTGCAGAACGTGGCGCAGGCGCTC
GGCACCTTCGTCCCCGAGCAGGGAAAGTGCGGCATCCTCTTCGTAGCCACGGTGGCGCAGTGCGCGCTCTTCGCGGA
GACCATCGAGGCCAAGCACCCCGGGCTGCTGGTGCGCGTGGTGCACGGGAAGGTGCCCTCCGTGGCCGCGGTGCTCG
AGGAGGTCTACGCCGCGGACCGGCCCGCGGTGCTGGTTTCCACGCCGTACCTGGAGTCCAGCGTGACCGTGCGCACC
GCCACGCACGTCTACGACACTGGGCGCGTGTACGTGCCCGAGCCCTTCGGCGGCCGCGAGACCTTCGTCTCCAAGTC
CATGTACACGCAGCGCAAGGGCCGCGTGGGCCGCGTGGCGCCCGGCACCTACGTGCGCTTCTTCGACACGCGGCTCC
GCTGCCGCTGAAGCGCATCGACTCCGAGT TCCTGCACCCGTACGTGCTTTACGCGCGCATCTTCGGGCTAAGCTGCC
CGATGACCTGCTCGTGCATCCCAGCGACCTCGCGCTGCTGCGCCGCACCGAGGAGTACGTCGACGGCTTCGGCATCA
GCCTCTCGCGCTGGACGCAGCTGCTGGACCGGCACTACATGCACATGGTCGAGTACGCGAAGGTGTATGTGCGCGGC
GGGCGCCTCGCCGCCGCGCTGGACGCCTTCGAGCGCACCGGCGTGATGACGCAC GAGGCCACCGAGGCCATCCGCGC
CGTGGACATGCTCGCGGCCGTCCTAAACGTGCGCAAGTCCAAGGACCGCTACCGCGCGGAGTGCAAGGTGCTCTTCG
GGCCCTTCGCGGGCAAGAAGTTCGTGGTCGCCGGGCGGCGTCCGCCCGGCTCGCACGTGCTCATGGTCACAGACCGC
GTCTTCATCGAGGCCGAGCCCCCATTCTGAGGACCACCTTCTTGGAGACGCCCGAGAAGTCGTCGGCGACGCCGCGG
CGCGCCACCACAAGGCAGTACGAGGTTACGTGCGGGCAGCGCGCGATGCAGCGGAAGGCTTCCTCCTGCGACAGCGA
GAAGGCGAACACGTAGAAGGTGTGCGGGGACTTCAGCGGCGTGTGGTCCATCGAGTAGATGACACCGAGCTTCTTCA
TGCGCCACATAAGCGCGTTGATGTGGTCGGCGCGCAGCGCGCGGCCCTTGAGCACGCCGCAGACGAAGCTCGAGCAG
GCCACGACGTCGTAGCGCGTGTTCCTGCTGAAGACCAGGTGCGGTGCGCCGCCGGCGCGCCGCGCGGCCGCGCGATT
CTCCACGATGTCCTCTATGGAGCGCTCGCTCGCAAAGAAGTCCAGGAACATGTACTGGTAGGCCACGGCCGGGCGCG

FIG. 29J

ACTTGCTGAACTTCATGAAGGCGTCCGAGTCCATGATGGCGTCCATGTCCTCGGCGGCGAGCCGGTGCTGCAGCCGG
ATGCCCTCGAAGGTGTGGAAGAGCCGCGCGTCCGCGTGCATGGACAGCGCGA GAGTGACGAAGTCGAGAAGGTCCGC
GTCGCCGAAGCGCACGAGCACGTTACCGGGCGTGCGCGTCTTGCGCATGAGCCGCGCGGGCGCGCCGTCGTTGTGGC
TGCGGCGGCGCATTTTGTCGCCGGGGGACTCGGGCGGCAGGTCGATCATGACCAGCCGGTGCCGCTGCGCGTCCTCG
GCGTTGAAGATCGAGGACGTGAAGCCCGGGTACAGCACCACGCAGTCGCGCTCCGAGATGGCGTGCAGCACGTCGCG
CTTGAGCCCGGCCACCAGCCGCTCCGCGTTCTCAACGAAGTAGTTCTCGTAGTCCAGGATGTCGTGCGCCATCCAGG
GGAAGTTCAGGTACGCGTTCATGGCGTAGTCCTCGGCGTCGAAGCAGATGCGCGTGTCTGGCGTCGCCGCGATCGGA
AGGTCCTTGATGCCGCGGAGCAGCCCGTCGTAGTCGGACTCGTCTACGAAGGAAAGCACCACAAAGAGGTCCTCGCC
CACGGTCTCGTAGTCGAAGAGGTGGTAGAGCTCTCTTAGCGCCAGCACGGCGAGCGCGTTGTCCAGCGAGGCGTGCA
CGCGCGCCAGGATGCTGTAGAAGGGCGTGGCCATCATCACGGCCTTGCCGCCCTCGCAGGCGACGGCGCGCGGGAAA
ATGACCTCCGGCGTGCGCGGCAGCCGCCCGAACGTCGCGTTCAGCAGCGCGACCGTGGCCGCGTCGCTCTGGCGCAG
GAACACTACCACCGAGGGGCCCGAGATGCTGAGCATGCGCTCGCGCATGC GCGCTGGCAGGTCCGGCGTGGTCACGA
GGTCCGCGAAGCGGCCGCCGTTGTAGAGGTCGCCGCCGCCGAGGAAGGTGAGCACGTCGAAGCAGTGCAGCACCTCG
TTGCGGAAGTAGTACTCGTTCTCGAGCTCCTTGGCGTACGCGCGTATGTCCACGTTCTCGAAGTTTGTTCGCAGACC
GCCGCCGTCGAAGAACCAGGACGCAAGCTCGCGGACGGCGTCCGCGGGCCTGTTGCGGCGGCTCTTGCACCAGAA GC
TCATGTAGTTGCGCGAGGTGGAGGCGTTCGCCAGGAAGAAGCGGTGGTCGAAGGAGATGAGCACATGCTCGAGCAGG
TGCGCGAGCCCCAGGACCGCGCCCACGTCGCGCCCAAAACCGAAGTTTGATATCCCCAGGTAGACGTCCCGTTTCAT
AGACGGCCTCAGGAACACCCTGACGCCGTTTTCCAACACTATCATTCTCCGGTATTTACTTACCCAAAAGTAGTATT
GGGAGAAGTGTTTGAACGTCCCCTCGCCTTTTTAAATCAAAAGTAGACTTCTCGCGCCCGTGCGCCACCGTCACGCG
CGCGCGGCGCGAGTCCATACCGGCGATCACCGCGCTGCTCTGCGGTGCGTCCGGCCGCGGGAAGAGCACGGACTCGG
AGATCCCGTCCAGCTGCGCGTCGGTGCGCTGTCGCCACGCGTGCGCGTCCGCGAGCTCGCGCACGGCCAGCTGCATC
TTGTTCGTCGGCAGGAACGTGAACACGTACGCCGCCGCCAGGAAGACT GCGAAGAGCACGAACTCAACCGCCCATGA
CATTTAGGGAGCTGATTTTGTTCCACGCGGCGACGCACGTCGTGACGGGCGACCCCGAGGCGCCGCGGCGCGCGGCC
TCGCTGTGCCGCGGCTTCGGCGTGGACTTCCGCGCGATTCACGCGGAGTTCGCGCGGCGGTACCCGCGCACCGCGGC
CGCCGTGGAGCGCGCGCAGCCGCTGCCCGAAGTCGACGCCGCCTTTCCGCCGGACGCGCGCCGGCAAGTCGTG CGGC
TGCGCCTCGAGGCTGCGGCGCTGGTCGTCAAGGAGTCGCGTGCGCTCTCGGCCTCCATGCGCGGCGTGGCGGTGGTC
GACGGCTGCTGCGTGCGCGTGTGCCGCGCTAACGACGAGCTGCTGGGGTTCCTCGCGCGGCGCTACGACCCCGCGGT
CTACCGCTACGCGGAGGTGCCCTCGCCGAGCGTGCGCCCGGGCTCGAAAGTCTTCGCGTGTGCGGGCCGCAGCGTCA
CCTTTGCGGCCGCGCACCGGAGCCGCATCACGGCCAACCGCCCGCTGCGCGTGGTCGTGACCGAGGCCTGTGTGGAC
GGCGTGCTCGCGCGCGGCGCCGCGGAGGTATTCGACCGCGGCTCCGGCGTGCTGCCCCGCGCGCTGCGCGAGATCTT
CTACCGCCTCGACGAGGACGGCTGTCCCACGGGCCAGACGCCAGGCTTCGCGGACAGTATGGCGTCGCGCAGCTGAT
CTATGTCCACCTTTTTCTCGTCGATCTGCGCCACGACCACGAAACT GCGAATGTCCACAGCGGCCATGGTCTTGGCC
ACCGGGTCGTACTTGAGGAGCAGCACGTACTCGTTGCCGAAGTGCTCGGTGACCTCGGTGATGAGCCGGTACACGCC
CATGCCGAGCACGTTCACCGCACCGTCCTTGGCGAAGAGCGAGAGGATGTTCACGCACTTCAGCTCCATCTCGCCCT
CGAGGCGCGCGAGCATGCGCCGGGTGACCTCGCATACTGAACAAAGAGGCTTACCTAGTAAGATAAGCGTT AGCTTA
GCCGCGGTCGGTGACGCGTCGGAGGCCATTTATGGGGATCAAAAACTTAAAGGCGTTGCTGCTCAGCCACGGCGCGC
TGACCCCGCACGAGCCGGGCGGCGACGAGCGCTTCCCTGCCGTGTTCGTGGACGGCTTCAGCGTCATGATGACCATG
GCGTACTCGTGCGCGGACGAAGACGAGTTCCGCGCGGCCGTCGAGGAGCGCGTGCAGCACTGGATGAGCGTGTCCGA
GAGCGGGCGGATCGTGGTCTTCCTCGACCGCGGCGAGATTCCGATCAAGCAGCCGCTGCGCGACCAGCGCCGCAAAG
CCACGCGCGACCGCGCCGCGCGCCACCGCGAGTTCATCGCCGCCGCGGAGGCAGAGGCGGCGGCAGAGGCCGTTGGC
GCCCGCGAGGACAAGCAGGAGGACGAGCACGCGGAGTTCGCCGAGGAGATCCGCGCCGAGAAGCAGCTAAAGCTGCA
GCGCATCCGCTTCCAGCTCAGCATCGCCAACCACGAGGTCGTTAAGTCGCTGATAGAGTCCACGCTCGCGCGCGCTG
GCGATGCCGTGGAGATCGTCTTCTGCGACGGCGTCGACGCGGAGATGGTCATGTGCGCGCGCGGACGCGCCGAGGCC
GAGCGTCGCGGGCGCTGGCCGCTGCTCGTGACCACGGACCAGGACGCGCTTTTGTTCACGTCCACCGATCGCGACGA
GAAGATAGTGAGCACCGTCTCCGCCTGCTACGCGTTCAGGCCCACCGAGACGACCGAGTACCTGTGCAA ACTTGCGG
CGCTGGCCAACGGCTGCGACTTCTTCCCCGGGCTCGGCGGCATATGCGTGAGTGTGGAGTCGCTGCGCCGCGCCACG
CTTTTCCCGGAATTCTCCGTGCGCAACGCCGCCGTGAGTCTGTGCACGCGGCCCATGCGGCTGTCCACGCAGGACGC
GCTGGAGCCAGAGGCCGCCGCCGAGGTCGTGGAATTCATCAGGCGGTACGCCGCCGGCGACGAGCGCATCTACCGCG
AGGTGCCGCCCGGCGCGTGCTGCGGACGCGCGTTTGTGCGCGGAGCGCTCGCGGCCGAGTGGGCCGAAGCGCTGCCG
GCGGCCACGGGTCTGAGCGTGGTCGCGGACATGATCGCGTGTCTGCCCGCGCGGCGGGACCCCGCGCCCGAGGAGGT
AGAGCGGCTGCTGGCGCTGGAGGCGCGCGCGCGAGGCGCGCGCGTCACGGATGCGATGCTCGCGCAGACTGCGCAGC
TGCTGGGTTACGGCGCGAGTGCGGGCGCCGACGGCGCCTCCGCCTTCGCGGTCTCGGGCGCCAAGGGCCTGATGTGT
CGCCTGCGCGGCACGGCCATGTTCTTCAACGCGGAGTACGTGGAAATTGAAAGCGAACCCAGACTGTTAAAGCTGCG

FIG. 29K

GTAGCATGGTGTTCCCGATCGTGTGCTCAACGTGCGGCCGCGACCTGTCGCACGAGCGGTTTCTGCTCATCGTGCGA
CAGCGGCCGCTAAAGGTTGTTTTGCGGACGGTGCGCAACGTCTGCTGCCGTATAAAGTTGTCTACAC AAATAGAGCC
GCACCGGAACCTGACGGTGCTGCCCATGCTCGACATAAGCTGATTTTTCTTTTCCGCTCTGTATGCGCGAGTTCGGA
CTCGCGGCGCGCATGGCCCGCGCCATCGAGGACGTGTGTCCGCGCGGCGCGGTGATATTCGTATCCAGCGCCGCGTC
CATGACCGACTGCCTTAACCCGTCGGTGTTCAAGCACGCGGCGATATACGCGGGGCGCGTGGACCGCGCGCCGCTGC
CGCCGCCCTCGCCGGTCCCGGCGGAGGCCGTGACGGAGCCCTGCGCGATAGACGCCATAGCGCCTTACGGCGCGCGC
GTGGTCCTGCTCTCGGAGCTGCTGCGGAGCTGCGTGGCCGTTCAGGCCTACCGCCTGGCAGTCCCCGGCGCCCTCGC
GCTCATGAACCTCGCGGCCGACGCGGCCTTCGAGCTCGTGGGCACGCCCTACGGCTTTAACAGCGACCGAACGTACT
GCTTCAAGCTCGTTGCCGACTGCTTTGCTAGCGTGGGCGT GACAACGAAGACCAGGCGCATCATGGGTCGCGACGTC
GTGCTCAGCCAGGACTTCCTGGAGAGCGGCATGTGGACCAAGGTGCTGGACTCCGCCCGCGGAGCCGCCGTGGCTGGT
CTAGAACAGCGGCGGCGCGCGGGTCCCGAGAACGGGCCGCGCCACCTGCAGCCGCTGCTGCAGCGCGCGGCACTGCG
CCTCGGCGTCGGCAGTCTCGGCAGGGTCGACGGGCGTCGGAGTCGGGAGGTGGTCCTGAACGGCT GCGTGTTCACCG
AGACGCGGATGCGCTCCTTGCAGGAGCGCTGCTCGATGCATTGGCCAGCATCTTCATCACGTGCAGGTACTCCAGCA
ACACGAACTTTTCGAGGGTGATGCCGTCGAAGGGCGACGACCCCACCACGCCCAGCGGGCTGGACACCGCGCCGTCG
AGCACCTCGCCGCGGGACTCCTTGCGCGCGCGCTCGAGCAGGTCCTCTGTCCGAGCCACCACGCTGCCGAAGTCGGC
GGCCGCGGGGGCGGGAACAGGCGCAGCAGCTGCGCCGTCCGCGTCCGCCGGCATCTCCTCGATCTTGAGACCGGCCG
CGAACTCCGAGGCCGCGTGCACGGGCGAGGCGCCGCGCCGCACCATGAAGTCGCACAGACGCGATAGCGCGGAGGAG
CGCACCGGCATGTCGAGCAGGCGCTCGGCCTCCATCTCGGCGACCGAGTCGGCGCACGCGTCCGGCGCGCCCGCCCG
CACGAGCTCGTCGCAGCACCCCGCCTCCTCCATGAGCGCGGGCATGAGCTTGTACTGCGCCATGTTCACCAGCCCGT
ACTTGAGCTCGAGCAGGTCCGCGAGCTCGGAGGCCATGGGTCGGTTTTTGGTGTAGATGACGCGCTCCACGGCCTCC
GCCATGTCCACGGCCTGCATGAGCTCGCCGACGAGCACGCTGGCCACGAGCGTGGCCAGCGTGACGCGCACGGTGGG
CACACAGACCGCGAAGAAGGAGGTGGAGTGGGTGAAGCGCATGAGCGCGCCGTGCAGACGCGC GAGGTCCGCGCTGT
TGCCCGCGTGCACGAAGCGCCGGCGCAGCCGCGCCAGCGCCTCCACGAGGTCCTCGCGCGTGGTCACGCGCACGTTC
GCGATGCACAGGTCGTGGATCGCGTTGGCGATCTGCGCGCGGCGCTGCGGCGAGCTGCCGGGCAGCAGCCGCGCCTT
GGCCTCGACGTCGACGGTGCTCGAAAGACAGCCGCAGGCGGCGCCGCGGACGACGAACTTCAACAACGACTCGAACA
CGCGCGCGCCCGCGCGGGGCGCTTGCTTGGACGACTCCATTTACTTTAAATAATTTACGAGATCAAAATAAAATGAC
TCTGCGCATCAAACTCGAGAAGCTCAAGCAGATCGTAACCTACTTCTCGGAGTTCAGCGAGGAGGTCTCGGTGAACG
TGGACGTCGGCGATGGCCTCATGTACATATTCGCGGCGCTGGGCGGGTCCGTGAACATCTGGACCATCGTGCCGCTC
AGCGCGAGCGTGGTATACGACGGCGATGTCAGCCGC GTGTTCAACCTGCCCGTGCTCAAGGTGAAGGCCTGTCTGTG
CAGCTTCCACCCCGACTCGGTGGTGAGCCTGGAGCCCGACCTCGAGGACAACGTGGTGCGGCTCTCGAGCCACCACG
TGGTCAGCGTGGACTGCGACAACGAGCCCGTGGCGCACCGCACGAACACCGCCATCTGCTTGGGCATTAACCAGCGC
AAGTCCTACGTGTTCAACTTCCGGCGCTACGAGGAGAAGTGCTGCGGCCGCACCATCGTCA ACCTGGACCTGCTGCT
GGGGTTCATCAAGTGCATCCACCAGTACCAGTACATCACGGTCTGCTTCCGCGACAAGAAGATGGTGCTGCACACGC
CCGGGAAGGTGGACAACTTCTTCCGCGAGTACTCCATGACCGAGTGGGCGCCCGACCTCGAGCGCTTCTCGTTCAAG
ATCCCCATCTCCTCCGTGAACAAACTCCGCGGCTTCAAGAAGCGCGTGGTCATGTTCGAGTCGCGCGTGGTCATGGA
CGCCGACGACAACATCATCGGCATGCTCTTCACCGACCGCGTGGGCATGTACCGCGTTAACGTGTTCATGTCTTTCA
GGACCGGTCTCTTTCATGCGACTAAATACCCTCATGGGCGGGTCGGTGAGCCTGCCCTCGCGGGACCTGCCGCCGCC
GGTGCGCACGCCGGAGATGAACATCGTGCCCGAGCGCGACCTCGCGGACACGATGGCGCGCCTCTCCACCGCAGACC
CGCCGCAGCCGCTGGGCGTCGGCGACGACGCGCGCATGGCCGTGCTGAAGACGACCTTCCCCGAGTTCGCGATATCG
CGGCCCGCGACGGGCATGCTCGCCGCGCAGCGAATCAGGTACGACGGCGACCCGCGCGTCTGCTGCGGCGGGTTCGG
GATCTCACATTACTGGGAGAGGGGGGCGCGCCCGATCGAACGTCGCGTTCGAGGGCGCGGCGCTGCGCACCTGCGACC
CCACGCGCTTCGACGCGGGCGCGTGCGACGCGCTGCTCTTCCGCGAGTGCGCCGCCGGC GGCGTCGACGCGGACTTC
TGCGCGCACTGGATCAACGCGGCCGTGACGCGGCGCACGGACCGACAGTCGCGCGCGCGGCTGAACGACATGTTCGT
GCGCGATTGCCAAAACGACGCCGCCCGGCCTCACTGCGTGGCCTGGATCCGCGCGATGCGAAGCGCGCGCGCGACGG
CGGACGACGGTCTAATAGACGCCGTGCTCTCGGTGCAGAGTCCCGAGTTCAAGGGCAAACACATGCGCTGCAGCTAC
CCCTCGCCGGCCACACTCGCCATGGCCGCGAACGTAGACGAGCCGCGCGAGTGTTGGGACCCCGAGTGCGTGGCCGG
GAACGTGGACTTCATGCTGAGCGATAACTACACGAACCTGGGCCTGTGTCGGCTCTCGCGCTGCTCCATCGGCGTCA
CACACCTGCGGATAGACGCGCGTTCGCGGCTGCGCATGCGGTGCGCCGGCGCGCTTGCCGGGCTCACGAAGGCGCCC
GTGAACCAGACTGTCGTCGTCGGCGACAACCT CGCGCGCGCCTTCGAGCCGCGCGTGGAAACGCTCGGCGTGTTGGC
GCTGTGCGTGGTGTATCTGCTAATTGTCTGGCTCTAAATGGGGGCCGCCGCCAGCATTCAGACCACGTGACCACCGT
CAGCGAGCGCATCCGCAACGAGCTCGAGCAGAGCGCGAGCGCTAGCGCGACCGCCGACTGCCGTCACCATCGGGAGT
CTGATTATCCGCAAGAACCTGGGATGCAGCGTTTCCGTCCGGAACATGTGCTCGGCC AACGCCGGCGCGCAGCTGGA
CGCCGTCATGAAGGCCGTGAGCAGCACCTTCAACGACCTCTCGTCGGACCAGAAGGCCTACGTGCCCGGGCTGCTCA

FIG. 29L

CGGCCGCGCTCAACATCCAGACCACGGTGAACACCGCCGTCAAGGACTTCGAGACGTACATGAAGCAGACCTGCACG
GCGGACGCGGTCATTCACAACAAAATCAAGATCCAAAACATCGTCATGGAAGAGTGCGCCTCTCTGCCAGGGAGTCC
GGCCACGCACCTGGAGTTCGTGAACACCGGCACGGCCGTGGGCAACTGCGGCGTGAAGGCCGTGATGGACGTGCTCG
CGAAGGCCAGCACCACCGTGCGCAACGACCAGGAGGCCGGCAAGGGCTACCAGACCATCATCATCGCGATCGTGGTC
GCCATCCTGGCGGCCATCTTCGCCTGGTACGCGCGGCACATGCTATTCATGTCCACCTCCGACAAAATCAAGCTCGA
GCTCGCCAAGAAGCCCGTGGTGCACTGGACCACCTACCTGGACACCTTCTTTACGGAATTTCCGCCGTCCGTCTAGA
TACGCGCAACATTGAAACATTATATCCACCTCTCAAACGGCGGTATGGTCCGACGCGTCCTCCTCGAGCGCGTGGAC
GGCATCGTCGAGCACTCGCGCGCAGACCGACGCTACTTGGAGGCCATTCAGCGACACCTCGAGGGGTCTACGCCCGG
GCTGCGGCAGATGTGGCGCTTCCTCTACGACCTGCTGCTGACGGTGTTCGTCGTC ATGTACATCGTCTTCCGCCTAA
TCGTGCGCAACCCCGGCATCTGCGCCATCCTCGCGCTCGCGGCCGCGGTGTACTACCTGTTTTTGTGTCTCTTTAGC
ATGGACTGATGGCGATCACAGACAGACCATCGCCCGCGCGCGCGTGACCAGCTCCGGCGCCGCGAAGACGTCCTGCA
CCGGGAAGTCGTCGATCTCGAACACGGAGCCGTCCGCGGACCAGATCACGCGCACGTTGTCGCTCACCGAGACCTCG
GTCAGCGTCACGCCCAGCACAACCGCGTCGTTGGTGCTCACCAGCACCAGCGCGCCGGGCTCCGCGCGCCGGTGCAG
CGGCGGCCCCGAGACTGAGCGCCGCTGCACGCGGAACATGTCCGCGAACTGCTTCGAGAGCAAGTCCAGGTGGTTGC
GGATGATCCACTCGAAGAAGTACGCGCAACCTCCGCCGCCGCACAGGAAGCGCGAACCCGCGGGCATCAGCAGCCGC
ACAACGTCCATGTAGCAGGCCTGCGGCAGGCTCGCGCGGTACAGCCGCGTCTTCGGCGAGAGCACCACCAGGCTGGA
GGTGCTCATCTGGAAGACCAGCTGGCTAACGGAGACGGTGAGCGTGCACGCGGGCACGGAAACCACGTCCAGGCAGA
TGTCGTCCAGAAAGATGCTCCGCTGGTAGAGGTGGTACAGGATGGCCACGATCTGAAAGGCCGTGGCGTCGCTGATG
GCGCAGGGGCGGTCGGCGCAGCGCATCTGCGCGCAGGACCAGCCCCCGAAGGA CTCGAAGCAGACGGTGATCATGCC
CGTGCTCGGACAGTGTGGCGAGCGCCGACACACCGGAAAGCCCACGGCCTTGCGGCAGCGCACCATGGTCGAGAGCT
CTATCCAGCAGCCTGCCTCCTCCTCGCCCATGCCCATGGCTACCGGCGTGAAGGCCGTGACGTCGTCGCAGATGCGC
CGCTCCAGAAACCCCACGCCCGAGGAGGGGTGCGCGGCCGGTGGCGAGGTGATGCGCGCCGGGACCGGCTCGGAGCG
GGCTCGGGAGGCGAGCTGCGCTCGACCCGGGCAGCCGCCGCCGGCCGCGATGCCCTGCGCGCGGGCGCGCGTTCGCG
CGACTTGTTTGACTTGCTGGCCTCGTCGCTAGCGTCATCGAAGCGGTCGTTCCTGTCGCCGCGGACGTCCGCCTCGT
CGCCCGCCGGCCGCGCGGCGGGCGACGTGCCGTCCGCGTACGGCCCGCGTTCGGCGCGAATGTCACGCGCCGGTGCA
CGTACGGCTCCGTAGAGCCCGTGGGGGCGCCGCGCCCGCGCCCTCGGCGGAAGGCCTGCCGGGACGCGCCGAAGCGG
GCGAACTCCCCCTTCGCCCGGCCCCTTTTTTCTTCCATGATATTTATCACAAAAAAAACTTCTCTAAATGACCAATC
TGCTTTCGTTGGTCGACCCGGAGGACCTGGCCTTCTGCGCCGGGTTCCCGTCCTTCGACGAGACCATGCTCGTGATC
GCGGGGGCGCGAGTGCGCTTCCCACGCTCGCTGCTCTCGCTCTTCAACGTG GTGCCGCGCACCATGACGCGCTACGA
AACCGAGCTCGTGGGCACCGAGATGGTGGTGGGCGCCGTGTTCACCACCGCGTACAACGTCCGCCGCAACCTAGGCC
TCGGCGAGGAGCCCGTGACCATGCGCGACATCGAGAAGTACTTCCTGGACTCCGAGAACGAGGTGCTCACGCTCATC
GTGCACAACACCGACTTTTCCGCCATGAGCGGCGTGCGCCGGCGCGGCGGCCGGCGCATCGCCAACCCCGTCATCT T
CCGCAGCGGGTCCACGCCGCTGCTCATCGTGATGGAGTCGCGCAAGAAGACCAACATCTACCGCGAGCGCACCGCGG
AGCAGGCCAACGCCTCCTACAGGGAGGTCGGCTCCTCGCTCGCGCTGGTCACTCGGTACGCGGGTCTGCAGCTGGTC
GACGTGCACACGCCCAGCTCCGTGCTAACGGTCTCCGCCGTCTACGGCTTCACCGAGGACAAGGGGCTCAAGAAGCT
GGGCTCCGCAAGGAGCTCGCGGAC TACCAGTCCACGCCGCTCACCGACCCCATCCGGCTCAGCGACTTCTCCAATAT
ATTGACGGCGTCAAGAAGAGCATCCAGCTCACGAACGTGCCCGTGCCCTCCGCCGGCGCCGAGGCCGCGCCGTAGGC
TTTCATGCGCGATAAATCGGATGGCGGCGCCGACGACGCCCGTGGTGCACCTCACGCCGGTGTTCGTGGAGCCTACG
ATCGCGCACTCGCTGCTGCGCGCAGAGTCCTACCTCGCGATCGCGGTCC TTGAGCTCGTGCTCGCGCTCGTGCTCGC
GCTCGTCTTCTTCCGCGACGAGCTGGGCGCGCTATTCCGCCGCGCGCCGCGAGCGCCTTCGCCGCTGGACGCGTACC
TGCAGGCGAGCCTCGTCTGCGACGGCGACGCGCTGCTGATCGAGCTGCCCGAAGGCCGGGTGCCGGCGCTCGCGCTG
GACGGGCGACCCGTCGCGTTCCCGGGGTGCGAGAGCCTTTTGTACCGCATAAATGGACCACGAAAAGTACGTCT TGT
CGATGTTCTTGGAGGAAGATAACTCCTTCTTCTCGTTCGTCGCCGCGCTGTCCGATGACGAGGCGCTCGGCGCCGTG
CAGTCCGCTGCCGCCCTCCTGGACTTCCTGCTCTCCGTGGTGGTCCGCGGCAAGGAGAAGCTCGCCGCCGCGGGGCA
CCACTACGACTCCATCGCGGACGGACGCGCGCGCGCCGCGTTCGAGTTCCGAGACCTGCGCGAGCTGGCGCAGCTCT
TCGACCGGCGGCCCTGCGGCGTCCAGGACCGCGTGCGTGTGCGCGACGGGCCCGCGCGCGCCTTCGTGGACGCGGCA
CTGGGGCTCATGCGCGAGCGAGGCTTCGACGGCACGCAGGCCGCGGAGCGCGCGCGCTACATCGCGCCGAACGATCT
GCCCGCGCTGGGGGCAATATCGGCCACGCTCTCGCCGGGTCTATAACGTAAAAAATATTAGTAAAATTCTGAAGGTC
CGTGTGTTTCGCGGGCGGCCAACAAACCAGTCGCTTAAATGGAGGGG GTGGAAATGGACAAGCCGCTCCTCTACTTC
GACGAGATCGCGGGCGCGCGCGACTACGACGCGGCCTTCGCGGAGAAGCACGAGCCGCCCAAGATCCCCGGCCGCGG
ACAGATGAAGCTGCTGGTCTGCGAGCTCGTGTTTCTCAACCGGCTGCACCTGCACGGCATGCTCGACGGCAGCGTCA
TCGTGTACGTGGGCTCCGCGCCCGGACGGCACATCTGCTGCCTGCACTCGCACTTCCAGGAGCTCGGCGTCT CGCTT
AAGTGGGTGCTCATTGACGGGCGCAAGCACGACCCCTGTCTCTCGGGGCTGCGGAACGTGACCACGGTGACGCGATT

FIG. 29M

CGCGGACGAGGCCTACCTCCGCGAGCTGCGCGGCGAGCTGCGGCGCGCCAAGATCGTGCTCATTTCGGACATCCGCT
CCAACCGCGTGGACACAGAGCCCACCACCGCGGACCTGCTGCGCGACTACGCGCTCCAGAACACCATGGTGAGCGTG
CTCAAGCCCGTGGCCTCCAGCCTGAAGTGGCGCTGCCCCTTCCCGGACTCCTGGGAGAAGGACTTCTACGTGCCCTG
CGGCAAGGAGATGCTGCAGCCGTTCGCGCCGCCGTTCTCCGCGGAGATGCGGCTGCTCACCGTGCACTCGGAGACGC
GCCCGAAGCTGCGTCTGATCACGCTCAGCGACGCGGTCAACTATGAAAAGAGGATGTTCTACCTCAATAGCGTGGTC
CGCCAGCGCGTAATTCTGAACTTTGACTATCCCAACCAGGAGTAC GACTTCTTTCACATGTTCTGTCTGCTCTCGTC
GGTGGTGTGCTCGTGCGAATTTAAATCGCCCAAAGAGAAGGTGCTGAGCCTGCAGAACCGCTTCTTCCGCTTCCTGC
GCATCCCGCCCTCCATCACGCTCGGGCTGCGCCGGCACGATGAACCGCCACAACACGCGGTACCTGGCCAAGATCCT
CTGCCTAAAGGCCGCGGTAAGAAGCGACCCCTTCGCGGTGGTAAGTAGGGACACCGTGCGCATGTACGAC ATCGAGG
TCGAGTACGGCGACCTCGTGACGGTGGTCACCGTCACGCACAAACTCGAGACCAGCCGCACCGTCTTCCAGGTCTTC
AACGAGACCTCGGTCGCGTACTCGCCGCTGCCGGACGACTACGGCGAGCCCATCGTGCTCACCACGTACATGCAGCG
CGAGCACACCAAGTTCCCGCTCTCCATGCTCTACATCGACGTGGTCGCCTCGGACATGTTCCCCACGTTCAAGCGCC
CCACCGAGGAGGAGGCCGCGGTGGTCGCGGCCATGCAGCGCGTGGGCGGGCGCCGCGATCCCGTGCTCAAGCTCCCG
CGCATGCTGGACACCGAGCTCGTGTGCAAGATACTGCACCTGCCCGAGCACCCGCTGCGCGTGGTGCGCTTCCTGCG
CCGAAACATGTTCACGGGCGTGGAGGTCGCCGACCGCTCGGTGTCCGTGGTCCTCGACTGACGAAGGGCAGCACGGC
CAGCGAGGCCGCCGCCACCAAGCACAGCGGCAGCCACGCGCGC GGGTCCGCCACGGGCACGAAGACGTGCTGGTTCA
GGTATTTCGCCTGGAAGCGCTCCGCGGTGGAGTCCACCTTGGACCCGCAGGCGTTGGTGAGGCGCACGACCGCGTCC
GCGACGCGCACGTCCCCGAGCGATATCACGCAGTCCGAGACGTTGCACCCGGCGATGTTTTTCTTCAGCGCGCGCGG
TAGCAGCGCGTCCGCGCGCTTGCAGGGCGCGTACCAGCAGTAGTAGGGCAGGCGCGTGTCGCGGCCGG TGTCGACCA
CGGCCTGGCTGGGCTTGAGGCACGCGCAGCGCTCGTCGTCCGGGTGCGCGTCGCAGAAGGCGTAAATCTCCTCGTCG
GGCGCGTCCGGCCCGGGCGCGGTCGGCGGCCCGCGCGACGGCGGAAGAACATCTCTGAAAAAATACTTCGACCAGAA
AACGACCACCGATCTTATTTCAAAGTAAAAATACTATTAATACGCACTCGGAGAATCATGTCGGTGGTGGCGCGCGT
ATCGTACAGCCTGTACTCGCAGAGCGAGATAAGCGCCACGGACGTGGTCATCAGCCAGTTGAAGAACGACGAGGACC
TGGGCACGGTGAAGGACCCGCGCCTGGGCGCCTCGGACGGGTCCATATGCCGCACCTGCGGGCTCACGGAGATGGAG
TGTTTCGGGCACTGGGGCAAGGTGCGCATCTACGAGTCCTACATCGTGCGCCCCGAGTACATCCCCGAGGTGGTGCG
GCTGCTCAACCACCTCTGCGTGCGCTGCGGGCTGCTGCGCT CGCGCGACCCGTACACGACGGACGTGGCCGCGCTCA
GCGTGCACGAGATGCGCAAGATGAAGGACCGCATGATGTCCAAGAAGAAGGCCTGCTGGAACAGCAAGTGTCTGCAG
CCGTACCAGAAGATCGTCTTCTCCAAGAAGAAGATCTGCTTCGTGAACAAGGTGGACGAGATACCCGTCCCCAACGC
GCTCATCTACCAGAAGCTGACCTCCATCCACCGCAAGTTCTGGCCGCTGCTGGAGGTGTTCCAGGA CCCCGCGAACC
TGTTCTACAAGGAGTACATGCCCGTCCCGCCGCTGCTCATCCGGCCGGCGATCAGCTTCTGGATAGACAACATCCCC
AAGGAGACCAACGAGCTCACCTACCTGCTGGGCATGATCGTGAAGTACTGCTCCATGAACGCCGAGGAGCAGGTCAT
CCAGCGCGCCGTGATCGAGTACGACAACATCAAGATCATCTCCTCGAACTCGAGCAGCATCAACCTCTCCTACATCA
TCGCGGGCAAGAGCAACATGCTGCGCAGCTTCGTGGTCGCGCGGCGCAAGGACCAGACCGCGCGCTCGGTCATCGGG
CCCGACTCCGCGCTCTCGGTGTGCGAGGTCGGCATCCCCGACTACATCCGGAACACGCTCACGCAGAAGGTGTTCGT
GAACTACCTCACCAGCAAGCGCGTGCGCGCGCTGTTCGAGGACCGCGCGGTCAAGTTCTACTTCAACAAGCGGCTGC
GCCAGCTCACGCGCATCAAGGAGGGCAAGTTCATCAAGGACAAGATCCACCTGCTGCCCGGCGACTGGGTGGAGATC
CCCATGTCCGAGGGCACGAACGTGATATTCGGCCGCCAGCCCTCGCTGCACCGACACAACGTCATATCCTCGACCGC
GCGCGCCTCGCCCGGCTACACCATCAAGATCCCGCCCGGGATCGCGAACTCGCAGAACGCGGACTTCGACGGCGACG
AGGAGTGGGCCGTGCTCGAGCAGAACCCCAAGTCCGTGATCGAGCAGAGCGTGCTCATGTACCC GGTGACTATCTTC
AAGCACGACGCGCACGGCGCGCCGGTGTACGGGTCCATCCAGGACGAGATCGTGGCCGCGTTCTCGCTGTTCCGGCA
CCAGAACCTCTCGCTGGACGAGGTGCTGAACCTGCTCGGGCGCTACGGGCGAGACTTCGCGCCGGAGCCTGGCCAGA
AGACCTTCTCGGGCGCCGACGTCTTCCGATTCATGATAGGCGCGGACATAAACTTCAAGGGCGTGCTCGAGAACGGG
CGCGTGGTGGCGCCGAACGTCGACAGCGACCTCGTGGTGGCCATGCGCGCAACCTCGCTAGCGGGGCTGATCGCGGA
CTACGCCACGAACGTGGAGGGCGTGCGCTTCGTGGACATGGCCTCCTACGTGTACAAGCGGTACCTGGCCATCTACG
GCTTCGGCGTGACCTTCCGCGACCTGCGCCCGGACCCGAGTCTGGTTCGCCGGCTGCACGCGCTGAACACCGAGAAG
ATAGAGCAGATCAAGGACGCGTACTCGCGGTACCTGCAGGACGTCGCGGACGGGAAGCTGGTGCCGATGGCGCCCGC
GGACGAAGCCGACGCGCTGGACTCGCTGCTGGCCAACCTGACCAACCTCAACGTGCGCGAGATCAACGAGTACATGC
GCGAGACGCTGGAGCGCAACCCCGATAACAGCCTGCTCAAGATGGCGCGCGCCGGGTACAAGGTCAACCCCACAGAG
CTCATGTACCTGCTGGGCACCTACGGGCAGCAGCGCGTGAACGGCGCCGTCGCCGAGACCAA GATATACGGGCGCGT
GCTCCCGTACGCGTTCCCCGACTCCGCGGACCCGGAGGCGCGCGGCTACATCATCAACTCGCTCATGAACGGTCTCT
CCGGCTCGCAGTTCTACTTCGCGATGCTGGTGGCGCGCTCGCAGTCCACGGACATAGTCTGCGAGACCTCGCGCACG
GGCACGCTCGCGCGCAAGGTCATCAAGAAGATGGAGGACACGGTCGTGGACGGGTACGGACAGATCGTGAGCGGCTC
GGTACTGCTCAAGTACGCGGCCAACTACGCGAAGATCCCGGGGTCCACCACCAAGCCCGTGGAGCTGCTCTTCCCGC

FIG. 29N

ACGAGAGCATGACCTGGTTCCTGGAGATCAGCGCGCTCTGGACGAAGATCCGGCACGGGTTCGTGCGCATGCACCGG
CAGCGCCTGGCCACCAAGATCCTGGCGCCGTTCAACTTCCTGGTCTTCGTGAAACCGGCGCCCTCGGAGGCGGAGGC
GCTCTCCGCGCGGGACCTGTACCACATGATCCAGC GCGTGATGAACGACGTGCGCGAGAAGTACTTCTTCTCGCTGG
CGAACGTGGACTTCATGGAGTACGTCTTCCTCACGCACCTGAACCCCTCGCGCGTGCGCATCACGCGCGCGACCGCC
GAGCTCATCTTCCGCAAGCTGTACCAGAAGCTGAACGCGCTGCTCGGCGGCGGCACGCCCGTGGGCATCATGTCCGC
GCAGGTGCTCTGCGAGAAGTTCACGCAGCAGGCGCTCTCGAGCTTCCACACCCCGAGAAG AGCGGCGCCGCGAAGGT
GAAGCTGGGCTTCAACGAGTTCAGCAACCTCATCAGCATGAGCCGCACACACCGAGATAGTGGCGCTGACCGCGCCG
AGCCCGGATAAGCTGATGCCGCTGAAGGTAAACTTCGAGTTCGTGTGTCTGGGCGAGCTCGTGCCCGAGATCGAGAC
CCGGCCCTCGGGACGGCCCTCCGTGCACCGCGTGGACATCACGGTGCACCGCCTGCGCATCAAGCGCGCGCACCTGA
CCGAGGTCCTGGTGGACACCATCATCGAGCGCTTCGTGTCCTTCAACGTGCTCGTGAAGGAGTGGGGCAGCGACATG
ACCGTGGAGGGCGACCGCGTCACGTACACGCTGCTGCTGCGCTTCGTGGAGCCGGAGCAGCTCAACTTCCACAAGTT
CATGCTGGTGCTGCCCGGCGCCGCGAACAAGGGCAAGGTGAGCAGGTTCAAGATCCCGATCACCGAGACCACGGTCT
ACGACGACTTCGACGCCGCGCGCAAGGCCTACC GCATGAACATCGAGCTCATGAGTCTGAAGGAGCTGGGGATATTC
GACCTCGAGGACGTGAACGTGGTCCCCGGCATGTGGAACACCTTCGACATATTCGGCATCGAGGCCGCGCGCGGGCA
CCTCTGCGAGAGCATGCTGGACACCTACGGCACGGGCTTCGACTACCTGTTTCCCTCCTGCGACCTGCTCGCGAGCC
TGCTCTGCTCCGGGTACGAGCCCGAGTCCGTGAACAAGTTCAAGTTCTGGAACGCGAG CGCGCTGAAGAAGGCCACC
TTCGGCGACGGCCGCGCGCTGCTGAACGCGGCGCTGCACAACCGCACCGACGCGGTCGCGGACAACAGCAGCTGCCA
CTTCTTCAGCAAGACGCCCTGCGTGGGCACGGGCTACTACAAGTACTTCGTGAACGTGGAGATGTTCATGCGCATGG
AGCGCGAGATCCAGGCGCGCGTGGCGGCGCGCAAGATGGAGGAGATCGAGGAGGCCGCCGAGGAGGAGTTCTAGGCG
CGACAGCGCCTTACTTTGCGACCGTGTTACGACGACACGACACGGTTAGGACGGCGAGTCGCAGACGAACATTTTTA
TGAGCTGGTAGCGGAAGTTGGCGTTTTCCAGGAAGGCGCCGCGGAGGTCCCGGATCTCGTAGTAGGTTTTGAGGAAG
TACACGAAGCGCGCGGGCTGCGTCATAGTCGGGTTCTCCGCAAGCCGCTTGTGCATCACGTACCCCATGGCGGCGGC
GCCGCTGCGGTTGACGCCGGCCACGCAGTGCACGAGCGTGGGCTTCTGCTCGGCCTCGAGGCGCGCCAGCAGCTTCA
CGAGCGCGGGCATGATGGAAGCGATGTTCGTCGTGTCGTCGTCTCTCAGCGGAATGTGGTACGCCGTTATCCCCGCG
GGCGTCGAGTACTTGGACATGGTCATGTTAACCAGGCACTTGAAGTCGACGCCGGAGTCCCCCCGCAGCACGGCGCG
CGCGTCCTCGGCGCTGCCCAAGTACACGTGGTCCGTGAGCCGCGTCATGCCCGAGG GCAGGGCCAGCGGCGGCCCCG
CGCGCGTGCACCGCAGCAGGAGCCTGGCGTACCACTCGCTCTTATCGCCCATATTTATTTATATGATACAAATGGCA
GACGTCACAACACTGACGGCCAACGGTCTGACCCTGGAGTTCGCGCGCGAGCGCGCTCTGCGCAGCCTGCGCGCCGC
GCGCACCTCCACGCTGGTGTTCTTCACGCTCACGCTCGCGGCCTCGCTGTTCGTGCTCTGGCTGCAGCTAACCGAGT
TTCCCGTCTTCGAGGAGCTCGGCAAGTACGCGCGCATCAAGAGCGCGGTGCGGTCCTGGCGCCCGCTGGTGGAGGCT
AAGACCGAGATCGAGTCCGACCTCGGCCGGCAGAAGACCGCCGACCGGCCCGAGCTCTTCGAGTTCAGGTGCGTGGA
CTTCGGCAAGTTCTACCTGCCGGTGAGGTACAGCCCCACGACCTTCCTGCCGCAAGCCGTGCGCCGCGGCGCGGGCG
ATGGCTGGATGGTGCACAAGGCGGCGGCC GTGGACCTCGCCGCGCAGCAGTTCTGCGAGTCCGTGCTGCGGCACCGC
GCCAACAACGTCATCACATGCGGGTCAGAGATGATGCGGCTGGTGGGCTACAGCGGCTACTTCGAGGACGACCACTG
GTGCGCCGCGACGTCCGGCGTGCTGACGTGAACGATCACACGATGGCCGTGACCAGCAGCCCGGCGATGAACCACAG
CAGCCGCGAGTTCGGCAGCAGCAGCACGAGCACCAGCAGGTATGCCAGGATGAA GATGTCGACCACGTCCACGTCGA
AGAGCCCCATGAAGGAGAAGAGCGGCGTGGTGAGGAAGTAGATGGCGCCGGGCCAGAAGCGCGCTAGCCACGTGGCG
AGCAGCGACCACAGGGAGGGCGCGCCGCTGAGCCGCGTCTTCACCTGTATGTAGTACTCGGGGTAGACCACCTGCTC
GGCGCCGGAGAGCACCACGCGCGCCAGAGAGAGCCGCTTCTCCAGCGTGAACACCTCGGTGAGCAGGCCGCTGCGCA
GCCCTCCCTCCTTGATGATCGCGTCGTAGAGCTTCTTCATGCCGCCGACGCTGATGATGTAGGCGTCTAGCGAGACG
TCGTATCCGCCGGGGTAGACCATGAGCTCGGGGTCGCCGGTGCCGGGGACGTTGGTGGCCAGCGCGCCGGTCATGTA
GGTCTCCTTGAGCTGCGTCATGTACCAGCCGTTCGCCTTCATCGCCTCGATGAGCGGCTTTACCATCTCGGGCTTGC
GGAAGGTCATGTCGTTGTCGACCACCAGGATGAAGTCATCGTCGGAGTACTTGGTGGGGACAGTGCCGGCCGATATG
CTCTCCCAGAGGTTGAGGTGGTGCGCCGCGCGGCGCTGCATCTCCTTCGGACACGTGGACTTGCACATGTCCGTGAA
GAAGTGCGGGTAGTCTTTGGAGTCCACGTCTTTCCATTCCACCGCCTTGAGCACGTGGTCGCCCTTGGGGTGCGGCG
CGGGAGGAGATGGCTTGGGTGCCGGCGCGGGGGCCGGCGCGGGGGCAGGTGC AGGGGCCGGTGCAGGAGAGGGAGCA
GGCGCGGGTTGAGGCTTGGGCGGGTCGTCGGCGAGGCCCACCAGGTACGGCAGCGTGGGGAACACCTCCTTGGTCCC
GCGGCCTTCGGCAACCCCGATTATGTAGGCCGTGATTTCGGGTGGATCCATTTAGTTATTAAAATTAATCATATACA
ACTCTTTTATGGCGGCTATGGATTCGGCTATCCAGTCCTTGACCGAGCCCACGATGCCCGCCAGGAACAGGAAGAAG
GCGAACTCCAGGTCCACGCGGTTCAGAGAGTCGCTGAAGTACACGAAGACGTCGCTGTCCGGGAAGAAGCTGCGCCG
GAACATGTTGTACCCGTTGACCTTGTGCGCGACGTGCTCCGCGCTCAGCAGCGTCTCGTCGAAGGGGTACGGGTCGC
TGAAGCGGAACACGTACATGGCCGGGTTCGCGTAGTAGTACTTCATGGTGTTTGTGACGAAGAGGCTCGCCAGCGAG
ATGATGATCTTTTTCTTCTCGATCTCGATCTTGATGTGGTCCTCGAAGCGCTTCATGTTGTAGGCGTTGGTGTCGTG

FIG. 290

CACGCGGATGAGCACGCGCGAGTCCGACATGATGTCCTGGAACTCCGCGCGCGTCGGGGCTCTCGGCGGGCGTCT
CCGCGGGCCGCGCCACCTCCGCGCACACCGTCGGCCTAGCGCGCGGCGGCGTGCGCATGGGCCGCGCCCCCACGCGC
TGCGAAGCGAAAAACTCCACGGCGCGAGCCTCGCCCGCGTCCGCGTACGA CTCCACCAGGTAGTTGCGGCTGCGCGT
GGTGCGGCCGATGGTGTTCAGCCGGTGCAGCTCCGCGACCAGCCGGCGGTAGTGCGCCTCCAGCTCCTCGGGCATGA
TGGAGGTGTACACCTCGGTGAGCAGCATCACGGTGTCGAAGTCCTCCTTGCCGCAGACGCGCGTCTTCACGAGGAAG
TGGTGCACAGCCGTCGCGATAGAGAGCCGCAGCGTGGACTCGGTGACCTCAACGCTGGCGTCCTTGGTCTTCTTC GC
GCTCCGCGAGGCCATGAACGAGACGAGGAAGTCCGCGCTGCTGTTGAGCACGATGACCAGCGCGACGATGAAGTTGA
GGTTCAGCGTCTTCGCGGACTGGAACAGCTCGGTGGCCGACGCGTGCACGTCGAGCAGGTTCGCGGAGAGCCGCAGG
AAGAACACGCCGCGCTTGATCTCGGCCGCGAAGCGACGTTCGTACTCCTGCCGGCGCGCGTTGATCGCGATGAGGAA
GTTCAGGATGAGCCGGTTGATGTTGTACTTCACGGCCCAGGTCTGCGTCTTCATGATGGTGTCGAAGGACATCACGA
TGTTGAAGATGAAGCGCTGGCTGTGCGAGAAGTAGCTGTAGGGCTCGCTGAGGAAGATGGACTTGTTGGTCGCGGGC
ACTACCACGCCCGCGCGCGCGCCGGACGCGTCGGTGTTCAGGTCCGGGATGTTCATGCCGCAGATGCGGCAGTAGGC
CATGCCGTCCTCAAAGTACACGAACTCCTCCACGAACTCGTTGATCTT GGCAAAGTAGTCCACGTCCACGCGCATCG
CGACCGCGAGCCGGATCTGGTGCTCGCAGGGCGGCGACTCGAAGCGCACACCCTCGCCCCAGCCCGGCGGCTCGCGC
ACGACCAGCGCGGTGCGCGAAGCCGGGCGGAACTTGGCGTCGCGCGCGTTGAGCAGCGCCGGGAAGAGGTCGCAGAG
GTGCCGGCTCGAGAGGAACACGTACTTGTACAGCAGCCGGCGCGCGTCCGCGGCCATGGCGTCCACGAAGGCG CGGC
CCCACTCCGCGACCGCGGGCTGCTCCTCCGCAAAGTTGTTCGGGTAGACCTTGTCCGTGGCCGCGAGGAACACCTTC
TTCACGTCGAGGAAGTCGCGGATCACGATGGGGACGCGCGCGCCGTCGAGCTCGTACATGAACACGTAGCGCAGGTT
GAGCTTGCGCCGCGAGACCGGGATGCCGATGTGCCGACACAGGTACGCGAACTCGAGGTACTTCTTCGAGAAGCGGA
TGCGGTCCAGGTTCTTGGAGACGTACTGCAGCATGTTGCGCATGTTGAAGGGGATCTCGCGCACGGCGGGCTCCGCG
GCGTCGTCGAAGGCGGTGCGCAGATCGCTGGTGCGCTGCACGACCACGGCTTCGCCGGTGGCGTCGTCGTGCACCAG
CACGTTAACGCGCCGCTGCCGGATGACCATGTCGAAGGTGTTGAAGAACATCTCGTACATGCTGTGCCGAGTGTCGT
CCGCGATGCGCTCGCCCACCGAGAGGCTCGCGGTGGCGTCGTCGCG CACCTGCTTCTCGAACTTGTACCCGATGTAG
GAGAATATCGAGATCAGCGTGGCGTCGTCGGCGTCGGGGTTCTGCTCCATGGTCGCGAAGAGCAGGCGGATGTCGTC
CTCCGTGATCGCGTCCACGTTGTACAGGTTGACCACGAAGATGGACTTGTTCTCGGCGATGAAGTCAGTGTAGGACT
TGGTGGCCGTGTTCGGGTCGCGCATGTACGCGCGGATCTTCGGCACGATGCTCGCGAGGATGGACTCCCTG GAATCC
ATTTAAGGACGGCAAGGGCGCGCGAGACCGTCTCAAAACTGAAATCGTATAAACTCTTAAAAAATTGGTATTGAAAG
TACGCACCACCAAATAAAGCGTCGAGGTCGGGCATGTCTTCGTGGCGACTCAAAATGAGCAAGTGTTCAGGTTCCAG
CAGCGTCCAGACTCTCGAGGATCTGCGTAATCGTCTTCGCTCCGAGGCCTTGGGCAACGATTTCCAAGAGCCCCGCG
ACGACCTCTTCCCCAGCGGCGAGGAGTGTCTGGACATCGACGGGCCCTGCCCTTGCGATGAGGCGGAGCAGGAGATC
GACCAGGAGCAGTTGCCTGTGCCCGAAACCGTGCCCGAACCGCCGGCCAAGACTCCTAAGCGCCGACCAGTGAAGAA
GGATAAGGCAGATAAGGCAGATAAAGACAAGTCGACCAGAGGCGCAAAGAAACCGTGCCCTTCGGACGACAAGGATG
ACGAGCTCAAGAGCAACGACGTCGACAACAACGAAGAGTCCGGC GACACAGATGGCGGCGCGAGCGCCCGAAGCCCC
AGCGACATCGACAACGTGGACGAGATGGACGACTCCGACCTCATGGTGGCGTTCTCCACCATCCTCGCAGACTTCAA
GGACATCACCCAACGAGTGAAAGCTCTTTCGTCCGTACTCACGGACGTACAGGCGGCCGGCATACGCAGGTGCTTCT
CGACGCTCGGCAAGGCTCTGACGGAGGCGGCCCACATCGCCAACACCGGAGCTAAGCCAGTCACCGCGC CTCGCAAG
AAGAAGGCCGCCACCTGCAAGAAGTAGGCGCACTAAATAGCGAGGCTCGGTATGCGGGCGCTGCACCTGTCAGACGG
CAGACTTTTTTTTGACAAGGAGCTGACGCAGCCGGTCCCCGACGACAACCCCGCGTACGCTGTCCTCGCGAAGATCC
GGATCCCACCGCACCTCTCGGATGTGGTCGTGTACGAGCAGGACCTCGAGTCCGCGCAGCAGGGCCTCATCTTCGTC
GGCCGCGACGCCAAGGGCCGAAAGCAGTACTTCTACGGGCGCGGACACGTGGAGCGGCGCACGGCCGTCCGCAACGC
CGTGTTCGTGCGCGTGCACCGCGTCATGAACAAGATAAACGCCTTCATCGACGACCACCTCGCCTCCGGCAGCGAGG
CCGAGGCGCAGATGGCCGCCTTCCTGCTCATGGAGACGAGCTTCTTCATCCGCGTCGGCAAGACGCGCTACGACGCG
AGAGCGGCACCGTGGGCATGCTCACGCTGCGCAACAAGCACC TCGCCGAGGCCGAGGGCGGTGAGGAGATCCGCGTC
GCCTTCGTGGGCAAGGACCGAGTCGCGCACGAGTTTGCCGTGCGCGAGGGGCAGCGGCTCTTCGCGGCGCTGCGTCG
GCTCTGGGACCCGGGCGCGCCCGACAGGCTGCTGTTCGACCGGCTGAGCGAGCGCCGCGTGTACACCTTCATGCGAC
GCTTCGGCATCCGCGTCAAGGACCTGCGCACCTACGGCGTGAACTACACCTTCCTGTACAACTTCTG GTCCAACGTG
CGCTCGCTGGAGCCGCGTCCCTCCGTGAAGTCGCTCATCTGCACCTCCGTGCGGCAGACCGCCGAGACGGTGGGGCA
CACGCCCTCGATCTCGCGCAGCGCCTACATGGCCACCGCGGTGCTCGAGCTCGTCAGGGACGGCGCGTTCCTGGACA
GAGTCGCCGCCACCGACACGCTCGACGACTTCGTGGACATCGTCGTGGACTATGTAAATAACTCTGAGCAGGTAAAT
GGATGAGGCGCTGCGCGTGGCGGCGCGCGTCGTGGACGGGCTCCGGCCGCTGGACGTGGCCGTGTGTCTCACGCAGC
TGCGCGGAGCCGCGCCCGAGCGCCGCTTCCCGGCGCTCGACGAGTGCTCCGGCGAGGCCTTCCTGGACTTCGAGTTC
GCCGGCGGGGACGTGGCGTCGCGGTACCTCTCCGCGCACACGCGCGAGCTCCGTGCGGCGGAGCGGCGCGAGCACAT
GGCCGCGATCGCGCGCTGCGTCACCGAGGCCGACCTGGCGCTCGCAGACCGCCCCCGGGGCAAGGCGCGCGCGGCGC

FIG. 29P

TGCGCGTGTGCCGCAACCGCGAGAAAGTCGCGCGCTTGGCGAGGCTGCTGCGCGACGCCGAGAGCAGCGGCGCGGAC
TTCGCCTTCATACGCGCGGCCGTGGCGTAGCAAAACGTAAAAACAACACATTCCCTAAATCGCCATGGACGCGCCAA
GTCTCGACTGCATGCTCGCCGCACTCGCGGCGAAGGCGTCTTCGGTGGACCGAGGCGCCCCCGAG GACGAGGTGCAC
CACGAAGTGGAGCTCGTGCTCGTAGACCCGCCGCTGTCCACCCTGGCCGCCACGCTGCGCCTGGCCTCGGAGACGGA
GTCCTTCATCCTCTTCACGGTGACCGCGCTCGCCAAGGAGGAGGGCAAGCTGCGCGCGCGCGTGCCCATGTCGCGCG
TCGTCGGCCTGGACGTGAAGAACGTGCAGCTGGTAAACGCCATCGACAGCATCGTCTGGGAGCGCAAGGCGCTCGTG
GAGGAGACCGCGCTGCAGGAAGGCTGTCTGCTGCGCCACTCCACCGAGCGGCGGCACCTCTTCGTGGACTACAAGAA
GTACCTCTCGGCCATCCGCGTGGAGCTGGTAAACCGCGTGCGCGTGCGCTCCAAAGAAGTCGTCGCGGACTTCAAGT
TCAAGTACTTTCTGGGGTCCGGCGCGCAGGCCAAGAGCTCGCTGCTGCACGCGCTCAACCACCCCAAGGTGCGGCCC
TCGCCCACGCTGGAGTTCGAGGTCGTCCCCGCGGGCGA GGCCGTGGACGAGGCCGCCGTGCTCGCGGAGCTGCGCGC
CGTGGCGAAGGCGCTCTTCATGGCGCCCACCGACGCCGTCTTCCTGGCGCCGCCGGCCGAGATGCCGGTGCGCACGC
TCATGCTGCAGAAGCAGGAGATCCCCGCGCTAGACCTCGACGGCCTCTTCGCGGTCTCCAAGACGGACGGCGTCTCT
GCGAGCGTGCGCGTGGACGAGGACGGCGTCTTCTGCGCGTTCTCGCACCTCGCGTACACCATC CGGTACCCGCTCGC
GCGCAAAGTGCAGGGCCGGTACCGGCTCTGGTGCGAGGCCGTGCGGCCCGTGGGCGAGCGCGTGTGGTCCATGTTCG
TGCTGGTCGTGGAGGAGCCTGCGGGCGATGACCGCGTCGCGGCCGTGGCCGGCGCCGTGGAGGCGCTGCGCGGCGTG
TGTGCGCGCGTCGAGTTCAAACCCAAGCGCGTGGACGGGCCCTTCTCGGCGACCTCCGAGCTGGTGGAGCACATCAA
GAGCGCGCTGCAGACGGAGCCAGAGGGCGTGGTGCTCTTCTACGCGCGCGGAGAGAAGTCCAAGCGCGACCTCAAGG
TCAAGCGCGACAACACGGTGGACCAGACCACGAACGTGATGTTCCGGTACATGTCCAGCGAGCCCATCGTCTTCGGC
GAGGGCTCCACCTTCCTGGAGTTCAAGCGGTACAGCAACGACCGCGGGTTCCCCAAGGAGTACGGCGCGGGGCGCAT
CTTCCTGCGCGAGGACGTGGTCTACCACAACAACAT CTACTGCATCGAGTTCACGAAGACGCACCTGGAGGTGGGCC
TCCGCAGCGTGGTCGTGCCCGTGAAGTTCATCGGCGAGTTCTCGCAGGAGGGGTACCTGCTGCGGCCGCGGCTGGCC
AAAACGGAGTGCTACTTCCGCAACCCCTCATTCTACGGGAACCAGCACTCGGTGGTGCTCGAGCACACTCGCGACCA
GCTGCTCTCGGTGGGGGACGTGTTCGACGAGAGCCGCATGGCCGCCGTCGGGCAGACGCTG GCCAACGACGCCTTCC
GCCTGAACCCGGACACGCCCTACTTCACCAACCGACGCACGCGCGGGCCGCTGGGCGTGCTCTCCAACTACGTGAAG
ACGCTCATGATATCGCTGTACTGCTCGAAGACCTTCCTGAACAACGCCGAGCGACGCAAGGTGCTGGCCGTGGACTT
CGGCAACGGCGCGGACCTGGAGAAGTACTTCTTCGGCGAGATCGCGTCCATGGTGGCCACGGACCCGGACGCGCGCG
CGATCGAGCGCGCCATGGAGCGCTACAACCGCCTCAACGCGGGGCTGAAGTCGCGCTACTACAAGTTTAACTACATC
CAGGAGACCATCCGATCCGAGACCTACGTGGAGAGCATCCGCCAGGTCATGTACTTCGGGCGCTTCAACATCGTGGA
CTGGCAGATGGCCATCCACTACTCCTTCCACCCGCGGCACTTCGCCACGGTGATGCGCAACCTGCGCGAGCTCACCG
CGCCCGGCTGCAAGGTGCTCATCACCACCATGGA CGGGGACTTCCTGTCGACGCTCTCCGAGAAGACCAGCTTCGTG
ATCAACCGCAACCTGCAGGAGAGCGAAAACTTCATGTCGATCGAGCGCGTGGCCGATGACCAGGTCATGGTCTACGC
GCCCTCGACCATGGCGCAGCCCATGACGGAGTACATCGTGCGCCGCGCGGACATCGTCAAGCTCTTCGCGGACAACG
GCTTCGACCTCGTGGACCACGCGAACTTCGAGACCGTGATCCGGCGCAGCCGCCGCTTC GTCGAGGGCGTCTCGCGG
CTGGAGACGCGGCCCTCCACCAAGAACTTCTTCGAGCTCAACCGCAACGCGCTCACGGAGATGGACAGCACCGACGT
GGCCGCGCTGCTAAAGATCTACGTGCTGTACGTCTTCAGCAAGCGGTAGGCAGAACCAGGGCGTCGATTCCGCGCCC
GCGCCGGCGCGGAAGGCGTTGAACAGCTCCGCCAGCCAGGCTGCGGTCTCGCGCGCGTCGATCGGGCCGCCGTCGTC
CGGCGGCGGCTCGCGCGCCGCGCGCAACACCAGCGTCTCCGCGGGCGGCAGAGGCTCCAGAGCCTCGAAGACCGCGC
GGCTCGGGAACAGCGCGCGCATCATGCGCGAGCGGTGGCCGAACACCGCCTTGACCGCGCGCAGTGCCGAGCGGTTG
TCCAGCCGCAGCGCTCGGTCAAAACGATGCACGCGCGCGGGCGCGCCGCGGTGGTCGCGCTCCACGAGCACGTGCCG
CCACGCCAGCGCCGCGCCGACGCGGTCCAGGC TGGGCGCGAGCGCCACCAGGCTTTTCAGCTCATGTAAATCTCCGC
GCATGGCCGACGGCTCCATTTACTACTGCGGAGGAACGCACGTGGTCGCGGCCGCGCCGGGCGCCGCGCTTGTGGTG
CTGGACGCGCCCGGAGCGGTAGCGGCGGCCGCGCCCGCGGGGCAGCGCGTCTTCTTCGCCGAGTACGGCCTCGAAAA
GCGGGCCAACGGCCCGATCACGGCGCGGCTGCGACGCTCCGGGTTCCGCGGCGCCGC GAACGCCTGGGCCTCCGTGG
CGGACTTCGAGGCCGGCGGCCGTCCCTCCGCGTGGACGCTGCGCGCGGAGGAGGCTTCGCGCGTACCGCTGCCGACG
GACGCGGCGCTGGTCCTGGCCTGGGGCGCGCGCGAGGAGCCGCTGCGGGCGTGCGTGCTGGCGCGCGCGGCAGACGC
AGAGGCGCCGGTGGGCGCCGCGCTCAAGGAAGCCGCCTTCGACGCGCGGGCGCCGGCGGCCGCGCTGTTCGCGGCGC
TGGGCGCGCCCGCGCTCGCGCCCCCGCTGCGGGCGCGGCTAGTGGCGCCGCCGGGCGCGCCGCCGCGGACGCGGCTC
TGCGAGAACCCGGCCATGCTGCGCGCGTTCGCAGTGGGCTGGTTCGGCGCGCAGCTGGGCGAGGCTTCCGAAAATGA
AAAGGTATTTGCCGCCTTTGATAAGGCGAGGTCGTGTTTGGACGACCGCTGATGGCGACGCCCGCGAACGCACCCGC
GCTGCTCGTCGCGGTGCTGCGACACCGCCCGTACCGCGTGGAGTACCACCCGGACTGGGAGCCGGTCATCGAGACGC
TGGTGGACGAGTACGACGCGGTCGCGCCCTGGCTGCTGCGCGACGCGACGAGCCCCGAGCCCGAGCGCTTCTTCGCG
CAGCTGGCGAAGCCGCTGGCGGACAAGCGAGTGTGCGTGTGCGGCATCGACCCGTACCCGCGCGGCGGCACCGGCGT
GCCCTTCCAGTCCCCGGACTTCAGCAAGAAGACCATCCGCGCGATCGCGAGCTCG GTCGCGCGCACGACCGGCACGC

FIG. 29Q

AGGGCTACGCGAACTACGACCTGGACGCGGTTCCGGGCGTGCTGCCCTGGAACTACTACCTCTCCTGCCGCGAGGGC
GAGACCAAGAGCCACGCGATGTACTGGGAGCGCATCTCGCGGCTGCTGCTGCAGCACGTGGCCAAGCACGTGAGCGT
GCTCTACTGCATGGGGCGCACGGACTTCCAGAACGTGCGCGCGCGCCTGGACGTGCCGGTGACGCTGGTGGTGGGCT
TCCACCCCGCGGCGCGCGACGGGCAGTTCGCGCGCGAGCGGGCCTTCGAGGTCATCAACGCCTTATTGGAGCTCAAC
GGGAAGTCTCAAGTGGACTGGGCGCGAGGATTTTCTTTTTATAGTGAAAATTAATCCGTGGTCCTAAATGGCGGCGC
CCATATGCGATAACTCTCACGTGTTCCTCCTCAAGCGCCTGGGCGTGCCGTCTTCCTGCCGGCGCTCGGAGGACCCG
CGCTTCGTGGAGATCCTGACTCCCTTCGAGCTCGCAAACTACATCGAGCGGCACCCGGGATGCTGCCTCTTCGAGAC
GCTGCGCGACGAGGAGGACTGCTCCGTCGTGCGCGTCTTCGCGGACGTGGACATGGACAGCGTGCTCGAGGAGGAGG
ACTTCGTCGCGGCGCTGGAGGACCTCATCGTAGAGCTCGCGGCCTTCTTCGACCGCTTCGCGAGCGGCTCCTGCGGC
ACCGTGCCCGGCGAGGTCAAGCGCGCCATGCTCGCGAACTTCTCGGTCACGCGATCCACGGCCGAGCACAAGACCAG
CTTCCACCTGATCTTCACGGAGACGTACACCACGCTGGACACGCTGGTGGCGGCGAAGCGCCCGCTGCTGGACCTGT
GCCGGCGCTCGGACAACGTGCTGCTGCGCGCGCTGGACACGGCCGTGTACCGCCGCGGCGCGACGCTGCGCGTGGTG
GGCACGCGCAAGACGCCGGAGTCGAGCGCGGTCCACTGCATGCAGTCGCCCGACGACGACATCAAGGACTACCTGTT
CACGTTCGTGGAGCTCTCGGACGCGAGCGTGTACTTCGAGCTCGCGGAGCGCGAGCAGCACACGCTGAGCACCGTTT
GCTGGGAGACCTCCTACATCCCCTTCGGCGACGCGATGCGGCGCGTGTGCCAGGCGGTGGTCAACGACATCGTGAAC
CTCCGCGACATCACCGAGGACAACTTCCTCGACACGCCGCTGGTCATCGACTACGCGACGCGCTGCGCGCTGTGCAA
GAAGCCCAAGCACAAGCACGCGCACCACATCACCATGGGCAACGGCTGTCTGCGCCTGGTCAAGGGCGGGAACGCGC
ACAGCTGCAAGGTCAAGATCATCCAGCTCGAGGGCAACCGGCTCTTCACGGCCGCGCAGATCATCATCGCGTCCGAG
GTCGTGAAGCTCACCGAGCGCAACGACTACATCGTGTGGCTGAACAACTCCTGGCGCTTCAGCGCGGAGGAGTCGCT
CATCACCAAGCTCATCCTGGACGTGCGGCACTCGCTGCCCGCGGACTACGC CAACGACATGCTGTGTCCGCGCAAGC
GCAAGGTCGTGGAAACCAACATCCGCGACATGCTCGTGGACATCTCCGAGACGGACACGCAGTACGACAAGCTGCCC
TTCACGAACGGCGTGCTGGACCTGGCCACGGGCGAGTTCCTCACCGGCGACCGCGCGAAGGCCTGCGTGTGCACGGT
CTCCACCGGGTACGCCTTCTCGCGCGAGGAGTTCGCGGCCGCGGCGGACTCGGAGGCCATGCGCCGGCTGGTTGGC G
TCATCGACGACATCCAGCCGGACACGCCCGAGAACGCCGATAACCGCGCGCTGTACGAGCGCGCCATGTCCAGCGCG
CTCTGCGGCGCCACGAAGACGGTCATCGTCTTCTTCTACGGCGACACCATGACCGGCAAGTCCACGAGCAAGCGTCT
GCTCATGTCCGCGCTCGGCGGACTCTTCATCGAGACCGGGCAGACCGTGCTCACGGACGTGCTCGACAAGGGCCCGA
ACCCCTTCGTGGCCAACATGCACCTGCGGCGCGCGGTCTTCTGCAGCGAGCTCCCGGACTTCGCCTGCAACAACGCG
CGCAAGCTGCGCTCCGACAACTTCAAGAAGCTGACCGAGCCCTGCATCGTGGGCCGGCCCTGCTTCTCCAACAAGAT
CCACAACCGCAACCACGCCACCTTCATCATCGACACCAACTACCGCCCGGTCTTCGACCGCGTGGACAACGCGCTCA
TGCGCCGCGTGGCGCTGGTGCGCTTCCGCACGCACTTCTCCTCGTCGGC CACTCGCGCGGCCGCCGCGCACAACGTC
GAGTACAGCGCGGTCAAGGAGATGGACGAGAGCCTGGACACCAAGATCCAGCGCAACTACTTCCGCTACGCCTTCCT
GCGCCTGCTCGTGCAGTGGTTCGGCAAGTACCACGTCCCGCAGGTCTCGCTGGCGCCCACGCCCGACGCGGTACCCG
ACTTCGCCTTCCACCGCCGCGTGGCCGAGCTGGTGGTGGCCAGCAACGACGCGCACCGCCGCGCGATGGAGTCG CTG
TCCAAGCTGGGGTACGTGCTCGTGGGCGGCAACGTGGCCATGCCCGCGGACGCCTTCCGGCAGCGGCTGGCCGCGCA
CTTCAACGCGCGCGTGCACGGCGGCGACATAGACGCCTTCATGTTCAAGCACAAGAAGGTCGTCAACGTAACGGAGG
AGTACGTGGAGTACGTATTCATCGAAGATGTCGAGAATAAATAGGCGGGCATGAACTCGGACGTGATCAAGCTCTTC
GCCGGGCACGACGAGTCCGTGCCCGGCATCCTGCCGCACCAGCTCGCGACCGTGGACTTCCTGATACGCCGCGTTCT
AGACGACAACGTCAGCGTGCTTCTCTTCCACATCATGGGCTCTGGGAAGACCGTCATCGCGCTGCTGTTCGCGATGG
TGGCCTCGCGCACCAAGAAGGTGTACATCCTGGTGCCCAACGTGAACGTCATGAACATATTCAACTACAGCATGGTC
ATGGTCGCTAACCTGTTCAACGCGCCCTTCGTGGCCGAGAACATATT CGTGTACTCGACGACTAGTTTTTATTCGCT
AAACTGCAACGACGGCGTCATAAACTACAACGGCCTCGGCAAGTACGAGAACTCGGTCTTCGTGGTCGACGAGGCGC
ACAACATCTTCGGGAACAACACCGGCGAGCTCATGATGGTGATCAAGAACAAGACGCGCGTGCCCTTCCTGCTGCTC
TCGGCCTCGCCGATCACGAACACGCCGCTCACGCTCAGCAGCATCATCAGCCTCATGTCCGATAAGGACGTG GACGT
CGGCGACATCGTGGTGCAGGGCAAGAAGGTGTTCCAGATCCTGCTGAACGAGCACGGCGTGCGCGTGATCCGCGAGG
TGCTCAAGGGGGCGCATCTCCTACTACGAGATGCCGGACACGGACATGCCCGAGGTGCTCTACCACGGGCGCCGCTTC
CTGGACACGCGCGTGGTCTACTGCCGCATGTCGCGCCGGCAGGAGGACGACTACCTCACTGTGCGCCGGCTTTGCAA
CAACGAGATGTTCGAGAAGAACATGAACAACGTGTCCATGGCGGTGCTGGGCCCGCTGAACCTGGTGAACAACCTGG
ACGTGCTCTTCCAGGCGCAGGACAAGGACCTGTACCCGAACCTGCGCATCAGCAACGGCGTGCTCTACGGGAACGAG
CTCACCAAGCTGGACATCAGCTGCAAGTTCAAGTTCTTCATCTCGAAGGTGGGCGCCATGCGCGGGAAGCACTTCAT
CTACTTCTCCAACTCGACCTACGGCAGCCTGGTCATCCGCAACGT GATGCTCAGCAACGGGTACTCGGAGTTCGGCG
GCTCGCAGAGCAACAACCCGCACACCACGCCCGACGGGCGCGCCAAGACCTTCGCGATCGTGACCAGCAAGATGAAG
GCCTCGCTGGAGGAGCTGCTCGAGGTGTACAACTCCGCGGAGAACAACGACGGCGGCGAGCTCATGTTCCTCTTCTC
CTCGAACATCATGTCCGAGTCCTACACGCTCAAGGAGGTGCGGCACATCTGGTTCATGACCATCCCCGAC ACCTTCT

FIG. 29R

CGCAGTTCAACCAGATCCTGGGCCGCGCCGTGCGCAAGTTCTCCTACGCGGACGTGGCCGCGCCCGTGAACGTGTAC
CTCATGGCGGCGGTGTACTCGGACTTCGACGAGGACATCGTCTCGCTGGAGGACTACAGCGTGGAGGACATCAACGC
GCTGCCCTTCGACGTGAAGAAGCTCTTCTACCTCAAGTTCAAGGCCAAGGAAACCAACCGCGTGTACGCCATCCTGC
AGGAGCTCTCGGACGCGTACTCCGCGCGCCCGCACCCGCAGCTCGTGGACGTGGTGCTGGGGGAGATCGTGCGCCAG
TTCTTCGCGCGGCACTGCCGCGTGCCCGCCGAGGACGCCGCGCTCGTGGCCGCCGTCGAGGCCGTTCTCGGCACGCG
CGAGGCAGCGGCCGAGTACATCCGCGCGATAGTGGACGGACACTTCTTCGTGACCAACAAGACCTTCGGGAAGTGCC
TGCTCTTCCGGCACGAGCGCGACATCGTGACCGTGCCCTTCGA GCTCGAGCACGACCCCTTCGCGTGGGCGATCAAC
TTCCGCAAGGAGGTCAGTGTGGTGAATATATAACGGCAAACATAAATAGAAAGACCGTCCTCGCGCGCGATGTCGAC
CTTCCGGCAGACGGTGTACCTGGCGGTGACGCTGCAGCCGCACGAGCTCACGCTCGACTTCCGCGGCAACGTCGCGG
AGGCGGTCATGCGCGAGTACCTCTACAAGGAGAAGGGCGGGCTCATGGCCACCGACATCGAGGTCTGC CTCGGAAAC
GAGATGCCGCTGGGGCGCATAGTGAACAACGCGGTTGTGGTCTCGGTGCCCTGCAACGTGACCTTCAAGTACTACCG
CGTCGGCGACACCGTGAGCGGCACGCTCAACGTCGAGGACGAGACCAACGTCTTCGTGGACTGCGGCGACCTCATCT
GCCAGCTCGGCAAGAGCTCGGGCGGCGTGACCTTCAACGAGTCCAAGTACTGCCTCGTGCGCAACGGAGTCGTCTAC
GAGCACGGCAGCCGGGTCTCGGCTGTGCTGCGCGAGGCGCGCTCCGGACGCGAGTCCGCGTTCGTGTTCTCCGCAGT
GCTGCTGGACGGCGTCCCCGCCGAGGAGAAGGACGAGAAGAAGGACGAGGGCGAGAAGCCCGCGGAGAAGGAGACGC
TTGCGAGCCCCGCCGCCAAAAACTAGCATTATTGGGCCGCGCGAACCTTCGATAAATGCGCACGTACACGTCGCTGC
TCTCGAAGCTGCTCAAGAGCAACCGGCGGCTCGGGAGCACGCGCGTCTTCCGCGACCCGCTGCAGCACATCAGCGCG
ACCGCCTTTGTGCACCGGCGCATCGACCGGCACCGGCGCGTCTCCATCTGCGCCGTGCTCACCACCACCGACGGGCT
CGTGGTCGCGTGCCGGCGCCGGTACTCCTTTTTGTCCTCCGAGCTCGCGGAGACGCGCTCGCCCGCGCGGCGCGTGC
TGCTCGCAACCAAGCACGCGGACGCTCTCGCGCGCCTCGGCGCCGCGCGCCCGCGCGACGACGTCA TGTTTCCGGGC
GGCGCGCCGCTGTCCGGGGAGTCGCCGCTGGCGTGCGTGCTGCGCGAGGTCGAGGAGGAGACCGGGCTGCGCGGCGA
CCAGGTCAGCGTGGACGAGCGGCTGTTCGTGCACGCCTTCATCGACGACCTGGTCTCGGGCCGCGACTTCGACGCGA
TCATCTTCACGGGCGCAGTCGCGCTTTCGAGCGCGGAGGTGGCGAAGCAGTTCCGGCCCAACGACGAGGTCAAGGGG
CTGGTTTTCCTGCACCCCGAGGACGCGGAGGGCGTGGGGTGATGGCGCGGCTGGCGGCGTTCGCGCGCTGCGCGGCG
CGCCTGCGCTGCTGGGGCGCGGCCGTCACGCGAGAGGCGGGGTCCACCACGTACACGAGGCGCCCGCCGCTCACGCG
CACGGTGGGCGGGTCGCCCAGCGCGGTCAGGAAGTTCCCGTCGTCGTCGAAGAGGCGCCCGCCGCGCTCGAGGAAGC
CCTTGCGCACCGTGACCAGCGCCGTGGAGGTGGAGTACCACACGCTCTGCCCGTCCGCGAGCCGCGCCGCGCGCGCG
GGCCCGCGCGCGTCCGCCGGGCGCGCCACCAGCGCGGACCAGCCGGAGTCGTCCTCCAGCGGCGCGAAGTCCGTGAA
GGCCTCGCGCACCCACTCCAGCGAGCAGCGCTTGAGCACGCGGAAGAGCTGCGTGAACTGCCGGGACTTGTCGCGGA
TGAGGGCCAGCAGGTCCTCGTCCACGGTGGCGGCGCCGGAGTCCTGGCGCGCGACCACGAAGTG CACGTTCACGTAG
CGGCGGTCGGGCGGCGTCATCTCGTGGCTGTTCAGGCGCACCGCGCGGCCCACGATCTGGCGCAGCGAGGCCTCGTT
CCAGGTCATGTCCAGGATGAAGATGTCGTTGATGGAGAGGAAGCTGAGGCCCTCGGAGCCGCTCAGCGAGAACACGC
AGACCTTGATCTTCTCGCCGTCGGTGTTGTCGCAGGCGTTGAAGGCGTCCACGAGCTTGGCGCGCGTGTCGCGCGTG
CGCGAGGAGAACTCCACGCTGGAGACGCCGAAGGCGCGGAAGTAGAGCAGCAGCATCTCGATGCCGGTCACGTTGAC
GAAGGGCTCGAAGACCAGACACTTGCCCGGCGAGGCCAGGATGCGCAGGCAGACCTCGGTGTACTTGCAGCTGCGCT
CGCGCAGCTCCGCGAGCAGCGAGACGTCCGCGGAGGTCATGCGGTCGCCGCTGACGGGCGCGCCGCTGCGGAAGAGC
CGCATGGCCGCCTCCGAGAAGACGCGGTCCTTGACGGCGCGCGCGAAGTCCAGGAAGAGCGCGGCCACGGCCTCGTC
GTACTCCTGCTTGGAGAGCACGGACTTGTCGGGCGCGTCCTCGAAGGCGAAGGTGGCCGCGATGCGCCGGTACACGC
GGAATACCGCGGCGCCGGACTTGCGCTCCATGGCGGCCGCGCGGCGGTAGGCCTCGGTCTGCTTCGCGGTCATGTCC
ACGTACATCATGCGCACGCGCTTGCGCGCGAAGGCGGCGGAGCCGTCGACGTCGTCGAAGAT GGAGGCCTCGTTGGT
GACTAAGTACGAGCACAGGCCGCCGAGCTTGTCCACGAGGTCCTCGGGGTTCGCGAGCGCGCCGCCGTTGAAGAGCG
GCGTCTGCCCGACCACGCCGGGGCGCAGCAGGTTCACGGCCATGGAGAACTCCTTGACGCTGTTCACCACCGGCGTG
GCCGTGAGGCAGAGCAGCTTCCCGCGGCCCATGGGGATGTTCTTCGCGAGGTAGTTGTACACCGTGCGCGCGGGCCG
CTGGCGCCCGTCCTCCTTGGTCAGCGACATCGAGATGAAGTTGTGGAACTCGTCGATGACCACGCAGACGCGGCTGC
TCGACGAGGCGGTCTTCATCAGCGTGAAGAAGCGGTGGTGGAAGCGCGGGTCGTCGTAGTTGATGAAGGTGCACCCG
GGCACGGCCTCGGGCGCGAAGCGCATCATCGTCGAGGTCCAGGGCTGCTCCACGAGCGCCTTCTTCACGAGCACGAC
CACCGTCCAGTCCGTGAAGACGTCGCGCAGGTGCT TGAGCACGTACACCGCGGTCACGGTCTTGCCCACGCCCGTCT
CGTGGAAGAGCAGCAGCGAGTGCATGCTGTCCAGGCCCAGGAACACGCGCGCCACGAAGAGCTGGTAGTCCTTGAGG
CGCACGGACTCCTCCACGCCCTGCATCTCGGAGGGCATGTGCGCGGTGCGCCGCAGCGCGTAGTCGATGTAGGCCGC
GTGCGCGCTGGTCATGGCGACGGTCGGCGCTCCTTTTACGGGGTCTGTCGTCTATCTATT GTCGGCGCGGGTCTGAT
TTAGGGGCAGTAGTTACAAAAACGTTTCCGCTGCTCGGCGCGGCGTTTGGAGGAGCGGTTGCGGCCGCGGCGGCGCA
GCCGCGCGCGGCGCGTCTTCGTGGTGCGGTGGCCGAACCAGCGCCGGTGCATGACCGGGTGCGCGACCGCGGCCGCG
CGATCCGCGCTCATGCAGGTTGCGTAGGTGCGGCACATGCTGCGCAGCACGCGCCGCGTGCGCCGCTCCACGGCGTC

FIG. 29S

GAGCCGCCTCGCGACGATGGGAAAGAGCCGGCGCCAGCCGCGCACGGCGAAGAGCGGGCGCTCGCAGACCGGGCGCG
CGAGCGCGTGGTAGGCGCCCAGCAGCCGCGGGTCCAGCGAGCGCACGTAGGTCTCCACGAAGCCGTTGCCGAAGACG
ATGGCCTGCGCGCAGAGCGGGTTCGTCATCTCCCTCTTGGAGGCGATGGCGTCGCCCACGAAGGCGCGCACGCCGCA
GTGCCGCAGCACCAGGCGCCGCCGCGGGAAGTGCAGGTGCGGGCCGAGCGCCGCGCGGGCGGCGGGGATGTGCAGCC
GCGGAGAAAAACGCGCGCGTCCCGCCATGGCATCGAAGCGCTCCGTCTGTTTTCAGTTATAGCGCCGCGGGCGGCTA
CTGCAGCAGCAGCTTGAGCTTGCGCTGACTCTCGTTCTCGATGCTCTTGGACTCGGAGGTCATGCTCTCGTAGAGCA
GCGAGTGCGTGACGTAGAGCGCCTCGTACACGCGGCTGGCGAAGGCCACGAAGCGGTC CACGAACTCGCTCTCTACG
GGGTCCTTGAGCACGCGGAAGGGCACGGCCAGCGCGTCGCGCCAGGCGGCGGCCTTGGTGCGCTCGCGCACGTGCGC
CACGAAGGCGGCGATGGCCGCGCGCCGCGGCTCGCTGGCGACCATGACGGCGCTGTCCTGAGCCAGCTGTCGCTCAC
GCACTTGAAGAGGCGCACGGTGCCGAAGAGGCTGCAGTACACGCGCAGCGCGTGCCACGTCGGTGCCGAAGAGCGTG
GGCAGCTTGAGCACCACGAAGCGCTCCTGCGTGATCTCGAGCAGCGGGCGCATCACCTCGAAGGTGATCGCGTGGTA
GTCGGCCACGTAGAGGTTGTTCTCGGTGAGGTGGTTGTTGGAGCGGATGGCGCCGCGCTCCTTGCGGTAGAGCCGGT
TGCGCGCGCTGAGGTCGAGCACGACCGCGTCGGCCTTGCCGCGCGCTCTGGAGCGCACGCTGGTGATGCCGTGCGCC
TCGAGCACCTTCTCGACGTCGCGCTCGTCGATCATGAGGTCGTGCGTGTACAGACTCAGCATCTCCGTGGGCATGCG
GTTGATGTCGTTCACCCGCGAGCACTGCAGGAAGTAGTTGGTCCCGTAGGCCAGGCTGGGCAGGTGCCCGACGCCGA
GCTGCAGGTCCAGCGCGGGCGTCGAGTCGAAGGTGGGCAGCGTCACGCTGAGCCCCTCGCGGATGCTGCGGCGCACG
GCCTCCACCGCGTCCATGGCCGATTTATTGGACGCACAGTCTGTTTTCATTTCGCG GCTACTGCGCAGTCACCTTCT
CGGCCACGATCCCCGCGTCGTAGCTGAGCCGGTACACCTCGTTGCACACCACGACCATCTGCCGCGGCACGTACATG
AGCGGGTTGTGCGCCTCCATGTGCGCGGTGGTCACGCGCACCGCCAGCTTGTCCTTGCCCCTGGAGACGTTGGAGTT
CAGCGCGGTGGGCGAGAAGAAGGTGCTGGGCGTAAAGTTGAACTGCAGCGTGCGCACGCCGGGCGTCTTGCCGAGGA
TCTCGCCGAAGACGCGCGAGACTGCGCTGTTCTCCGAGTACAGCACCTCGTTGCCGAAGCGCACGTCCATGCGCGCG
ATGACGTCGATCTTGTTCTTGAAGTCCACGCCCTTGAGGAAGGGGTCGGCCACGAAGAGGTCCTTGGCGCGCGCCTC
CGGCGAGCGGTTGTCGCCGTTGTACACGTTGCGCTGGCAGGTCCACACGCCCACGGGCACGGAGGCGTCGCCGATGT
TCACGGAGTGGATGGCGGTCGTGAAGCGGATGCGGGAGGTCGCGCGGCTGTAGGCCCCCGTGATGGCGGAGAACTTC
TTGGACATGTTGTACACGACGGAGTTCTTCCTGGTGGCGAACACTAGGATGTTCGTGTGCAGGAACACGCGCATGCC
CACGGGCACGTCGTCGATGCGCACGAAGACGTCGGTGTCCTGGATGGACACGACGCCCGACGGGGGCACCTCGACTA
TCTCCGCGGTCTCGGGGAAGCCCTCGGGGTAGCAGTTCGAGACGATCACCATGT CCTCCAGCAGGCGCTCCACGAAG
GCCATCACGAAGTCGCCCTCGGACTGCTGGAAGCCGGGGTACGATATGAAGCGGTTGTTGGCGTCGCTGAGCACGGG
CTTCATGTACACGGACAGGGAGGTGCACGCGTGCACGTCCGTGATCACCGCGGTGGTGTGGTTGATCTGCTCCACGC
GCCGCCGCGGCATCTCGATGAAGGCCGGGCGCGGGCACAGGTTCTTGACCATGTAGCCGATGAAGCTCAGCTCCATG
GAGTAGGGGAACTCCTTGGCGAGCTTGGCGGCGTCGAAGGTCTCGTCGTAGACCATGACGCAGGCGACGGGGTTCAG
CGTGACCGTGACCGTGACCTTGCTGTCGCTGAGCTTGAGCGTGCTGAAGGTCTTGTCCGCGTCAAAGGGCGTCTTGA
TGTAGGCGTGCACGCAGGCGGCCTCCTTGATGACGTCGTTGGGCGAGCTCCCGGTGGAGAGGTCGTTGAGCTCGCGC
GAGAAGCCCGAGAGCTCCATCACGCGCTCGTTGTCCAGGCAGGAGTCGAACAGCTCCTCGCCGGAGGTCTCCCAGAT
GGTGTCCGCGGCGGAGTTCACGGCCACGTGGCGGATGAGCTTGTACGCGATGTAGGGCACGTAGCACATCTTGCCCA
CGCCCTTTATCTCGGGCAGGTCCACGCTCAGCACGAAGTTGTTCATGGCCGAGATGTACTTGTCGCGGATCTCGAAG
GTCACGGTGACCGCGTCGCTGGTGGTGTCCACCACGCCCTGCGTGGTGATGT ACTGCGGCATGTACACCGTGGGCGC
GCGGTGGTCCGTGGCGAACACGCTGGCGCGCCGCACGGCGTCGTCGCCGCCCACCAGGCTCACCACGGAGTTATTCA
TTTATTCCCTGGGAAAACCAGTTAAATAAGGCTCTTCAGAGCCATGCGCACCGTCCGGCCGTCGGGCTCCAGGTAGC
AGCGCCCGTAGACGCCCTCCGTGGCGCGCGTCTCGTTGATGAGCGCGCGCACGCGGTCGGGGTCCGCGTACATCTCC
AGCGGCAGCAGCTCGATCTTGGGCTCCTCGCGCAGCGCGACGAGGTGCCGGATGGAGCCCGCGAAGGAGTCGCGGCA
CAGCCGCGAGCAGAACTCGCCCACGGCGCCGCCGTCGAGCGTCTCCACGGCCAGCGCGGCCGTGCCCACGCGCTGAC
GGCAGAACCAGCACGTGCCGTCCGCGGCGCGCAGCGCCAGCCGCTCCGCGGACACCGTGTTGAAGTACTTCGGCAGC
ACGTACTCGATGCGGCACGCCGCCGGCGGCGCGCAGGCCGACGCCCGCGGCGCGGATATGTCCACCCGCGAGAGCGC
GATGCGCTTCATGGGCGGCGGTGGATGCTATTTATGTCGCCCGCGGCTTTTCAAAGGTCGAGCGAGCACGCCGCGAA
GCGCGCGGGCGAGAACACGTACTCGTGGCCGAACTCCGGGATCTGCGCGGCGCGCTTGCGCGCGCGCATGTGCGCGA
GGAAGTTCTCCCAGGTGAGCTGGTTGCTGTTGTTCTTCGCGTAGTTCTTC ACGGTCTGCGGACGCAGGTTGCGCGTC
ACGCCCGTGACCTCGAAGATCTTGTCCAGGAAGAAGGAGTAGTTGATGGTTTTGGTGGGCGTGATCTCCTGGCAGAA
GAAGACCAGCTGCTTGAATATCTCGATGACCTCGTTGATCTTCTCGGTGCTGAGGTCCAGCTTCTCGTTTTTGACCT
GGTTGATGATCTCGAAGACCAGCTTGTAGTCCTTCTTGTTGATCATCTCGCTGTCCTTGAGGAAGCTGGAGACGT AG
TTGGCGTCCACGTCCTCGGGCCGGATCTGGTGCCGGTCCATCATCGCGCGCAGGTCGCGGATGACCTCCTCCGAGCA
CTGCTTGGAGAGCAGCCGCCGGAGCACGTTCCGCAGGTGGATGAGCTTGTTCGACACGTGGAAGTTGGACCTCTTCT
GCACGCGGATGCCCATGGGAAACACGGTCTCGCAGAACAGGCAGAACTCGTAGTCCGCGTCGGACACGAGCCCGTTG

FIG. 29T

CGGCGGCAGCCGCCGCACATGCGCAGGTTCATGCTTGCTCCAGCCCCAGCACGCGCAGGATCTCGCGGTCCAGCACT
TTAGTGTCCAGCGTGCGGGTTCTACAGAACTGGAGGAAGCCCGCGAGCGCGCGCGCGCGCCCTGGCTGCGAGAGCAG
CAGCATGCGCGCGTTCCCGGGGTCCTCGTTGATGAAGCGCGTGAGGTTCAGCGAGCACCGCGTGCAGCGCCGCGGCG
GGTCGAGCTCGACCGAGTACGCCGCGAACCAGACGTTGTCGCCCATGTATTATTTATTAACACAGAACGTCGCACAT
GTTGCGCGAGGACATGTACGGGTCGTACTCCTGCCCGTAGATGAGGATGGTGCAGTACCGCGAGATCATGAGCATGG
CCTCCTCCATGGTGAGCAGGTCGTCCTCGAACATGGCCTTGTGCTGCATGTGCTGGCTCTGCTTGGCGGCCATCGCG
GCCGCGCCGTCGCCGCGCAGCCACTCGTTCAGACACTGGCCGTCGCCGGCGCCGCTCTCCTGCGCGAAGGTGT TGCG
CATGGCGCGCATGAGCCTGGCTTCCCTGGCCGAGCGGCTGAGCACGGTCATGGGGTCGTAGAGCCAGGGGCCTGCGT
CCGTGAACAGGATGGTGCAGTACCCGTTGGCGAAGGCGTCCGCGCCGCTGCAGTTGTCGATGCCGTCGCCGACCCTG
TAGCACACCGCGGAGACCAGCCGGTACATGATGCCGTTGAGCATCATGTCCTGCGACACCTCGATGGGAATGTCGCT
GATCACGGGCCGCATGTTCGTGAAGCAGTCGCCCGTGCTGGCCATGCCCCCGCGCCGGTTCACCAGGAACACCAGCA
CGCCGTTCGTGATCACGGGCGCGCGGTCGCGCTCGTAGAGGTAGCCGCTCGCCGCGCACACGGCGGACGCCACGTCC
GTGCGAGAGACCGCGCCCATGTTCTGGGCGGGCATGTACAGCACTCGCCCGGCCTCCGCGGTGCACGAGAAGGGCTG
CTCCCCGCCCACGTGGATGGGCGCCGTCGATGTCGTGATCATCTTG CTGGAGTCCACCACCAGGTAGGGCACCGTGT
GCATGGCCATGTCGCCCATGCCCCCGATCCCCGTTCCGAACGACGGCCGCGACACGCTCACGAGCGTCGGCTTGAAC
GAGACTATGGAGAAGATGGAGGCCAAAATCTGCTCCTCGTCGGTCATGATGGAGGCGCACGAGGGGTGGATGATCTT
CATTAGGGCGTTGTCGATGGACTCGTCGCTCTCGCAGTAGAAGACGCCCATGCGGAGGTTCAGGATGCACC GCCGCA
GGTTGGTGTGCAGCACCGCGCGCTGGATCTCCATGGACACGGAGTCGCCGACGCCGGGCATCACGATGGGCGTTTCC
TCGGTGAGCTTGTTCACCAGCAGCTGGTAGTTGTTGGGTCGCACGCGGCTGTTGTGGTGGAGCTGCGCCAGGAGCGA
GAGGCTGTCCCCGTTGACGAACGCGGACTCGATGGCCGGCAGCTTTACGCCGAACAGCGCCATGGCGATGGGGTGCA
CGAAGCCCACGGAGTCGGACGACTTGAACGAGAAGAGCAGGTCGCCCGAGGAGCTCATGTCTTTGAAGTGCACGGAC
TGGAACTGCGTGGCGGAGAGCAAGTTCTGGTAGCTGGACATGCTCTGCAGGTCGTCGATCTCCTTCATCTGCTTGTT
TACGCGGGTCGAGTTCCTCCCGTAGATGATCACCAGCGGGTGCGTCTGGCTCACGGATAGCCCCGAGTCCGTCATGG
CGGCGCGCACGCTGTTCAGCAGATCGAACAGCTCCGACCGGTCT CTGTTCTGGATCCCGACCTTTGCCATCACAGAC
ATGAGCTCCTGGATGGTCATGTTCTTGTGGTCTCGGCGCGTGGACCGCAGGTAGTCGGCGATCATCTCGCCTTCCTT
ACGGATCTTCATCTGCCAGTCGTGCATGGAGGTCATGCGGTCCACAGGCATGAGCACGCTGTCGGAGGACGACTGCG
CGGCGCTGCCGGACTGGCGCGAGCCAGGGCGCGCGGACGACGGGCGCGCGGAGCTGCCGCGGCTGGAGG AGGACCTG
GACCTCCGCGAGGATCTTCGCTGCGAAGAGCTGCGCACGGGCCGCTGGGCGCGCGCCCCGGCGGAAACCATGTCCTC
GCGGTTTATGCTTAGGAGCGAGCTGCAGACCGCGCACGACAGCGACTGTTTTGGAATGTGGATGTGGTCGCACTCCA
GTGACATGCCCGCATTGTCGTAGCCCGGGACCAAGTCGAACTTTGCGTTAAAAAAATCTGATGCGCACGCGGGCGAT
TCCATTTATACCGGGAGTTTTTATGAGGTGCCGGTATTATCCACGCGATCTCGCAGTGTGCTGGGAGTATCTCGCGT
AGCCGCCCCCGTGAGCAAACGACGCAAGTCGTTGATGGCCGACTGTGTTACGGACTTCGCCGTCTCGATGTCGCGCG
TAAGGCTGAGCGACTCGGCGTTGAGGTCGCGCACGCTGTCCGCGATGTCGGCCAGCTCCTTTTTGATGAAATCCTTA
TCATTATCGGCGTTGATGACTTTGTCCGGCACTCTAGACTCT AGAACCGGTGACGCGGCGGGCGCCTTGATCGTCGG
GCAGCTGGACGCCGGGTACTGGGGCGGCGGCAATGATTGCTGTAGGAAGACGGGCTTAGCGGCAGGCGCCGGTTTTG
TCGGCAAGGGCGGCGCCGGCGGGCACTGTCGTGTAGACGGCGGGCACGCCGGCGCGGGGCACGCCGCCGGTGGCGGA
CATGTCGGCGCAGTTGCGGGTGGACACGCGGGCGCGGGCGCCGGCGCGGGGCACGGCGCGGCAGGCG CAGGGCACGC
GGGAGCCGGAGCTGGAGCCGGGCACGGCGCGGCAGGCGCAGGGCACGCGGGAGCCGGGCACGCCGGCGCGGGAGGAC
ATGCCGGCGCAGCGGCAGGACAGACCACCGCTGTCGCGGAGCACGCGGCAACCGGCGTGGAGCACGCGGCGGGCATT
ACGTTCAGAGGCGTCGACTGGACCTTGGCACCACGGGGCAGTAGCGATGGCGCTAGGGGCGACTGTCCGGTGGTTGG
ACGCTGCATGCAAGCAATCGCAGATTTCAGACGGGACTGGTAATACCTGCCCGCTTCCTTCACCGTGTACTTGTCGA
CGGAGTCTACCTCCTCATCGGGAGGACATGGCTGCTCCGGTGCGGGAATGACTGCTTGAGGACACTTGGTGAACAGA
CTGGAGCTGGTCTCCGCTAGCACCAGTTTAGACTTGGCCAAGTCGGAGGCAAACTTTCTTCTGAGATCCATTTAAGC
CTTCAAAATTGAACGTGTACGCCGACCGCTAAATGGAAGAATCGGTGGCCGTCGAGTACGCGGACGAGGACGAGGAT
GAGATTGAGGAGTACGAGGAGGAGGACGAGGACGAGGAGGAAGAGTCTGCCGAGGGCGCCGCCGCCTCCTCGGTCAG
CGACGTAGCGCTCTCTGCCGCCGAGAAGCTGGTGGCCTCGGAGGTCCCGGACGACGCGGCTGCCGCGGACACCAACG
TGCGTCAACGCGTCACCGCGCGCGTGGAGGAGCTTAAGGCGCGCTACACACGGCGGATGAGTCTA TTTGAGCTCACC
GGAATTGTAGCAGAGAGTTTCAATCTTCTGTGTCGCGGGCGGCTGCCGCTCGTGGCGGACGCCGCAGACCCGGCGCT
CGACAACGAGCTCAAAGTGGTGGTTCGGGAGCTCGAGGAGGGCGTCTGCCCCATCGTCATCGAGAAAAACGGCGAGT
TCCTCTCGCCGGGCGACTTCGACCCCGAGTGCCTGCGCTACCACCTGACGTACATGACCGACCTCTGGAAGTCCCAG
GGGCGCATGTAGCCGCGGCTACTCCGACTCGGCGGCCTCCGCGATTTTTTCTTTTATCATGTCCAGCAGCTCGCGCA
CCACGATGGGGCGGCCGCAGTACGTGATGCCGTTTTCGGATATCACGCTCTGCGCGATGTCCACCAGCGAGCCCTCG
CGCTCCCAGTACTCGCGCGCGAGCACCTCCTTGTACAACGCGCGGTGGTTGGCCACGTACCGCACCAGCGTCTGGAT

FIG. 29U

GTTCTTCACGCCCACGCTCTTGAGGTCCTGCGGCGAGAACTTCTCGCGCAGCGACACGAAGACGTCCCGGACGAGCT
TGCCGATCTCCACGTTGGTCTTGAACTCGTTGTACAGCACCACGTAGAGCTTGCACACGACCGTGGCGAACTTCGCG
GGCTTGAGATCCTTGTTCTGGAAGACCAGCATGCTGCTCATCACCTTCTTCATGAAGGCCAGGTACTTCGCGCGGTC
GCCCTCGACGCTCACGCTCCCGACCTCGAGATCGGACACGCAGCGGATTCCGTGCTCCGCGCT CTCCGCGGAGACGC
GCAGCAGCTCCTGGTACTCCTTGAGCTTCTGCTTGTCCGTCATCAGCGAGTTGTCGAATACCGCCACCAGCTTGAGC
ACGTAGTTCTCGTCCGAGAAGACCTTGTTCAGACACTTCACCAGGAAGCTGTAGTGGCTCTGCAGGATCTTCATGAC
CGCGTTGGCTCCGCTGGCTCCGCGGACGTGCGATATCATCTCCATGATCTTCTTGGAGTCGTCGATGATCTCCTCGG
TGTCGTTTCGCATGTTGCGGTACATCGCGTTCAGCGAGACCAGCGTCTGCGCGGCCAGGAGCACGTCGCGGAACACG
CGCGCGAACTCGCGCTTCTCCTCCGCGTCGGCGATGCTGTTGTACACGGACTTCGCCACCGCGTTCGACTTCAGGAA
CCAGAAGGAGAGCGCCTGGTAATTGAAGTGCTTCATTAGCGCCAGCACGTCCGCCTCGCTCATTTCCGGCGCAATGG
GGCACACCGAGCTTTCGAGCACGGGCACCATGCTGA CGAGCGTGTCCACGTCCGTGTCGAAGTCCAGGCAGTCCACG
CAGAGCCCGGTGCCGCGGCTCAGGTGATCGCGGCTGATGTTGTAGAAGCGCTCGTAGCAGGTGCGGAGGCGGTCCAT
GTCGGCTGCGTTTTAGGGAGACACACACTCTTGAATTATGGCTGCGGGTAGAACTCCTGCAGCAGCGCCGGCGCACG
CGCGGAGTCCGGCTCCACTCCCAGCTTCAGCGCGCAGTTCACGGACCAGGTCTTCATGAAG CGGTCGGGCGCGTCCG
TGACCACGTGCCGGAAGAGCTTCGCGAAGTGGCGGCTCACGGCGTTGGGCACGGTCGCGTTGCGCACGAAGGCCGTG
AAGCGCGAGGTCAGCTTCGGCGCGAAGCGCTTGCCGTCCACGAAGAAGCCAGAGGTGGTGAGCGAGAGCCCGTTCTC
CTCGCGCACCACGCGTCGCGCGGCCTTGTGCGGAAACATGCTCGCGAGGCGCCCGCTCGCGTCCTGGTCTAGGTGGA
TGGCGTCCGTGGCCGCGTCCTTGCGGATGCGCACCACGTCGTGCACGATCTCCTGGATGAGGATGCGCGTGGCTGCG
GTCTCCGTCAGCCGCATGGGGAAGTAGACCATGTCCCCGGAGATGAGCACGTTCCCGCTAGCGTTTACGTAGCTCAC
TATCTCGGACACGGTGCGCAGACGCACGATCGCGCCTTCGCAGCAGTGCACCACGTAGTACCCGGCGGTGGCGCGCA
GGCGCTTGTTGTCCGCCTCGAAGTCCGCCTCCAACCCCTCGTTGAAGTACTTGTCGAATATGATGGGCAGGAAGGAT
AGTTTTGACTCGGTGACCACCTTCCCGAAGTTGAGGATGTACGGGTTCAGCGCGCTGCGGTCGACCTCTTCGTCGTA
CACGCAGGACTTGAAGGTGTCGGTGTGCGCCTGGCTGCGCAGGAAGCAGCACGGAATGCAGATGCGCTGCAGGCGGT
GGAAGATGGAGAGGAAGCCCACGCTGTTGTAGCGCCCGTCGGGGTCCATGCACGAAAAC ATGACGCCGTTTCCGTTC
ACGAAGACCTCGCGCGTCTCGGACTTGAAGAAGTTGTTGCTGACCTTGGCCATGTCCGCGTCCAGCGACTGCACGAT
CACGGGCTTGCGGTTCTTGGTCTTGGTGTTCTGGCAGATGCGCGACCAGTACACGGTCTCCACCTTGGTGAAGTCCG
AGGACTGCTTCACGTTGTTGAACATCACGCTGATGGCCACGATCAAGAACGTGAAGTACTTCTCGATGTTCGGGATG
TAGTTCTTGACCTTCACGGACACGTGCGACTTCGCGAGGATGATCGAGATGCGCTTGTCCGTGGAGAGCAGGATGTT
GTTGGTCGCCGTCTCCACGAAGATGAAGCTCGTTTCCATGTCCAGCTTCATCTTAGACGTGATGGTCGTGTTCAGCG
ACACCTTGTAGGTGATGTCGCCCTTGACGCGGTCCATCTTTACGTCCATGCTCTCGATGAGCTTCGTGAACAGACTC
ACGTCGTTCACCGTGAGCGTCTTCCCGTCGCT CGAGATGACCAGGTCGCCTTCCGGGCCCCACACCGAGAGGTTCAG
CGGCTCGTCCACCAGCAGGAAGCGCGTCCCCGTCATCGACACGAAGAAGTCGTCCGTCTTCGAGAGCAGGATGTCGA
AGTCGCCCACCTCCGCTCGCTTGTCCGGCGACTGCTGCGCGATCGCGCGGAGCCCGGACTCGCGCAGGTTCGTGCGG
AAGATGTTGTTGAACTTGGTCTCCACGTTCATGTTTAGGTCGAGGTTCGCGAACTCG CGGATGAGCCGCTCCTCGAA
CTTGAGGATGGAGTCGTTGGGCTCCTCGAAGGAGCCGAACTCCGGCGCGGAGGTGTCCGCCGCGCGCGCCACCCAGA
CCACCAGGAAGTTGCACGCGTCCGCGTACGCGTTGTAGAGGATGCCGTCCGTGCGGATGAGCGTTTTCTTTTGCGTG
GGCGAGAACGGGTTGAAGATGGTGTTGTCCACGTAGCTGTACTCCAGGTTGTTCTTGTGCGAGTACACGATGATCTC
GTCCTGCAGGCCCAGCAGGCTCCCCAAGTACCCCTTGAGCTGCCGCACGCGCATGGTCAGCAAGATGTGTCTGCGCA
CGTGCTCGGGGTCCTTCTGGATGTACTGCTTCGCGAAGAAGTAGATCGGCGAGGCCTCGTCCACGGAGTCGTACAGC
GACAGGTACAGCACGCGCTCGATCTCCTGGTGGCGCCCCACCAGCACCACCAGCTGCGGCGCGACGGTGTAGAGCAT
GGTCGCGCGGGCGTATTTATAGCCGGCGTTAAACTGAAATAAAATACGCGGGTCGCGAGGCAGCGCCATGTTCCAGC
CGGTGCCCGACATGGCCGCCGAGGCCGACATCGACCTCGGCGACGTCAGCGTGGACGCGACGCGCGCGGGCGCGCGC
GAGAAGACCGTCTTCTTCGCGCGCAACAAGCGCATGTACCCGCACCGCAGCAAGGACGAGGAGCGCAAGCTGTCGCT
GGGCTTCTTCTTGCAGCGGCTGGACTTCCTCACGTCGCGCGAGGTCAACCTGCAG TTCCGGTCGCTGGACGCGCTGC
GCACCGAGAACGTCATGAAGAAGAACAACGTGCTCGTGGCGCCGTACATCCTCATCGCGACGCTCGCGGGGCGCGGC
TTCCGCATGACGGAGACCATGGTCGAGCTCTACTTCCCCGAGCTGTACCGCGAGACCAGCAAGCGCTTCCGCTTCTG
CGCGCAGATAAAGGTCATCCAGGACTTCCTGGGGTTCGCCCACGACAGCTACCACACTTACGACTTCGAGACGTACT
TCGCGTTCGTGGCGCTGGTGCTGCGCGGCGCGGACTCCGCGGCCGAGGCCTTCGACGTCCGCGCCGAGAGCGGGCTT
GTGCGCAGCCTCACCGAGATCACGTACCGGCTCTACGTGATGCAGCTGCGCTCCGACGCCGCGCAGTGGAGCGTGAG
CACCGGCGCCGTAGTCTCGCAGGCGGTGAACACCGTGCTGTCGGTCGTCGGCGACCTTGCCGCGCGCGCGGAGGCCG
AGCGGCTCACGCCCGTGTGCGACCTCGCGCGCGAGAACCCGCTCTCGCTCGAAGACCTGCGCAAGTACGGCCCGCGG
CTGCGCTCGCTGCTCACGACCATGGCGCGCGCGCGATCCTTCAAGACGAACCGGCGGGACAAGGACGCGCTGTCCCG
GTTCTGCCGACTGACGGCGGGCCCTAGCCCGTCTGCGTGCCGCGCGTCGCCATAGGCGTCGGCGCGCGCTCGCCGCC

FIG. 29V

GGAACACTCGGGGTCGCTGAACATGTAGATGAGCGCGACGCCTAGCAGCAGGTACATGATCATGCTGATCACGGTTT
TGAACACGACGGCGGCGAACGTGTTGGACCGCAGTCGGTGCTCGCAGAAGTGCATGAACAGGTGCCGCATGAGGTCG
ATGGCCCCGTTGGCCACCTGGAAAAGGGCGAGGCCGCCGATGGACTTGATCACCGTCACGTAGCACGGCCGCATTCG
ACGACGCTATTTACTCACTGTCAAAAGAAACGGCGCCATCCGACCGGAGGTTGAGGTTGCGCTTCATGTTCCAGTAC
ATCTCGCCGATGCTCGAGTAGTACGCCGTCAGCCGCGATATTTTTTCTCGGACCAGCTCGTAGGCCTTCTGCATCTC
CGCAACGCCGATCTCCGCGTCGCCCACGTACCGGCCGCTGCGGCGCACGATCAGCAGCAGCGCCTTCAGGTTCTCCA
GCGCGATCATGTCCATGTACAGCGACTTCGAGAGCTGCACGAAGAGGTTGTACCGCTCCAGGATGCTGTTCTTCACC
TCGTCCGCGATCGGGACTCCGAAGATGCGCTCCGTGGTGTACACGGACTGCGTGAGCTGCTTGAAGAGCGCGGAGAT
GCAGCAGGTCGCGCGCTTGACGGCGTCGAGCTGCTTCTCGGAGCGCGCGCTCGCGATGCTCAGCGCGCTGTTCACGA
CGTTGCTCGTGTCGCGCACGTAGCGCGTCTTCAGCGCGGCGTTGATGGCATCCGCGATCTCGTTGCTGCTCACGCTC
GAGTCGTCCGAGCTGCCCGAGACCTCGTCCAGCAGCCCCGAGATCGTGATGTCGGGCGAGCCGCCGACGGTCACCAG
ACGGTCGAGCAGGTTGCAGGGCATGGACATGAGGATGCCCTCGCTCGAGAGGCAGCCCTCGTCGATCATGCTCTGCA
GGTTGCGCTTGAAGGCCGTGTTTTCGGGCATGAACCCGTCCACGCTCATGAGCTCGTCGACCGTGCTCGCGGAAAAG
ATGCCCCTCACGTTGATGCGGTCCAGCATGCCCATGTCCTGCGAGCACAGCACCACCGACTGGTCGGCCGTCTCGGC
GGCGTCCTTGGCGCCGCCGTAGATGATGCGCGGAAACCGCCAGCTCGCCGGAAAGGAGAAGGAGGGAAACCGGCACT
GCGCGCTCGGGCCTCGGTAGCCCTGCGCGTCGCGCACGTTGGTGGCCGTGACCATGAACTGCAGCAGGTCGTGCGCG
GACGCCATGATCTTCTCCACCTCCTCCTTGCTGCAGCAGACCTTGCCCAGGCTGCGCGCGATGTTCGTTTTGCTCAC
CGAGGGCGAGACCGTGACGGCGGTGTGCCGGCGGCTGCCGAGCGTGTACGCGCTCACGCTAACGCGGTACCCCATGG
CGCCGAAGAGCAGCTTCACGAAGTCCAGGTAGCTCTCCTTATTGATGTAGTGCGGCGCGCCCTTGTCTTCCATCCTC
AGCCCGGCGTAGGCCATGAGCACTTCCTTCATCGCCGTCTCGGGGTCCGAGTTGCACACCAGCCGCAGCATCTGGAA
GAACTGCGTGAAGGCGCGCTGCGAGAGCCCGATGTGGTGGTTGGGCTGCGTCGACCGGCGCGGGAACTCCCTGGGCG
TCATGGCGTTGATGCCCGAGAGCGTCTCCATCACGAGCGCGCCCACGGTCTTCTGGCCCATGACGCGCGGGTAAAAG
CACACGCGGAGGGGCTCCTTGCCGGCCGCGAGCGCGTCCGAGAGCAGCGAGCAGTACGTGACGTTGTCGTGGTCGAA
GAGCGCGAAGGTGTAGCAGACGGAGCTCATGAAGAGCGAGTCGGCGGTGCTCATGGACTTGAACTCCGTGTACGCGA
TTCCGTCCCAGAACAGGCTCTTTCCGGGCGCGATCAGCGGGGACGCGCGGTCGGCGCGCATCAGCATGGAGAGCAGC
GTCACGTAGTAACGGATGTTGGCGGAAACGTCTACGAACTGCATGCCGGGCGAGGCCACGCGCAGGGTCGCGCCCGA
GGTAGTGAGCACCTCCAGGCTGTCCATGAGCGTCACGCTGGGGTGCAGCTGCGCAAGGCGCGCCAGCTGGCTCTGGT
AGAAGATGGACACGGCGAGGCTGGCCACGCTGCCGCGCGCCATGCGCAGGTTTTGTCCGTTGAAGGTGAGCTGGCGC
AGCGAGAACACGGAGTCGAAGTACTGGAAGAAGGTGAGCAGGTACTTGAGCGGCATGGTCGTCAGCTCGGTATCCAC
CTGCGGCGTCTGCGTGAGCACGATTCCGTTCTTGGCCGCGGCGTCGGGGATGTCGTACATGGCGTCCATTCTGGCGC
GGGAGGCGTCGGTGAGCAGCGCGCGCACGTTGAGCAGCATGAGCAGGTCTCGCGCGAGCATGGTCCCGTCGACCAGC
CGGGCGCGAAAGCCGATCTCGGCGGGGCCGGCGATGTTGGGGTAGATCAGGTTCAGCAGGTACGTGTTGTCGAAGCT
CAGCGAGGGGAAGGAGATGGGCGACTTCGCCGGGAGGCCTGTGGGGTAGCGCACGTAGCCGCCGCAGATGCGCGCGT
GCGCCTCAAAGCTGGTCACGCGAGTCTTCAGCAGGTTGCGGGTGAAGGGCGGCACGTCCTTGAAGGACTGCGTGCAG
ATCACGGGGTTGGCGGTGTCGGTCAGCTTGAGGTTGGTGGGCTTGAGCTCCGCGAAGTTGGGGCCCAGCAGCACGGG
GACGAGGTGCGAGTTGGCGGCGCTGTCGAGCAGGAAGTTGATGCCGAACTGCTTCACGGCGACCTCGGTTTCCTCGT
CGCTGGCGAGCTTCTCCGCGTCCTCGAGGAAGAGCGCGTCCAGCGGGTGCACGTACGTGCGGTTGACGTCGTAGCTG
GGCTTGAAGTCCGAACACAGCGTGGGGAGCACGGTGGAGACGAGCTGGAACATGTATTCCGCGCCCTCCACATGGTG
CAAGGCCATGTGCACGTTTGGGGCCGTCATTTATTTAGTATTAAATGACGGCCGTACCGGTAACCGATATTCCTGGA
GACTACGGGCCGACGTCCTTTTCGGAGGACAACTACCCGCTGAACAAGCACTACGAGCTCACCAAAGGCCAGCTCTC
GATCCTGCGCACGGTCAACGACAAGCTGCTCGCGCGCACCGTGCAGCACTCGGACGGGGAGAGCGATGAGAGCGAGA
GCGAGGAGGACGACATCTCAGTCCGCTGCCGCCGGACGAGGAGGAGCCGGACTCGTGCGTGGCCCGAGTCATGCCGC
GGGACGCGGACCTGCGGCGCCAAAAAAGGCCGACGGCTACATCATTGCCGCCGAGCAGCAGCGCCAGCAGCGCATAA
ACATTCTGGTATCCGATCGAGAGGCCGTCGTGGAGCGGGAGCCGGTTCAGACGTCGTTCGCGCGCGTCTCGGCTATC
CCGATCCACGGGGACGGCGCGCGCCGCACCACCGCCTCCTTCTCCGCGACCACGCCGTCGCTGGGCGCCGTGTTCGA
CGACGCCAAGCGCGTGCGGCTGCTGGAGGAGGAGGTCAAGGAGCTCCGCAGAAAGTGCGCGACCTCTCAGGATAACG
GAAACCTGGAGAACTTCACCAAGGTGCTGTTCGGCAAGGCGCCGCGCGCGAGCGAGCTGAACAAGCGCGTGGTCATC
GTGAACTACGCCACGCTGAACAACGTGACGCTGTCCATGGATGACCTCGAGAAGTGCTCCGACGAGGAGGTGGACCG
CATGTACTCGGTCATCCGGCGCTACAACGAGACGCGGAAGAAGAAGATCCTGGTCACGAACGTGGTCATCATCGGGA
TCACCGTGCTCGAGCACGTGCTGGTGAAGCTTGGCTTCTCGGAGGTGCGCGGGCTCAGCGCCGACCTCTCGTCGGAG
CTCATCGACGTGGAGATCGGCGAGGACTGCGAGCACATCGCGGAGCGCCTGGGGTTCGGGAACAGCCCGGTGCTAAA
CGTGGCGCTCTTCGTGGTAAAGCTGTTCGTGCGGAAGCTGAACCTGATCTGATCAACACATGCCGCCGTCGAGGTCC
ATGGCGTTCATGAGGTTGGAGGCGCGGCGGCGCGCGCCGGTGGAAGCGGTGGAGGCGCTCGAGGTCGTGGAGCAGGG

FIG. 29W

AGTGTTGCCGGAGGAGGCGCGGCGGCGGGAGCTAGAAGCAGAACTCGAGGTTCCGCTGGTGGTGCTGCGGCGACTCG
TGCCGCTCGTGCCGCTCCTGCCAGTGCCAGTGCCGCTGCGGCGTGAAGTACCGGTGCCGGACCTGCCGCTGGAGCTT
TTCTTGCGGCCGCCGTTAACGCTGTCGATGCCGAGCAGGTCCTCGCACACCTCGCCGACGGTTCCCTGCACGTCCAA
CTTGCCGTTCTTGACAACCCCGTACACGATCTTGCCGCAGTTGGACACAGCCTGGATGGTGGTCTCGTCGCTGTCAA
AGGCGTTCATTCCGCCGCACGCGCCGTCGTTGTTTCTTCGAGAAGGCGCGCCGCTGCGGCGACTCCGGGTGCTGGCG
CTGGACCGAGTTCCGGAGGACCTGGAGCCCGTGGACCGGCTGCCGGTCGACCTGGTGCCGGTAGTGCGCCTTCTGGA
CGAAGAGGAGGAGGCGCTTCCGCGGCGGGTGGACGAACTAGCCTCCAGCGCGCCGGCGCCGCCCACACAATCCACGT
CGGCGGCGGCAGCGCCTCCGCGAATGACCTGCTCGTTGTTGAGCTGCGTCAGGAGAGATCGCAGCTGCGGCGCGATC
TTCTGCAAGGTGCTCACGTAGTCGTCGTAGCTGCTCTGCGGGCGCTGCGCCATTTTTTCGGACGCCATTTATTACGC
GGAATATCTACGACGACGCAGCACTGAATCGGTTTCTCGCGACGGGAGATTCCGCGGTCGGCGCCGGTGCGGTGTTG
TCGCCGGGCGACGAGGTAACCAGCGCGTGGAAGGCGCGCACCTGGTCGTCCGTCATCTTGTCCTCG AACGAGGACGC
GCCCGGGGGAAGCAGGTCCTTGTTGCGCGGAACGGCGGGCGCCGAGACGCACGACCGGCGGTACATCATGATGACGA
TGTAGCACACGATCGAGATGACGATCACGGTCAGCAGCGCGTCGAGGAGCCCCATTTATTACCTGTATATGCCCGCG
TTTACCGGGCGGTGAGCTCAATGTCGGTGTTGTTTAGCCGGGCGTACGGGACGCTGCCGGAGCACTTCCTGTACATG
CTGAACACGAACAGCCCGAGCAGCAGCACGGCGCCCACTATGAAGCAGGTTACGCACAGCGCGCGCCACACGTAGTC
GGTGACGTTGGTGTTCTTGCTGAAATCCACGAAGGCGAAGACGCAGGCGGCCGTCAGCAGCAGCACGCCGCATATCA
GCACTCCGGAGTAGTAAGAGCTCAAGGTCTCGAATATGTCCATTTATCTGAGGAGAAATTTAAATTACTGAATGGAC
GAAGTGGAATAGAAACCACGAGAACACGACGGACTGCAG CACGAAGATGGTGCTCAGCTTCGTCTTCATGGGCATGC
AGAAGTTCGCGGCCAGCGCCATACAGAAGATGAACACGAGCACCGCCGGGTCGTAGTCGGACACCATTTACACTACG
CTAAAAGGCATATCTCGGCGCGCGACGTCCACGAGCACCAGCACGCGGACGCCCGCGGGCGCGCCGGCGGCGACCGC
GGCGAGCTGCCCGGCCGTGGGGTTCACCAGCAGCAGTGCGCGCGCGGTTCGCGGGACAGGGTCC TCGTAGGACATGG
TCGGTGTGGACCCGGGACGCAGCGGCCGCCCCTGTCTGTCGAAGAGGCCCTCGGGAAACGAGGTGCCCGGAACGGCC
ACGACGACGGTGTCGCTATCTAGAAACATTTATGGTCTTGGTTTCCACGGATCGCCTCGAGTAGACCGCCACGAAGT
AGAAGATGACGCCCGCCGCGAGCGCCGCCACCAGGAAGGGCGGCACGGCGGGCAGGTTCGCGGACGCGTTGTCGCGC
ACGCCGGGGTCCGGGTCTGCGTAGCCCGCGCCCACGGCCTTGCCGCAGTCGGCGATCATGTGCGCGCGCGAGTTCTG
CATGACCAGGCTGTCCACGTCGATGCGGCACCCCACGTAGCGGCACCGCGAGCGCTGCTCGTCCTGGCTGAAGAAGA
GCCACTTGCGGTCGCGCGACTGGTCCGTGCACTCGTGCGCGCGGCAGACGCGCGGGCCCAGGTACTTCCCGAGCGTG
GTGCCCGCGACGCACGCGCACTCCGGCGCGGCGCGGT GCGCGTCGCAGTAGCGCCGCAGCGCGGAGTCGCCGAAGGC
GAAGGAGGCGGGCCGCGCCACGCGCACGAATTCCGAGCAGAAGCGCGCGTCCATGTGCTTGGCGCAGAGCGCCGCGT
AGGTGTCCAGCGCCGCGTAGCGGCCCGTGCGCAGCCAGGCCATGCACTCGGGCGCGTCAGGCTCCACCGCGCAGCGG
CTGGCCATGACGCCGTCGCAGTGCGCGGTCTTGTACCCGTTCGCGAACACGGACGGGCACCC GGGCCCCGGATTTGT
GCAGCAGCGCGCCATGGCGGCGTCCGTGGGCGGCGCCGAGGCGCCGATCTCGAACGCGCACATGGTGCCCTGGCGCA
GGTACGGCTTCGCGATCTCGGGAACGTAGTCTGCGCGCAGCAGCGAGCCCGGGCGGAAGAAGAGCGAGTCGCAGGGC
GGGCCTCGCACGAGCCGCGCGCGGCTCGCCAGCTCTGGCGAGAGGAAGCGCCCGCACTGCCCGGGGTCCATGGTCGG
CAGCAGACAGAACCGCGGCCGTACGGTCTTCAGCTTCGGGTCGGAGAAGGTTTCTGATTCTTCCGCGAAGGCGAAGG
TGTCCGTGGCGCTCGTGTGGGTGACGCGCAGCGCGTACTCGCCGGGCGTCGGCGTGTCGAGCACCTCCACCTTGGAT
ACGGTGTCCCCCATTTGAAGACGCTATTTACGCCGCTGCCTACTCGGCGAAGAATAGGTCCTCCGACTTGGCGCCCG
CGTACACCGGGCAGGCGGGCGCGGCGGAGCGAGTGCGCACGATACCGCGGCCAGTGAGGCGGAAGGCGTAGATGGCG
AACAGCAGGCCGAGCACGATGTACATGAAGGTGGTGGCGCCCACGGACCCGGTCACGTGCGTCACGATGATGGTGAC
GATGGACATGATCGTGCACACGATGGCCATGCCGGTGTTGTTGGCCGCGTAGGGGTGCATGATCTGCATGGCCGCGC
AGTATCCGATGACCAGGCACGGCAGCGGGAGGATAAGTGAGGCAATACCTATCATTACTA GAGCGAGCACGGGGGTG
GACGTCAAGGCCAATACAAAAATCACAATACCTGTTAGTATGCGGATATCCTCGTACTGGAGGACGCTGTAAGGCGC
GATATTCCCTCCAGGCACTGGCCGGGGGGTAGCCGGGACTAGGGGGGAGTCGGCAGTGCCGGGGTCTTTGGGGAGAA
AGGCATTCTGCTCCTCCGGGCTGAAGAGCTCGGCGTCCTGAACGCCGCCGGCGGTGAACTCGTCGTTATAGTAACTA
AAGTAGCTTTCCATTTATATGTTGAAAAATGTTTGGAGGCGTACAGGTGGACGACAAACTCTACGCGTACCTAAAAA
AACTCGCCGGACGCGGGCGGCCGCTGTGTCTGTTCCGCGACAACGGCGAGTTCGTCGAAGTCTTCGCGGGGTCCGCG
TTCCGCTTTGTGCTGCCCGTGGGCCTCTTCGCGGACCTGCGCGTGCGCACGCGCGGCGTGGCCTTCCCAAAACTGCG
CGACTCCGCGCGCATGCGCGGCGTGCGGGTGGACGCGCACACGCTGCCCTCGCTGTACCCCAACCAGCGCATCGTGG
TGGACGAGGTGCTCGCGGCCCGCGACCAGTTGCTGGCCGCGGGCCGCGCCGTGTACGTGACGCTGCATCTGGCTTGC
GGCTTCGGGAAGACGCTGACCGCGTGCCACCTCATCGCCACGCACGGCCGCCGCGCGGTGGTGTGCGTGCCCAACCG
CATGCTGGTGCCGCAGTGGCGCGCGGCCGTGGCGGAGCTGCGGGTGCCCTTCGCGGTC TCCTGCGACGGCGCGGCCT
CGCTGCTGCGCTCGGGCGAGCTCGACCGCGCCATGGTGGCCATCGTGGTCAGCCGGCACTTCGCCAACGACGACTTC
TGCCGCGCGGTGAGCCGGCAGTTTGACGTGCTCGTGCTCGACGAGTCGCACACATACAACCTCATGAACAACACCGC

FIG. 29X

GGTCTCGCGCTTCTTAACCAAGTACCCGCCGCCCATGTGCTTCTTCCTGACCGCGACGCCGCGCACGGCCAACCGCA
TCTACTGCAACCGCGTGGTGAACGTGTCCGTGGTCAGCCGCCTCACCAAGGTGGTGCGCGTGGTGGACGCCTTCTTC
GAGCCGTACACCACGCCCAAGATCCGCACGCTCGAGCGCAGCCTCGATGGACCTCAGAACAAGTACCACGTCTTCAC
CGAGAAGATCCTCGGCGAGGACGTGCACCGCAACAAGCTCATCGTGGACACCGTGGTCGCGGCCATGGCCGCGGGCG
AGGCGCGGCGCGTGCTCGTGCTCACCAAGCT GCGCGAACACATGGTCGGGCTGCACGCCGCGCTCTGCGAGCGCCTC
GGTGCGGAGACGGTCTTTCTCGGCGACGCCAAGAACAGGAAGACGCCCGAGGTCACGCGCGCACTGCGCGACAAGGA
CCGCTTCGTGCTCGTGTCCACGGTCTTCTTCTCAGGCACGGGCCTGGACCTGCCCAACCTGGACGCGCTCGCGGTGG
CCGCGGCCGTGCTCAACCGCATGGTCATGGAGCAGATGATCGGACGCGTGTGTCGC GAGTCGCACGCCAACACGCGC
ACGCTGTTCGTGTTCCCGGACTCCTCCGTGCGCGCGATCCGCGACACCGTGTCTGCGTTTGCGCAGCGGCTCGTGGC
GCTGGCGGTGGACGGGCTGGGCTTCGTCCGCGAGCGCGCCGCCGCCGGCGCGAAGAACGAGCCGGCGCTGTACAGCG
CCATCAGCGGGCGAGATCTCGCAGCGGTGTAAGCGCGGACCCGCACGCCGCGCACGAGAGCGTGCTGGAGCAGGCGA
GTCCCAGCGACAGTGTGGACAGCCTGTCCACGTCCTTGATGCTCACCAGCCGCGAGTTGCACGAGAGCACACGGGGT
CGCTACTATCATCGACCACTGTGGTGACGCGGCGGCGTCTGCGCTTTTTGTTTCCAGCGCGACATCGACCACGCCTC
CCTTAGAGCCCCCCTTCGCCCCCGCCTTAGCTTTCACCGCGCTCATCTTTTATTTATCATAAAAACACGTCTGCGTA
CGCGTTCGCGCACACGTCCCGCAAATCCGCGCGCGCGCCGCAGCGCGTGAAGCGCGCGGCGTCCGCCTCCGCGATCC
GCGCGCACGGCAGCGGCGCGCCCTTCTCGTCCGCCATCACGCGCGCAGAGATCCCGGTGGCCCCCAGCGCGTACGAC
ACCACCACGTCGCCGACGCAGCGGTACACGTTGCCGGAGCCGGCGAGGCGGTCGAACGCGGCGCCCTCCTGGCGCAG
CTTGTCGAATATGCGAGGAACGAGGATGTTAAAAATGAGAACGAAATAGCAGAT CAGCAAAAACAGCGAGATCATGA
CCTCCGAGAGCGATTTATATACCTTGAAAGAGCTAATACGACTTCGGGACTCGCTGCACCTCGCCACCGGCGCCGCC
GTCGAGCGCTACAACGCGCTCGTGGAGTGGGCCGCGCGCACGTACTGGACGGTCGCGGTGCTGCCCTCCGCACCGTG
CGCCTCCATCGAGAAGTACTACTGCGTGTGCAAACCCGACTGCGCGCTCGAGCCCGGCGAGTACTCCGTGAGCCGGC
TGCACTTCGGACTCACGCACGCCTGGGTGCGCGGCGCCGCCTTCAACTCGGCCAGCGGCGCCGAGGTCGAGCCGCCA
GAGGAGGTGCGTAGGGCCTGCGAGGCGCTCGACGCCGCCTTCGCGGACCTCACCTTCGTGCGCTTCTCGGTCTTCGG
CCGCGAGTGGACGGTCGACGACGCCGTCACAGACCACTCCTCGCGCGACGAGGTGTTCGCCGCGTGCGCCGCCTCCG
GCGTGCGCGTCGCGCGCACGCTGCGTGTGCGCGTGCGGGCGGGAGAGTCCTTCGCGCGCGCGGACTTCGACGCGGTG
CACGCCGCGCTGCGCGCGGAGGGCGACGTCGCTCGCGGCACCGCGGTCTGTCTCGCGCTGCGCGGGTCATCGCGCCG
CTGGATAGCGGACCGAGCGCCTCGATGCTTCATGCGCGTGCGCCGCGTGGAGCTCGAGCCCGTGGACGCTCGGCACC
ACTGCCCGGTGCTGATCTCAGCGCGCGGCGACCGGGTGCTCTGCCGCGGCGT GGGGCACCTCGCGGACGCGCGCGCG
CGCGAGGGCGTCTTCGTGGCCGTGCGCAGGTACCCGGAGTGTCTGGTGCTCTGCGACGAGGCGGCCGCCGGCGCGGC
GGAGTGCTCGCGCGAGGAGGCGCTGCGGCTGCTGGTGCGCCGCTTCGGGCGCGACTTCGCCGTCAGCGAGGAGGGCT
ACGTCTTCCGCGTGCAGGACATGGACCTGCGCGGCGTGTCCGCGCGACTGGGGCTCGCGCCCTGCGCGAGCCTGGAG
GATCTGCGCCGAGCGGTGGAGCGCGACCGCGCGCTGATGCGGCGGCTGCGCGCGGAGGGCGCCGTGCGCCTCGCGTG
CGAGTGCGTGGGATACCCGCGCCAGAACGCGGTGGAGCTCATAAATAATATGCGCTTTCAAATAACGGAAGAAGGCG
CGGTGGCGAACTTTGAGCTGGCGAACGCGAGCTGTCTCGGCAACCCGACCGCGGAGTCCATCTTCGCGAGCTTCGCG
CAGTTCGTGCCGATCTTCAACGTGC TATCGGCGATCGCGCGCGCGCAGCCATGATCGTGGCGGCCTTCGACCTGGGC
ACGCGCAACCCCGCGCGCACCGTGCTGGAGGTGCTCGACGGCACGGTGCGCGTGGTGGACGTGGCCAAGCTGGACTG
GAGCCGCGACTGGGAGAAGCGCGTGCACCGCGACGTGACCGCCTTCCCCGCTAACGTGGTGCTCGTGGAGCGCCAGT
GCAAGATGTCGCCTTTTTCTAAGTTCATATACTTCATACGCGGGCTGCTC TACGACGGGCGGCGCCGCACGCGCGTG
CTCGCGGTGCCGCCGGCCATGACCGGCAGCACCTACCGGCAGCGCAAGCGCCGCTCGGTGCGCACCTTCCTCGCGCT
CGCGGAGAGCTTCGGCATCCTGGACGCCGTGCCCGCGCGGAAGAAGCTCGACGACGTCGCGGACAGCTTCAACATGG
CCATCAATTACGTGCTCCGAACAAACTGAAATACGACTGAACGAATAAGTCATGCTGGCGCTGTTCGAGTTCCTG CG
GTCCGTGGAGGACTGCTACCGGCGCACCATCTTCAACTTCCACATCGCGCACAGCGCCGAGGCGGGCGATGTCTACG
GCGTGCTGCGCGACCGCATTTTGGCGGCCACGCGCTTCGAGGAGGTAGCGCCGCCGGGGCTCGCGGACGCGCTGGCC
AAGGTGGTCTACTGCGACATAAGCACCACCAAGCACCTGGTCAACCACGCGGCCTTCGCGGCGCGCGCGCGGCCGGC
GCGGCGCGGAGGCAGCCTCGCGCAGTTCTTCGACGTGCACGTGGGCGAGGACGCGGAGAGCCGCCGCACCGCAGAGA
TCTTCGACCGCGAGCGCTCCTCGCTGGTCTCGTACGTGAAGACCACGGCCAAGCGCTGCAAGATCGACTACGGCGAG
ATCAAGCGCACCATCCACGGCGGGCGGCAGACCTACTTCTCGGGGCGGCGCTCGGACGACTTCTTGAGCACCACCGT
GCGCGCGGACCCGAGCAAGCCCTGGATCAAGTCCATCTCCAAGCAGCT GCGCGTGGACATCCTGCACCACGCGATCT
GCACGCGCGGCAAGAGCTCCATCCTGCAGACCATCGAGATCGTGCTCACGAACCGCACCTGCGTGAAGATATTCAAG
GACTCGACCATGCACATAATCCTCTCCAAGGACGACCGCGAGCGCGGGCTCGCGGACCTCGCGGACAAGCTCTTCGG
GACCTACGCGACCACCTTCCGCGTCATCGCGGCCATCACCGGCAACGCCTGCTTCGCGGCGGTGGCAGACGCG GCCG
CGCGCGTGGTCGCGCTCCCGGACGCGGACGCGAAGCTGGCGGCGGTGCGCGGGCTCGCGGAGTGCTACGGCGTGCGC
AACTTCAAAATCGGCATGTTCAACCTCACCTTCACGGGCGCCATCGAGCACACGGTCTTCCCCTCGCTGATCCCCGC

FIG. 29Y

GGAGAGCAAGATCAAGTTCTTCAAGGGCAAGAAGCTTAACATCGTCGCGGTGCGCTCCACCGAGGAGGGCCGCGAGT
GCGTGGAGCAGGCGCAGGCGCTGCTCGCGGCCATGCGCGAGCGCTCCGCGCGGCTCGCGGCCGCGGACGTGGCCACC
GCGAGCGTGGACTTCCTCAAGGAGCTGCTGGGGCCATAGTGAAATAATACTGATTTCTTAAATATGGAGCAGGCGCT
CGGATACAAGTTTTTGTTGCCCGACCCCAAGGACGACGTCTACTACCGCCCGCTCCACTTCCAGTATGAGTCCTACG
CCAACTTCATCAAGCACCGGCTTAAGGACATCCTCACGGTGCGGCG CACGCTGCTCACCTTCAAGAACGGCACCGAG
TCCATCGTGCTCGAGATCGACGACGTGAAGATCTCGGCGCCGGAGTTCTCGCCCATCGTGGCCAGCATCAAGGGCCA
CAGCTACGAGGCGCTGGTCACCTTCACGGTGAACATCTACCGGCACGTGATGACCAAGGACGGCCTCACCGTGACCA
AGATCAACAGCTACGAGGGCACCGACTCGCACCTCGTCAAGCTCCCGCTGCTCATCGGCTACGGGAACAAG AACGCG
CTGGACCCCTCCAAGTTCGTGGTCCCGAACGCCATCGGCGGCGTCTTCATCAACAAGCAGTCCATCGAGAAGCTCGG
CATCAACATGATCGAGAAGATCACCACCTGGCCCAAGTTCCGCGCCGTGAAGGCCAACTCCTTCACGCTCTCCTTCT
CCTCGATCTCGCCCGTGCACGTGATGCCCGCGCGGTACCGACACTACAAGATCCTGCTCGACGTGAACCAGCCCGAC
AACTTCGTGATCTCCTCCGCGAAGACCTTCATCACCGTGAACGTGATCGTGATGGTGCAGTTCCTCGCGGACGTCAC
GCTCGAGTTCGTTGCGCGCAACCTCTGCTTCGACATGCCGCCCGAGGCCGCGCACCTGGCCACCGCGCTCGTGGAGA
GCGCGAAGACCGTGCCCGCGGGCGCGGACGTGGCCGAGTACGTGAACGCGCTCATCGCGGCCGAGCACGCGAAGCAG
AAGTCGACGCTGTCCAAGGAGGAGTTCCGCTACGAGATGCTCAGCAACTTCCTCCCGCACATGCAGGACAGCGCCAA
CCAGCTCAAGGGCCTGTACCTGCTCTCGCTGGTGCGCAAGATGGTCTTCTGCGTGTTCTTCCCGAACCGGTACCCGG
ACCGCGACTCGCTGGTCTGCCACCGCGTGTACACCTACGGGCGCTACTTCGAGGCGCTGGCCATGGACGAGCTCGAG
ACCTACATCGGGAACATCCGCAACGACATCCTCGCGAACCACAAGAACCGCGGCACCTGCACCGTGAAC ATCCACGT
GCTGACCACGCCCGGCTTCAACCACGCCTTCGCGGCGCTGCTCAGCGGCAAGTTCCGCAAGTCCGACGGCAGCTTCC
GCACGCACCCGCACTACTCCTGGATGCAGAGCATCTCCATCCCGCGCAGCGTGGGCTTCTACCCCGAGCAAGTCAAG
ATCTCGAAGATGTTCAAGGTGCGCATGTACCACCCCAGCCAGTACGGCTTCTTCTGCGCCTCGGACGTGCCCGAGCG
CGGGCCGCAGGTCGGGCTCATCTCGCAGCTCTCCGTGCTCGCCTCCATCTCGAACATCCGCACCGCGGACTTCGTCG
AGCTCACCAAGCGCGTCTGCGACTACGTGCGCTCCTACCCCGCGCGCGACATCAGCTACTTCGAGACCGGGTTCGCG
GTCACCGTCGAGAACGCGCTCGTGGCCTCGCTGAACCCCGCGATCGTGGACGCGTTCGTGCTCGACCTGCGCCGGCG
CAAGCGGCTCGGCTTCTTCGGGAACCGCGAGATCGGCGTCGC GCTCGTGCGCGACCGCATGAACGAGGTGCGCATCA
ACTTCGGCGCGGGCCGGCTCATCCGCCCGCTGCTCGTGGTCGAGAACGGCGTGCTCGTCATGGACGCGGAGGCGGAG
CGGCTCGAGCGCGACCTCTCCGCGATGACCTTCTCGGACGTGCTGCGCGAGTTCCCGCACGTGATCGAGATCGTGGA
CGTGGAGCAGTTCAGCTTCAGCAACGTCTGCGACTCCGTGCAGCGCTTCCGCACGCTGCCGCCCGAG GAGCGCGCGC
TCTTCGACTTCTGCGACTTCCCGGCCGAGTTCCGCGACGGGTACGTGGCCTCCTCGCTCGTGGGCATCAACCACAAC
TCCGCGCCGCGCGCCATCCTCGGCTGCGCGCAGGCCAAGCAGGCCATCTCCTGCCTGAGCGCGGACCTGCGCAACAA
GGTCGACAACGGCATCCACCTCATGTTCGCGGAGCGGCCCATCGTGGTCAGCAAGGCGCTGGAGACCTCCAAGATCG
CGGACAACTGCTTCGGGCACCACGTCACCATCGCGCTCATGTCCTTCCGCGGCATGAACCAGGAGGACGGCATCATC
CTGAAGCGGCAGTTCGCGGAGCGCGGCGGGCTCGACATCCTCACCTGCAAGAAGTACCAGGTCGAGATCCCGCTCGA
GAACTTCAACAACCGCGAGCGCGTGCGCTCCGCGGCGTACTCCAAGATCGACGTCAACGGCGTGGTGCGCCTGAACG
CCTTCCTCGAGCAGGGCGACGCCATCGCGCGGAACGTGTC CTCGCGCACGCTCGACGACGACTTCGTCGCTGACAAC
CAGATCAGCTTCGACATCGCGGAGCGGTACTCGGACATCTACGCCGCGCGCGTGGAGCGCGTGCAGGCCGACCTCAC
CGACAAGGTCAAGGTGCGCGCGCTGACCGTGCGCGAGCGCCGCGCCATCCTCGGGGACAAGTTCACCACGCGCACCA
GCCAGAAGGGCACGGTCGCGTACGTGGCCGACGAGACCGAGCTGCCCTACGACGAGAACGGGATC GCGCCGGACGTG
ATCATCAACTCGACCTCCATCTTCTCGCGGAAGACGCTCTCCATGCTCATGGAGGTCATCCTCACCACGGCCTACGG
ACACAAGCCCTTCGCCGAGGACGGCTCCAACCGCCCGATCTGCTTCCCCAGCACCAACGAGACCGACTTCGAGACCT
ACATCGAGTTCGCGCGGCGCTGCTACGCGCTCTCGCACCCCGAGGCCGCCGCGGACGACCCCGAGTTCGAGCACCGC
GTCTTCTGCGAGCGCGTGCTCTTCGACCCCGAGACCGACGAGCCCTTCGCGGCGCGCGTCTTCTTCGGGCCGCTGTA
CTACCTGCGTCTGCGGCACCTCACGCTGGACAAGGCCACGGTGCGCTGCCGCGGGCGCAAGACCAAGCTCATCCGGC
AGGCCAACGAGGGCCGCCGCCGCGGCGGCGGCATCAAGATCGGCGAGATGGAGCGCGACTGCATGATCTCGCACGGC
GCGGCCTTCACCGTCGCCGAGATCCTGCGCGACTCCGA GGAGGACGCGCAGGAGGTGCTCGTCTGCGAGAACTGCGG
CGACATCGCGGCGCGGCTCAACGGCACGCACGTCTGCATCCGCTGCTCCAAGATGAGCCTCTCGCCGGTGCTCACGC
GCATGGACTCCACGCACGTGAGCAAGGTCTTCACCACGCAGATGAACGCGCGCGGCATAAAGATCCGCGTGGAGTTC
GAGAAGCAGGACCCCTGCTTCTACGGGACTCCGAAACGGTTCAGCCTCGCGCCCGACGAGTCG CTGTTCTCGCCGGA
GGACTGAACCCGCCGTCGCGACCGCGTCGCTACGACTAGCTTATCGTTCGACTGATGCGAAACGCGCGGCGGCGCCG
CGACTTAGCTTATATCGACTGATGCGAACGCGCGACCTCTCGCGACTTTCTAGCTTCTCAGACTGATGCTACCATAT
CGCGGCGTGCTGGCCCCACCACCAGGGCTTCTCGCCGTGGCTGACGCGGGGCTGGCTGCGACGCGCGCCGCAGTAGC
TGCGCGCGCCCCAGTCGCCGCGCACGTGCGCCGGGGGCAGGCTCCCGTCCAGCGCATGCCGCGTCACCTCGGCGCCG
GGCCGGCGGCACGTGTGCACGTCCGTCTTGTTGGAGACGAGCACTGCGTACTGCCGCATGGTCTCTATGTGATGCTC

FIG. 29Z

CAAGTGCTTGCCCGCCTTCCGGTTGGACTCACAGCACGTTTTTGCTTCGGCTAAGGTTTTTTCTAGAGGGGCTAGTA
GCTTATCCACGCGCTCGGGCAGGACGCACGCGGAGC CGTCGAGCCCCACGCGGAACGGGGTCACCGGGATGTTCCCG
TCGTAGCGGTCCCACAGCATCCTGAGGTAGGTTGTGCCGTCGTCGTCGGCGTGCGTCCACACTCGACGATGTTCGTG
GCAACGACCGTCGTATGTAAGTCTGTCTCGACGCTCGTAATAGTTTCTGCTTATATTGTACGCGTCTCCGTACTCGA
AGTAGTATATATCTCCGGGTCCTGGACTTGCTATATTGTTTTCGTCGTTTCTACGATGTAT ACCGTCTGGATAATAC
GATATTCTAACTGCACTGCAATCCACCGTAGAAGGTTTAGGTAACTTTTCTAATTCTCCTTGTTGGTCATGGTCAAC
TGACTTGTACACAGCTCCGTCGTGTTCTGAGGGAGTTATAAATATATCCATGGTGAAAGAAGTTCCTCGTTTTGAGA
ATTTGTCCCATGCGGTAAAACAAAGGCCGTCCATCATAAACTCCGGTACACTCATAACAAACCTGCACTTGTGATCA
TCAAATGATATTTTAACATGGTCTTTGTCTTTTACGTCCGTACCGTTAACTTCTTTCATAAACTGTATAATTGCAAG
AACTCCTCTTGCGTATTCTATAGTTCTGGTATCAGACACCAACTTTTCTGTTTTAATATAAACGTCGTTTACATCTA
CACCGTACCACCAGTAAATAGGAAGTCCTATGTAGATGGCTGTGTTTCTAAAATGGGATGCAAGCGTACTTATGTCA
CGGAAAAAGGCCACACAAAAAAAATCCTGTTTTTGAATCTATAATTTTTCTGGTGCTGTCCTCTGTAACTCCTAAAAT
GTCCATAATTCTTTCGTTGTGAAGAGTAAGGTGACCTGTCATTATGCTGTATACGACCATTAAGTAAAACTTTCCAA
GCGTGTCTACGTTTATAATATTTATCTTAGCATGCTCGCATAGCATAGTTACGTGGACCTTCATCCATTCGTCGTCA
ACAAACATATTTTTGTACATAGTGTTTTGGTTTACGTATTTGCTAAAATACAGGTTTAC AGGTCTACGAGATACTTT
CGTTCCATCTACTTTTGGTGCGCTTCGTATGTACTCGCGCAAAACGTCTCTTATAATTTTTCTATGAGTACGTGGTA
TACATATTACCGTCCCAAGTGGATGATGCCACTGACGCTGAACGATATCTTTAAATTCAGATACCAACGAACTGTGG
TTCTCCATTTATAATTAAATAATTAGACCATATCTACCACAGACCTTACCAAATGGCGCCGTGTCTTTGACGACGCC
ACCAAGCATCTAAATTATAAGTATTGTATGGATTATGTCTATTAAAGATGGATGTGCGAGGAGTTCTTGTCCATGTT
GGTCTGTAAGTCTCTCTCACTATGGGGTAATTGCTGCTCGTTGTATTGGAAGACCCTAGCCCGACTGGAATTTTTGA
ACAGCAAGGTTTGTCTTTAACGTAATTTTCTAGAGGAGATATAAGTTTGTCTAGTTTATCTATGTCCATACACAAAG
GATTATCGTTATTATCTTCATCGTCTATGACT TCTACTTCCGATAGAGGAGGCTTCACGCTCAATAATCCAATGAAC
CTGTCTCTTAAAATTCTGTGATATGATGTCTTATCATCATCTATGTCTCCATCAAAACGATGTTTTAAACACACAAC
GTTATCGTATGTTAATTTATCCCGGCGCTCAAATTCATTGTTCGCAGAGTCTTCTGTGTGGCTATAGTAGTGGTAGT
CTAAGTAGTACCCGTTGTTTTCATAGTTTCTAGTAAAAATGGTAGGCGTTTGGTTAT TATCAACATCATGTTGTTTA
ACATAAGTATCTTCTTTGTAGTTAGGGTGTCTGGCAGTAACACCATCTTTAGGTACGTAAGAAATACGCCTGCTAAA
ACTAGGATGAAATTTAAATCGTATAGCGCCTCTATTTCCTACGTCATCTTTTGTTATACCATCAACAACACCTTGTT
TGGAATGATCTAGTGTTTTATACGTAAATCCGTTATATCTAGTTGGATTCATAAAAACATCTAGATAAAATGTAGTT
CCGTATTTAGTTATTTTATCATATACTGTATAACAAAGGCCGTCTAAAATGAACTCTGGTACTGACGATATAAAGTT
TGTGCTAAAACCACCAAATGATATATTTATATGCGGTGTGCGAGTAGAATAATCTCCGACTTTGTCATAAGTTATAT
ACATATATCTAGCAAAAGTCACTGCACCGTTAGAATTCTTTTTAGGATCCTCTTTATTAAAATAATCATCGAGTAAC
GTATGTACGTTTGTACTAAGCCCATCACCT CTCCACCAATACATAGGTATTCCAAAAACTAATGACTTGTTATTGTA
ATAAAACGCTACAGAACCCATATACCACAAAAAGAGATAACAAAAGTAATCCATTTGTGTATCTACATCTCTGGGGT
CGTTTAAATTCATATTATCCATAATAAACCCATTGTCCGTAGCTCCTGTCATTATCCTGTATACTACCATTAGCAAA
AGCCTACCCACTGTACTCACGTCTGTAAAAGTTTTTATAGCCACAGCACTTTCGT ACATCCATACATTGTTTCTAAA
AAGCTCAACATAAACAGGATTTTTGTCAACATATTGTTTCATAATCAAATTTAGTGGCTTTCCAGTTTTTTTATGAG
TGTCGCTTAAAGAAGGAGCATTCTTAATGTACTCTCGAAGCAAATCTCTCACAAGCTTTCTTATCTCTATAGGAATG
CATGTTTGGCTGTTTAATTCTTTATACCAGTTAGCGCTAACAAACGTTCTAAACTCGTCCACGAGCTTCTCCATTTA
TAATTAAATAATTACAGACGGCAACACAGCGGTTATCTAATATCTACCGTATCCTGTCTGTACATCTATTTTTTTGT
TGAGATCAAGAAGAGCTCTACGTAGACTCTCCAAGTGTCTTTCTAGTCTGTCTAACCGGTTACCTGTTTCTCTGCAG
CAATCAGTTATAGTTTTGTAACTGTCTAACAAGCTTACGAGGCGCTCTTCCACACTTTCTTTAGTTGGAGCTCCAGC
CGCGTACACTCCGTTGGTTGAATTGCCT GTATCATCATCAGGCGGAGCCAATAGGTTTTCTCCGTCACCTTCCTCCA
TATTGAATCCAACGAACACAAACGCGTAAGTGTTCCTCTATTTAAAGTATTGATTTTAGAAAAAGGCAGGCCTCGCT
GCCCTGATTCGGTGGCAAACACGGGTTGAACACGCGGAAGTCGCTCGCGGCCGTGAAGATCTCGTCCGCGCACGCCT
CCACGCTCGCGAAGCGCGCGGGCGAGACGCCGTCGTGCGAGCGGAACCCGAAC TCCGAGGCCGCCACCGCCGCGCCC
TTGAAGAGCACGCAGCGCCACTTCTTGCGGACGTCGAAGGCCTCGTCGTTGGGGTCGAACACGCGCCGGTCCACGCG
CGGGCCGCCCGCCGTGCGCGCGAACTCCAGCGCCGCGTTCGCCGCGTTGAACTCGCGGATGTTGTCGTAGTTCTCGT
AGACGGCCCAGAGCTGCAGCGCCACGAACATCGCGGCCGCCGCCGCGAGGGCCACGCAGAGCGCGGACACCGCGTCC
ATCTTTTATGTGCAGAATTATTCGTCGGCGCGGAGCTCGCGCAGCTCCGCGGCGCGCAGCCGCGCGAAGGCCGCCTT
GAGCGCGCGCAGCAGCTCCTCGGTGTCCGCGCGCAGCATGTCGAAGCGGTGGTAGCTGTCCAGGCGCGCGCGGCAGC
CGAAGAAGCGCGCGACGCACGCGGTGACGATGTCGTTCACGTAGAGCACGCCCGAGGCCGTGCAGTACACGGAGCGC
GGCTCGCGCGGGTCCGGCGGCACGTC CACGGCGACCGCGTGCGCGGCCACGTCCTCGAGCACCTTGCGCTCGAGCAC
GGCGAGGAAGTCGCGCAGCTGGCGGCGGTTGTCCAGCCAGGCGTAGGTGGTCGCGAAGAGCGTGAGCCGCCCGCGCG

FIG. 29AA

GCGCGATCGCGGTGTAGGGCGCGTACCCGCGGAACTCCCGGGGGTGCACGACCTTGACGTTCTCGTGCTCGCGGCGG
AAGGCCTCAGTGTCGAGCAGCGCCGCGAGCGCGTCCACGAGCTTGTCGGAG ACCTCCACGCCCGCGCCGAAGGCGAT
GAGCTCGATCTTCTGCTCGCTCTTGGGGCGGAAGTCGTGGAAGGTGTGCAGCAGCATCTCGCGGAGCTGCGGCGGCT
TCTCGACGGCCTCGAGCGCGTCGCCGCGGACGAGGAAGTAGTCGAGGTCGTGCAGCGAGACGTGCTGCCCGGCGGCG
CTCTGCGCGAACTTGAGGAAGACGCAGAGGCCCGCGCGGCGCTCGAGCACGTCCTCGACGTGCGCGTGGAACACGT G
CCGCGAGGGCATGGCCTCGATCGCGGAGAGCCACTCCTCGTTGACGCAGGTGGTGGTGTTCTCCAGCACCACGCCCT
GCGTGAGCGAGGGCCACTGCAGGTGGAAGGCGAACTCGTGCTTGATGAGCGAGGCCACGGCCGGGTCCAGGTCCACG
GCCAGCGCGGCCTCGCCGACGAGGGGAGCGTCCGCCATCACGCGGAGGACGCCTGGCCCATCTCCTTTTTCGCCTTT
TTATTCAGGATCATTATTCTTTCGTTGACCAGGTCCATGAGCATCTTGATGGCGGCGGCCGCGGCCGCCGCGTCGCC
GCCGCACATCTGCGCGATGCGCGTGAGCATGTGCAGCAGCGCGGCCTCGTTCAGGTCCTCCTCCATTTAGAGGCCGT
AAGGGCGCGCGTCGTCGCGACGAGGGGACGCCTCCCGCTGCAGCGTGGCGCGCACGGCGAAGGCGAGCAGCGCGCCG
GCGCACTGCGTGAGCACGCACTCCGCGAGCGCGACGAGGAGCTCGGAGA GCACGAGCACCATTTAGAGGCGCGCACG
GGTTTAATTGCCGCCGTCAGAGTCGGCATCTCCCTTGTCGCCGCCGTCCTTGCAGTCGCCCTTGGCGTCGCCGGCGT
CGACGATGTCGGCGAGCCGCGTCTTCATGTGCGAGAACTGCGCGAGCAGGATGCCGGGGTCGAGACAGCGCTTGACG
ACGCTCTCGTCGGCGAAGTCGTAGCAGATGCGCTCCTGGTTCTGGCAGAACACCGAGTCTTCGATGATCAACAC CCT
CCTGGTCCCGGCCGACCGCATGATGGCCATGGCCCGGATGAGCCTCTTCTTCGATCCGCGTATGGACATGGACCGGA
GCACGTTCTCCACGTCGGAGTCGGAGACGTTGCAGCAGCAGAGGTGCGTGATGCTGGCGCGCCCGTTGACGGGGATG
TGCTTGTAGGTCTGGCAGAGCAGCACCAGCGACACGTTGATGTGCCGCCCGTAGTTCATGAGGCCCAAGAGTGTGGG
CGACCGCGTCTGCGTGTCGCCCATATCGTCGAGAATGATGAGGAACTTCTGCTTCTTCGTCTGCGCGTGCCGCTCGA
TCTTGCGCTTGGCAACCGAGAGGTTGTACTCGAGCTCCTCGTGCGTGGTGACCTTGTGGATGTGGTCCGGCCACACG
AAGCCGTCGTAGGCGGCGTTGTAGACGGGCGTGAAGAGCAGGATGTGCTTGAAGCGGCGCACGAGCGTGCGGAAGAG
CGAGAGCAGGTAGGCGGTCTTGCCGGAGCCGGAGCCGCCGACGAGCG CCATCCTGAAGGGCGCCTCAATGAGACTCT
CCCGCTTGAAGCGCACCTCCTGCACGACATCCATCGTATATTTACTGTCACTAAATTACCGGCTCCGAGAAATATAG
AAATTAGAGCCTCCTAGAGCACACCGAGGCTCATCGGCAAGATGGCACATAACACGTTCGAAAACGATAGCGAGACG
GCTAACAACCAGTACGTGGCGTCAGTCAAGCGCCAGAAAATGATTCGGCGATACATTAAGATGTTCTTCCGG TTCGT
TACGGCGATAGCTATCATTGTCCTGGCTATTCTAGTTGTGATCCTGTCGCTATCTCTAGACGAATGTCTGCACAGAG
AACACCCTCATGACTATTCGCATGTACAAAATTCAACATGTCCCGGAATTCCATTGGGTGATAAGTGTTTAACACTT
AACACACCGTCTACATGGGAAGATGCTAATCAAATGTGTAGCAATCTAGGTTTCAGTTTACCATCAAAAGGACTACT
TAAAACGCCGTGGCTCACAGATTACCTTGATGGAACTTGGGGAAATAAACTGGGAAATGTCTTTGGACCAACTGGCG
AACTCGAGCAGGTCATGGGACAGCACGAAACCCGCAAATATTTTTGTGTGTCTGGTTAGATGATTAAATCTAATAAA
TGGGTTGCTGTAAGGTCCCTAACCGCCAGTCTATAAGGACTTTGAAAAAGGTGTCCTGCCCGGTCGCCAGCCTCGTT
ACCATTCTCTCCCTAGCTACCAGCCTCTGTGCGATAGTCAGATAC ACTAATTTTTTTCTAAAAGAGGCGTGTGACGA
AGGATGGATGCCAATAAAAGACATATGCATTTTAAACACGCACTTTAAAGCCACCAAGGACGACGCCCACAGAATAT
GCGAAAGCCTAGACGGAAATCCGCCGGCCATCCCCAATCCCACTCTGCTAAAGGGTGTAATGGTTCTCACCGGAGAA
AGACAGTTTTGGATGACTCACCACCCGGACTACACATCTGTATACGAGCATAATGAAAAGTTGCAAATTC CAAAAAA
CACTAAGTACGACAAAGATAGACACATTTGTTTGATGAGCGAGGACGGATTGATACACCATAACTGCATGATGAACG
TAACCGTGGTATGCATGAAGGAGATGCACGGATAACTGAAAATATACTGTTTGAACGCAAAGACGCCATGTCGCGAC
TTCAAATACTGACCTCATTTGGACAAATCTACGCACCCGACGAAGCTCGGCTGCGCGAGATCGCGCGTGATTTGGGA
ATATGCACCATAAAACGCGCATTCGGCGACATGCTGTACGGCTTTATAGACTTCAACCCGGTGCCCCTGACCCAAGT
AAACATGCTCATGTCCAACTGCTACTTCGCGGTCAACGGCAACCTGCTTCCGTGCACGGAGGACTTCCGGCTCAGAC
TCCCGGCAACGGAGATCTCTGCGGCCTACCTGACGAGAACGGGACGGACGATCCTGTGCGGCAAAGACTTCAACATA
GTGGCGCCGTCAGGGTTCAAGCCGTCCATGCGGCTGCGCGACC TTAGTCACGTGTCTGCGCTTGTAGAGATCCTGGA
GCTCTACGACGAGTCCGGGGATTACCAATTCGTGCTCGGCCCCAGCGCGCAGTTCATGCTGCGGCTGATGGAGAAGG
AGAATGTCTGTCTGTTCGGCAACGGTTGGTGCATAGTGGACCTGCGCAAGCTAGACGTAACCATATAATTGCTGCTG
CTATGTCGTGCCCGACTCTGTGCGACAAAGACAGCGGCTAACCAGACTCTTCGTCCCTGTTCTCCAAG CAAAAACT
GGAGTGAGTTGCCATTTCCGTCTCCAACCATATAATTAGCATCCTTGTTTTTATCCTGTATTTTTATCAGTTTTTAT
GCTAGTTAAAACATAAATAGTAAGGCTAAAAAGAAGAGTTCTAGAATCTTGCAACAACCAAGATGAAGGCGGCGGCG
GTGTTGTTGCTAGCGCTACTGGGAGCGTTCACCAACGCAGCGCCCGTCAGCAACCAGCGTCTTGGCAGTGAGGAGAA
AGAAAAATTCTGCTCGACTCATCATGACGAAGTGTACGCCAGGTTCCGGCTTCAGATGCGCGTGGGTGTACGACACA
GTCCGCTCTACGTTCCCAGCAACATGTGCATGATGGACATAGAAGACTCTACGGATGACATAGAAGAGTCCACGGAG
AAAGAATACACGTCTACGGCTACGGGTGAGGCGGCCGGAGTGAACGTGTCCGTGGCACTAGTGGGAGAAGGCGTGAA
AATACCGTTTAGTTACATAGGCCTTGGATTCAACCCATCTA CAGATGGCTACCTGTACGTCAACGTCTCGTCACGAG
CTCCTTGGGTTCAACAGACTCCAGACCTATCCGCGAACAGCGGCTGGGGTATTAAACAGGTTCTAGAAAAAGAGTTA

FIG. 29BB

CTGGCCATCCAGATAGGGTGCGACAACCAAAAATTTCCCGAAGAACCCACAACTACCCCCTCACTTGTCACGACAAC
GCTTTCCCCAACAACGACTTTAAATCCGAATAACGAAAACACAGACACTACGCCGACGCCCACCGG CGCCAGTGTAG
ACGGAAAGCGCAATCCAGATGACATTGACTTCTCGCTGATCGTGGACCCCCGATGCGTGACCTCTGTAAACCTGCAC
TTCGAGCTCAAGGACGCGTGCATGGACTACAAAAAAGAGTCGCCGTTGTCGCTGAAGGGGAAATATGGAGACAGTGA
ACTAGTAAAACAGGAGATTAAAGACGTGGGAAAGAATCACAATATGTGCAGTCTTAACCTCAGCCCTGGCCATTGAG
CTGTTTTTATTCGGCAATATAATAAGGTGATTATTGAACATTAAACAAAACTTATCCCACAACGCCGCAACAATGGA
AGTGTTGGTGATCGTCTCCATTATCGTCGCCGTAATATGCTTAACCGGAGCGGCGATGTACATCCTTATTGAACTCG
GCTTAGCCGCCGAGCGCGCTAACAAACGCGCGCGCGTGAAGAAAAATATGCGCAAATTAGCCACTCAATTGGGAAAT
GGATCTGTCGACTCCGGCATAGGCATAGGCCCGTGCATAATGTCGCGCACCATGGACTCTGGACCCAGTCGCTGGGA
CAGCGACAGTGAGGGTGACGGAGACAGCCTGTCCACGACGTCCACCAGCGAAGGGGGGACTCTCACCCGAGTGTGGG
TTGGGAGCGGGTCCGGGCCCATGTACGAAAACTTCTGCGGGAACGGCACCCACCGCCACTCTCCCACCAACGACCCT
GGCTACCACTCGCGGGAGACTCTCTGCAGCGGACCTCCCCGTCAGGCGCCGGCGCTACCGCCCA CCCCGAAGCCCGA
CGAGGTAACGGTGGACGTGGGGCCCAGACCCAACGACCAACACGGTCCGTACGAGGAACCTGATCCCATTCCCCTGC
AGGAACCCGAGCCGCCGATGCAGATCGAGGTAACCATCAACGGGCCCGGTGAAGAAGGCGAGGTGGAGGGAGAGTTT
TTCTACGACGAGTAGCCGCCAAAACTGAATAACTATCGGGCTTCGTAAACGCGCAGACATGCCGCTGTTCCGGAAGC
TCATGGTTTCGCGCTCCCTGGTCAAGGAATGTCTGACTCTGGACTTCCGGCAGGGCGAGCGTCTCCCCACCCGATGC
TTCCTCCCGGTGCCCGCGGGGACGACATTCCACAGAGTCTGCGACACCTCGCCGCTGACGGACGAAGTATCCCGGCA
CGTGCAGGAGCCCGTCATGGGCACCGGACGGGTCCAGTACTACTACTTCGAGAGCGGGCAGGGCATGATCGGCGACA
ACGCGGGCATGTCGCGCATGCTCGTGTGCACGCGCTC GGCGTACAACGGCGGCGACGTCGTCGTGCGGTCCACGCGG
AGCAGAGCAGACAAGACCGTGGTCGCGCCCTGCCAGGGCATGGCGCTGCTGCTGAGCCCCTTCTGCGCCTTCGACAT
CACGCCGGTGGAGAGCGGCTCCGCGATATTCGCGGAGGTCATCGTCACTTCGCCCAGCATGGACCACGTCGAGGCGG
TCACCGGCACGGGCGAGGCGGCCGTGCGGATATTCAACTCGCACCACCCGCTCTGGCCGCGA CACGGCTCGAACGTC
TGCTTCGCGCTGCGGTTGCTGCGAGACGTGCGCACGGGCGAGCGCGTGGTCGAGCAGATGTTCATGGACGGGCGCTG
GCACACCGTGCTGAGGACGTCCTGCGGCAACAAGGTCTGCGTGCCCGCCGACCTCGTGGGCCAGACGAACCTCGAGG
AGGTGCCCTTCTGCGACGTGACGCCCGAGATCATGCGCCGCGCACTGGCGATCGACCCGCCGTACGAGGCCGTGGCG
CACCCGCGCCGCTGCGTGTACGGCGCCATGGACGTCCGGTGCGCGAACGAGTACCTCGTGTACTGCACCTTCAAGAC
GGAGCCGGCGCGGCGCAGCACGTCCTCGCCGGGCCCGGACGGCCCCCTGTCGCCCGCGACTCCGTCGACCTCGCGGG
CCGCGGCTGCGCGCGCCCCCACGACGCCGCAGGAAGTGGCCTCGCCGACCACGAGGCTCGTGGAGACCTGCCTGCGC
GACGCCCTCGACGGACTCTGACCCGAAGGACCCAC CGTCCACTCACATTCCACTGCCAGACAACTCAAGCTTTTTCT
GCATCTACCTCGCTAATAATTGAATTGTTATAGTACAAACAGGCGCACTCGAGCACAATGGCGTGTTTTATCGAATT
GTTAGACTCCATCTTCAACCGACACCACCGTAATTTCGGGCCGGAGGACATGTACAGGCCCTCTGACGCCCCGCCCC
CCAAATCTCACACGCCTCGCACTCCCCGCACCCCGCGGACCCAGTGTCCCGGACACCCGC GGCGACAAAGCTCCTCT
CCCATCTACGGTGCTTATGTGGACTCCCTGCCGAGGAACAGAAAGCGGTTCCAGAATCAACACAGTTGTCCCGGAGA
TTACGAGCGGTGTCAACTCCAGGACACTATCAGCCTGGAGGCGACGCTACTCACGGTTACCTCGACTTCCATCTCCA
GCATATCCAGCTCTAGTAGCTCAGACTCTAGCTCATTGGGGCAGTGCAGACTGTCCATTGTGTCCGCGACATCGACC
TCCACGACCTTCTCCTACTCGTCCTGAGCGCCACACTTATTTTTGTATAATAGTTTGTATTGAACCTTAGAGACATC
CACAAATAGTTAGGAAGCATGAGTAGTTCAAGTAGCGAGACCACCCCTAAGCCCAAGCCCATCCCTGCTCCTCCCAT
GACTCAGGAGGAGTTTAACAAAGAAGTGAAGAAACGAAAAGAACAGAAAAAGGAAAAATCTAGAACCGTTGAACGTG
AGTCAGAAACCGTAACTGTATCTTCCGACGGAT CAGAGATAAAAAAGACTTACGAGCGCGAGTCTGAGAGAACAACC
GAAACAGAAAAGAACAACACGTCAACCGATGATGATAATAAGCAGAACACCCCTGTAGAGAAACCAGAGGAAACTAA
GCCTGCTTCTACTCCTGAAGGTGAGAAGCCAGCTGAAACTCCTGCCCCGACTACTGACCCCCAACCCACTACACAAC
CACCCGCAGAATCAGGCCCTGGAAGTCAACCCACACCTGTTCCAGAACCAACCCCCGC ACCTGAGCCTGCACCGGAA
CCCACTCCTGCCACTCAGCCTGCATCAGTAACTCAACCCGCTCCAACACCAGAGCCAAGTCCAGCCCCTGAAACTAC
TCCGGCTTCCGAACCAACCCCTGCACCAGAACCCACTCCCGCTCCAAAACCTACACCAGCCACAGAACCGACTCCTC
AACCAACCGTAGAAACAACACCATCTGCTCCAGCACCAACTCCCGAGGCCCAACCACCCGCCAACAATCCCACTACT
GAAACTACCACTGGTACCAGCACCTCCTAAGTGAGTACGTAAGCATTTCGGAGTAACGTCGTAGCAAGCGCTAGTCC
GCCGCGAGCGGTTCTTGCAAGTTTTTTCGGGTAAAAAGCGTACACCGTCGCCTTGTAGCGGCGGTGTACGCTTTTTT
CACGCCCTTTTTGCAAAATTTAAATTGTACCCGCGCCGGCTCTAGGAAAGATGGCGTGCCTCAGGGTGTTCTTGGCG
GTGCTCGCGCTGTGCGGGAGCGTGCACTCGGCGCAATGGATCGGCGAGCGCGACTTCTGCACGGCCCACGCACAGGA
CGTCTTCGCGCGGCTGCAGGTGTGGATGCGCATCGACCGGAACGTGACCGCCGCGGACAACAGCTCGGCCTGCGCGC
TGGCGATAGAGACGCCGCCGAGCAACTTCGACGCGGACGTCTACGTCGCCGCGGCCGGCATAAACGTCAGCGTGTCC
GCGATCAACTGCGGCTTCTTCAACATGCGCCAAGTAGAGACAACGTACAACACGGC ACGCCGGCAGATGTACGTGTA
CATGGACTCTTGGGACCCCTGGATGCTCGACGACCCCCAGCCGCTCTTCAGCCAGGAGTACGAAAACGAAACGCTGC

FIG. 29CC

CGTACCTGCTGGAGGTTCTGGAGCTAGCGAGGCTGTACATTCGCGTGGGCTGCACGGTGCCCGGAGAGCAGCCCTTT
GAGGTGATCCCGGGGATCGACTACCCCCACACCGGCATGGAGTTTCTCCAGCACGTTCTACGGCCGAACCGCCGGTT
CGCTCCGGCGAAGCTGCACATGGACCTCGAGGTGGACCACCGGTGCGTGAGCGCCGTCCACGTGAAGGCGTTCCTGC
AGGACGCCTGTAGCGCCCGCAAGGCGCGGACGCCACTCTACTTCGCGGGGCATGGCTGCAACCATCCAGATCGCCGG
CCAAAAAACCCAGTACCGCGCCCTCAGCACGTGTCGTCACCGATCTCCAGGAAGTGCAGCATGCAGACGGCGCGCTG
AGGGCGCTCACCGCGCTGACGGCGGCCGT GGTGTGCGCGATCGCCGTTGCGCTCGAGCGCGGGGCGGAGGCCGACGC
CGTGGACCTTATCCTTATAAAATTTTCAATGATATGCTAGTTTTTATGCGACCTTCCTTAGAAAATTCGGAATTCAA
AAATGAAATAAAACGGCGTTTAGCACGCATATTATTAATACCGACCACCATGGCAGGCGTCCGCAGCTGCCAGAAGA
AAGTCCCTTCTACTGCGGGCTCCATGTCATTTCAACGGGGCAACCGGAGCATCC AGCCTGCGATGTCCGAGGCGTTG
CAGAATGATTTCAGCTACAACCCGCGACCGCCTCCGCCGAGCGCAGAAGAGATTGACTTCTTCTGCGTGGACATGCG
CAAAGTACTGATGGAAATTGAGGCCAAGCCCAACAGCTCCAAGTACCCCAATTTCATCCACCCGGTTGACAGCAGCC
CGCCGTGCACGCCGGCGCGCAAGCGCAACGGCTTCGGCCGCAAGGCACTGAACAAGACCCCGGTGCCGCAGCAGGCC
AAGCGTGACGGCTACTCCCGCTAATGCAGTCCACACACTTCACACACTACATCAGCACTCAAGCTTATAATCACCAC
ACAATGAATTAGCCCAGCCCACACACGTGCCAAGCACACATAAAATCACCCACCTGTCCTGATCGTTCCCAATTACT
CCCAATCACCCGTGCTTTACACGCACGTAAATCACCCTCTCCTTCGTTCCTGATCGCTCCTCCTCCTTAATCACACA
TACACCCCGTAATTTTGTACTTTTGTACTTTAATTTGTACACTTTACACACTGACTTTGTACTGCCTTTGTACTTTA
TTTTTGTACTGAAATTGGACGATACTTATCTTTGTATTCACATCCAAGTTTTGCAAATTCCACAGCCGGTCGCGAAA
AGTGAAATCGTACCGTTTTAGGCTTCGATCCCCCTCCCGCGCGAAGACTCGCCAGCATGGACTCTCGTAGGCTCGCT
CTTGCCGTCGCCTTCGGAGGCGTCCTCGCCAGCATGACACAGCGCCGCCGCC TGGCTTCTCTCATCGCCAGCATCGG
CCAACGGCTGATGGGCGGCGACGGCATGCGTCGCGTCGCCGTTCGGTTGATCGACCAGCTCATGGCCGGACCCCCGG
ACATCAACGACGAGGCCTTCCAGCGCGAGATCCGCGTGGGCGAGCTCTTCCAGGCGCTCCACCGCGTGGTCGAGCAG
GCACGCCGAGAGAAGTACTTCGAGGTCTGCGGCGCCGGCAACGACGCCGACGCGCCCGTCGTCGAGATGGACACCGC
GGCCGCACCCCCGCAGCCCCAGCCCGCGCCCTTCGTGGTCACGCCGCAGAACGCGTTCATGTTCGTGCCGCAAGGCA
GCCACGTGCACGTGGACGAGAGCGTGGACCCGTTCTTCGGCATGAGCCCCTCCATCTTCGGGCGCGACCTCCCCCTT
CAGCCGCCCGAGGAGCTGCTGAGCGACCACGACCCGCTCATGAGCCAGGCCGGCGAGCCGCCGAGCCCGCGGTCGCC
CTGCGAGGCCGACCTCTGGTGCTTCGAGACGCTCGGCGACAGCGACAGCGATTGAGCCCGCACCACACCCCACCTCA
CCCACCCCACACTCCACCTCACCTCACCCTAACACCAACACCCTAACACCCAACACCTCAACCGGACAATGAAGGAG
TCCCACATTTCACTGAAGGACGCGGATGAAGCCGCACATCCCCACATGAAGGATTGGCAACGGTCAAACATTTCACC
TGCAATGAAGGACGATGCGCGGTCGCATTGGCCTGCGACCGACATCGCAC ACATGAAGGACACAATTGGTTTGTTAA
TCCGGACAATGAAGGACAAATTGTTTTTGTTAATCAGGACAATTGGACACAATCAGATTAATTTTTGTACGATCATA
AAATCGATATTTGATGCACATATATTAGTAAGTATATTAGACTAAATTCTCCGGGGAGGCAAGCAGTTGGATACGGC
GGGGCGGGGCACGACGTGCACGGAGAATTCGGGCGGGTCCCCCTTCCCCCCACCCCCACGCACCACGATGCGTCT AA
TCTTAGCGCTCGTGGCCTGCTTGTTGGCGGCGCCGATGCCGTTATCGGGTCGTTCGACAAGCACCCCAAACACACAG
TCCGTACTCGGCTCGACGAGTTCGGAACCAAGCTCGGAAGACGCTGTGGCTTCGAGCACAACGACAAGCACACTCAC
AAGCACTACAAGCACACTCACTATGTCCACAAGTGTGGACACCACTACTACCTCGGGCGCTACGACGTCCACAAACA
GCACTCCTGCAGCGAGTGTGAGT TCTTCCACACCCGCAGCCACTGAGGCATCGACGGCACCAACGACGCCGTCGACG
CAGACGACAGTGAAGGTAACGAAAGACAAAGACACGAAGGCGTCTGCCTACCTCGTTTTACTAATCACGTTCATGGT
CATGACAACGCTAGTGATGGTTGTGGTCGTGGTCGTGATCGTGTACAAACAGGGACTTTGTGACTGCTGCTGTAAGA
TGTTTCCCTGCTGCAAAGAGCTCAAGGACTACCTCGACGAGGAGGAGA GCGCCGGGCTGTACGACGCCTTGACGTGG
AGCCGCTCAGACCCCGGCCTCCGGCTCGTCGTGCGCGCGGACCCCAGATGATGAGGATCGGATAAGATCGGCGTGTT
TTTCCCGCCCGTCGCGAACATTATGCCTCTAAATGCCGAGAATTAACTGAAATTCAAACACGCTTTGGGACTCAACT
CTGTGGCCCACACAACCAAGCTTGCATGCCTGCAGGTCGACATCTATATACTATATAGTAATACCAATACTCA AGAC
TACGAAACTGATACAATCTCTTATCATGTGGGTAATGTTCTCGATGTCGATAGCCATATGCCCGGTAGTTGCGATAT
ACATAAACTGATCACTAATTCCAAACCCACCCGCTTTTTATAGTAAGTTTTTCACCCATAAATAATAAATACAATAA
TTAATTTCTCGTAAAAGTAGAAAATATATTCTAATTTATTGCACGGTAAGGAAGTAGAATCATAAAGAACAGTGACG
CCTCGAGGAATTCATGATCCTTCAGGCCCTTCTGTTTGTGCCTCTCCTAATCTCTTCGTTGTGTCTCGGGAAATTCC
CCATCTACACAATACCAGACAAACTTGGTCCTTGGAGCCCCATCGATATACATCACCTCAGCTGTCCAAATAATTTA
GTTGTGGAGGATGAAGGGTGCACCAATCTATCAGGATTCTCTTACATGGAACTAAAGGTGGGATACATCTCTGCCAT
AAAAGTAAATGGGTTCACTTGTACCGGTGTTGTGACAGAGGCTGAAACCTATACCAACTTTGTTGGTTATGTCACCA
CCACATTCAAGAGGAAACATTTCCGCCCTATACCGGATGCATGCAGGGCTGCATACAACTGGAAGATGGCTGGTGAT
CCTAGATATGAGGAATCTCTTCAAAATCCTTATCCTGATTACCACTGGCTACGGACCGTAAAAACCACTAAGGAGTC
TCTTATCATCATATCTCCGAGTGTGGCTGATTTAGACCCATACGACAAATCCCTTCATTCTAGGGTGTTCC CTGGTG
GGAAATGTTTGGGAATAACGGTTTCTTCCACCTACTGCTCAACCAACCATGATTACACCATCTGGATGCCCGAGGAA

FIG. 29DD

CCAAGACTCGGGACATCTTGCGACATTTTTACCAGCAGCAAAGGGAAAAAGGCATCTAAAGGAGGCAAGACTTGCGG
ATTTGTGGATGAAAGGGGCTTGTACAAGTCTCTAAAAGGAGCGTGTAAACTCAAGCTGTGCGGAGTTCTCGGACTTA
GACTTATGGATGGAACCTGGGTTTCCATTCCAACATCAGACGATACCAAATGGTGCCCTCCGGATCAATTGGTGAAT
CTACATGACTTTCACTCAGACGAAATAGAGCATCTCGTCGTGGAGGAGTTGGTCAAGAAGAGGGAAGAGTGTTTGGA
CGCATTAGAGTCCATCATGACCACCAAATCTGTAAGTTTTAGACGTCTCAGCTATTTGAGAAAACTTGTCCCTGGGT
TTGGAAAGGCATACACTATATTCAACAAGACTTTGATGGAGGCT GACGCCCACTACAAGTCAGTTCGGACTTGGAAC
GAGATCATCCCCTCCAAAGGGTGTTTGAAAGTCAGAGAGAGGTGTCATCCTCCTGTGGACGGAGTGTTCTTCAATGG
CATAATTCTGGGTCCAGACGGGAATGTCCTGATACCAGAGATGCAATCATCTCTACTTCAACAACATATGGAGCTGT
TGGAATCTTCTGTAATCCCCTTAATGCATCCCTTGGCGGACCCGTCAACAGTCTTCAAGGAAGGGGATG AAGCGGAG
GATTTTGTTGAAGTTCACCTCCCTGATGTTCACAAACAAATCTCAGGGGTTGACCTTGGTCTCCCGAGTTGGGGGAA
ATATCTCCTGATGATTGCAGGTGGTCTGGCGACTCTAGTTCTGATAATCTGCTCGATGGCATGCTGTAGAAGAACCA
AGCGAACAGAGTCAAGAAGACGAGGCTCTCGAGAGTCAGAGAAAAAGGTAACGGCAACCCCCCAGACTAGGAAAGTC
GTATCTTCATGGGAGTTATACAAGAGTGAAGGCGATGCCAGGCTGGATTACAAGGATGACGACGATAAGTGAGCGGC
CGCGCAGCACTGCTCGGAGGAGTGCTGCAAAGTGGAGGAAGTTCTGTGAGAAAGTGCGTTTTTCTGTAATGTGAAAT
AAGATAGCCTTATGTGTGCACAGACATGGCGAACAGGCTTGTGTTTCTCGACCCCGAGACCCTAGCCGAGGCCGACG
GCATCCCCGGCTATGGGGTGTTCGAGCCCGGCAAGAAGAAAT GCATCTTCACAAAGATCCGCACCAGCGTCGCACTC
GCGTGCCGGTACGCCGTCTCGGACGGCGGCCTCATCGACGAGTTCGTCATGGCGACATACGGGACCAGACGCGCGTG
CCGGCTCGTCCGGCACCTGACGATAAGCGCGGAGGGCGTGATGACCCGGCCCGCCAGCAACTGCGCGCCGCACATGG
TGCTCATCTGCCTCAGAGGCGTGGCCGCCGTGTCCAGCGAGGACATGGGCTTCGGTCGCTGCATCAT GGAGCGCGGC
ACCATGTTCATGGTCAAGTCCGCGCACAGCGCCGTCGTCTGCGGCAACCCCGCCTGCGAGCTGCTCGTCCTCTTCTA
CGACTACTTCACCCCCATCCCCCGGCCGCTCTCCGGAGACGAGGTGCTGTTCACCCGCGACCTCGCGCACGTGGACT
ACGCCCCCGAGTCGGCGGTCGTCTTCAAGATGGATTACAACCTCGAGACCGACGTGGCCACGCTGTTTGTCGGGGGG
TACATATTCCGCGCCAAGGGCCTGATGATGGAGACGCGCGAACAAGTGGGCGACGAGTGCGACTGCTGCCGCCACAG
CTCGCCGGTGCTCGTCATGGATCGCGAGAAGATGATGTCGTCGCTGCGCATGATCCCCAGCATCGTGCCCGGCCAGC
GGGAGATCTGCCTTCGCGAGCGCGGCTGGGCCGTCCTCGAGACGGACGCCCGCGGACACTGCGAGCCCGGCGTCCTG
AGGCTGGCGCTCGCCGGCCTGCGGCTGTTCGCAGGATGCC TGCGCTCCGTCGTGGGGCGGCGCGAGCTGTCGCTGTT
CTGCTACGGCATCGCTCCCAAGTTCGGCGGAGAGTTCGAGGACGCGCCGCGCCCCATGGAGATCGACGGTTAGTTGT
TTTTATCCCTGTACATACGCCGCAAACTGAAACTTTAGGGCACCGCGTAATAGTGCACGAACGCCCAGTGGACCGCT
TCCGCAGCCATGGAAAACAACGAAGGCAACGAACGCAACAACGAACACCCGCACGTTCGAGAATT CAAGGAGGCGTC
CCTGTACGGGTTTCTGGTGTCGGCCGCGGACGTGACCGTCGAGGACGTGCGCCGGTACCTTCAGTTCGGCGCGGACG
TGAACTACAGGGGCGCGTACCTGTGCACGCCGCTGCACGCGTACCTGCAGTCCGGCTGCGAAAAGCGCCTAGACGTC
GTGGACGCGCTGCTGGACGCCGGCGCAGACATCAACGCCAAGGAGATCTGCGGGCTCACGCCCGTGCACCTGTACGC
GAGCTACGCGGATGTGGACGTAGAGTTCATGCGCGGGCTCATCGAGCGCGGCGCGAGCGTGTGCGGCGAGAGCTCGG
TCACGGGCTGCCTGTACTCGTACCTGTACACACACAGCGTGGACGGCGGCGCGCGCCTGGACGTGGTCGAGCTGCTC
GTGCAGGCGGGCGCGGACGTGAACGTCCGCGGCGAGGCGCGCAAGACGCCGCTGCACGTGCACTGCGCGGGCTTCGA
GGTGGATTCGGACATCGTGGAGCTGCTGCTGCGCGCGG GCGCGGACCCCGAGGCGCTCGACGAACACGGGCTCACGC
CCGCGGACGTGCTCGTGAAGTCCGTGGGCGCCAACGTGGCGACGCTGCGGCTCTTCCTCGACGCGGGCGTGAGCGTG
GCCACGTCGCGCGACGCGCGCGGACGCACGCCGCTGCACCACCACGCGGACTCCTTCCGGGCGAGTGCGGTCATCGT
GCGCGAACTGCTCGCCGCCGGCTGCGACGCGGCGGCCACCGACGACCTCGGAAACACGCCCCT GCACAGCCTCGCCA
CCTTCTGCTCGTGCCGGCGCTCGGTGCTCGACCAGCTCATCGCCGGCGGCGCGGACATCAACGCCCGCAACCACTAC
GGCCACACCTGTCTGTACTACGCGTCCATCTACAACCCCTCCGTCTGCTCGAGGCTCATCGCCGCGGGTGCGGACGT
GACCGCGCGCACGCCGGACGGACGCACGCCGCTCTCGGGCATGATCATGCGCAAGCACACGCGCGCCGTGCGCGCCG
CCCTGGCGACGCGGCCTCCCGCGGACGCCGTCGCCGCGTCGCTAGACGTCGCGGTACAGCCCGAGCCCACGGACGCC
ACTCGCGCGTGCGTGCGGTACGTGGTGCTCTGCGGCGGCACGCTCTCGGCGCGCGTGCGGTCGCGACACGCGGACTT
CGTGCGAGAGTGCGAAAGCGAGGTGGTCGTGCTCAGAACCACCGTGGTGGGGCTGCCCGGCACCTCGCTGCTGGACA
TCGTGCGTGCGGCGCAGCCGCCGCCGGTACTGCTCT CCCCGCGCGTGCACCACGTGCTGCAGAAGCTGTGTGTGTAC
GCGGAGTTGGTAGACGCGCGGCTGCGCGAGATGCGGCACAAGACCAACCTCGTGGACGCGGTGTCGCGGCTCGTGTG
TCCGTGCGCGCTGCCGCCGGAGGTGGTGCGCGGCATCCTCGTGCACGTGCCGATAGACAGCCTGCGGCACACGTTGA
CCCTCGGCGTGGCGCAGGCCTTGCGTTTCCTTCCCTCGCATAAATGAAATATTATTTTTTG TGGTAGACCGGATCTC
CCCGATGGACCCCGCCGGACAACGACTGCGCGCGCCAGGGCCGTGGCGCCTGAACCCGCCGACCGCGGCCGCGCTGG
AAAGCGCGCTGCTGCGGCCCGCGGCGTCGGCGGGCGCCGACCGCTGCGCGAACGCGCACGTGGACAGCCGCAACATG
GGCGTCGGCGAGGGCCGAGAGGTGCCCGCGGACGTCGAGGGGCTCATGACCGAGATCCACCTGCGGTACGGAATGAC
GCGCGTCCACCGGAACGTTCACTTCGTGCAGTTCTGGCACGGCGAGCACGTGCGCCGGCGCCCCGCGCGACACGTGT

FIG. 29EE

TCACGGTCTGGATCTGCCTCAGCGGCGAGGTGCGCATCTACGCAGAGTGCTGCCAGGCGGGGCACGGCTTCGTGCTC
TGCCGCCAGATGGCGGCCGGGTACATGTTCGTGACCGAGCCCACGGACTCGGTCACGGTCTCGGTGCCGCACCGGCT
GCGCAACTCGCGGTCGCCGGTGTGGCTGGCGGCGGTCTTCGCCACGCGGCACTTCGAGCCGCTGCCGCCGCCCATGT
ACGCCGTGCCCGGGCACGTGGTGCTCGCGCGCAGCGCCTCCATGCTCTGCGACTGCTGGCCGTCGGACCCGCGGCGC
CGCAACGTGATCTTCTACATGCGGCTGTCGGGCGCGATGGTGCGCGTGGTCGTGCCGGGCGCGGAGCTTGAGATCGA
GTGCACCTCGGGGTTCCGGCCGGACCACTTCTCCATCGACGACGAGTGCGTGTGCTGCG AGCGGCCGCACGTCGCGC
GAACCGCGGTGTGGACGCTGGCGGAGATTTGCCGCGGCGCCACGGTGGTGCTCGCGCCGCCACTGCCCCGCGACCGC
GCCGCGGGGCTGCTCGCGGAGATCCGCCTGGCCTCGCTGCGATGGGTGCGCGTGCGTGCGGTCCGCAGCGGCAGAGA
AAGCGTGGGCCCGTTCCCCTCGGTGGTGTGGGCGGCGGTCTTCTCCGCCGTTCGGCTCTTCCTGGACGGAACCGTGC
CTGCCTTCCCGGCGTGTGTGGAGAATGGACGCGCGGCGTACGGCATGGTGTACGTGCCCTCGGAGGAGCCGCGGATG
GACGGGCTCTGTGTGTTCCCGACGCCCGCCGAGCCGGCGGCGCTCTTCGTCCGCGGAGACCAGGTGCTCGAGGCCGG
CGCGGCCGCCGCCATAATCGCGGCCGCTGAGAAGCGCGTCCAGGCCGCCAATGGGTCTCCTGCTGCCGCGGAGGAGG
ACATAGGTGCGGCGGCCGATGCCGCCGCAGAGAGCGTGGAGCAGGACCAGCGCGTCGAGTTTGACCTTGGGCCTGGG
CCTGACCCCAGCCAAGAAGCGCCCGCGGACGCGCAGCGTGCCGATTCGGACGACGACACCGGCTCCGAGACTGAGAC
CGGCGACGAGAGTGTGGGCGGCGAGGATGACAGCGACTCCTCCTCCTCTTACTCGGTGATGTCGGACGACGAAAACG
ACAGCGGCGACGAGGGCTGGGGCGACTCTAGCGACTCCGGCATCGAGGACGACGACG GCGGTGTCGGCCAGGCCGCC
GAGGAAGAAGAGGAGGAAGAGCGCGACGTCCTCGGCGCAGCGGCCCAGATGCTCGGAGACTGACCGGTGGTGAAAAC
ATAAAAATAAACTGTTCAACACTTGTACTCCGGGCACCAACACTACTATCCATACCCACCCTCCCTCCACACACTAC
AATGGCAAACAGAGAAGAGATTGACGCCTCCGCCGTCATGGCTGCCTACCTCGCGAGAGAGTACGCGGCGGCTGTAG
AAGAACAGCTGACGCCGCGCGAGCGCGATGCGCTCGAAGCCCTTCGCGTTTCCGGCGAGGAGGTCCGGTCGCCGCTG
CTGCAAGAACTCTCGAACGCGGGCGAGCACCGCGCCAACCCCGAAAACTCGCACATCCCCGCCGCCCTCGTCTCCGC
GCTTCTCGAAGCCCCCACTTCCCCCGGCCGCATGGTCACTGCGATTGAGCTCTGCGCGCAGATGGGCCGGGTATGGA
CGCGCGGCCGCCGGCTCGTCGACTTCATGC GGCTCGTGTACGTGCTCCTAGACCGTCTGCCGCCCACGGCCGACGAG
GACCTCAGCGCCTGGCTGCAGGCCGTCGCGCGCGTGCACGGCACGCGGCGCCGCCTGCACCGCGTTCTCGGCGTCGG
GGCCGTCATGGCAGGCGTCGGTATGCTGCTGCTCGGCGTGCGCGTGTTGCGGCGCACATAACTTTTTATCTCGGCTC
AAACTGAAATACGACATTGGACTACGAAACCTATAATTTTGCCCACGGCCGCGCG AGATAGGATAATAAATAACCTC
TGAGCAACTAACATGGCCGATGAGAGAGAGGCCGACGGCGCGCTGTTCCGGTACCTGGAGAGCGAGGACCGTCCGGA
CGTGGAGCACATGCGCCGGCTGCTGGACGAGGGCGCGGACGTGAACTACGCGGGCCCGCGCGGGTACGCGCCGCTGC
ACATGCTCATGCGCGGCAACCCGCTAGACCCCGACGCGGTGCGACTGCTGCTCGCCGCGGGCGCGGACGTGAACGCG
ACATCGCTCTGCGGGTTCACGCCGCTGCACTCCTACATGTGCTTCGGGACCGTGACGCCAGACACGCTGCGTGCGCT
CATGCGCCACGGCGCGAGCGTCAGCGACCTCGAGCGCAACATCAACGCGCTGATCGAGTACTTCAACCGCGACGGCT
GCATGGGCGGCGCGGAGGCGACCGTGATCGCACTGCTGGCGGAGCACGGCGCGCACGTGAACGCCAAAGACGACCTT
GGACGAACGCCGCTGCACATCTACCTGT CCGGCTTCTTCGTGTCGGCACCGGTGGCGCTCGCGCTGATCGCGCTCGG
CGCGAACCCGAACGCCACGGACGCGTACGGGCGCACGCCACTGCACGCCTTCCTGCGCTCCCGCGACGTGGACCCCG
CTGTGCTGAAGACGCTCATAGCCGCGGGCGCAGACCCGCTCGCGCGCGACATCATCCGGCGCACGGCGCTGCACTAC
CACTGCGAGTCCTTCAAGACGCGCGCTAGTGTTATCGAGACGCTGGTGGCCGC CGGCTGCGACCCCGCGAGCACAGA
CCTGCTCGACAACACGGCGCTGCACAGCATGGCCATGGGCAGCTCCTGCCGCGCCTCGCTGATCCGCCCGCTGCTGG
CCGCGGGCGTGTCCGTGAACGCGCGCAACGCGCGGCTGCAGACGCCGCTGCACCTCGCGGCCGTGTTCAACCCGCCG
GCCTGCGCGCGGCTGCTGGCCGCGGGCGCGGACCCCGCGCTCGCGGACCTAGACGAGACAACGCCGCTGCTGAGCAT
GGTGCGACACAACTGCGCACGCGCGCTGCGCACGGCGCTGCCCTTGGCGCCGGACGCGCTAGTGGCCGGCGCGGTTA
ACCGCGTGAACGCGCGCACGCCGAGCGCGGCCACGCGCGAGTGCGTGATGGCGCTGGCGCTGCGCGGCGCGCTGGAC
CTGCTGAGCGCGGAGAGCGTTGCCACCCACGCGGCCGCGATCCGCGCCTGCGAGGCGGAGGTCGCGCTGCTGCGGCG
CACGCGCCTGGGCGCGCCGCCGACGACGCTCTTCGCGCTGCTGACAGGACGACCGAACACGCTGGTTTCCGCAAAGG
CGGCGCGACGCGCGATGGCGGACGTGTGTGTCTACCGCGCGGCGCTGGCCGCGCGCGTGGAGCGCGTGCGCCGAAAG
TCCTCGCTGGTCGAGCGCCTCACCGCCATGGTGTGTCCGTGCGCTCTGCCGCCAGAGCTAGTGACGCGCATCCTCGC
GCTCCTGACCGTGGAGGAACTCGCTTGCGCAATGCGCAAATAATAATGAAC TATAACTAGGCTTATTAGAGGCACTA
TTTGTGCAGAGTCGTTAGTTATAGTTAGTGTACTTACAATTGGAATGTCGAAGAACAAAATTCTGGTGTGTGTTGCG
ATTATTCTTACTTATACATTATACACAGATGCGTATTGTGTTGAGTATTTAGAAAGTAGGGAAGATGAACAACAGTG
CAGCGGTAGTAATGGTGCGTCTGCGAGTTTACCGCACATGCTCAGAGAACTCAGGGCCGCGTTCGGAAAGGTAAAA A
CTTTCTTCCAGATGAAAGACCAACTGAACAGTATGCTACTCACACAGTCGCTCCTCGACGACTTCAAAGGCTACCTC
GGGTGTCAGGCACTTTCCGAGATGATACAGTTTTACTTGGAAGAGGTGATGCCGCAGGCGGAAAATCACGGGCCGGA
CATCAAAGAGCACGTTAACTCGCTGGGAGAAAAACTCAAAACGCTGCGTCTTCGACTGCGTCGCTGCCACCGCTTCC
TGCCGTGTGAGAACAAGAGTAAGGCCGTGGAGCAAGTCAAACGCGTGTTCAACATGCTGCAGGAACGAGGTGTTTAC

FIG. 29FF

AAGGCCATGAGCGAGTTCGACATATTCATCAACTACATAGAATCATACATGACTACTAAAATGTAAAAATGTATATA
ACTTTTAGCTATCGTTCGGATTCTCGTATCGTTCTGCTACAATGTATATAAAAATGTATATTCACATAGTTACAGTT
ACAGTTACAGTTACAGTTACAGCTATATTTTTATGCTCACAAGATGCTA TATAATTGAAAGGAAATTGTTCACTCTC
TGTCAGGGCGCCATGGACTTTCTAGGCGCCGCGCTTCACGACTACGTTGCCGACGCGGAAAATGTCCGCGTTGACGA
GGTGCGGCGGCTGCTGGCCGCAGGCGCCTCTGTGGAGTACGCGGGCGAGTTCGGGAAGACCGCGCTGCACCAGTACA
TGGGCCGTTCCGGCGCGGACCCCGACGTCGTGCGCGCGCTGCTGGACGCCGGCGCGCGCGTGGACCTCCCGGAG ACC
TGCTGCGGCTGCACGCCCGTGCACCTCTGTCTCATGGCCGCCAATATCGACGTGGAGGTTCTCCGCATGCTCGTCCA
CGAGGGCCGCGTCGAGGACTGCGGCCGCGCCGAGCTTGCCTCCGCGGTGCTCAAGGAGTTCGTGGTGAACCGCGCCT
TCGACGAGAACGTCACCGAGCGAGTGATGCGCGTTCTTGTGGCCGCGGGCGCGGACGTTAACGCCACCAGCGTGGTC
GACCGCACGCCGCTGCACGTCTGCCTCACGGGCATGTCCACGCACCCGGGCACCATCGCCGCGCTGCTGCGCTTCGG
TGCGGACGTGAACGCCGTGGACCTCTGCGGCATGTCGCCGCTGGCGGTGCTAGTGCGCTCGCGCGCGGCGACCGCAG
AGCTGGTGCGCATGCTGCTCGACGCGGGCGCAGACGCACACGCGGTCGACAGTCGCCTGGACTCGCTGCTGCACCAG
CACTTTCAGTCCGCGCGCCCGCGGCCGGAGGTGGTGCGCGAGCTCAT CCGCCACGGCTGCTCGCGCGGGCGCGGAAC
CGAATCGGCAACACGCCGCTGCACGAGGCCGCAAAACACTCCTCCTGCAAACACTCGCTGGTGGGGCCGCTGCTGGC
TGCCGGCGCGAGCGTGGACGCGCGAAATAACACGGGCAAGACGCCGCTCCACTTGGCGGCGGCGTCCAACCCGCGCG
CGTGCCGCCGGCTGATCGCGCTTGGGGCGGACGTGGTCGCGCGCAGTTACGCGGGCGTCACGCCGCTGGCGC AGCTG
GTCGCGGACAATAACTCCGCGCTGGTGACCGCGGCGCTGGACACGCAGCCCGAGCCGCGGGCCGTGGCAGAGTCGCT
GCGAGCTACCACGCCCGTCGGCGAAACAGCGTGCTCGCGGCTCTGTGTGGCGTACGTGGTGGCGCGCGTGCCGAGCG
AGGTCCTCGGCGAGCCCGAGCGCGCCCTGCACGCGGCCTTCGTGGCGGAGTGCTTAGCGGAGGTAGCGGCGATACGC
CGTGCGCTGCGGCACACCTCCAGTCTCGCTGCTGGAGATCCTGGTGGCCGCGCGCCCGCCGCGGAGCCTGCTCTCGC
GCCGCGCGCGGCGGCTGGCCGAGAGCCGGACGACGGTCTACCGCGCGCCGCTCCGTGCACGCATCGCGGCCATGCGC
CATCGCTCGCGACTGGTGGAGCGCGCGCTGCGCACGCTGCGCGGCTGCGTGCTCCCGCGCGAGGTGCTGGAGCGCGT
GCTGCGGTGTCTGTCCACACAGGACCTGCGGACATCCGGACTGGC CGAGTAGCTTTTTCTGAGATAAGTGAATAAAC
ATGGTGGGATTCGATCGCGCCGCCAACGCCACGCCATGGACGCCGCCGAGATGGAGGAGCTCGACATCAACGCGGAG
TCGGCGCTGTACGACTACTTCATCCTGAACGCGGACAGAGCCCGCGTGGGCGAGGTGGTCATGCTTCTCGCACAGGG
CGCGGAAATAAACTACGCGGACAGCTTCGACAAGACGCCGCTGCACCTGTACTTGCACACGCGACACCCG CGCTCGG
ACGTGATTCTGGCGCTGATGGAGGCAGGCGCGGTCGTGGACACGCCGGAGCGCTGCTGCGGCGCGACCGCGGCGCAC
CTGTACATCCTCAACGCGGCCGAGGTCGACCTGTCGGTGCTGGAGGCCATGCTGACCTGGGGCGTGCGCCAGAACGA
CCAGCACTCGGAGCGGCTGCTCTCGAGCTTGTTGCGCGAGTACGTGGTGACCCGCGCCTACTCGGATCAGACCGAGC
CGATCATGGACTTGCTCATCGGCATGGGCGCCGACGTGGACATGCCGGTCGGCGTGAGTCGCACGGCGCTGCACGCC
TGCCTTACGGGCCTGAACACGAACCCGTGCATGATTCGCGCGCTGCTTCGGCGCGGCGCCAGCGTGACCGCAAAAGA
CACCTACGAGATGACGCCGCTGGCGGTGCTGCTGAAGTCTGCGAGCGCGACGCCGGAGCTCGTGCGCATCCTCGTGG
AAGCAGGCTCCGACGTGAGCGCCACCGACTTCCGCCTCAACGG CATGCTGCACCAGCACGCGCAGTCCACGCGCCCG
CGCGCGAGCGTCATGCGCGAGCTCATCCGGCTGGGGTGCAGCCCAGCGGCCAAAAACATGTTTGGTAACACGCCGAT
GCACATGCTGGCCATGGAAAGCTCCTGCCGCCGCTCGCTGATCCTCCCGCTGCTGGAGGCAGGGCTTTCCGTGAACG
AGGAGAACCCGCACTACGGCACCGTGCCTCTGCACGTGGCCTCGGGGTACGACAACACGCAGGGCTGC CTCAAGCTC
CTCCGGCAGGGAGGAGACCCCGCCGTCGTGTCGGCCGCCGGACGCACGCCGATCTCGAACATGCTCGTCAAACGCAA
CCACGTGGCGGTCGCCGGCGCGCTGTCGACACACCCGAGCGCGGTAGTGGTCGTGCAGGCTCTCGAGCAGGCTCTCG
AGCACGTGCTGAACGCCGGGCCCAGCGAGGCCTCGCGGCTCGCCGTGGCCTTTGTGGTGGCGCGCGCTGGCGCATCC
GCGCTACCGGAGGCCGTGCGCCGTCTGCACGAGGGCTTTGTCGCCGACTGCGAGCGCGAAGTCGCGCTGCTTTCTCA
AACCATGCTCGGCACACCGGCCGTGAGCGCGCTGGCCGTGCTGGTCAGCAAGGAGGTCTTTGGCACTGTTATCTCCT
CGCGTGCGCTGCGTGTCGCGCGGGAGGTCCGCGTGTACGCAAGGCCGCTCCGCGAGGCGCTCATAAATCTGCGCCAC
AAATGCCGCTTAGTTTCCAGCCTTAAAAGGCAGGTGGGACC TTGCTCGCTGCCCGGCGAACTGGTGGAGCGCGTGCT
CGCGACCGTGCCACTGACCGACTTGCGCCGCTCGTGCGGCCGCCGCGCGCCCGAGTGACTGCCCATCCCGTTGCTAC
GCGACTCGGTGACTGCCCGCTGTTTTTCTTTCCCCGTTTCTTCTTATTAGGAGTTGTTGCCCGCCTCCATGATCCTC
GCGCGCGCCGGCGGGCGACCTCGCACGCCCGCGGCGGCCGCGGCCGCCGCCGAGGACGGAGAGCAC AGTGATCGCCG
GAAGCGCAAGCGCAAGACGCCCAACTGCGAAGACGCCGACAACTCCGACGACGAGCTAGCGCAGACGCCGTGTGACC
GCGAGTGGCCGGACTGTCGCGCGAGCTCGATCACGAGCTCCGACTCGGTCTCTCTCGGCGACGAGATCTACCTGCGA
TACGTGGCCTCGCAGGTGGACTTCGCGCAGACCTGGGCCCCGCCGGTGCGGCTGCTGCGCTTCTTCGGGAACTTCTC
GAAGGAAACGCTCAACCGCATGTCGCGGCGCGGGTACGTGAACCGCTCCTACTTCCAGATGGCGCACGCGCGCTTCT
CGCCCACCAACGACGACATGTACCACATGGCCACGGGCGGGTACGGCATCGTGTTCCGCTTCGACCGCTACGTGGTC
AAGTACGTCTTCGAGCACCGCAACGGCATGTCCGAGATGGACGCCTCTACGGAGTACACAGTGCCGCGGTTCCTGCG
CAATAACCTCAAGGGCGACGAGCGCGAGTTCGTGGTCTGCGCGCTGGCCATGGGGCTGAACTACCGGCTGGGCTTCC

FIG. 29GG

TGCACTCGCTGTACCGGCGCGTGCTGCACACGCTGCTGCTGCTCATGCGCGTGGAGGAAGGCCAGCGGCCCTCGGTG
GAGATGTCCAAGAAGCCGCTGCTGCGCTGGTTCGAGGCGCGCAAGGACAGCGAGTCCTTCGTGCGCCTGATCTCGTA
CTTCTACCCCTCGGCCGTGCAGAGCAACGTGAACCTGATCAACAACTTCCACCACCTGGTGCAC TTCTTCGAGCACG
AGAAGCGCGCGCGGTACGTGTTCGACCGCGGGGCCGTGATCGTGTTCCCTCTGGCGCGCGGGTCCGCGGACTCGATC
TCGCCGGAGGCGGCGGCGGCGCTGGGCTTCGCGCCGCACTCGGAGTTCCTCAAGTTCGTGTTCCTGCAGATCGCGCT
GCTGTACCTGAAGATCTACGAGCTCCCGGTCTGCACGAACTTCCTGCACGTGGACCTGAAGCCCGACAACGTGCTCA
TCTTCGACAGCGCGCGCGCGCTCAGCGTGACCGCGGCCGGCGCGACTTTCCGCTTCGAGGAGCCCGTGCGCGCGGCG
CTGAACGACTTCGACTTCGCGCGCGTGGCCACCATCGAGAACCGCAAGATCTCGGGCAGCGTCCGCGTGCCGCAGAA
CTGGTACTACGACTTCCACTTCTTCGCGCACACGCTGCTGCGCGCGTACCCGCACATCGCCGCGGAGGACCCGGGCT
TCCACGCGCTGCTCTCGGAGCTCACGGTCTCGTGCTC GCGCGGGACCTGCGACCGCTTCCGGCTGCGCGTGTCCTCG
CCGCACCCCATCGAGCACCTCGCGCGGCTGGTGCGCCGCGACGTGTTCTCCCGCTGGATAAATGCCGCTGCAGACGC
CCCCGACGCCGCCGCACTCTCCTGAGCCCACGCCCGCGGCGCCGGGCTCGCTGTACGACGTCTTCCTCGCGCGCTTC
CTGCGCCGGCTGGCCGCTCGCGCGGCGCCGGCCTCGGCCGCCTGCGCCGTGCGCGTGGGTGC GGTGCGCGGCCGCCT
GCGGAACTGCGAGCTGGTGGTGCTGAACCGCTGCCACGCGGACGCGGCCGGCGCGCTCGCGCTGGCCTCCGCGGCGC
TCGCCGATACGCTGGCGGAGCTGCCGCGCGCGGACAAGCTCGCCGTCGCGCGCGAGCTGGGCGTGGACCCCGAGCAC
CCGGAGCTGATGCCGGACCCCGCCTGCGCGGGCGAGAGCGCGCTCGCGCAGAACATCGACATCCAGACGCTGGACCT
GGGCGACTGCGGAGACCCCAAAGGCCGCCGACTGCGCGTGGCGCTGGTGAACAGCGGCCACGCGGCCGCGAACTGCG
CGCTCGCGCGCGTGGCGACCGCGCTGACGCGCCGCGTGCCCGCGAGCCGGCACGGCCTCGCGGAGGGCGGCGTGCCG
CCGTGGACGCTGCTGCTGGCGGTGGCCGCGGTGACAGTGCTCGGCGTGGTGGCAATCTCGCTGCTGCGGCGCGCGCT
GCGGGTGCGCTACCGCTTCGCGAGACCGGCCGCGC TGCGCGCGTAGCCGCGCAAAATGTAAATTATAACGCCCAACT
TTTAAGGGTGAGGAGCCATGAAGTTGCTCGTCGGCATACTGGTAGCCGTGTGCTTGCACCAGTATCTGCTGAACGCG
GACAGCAGCACGAAAAGATGGTCCGAAGTGCTGAAAGGTAGCGAGTGCAGGCCTAGGCCGATTGTTGTTCCTGTAAG
CGAGACGCACCCAGAGCTGACTTCTCAGCGGTTCAACCCGCCGTGTGTTACGTTGATGCG ATGCGGCGGGTGCTGCA
ACGACGAGAGCTTGGAATGCGTCCCCACGGAAGAGGCAAACGTGACGATGGAATTCATGGGTGTAGGTGTGTCCAGC
ACTGGATCTAGTGTGAGCACTCAACATCTGGAATTCGTGGAGCATACAAAGTGCGACTGTCAGCCGCGCGGCGGACA
GCAGACGACACCGACGCCACCTAGACGGCGCCGAAGGGCTTATTAGCAGCAGTTTTTGTAGCGGGACGTTTCTGGGT
TTCCTTGCGCGCTCGGCGGCGGGGCTGCTGCTCGCGGCGGGCGCGCGGTGGCGGCGGCTGGCCGCGGCGCTGGCGGC
CGCGGGCCGCGCGGCGGGGTAGCGGCCCGGCCCGGGCCCGCCGCAGCCCTTCGCCTGCGGAGGAGGCGCCACGGCGC
AAAGTGAAAAAGGACCGCCTAGCAGTCGAGACCCTCCCGCCACAGCCGCGGACACCCACACCCGCCCTCCACACCAC
AGCCAGCAAGCATGCACCCCTCGCCGCGCAGGC TGCTCGGCGCGCTCGCGCTGGTGGCGCTGGGCTTCCTCCTCGGC
GGGCTCTTCCGCCCCGCGGCGCCGCCGCTGCCGGCCGCCCTCGTGGAGGCGGGCCCCGTCCGCGCGAACGGCTCCGC
CTCGGTGACCTGCCTGACCGTCGGCGGCGACGGGCGGCACATGGCGGTGGTCGCGCACGGCGGCGGGACGCTCTCGC
CGGTGTACCCGCTCGCCGCCGGCATGCACGCGACCTTCGCCTCGCTGCGCAAGGGCGC GCTGCTGCTGAACGTCGCG
ACCGTGCACATCTACGACGTGCGCGAGCTCGCGCCGGAGTTCGAGCTGACCTGCGTCGCGGTGGCGGGCGGCTACAA
CGCGGCCTGGGCGGCCACGCGGCCCGCGGCCGAGTGGCGCCGCCAGCTGGCGCAGATGCACCGCTCGGAGCTGTGAC
CCTCTCCCCGGTCTCCCATCCGTTTTTGTATTCGGCCTTAGTAGATTAGACCAGCATCCCGCGCCCCTTGCGCCGCC
CTTCGCTCGTGAACGAGCGAATCAGTCAATTAATTATTTTTATCGCCGCCCGCTCACTCCGGTAAGGGAACGCGGTT
AACTCACCCACGAGAACAAGCAACCGCTCACTCACGAGGTAAGGGAACAACAGTTAACGTCAACTCACTCACGAGAA
CAAGTTGACCACTCTCGAGGCAGAGACGAGAAAACAAGTGACCGTACTCGCTCACGAGAACAAGTTGACGCACCACT
CGCCGAGGTAAGGGAACAGATAACAAGTAACAAGTAACCGTTACATCACTCGCTCACTCCTCGGAAAATAGAACGAG
AGAACGAGAGAACGAGTTAACTTACTCACTCGCTCACTCGGTGTGAGAGAACGAGAGAACGAGTAGCTGTTGCTCAC
TCAATCGCCCCTCGGAGTAAGGGAACAAGAGCAGTCAACGCACCCACTCAGTCTTGGAGTGAGAGGCAGAGGACGAG
CTAACGAGTTGAACAGTTAATCTCTCACCACTCAGAGTGAGAGAGCGAGAGAGTGA GGACGAGTTAACAAGTCAATC
CTCACTCAGAGCGAGAGAGTGGAGGACGAGTTAATAGTTAACGGTTAGTTATCACTCACTCAGAGTGAGAGGAGGGC
GAGTCAACCACTCGCTCGCCCCTCCGAGTTAGAGAGGAGAACCAGTGAGCGAGTTAACCCGCACACGAGCGAGAGAA
CGTGAACTCGCTCGCGCGCGCTCGGCTAACAGTCGGCCTCTCCCAAAACTCTTCGTAAACTTTTCCCGTGACAGGTT
CGTCCTTCCAAAACTAAACTGTCGGGTCGGCCTGCCTCTCAACTCTCCGTAAAACGTTTGTAAACTGTTCGGAGGTC
GGTGACCCGCTCAACCCGTCCGCGAAAACTTTTCGCAGGCAGTGTCTGCCTCTCTCGGACTCTCCGCAAACACTTTC
GCGGAACCTCGGGGGTGGTCGACCTCTCTCCAAACTTTGCAAAACTTTTTCGCGGAGCCTCTGGAGGCCAGTCCTCC
CTCCAAACTCTTTGTAAGATCTTTTCGGAGGCCAGTCCTCCTCTCCAAAACGTTCCGCAAAATCTTTGGGAGGTCGG
CCTCTCCTCTCCAAAACGTTCCGTAAACTCTTGGACGGCCGCCCGCGGCACGCGAGGCGGAGGATCCGGGGGTAGTC
GACCTCCCTCAAAAACTTTGTAAAAACTTTTTATAAAACTTTTCGCGGAACCTCGAGAGTAGGTCGACCTCCCTCAA
AACTTTTATAAAACTTTTTAGCGGAACCGTTGGAGGCAGGTCGACCTCCCTCAA AACTTTTATAAAACTTTTTAGCG

FIG. 29HH

GAACCGTTGGAGGCAGGTCGGCCTCTCAAACTCTTTGCGAGAACTCTTCGATAACTTTAGGAGGTCAGGTCGACCTC
CCAAAACTTTTGCGAGAACTCTCTGAAAACTTTAGGAGGTCAGGTACCTCTCCAAAACTTTTATAAAACTTTTTCGC
GGAGCCTCTGGAGACGGGCCGCCGCCCGCGACCGCGGGAGCGGAGAGGCCGACCTCCCGAGACGTTCCGCGTTACCG
TCGGGGTAGGCGTCCTCTCGAGAACGCCAAAAGACTTCGTGCAAAAACTTTTCGGAGGGGCGCGGAGGGCGGGCGGC
TCCCGCGAACTCCCGCAGAACCTTTTCGCGCGACCGCGAAGGCCGGCCGCCTCTCCCGAACACTCTCAAGAGCTTTT
CGGAGGAGGGGCAGGTCGCCCCCACCTCTCCGACGCTTTGTAAAAACGTTTACGCGGAACCTCGAAGGCAGGTCGCC
TCCCTCGAAAACTCCTCGCGAAACCTTTAAAAACTTTTGCGAAAACTTTTCGGAGGATGTCGGAGGGCGGGCGGCTC
TTCCAAACCTCCGCAGAACCTTTTCGCGCAACCGTTGGAAGACAGGTCGGCCTCTCTCGAAAACTTTTAAAACTTTG
TAAACGCGTTGGCGGGACCGTCGCGGGAGAGCGGCCGCCCGCGGCACGCGAGAGGAGGAAACGTTGGAAGGAGTCGG
CCTCTCCCGAAAACTTTTTATAAAAACTTTTCCGCGGAACCGTGGAAGGCGGTCGGCCTCTCCCGAAAACTTTATAA
AAACTTTTTGCGGGACTCGGACGGCGGGTCACCCGACCACCTGACTCCTGTCTACCCGACTACTTGACTTCTGTCTC
CCGGGCTCCTGACTCCCTGACTCCCGGACTCCCTGACTCTAGAGCGAGGTCTCGCGGCTGCGGGGTGCCGCCTCCGC
GGAGTCGCGTTCCCGCGGACGCCCGTCCTCGAAAGCATTCAGCAGTTCCAGCCTCTGCCGTAGCTCCTCCCGCAGGA
ACTCCTGGTCCGCGTTCTCG

FIG. 29II

ORF VIRUS-BASED PLATFORM FOR VACCINE DELIVERY

CROSS REFERENCE TO RELATED APPLICATIONS

This application claims priority under 35 U.S.C. § 119 to Provisional Patent Application Ser. No. 62/311,013 filed Mar. 21, 2016, herein incorporated by reference in its entirety.

FIELD OF THE INVENTION

The present invention is directed to novel vaccine delivery platform based on the Orf virus (ORFV) genome which is effective for prevention of infections, diseases, and other conditions in animals.

BACKGROUND OF THE INVENTION

Herd health is a constant concern for the livestock industry. Effective vaccines are necessary to keep animals safe from a multitude of infectious diseases. Protection elicited by vaccines is necessary to ensure that the food supply is safe and affordable for human consumption.

Several important diseases and conditions impose a burden on livestock, requiring the investment of significant resources for their prevention. Often, these diseases include an infectious agent, such as a virus, bacteria, or other microbe.

Porcine epidemic diarrhea (PED) is highly contagious and is characterized by dehydration, diarrhea, and high mortality in swine, particularly young piglets. The causative agent, porcine epidemic diarrhea virus (PEDV), is a single stranded, positive sense RNA virus identified to the *Alphacoronoavirus* genus of the family Coronaviridae. PED was likely first observed in Europe circa 1970, and the causative virus was subsequently characterized (see for example M. Pensaert et al. Arch. Virol, v. 58, pp 243-247, 1978 and D. Chasey et al., Res. Vet Sci, v. 25, pp 255-256, 1978). PED disease was generally considered exotic in North America until 2013, at which point widespread outbreaks commenced, and severe economic losses to the swine industry resulted. Since its initial detection, PEDV has killed over seven million piglets (~10% of the swine population) causing significant economic losses to pork producers throughout the country.

Among the reasons that contributed for the rapid spread and devastating effects of PEDV in the US are: 1. the fact that the swine population was naïve to the virus; 2. there was no vaccine available to control the disease. Recently, two PED vaccines received conditional license from the USDA and are now available to pork producers in the country. However, the efficacy of these vaccines in the field is still unknown. Effective vaccines are critical to control PEDV and to reduce the economic losses posed by the virus to the US pork industry.

The rabies virus is transmitted through broken skin by the bite or scratch of an infected animal. Exposure to rabies virus results in its penetration of peripheral, unmyelineated nerve endings, followed by spreading through retrograde axonal transport, replication occurring exclusively in the neurons, and finally arrival in the central nervous system (CNS). Infection of the CNS causes cellular dysfunction and death (Rupprecht & Dietzschold, Lab Invest. 57:603, 1987). Since rabies virus spreads directly from cell to cell, it largely evades immune recognition (Clark & Prabhakar, Rabies, In:

Olson et al., eds., Comparative Pathology of Viral Disease, 2:165, Boca Raton, Fla., CRC Press, 1985).

The rabies virus (RV or RABV) is a rhabdovirus—a nonsegmented RNA virus with negative sense polarity. Within the Rhabdoviridae family, rabies virus is the prototype of the *Lyssavirus* genus. RV is composed of two major structural components: a nucleocapsid or ribonucleoprotein (RNP), and an envelope in the form of a bilayer membrane surrounding the RNP core.

The RV G protein, is involved in cell attachment and membrane fusion of RV. The amino acid region at position 330 to 340 (referred to as antigenic site III) of the G protein has been identified as important for virulence of certain strains of RV. Several studies support the concept that the pathogenicity of fixed RV strains is determined by the presence of arginine or lysine at amino acid residue 333 of the glycoprotein (Dietzschold et al., Proc. Natl. Acad. Sci. USA 80: 70-74, 1983; Tuffereau et al., Virol. 172: 206-212, 1989).

Rabies continues to be a threat to domestic animals and humans through transmission from wildlife. Therefore, there is a need for more safe and effective rabies vaccines.

Parapoxviruses

Poxviruses present many features that make them excellent vaccine vectors for delivery of foreign antigens in humans and animals, including: i) their natural immunogenicity; ii) their ability to induce long-lasting humoral and T cell responses against foreign antigens; iii) the flexibility of their genome that allows for large genome segments to be deleted and foreign DNA to be inserted, thus enabling construction of multivalent vaccines; iv) their ability to induce robust immune responses in both permissive and non-permissive species; and v) the ability to differentiate naturally infected from vaccinated animals (DIVA-compatible). To date, multiple poxviruses have been empirically developed as vaccine vectors for use in human and veterinary medicine. Among the most widely used poxviral vaccine vectors are the orthopoxvirus vaccinia virus (VACV) and the avipox viruses, fowlpox virus (FPV) and canarypox virus (CNPV). Orf virus (ORFV) is the prototypic member of the *Parapoxvirus* genus, and has a worldwide distribution causing acute dermal infections in its natural hosts: goat and sheep. Despite the use of these viruses as vaccine vectors in humans and many animal species, little is known about the immunomodulatory mechanisms underlying vector-elicited host immune responses and how these interactions drive the adaptive immune responses against foreign antigens delivered by these vectors.

The parapoxvirus Orf virus (ORFV), represents a promising and perhaps superior alternative to other poxviral vaccine-vectors currently being used in veterinary medicine and agricultural industry. ORFV has been long used as a preventive and therapeutic agent in veterinary medicine due to unique immunomodulatory properties of the virus. ORFV immunomodulators (Baypamune®, Bayer; Zylexis®, Zoetis) have been used for prophylaxis, metaphylaxis, and therapy of various diseases, including infectious diseases of several animal species. Inactivated ORFV has been shown to induce an autoregulatory cytokine response in mice, involving up-regulation of Th1-type cytokines (IL-12, IL-18, and IFN-γ) and their subsequent down-regulation, which is accompanied by induction of Th2-type cytokines IL-10 and IL-4.

In addition to the general properties described above for other poxviruses, ORFV presents many unique features that may favor its use as a vaccine vector for veterinary applications, including: i) its unique immunomodulatory properties; ii) its narrow host-range (sheep and goats), iii) the ubiquitous nature of ORFV; iv) the benign nature of ORFV infections, which are self-limiting and restricted to the skin with no evidence of systemic dissemination, and v) its ability to re-infect its hosts, which allows repeated vaccine administrations and immunizations boosts. Together these observations indicate that ORFV has promising potential as a vaccine vector platform for use in multiple animal species.

There is a need for a vaccine delivery platform with broad applicability for prevention of multiple infections, diseases, and conditions in various subject species to enable construction of safe and highly immunogenic constructs. The compositions and methods of the present invention involve novel polynucleotide constructs that meet these needs and address the economic burden of treating and preventing disease in subject animals, in particular cattle, swine, and horses.

The compositions and methods of the present invention provide for safe and immunogenic vaccine delivery platforms, of particular use in cattle, swine and horses. The compositions and methods of the present invention for vaccine vectors provide flexible platforms that allow insertion and expression of protective antigens for other infectious disease agents affecting cattle, swine and horses. The compositions and methods of the present invention can be used as a vaccine delivery platform for multiple infectious disease agents affecting cattle, swine and horses. The ORFV-based constructs and vectors can be used for vaccination against a variety of diseases and conditions, including, for example, rabies and porcine epidemic diarrhea virus. There is a strong need for effective, inexpensive rabies vaccines for use in cattle in South America, and for PEDV vaccines in the US, Asia, Europe and other countries in Central and South America.

Other objects, advantages and features of the present invention will become apparent from the following specification taken in conjunction with the accompanying drawings.

BRIEF SUMMARY OF THE INVENTION

The present invention relates to compositions and methods for vaccine vectors with enhanced immunogenicity in cattle, horses and swine. According to the invention, Applicants have developed ORFV-based vaccine vector platforms for use in multiple animal species for delivery of a variety of specific antigens.

In one aspect, the present invention encompasses novel polynucleotide constructs. In one embodiment, the polynucleotide constructs may be viruses, viral vectors, plasmids, and infectious DNA molecules, including, for example, ORF-based viral vectors. In a further aspect, the viral vectors of the invention may be used for whole virus, attenuated live vaccines. The novel viral vectors have several modifications in nucleic acid sequence from currently known ORFV strains. In some embodiments, the viral vectors cause reduced immune response when administered to subject animals. In other embodiment, the viral vectors induce an enhanced immune response when administered to subject animals. Thus, the invention comprises a viral vector of the invention, preferably live and attenuated, or an immunogenic fragment thereof, one or more adjuvants, and optionally one or more excipients. The immunogenic compositions of the invention protect animals from infection by ORFV, and are effective in single doses, in two-dose programs, or in vaccination programs involving multiple doses, which may be spread apart by at least a week, and optionally at greater intervals of time, such as one to several months. It should be noted that depending on the level of epidemic threat in a particular animal population, the vaccine dose program of one, two, or multiple doses may be repeated, from time to time, as a precautionary measure.

In another aspect, the present invention provides polynucleotide constructs that have been modified to include a heterologous antigen, which can be used to treat or prevent one or more diseases, conditions, or infections. In one embodiment, the polynucleotide constructs are ORFV-based viral vectors. The viral vectors of the invention may be used for whole virus, attenuated live vaccines. The novel viral vectors comprising one or more heterologous antigens induce enhanced immune response to the vector, heterologous antigen(s), or both, when administered to subject animals. Thus, the invention comprises a viral vector of the invention comprising at least one heterologous antigen, preferably live and attenuated, or an immunogenic fragment thereof, one or more adjuvants, and optionally one or more excipients. The immunogenic compositions of the invention prevent, or treat an animal for, one or more diseases, conditions, or infections associated with the heterologous antigen(s). The immunogenic compositions are effective in single doses, in two-dose programs, or in vaccination programs involving multiple doses, which may be spread apart by at least a week, and optionally at greater intervals of time, such as one to several months.

The recombinant constructs of the present invention can be used to treat or prevent one or more diseases or conditions. The nucleotide constructs may be modified to encode one or more heterologous antigens associated with a disease, condition, or microbe. In an exemplary embodiment, the nucleotide construct has been modified to remove one or more genes or open reading frame. In a further aspect, the heterologous antigen or antigens are inserted into the insertion site created by deletion of the gene(s) or open reading frame. In an exemplary embodiment, the deletions are to one or more of ORFV002, ORFV024 ORFV073, ORFV113, ORFV118, ORFV119 or ORFV121 in the ORF virus, and one or more antigens are inserted into the deletion sites. The antigens may be associated with an important agricultural livestock disease, including, for example rabies virus G protein and/or PEDV S protein.

The present invention provides methods of treating or preventing a disease, condition, or disorder in an animal by providing to the animal a nucleotide construct as described, encoding an antigen associated with the disease, condition, or disorder. In a further aspect, the invention provides methods of treating or preventing more than one disease, condition, or disorder in an animal by providing to the animal a single nucleotide construct as described, encoding one or more antigens associated with the diseases, conditions, or disorders to be prevented. In an exemplary embodiment, the nucleotide construct is an ORFV-based viral vector encoding rabies virus G protein and/or PEDV S protein.

The present invention also includes the option to administer a combination vaccine, that is, a bivalent or multivalent combination of antigens, which may include live, modified live, or inactivated antigens, with appropriate choice of adjuvant.

Representative embodiments of the invention include an isolated polynucleotide sequence that includes a polynucleotide selected from the group consisting of:

(a) SEQ ID NO: 4 or 5 or a fragment thereof that encodes an ORFV-based viral vector;

(b) the complement of any sequence in (a);

(c) a polynucleotide that hybridizes with a sequence of (a) or (b) under stringent conditions defined as hybridizing to filter bound DNA in 0.5M NaHPO4, 7% SDS, 1 mM EDTA at 65° C., and washing in 0.1×SSC/0.1% SDS at 68° C.

(d) a polynucleotide that is at least 70% identical to the polynucleotide of (a) or (b);

(e) a polynucleotide that is at least 80% identical to the polynucleotide of (a) or (b);

(f) a polynucleotide that is at least 90% identical to the polynucleotide of (a) or (b); and (g) a polynucleotide that is at least 95% identical to the polynucleotide of (a) or (b)

Preferably in combination with at least one heterologous sequence encoding an antigen.

The invention further provides RNA and DNA molecules, their complements, fragments and vectors and plasmids for the expression of any such RNA or DNA polynucleotides, and for and ORFV-based viral vector that is expressed from such nucleotide sequences, wherein said virus is live, or fully or partially attenuated.

The invention also provides a vaccine that comprises a polynucleotide sequence as aforementioned, and corresponding nucleotide sequences.

The invention also provides for novel full length variant ORFV genome sequences that can replicate efficiently in host animals and tissue culture, and can be used as a whole virus live, preferably attenuated vaccine composition, and be modified or adapted to include heterologous antigens for immunization.

The present invention encompasses immunogenic compositions comprising viral vectors. The viral vectors ORF-based viral vectors and may be used, in one embodiment for whole virus, attenuated live vaccines. Thus, the invention comprises an immunogenic composition, suitable to be used as a vaccine, which comprises a variant ORFV strain of the invention comprising one or more heterologous antigens, preferably live and attenuated, or an immunogenic fragment thereof, one or more adjuvants, and optionally one or more excipients, in an amount effective to elicit production of antibodies in animals. The immunogenic compositions of the invention protect animals from infection by one or more microbes or development of particular diseases or conditions, and are effective in single doses, in two-dose programs, or in vaccination programs involving multiple doses, which may be spread apart by at least a week, and optionally at greater intervals of time, such as one to several months.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 8 shows immunogenicity of recombinant ORFV according to an exemplary embodiment of the present invention in cattle. Cattle were immunized with ORFV-024RabV-G or ORFV-121RabV-G on day 0, and immunized with the same recombinant virus again on day 21. Inoculation was either subcutaneous (SC) or intramuscular (IM) Blood and serum was collected from animals on days 0, 21, and 42, and rabies virus-specific antibody titers were determined.

FIG. 15 (A-C) shows replication characteristics of ORFV-PEDV-S in ovine, swine (ST) cells and porcing (PK15).

FIG. 16 (A-C) shows Immunogenicity of recombinant ORFV-PEDV-S in pigs.

FIG. 17 (A-B) shows the protective efficacy of ORFV-PEDV-S against PEDV challenge.

FIG. 19 (A-D) show serological responses following challenge infection with PEDV.

FIG. 20 (A-B) show serological responses in gilts immunized with ORFV-PEDV-S.

FIG. 21 (A-B) show PEDV specific antibody levels detected in colostrum and milk of immunized gilts.

FIG. 22 (A-c) show antibodies detected in serum of piglets born to immunized gilts.

FIG. 24 (A-B) show clinical outcome of PEDV infection in piglets born to immunized gilts.

FIG. 25 shows the recombinant plasmid sequence used to generate ORFV-024-RabV-G (SEQ ID NO:1).

FIG. 26 shows the recombinant plasmid sequence used to generate ORFV-121-RabV-G (SEQ ID NO:2).

FIG. 27 shows the recombinant plasmid sequence used to generate ORFV-PEDV-S(SEQ ID NO:3).

FIG. 28 shows the OVRF-024-RabV-G genome (SEQ ID NO: 4).

FIG. 29 shows the OVRF-121 RabV-G genome (SEQ ID NO:5).

DETAILED DESCRIPTION OF THE INVENTION

Figure 1:
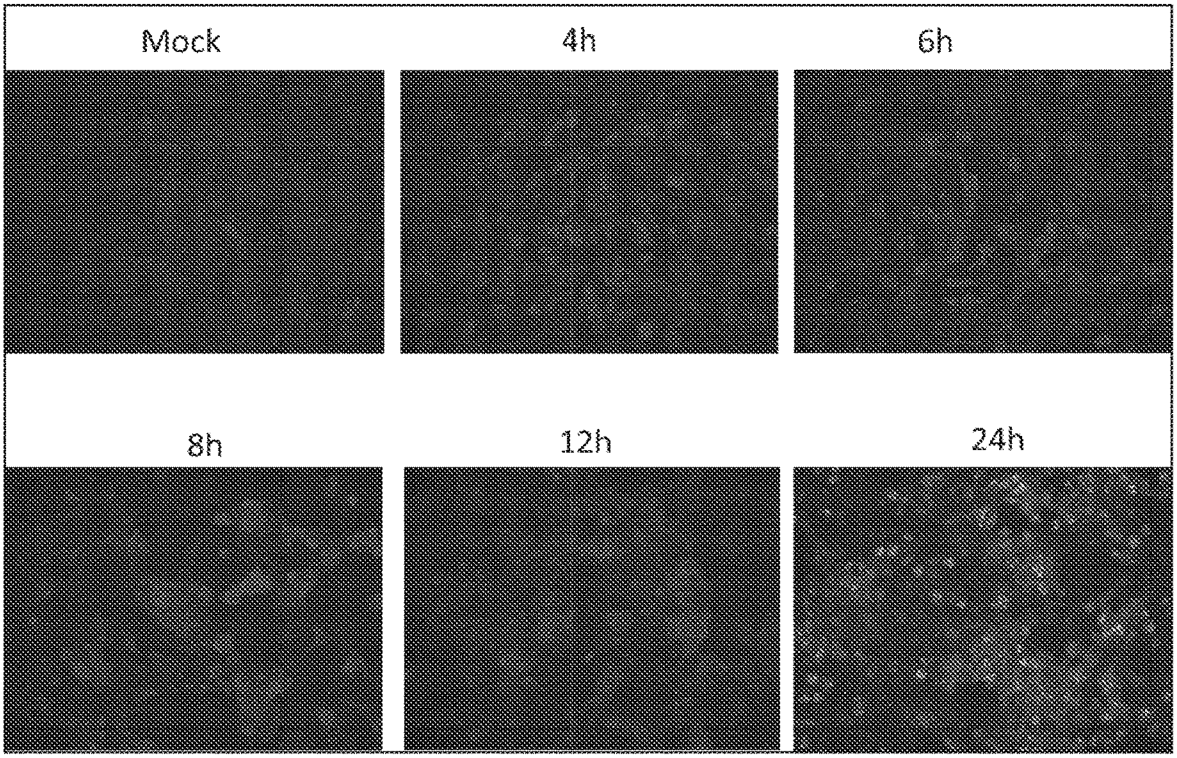
FIG. 1 shows expression of rabies virus G protein (RABV-G) in cells exposed to nucleotide constructs of the present invention. ORFV was modified to delete the ORFV24 gene, creating an insertion site into which a polynucleotide encoding RABV-G was inserted (ORFV-024RabV-G), according to an exemplary embodiment of the invention. Expression of RabV-G in Ovine fetal turbinate (OFTu) cells exposed to ORFV-024RabV-G (MOI=10) was assessed by immunofluorescence microscopy, using anti-flag primary antibody and anti-mouse secondary antibody conjugated to Alexa 594. Expression was assessed at 4, 6, 8, 12, and 24 hours following exposure to virus, compared to mock exposure.

The following definitions and introductory matters are provided to facilitate an understanding of the present invention.

Numeric ranges recited within the specification, including ranges of "greater than," "at least," or "less than" a numeric value, are inclusive of the numbers defining the range and include each integer within the defined range.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction.

A "nucleic acid construct" or "DNA construct" refers to artificially constructed segments of nucleic acids. These constructs are generally intended to be transplanted or introduced into a target tissue or cell. Generally, such a construct contains a DNA insert with a gene sequence encoding a protein of interest.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With the term "induction of an immunoprotective response" or "conferring immunity" is meant a (humoral and/or cellular) immune response that reduces or eliminates one or more of the symptoms of disease, i.e. clinical signs, lesions, bacterial excretion and bacterial replication in tissues in the infected subject compared to a healthy control. Preferably said reduction in symptoms is statistically significant when compared to a control.

The terms "percent similarity", "percent identity" and "percent homology" when referring to a particular sequence are used as set forth in the University of Wisconsin GCG software program.

A "replicon" is any genetic element, for example, a plasmid, cosmid, bacmid, plastid, phage or virus that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" refers to a nucleic acid segment that may possess transcriptional and translational control sequences, such as promoters, enhancers, translational start signals (e.g., ATG or AUG codons), polyadenylation signals, terminators, and the like, and which facilitate the expression of a nucleic acid sequence in a host cell or organism.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

An "infectious DNA molecule", for purposes of the present invention, is a DNA molecule that encodes the necessary elements for viral replication, transcription, and translation into a functional virion in a suitable host cell.

The term "isolated" is used to indicate that a cell, peptide or nucleic acid is separated from its native environment. Isolated peptides and nucleic acids may be substantially pure, i.e. essentially free of other substances with which they may bound in nature.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

"Regulatory sequences" are segments of a nucleic acid molecule which controls expression of a gene. Regulatory sequences include, for example, promoters, terminators, enhancers, and ribosomal binding sites.

"Native" refers to a naturally occurring ("wild-type") nucleic acid sequence.

"Heterologous" sequence refers to a sequence which originates from a foreign source or species or, if from the same source, is modified from its original form.

As used herein, the term "endogenous," when used in reference to a polypeptide, nucleic acid or gene, refers to a polypeptide, nucleic acid or gene that is expressed by a host or already present within a host organism.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequences also refer to sense and antisense strands, and in all cases to the complement of any such strands. For purposes of the present invention, a polynucleotide molecule is useful in practicing the present invention, and is therefore homologous or has identity, where it can be used as a diagnostic probe to detect the presence of PEDV or other viral polynucleotide in a fluid or tissue sample of an infected animal, e.g. by standard hybridization or amplification techniques. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova T A and T L Madden, "BLAST 2 sequences—a new tool for comparing protein and nucleotide sequences." (1999) FEMS Microbiol Lett. 174:247-250.]. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 325 89:10915-10919.1992). The percent identity is then calculated as: Total number of identical matches×100/divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90% and 95% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tryptophan and phenylalanine.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 (or any other particular polynucleotide sequence) if it hybridizes to the complement of SEQ ID NO:1 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a PEDV virus as defined below. Modifications in hybridization conditions can be empirically determined or precisely calculated based on the length and percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

In another embodiment, a second nucleotide sequence is homologous to a target or reference sequence (of the invention) if it hybridizes to the complement of the target or reference sequence under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C., as is known in the art.

A "coding sequence" or "coding region" refers to a nucleic acid molecule having sequence information necessary to produce a gene product, when the sequence is expressed. A gene product is said to be "encoded" in DNA in three-nucleotide sequences called codons which are read to produce a functional protein.

In another embodiment, a second nucleotide sequence is homologous to SEQ ID NO: 1 (or any other sequence of the invention) if it hybridizes to the complement of SEQ ID NO: 1 under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C., as is known in the art.

"Mammals" include any warm-blooded vertebrates of the Mammalia class, including humans.

The term "ungulate" refers to any mammal with hooves including odd-toed ungulates such as horses and even-toed ungulates such as cattle and pigs. In the context of the present invention the term "ungulate" excludes cetaceans such as whales or dolphins.

The term "livestock" refers to domesticated animals raised for a commercial purpose, such as food, fiber and labor. Such animals may include cattle, swine, lambs, goats, poultry, and equine.

The terms "porcine" and "swine" are used interchangeably herein and refer to any animal that is a member of the family Suidae such as, for example, a pig.

A "susceptible" host as used herein refers to a cell or an animal that can be infected by a particular microbe or can develop a particular condition. When introduced to a susceptible animal, a viral vector according to the present invention may also induce an immunological response against the viral vector and one or more antigens encoded by the viral vector, and thereby provide the animal immunity against one or more microbes, prevent or treat infection, or prevent or treat a disease or condition.

An "antigen" is a molecule or substance that induces an immune response in an organism. Such immune response involves the production of antibodies that bind to the antigen. Antigens typically originate from the external environment of the organism, and are considered to be "foreign antigens." Alternatively, antigens may originate within the organism ("self-antigen"). Antigens may be, for example, peptides, polysaccharides, or lipids. Antigens may also include parts of bacteria, viruses, and microorganisms, such as coats, captures, cell walls, flagella, fimbrae, and toxins. The term "immunogenic fragment" and "antigenic determinant" as used herein are interchangeable, and refer to a polypeptide or a fragment of a polypeptide, or a nucleotide sequence encoding the same which comprises an allele-specific motif, an epitope or other sequence such that the polypeptide or the fragment will bind an MHC molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

The term "vaccine" refers to an antigenic preparation used to produce immunity to a disease, in order to prevent or ameliorate the effects of infection. Vaccines are typically prepared using a combination of an immunologically effective amount of an immunogen together with an adjuvant effective for enhancing the immune response of the vaccinated subject against the immunogen.

Vaccine formulations will contain a "therapeutically effective amount" of the active ingredient, that is, an amount capable of eliciting an induction of an immunoprotective response in a subject to which the composition is administered. In the prevention of infection and disease, for example, a "therapeutically effective amount" would preferably be an amount that enhances resistance of the vaccinated subject to new infection and/or reduces the clinical severity of the disease. Such protection will be demonstrated by either a reduction or lack of symptoms normally displayed by a subject infected with a particular microbe, a quicker recovery time and/or a lowered count of bacteria or virus particles. Vaccines can be administered prior to infection, as a preventative measure against a particular microbe, disease, or condition. Alternatively, vaccines can be administered after the subject already has contracted a disease. Vaccines given after exposure to a microbe or development of a disease or condition may be able to attenuate the disease, triggering a superior immune response than the natural infection itself.

A "pharmaceutically acceptable carrier" means any conventional pharmaceutically acceptable carrier, vehicle, or excipient that is used in the art for production and administration of vaccines. Pharmaceutically acceptable carriers are typically non-toxic, inert, solid or liquid carriers.

"Dose" and/or "administration" refers to a vaccine or immunogenic composition given to a subject. A "first administration" or "priming vaccine" refers to the dose of such a composition given on Day 0. A "second administration" or a "third administration" or an "annual administration" refers to an amount of such composition given subsequent to the first administration, which may or may not be the same vaccine or immunogenic composition as the first administration.

An "epitope" is the specific site of the antigen which binds to a T-cell receptor or specific antibody, and typically comprises from about 3 amino acid residues to about 20 amino acid residues.

"Excipient" refers to any component of a vaccine or immunogenic composition that is not an antigen.

"Fragment" refers to a truncated portion of a protein or gene. "Functional fragment" and "biologically active fragment" refer to a fragment that retains the biological properties of the full-length protein or gene. An "immunogenically active fragment" refers to a fragment that elicits an immune response.

The term "G protein", as used herein, refers to protein in the glycoprotein projections that cover the outer surface of a rabies virus.

The term "multiplicity of infection" (MOI) refers to a ratio of the number of organisms per cell, which details how much inoculum can be used in a given infection.

The terms "*parapoxvirus", "parapoxvirus* strains", as used herein, refer to viruses belonging to the family Poxyiridae and the genus *Parapoxvirus.*

The terms "*Parapoxvirus ovis*" and "*Parapoxvirus* ORFV", as used herein, refer to viruses belonging to the family Poxyiridae, the genus *Parapoxvirus*, and the species *Parapoxvirus ovis*. These viruses are also called ecthyma contagiosum virus, contagious pustular dermatitis virus, or orf virus. They possess a unique spiral coat that distinguishes them from the other poxviruses.

Virus and Vaccine Compositions

In one aspect, the present invention involves nucleotide construct for delivery of one or more antigens to target animals. Nucleotide constructs can be viruses, viral vectors, plasmids, and infectious DNA molecules. In a preferred embodiment, the vector is a viral vector, most preferably an ORFV-based recombinant viral vector. The term "viral vector" refers to a genetically modified virus used for the delivery of genes into an organism. The viral vectors carry the viral genome. The viral genome comprises the nucleotide sequence that includes one or more deletions of viral genes or open reading frames, and/or one or more heterologous polynucleotides encoding an antigen. An ORFV-based recombinant vector can be any virus or polynucleotide construct that is derived from parapoxvirus ORF virus. For example, the ORFV-based recombinant viral vector can be a recombinant ORFV virus with one or more attenuating gene deletions to ORFV113, ORFV118, ORFV119 or ORFV121. In another aspect, the ORFV-based recombinant viral vector can be a recombinant virus that is not an ORF virus, but incorporates at least part of the ORF virus genome. For example, the ORFV-based recombinant viral vector can be a poxviral vaccine vector, such as orthopoxvirus vaccinia virus (VACV), avipox viruses, fowlpox virus (FPV) and canarypox virus (CNPV), into which one or more polynucleotide sequences have been inserted corresponding to one or more attenuating gene deletions to ORFV002, ORFV024, ORFV073, ORFV113, ORFV118, ORFV119 or ORFV121.

In another aspect, a nucleotide construct of the present invention may be a plasmid. In another aspect, a nucleotide construct of the present invention may be an infectious DNA molecule. An "infectious DNA molecule" for purposes of the present invention is a DNA molecule that encodes the necessary elements for viral replication, transcription, and translation into a functional virion in a suitable host cell.

In a further aspect, the viral vectors of the present invention comprise modifications that confer enhanced safety, immunogenicity, and delivery capability in multiple animal species. In a further aspect, the viral vectors have been modified to enhance the delivery of foreign antigens to an animal subject. In one embodiment, the modification to the viral vector is achieved by including an adjuvant. Adjuvants may stimulate the immune system's response to the target antigen of a vaccine through various mechanisms. Adjuvants may include, for example, inorganic compounds (alum, aluminum phosphate), mineral oils, bacterial products, cytokines, and food based oils.

In a further aspect, the viral vectors of the present invention incorporate or include one or more antigens or antigenic determinants. The antigens or antigenic determinants can be derived from or associated with a specific microbe, disease, or condition. Preferred antigens are those associated with diseases common in livestock, for example, the antigen can be rabies virus glycoprotein G (RABV gG) or PEDV spike protein (PEDV-S). Viral vectors may incorporate two or more antigens to provide immunity against multiple antigens and conditions. The virus is utilized to carry the antigenic DNA into the cells of the animal being treated and the antigen is then expressed as protein once inside the animal and the animal's immune system produces antibodies to the antigen. The viruses utilized are typically live attenuated viruses that carry DNA encoding protein antigens from an unrelated organism. Such vaccines may be called "subunit vaccines" because they only use portions of antigens that best stimulate the immune system. Recombination subunit vaccines combine multiple portions of antigens to produce the most effective immune response.

In a further aspect, the viral vectors of the present invention may comprise a polynucleotide construct, at least a portion of which has a sequence that is at least 80% homologous, at least 85% homologous, at least 90% homologous, at least 95% homologous, or 100% homologous to SEQ ID NO:4 or SEQ ID NO:5.

The invention also relates to an immunogenic composition, suitable to be used as a vaccine, which comprises a variant ORFV strain according to the invention. The immunogenic compositions according to the invention elicit a specific humoral immune response toward the ORFV-vectored antigens comprising antibodies and including neutralizing antibodies.

The preferred immunogenic compositions based upon the variant strains disclosed herein can provide live, attenuated viruses which exhibit high immunogenicity while at the same time not producing dangerous pathogenic or lethal effects.

The immunogenic compositions of this invention are not, however, restricted to any particular type or method of preparation. These include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

The present invention preferably includes vaccine compositions comprising a live, attenuated ORFV-based viral vector of the invention and a pharmaceutically acceptable carrier. As used herein, the expression "live, attenuated ORFV-based viral vector of the invention" encompasses any live, attenuated ORFV strain that includes one or more of the variations described herein. The pharmaceutically acceptable carrier can be, e.g., water, a stabilizer, a preservative, culture medium, or a buffer. Vaccine formulations comprising the attenuated ORFV of the invention can be prepared in the form of a suspension or in a lyophilized form or, alternatively, in a frozen form. If frozen, glycerol or other similar agents may be added to enhance stability when frozen. The advantages of live attenuated vaccines, in general, include the presentation of all the relevant immunogenic determinants of an infectious agent in its natural form to the host's immune system, and the need for relatively small amounts of the immunizing agent due to the ability of the agent to multiply in the vaccinated host.

Attenuation of the virus for a live vaccine, so that it is insufficiently pathogenic to substantially harm the vaccinated target animal, may be accomplished by known procedures, including serial passaging. The following references provide various general methods for attenuation of coronaviruses, and are suitable for attenuation or further attenuation of any of the strains useful in the practice of the present invention: B. Neuman et al., Journal of Virology, vol. 79, No. 15, pp. 9665-9676, 2005; J. Netland et al., Virology, v 399(1), pp. 120-128, 2010; Y-P Huang et al., "Sequence changes of infectious bronchitis virus isolates in the 3' 7.3 kb of the genome after attenuating passage in embryonated eggs, Avian Pathology, v. 36 (1), (Abstract), 2007; and S. Hingley et al., Virology, v. 200(1) 1994, pp. 1-10; see U.S. Pat. No. 3,914,408; and Ortego et al., Virology, vol. 308 (1), pp. 13-22, 2003. In preferred embodiments, attenuation of the virus as described herein is achieved through targeted deletion/insertion using standard genome editing methods known in the field.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective responses in animals (e.g., proteins derived from ORFV002, ORFV024, ORFV073, ORFV113, ORFV118, ORFV119 or ORFV121, etc.). Various subtypes or isolates of the viral protein genes can be subjected to the DNA-shuffling method. The resulting heterogeneous chimeric viral proteins can be used broad protecting subunit vaccines. Alternatively, such chimeric viral genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product.

The nucleotide constructs of the present invention may further comprise one or more sequences encoding an antigen or antigenic determinant associated with infections, including infection by a virus or microbe, that is significant for livestock, such as, for example, porcine epidemic diarrhea virus (PEDV) and rabies virus. Diseases that can be treated or prevented using the present invention include, but are not limited to, foot-and-mouth disease (FMD), Ovine rinderpest (peste des petits ruminants; PPR), Rift Valley fever (RVF), rabies, EHD and BT virus infection, African horse sickness (AHS), African swine fever (ASF), Classical swine fever (hog cholera; CSF), Contagious bovine pleuropneumonia (CBPP), anthrax, East Coast fever and corridor disease, Newcastle disease, Trypanosomiasis (trypanosomosis), Bovine babesiosis, Heartwater, Bovine anaplasmosis, avian influenza, brucellosis, cattle fever tick, Chronic wasting disease, contagious equine metritis, Equine herpesvirus, Equine infectious anemia, Equine piroplasmosis, Equine viral arteritis, Johnes, New World screwworm, Piroplasmosis, Pseudorabies, Schmallenberg Virus, Porcine Reproductive and Respiratory Syndrome Virus, Porcine Circovirus, Senecavirus A, Swine Influenza, Tuberculosis, Brucellosis, Vesicular stomatitis, and West Nile virus.

If the clones retain any undesirable natural abilities of causing disease, it is also possible to pinpoint the nucleotide sequences in the viral genome responsible for any residual virulence, and genetically engineer the virus avirulent through, for example, site-directed homologous recombination. Homologous recombination is able to add, delete or change one or more nucleotides. An oligonucleotide is synthesized containing the desired mutation and co-transfected with the target ORFC virus into mammalian cells. The hybrid molecule, which results from that procedure, is selected by limiting dilutions or plaque assays. Then the recombinant virus, is isolated containing the appropriate mutation Vaccines of the present invention can be formulated following accepted convention to include acceptable carriers for animals, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention may further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, ionic polysaccharides, and Avridine lipid-amine adjuvant. Non-limiting examples of oil-in-water emulsions useful in the vaccine of the invention include modified SEAM62 and SEAM ½ formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM ½ is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines.

Additional adjuvant systems permit for the combination of both T-helper and B-cell epitopes, resulting in one or more types of covalent T-B epitope linked structures, with may be additionally lipidated, such as those described in WO2006/084319, WO2004/014957, and WO2004/014956.

Adjuvant Components

The vaccine compositions of the invention may or may not include adjuvants. In particular, as based on an infective virus, the modified live vaccines of the invention may be used adjuvant free, with a sterile carrier. Adjuvants that may be used for oral administration include those based on CT-like immune modulators (rmLT, CT-B, i.e. recombinant-mutant heat labile toxin of *E. coli*, Cholera toxin-B subunit); or via encapsulation with polymers and alginates, or with mucoadhesives such as chitosan, or via liposomes. A preferred adjuvanted or non adjuvanted vaccine dose at the minimal protective dose through vaccine release may provide between approximately 10 and approximately $10^6$ $log_{10}TCID_{50}$ of virus per dose, or higher. Adjuvants, if present, may be provided as emulsions, more commonly if non-oral administration is selected, but should not decrease starting titer by more than 0.7 logs (80% reduction).

In one example, adjuvant components are provided from a combination of lecithin in light mineral oil, and also an aluminum hydroxide component. Details concerning the composition and formulation of Amphigen® (as representative lecithin/mineral oil component) are as follows.

A preferred adjuvanted may be provided as a 2 ML dose in a buffered solution further comprising about 5% (v/v) Rehydragel® (aluminum hydroxide gel) and "20% Amphigen" ® at about 25% final (v/v). Amphigen® is generally described in U.S. Pat. No. 5,084,269 and provides de-oiled lecithin (preferably soy) dissolved in a light oil, which is then dispersed into an aqueous solution or suspension of the antigen as an oil-in-water emulsion. Amphigen has been improved according to the protocols of U.S. Pat. No. 6,814,971 (see columns 8-9 thereof) to provide a so-called "20% Amphigen" component for use in the final adjuvanted vaccine compositions of the present invention. Thus, a stock mixture of 10% lecithin and 90% carrier oil (DRAKEOL®, Penreco, Karns City, Pa.) is diluted 1:4 with 0.63% phosphate buffered saline solution, thereby reducing the lecithin and DRAKEOL components to 2% and 18% respectively (i.e. 20% of their original concentrations). Tween 80 and Span 80 surfactants are added to the composition, with representative and preferable final amounts being 5.6% (v/v) Tween 80 and 2.4% (v/v) Span 80, wherein the Span is originally provided in the stock DRAKEOL component, and the Tween is originally provided from the buffered saline component, so that mixture of the saline and DRAKEOL components results in the finally desired surfactant concentrations. Mixture of the DRAKEOL/lecithin and saline solutions can be accomplished using an In-Line Slim Emulsifier apparatus, model 405, Charles Ross and Son, Hauppauge, N.Y., USA.

The vaccine composition can also include Rehydragel® LV (about 2% aluminum hydroxide content in the stock material), as an additional adjuvant component (available from Reheis, N.J., USA, and ChemTrade Logistics, USA). With further dilution using 0.63% PBS, the final vaccine composition contains the following compositional amounts per 2 ML dose; 5% (v/v) Rehydragel® LV; 25% (v/v) of "20% Amphigen", i.e. it is further 4-fold diluted); and 0.01% (w/v) of merthiolate.

As is understood in the art, the order of addition of components can be varied to provide the equivalent final vaccine composition. For example, an appropriate dilution of virus in buffer can be prepared. An appropriate amount of Rehydragel® LV (about 2% aluminum hydroxide content) stock solution can then be added, with blending, in order to permit the desired 5% (v/v) concentration of Rehydragel® LV in the actual final product. Once prepared, this intermediate stock material is combined with an appropriate amount of "20% Amphigen" stock (as generally described above, and already containing necessary amounts of Tween 80 and Span 80) to again achieve a final product having 25% (v/v) of "20% Amphigen". An appropriate amount of 10% merthiolate can finally be added.

The vaccinate compositions of the invention permit variation in all of the ingredients, such that the total dose of antigen may be varied preferably by a factor of 100 (up or down) compared to the antigen dose stated above, and most preferably by a factor of 10 or less (up or down). Similarly, surfactant concentrations (whether Tween or Span) may be varied by up to a factor of 10, independently of each other, or they may be deleted entirely, with replacement by appropriate concentrations of similar materials, as is well understood in the art.

Rehydragel® concentrations in the final product may be varied, first by the use of equivalent materials available from many other manufacturers (i.e. Alhydrogel®, Brenntag; Denmark), or by use of additional variations in the Rehydragel® line of products such as CG, HPA or HS. Using LV as an example, final useful concentrations thereof including from 0% to 20%, with 2-12% being more preferred, and 4-8% being most preferred, similarly, the although the final concentration of Amphigen (expressed as % of "20% Amphigen") is preferably 25%, this amount may vary from 5-50%, preferably 20-30% and is most preferably about 24-26%.

According to the practice of the invention, the oil used in the adjuvant formulations of the instant invention is preferably a mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.), USB Corporation (Cleveland, Ohio). Preferred mineral oil is light mineral oil commercially available under the name DRAKEOL®.

Typically, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80 etc), if any such emulsifiers are present.

Non-natural, synthetic emulsifiers suitable for use in the adjuvant formulations of the present invention also include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate). Generally speaking, the emulsifier(s) may be present in the vaccine composition in an amount of 0.01% to 40% by volume, preferably, 0.1% to 15%, more preferably 2% to 10%.

In an alternative embodiment of the invention, the final vaccine composition contains SP-Oil® and Rehydragel® LV as adjuvants (or other Rehydragel® or Alhydrogel® products), with preferable amounts being about 5-20% SP-Oil (v/v) and about 5-15% Rehydragel LV (v/v), and with 5% and 12%, respectively, being most preferred amounts. In this regard it is understood that % Rehydragel refers to percent dilution from the stock commercial product. (SP-Oil® is a fluidized oil emulsion with includes a polyoxyethylene-polyoxypropylene block copolymer (Pluronic® L121, BASF Corporation, squalene, polyoxyethylene sorbitan monooleate (Tween®80, ICI Americas) and a buffered salt solution).

It should be noted that the present invention may also be successfully practiced using wherein the adjuvant component is only Amphigen®.

In another embodiment of the invention, the final vaccine composition contains TXO as an adjuvant; TXO is generally described in WO 2015/042369. All TXO compositions disclosed therein are useful in the preparation of vaccines of the invention. In TXO, the immunostimulatory oligonucleotide ("T"), preferably an ODN, preferably containing a palindromic sequence, and optionally with a modified backbone, is present in the amount of 0.1 to 5 ug per 50 ul of the vaccine composition (e.g., 0.5-3 ug per 50 ul of the composition, or more preferably 0.09-0.11 ug per 50 ul of the composition). A preferred species thereof is SEQ ID NO: 8 as listed (page 17) in the WO2015/042369 publication (PCT/US2014/056512). The polycationic carrier ("X") is present in the amount of 1-20 ug per 50 ul (e.g., 3-10 ug per 50 ul, or about 5 ug per 50 ul). Light mineral oil ("O") is also a component of the TXO adjuvant.

In certain embodiments, TXO adjuvants are prepared as follows:

(a) Sorbitan monooleate, MPL-A and cholesterol are dissolved in light mineral oil. The resulting oil solution is sterile filtered;

(b) The immunostimulatory oligonucleotide, Dextran DEAE and Polyoxyethylene (20) sorbitan monooleate are dissolved in aqueous phase, thus forming the aqueous solution; and (c) The aqueous solution is added to the oil solution under continuous homogenization thus forming the adjuvant formulation TXO.

All the adjuvant compositions of the invention can be used with any of the ORFV strains and isolates covered by the present Specification.

Additional adjuvants useful in the practice of the invention include Prezent-A (see generally United States published patent application US20070298053; and "QCDCRT" or "QCDC"-type adjuvants (see generally United States published patent application US20090324641.

Excipients

The immunogenic and vaccine compositions of the invention can further comprise pharmaceutically acceptable carriers, excipients and/or stabilizers (see e.g. Remington: The Science and practice of Pharmacy, 2005, Lippincott Williams), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as Mercury((o-carboxyphenyl)thio)ethyl sodium salt (THIOMERSAL), octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), TWEEN or PLURONICS.

Vaccines of the present invention can optionally be formulated for sustained release of the virus, infectious DNA molecule, plasmid, or viral vector of the present invention. Examples of such sustained release formulations include virus, infectious DNA molecule, plasmid, or viral vector in combination with composites of biocompatible polymers, such as, e.g., poly (lactic acid), poly (lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: Drugs and the Pharmaceutical Sciences, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. Nos. 3,137,631; 3,959,457; 4,205,060; 4,606,940; 4,744,933; 5,132,117; and International Patent Publication WO 95/28227, all of which are incorporated herein by reference.

The compositions of the present invention can further comprise liposomes, which can be used to provide for the sustained release of virus, plasmid, viral protein, or viral vector. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

Methods of Prevention

In another aspect, the present invention involves methods control and prevention of disease for animals in need thereof. In one embodiment, the methods involve administration of an effective amount of a nucleotide construct according to the present invention, to an animal.

An effective amount of any of the above-described vaccines can be determined by conventional means, starting with a low dose of virus, viral protein plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a veterinarian based on analysis of all relevant factors, some of which are described above. An immunologically effective amount of the vaccines of the present invention is administered to a pig in need of protection against viral infection. The immunologically effective amount or the immunogenic amount that inoculates the animal can be easily determined or readily titrated by routine testing. An effective amount is one in which a sufficient immunological response to the vaccine is attained to protect the animal exposed to the ORFV-based viral vector. Preferably, the animal is protected to an extent in which one to all of the adverse physiological symptoms or effects of the disease or conditions are significantly reduced, ameliorated or totally prevented.

The effective dose amount of virus, protein, infectious nucleotide molecule, plasmid, or viral vector of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ tissue culture infectious dose 50 ($TCID_{50}$), more preferably from about $10^2$ to about $10^8 TCID_{50}$, and most preferably from about $10^3$ to about $10^7 TCID_{50}$. The dose amount of a viral vector of the present invention in a vaccine of the present invention preferably ranges from about $10^1 TCID_{50}$ to about $10^9 TCID_{50}$, more preferably from about $10^2 TCID_{50}$ to about $10^8 TCID_{50}$, and even more preferably from about $10^3$ to about $10^7 TCID_{50}$. A suitable dosage size ranges from about 0.5 ml to about 10 ml, and more preferably from about 1 ml to about 5 ml. In one exemplary embodiment, the methods involve immunization of cattle with an immunogenic composition as described, at day 0 followed by a booster immunization at day 21 or day 30, wherein said immunization is by subcutaneous or intramuscular injection at a dose of $10^{7.8} TCID_{50}$, and wherein said immunogenic composition is ORFV-024- or ORFV-121 comprising one or more heterologous antigens suspended in cell culture medium.

In a further preferred example, the animal is vaccinated intramuscularly, subcutaneously or orally at 5-weeks pre-farrowing and then 2-weeks pre-farrowing. Under these conditions, a protective immune response can be demonstrated in vaccinated sows or cows in that they developed antibodies to one or more antigens encoded by the nucleotide construct (measured, for example, via fluorescent focal neutralization titer from serum samples) with neutralizing activity, and these antibodies were passively transferred to their piglets. The protocols of the invention are also applicable to the treatment of already seropositive sows and gilts, and also piglets and boars. Booster vaccinations can also be given and these may be via a different route of administration.

At least one vaccine or immunogenic composition of the present invention can be administered by any means that achieve the intended purpose, using a pharmaceutical composition as described herein. For example, route of administration of such a composition can be by parenteral, oral, oronasal, intranasal, intratracheal, topical, subcutaneous, intramuscular, transcutaneous, intradermal, intraperitoneal, intraocular, and intravenous administration. In one embodiment of the present invention, the composition is administered by intramuscularly. Parenteral administration can be by bolus injection or by gradual perfusion over time. Any suitable device may be used to administer the compositions, including syringes, droppers, needleless injection devices, patches, and the like. The route and device selected for use will depend on the composition of the adjuvant, the antigen, and the subject, and such are well known to the skilled artisan. Administration that is oral, or alternatively, subcutaneous, is preferred. Oral administration may be direct, via water, or via feed (solid or liquid feed). When provided in liquid form, the vaccine may be lyophilized with reconstitution, or provided as a paste, for direct addition to feed (mix in or top dress) or otherwise added to water or liquid feed.

In a further aspect, the treatment methods of the present invention involve administration of a viral vector for the prevention of one or more infections, diseases, or conditions. Such infections include infection by a virus or microbe that is significant for livestock, such as, for example, porcine epidemic diarrhea v is (PEDV) and rabies virus. Diseases that can be treated or prevented using the present invention include foot-and-mouth disease (FMD), Ovine rinderpest (peste des petits ruminants; PPR), Rift Valley fever (RVF), rabies, Bovine spongiform encephalopathy (BSE), EHD and BT virus infection, African horse sickness (AHS), African swine fever (ASF), Classical swine fever (hog cholera; CSF), Contagious bovine pleuropneumonia (CBPP), anthrax, East Coast fever and corridor disease, Trypanosomiasis (trypanosomosis), Bovine babesiosis, Heartwater, Bovine anaplasmosis, avian influenza, brucellosis, cattle fever tick, Chronic wasting disease, contagious equine metritis, Equine herpesvirus, Equine infectious anemia, Equine piroplasmosis, Equine viral arteritis, Johnes, New World screwworm, Piroplasmosis, Porcine Epidemic Diarrhea Virus, Pseudorabies, Schmallenberg Virus, Scrapie, Spring viremia carp, Swine Influenza, Tuberculosis, Brucellosis, Vesicular stomatitis, Porcine Reproductive and Respiratory Syndrome Virus (PRRSV), Porcine Circovirus 2, Senecavirus A and West Nile virus.

In a further aspect of the invention, the methods can be used for prevention of diseases, conditions, and infection in a variety of animals. In a further aspect, the methods can be used for prevention in livestock. Livestock to which the methods of the present invention can be applied include, for example, alpaca, bison, camel, cats, cattle, deer, dogs, donkeys, gayasl, goats, guinea pigs, horses, llamas, mules, pigs, rabbits, reindeer, sheep, water buffalo, yak, aquatic animals (i.e., fish, crustaceans, molluscs, and aquatic plants), chickens, turkeys, ducks, geese, elk, and moose. In a preferred embodiment, the livestock treated using the present methods are cattle or swine.

The compositions of the present invention described herein can be distinguished from Wild-type strains in both their genomic composition and proteins expressed. Such distinction allows for discrimination between vaccinated and infected animals. For example, a determination can be made as to whether an animal testing positive for parapoxvirus in certain laboratory tests carries a wild-type parapoxvirus strain, or carries a recombinantly produced parapoxvirus previously obtained through vaccination.

A variety of assays can be employed for making the determination. For example, virus can be isolated from the animal testing positive for *parapoxvirus*, and nucleic acid based assays can be used to determine the presence of a *parapoxvirus* genome, indicative of prior vaccination. The nucleic acid-based assays include Southern or Northern blot analysis, PCR, and sequencing. Alternatively, protein-based assays can be employed. In protein-based assays, cells or tissues suspected of an infection can be isolated from the animal testing positive for parapoxvirus. Cellular extracts can be made from such cells or tissues and can be subjected to, e.g., Western Blot, using appropriate antibodies against viral proteins that can distinctively identify the presence of either the recombinantly produced parapoxvirus previously inoculated, or Wild-type parapoxvirus.

Methods of Producing Nucleotide Constructs

In another aspect, the present invention involves methods of preparing a nucleotide construct of the present invention. The nucleotide construct may be a virus, a viral vector, a plasmid, or an infectious DNA molecule. In a preferred embodiment, the nucleotide construct is an ORFV-based viral vector. In one aspect, the nucleotide construct is modified by deletion of one or genes or open reading frames, for example ORFV002, ORFV024 ORFV073, ORFV113, ORFV118, ORFV119 or ORFV121. The ORV-based viral vector can be any of OV-IA82Δ002, OV-IA82Δ024, OV-IA82Δ073, OV-IA82Δ113, OV-IA82Δ118, OV-IA82Δ119, OV-IA82Δ121. Deletion of the one or more genes or open reading frames can be by any method known to a person of skill in the art, for example by homologous recombination or deletion by the CRIPSR/Cas9 system. The modified nucleotide construct thus comprises an insertion site, formed by the nucleotide sequences upstream and downstream of the deleted gene or open reading frame. In one aspect, feature, or improvement of the ORFV-based viral vectors provided herein is the use of wild-type/field strain, for example, ORFV(IA82) (GenBank Accession No. AY386263.1), and targeted attenuation through deletion/insertion to increase immunogenicity and safety of the vectorin contrast, tradition approaches have relied on passaging in cell culture in vitro which result in multiple genetic changes with non-specific, wide ranging gene-deletions, mutations and rearrangements to produce attenuation of the virus.

In a further aspect, the nucleotide construct is further modified to encode one or more antigens. Preferably, the one or more antigens are inserted into the insertion site, or insertion sites, formed by deletion of one or more genes or ORFs. The modification may be by insertion of one or more isolated, heterologous nucleotide sequences encoding an antigen, immunogenic fragment, or antigenic determinant into the construct. The polynucleotide sequence or sequences encoding the antigen or antigens may be placed at any of the deletion sites and downstream of a promoter. In one aspect, the heterologous polynucleotide sequences are operably linked to an endogenous promoter. In another aspect, the heterologous polynucleotide construct can be operably linked to a heterologous promoter, either from the same source as the heterologous polynucleotide, or a different source. Preferably, the promoter is the early-late VACV promoter VV7.5.

In a further aspect, the methods of the present invention involved selection of a nucleotide construct. Nucleotide constructs particularly suited for the present invention are suited for prevention of infections, diseases, or conditions in livestock. Such nucleotide constructs preferably are, or are derived from, viruses, viral vectors, plasmids, or infectious DNA molecules that cause disease in animals.

EXAMPLES

Example 1: ORFV Vector Expressing Rabies Virus Glycoprotein G RABV gG

Construction of ORFV Vector Candidates Expressing the Foreign Viral Antigen Rabies Virus Glycoprotein G (gG)

To assess expression and stability of viral antigens delivered by ORFV vector candidates, chimeric ORFV/RABV-G was generated by homologous recombination. The coding sequences of RABV gG were synthesized (GeneScript, Piscataway, N.J.; GenBank accession numbers AB110666 and ABD42929) and cloned into recombination plasmids containing deletions for the genes ORFV113, ORFV118, ORFV119, ORF024, and ORFV121. The RABV gG was cloned between ORFV113-, ORFV118-, ORFV119-, and ORFV024- and ORFV121-flanking genomic regions and downstream of the early-late VACV promoter VV7.5, which was optimized for high levels of poxviral gene expression.

Recombinant ORFV/RABV-gG vector candidates were obtained by homologous recombination between the available wild type strain of ORFV and the corresponding recombination plasmids. OFTu cells cultured in 6-well plates were infected with each gene-deletion mutant virus (MOI=1) and 3 hours later transfected with the recombination plasmids (2 μg) using Lipofectamine 2000. Seventy-two hours after infection/transfection, cultures were harvested, and cleared cell lysates used for selection of recombinant viruses by limiting dilution followed by real-time PCR. OFTu cells cultured in 96-well plates were infected with serial 10-fold dilutions of cell lysates from the infection/transfection and incubated at 37° C. for 3-5 days. Cells were subjected to three freeze-and-thaw cycles, total DNA was extracted using the ZR-96 Quick-gDNA™ kit (Zymo Research Corporation, Irvine, Calif.), and the presence of recombinant viruses was detected by real-time PCR using a PrimeTime® qPCR assay specific for the RABV gG (Integrated DNA Technologies, Inc., Coralville, Iowa). PCR positive wells, indicative of the presence of recombinant viruses were subjected to additional rounds of limiting dilution and real-time PCR screening.

Construction of ORFV-024-RabV-G and ORFV-121-RabV-G

The full-length coding sequence of the RabV glycoprotein strain BRbv39 (GenBank accession no. AB110666) was analyzed, and restriction endonuclease sites required for insertion into the ORFV genome (ORFV024 and ORFV121 loci) were removed through silent nucleotide substitutions. Coding sequences of the Flag-tag epitope (Flag) were added to the 3' ends of the G coding sequence. Additionally, EcoRI and NotII restriction sites were added to the 5' and 3' ends of the RabV-G construct, respectively. A single DNA fragment containing the full length RabV G-Flag coding sequences under the control of the VV.7.5 early/late poxviral promoter was chemically synthesized (Epoch Life Science, Inc, Missouri City, Tex.) and subcloned into the poxviral transfer vector pZippy-neo/gus (Ning et al., 2011) using EcoRI and NotI restriction enzymes (pZ-RabV-G).

To insert the RabV-G-Flag coding sequences into the ORFV024 and ORFV121 genome loci, recombination cassettes were constructed. ORFV024 left and right flanking regions were PCR amplified from the ORFV genome with primers 024LF-Fw(HindIII) (SEQ ID NO:6)-5'-TAAGGCCTCTAAGCTTAACCAGCAGACCTTCTT-CACCAA-3'; 024LF-Rv(SalI) (SEQ ID NO:7)-5'-CAGAATTCGCGTCGACCTTAGCTCTGTCTGAACTG-AAGCA-3'; 024RF-Fw(NotI) (SEQ ID NO:8)-5'-attct-tatGCGGCCGCgccggcttcatccgccgcagcata-3' and 024RF-Rv (BglII) (SEQ ID NO:9)-5'-CAGAATTCGCAGATCT-TACGGCGACACCGACTCCGTGTTC-3'. ORFV121 left and right flanking regions were PCR amplified from the ORFV genome with primers 121LF-Fw(SpeI) (SEQ ID NO:10)-5'-ATTCT-TATGCGGCCGCGCAGCACTGCTCGGAG-GAGTGCTC-3'; 121LF-Rv(HindIII) (SEQ ID NO:11)-5'-CAGAATTCGCAAGCTTGGTTGTGTGGGCCACAGA-GTTGAG-3'; 121RF-Fw(NotI) (SEQ ID NO:12)-5'-AT-TCTTATGCGGCCGCGGAGCACTGCTCGGAG-GAGTGCT-3'; and 121RF-Rv(BglII) (SEQ ID NO:13)-5'-CAGAATTCGCAGATCTATCATGCGCAGCGACGACAT-CATC-3'. Both ORFV024 and ORFV121 flanking regions were sequentially cloned into the vector pZ-RabV-G resulting in the recombination vectors pZ024-RabV-G and pZ121-RabV-G, respectively. Correct cloning of ORFV024 and ORFV121 LF and RF were confirmed by restriction enzyme analysis.

The full length RabV G coding sequences were inserted into the ORFV024 and ORFV121 locus within the ORFV genome by homologous recombination between a parental wild type ORFV and the recombination vectors pZ024-RabV-G and pZ121-RabV-G, respectively. OFTu cells cultured in 6-well plated were infected with ORFV (MOI=1) and 3 h later transfected with 2 μg of pZ024-RabV-G or pZ121-RabV-G DNA using Lipofectamine 3000 (Life Technologies) according to the manufacturer's instructions. At 72 h post-infection/transfection cell cultures were harvested, subjected to three freeze-and-thaw cycles and cell lysates used for recombinant virus selection by limiting dilution followed by real-time PCR selection. OFTu cells cultured in 96-well plates were infected with 10-fold serial dilutions of the cell lysates ($10^{-1}$ to $10^{-3}$), incubated at 37° C. for 72 h, total DNA was extracted from screened by real-time PCR using a TaqMan assay specific for RabV-G (PrimeTime® qPCR Assays, IDT). qPCR positive wells were harvested and subjected to several additional rounds of limiting dilution. qPCR positive wells from the limiting dilution were subjected to plaque purification. OFTu cells cultured in 6-well plates were infected with 10-fold serial dilutions ($10^{-1}$ to $10^{-3}$) of cell lysates from limiting dilution qPCR positive wells and overlaid with culture medium containing 0.5% agarose (SeaKem GTC agarose, Lonza Inc., Alpharetta, Ga.). Plaques were picked and screened by qPCR. The presence of PEDV-S and absence of ORFV121 sequences in the purified recombinant virus were confirmed by PCR screening. PCR amplicons were analyzed by electrophoresis in 1% agarose gels. Insertion and integrity of the RabV-G sequences were confirmed by whole genome sequencing using the Nextera XT DNA library preparation kit (Illumina, San Diego, Calif.) followed by sequencing on the Illumina Mi-Seq sequencing platform (Illumina, San Diego, Calif.).

Characterization of ORFV/RABV-gG Recombinant Viruses

ORFV-based recombinant viruses ORFV-024-Rabv-G and ORFV-121-RabVgG were subjected to DNA sequencing to confirm the integrity of the regions involved in the recombination process. DNA was extracted from cultures of ovine fetal turbinate cells (OFTu) infected with each recombinant virus using the GeneJET Viral DNA/RNA Purification Kit (Thermo Fisher Scientific) and the complete genome sequences of the recombinant viruses were sequenced using the Illumina MySeq sequencing platform.

Replication characteristics of ORFV/RABV-gG recombinant viruses were assessed in vitro and their ability to replicate in cell lines derived from target animal species was investigated. Multi- (MOI=0.1) and single-step (MOI=10) growth curves were performed in BT (bovine), #D (equine) and PK15 (porcine) cell lines. Briefly, cells were infected with recombinant ORFV/RABV-gG or parental viruses and harvested at different time points post-infection (pi; 0, 6, 12, 24, 48, and 72 hours). Primary OFTu cells were used as controls. Viral titers were determined by limiting dilution, calculated according to the method of Spearman and Karber, and expressed as log 10 $TCID_{50}$/ml.

Assessing the Expression of RABV gG by ORFV Recombinant Viruses

Expression of RABV gG by ORFV/RABV-gG recombinant viruses was assessed by immunofluorescence (IFA) and western blots (WB). OFTu cell cultures were infected with ORFV/RABV-gG recombinant viruses (MOI=5) and expression of RABV gG was determined at different time points pi. Primary OFTu cells were used as controls. For the IFA, cells were fixed at 0, 4, 6, 8, 12 and 24 h pi and stained using an anti-flag tag antibody followed by incubation with an Alexa-594-conjugated secondary antibody. For WB, infected cells were harvested on the time points indicated above and lysed with M-PER mammalian protein extraction reagent (Thermo Scientific, Whatman, Mass.) containing protease inhibitors. Protein extracts (30 μg) were resolved by SDS-PAGE in 10% acrylamide gels and blotted on nitrocellulose membranes. Blots were incubated with antibodies against flag-tag followed by incubation with an HRP-conjugated secondary antibody against mouse (sc-2005; Santa Cruz, Dallas, Tex.) and developed with a chemiluminescent substrate (ECL, Pierece-Thermo Scientific).

Determining the Stability of RABV gG Gene in ORFV Recombinant Viruses In Vitro

The stability of the RABV gG open reading frame in the genome of recombinant ORFV/RABV-gG viruses was assessed in vitro. Recombinant viruses containing the RABV gG gene were subjected to ten passages (p 10) in primary ovine cells (OFTu). Expression of the RabV gG was assessed by IFA at passages p 1, p 5 and p 10 as described above to access stability of RABV gG expression.

Evaluation of Immunogenicity of ORFV Vector Candidates in Target Animal Species

The immune response elicited by immunization with different ORFV/RABV-gG recombinant vectors was investigated in vivo. Immunization experiments with candidate vectors were performed in cattle, horses and swine. Rabies virus neutralizing antibody (RVNA)-negative animals of each species (n=12) were randomly allocated to four groups (G1: ORFV-024-RabV-G; and G2: ORFV-121-RabV-G) and immunized by intramuscular administration of 1 ml of virus suspensions containing $10^7 TCID_{50}$/ml (route and dose used in preliminary data). Animals were monitored daily for two weeks after vaccine administration. Clinical monitoring was based on visual inspection of the injection site. Serum samples were obtained on days 0, 21 and 42 post-immunization, processed for serological tests, and stored at −20° C.

Assessing Humoral Immune Responses Elicited Against RABV gG Following Immunization with Different ORFV Vector Candidates The RFFIT is the diagnostic standard for determining levels of rabies virus neutralizing antibody (RVNA). Serum samples harvested on days 0, 21, and 42 post-immunization were subjected to heat inactivation for 30 min at 56° C. and tested in triplicate using the RFFIT as previously described[37]. Briefly, five-fold serial dilutions of sera were incubated with 100 $TCID_{50}$ of the RABV strain CVS-11 for 90 min at 37° C. After incubation, BHK-21 cells were added to the wells containing serum/virus mixtures and incubated at 37° C. with 5% $CO_2$ for 24 h. Cells were fixed for 15 min in ice-cold acetone followed by incubation with an FITC-conjugated anti-rabies antibody (Fujirebio Diagnostics, Malvern, Pa.). Twenty fields of each dilution were examined by fluorescence microscopy and the number of fluorescent foci recorded. The RVNA titer was considered the reciprocal of the highest serum dilution able to prevent infection in 50% of the fields examined. The RVNA titers were transformed to international units per milliliter of serum (IU/ml) by calibrating to the RVNA titer of the standard serum sample (US Standard Immune Globulin), which was determined in parallel on each RFFIT.

Assessing Cellular Immune Responses Elicited Against RABV gG Following Immunization with Different ORFV Vector Candidates The frequency of RABV gG-specific IFN-γ-secreting cells in peripheral blood mononuclear cells (PBMCs) was determined by an IFN-γ ELISPOT. PBMCs isolated by density-gradient centrifugation from whole blood samples harvested on days 0, 21 and 35 post-immunization were tested for IFN-γ production by commercial ELISPOT kits specific for bovine- (Mabtech Inc., Mereimount, Ohio), equine- (R&D Systems, Minneapolis, Minn.) or swine-IFN-γ (R&D Systems). Approximately $5\times10^5$PBMCs were seeded in triplicate in the ELISPOT plates and incubated with 1 μg (in PBS) of recombinant RABV gG (MyBiosource Inc., San Diego, Calif.) for 24 h at 37° C. with 5% $CO_2$.

Negative controls (stimulated with PBS) were included in all assays. Cells secreting IFN-γ were detected with antibodies against bovine, equine or swine IFN-γ followed by incubation with an AP-conjugated secondary antibody. Foci of cells secreting IFN-γ were visualized by addition of the substrate BICP/NBT and the number of cells secreting IFN-γ were expressed as the difference between the number of foci per $10^6$ cells in cultures stimulated with RABV gG and the number of foci per $10^6$ cells in negative control cultures (PBS-stimulated).

Results

The prime-booster immunization strategy induced a robust immune response against the RabV G antigen in both swine and cattle. The prime-booster immunization strategy also induced immune responses in horses. Immunization by either SC or IM both resulted in similar immune responses in cattle. Overall, insertion of RabV-G in locus 121 of ORFV resulted in more robust NA antibody responses in pigs and cattle.

Expression RabV-G

Figure 2:
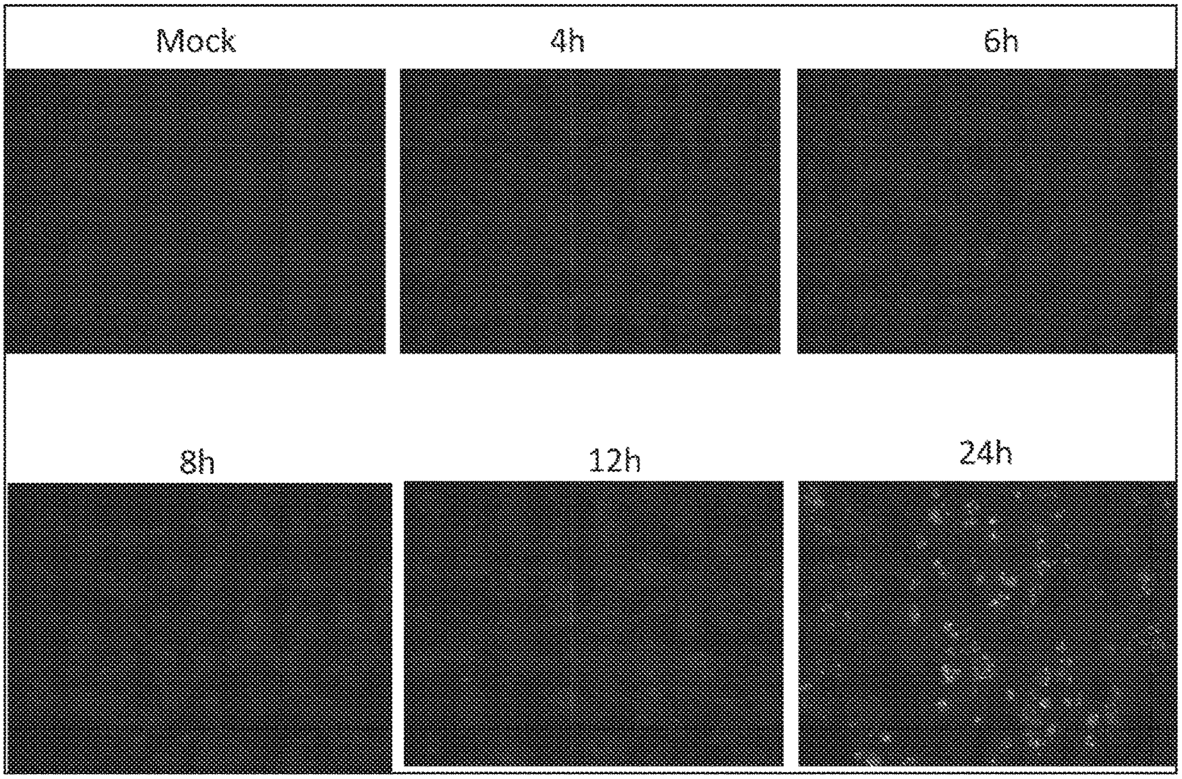
FIG. 2 shows expression of rabies virus G protein (RABV-G) in cells exposed to nucleotide constructs of the present invention. ORFV was modified to delete the ORF121 gene, creating an insertion site into which a polynucleotide encoding RABV-G was inserted (ORFV-121RabV-G), according to an exemplary embodiment of the invention. Expression of RabV-G in Ovine fetal turbinate (OFTu) cells exposed to ORFV-121RabV-G (MOI=10) was assessed by immunofluorescence microscopy, using anti-flag primary antibody and anti-mouse secondary antibody conjugated to Alexa 594. Expression was assessed at 4, 6, 8, 12, and 24 hours following exposure to virus, compared to mock exposure.
Figure 3:
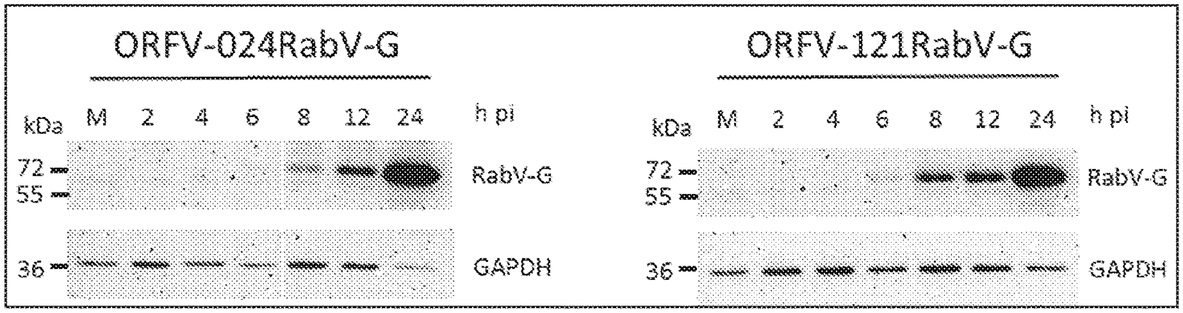
FIG. 3 shows expression of rabies virus G protein (RABV-G) in cells exposed to nucleotide constructs of the present invention. ORFV was modified to delete the ORFV024 and ORF121 genes, creating insertion sites into which a polynucleotide encoding RABV-G was inserted (ORFV-024RabV-G and ORFV-121RabV-G, respectively), according to an exemplary embodiment of the invention. Expression of RabV-G in Ovine fetal turbinate (OFTu) cells exposed to recombinant virus (MOI=10) was assessed by immunoblot, using anti-flag primary antibody and anti-mouse secondary antibody conjugated to horse radish peroxidase (HRP). Expression was assessed at 4, 6, 8, 12, and 24 hours following exposure to virus, compared to mock exposure (M).

FIGS. 1 and 2 shows expression of rabies virus G protein (RABV-G) in cells exposed to nucleotide constructs of the present invention. ORFV was modified to delete the either the ORF24 or ORF121 gene, creating an insertion site into which a polynucleotide encoding RABV-G was inserted (ORFV-024RabV-G and ORFV-121RabV-G, respectively). Ovine fetal turbinate (OFTu) cells were then exposed to the recombinant viruses, and RabV-G expression was assessed by immunofluorescence microscopy at 4, 6, 8, 12, and 24 post-exposure, using anti-flag primary antibody and anti-mouse secondary antibody conjugated to Alexa 594. Expression of RabV-G was confirmed by immunoblot analysis (FIG. 3).

These data demonstrate that the recombinant viruses effectively encode and express heterologous antigens that have been inserted into insertion sites created by deleting one or more open reading frames or genes.

Replication of Recombinant Virus

Figure 4:
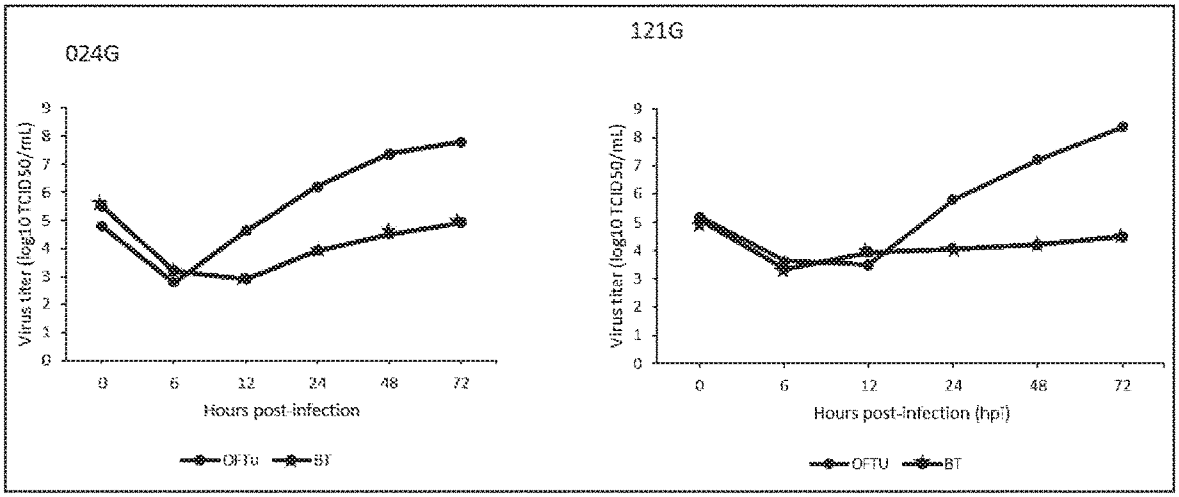
FIG. 4 shows replication kinetics of recombinant ORFV according to an exemplary embodiment of the present invention in primary cells. ORFV was modified to delete the ORFV024 and ORF121 genes, creating insertion sites into which a polynucleotide encoding RABV-G was inserted (ORFV-024RabV-G and ORFV-121RabV-G, respectively), according to an exemplary embodiment of the invention. Replication of recombinant virus in Ovine fetal turbinate (OFTu) and bovine turbinate (BT) cells was assessed at 0, 6, 12, 24, 48, and 72 hours post-infection.
Figure 5:
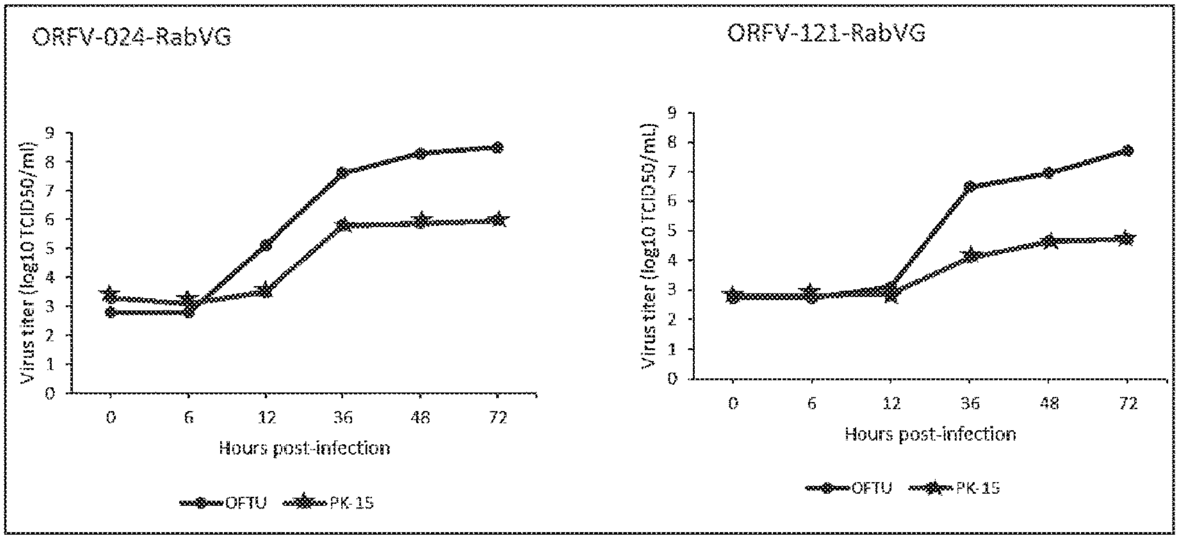
FIG. 5 shows replication kinetics of recombinant ORFV according to an exemplary embodiment of the present invention in primary cells. ORFV was modified to delete the ORFV024 and ORF121 genes, creating insertion sites into which a polynucleotide encoding RABV-G was inserted (ORFV-024RabV-G and ORFV-121RabV-G, respectively), according to an exemplary embodiment of the invention. Replication of recombinant virus in Ovine fetal turbinate (OFTu) and porcine (PK-15) cells was assessed at 0, 6, 12, 24, 48, and 72 hours post-infection.
Figures 6, 7:
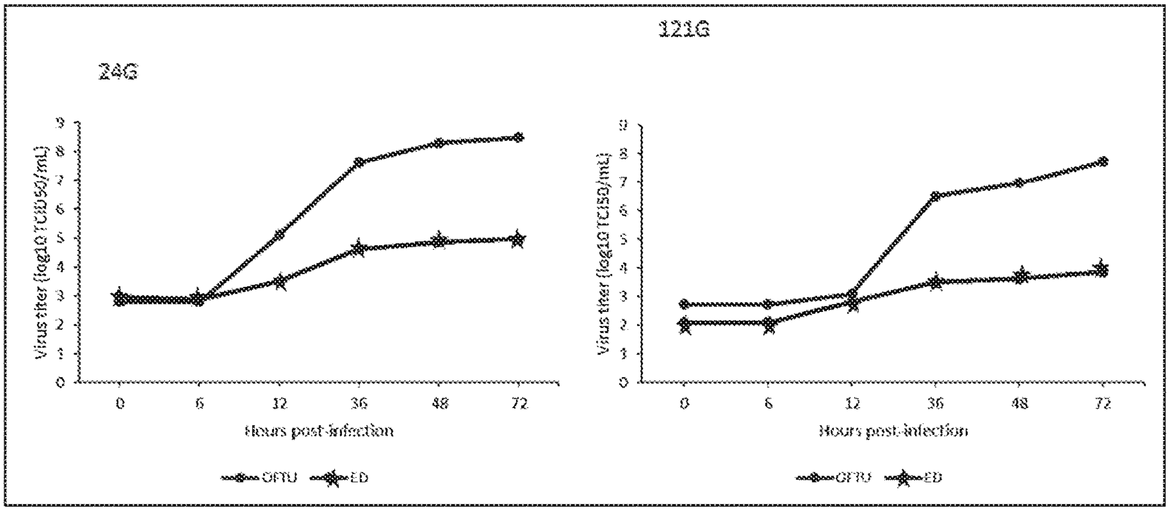
FIG. 6 shows replication kinetics of recombinant ORFV according to an exemplary embodiment of the present invention in primary cells. ORFV was modified to delete the ORFV024 and ORF121 genes, creating insertion sites into which a polynucleotide encoding RABV-G was inserted (ORFV-024RabV-G and ORFV-121RabV-G, respectively), according to an exemplary embodiment of the invention. Replication of recombinant virus in Ovine fetal turbinate (OFTu) and equine (ED) cells was assessed at 0, 6, 12, 24, 48, and 72 hours post-infection.
FIG. 7 shows immunogenicity of recombinant ORFV according to an exemplary embodiment of the present invention in cattle. Cattle were immunized with ORFV-024RabV-G or ORFV-121RabV-G on day 0, and immunized with the same recombinant virus again on day 21. Inoculation was either subcutaneous (SC) or intramuscular (IM) Blood and serum was collected from animals on days 0, 21, and 42, and rabies virus-specific antibody titers were determined.

ORFV-024RabV-G and ORFV-121RabV-G recombinant viruses were assessed for their ability to replicate in primary ovine and bovine cells. Ovine fetal turbinate cells (OFTu) and bovine turbinates (BT) primary cells were infected with ORFV-024RabV-G and ORFV-121RabV-G. As shown in FIG. 4, both of the recombinant viruses replicated in both ovine and bovine cells. Replication was also assessed in porcine PK-15 cells, compared to OFTu cells, showing good replication of both recombinant viruses in both cell types (FIG. 5). Further, replication was assessed in equine ED cells, compared to OFTu cells, again showing good replication of both recombinant viruses in both cell types (FIG. 6).

These data demonstrate that the ORFV-based viral vectors of the present invention effectively replicate in a variety of relevant animal cell types.

Immunogenicity of Candidate Vectors in Target Species

Figures 9, 10:
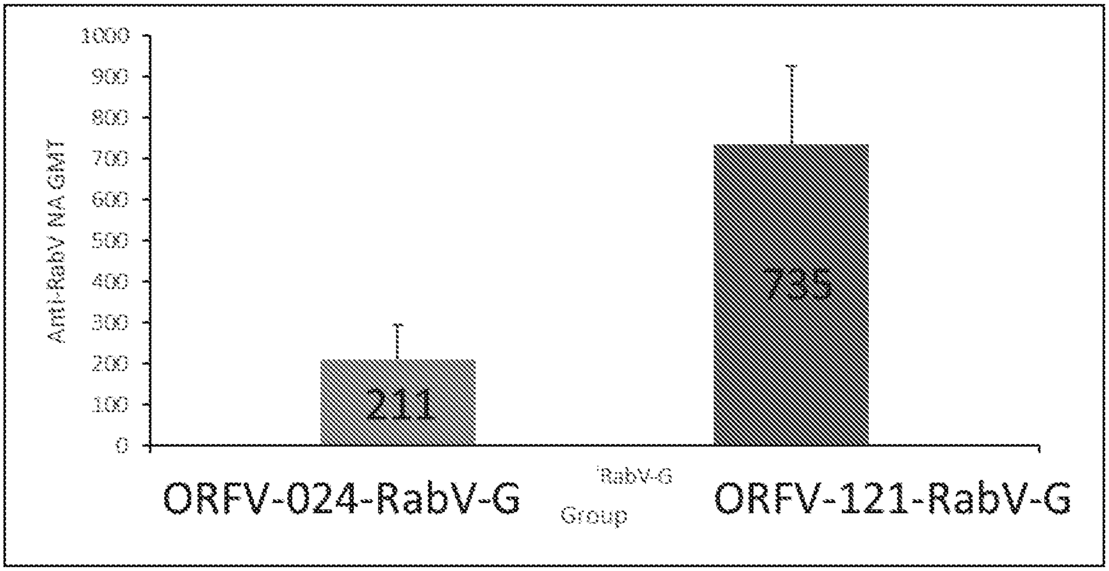
FIG. 9 shows immunogenicity of recombinant ORFV according to an exemplary embodiment of the present invention in cattle as the geometric mean neutralizing antibody titers against RabV determined from the results of FIGS. 7 and 8
FIG. 10 shows immunogenicity of recombinant ORFV according to an exemplary embodiment of the present invention in horses. Horses were immunized with ORFV-024RabV-G or ORFV-121RabV-G on day 0, and immunized with the same recombinant virus again on day 21. Inoculation was either subcutaneous (SC) or intramuscular (IM) Blood and serum was collected from animals on days 0, 21, and 42, and rabies virus-specific antibody titers were determined.
Figure 11:
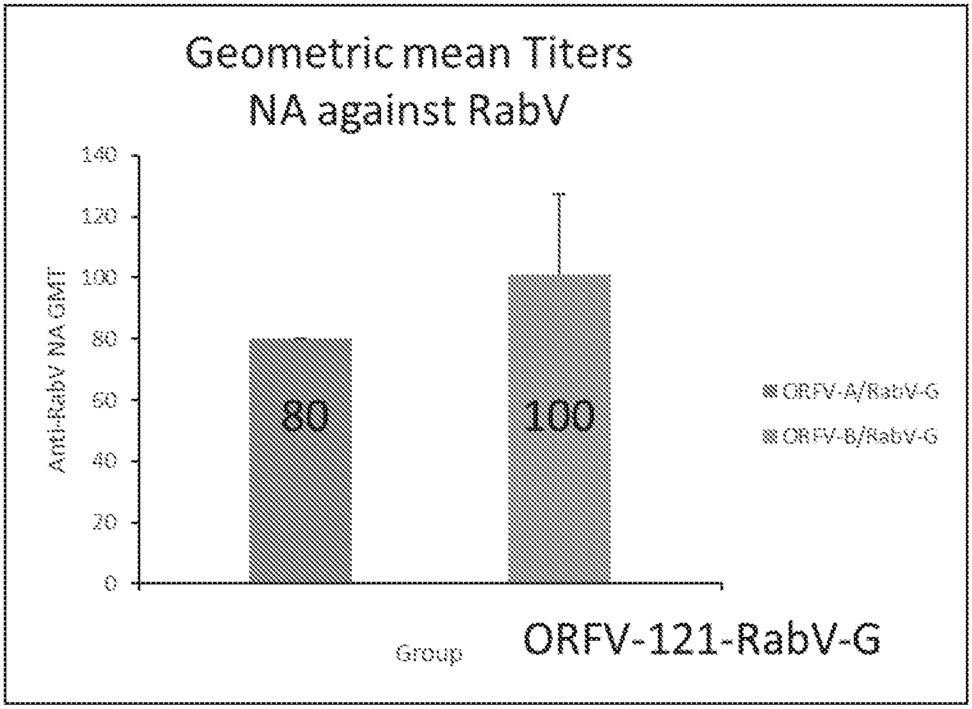
FIG. 11 shows immunogenicity of recombinant ORFV according to an exemplary embodiment of the present invention in cattle as the geometric mean neutralizing antibody titers against RabV determined from the results of FIG. 10.
Figures 12, 13:
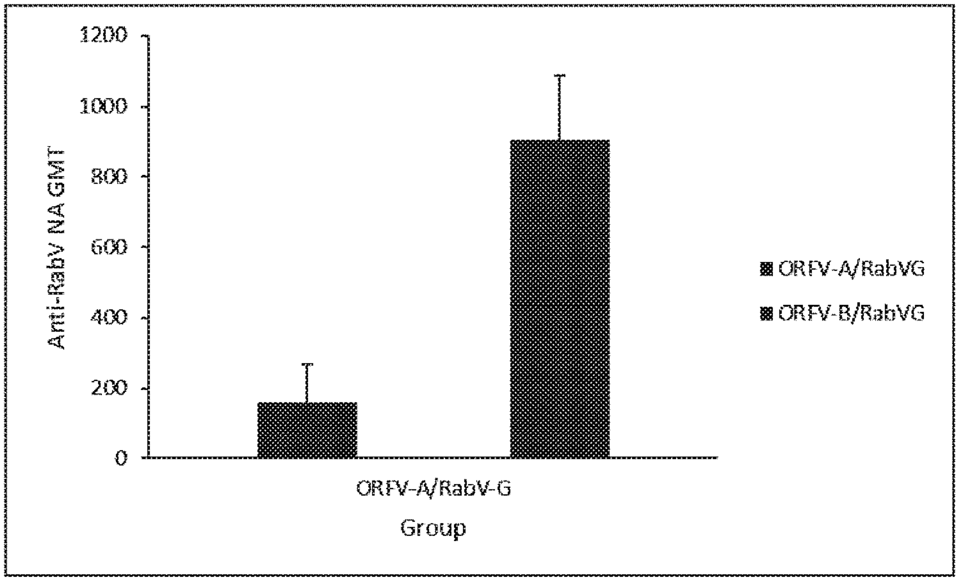
FIG. 12 shows immunogenicity of recombinant ORFV according to an exemplary embodiment of the present invention in pigs. Pigs were immunized with ORFV-024RabV-G or ORFV-121RabV-G on day 0, and immunized with the same recombinant virus again on day 21. Inoculation was either subcutaneous (SC) or intramuscular (IM) Blood and serum was collected from animals on days 0, 21, and 42, and rabies virus-specific antibody titers were determined.
FIG. 13 shows immunogenicity of recombinant ORFV according to an exemplary embodiment of the present invention in cattle as the geometric mean neutralizing antibody titers against RabV determined from the results of FIG. 12.
Figure 14A:
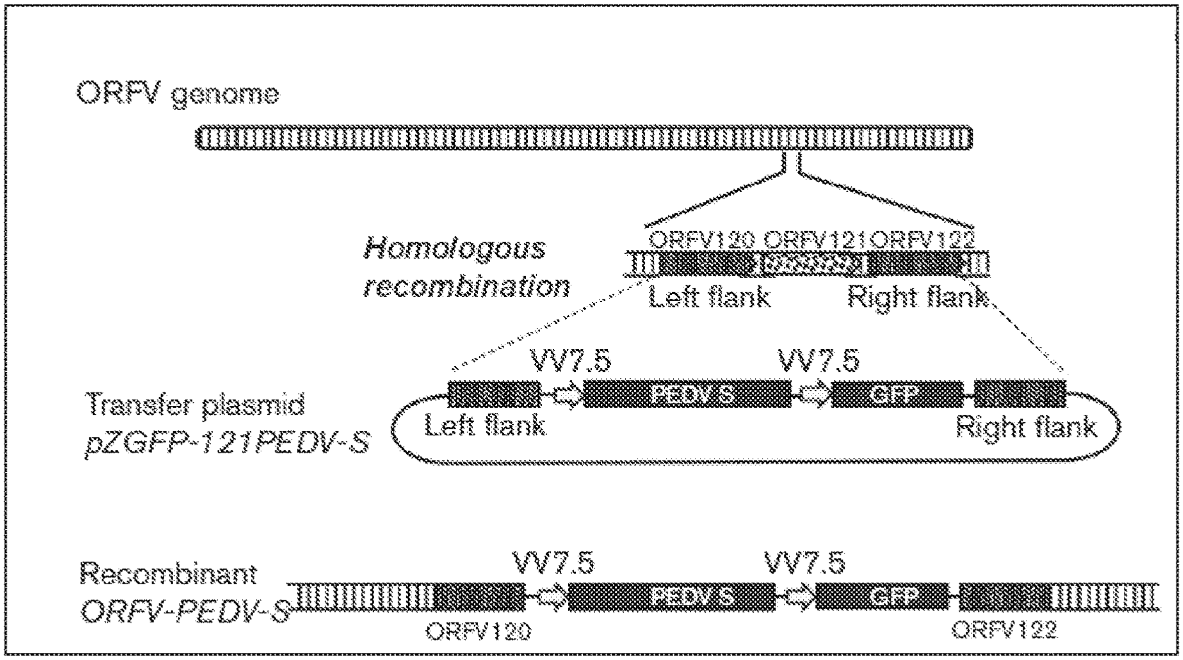
FIG. 14 (A-D) shows Generation of recombinant ORFV-PEDV-S virus. (a) Schematic representation of the ORFV genome depicting ORFV121 insertion site and flanking regions (ORFV120 and ORFV122) used to generate the recombinant ORFV-PEDV-S virus. pZGFP-121PEDV-S transfer plasmid containing the full-length PEDV S gene plus the GFP selection reporter under the control of individual early/late VV7.5 poxviral promoters. Recombinant ORFV-PEDV-S genome depicting insertion of the PEDV S and the GFP reporter gene into the ORFV121 gene locus.
(FIG. 14B) Agarose gel (1%) demonstrating PCR amplification of an internal region of the S gene (~150 bp) from the genome of the recombinant ORFV-PEDV-S gene and absence of ORFV121 gene sequences in the recombinant ORFV-PEDV-S virus. Wild-type ORFV DNA was used as a negative and positive control on the PCR amplifications with S- and ORFV121-specific primers, respectively.
(FIG. 14C) IFA demonstrating expression of PEDV S in cell cultures infected with the recombinant ORFV-PEDV-S virus. Left panel shows expression of the reporter GFP protein by the recombinant virus. Right panel shows expression of PEDV S detected with a mouse mAb against PEDV S.
(FIG. 14D) Western blot demonstrating expression of the full-length PEDV S (~150 kDa) by the recombinant ORFV-PEDV-S virus in cell culture in vitro. Cell lysates from cells infected with wild-type ORFV were used as negative controls. Blot was developed with an anti-His tag mAb.
Figure 14B:
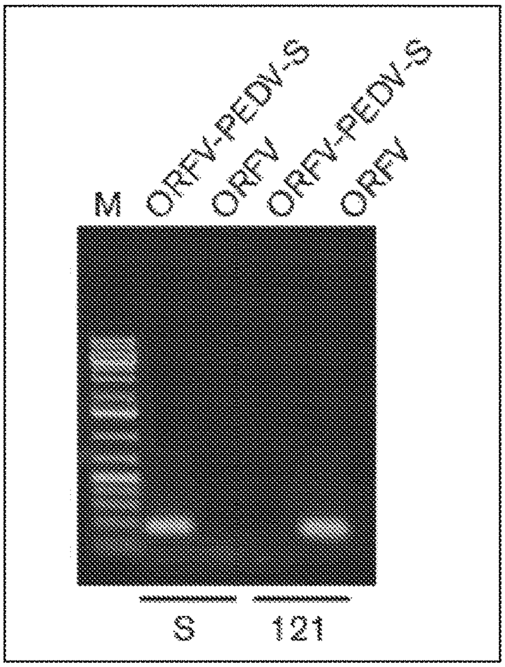
Figure 14C:
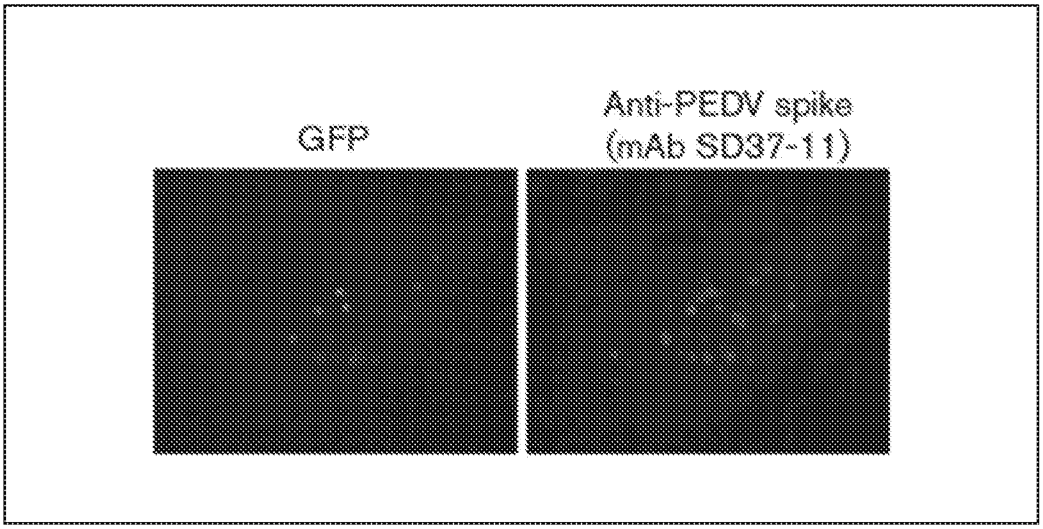
Figure 14D:
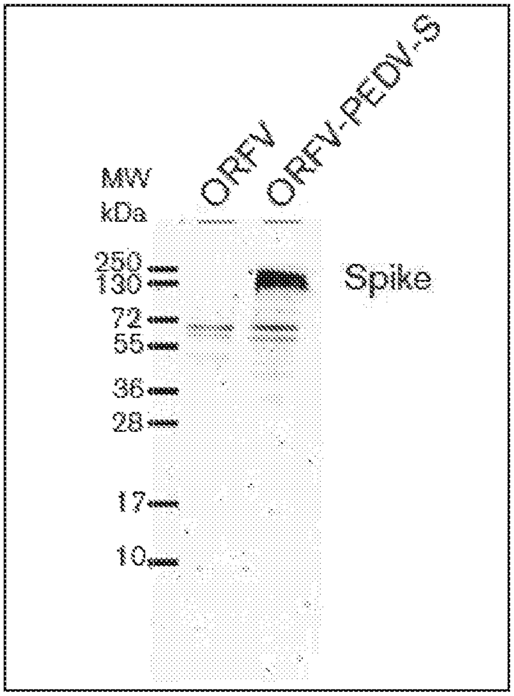

ORFV-024RabV-G and ORFV-121RabV-G recombinant viruses were assessed for their immunogenicity in several different model livestock animals. Cattle, pigs, and horses were immunized with ORFV-024RabV-G or ORFV-121RabV-G on day 0, and immunized with the same recombinant virus again on day 21. Inoculation was either subcutaneous (SC) or intramuscular (IM) Blood and serum was collected from animals on days 0, 21, and 42, and rabies virus-specific antibody titers were determined. As shown in FIG. 7-9, neutralizing antibody titers against RabV increased significantly in cattle following immunization with the ORFV-based viral vectors. Horses (FIGS. 10-11) and pigs (FIGS. 12-13) also exhibited significant immune response to the heterologous antigens expressed by the recombinant viruses.

Summary

These results demonstrate that the nucleotide constructs of the present invention effectively encode and express heterologous antigens that can induce an immune response for prevention of diseases or conditions in animals. A prime-booster immunization strategy induced robust immune responses against a model heterologous antigen encoded by the nucleotide constructs of the present invention. The immune response produced protective anti-RabV antibody titers (0.5 IU/mL=titers of ~1:50). Further Prime-booster immunization strategy induced immune responses in horses. Immunization by both SC and IM routes resulted in similar immune responses in cattle. Insertion of RabV-G in locus 121 seems to induce more robust neutralizing antibody (NA) responses in pigs and cattle. These results provide support that not all insertions sites in the ORFV genome result in equal immune responses in hosts. Endogenous ORF024 and ORF121 both encode immunomodulatory proteins that inhibit activation of NF□□ signaling pathway, thus aid in the regulation host immune responses. Therefore, it is unexpected that insertion of the same antigen (RabV-G) into ORF024 and ORF121 and immunization of cattle and pigs shows that insertion in the ORF121 site results in significantly higher immune responses.

Example 2: Recombinant ORFV-Based Vaccine Delivery Platform for Porcine Epidemic Diarrhea (PEDV) Expressing PEDV Spike Protein Construction of ORFV-PEDV-S The full-length coding sequence of the spike gene of PEDV strain CO13 (GenBank accession no. KF267450) was analyzed, and restriction endonuclease sites required for insertion into the ORFV genome (ORFV121 locus) were removed through silent nucleotide substitutions. In addition, early poxviral transcription termination signals (TTTTTNT) present within the coding sequence of PEDV S were removed by silent nucleotide mutations. Coding sequences of the His-tag epitope (6×His) were added to the 5' and 3' ends of the S coding sequence. The sequence of the VV.7.5 early/late poxviral promoter was added to the 5' end of the PEDV S coding sequence. Additionally, HindIII and SalI restriction sites were added to the 5' and 3' ends of the VV7.5-PEDV-S construct, respectively. A single DNA fragment containing the full length PEDV S coding sequences under the control of the VV.7.5 early/late poxviral promoter was chemically synthesized (GenScript®, Piscataway, N.J.) and subcloned into the poxviral transfer vector pZippy-EGFP (Ning et al., 2011) using HindIII and SalI restriction enzymes (pZGFP-PEDV-S).

To insert the PEDV-S coding sequences into the ORFV121 genome locus, an ORFV virulence determinant that inhibits the nuclear factor-kappa B(NF-κB) signaling pathway (Diel et al., 2011), a recombination cassette was constructed. ORFV121 left (LF, 1016 bp) and right (RF, 853 bp) flanking regions were PCR amplified from the ORFV genome with primers 121LF-Fw(SpeI) (SEQ ID NO:14)-5'-ATTCTTATGCGGCCGCGCAGCACTGCTCGGAG-GAGTGCTC-3'; 121LF-Rv(HindIII) (SEQ ID NO:15)-5'-CAGAATTCGCAAGCTTGGTTGTGTGGGCCACAGA-GTTGAG-3'; 121RF-Fw(NotI) (SEQ ID NO:16)-5'-AT-TCTTATGCGGCCGCGGAGCACTGCTCGGAG-GAGTGCT-3'; and 121RF-Rv(BglII) (SEQ ID NO:17)-5'-CAGAATTCGCAGATCTATCATGCGCAGCGACGACA- TCATC-3' and cloned into the vector pZGFP-PEDV-S resulting in the recombination vector pZGFP-121PEDV-S. Correct cloning of ORFV121 LF and RF and of PEDV-S were confirmed by restriction enzyme analysis.

The full length PEDV Spike coding sequences were inserted into the ORFV121 locus within the ORFV genome by homologous recombination between a parental wild type ORFV and the recombination cassette pZGFP-121PEDV-S. OFTu cells cultured in 6-well plated were infected with ORFV (MOI=1) and 3 h later transfected with 2 μg of pZGFP-121PEDV-S DNA using Lipofectamine 3000 (Life Technologies) according to the manufacturer's instructions. At 72 h post-infection/transfection cell cultures were harvested, subjected to three freeze-and-thaw cycles and cell lysates used for recombinant virus selection by limiting dilution followed by plaque assay. OFTu cells cultured in 96-well plates were infected with 10-fold serial dilutions of the cell lysates ($10^{-1}$ to $10^{-3}$), incubated at 37° C. for 72 h, and screened under a fluorescence microscope. Wells containing viral foci expressing the green fluorescent protein (GFP) were harvested and subjected to one additional round of limiting dilution. GFP positive wells from the second limiting dilution were subjected to plaque purification. OFTu cells cultured in 6-well plates were infected with 10-fold serial dilutions ($10^{-1}$ to $10^{-3}$) of cell lysates from limiting dilution GFP positive wells and overlaid with culture medium containing 0.5% agarose (SeaKem GTC agarose, Lonza Inc., Alpharetta, Ga.). Fluorescent plaques were subjected to five additional rounds of plaque purification. The presence of PEDV-S and absence of ORFV121 sequences in the purified recombinant virus were confirmed by PCR screening. Primers used for PCR amplification of PEDV-S sequences were PEDV-intS-Fw (SEQ ID NO:18)-5'-CGTGGTGGGTTTGGTTGATT-3' and PEDV-intS-Rv (SEQ ID NO:19)-5'-CTGCACGTGGACCTTTTCAA-3'; and 121int-Fw (SEQ ID NO:20)-5'-GGCGGACTACCAGAGACATC-3' and 121int-Rv (SEQ ID NO:21)-5'-GTCTTCCGGGATGTCGTAGA-3', respectively. PCR amplicons were analyzed by electrophoresis in 1% agarose gels. Insertion and integrity of the PEDV full-length spike sequences were confirmed by whole genome sequencing using the Nextera XT DNA library preparation kit (Illumina, San Diego, Calif.) followed by sequencing on the Illumina Mi-Seq sequencing platform (Illumina, San Diego, Calif.).

Immunization Protocols

1) ORFV-024-RabV-G/ORFV-121-RabV—Cattle
Immunization: day 0, day 21 (booster) or day 0, day 30 (booster)
Route: SC or IM
Dose: 10^7.9 TCID50
Formulation: Virus suspension in cell culture medium.

2) ORFV-024-RabV-G/ORFV-121-RabV—Pigs
Immunization: day 0, day 21
Route: IM
Dose: 10^7.8 TCID50
Formulation: Virus suspension in cell culture medium.

3) ORFV-024-RabV-G/ORFV-121-RabV—Horses
Immunization: day 0, day 21
Route: SC
Dose: 10^7.8 TCID50
Formulation: Virus suspension in cell culture medium.

4) ORFV-PEDV-S
Immunization: day 0, 21 and 45.
Route: IM, TC (note TC induced no response).
Dose: 2×10^7.38 TCID50
Formulation: Virus suspension in cell culture medium.

Evaluation of Immunogenicity of ORFV-Based PEDV Vaccine in Pigs.

Figure 15A:
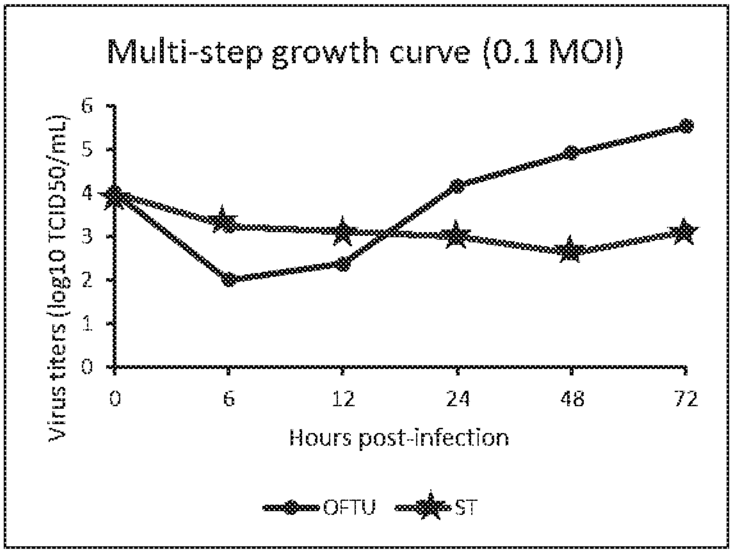
FIG. 15A shows Ovine (OFTU) or swine (ST) cells were infected with ORFV-PEDV-S (MOI=0.1) and virus titers determined at 6, 12, 24 48 and 72 hours post-infection. Titers are expressed as tissue culture infectious dose 50 per mL.
Figure 15B:
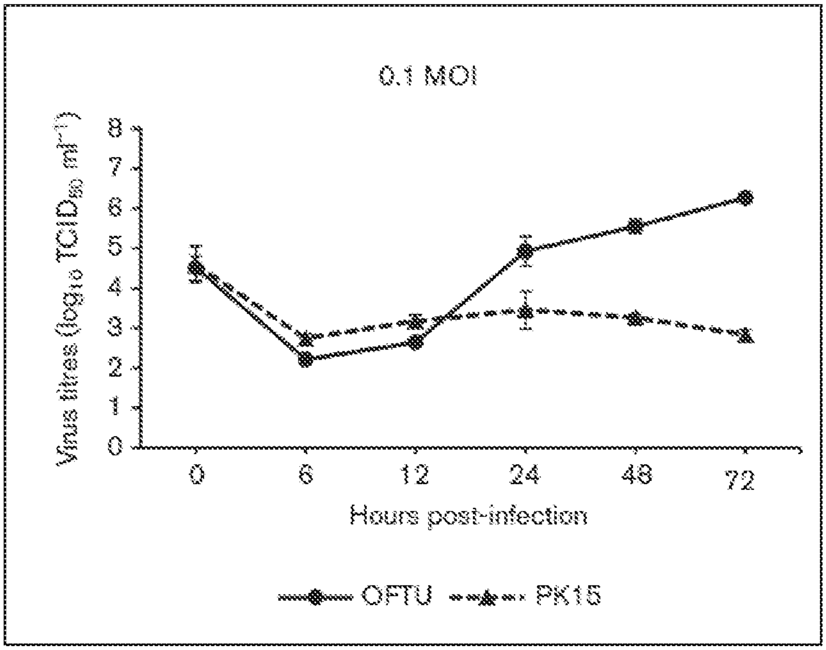
(FIG. 15B) is a multistep growth curve of the recombinant ORFVPEDV-S in primary OFTu and porcine kidney (PK15) cells.
Figure 15C:
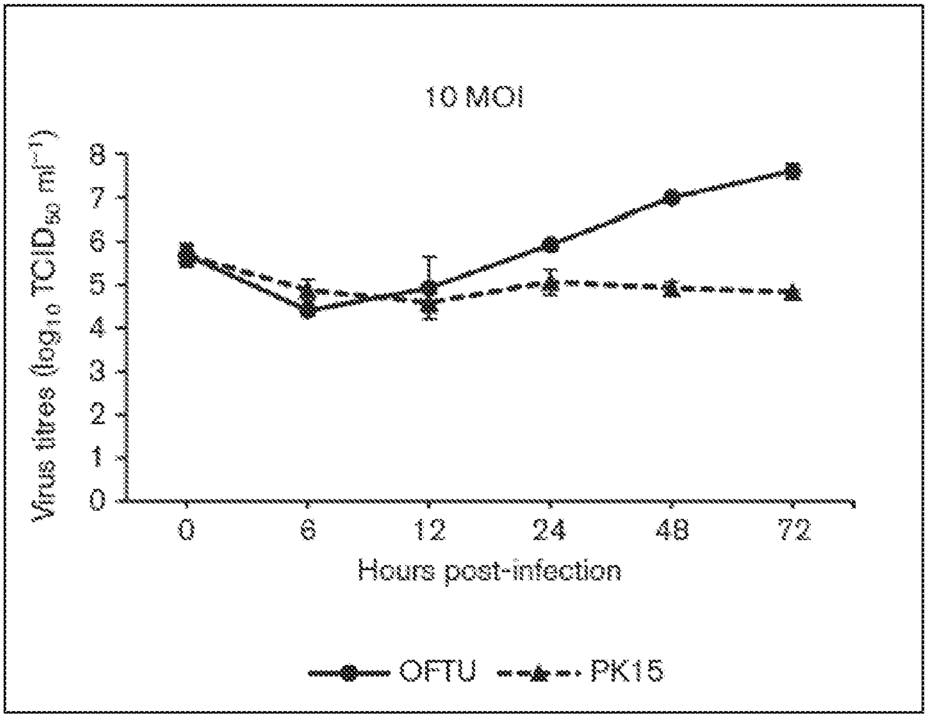
(FIG. 15C) is a single-step growth curve of the recombinant ORFV-PEDV-S in primary OFTu and porcine kidney (PK15) cells. Cells were collected at indicated time points and virus titres determined by the Spearman and Karber's method and expressed as log 10 tissue culture infections dose 50 (TCID50) per millilitre. Error bars represent SEM calculated based on the results of three independent experiments.

The immunogenicity of the recombinant ORFV-PEDV-S virus was evaluated in pigs. Sixteen 3-week old weaned piglets were obtained from a PEDV free farm. Animals were housed in BSL-2 animal facilities and randomly allocated to two experimental groups, consisting of sham-immunized (ORFV; Group 1-n=4), and ORFV/PEDV-S-immunized group 2 (n=4, transcutaneous immunization) ORFV-PEDV-S-immunized group 3 (n=4, intramuscular immunization), ORFV-sham-immunized group 4 (n=4). Immunization was performed by intramuscular (IM) injection (Group 3), transcutaneous application (Group 2) or both IM and TC (groups 1 and 4) of 2 ml of recombinant virus suspension containing $10^{7.5}$ $TCID_{50}$/ml in MEM. The first immunization was performed on day 0 and animals was boosted as above on day 21 and 42 post-primary immunization. Serum samples were collected on days 0, 7, 14, 21, 28, 35, 42, 49, 53, 56 and 60 post-primary immunization for evaluation of immune responses (FIG. 15).

Assessment of Protective Efficacy of the Poxviral Vectored PEDV Vaccine Candidate in Pigs.

The protective efficacy of recombinant ORFV-PEDV-S virus was evaluated in vivo. For this, piglets immunized as above were randomly allocated into 4 experimental groups on day 21 post-booster immunization (G1 sham-immunized-non challenged; n=4 [IM/TC]; G2 sham-immunized-PEDV challenged, n=4 [TC]; G4 ORFV-PEDV immunized-non challenged, n=4 [IM]; and G3 ORFV-PEDV immunized-PEDV-challenged, n=4; [IM/TC]). Animals from groups G2, G3 and G4 were infected orally with $2\times10^{5.0}$ $TCID_{50}$/mL of PEDV strain US/CO/2013. Animals were monitored daily and parameters of PEDV infection and disease (diarrhea, fecal shedding, and mortality) recorded for the duration of the experiment (14 days). Fecal swabs were collected on days 3, 5, 7, 10 and 14 post-challenge to determine virus excretion in feces.

Results

Intramuscular immunization with ORFV-PEDV-S induces serum IgG, IgA and neutralizing antibody responses in pigs. The animals are protected from clinical disease post-challenge infection and present reduced virus shedding in fecal samples. Intramuscular immunization with ORFV induces memory responses that rapidly and robustly become effectors after PEDV infection.

Expression of PEDV-S

FIG. 14 shows expression of PEDV-S in cells exposed to nucleotide constructs of the present invention. ORFV was modified to delete the ORF121 gene, creating an insertion site into which a polynucleotide encoding PEDV-S was inserted (ORFV-PEDV-S) (FIG. 14A). The presence of PEDV spike in ORFV genome was demonstrated by polymerase chain reaction (FIG. 14B). Expression of PEDV spike protein in cells infected with the recombinant ORFV-PEDV-S was then assessed by immunofluorescence assay (FIG. 14C). In addition, expression of PEDV Spike protein in cells infected with recombinant ORFV-PEDV-S was confirmed by Western blot (FIG. 14D).

These data demonstrate that the recombinant viruses effectively encode and express heterologous antigens that have been inserted into insertion sites created by deleting one or more open reading frames or genes.

Replication of Recombinant Virus

Ovine (OFTU), swine (ST) or porcine (PK-15) cells were infected with ORFV-PEDV-S(MOI=0.1 or 10) and virus titers determined at 6, 12, 24 48 and 72 hours post-infection. Titers are expressed as tissue culture infectious dose 50 per mL. As shown in FIG. 15 A-C, the ORFV-based viral vectors of the present invention effectively replicate in animal cells.

Immunogenicity of Candidate Vectors in Target Species

Figure 16A:
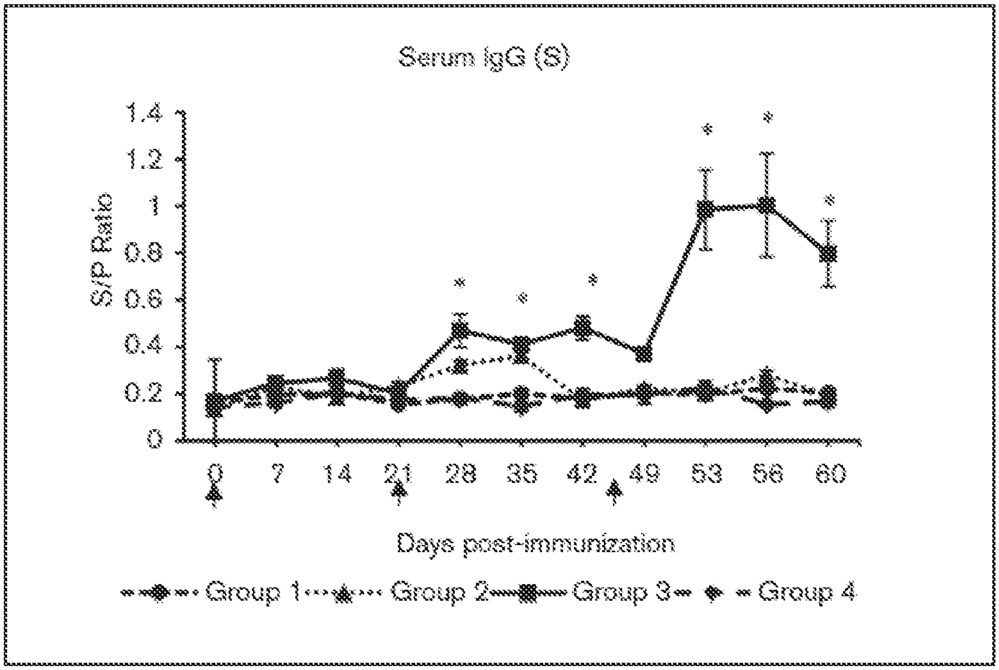
(FIG. 16A) Isotype ELISA demonstrating serum IgG antibody responses specific to the PEDV S protein.
Figure 16B:
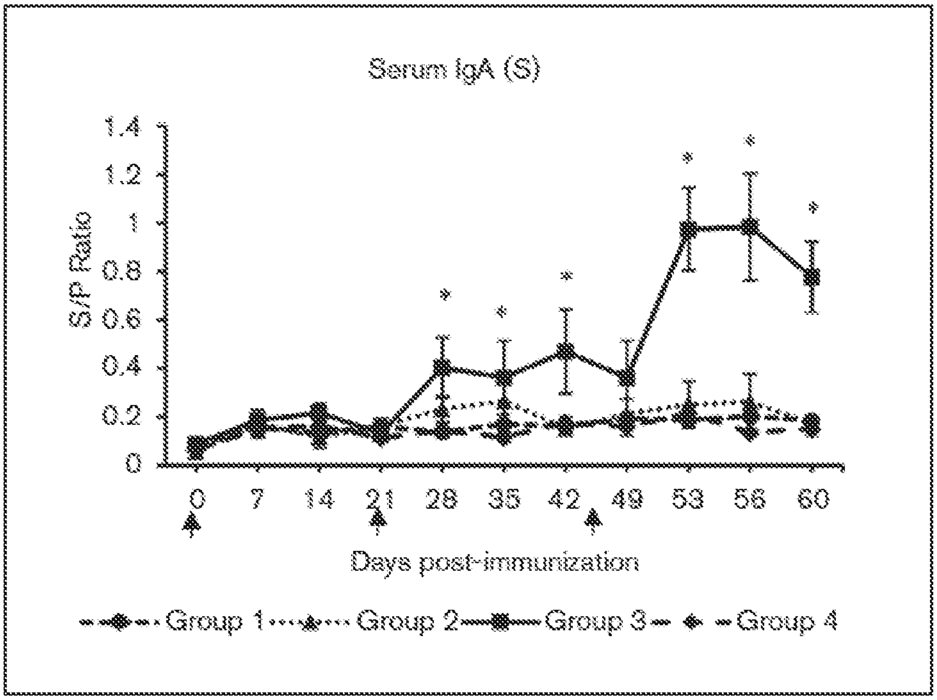
(FIG. 16B) Isotype ELISA demonstrating serum IgA antibody responses specific to the PEDV S protein.
Figure 16C:
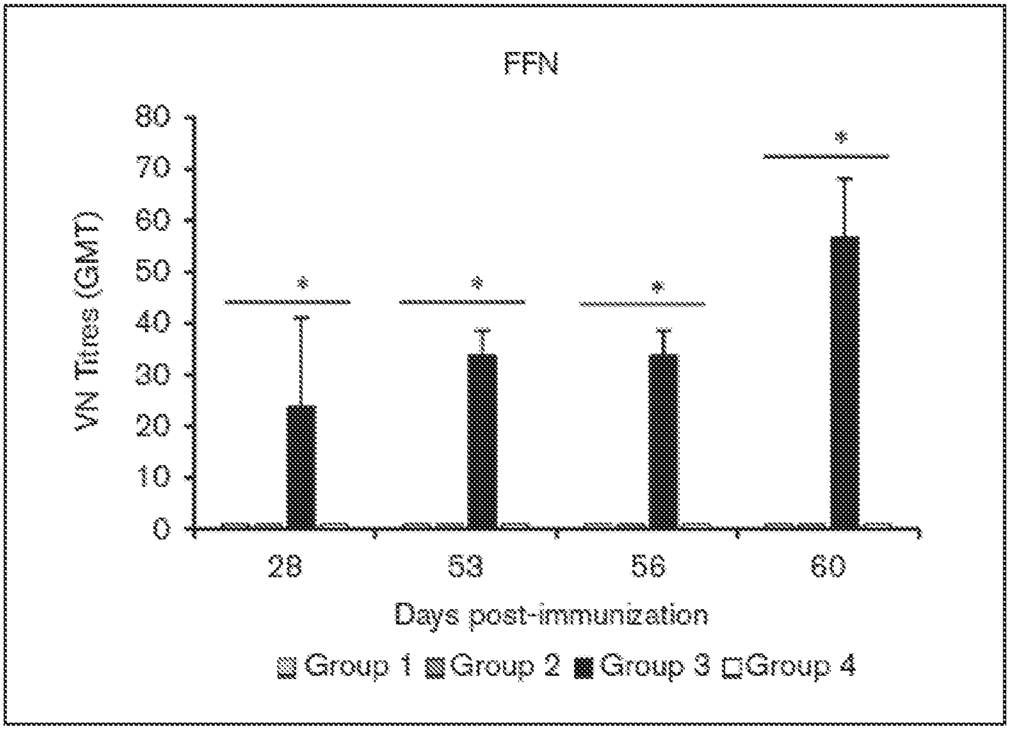
(FIG. 16C) Virus NA responses elicited by immunization with recombinant ORFV-PEDV-S. S/P, sample to positive ratio; GMT, geometric mean titre. Arrow heads represent immunization/booster immunizations (days 0, 21 and 45). Error bars represent SEM. Statistical significance was determined using one-way ANOVA and Tukey's honest significant difference (HSD). *Statistically significant at the 0.05 level when the mean of Group 3 was compared to the mean of Groups 1, 2 and 4.

ORFV-PEDV-S was assessed for immunogenicity in pigs as a model livestock animal. Piglets were immunized on day 0 and boosted on days 21 and 42. Challenge with PEDV was performed on day 60 post-prime or 21 post-booster immunization. *Blood was collected for serological assays on days 0, 21, and 45. Fecal samples were collected on days 0, 7, 14, 21, 28, 35, 42, 49, 53, 56 and 60. post-challenge infection to assess virus excretion/protective efficacy. The immunogenicity of the recombinant ORFV-PEDV-S was evaluated in pigs following IM or TC immunizations. While IM immunization has been shown effective for other ORFV-vectored antigens in pigs, proof-of-concept TC immunization was used given its efficacy in inducing mucosal immune responses in other animal species. Notably, animals immunized via the IM route developed robust antibody responses (IgG, IgA and NA) against PEDV, whereas no seroconversion was detected in animals immunized via the TC route. These results corroborate the findings of previous studies, demonstrating that the IM route is an effective route to deliver ORFV-vectored antigens in swine. Although no NAs against ORFV were detected in any of the immunized animals (data not shown), it is possible that local innate/inflammatory responses elicited by skin scarification may have affected the delivery and/or expression of PEDV S by ORFV-PEDV-S in the skin, thus, potentially preventing the development of immune responses against PEDV S in animals immunized via the TC route. Additionally, the dose delivered following skin scarification and topical application of the recombinant vector may not have been sufficient to prime and boost the immune system against PEDV S in animals from the TC immunized group. Given the natural tropism of ORFV for keratinocytes in natural hosts (sheep and goats), it would still be interesting, however, to explore more precise methods of TC delivery of ORFV-vectored antigens in the future. FIG. 16 (A-C) shows immunization of pigs with the recombinant ORFV elicits PEDV specific serum IgG, IgA and neutralizing antibody responses.

Figure 17A:
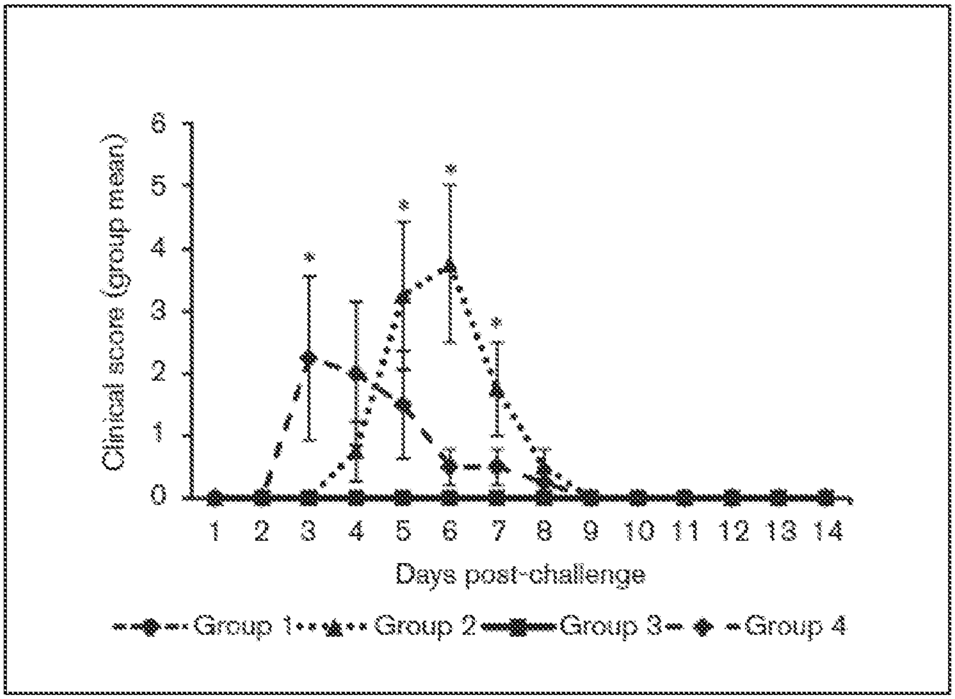
FIG. 17A shows average group clinical scores recorded post-challenge infection with PEDV strain CO13. Clinical signs were recorded and individual daily scores assigned to all animals based on the following criteria: 0, normal faeces; 1, pasty faeces; 2, moderate diarrhoea (semi-liquid); 3, diarrhoea (liquid); 4, severe diarrhoea (very liquid); 5, watery diarrhoea (profuse diarrhoea). Error bars represent SEM. Statistical significance was determined using one-way ANOVA and Tukey's HSD. *Statistically significant at the 0.05 level when the mean of Group 3 was compared to the mean of Groups 2 or 4.
Figure 17B:
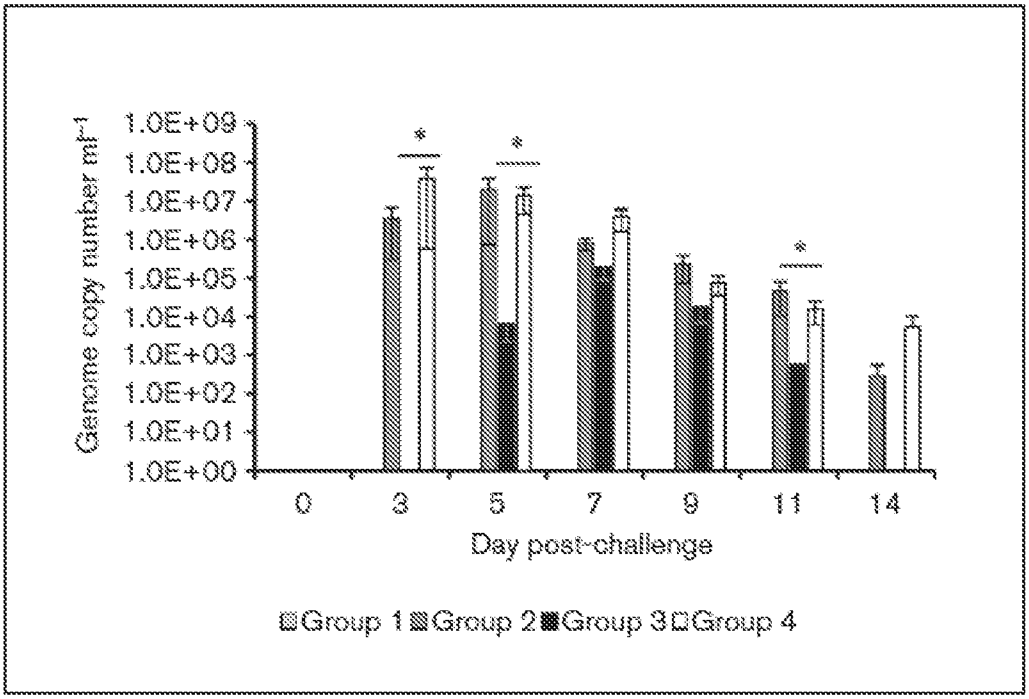
FIG. 17B shows virus shedding in faeces was measured and expressed as log 10 genome copy numbers per millilitre. Error bars represent SEM. Statistical significance was determined using non-parametric Kruskal-Wallis test between groups. *Statistically significant at the 0.05 level when the mean of Group 3 was compared to the mean of Groups 2 and 4.
Figures 18, 19A:
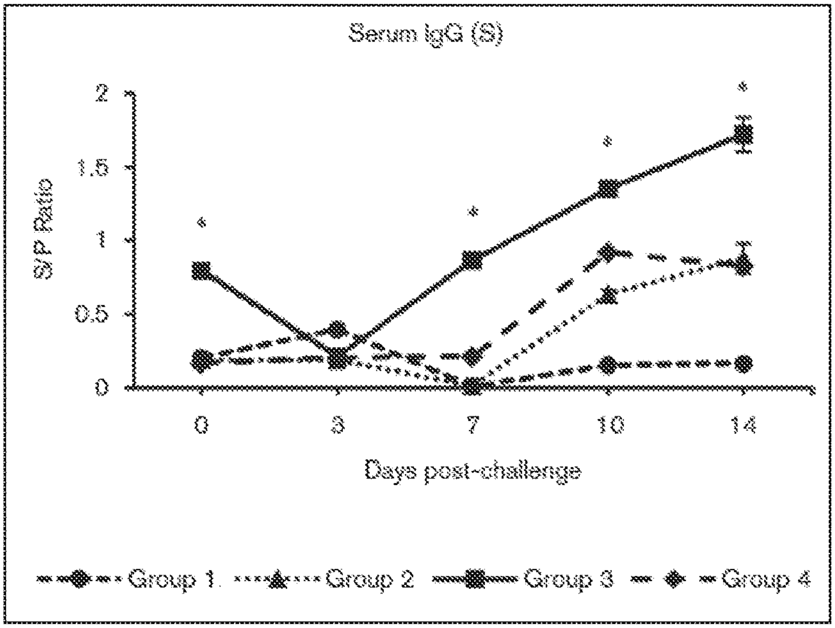
FIG. 18 shows intramuscular immunization with ORFV-PEDV-S results in reduced virus shedding. Real-time PCR was used to detect PEDV shedding in fecal swabs post-challenge. Group 1: Control, no challenge. Group 2: inoculation with ORFV-PEDV-S via skin scarification. Group 3: inoculation with ORFV-PEDV-S via intramuscular injection. Group 4: control, challenge.
FIG. 19A shows isotype ELISA demonstrating serum IgG antibody responses specific to the PEDV S protein.
Figure 19B:
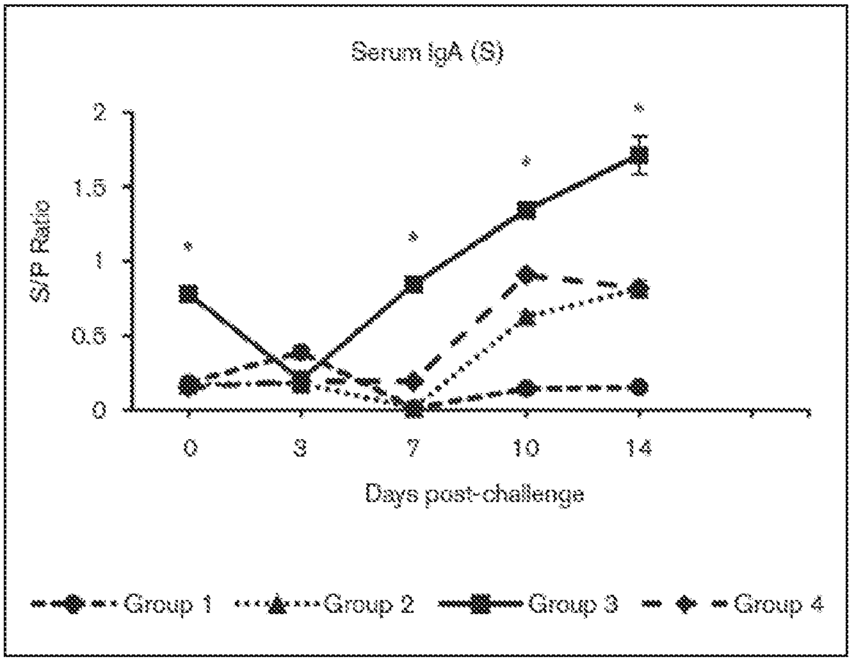
FIG. 19B shows isotype ELISA demonstrating serum IgA antibody responses specific to the PEDV S protein.
Figure 19C:
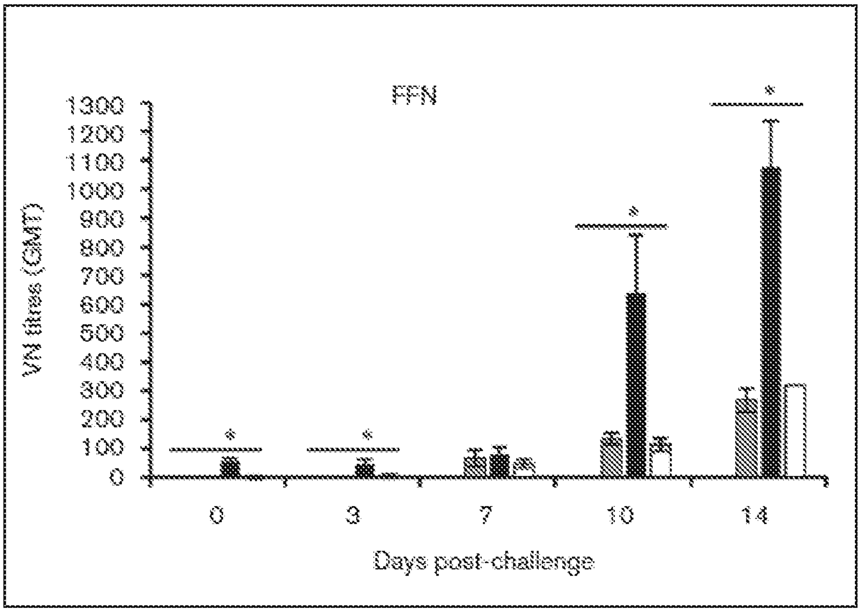
FIG. 19C shows virus NA responses.
Figure 19D:
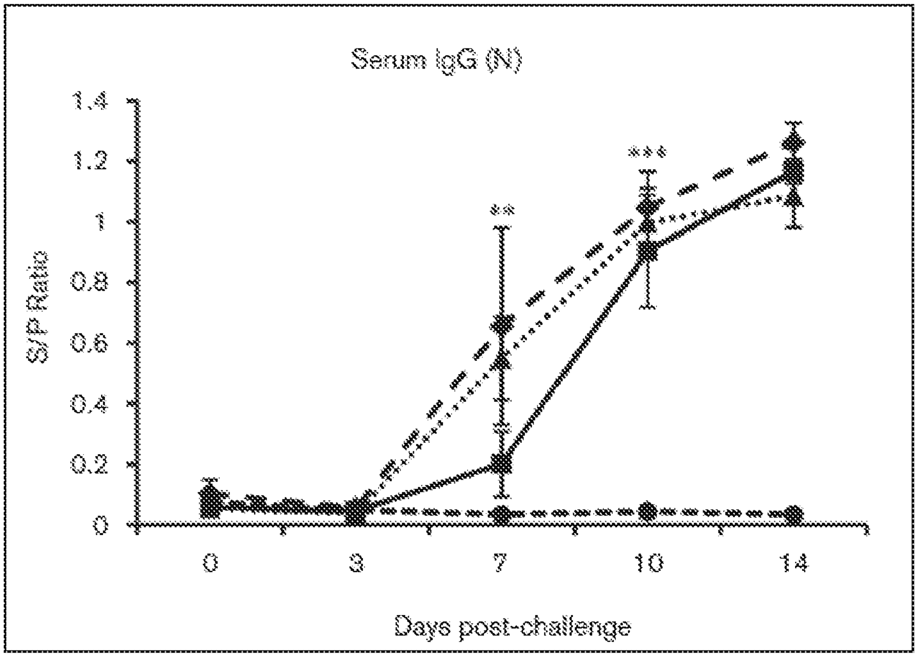
FIG. 19D shows isotype ELISA demonstrating serum IgG antibody responses specific to the PEDV N protein. S/P, sample to positive ratio; GMT, geometric mean titre. Error bars represent SEM. Statistical significance was determined using one-way ANOVA and Tukey's HSD. *Statistically significant at the 0.05 level when the mean of Group 3 is compared to the mean of Groups 1, 2 and 4; statistically significant at the 0.05 level when the mean of Group 3 was compared to the mean of Groups 2 and 4; *statistically significant at the 0.05 level when the mean of Group 3 was compared to the mean of Group 4.

To assess the protective potential of ORFV-PEDV-S-elicited immune responses, animals from Groups 2 (TC) and 3 (IM), and sham-immunized Group 4 (TC+IM), were challenged orally with a virulent PEDV strain CO13 ($2\times10^5$TCID$_{50}$). Notably, while 3 out of 4 (¾; 75%) animals from Group 2 (which did not seroconvert after TC immunization; FIGS. 15 A-C) and 2/4 (50%) animals from control Group 4 developed characteristic signs of PED, none of the animals from Group 3 (IM, which developed serum antibody responses to PEDV) were affected. Additionally, animals from Group 3 presented reduced virus shedding in faeces when compared to animals from Groups 2 and 4 (FIG. 17 A, B, and FIG. 18). FIG. 17 (A-B) shows immunization with ORFV-PEDV-S induces protection against clinical disease post PEDV challenge. Clinical scores post oral challenge with PEDV strain CO13. Animals were monitored daily for characteristic PED clinical signs. Clinical signs were recorded and individual scores for each animal calculated as follows: 0. Normal feces; 1. soft stool; 2. mild diarrhea; 3. diarrhea; 4. severe diarrhea, 5. watery diarrhea. Mean scores for each group were calculated for the duration of the experiment and plotted on the graph above. FIG. 18 shows intramuscular immunization with ORFV-PEDV-S results in reduced virus shedding. Real-time PCR was used to detect PEDV shedding in fecal swabs post-challenge. No clinical signs were observed in animals from Group 3 (IM). Results from the RT-qPCR performed in rectal swabs show a delayed onset and short duration shedding of PEDV by animals from Group 3 (FIG. 17B, and FIG. 18). Together, these results demonstrate that IM immunization with the recombinant ORFV-PEDV-S protected pigs from clinical PED and reduced virus shedding following oral challenge infection. The results here show a strong correlation between PEDV-specific antibodies in serum, protection from clinical disease and decreased virus shedding in faeces.

FIG. 19 shows efficient generation of immune memory via virus neutralization titers in animals following challenge with ORFV-PEDV-S. Animals immunized intramuscularly with ORFV-PEDV-S presented a robust neutralizing antibody response post-challenge. Serological responses that followed challenge infection with PEDV varied significantly between immunized groups. While animals from Group 3 presented a robust serological response, typical of a secondary immunological response, characterized by high levels of S-specific and NA responses to PEDV (FIG. 19 A-C), animals from Groups 2 and 4 developed delayed antibody responses, typical of primary exposure to PEDV (FIG. 19 A-C). In contrast, antibody responses to the N protein (structural protein not present in the ORFV-PEDV-S construct) were lower in animals from Group 3 (day 7 p.c.), suggesting an early inhibition of PEDV infection/replication in animals from Group 3 (FIG. 19D). Together, these results suggest that IM immunization with the recombinant ORFV-PEDV-S virus efficiently primed B cells, which rapidly and effectively responded upon exposure to the virus in the intestinal mucosa, leading to anamnestic antibody responses in immunized animals.

Summary

In summary, here we show the successful generation of a recombinant ORFV containing the full-length S gene of PEDV into the ORFV121 gene locus. Characterization of the recombinant ORFV-PEDV-S virus in vitro demonstrates efficient and stable expression of the heterologous protein in cell cultures infected with the recombinant virus. Immunization challenge studies in pigs, show that IM delivery of the recombinant ORFV-PEDV-S elicits robust serum antibody responses in immunized animals that correlated with protection against clinical PED and decreased virus shedding in faeces. These results further demonstrate that the nucleotide constructs of the present invention effectively encode and express heterologous antigens that can induce an immune response for prevention of diseases or conditions in animals. Intramuscular immunization with ORFV-PEDV-S induces serum IgG, IgA and neutralizing antibody responses in pigs. Animals are protected from clinical disease post-challenge infection. Further, animals immunized with the constructs of the present invention exhibit reduced virus shedding in fecal samples, and IM immunization with ORFV induces memory responses that rapidly and robustly become effectors after PEDV infection.

Example 3: Immunization of Pregnant Gilts with ORFV-PEDV-S and Antibody Transfer to Colostrum/Milk The ability of the ORFV-PEDV-S to induce lactogenic immunity was assessed in pregnant gilts. Six pregnant gilts were allocated into three groups: Group 1: sham-immunized control; Group 2: ORFV-PEDV-S immunized; and Group 3: ORFV-PEDV-S immunized/live PEDV exposed. The immunized groups received 3 IM immunizations of the ORFV-PEDV-S at 3-week intervals. The last dose was given at approximately two weeks prior to farrowing.

Figure 20A:
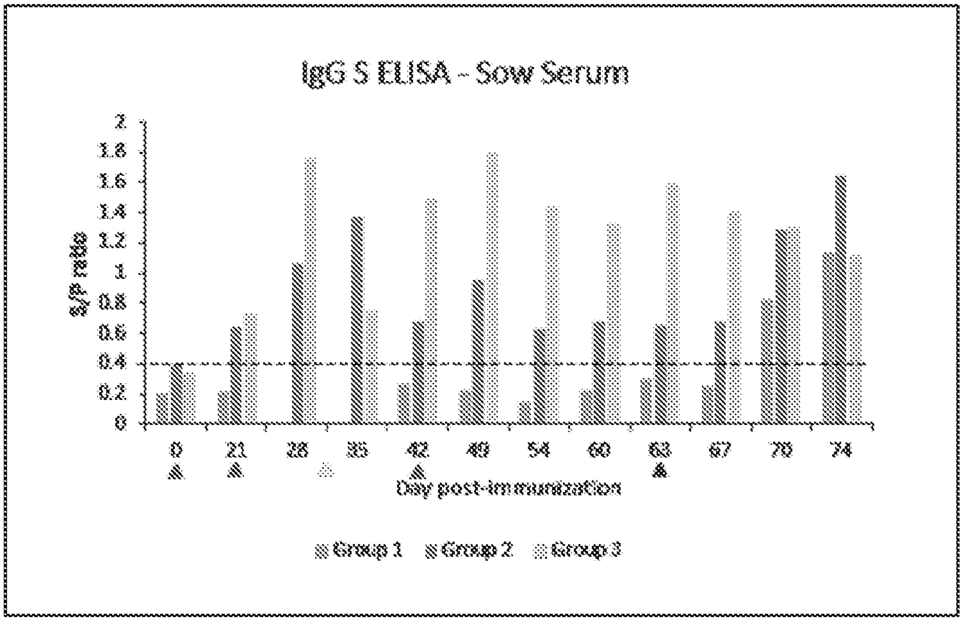
FIG. 20A shows serum IgG antibody levels as detected by S-ELISA.
Figure 20B:
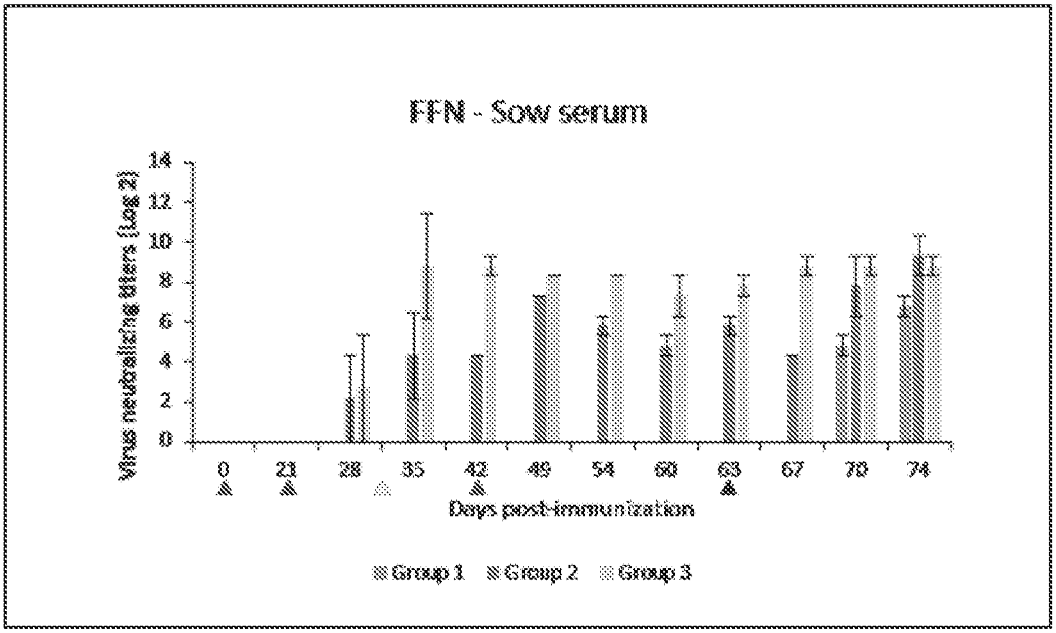
FIG. 20B shows PEDV neutralizing antibody responses as detected by FFN assays. Green arrow heads indicate immunization dates (ORFV-PEDV-S, IM); Yellow arrow head represent the date in which Group 3 animals were exposed to live PEDV; and red arrow head represents the date in which piglets were challenged.

Serological responses were assessed by PEDV IgG and IgA Spike ELISA (S antigen), and functional antibodies (neutralizing antibodies) by fluorescent focus neutralization (FFN) assays. As shown in FIGS. 20 A and B, intramuscular immunization with ORFV-PEDV-S induced IgG, IgA and virus neutralizing antibody (NA) responses in immunized pigs. Animals from Group 2 (ORFV-PEDV-S) and Group 3 (ORFV-PEDV-S+live Oral PEDV) presented IgG, IgA and neutralizing antibodies against PEDV. Group 3 was included in our experimental design due to the notion that local gut immunity is necessary for effective transfer of lactogenic immunity against enteric pathogens from the mother to the offspring in swine. The rational was that the immunity provided by the ORFV-PEDV-S vaccine candidate would be boosted by oral live virus exposure. As expected animals from Group 3, presented an anamnestic neutralizing response after oral exposure to PEDV on day 31 pi (FIG. 20C; day 42). Animals from the control group remained negative during the immunization phase of the experiment (first 54-56 days) and seroconverted only after the piglets were challenged with live PEDV (as seen on days 70 and 74; FIGS. 20 A and B).

Figure 21A:
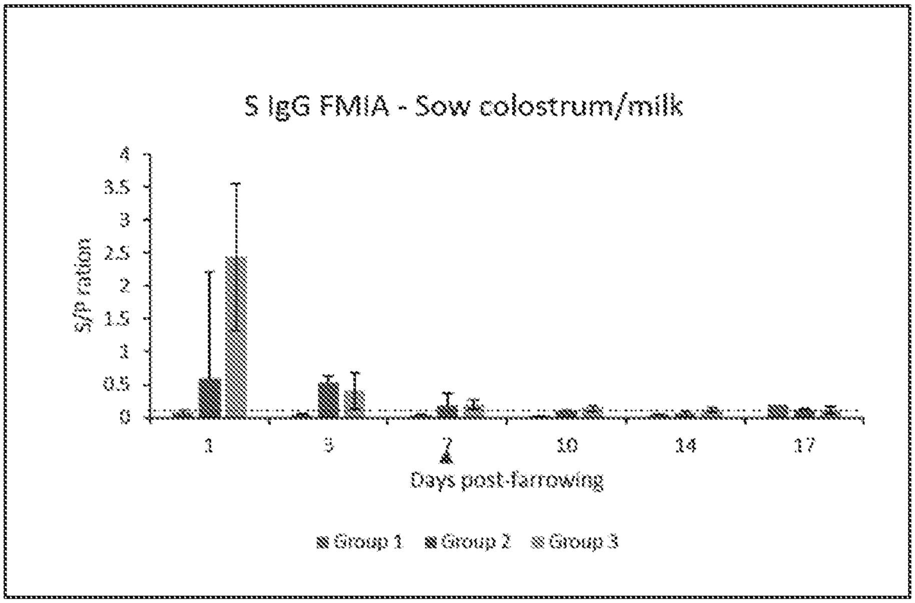
FIG. 21A shows S-specific IgG antibody levels detected in colostrum and/or milk after farrowing by using an FMIA assay.
Figure 21B:
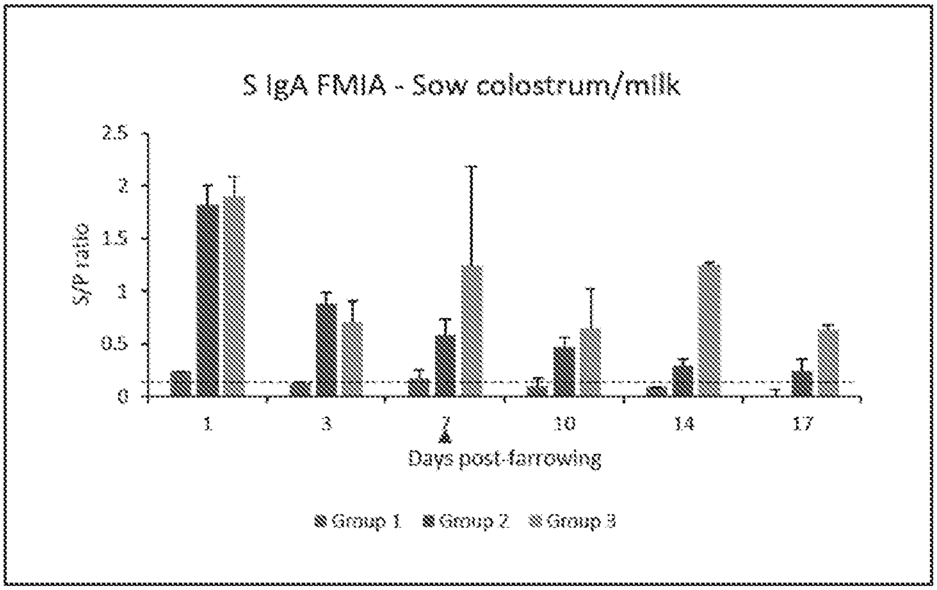
FIG. 21B shows 5-specific IgG antibody levels detected in colostrum and/or milk after farrowing by using an FMIA assay.

Antibody levels in colostrum and milk were also evaluated after farrowing. Colostrum was collect right after farrowing (day 1) and milk samples were collected on days 3, 7, 10, 14 and 17 post farrowing. PEDV specific IgG and IgA antibody levels were assessed by S-IgG and S-IgA-isotype FMIA assays. While similar levels of S-specific IgG and IgA antibodies were detected on day 1 post-farrowing on animals from Groups 2 and 3 (FIGS. 21 A and B). While the levels of S-Specific IgG and IgA antibodies dropped rapidly after day 3 post-farrowing, S-Specific IgA antibodies were detected in animals from Group 2 and 3 until day 10 post-farrowing. Animals from Group 3 presented S-IgA antibodies in milk up to day 17 pi.

Figure 22A:
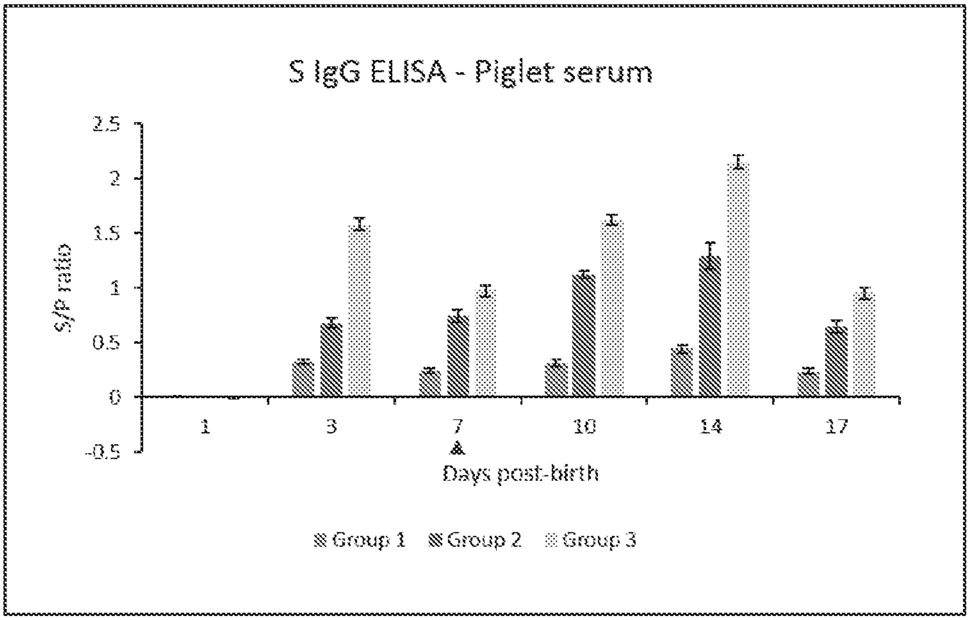
FIG. 22A shows S-specific IgG responses in serum from piglets as determined by ELISA.
Figure 22B:
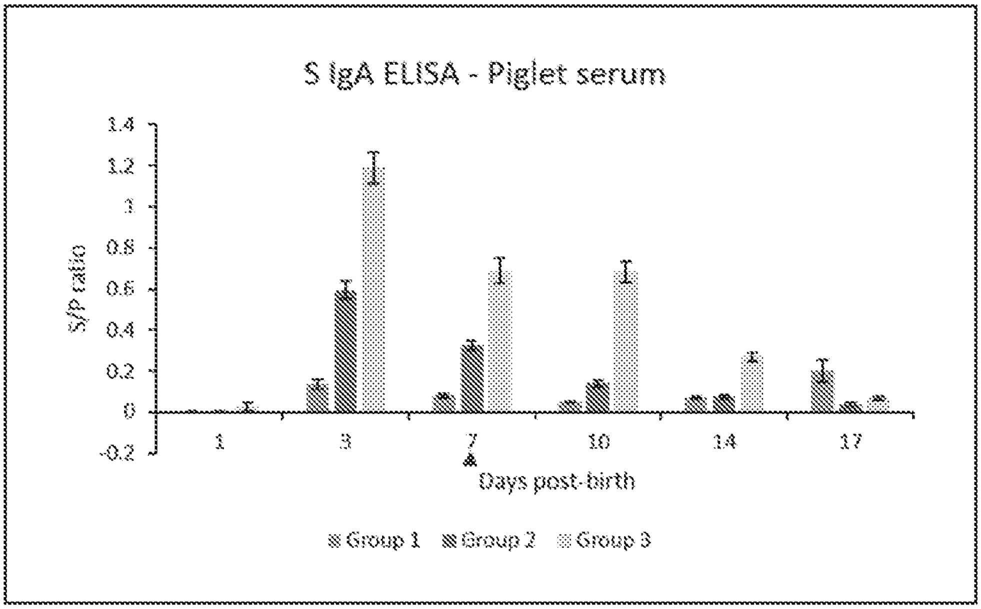
FIG. 22B shows S-specific IgA responses in serum from piglets as determined by ELISA.
Figure 22C:
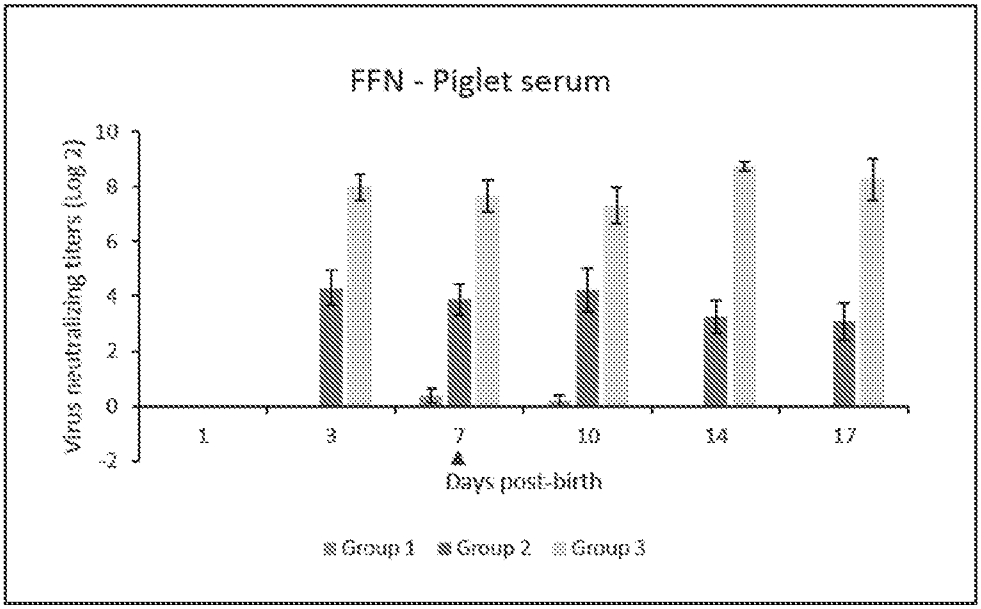
FIG. 22C shows neutralizing antibody responses in serum from piglets as determined by FFN assay. Red arrow indicates the day of challenge with PEDV.

Levels of antibodies transferred to piglets born to immunized gilts were assessed in serum. Serum samples were collected on days 1, 3, 7, 10 14 and 17 of life and PEDV S-specific antibodies were assessed by S-ELISA, while functional neutralizing antibodies were measured by FFN assays. Notably, piglets born to ORFV-PEDV-S immunized animals from Group 2 and to ORFV-PEDV-S-immunized/PEDV exposed Group 3 animals presented S-specific IgG and IgA antibodies in serum on day 3 of life. No antibodies were detected on day 1 prior to ingestion of colostrum. Similar to the results obtained in serum and milk of animals from Group 3, the levels of S-IgG and S-IgA antibodies were higher in piglets born to animals from this group (FIGS. 22 A and B). Neutralizing antibodies were also detected in serum of piglets born to animals from Group 2 and 3 (FIG. 22C), indicating successful passive transfer NA to through colostrum and/or milk.

Figure 23:
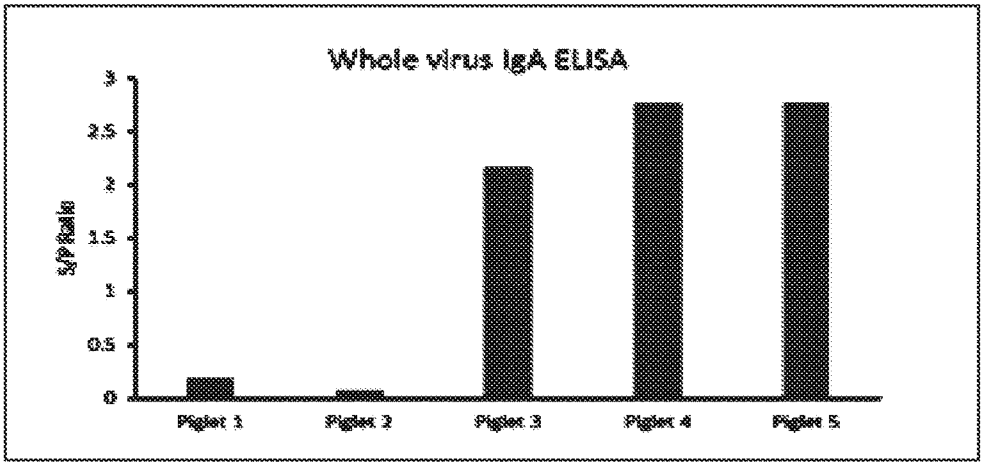
FIG. 23 shows detection of PEDV specific IgA antibodies in intestinal content of piglets prior to PEDV challenge. Piglets #1 and #2 were born to non-immunized gilts, while piglets #3, 4 and 5 were born to ORFV-PEDV-S-immunized PEDV-exposed gilts (Group 3). Results represent the sample-to-positive ratio on intestinal contents of individual piglets.

Intestinal contents from a few piglets born from Group 1 (n=2; piglet #1 and #2) and Group 3 (n=3; piglet #3, #4 and #5) gilts were collected prior to challenge infection on day 7 post-birth and tested for the presence of PEDV specific IgA antibodies by ELISA. No samples were collected from group 2 piglets because gilts from this group only delivered 24 piglets, which was the target n for the challenge experiment. These samples were tested for the presence of PEDV-specific IgA antibodies by an indirect whole virus ELISA. As shown in FIG. 23, high levels of PEDV IgA antibodies were detected in piglets from Group 3, whereas piglets from Group 1 did not present PEDV-specific IgA antibodies in the gut.

Challenge Infection of Piglets Born to Immunized Gilts.

On day 7 of life all piglets born to gilts in Group 1, 2, and 3 were challenged orally with 2×105 TCID50 of PEDV strain CO13. Animals were monitored and litter daily scores for characteristic clinical signs of PED were recorded. Additionally, mortality rates were recorded. Fecal swabs were collected on days 0, 3, 7 and 10 post challenge (pc; correspond to days 7, 10, 14 and 17 of life) and the amount of PEDV shedding in feces was assessed by RT-qPCR. On day 10 pc, all piglets that survived the PEDV challenged were euthanized and intestinal samples collected for histological examination.

Figure 24A:
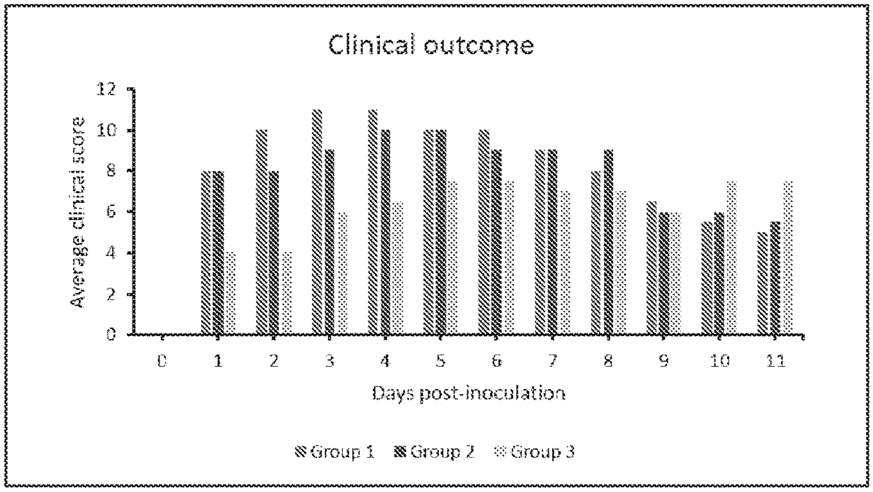
FIG. 24A shows clinical score observed during 10 days post challenge.
Figure 24B:
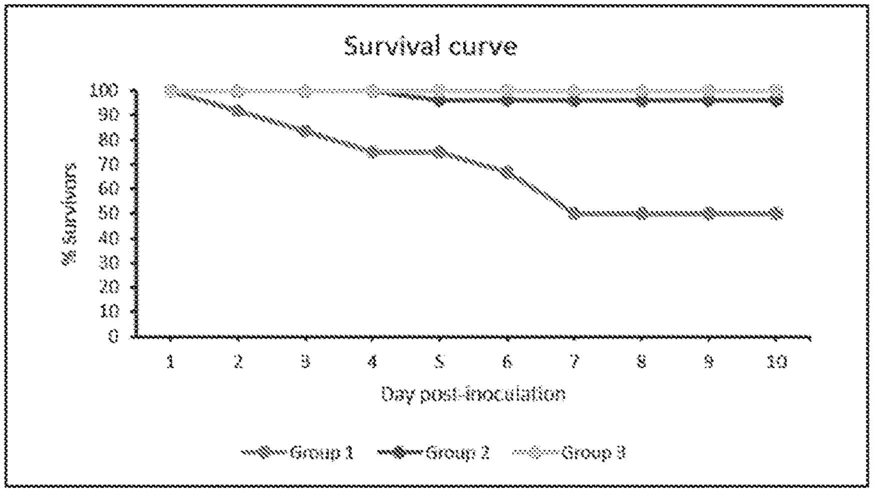
FIG. 24B shows survival curves post-PEDV challenge in piglets born to immunized gilts.

As shown in FIG. 24, immunization with ORFV-PEDV-S alone (Group 2) or with ORFV-PEDV-S or followed by PEDV exposure resulted in reduction in clinical signs and marked reduction in mortality rates when compared to control piglets born to non-immunized gilts (Group 1).

Discussion

Correlate(s) of protection for PEDV remain unknown, neutralizing secretory IgA (sIgA) antibodies are thought to play a major role in protection sIgA seem especially important in providing lactogenic immunity and protection during the first days of life of newborn piglets. One of the main obstacles in eliciting lactogenic immunity to PEDV, however, is the need for local gut stimulation of IgA secreting cells (plasmablasts) and their subsequent migration to the mammary gland where they produce sIgA antibodies which are secreted in the colostrum and milk and ultimately transferred to suckling piglets (gut-mammary-sIgA axis). This has been achieved by natural infection, oral vaccination of pregnant sows with live PEDV or, more recently, by a subunit vaccine candidate.

The potential of the ORFV-PEDV-S recombinant virus would to elicit lactigenic immunity and protection was explored using a pregnant gilt immunization model. Pregnant gilts allocated into three experimental groups, including a control sham immunized group 1, ORFV-PEDV-S immunized group 2 and ORFV-PEDV-S/PEDV exposed group 3. Animals from group 2 received three 3-week interval IM immunizations with the ORFV-PEDV-S with the last immunization being given at 2 weeks prior to farrowing. Animals from group 3 received two IM immunizations with ORFV-PEDV-S (days 0 and 21) followed by oral exposure to PEDV on day 31, and a final booster with ORFV-PEDV-S on day 42. Serological responses and the presence of PEDV specific antibodies in colostrum and milk were evaluated at several intervals post-immunization and post-farrowing.

Notably, animals immunized with ORFV-PEDV-S(group 2) or immunized with ORFV-PEDV-S and exposed to PEDV developed PEDV-specific IgG, IgA and NA responses in serum. Additionally, PEDV-specific IgG and IgA antibodies were detected in colostrum and milk. As expected animals from group 3 presented higher titers of levels of antibodies. Passive transfer of these antibodies to piglets was evaluated in serum samples collected at various intervals post-birth. PEDV specific IgG, IgA and NA were detected in piglets born from gilts in Group 2 and 3, indicating successful transfer of PEDV-specific antibodies from the gilts to their offspring through the ingestion of colostrum and/or milk. Additionally, challenge of piglets with PEDV on day 7 post-birth revealed that the antibodies transferred from ORFV-PEDV-S-immunized gilts (Group 2) or from ORFV-PEDV-S-immunized and PEDV-exposed gilts (Group 3) to piglets through colostrum and milk resulted in markedly reduced clinical scores and mortality rates when compared to those presented by piglets born to control non-immunized gilts (Group 1) (FIG. 24). Notably, the degree of protection correlated with the levels of antibodies detected in gilt colostrum and milk and in piglet serum.

Results here demonstrate the suitability of the ORFV-vector platform as a vaccine delivery platform for enteric diseases of swine. This vector represents a promising alternative to currently available PEDV vaccines.

Table of Sequences

| SEQ ID NO: | Sequence (or description) |
|---|---|
| 1 | pZ024-RabV-G (recombination plasmid used to generate ORFV-024-RabV-G virus) |
| 2 | pZ121-RabV-G (recombination plasmid used to generate ORFV-121-RabV-G virus) |
| 3 | pZ121-PEDV-S (Sequence of recombination plasmid used to construct ORFV-PEDV-S) |
| 4 | OVRF -024-RabV-G Complete Genome |
| 5 | OVRF-121 RabV -G Complete Genome |
| 6 | 024LF-Fw(HindIII) |

-continued

Table of Sequences

| SEQ ID NO: | Sequence (or description) |
|---|---|
| 7 | 024LF-Rv(SalI) |
| 8 | 024RF-Fw(NotI) |
| 9 | 024RF-Rv(BglII) |
| 10 | 121LF-Fw(SpeI) |
| 11 | 121LF-Rv(HindIII) |
| 12 | 121RF-Fw(NotI) |
| 13 | 121RF-Rv(BglII) |
| 14 | 121LF-Fw(SpeI) |
| 15 | 121LF-Rv(HindIII) |
| 16 | 121RF-Fw(NotI) |
| 17 | 121RF-Rv(BglII) |
| 18 | PEDV-intS-Fw |
| 19 | PEDV-intS-Rv |
| 20 | 121int-Fw |
| 21 | 121int-Rv |

What is claimed is:

1. A vector for vaccine delivery in livestock comprising: a nucleic acid sequence encoding an infectious Orf virus operably linked to a heterologous nucleic acid sequence encoding at least one antigen, wherein the at least one antigen encoding sequence is inserted into an insertion site created by a deletion in ORFV024 and/or ORFV121 of a wild type Orf virus strain, and wherein the vector comprises:

(a) SEQ ID NO: 4 or 5;

(b) a polynucleotide that hybridizes with a sequence of (a) under stringent conditions defined as hybridizing to filter bound DNA on 0.5M NaHPO4, 7% SDS, 1 mM EDTA at 65° C., and washing in 0.1×SSC/0.1% SDS at 68° C.;

(c) a polynucleotide that is at least 90% identical to the polynucleotide of (a); or (d) a polynucleotide that is at least 95% identical to the polynucleotide of (a).

2. The vector of claim 1, wherein the wild type Orf virus is Orf virus strain OV-IA82.

3. The vector according to claim 1, wherein the at least one antigen encodes a rabies virus G protein and/or PEDV S protein.

4. The vector of claim 1, wherein said vector is a viral vector.

5. The vector according to claim 1, wherein the livestock are one or more of swine, cattle, or horses.

6. A vaccine or immunogenic composition comprising the nucleic acid construct of claim 1, and a pharmaceutically acceptable carrier or diluent.

7. The vaccine or immunogenic composition of claim 6, wherein the composition further comprises an adjuvant, an excipient, or a combination thereof.

8. A method of delivering a vaccine in livestock comprising:

administering a nucleic acid construct comprising a nucleic acid sequence encoding an infectious Orf virus operably linked to a heterologous nucleic acid sequence encoding at least one antigen, wherein the at least one antigen is inserted into an insertion site created by a deletion in ORFV024 and/or ORFV121 of a wild type Orf virus, and wherein the nucleic acid construct comprises:

(a) SEQ ID NO: 4 or 5;

(b) a polynucleotide that hybridizes with a sequence of (a) under stringent conditions defined as hybridizing to filter bound DNA on 0.5M NaHPO4, 7% SDS, 1 mM EDTA at 65° C., and washing in 0.1×SSC/0.1% SDS at 68° C.;

(c) a polynucleotide that is at least 90% identical to the polynucleotide of (a); or (d) a polynucleotide that is at least 95% identical to the polynucleotide of (a.

9. The method according to claim 8, wherein the at least one antigen encodes a rabies virus G protein and/or PEDV S protein antigen.

10. The method according to claim 8, wherein the wild type Orf virus is an Orf virus strain OV-IA82.

11. A method of conferring immunity to an antigen in livestock comprising:

introducing to the livestock the vector according to claim 1.

12. The vector of claim 1, wherein the at least one antigen encoding sequence is inserted into an insertion site created by a deletion in ORFV024 of the wild type Orf virus strain.

13. The vector of claim 1, wherein the at least one antigen encoding sequence is inserted into an insertion site created by a deletion in ORFV121 of the wild type Orf virus strain.

14. The vector of claim 1, wherein the vector comprises SEQ ID NO: 4 or 5.

* * * * *

SEQUENCE LISTING

<160> NUMBER OF SEQ ID NOS: 21

<210> SEQ ID NO 1
<211> LENGTH: 5879
<212> TYPE: DNA
<213> ORGANISM: Artificial Sequence
<220> FEATURE:
<223> OTHER INFORMATION: recombination plasmid used to generate ORFV-024-RabV-G virus

<400> SEQUENCE: 1
gaactcgaga ctagtaggcc tgcgcgcaag cttaaccagc agaccttctt caccaagggg 60
ctcagtccgc tgatgcgcca cacctacatc tacaacaact acgcctacgg ctggattccc 120
gagaccgcgc tctggagcag ccgtctgggc gactaccgcg tcacggactt ctacccgata 180
tcgctgggca tgctcaagaa gttcgagttc atgttctcgc tgctggcgga ccccggcggc 240
gcctgccccg cgtacgagcc caagctcaac accgagttcc tgaaccgcgg ctccttctcg 300
ggccggtacg tgaacccctt ccaccgcttc gcggcgctgc ccgagcgcga gtacatctcc 360
ttcctgctgc tgagctcggt gcccatcttc aacatcctct tctggtttaa gggcgagacc 420
ttcgacactg ccaagcacag cctgctcggc gccgtgtaca ccacgcccga gaggcacatc 480
gagctcgcgc ggtacctgcg gcgcacgggc gactacaagc cgctgttcag ccgcctgggc 540
aacgacgaca cctactcgaa gcccttctcg gggttcacgc gcatcagcaa ccccacgccc 600
atcgggcggc tgccgccctc ggacttcgag acgctggcca acctgagcac cattctctac 660
tacacgcgct acgacccggt gctctgtttc ctggtcttct acgtgccggg gctctccgcg 720
accacgaaga tcacgcccgg cgtggagttc ctcatggaga agctctcgct cgcgcccgag 780
aacgtggtgc tgctgtagcc tcaaacataa aatataggcg cctctgatcg cactgcttca 840
gttcagacag agctaaggtc gacctgcaga tatactatat agtaatacca atactcaaga 900
ctacgaaact gatacaatct cttatcatgt gggtaatgtt ctcgatgtcg aatagccata 960
tgccggtagt tgcgatatac ataaactgat cactaattcc aaacccaccc gctttttata 1020
gtaagttttt cacccataaa taataaatac aataattaat ttctcgtaaa agtagaaaat 1080
atattctaat ttattgcacg gtaaggaagt agaatcataa agaacagtga cgcctcgagg 1140
aattcatgat ccttcaggcc cttctgtttg tgcctctcct aatctcttcg ttgtgtctcg 1200
ggaaattccc catctacaca ataccagaca aacttggtcc ttggagcccc atcgatatac 1260

-continued

```
atcacctcag ctgtccaaat aatttagttg tggaggatga agggtgcacc aatctatcag   1320
gattctctta catggaacta aaggtgggat acatctctgc cataaaagta aatgggttca   1380
cttgtaccgg tgttgtgaca gaggctgaaa cctataccaa ctttgttggt tatgtcacca   1440
ccacattcaa gaggaaacat ttccgcccta taccggatgc atgcagggct gcatacaact   1500
ggaagatggc tggtgatcct agatatgagg aatctcttca aaatccttat cctgattacc   1560
actggctacg gaccgtaaaa accactaagg agtctcttat catcatatct ccgagtgtgg   1620
ctgatttaga cccatacgac aaatcccttc attctagggt gttccctggt gggaaatgtt   1680
tgggaataac ggtttcttcc acctactgct caaccaacca tgattacacc atctggatgc   1740
ccgaggaacc aagactcggg acatcttgcg acatttttac cagcagcaaa gggaaaaagg   1800
catctaaagg aggcaagact tgcggatttg tggatgaaag gggcttgtac aagtctctaa   1860
aaggagcgtg taaactcaag ctgtgcggag ttctcggact tagacttatg gatggaacct   1920
gggtttccat tccaacatca gacgatacca aatggtgccc tccggatcaa ttggtgaatc   1980
tacatgactt tcactcagac gaaatagagc atctcgtcgt ggaggagttg gtcaagaaga   2040
gggaagagtg tttggacgca ttagagtcca tcatgaccac caaatctgta agttttagac   2100
gtctcagcta tttgagaaaa cttgtccctg ggtttggaaa ggcatacact atattcaaca   2160
agactttgat ggaggctgac gcccactaca agtcagttcg gacttggaac gagatcatcc   2220
cctccaaagg gtgtttgaaa gtcagagaga ggtgtcatcc tcctgtggac ggagtgttct   2280
tcaatggcat aattctgggt ccagacggga atgtcctgat accagagatg caatcatctc   2340
tacttcaaca acatatggag ctgttggaat cttctgtaat ccccttaatg catcccttgg   2400
cggacccgtc aacagtcttc aaggaagggg atgaagcgga ggattttgtt gaagttcacc   2460
tccctgatgt tcacaaacaa atctcagggg ttgaccttgg tctcccgagt tgggggaaat   2520
atctcctgat gattgcaggt ggtctggcga ctctagttct gataatctgc tcgatggcat   2580
gctgtagaag aaccaagcga acagagtcaa gaagacgagg ctctcgagag tcagagaaaa   2640
aggtaacggc aaccccccag actaggaaag tcgtatcttc atgggagtta tacaagagtg   2700
aaggcgatgc caggctggat tacaaggatg acgacgataa gtgagcggcc gcgccggctt   2760
catccgccgc agcataagaa aaacctgcaa cttcgcacac gcgcgcacgc acacggtcta   2820
cgtgtagtta ccctgtaaag acgggcttgc tcccgaacaa gcgctcgaag aagagcgtgc   2880
acatagcctt attgtccagc aagttgacta tctctgtaca cagcctcttg aagtacacct   2940
cgtacatgat ccgctcgttt ttatccagtc tgaaggtctt gtcgaccacg cgctcgtagg   3000
acttcacgtt cgcgatccgg cgccgccagg ggccctcctc gcacacgtac gcgaagaagt   3060
agcgctcgcc gatctcgatg gcctccgcgt tcgccgcgtt gtaccgcgtc accagcgcca   3120
cgttggggtt gtcgggggac ttgaagttct tgtggtgcgt tcggctcagc aggaaccagt   3180
ccagcggcat gctgcgcgcc tcgaactcga aggtgagctc gtcctccagc gagcgcagga   3240
tctccacgcc cacgttcccg gagccctcct ccgccagcgc gcggcagagc atgtccttgt   3300
acttgcggat catgagcttg tggaagggcg ccacgtcgcg gcgcgtctcg ctggtgccct   3360
tgctcacgcg ctcgctgccg ccgccgtcgc tcaccgcaaa cttgatcgtg gtgtacttct   3420
tcttggactg catgatcagg ttgcagtaca ccgcttcgaa ctccaccttg aagttcgcga   3480
agagcacgtg ctcgttgatc acgcgctcca gacagcgccc cacgcgccgc gagaacgcga   3540
tgtcggaggc gcccacctcc aggaacacgg agtcggtgtc gccgtaagat ctgccggtct   3600
```

-continued

```
ccctatagtg agtcgtatta atttcgataa gccaggttaa cctgcattaa tgaatcggcc   3660
aacgcgcggg gagaggcggt ttgcgtattg ggcgctcttc cgcttcctcg ctcactgact   3720
cgctgcgctc ggtcgttcgg ctgcggcgag cggtatcagc tcactcaaag gcggtaatac   3780
ggttatccac agaatcaggg gataacgcag gaaagaacat gtgagcaaaa ggccagcaaa   3840
aggccaggaa ccgtaaaaag gccgcgttgc tggcgttttt ccataggctc cgcccccctg   3900
acgagcatca caaaaatcga cgctcaagtc agaggtggcg aaacccgaca ggactataaa   3960
gataccaggc gtttccccct ggaagctccc tcgtgcgctc tcctgttccg accctgccgc   4020
ttaccggata cctgtccgcc tttctccctt cgggaagcgt ggcgctttct caatgctcac   4080
gctgtaggta tctcagttcg gtgtaggtcg ttcgctccaa gctgggctgt gtgcacgaac   4140
cccccgttca gcccgaccgc tgcgccttat ccggtaacta tcgtcttgag tccaacccgg   4200
taagacacga cttatcgcca ctggcagcag ccactggtaa caggattagc agagcgaggt   4260
atgtaggcgg tgctacagag ttcttgaagt ggtggcctaa ctacggctac actagaagga   4320
cagtatttgg tatctgcgct ctgctgaagc cagttacctt cggaaaaaga gttggtagct   4380
cttgatccgg caaacaaacc accgctggta gcggtggttt ttttgtttgc aagcagcaga   4440
ttacgcgcag aaaaaaagga tctcaagaag atcctttgat cttttctacg gggtctgacg   4500
ctcagtggaa cgaaaactca cgttaaggga ttttggtcat gagattatca aaaaggatct   4560
tcacctagat ccttttaaat taaaaatgaa gttttaaatc aatctaaagt atatatgagt   4620
aaacttggtc tgacagttac caatgcttaa tcagtgaggc acctatctca gcgatctgtc   4680
tatttcgttc atccatagtt gcctgactcc ccgtcgtgta gataactacg atacgggagg   4740
gcttaccatc tggccccagt gctgcaatga taccgcgaga cccacgctca ccggctccag   4800
atttatcagc aataaaccag ccagccggaa gggccgagcg cagaagtggt cctgcaactt   4860
tatccgcctc catccagtct attaattgtt gccgggaagc tagagtaagt agttcgccag   4920
ttaatagttt gcgcaacgtt gttgccattg ctacaggcat cgtggtgtca cgctcgtcgt   4980
ttggtatggc ttcattcagc tccggttccc aacgatcaag gcgagttaca tgatccccca   5040
tgttgtgcaa aaaagcggtt agctccttcg gtcctccgat cgttgtcaga agtaagttgg   5100
ccgcagtgtt atcactcatg gttatggcag cactgcataa ttctcttact gtcatgccat   5160
ccgtaagatg cttttctgtg actggtgagt actcaaccaa gtcattctga gaatagtgta   5220
tgcggcgacc gagttgctct tgcccggcgt caatacggga taataccgcg ccacatagca   5280
gaactttaaa agtgctcatc attggaaaac gttcttcggg gcgaaaactc tcaaggatct   5340
taccgctgtt gagatccagt tcgatgtaac ccactcgtgc acccaactga tcttcagcat   5400
cttttacttt caccagcgtt tctgggtgag caaaaacagg aaggcaaaat gccgcaaaaa   5460
agggaataag ggcgacacgg aaatgttgaa tactcatact cttccttttt caatattatt   5520
gaagcattta tcagggttat tgtctcatga gcggatacat atttgaatgt atttagaaaa   5580
ataaacaaat aggggttccg cgcacatttc cccgaaaagt gccacctgac gtctaagaaa   5640
ccattattat catgacatta acctataaaa ataggcgtat cacgaggccc tttcgtctcg   5700
cgcgtttcgg tgatgacggt gaaaacctct gacacatgca gctcccggag acggtcacag   5760
cttgtctgta agcggatgcc gggagcagac aagcccgtca gggcgcgtca gcgggtgttg   5820
gcgggtgtcg gggctggctt aactatgcgg catcagagca gattgtactg agagtgcac    5879
```

<210> SEQ ID NO 2
<211> LENGTH: 6028

<212> TYPE: DNA
<213> ORGANISM: Artificial Sequence
<220> FEATURE:
<223> OTHER INFORMATION: recombination plasmid used to generate
ORFV-121-RabV-G virus

<400> SEQUENCE: 2
gaactcgaga ctagtctgcg accgacatcg cacacatgaa ggacacaatt ggtttgttaa 60
tccggacaat gaaggacaaa ttgtttttgt taatcaggac aattggacac aatcagatta 120
atttttgtac gatcataaaa tcgatatttg atgcacatat attagtaagt atattagact 180
aaattctccg gggaggcaag cagttggata cggcggggcg gggcacgacg tgcacggaga 240
attcgggcgg gtcccccttc cccccacccc cacgcaccac gatgcgtcta atcttagcgc 300
tcgtggcctg cttgttggcg gcgccgatgc cgttatcggg tcgttcgaca agcaccccaa 360
acacacagtc cgtactcggc tcgacgagtt cggaaccaag ctcggaagac gctgtggctt 420
cgagcacaac gacaagcaca ctcacaagca ctacaagcac actcactatg tccacaagtg 480
tggacaccac tactacctcg ggcgctacga cgtccacaaa cagcactcct gcagcgagtg 540
tgagttcttc cacacccgca gccactgagg catcgacggc accaacgacg ccgtcgacgc 600
agacgacagt gaaggtaacg aaagacaaag acacgaaggc gtctgcctac ctcgttttac 660
taatcacgtt catggtcatg acaacgctag tgatggttgt ggtcgtggtc gtgatcgtgt 720
acaaacaggg actttgtgac tgctgctgta agatgtttcc ctgctgcaaa gagctcaagg 780
actacctcga cgaggaggag agcgccgggc tgtacgacgc cttgacgtgg agccgctcag 840
accccggcct ccggctcgtc gtgcgcgcgg accccagatg atgaggatcg gataagatcg 900
gcgtgttttt cccgcccgtc gcgaacatta tgcctctaaa tgccgagaat taactgaaat 960
tcaaacacgc tttgggactc aactctgtgg cccacacaac caagcttgca tgcctgcagg 1020
tcgacctgca gatatactat atagtaatac caatactcaa gactacgaaa ctgatacaat 1080
ctcttatcat gtgggtaatg ttctcgatgt cgaatagcca tatgccggta gttgcgatat 1140
acataaactg atcactaatt ccaaacccac ccgcttttta tagtaagttt ttcacccata 1200
aataataaat acaataatta atttctcgta aaagtagaaa atatattcta atttattgca 1260
cggtaaggaa gtagaatcat aaagaacagt gacgcctcga ggaattcatg atccttcagg 1320
cccttctgtt tgtgcctctc ctaatctctt cgttgtgtct cgggaaattc cccatctaca 1380
caataccaga caaacttggt ccttggagcc ccatcgatat acatcacctc agctgtccaa 1440
ataatttagt tgtggaggat gaagggtgca ccaatctatc aggattctct tacatggaac 1500
taaaggtggg atacatctct gccataaaag taaatgggtt cacttgtacc ggtgttgtga 1560
cagaggctga aacctatacc aactttgttg gttatgtcac caccacattc aagaggaaac 1620
atttccgccc tataccggat gcatgcaggg ctgcatacaa ctggaagatg gctggtgatc 1680
ctagatatga ggaatctctt caaaatcctt atcctgatta ccactggcta cggaccgtaa 1740
aaaccactaa ggagtctctt atcatcatat ctccgagtgt ggctgattta gacccatacg 1800
acaaatccct tcattctagg gtgttccctg gtgggaaatg tttgggaata acggtttctt 1860
ccacctactg ctcaaccaac catgattaca ccatctggat gcccgaggaa ccaagactcg 1920
ggacatcttg cgacattttt accagcagca aagggaaaaa ggcatctaaa ggaggcaaga 1980
cttgcggatt tgtggatgaa aggggcttgt acaagtctct aaaaggagcg tgtaaactca 2040
agctgtgcgg agttctcgga cttagactta tggatggaac ctgggtttcc attccaacat 2100
cagacgatac caaatggtgc cctccggatc aattggtgaa tctacatgac tttcactcag 2160

```
acgaaataga gcatctcgtc gtggaggagt tggtcaagaa gagggaagag tgtttggacg   2220
cattagagtc catcatgacc accaaatctg taagttttag acgtctcagc tatttgagaa   2280
aacttgtccc tgggtttgga aaggcataca ctatattcaa caagactttg atggaggctg   2340
acgcccacta caagtcagtt cggacttgga acgagatcat cccctccaaa gggtgtttga   2400
aagtcagaga gaggtgtcat cctcctgtgg acggagtgtt cttcaatggc ataattctgg   2460
gtccagacgg gaatgtcctg ataccagaga tgcaatcatc tctacttcaa caacatatgg   2520
agctgttgga atcttctgta atccccttaa tgcatccctt ggcggacccg tcaacagtct   2580
tcaaggaagg ggatgaagcg gaggattttg ttgaagttca cctccctgat gttcacaaac   2640
aaatctcagg ggttgacctt ggtctcccga gttgggggaa atatctcctg atgattgcag   2700
gtggtctggc gactctagtt ctgataatct gctcgatggc atgctgtaga agaaccaagc   2760
gaacagagtc aagaagacga ggctctcgag agtcagagaa aaaggtaacg gcaacccccc   2820
agactaggaa agtcgtatct tcatgggagt tatacaagag tgaaggcgat gccaggctgg   2880
attacaagga tgacgacgat aagtgagcgg ccgcggagca ctgctcggag gagtgctgca   2940
aagtggagga agttctgtga gaaagtgcgt tttctgtaa tgtgaaataa gatagcctta   3000
tgtgtgcaca gacatggcga acaggcttgt gtttctcgac cccgagaccc tagccgaggc   3060
cgacggcatc cccggctatg gggtgttcga gcccggcaag aagaaatgca tcttcacaaa   3120
gatccgcacc agcgtcgcac tcgcgtgccg gtacgccgtc tcggacggcg gcctcatcga   3180
cgagttcgtc atggcgacat acgggaccag acgcgcgtgc cggctcgtcc ggcacctgac   3240
gataagcgcg gagggcgtga tgacccggcc cgccagcaac tgcgcgccgc acatggtgct   3300
catctgcctc agaggcgtgg ccgccgtgtc cagcgaggac atgggcttcg gtcgctgcat   3360
catggagcgc ggcaccatgt tcatggtcaa gtccgcgcac agcgccgtcg tctgcggcaa   3420
ccccgcctgc gagctgctcg tcctcttcta cgactacttc acccccatcc cccggccgct   3480
ctccggagac gaggtgctgt tcacccgcga cctcgcgcac gtggactacg cccccgagtc   3540
ggcggtcgtc ttcaagatgg attacaacct cgagaccgac gtggccacgc tgtttgtcgg   3600
ggggtacata ttccgcgcca agggcctgat gatggagacg cgcgaacaag tgggcgacga   3660
gtgcgactgc tgccgccaca gctcgccggt gctcgtcatg gatcgcgaga agatgatgtc   3720
gtcgctgcgc atgatagatc tgccggtctc cctatagtga gtcgtattaa tttcgataag   3780
ccaggttaac ctgcattaat gaatcggcca acgcgcgggg agaggcggtt tgcgtattgg   3840
gcgctcttcc gcttcctcgc tcactgactc gctgcgctcg gtcgttcggc tgcggcgagc   3900
ggtatcagct cactcaaagg cggtaatacg gttatccaca gaatcagggg ataacgcagg   3960
aaagaacatg tgagcaaaag gccagcaaaa ggccaggaac cgtaaaaagg ccgcgttgct   4020
ggcgtttttc cataggctcc gcccccctga cgagcatcac aaaaatcgac gctcaagtca   4080
gaggtggcga aacccgacag gactataaag ataccaggcg tttccccctg gaagctccct   4140
cgtgcgctct cctgttccga ccctgccgct taccggatac ctgtccgcct ttctcccttc   4200
gggaagcgtg gcgctttctc aatgctcacg ctgtaggtat ctcagttcgg tgtaggtcgt   4260
tcgctccaag ctgggctgtg tgcacgaacc ccccgttcag cccgaccgct gcgccttatc   4320
cggtaactat cgtcttgagt ccaacccggt aagacacgac ttatcgccac tggcagcagc   4380
cactggtaac aggattagca gagcgaggta tgtaggcggt gctacagagt tcttgaagtg   4440
gtggcctaac tacggctaca ctagaaggac agtatttggt atctgcgctc tgctgaagcc   4500
```

-continued agttaccttc ggaaaaagag ttggtagctc ttgatccggc aaacaaacca ccgctggtag 4560
cggtggtttt tttgtttgca agcagcagat tacgcgcaga aaaaaaggat ctcaagaaga 4620
tcctttgatc ttttctacgg ggtctgacgc tcagtggaac gaaaactcac gttaagggat 4680
tttggtcatg agattatcaa aaaggatctt cacctagatc cttttaaatt aaaaatgaag 4740
ttttaaatca atctaaagta tatatgagta aacttggtct gacagttacc aatgcttaat 4800
cagtgaggca cctatctcag cgatctgtct atttcgttca tccatagttg cctgactccc 4860
cgtcgtgtag ataactacga tacgggaggg cttaccatct ggccccagtg ctgcaatgat 4920
accgcgagac ccacgctcac cggctccaga tttatcagca ataaaccagc cagccggaag 4980
ggccgagcgc agaagtggtc ctgcaacttt atccgcctcc atccagtcta ttaattgttg 5040
ccgggaagct agagtaagta gttcgccagt taatagtttg cgcaacgttg ttgccattgc 5100
tacaggcatc gtggtgtcac gctcgtcgtt tggtatggct tcattcagct ccggttccca 5160
acgatcaagg cgagttacat gatcccccat gttgtgcaaa aaagcggtta gctccttcgg 5220
tcctccgatc gttgtcagaa gtaagttggc cgcagtgtta tcactcatgg ttatggcagc 5280
actgcataat tctcttactg tcatgccatc cgtaagatgc ttttctgtga ctggtgagta 5340
ctcaaccaag tcattctgag aatagtgtat gcggcgaccg agttgctctt gcccggcgtc 5400
aatacgggat aataccgcgc cacatagcag aactttaaaa gtgctcatca ttggaaaacg 5460
ttcttcgggg cgaaaactct caaggatctt accgctgttg agatccagtt cgatgtaacc 5520
cactcgtgca cccaactgat cttcagcatc ttttactttc accagcgttt ctgggtgagc 5580
aaaaacagga aggcaaaatg ccgcaaaaaa gggaataagg gcgacacgga aatgttgaat 5640
actcatactc ttcctttttc aatattattg aagcatttat cagggttatt gtctcatgag 5700
cggatacata tttgaatgta tttagaaaaa taaacaaata ggggttccgc gcacatttcc 5760
ccgaaaagtg ccacctgacg tctaagaaac cattattatc atgacattaa cctataaaaa 5820
taggcgtatc acgaggccct ttcgtctcgc gcgtttcggt gatgacggtg aaaacctctg 5880
acacatgcag ctcccggaga cggtcacagc ttgtctgtaa gcggatgccg ggagcagaca 5940
agcccgtcag ggcgcgtcag cgggtgttgg cgggtgtcgg ggctggctta actatgcggc 6000
atcagagcag attgtactga gagtgcac 6028

<210> SEQ ID NO 3
<211> LENGTH: 9611
<212> TYPE: DNA
<213> ORGANISM: Artificial Sequence
<220> FEATURE:
<223> OTHER INFORMATION: recombination plasmid used to construct
ORFV-PEDV-S

<400> SEQUENCE: 3
gaactcgaga ctagtctgcg accgacatcg cacacatgaa ggacacaatt ggtttgttaa 60
tccggacaat gaaggacaaa ttgtttttgt taatcaggac aattggacac aatcagatta 120
atttttgtac gatcataaaa tcgatatttg atgcacatat attagtaagt atattagact 180
aaattctccg gggaggcaag cagttggata cggcggggcg gggcacgacg tgcacggaga 240
attcgggcgg gtccccccttc cccccacccc cacgcaccac gatgcgtcta atcttagcgc 300
tcgtggcctg cttgttggcg gcgccgatgc cgttatcggg tcgttcgaca agcaccccaa 360
acacacagtc cgtactcggc tcgacgagtt cggaaccaag ctcggaagac gctgtggctt 420
cgagcacaac gacaagcaca ctcacaagca ctacaagcac actcactatg tccacaagtg 480

```
tggacaccac tactacctcg ggcgctacga cgtccacaaa cagcactcct gcagcgagtg    540
tgagttcttc cacacccgca gccactgagg catcgacggc accaacgacg ccgtcgacgc    600
agacgacagt gaaggtaacg aaagacaaag acacgaaggc gtctgcctac ctcgttttac    660
taatcacgtt catggtcatg acaacgctag tgatggttgt ggtcgtggtc gtgatcgtgt    720
acaaacaggg actttgtgac tgctgctgta agatgtttcc ctgctgcaaa gagctcaagg    780
actacctcga cgaggaggag agcgccgggc tgtacgacgc cttgacgtgg agccgctcag    840
accccggcct ccggctcgtc gtgcgcgcgg accccagatg atgaggatcg gataagatcg    900
gcgtgttttt cccgcccgtc gcgaacatta tgcctctaaa tgccgagaat taactgaaat    960
tcaaacacgc tttgggactc aactctgtgg cccacacaac caagcttata tactatatag   1020
taataccaat actcaagact acgaaactga tacaatctct tatcatgtgg gtaatgttct   1080
cgatgtcgaa tagccatatg ccggtagttg cgatatacat aaactgatca ctaattccaa   1140
acccacccgc tttttatagt aagtttttca cccataaata ataaatacaa taattaattt   1200
ctcgtaaaag tagaaaatat attctaattt attgcacggt aaggaagtag aatcataaag   1260
aacagtgacg cctcgaggat gcatcatcac catcaccaca agtctttaac ctacttctgg   1320
ttgttcttac cagtactttc aacacttagc ctaccacaag atgtcaccag gtgctcagct   1380
aacactaatt ttaggcggtt cttttcaaaa tttaatgttc aggcgcctgc agttgttgta   1440
ctgggcggtt atctacctat tggtgaaaac cagggtgtca attcaacttg gtactgtgct   1500
ggccaacatc caactgctag tggcgttcat ggtatctttg ttagccatat tagaggtggt   1560
catggctttg agattggcat ttcgcaagag ccttttgacc ctagtggtta ccagctttat   1620
ttacataagg ctactaacgg taacactaat gctactgcgc gactgcgcat ttgccagttt   1680
cctagcatta aaacattggg ccccactgct aataatgatg ttacaacagg tcgtaattgc   1740
ctatttaaca aagccatccc agctcatatg agtgaacata gtgttgtcgg cataacatgg   1800
gataatgatc gtgtcactgt cttttctgac aaaatctatt acttctattt taaaaatgat   1860
tggtcccgtg ttgcgacaaa gtgttacaac agtggaggtt gtgctatgca atatgtttac   1920
gaacccacct attacatgct taatgttaca agtgctggtg aggatggtat ttcttatcaa   1980
ccctgtacag ctaattgcat tggttatgct gccaatgtat ttgctactga gcccaatggc   2040
cacataccag aaggttttag ttttaataat tggtttcttt tgtccaatga ttccactttg   2100
gtgcatggta aggtggtttc caaccaacca ttgttggtca attgtctttt ggccattcct   2160
aagatttatg gactaggcca atttttctcc tttaatcaaa cgatcgatgg tgtttgtaat   2220
ggagctgctg tgcagcgtgc accagaggct ctgaggttta atattaatga catctctgtc   2280
attcttgctg aaggctcaat tgtacttcat actgctttag gaacaaactt ctcttttgtt   2340
tgcagtaatt cctcaaatcc tcacttagcc accttcgcca tacctctggg tgctacccaa   2400
gtaccttatt attgttttct taaagtggat acttacaact ccactgttta taaatttttg   2460
gctgttttac ctcctaccgt cagggaaatt gtcatcacca agtatggtga tgtttatgtc   2520
aatgggtttg gatacttgca tctcggtttg ttggatgctg tcacaattaa tttcactggt   2580
catggcactg acgatgatgt ttctggtttt tggaccatag catcgactaa ttttgttgat   2640
gcactcatcg aagttcaagg aaccgccatt cagcgtattc tttattgtga tgatcctgtt   2700
agccaactca agtgttctca ggttgctttt gaccttgacg atggttttta cactatttct   2760
tctagaaacc ttctgagtca tgaacagcca atttcttttg ttactctgcc atcatttaat   2820
gatcattctt ttgttaacat tactgtatct gcttcctttg gtggtcatag tggtgccaac   2880
```

-continued

```
cttattgcat ctgacactac tatcaatggg tttagttctt tctgtgttga cactagacaa   2940
tttaccattt cactgtttta taacgttaca aacagttatg gttatgtgtc taaatcacag   3000
gacagtaatt gccctttcac cttgcaatct gttaatgatt acctgtcttt tagcaaattt   3060
tgtgtttcca ccagcctttt ggctagtgcc tgtaccattg atctttttgg ttaccctgag   3120
tttggtagtg gtgttaagtt tacgtccctt tactttcaat tcacaaaggg tgagttgatt   3180
actggcacgc ctaaaccatt tgaaggtgtc acggacgttt cttttatgac tctggatgtg   3240
tgtaccaagt atactatcta tggctttaaa ggtgagggta tcattaccct tacaaattct   3300
agctttttgg caggtgttta ttacacatct gattctggac agttgttagc ctttaagaat   3360
gtcacaagtg gtgctgttta ttctgttacg ccatgttctt tttcagagca ggctgcatat   3420
gttgatgatg atatagtggg tgttatttct agtttgtcta gctccacttt taacagtact   3480
agggagttgc ctggtttctt ctaccattct aatgatggct ctaattgtac agagcctgtg   3540
ttggtgtata gtaacatagg tgtttgtaaa tctggcagta ttggctacgt cccatctcag   3600
tctggccaag tcaagattgc acccacggtt actgggaata ttagtattcc caccaacttt   3660
agtatgagta ttaggacaga atatttacag ctttacaaca cgcctgttag tgttgattgt   3720
gccacatatg tttgtaatgg taactctcgt tgtaaacaat tactcaccca gtacactgca   3780
gcatgtaaga ccatagagtc agcattacaa ctcagcgcta ggcttgagtc tgttgaagtt   3840
aactctatgc ttactatttc tgatgaggct ctacagttag ctaccattag ttcgtttaat   3900
ggtgatggat ataattttac taatgtgctg ggtgtttctg tgtatgatcc tgcaagtggc   3960
agggtggtac aaaaaaggtc ttttattgaa gacctgcttt ttaataaagt ggttactaat   4020
ggccttggta ctgttgatga agactataag cgctgttcta atggtcgctc tgtggctgat   4080
ctagtctgtg cacagtatta ctctggtgtc atggtactac ctggtgttgt tgacgctgag   4140
aaacttcaca tgtatagtgc gtctctcatc ggtggtatgg tgctaggagg ttttacttct   4200
gcagcggcat tgccttttag ctatgctgtt caagctagac tcaattatct tgctctacag   4260
acggatgttc tacagcggaa ccagcaattg cttgctgagt cttttaactc tgctattggt   4320
aatataactt cagcctttga gagtgttaaa gaggctatta gtcaaacttc caagggtttg   4380
aacactgtgg ctcatgcgct tactaaggtt caagaggttg ttaactcgca gggtgcagct   4440
ttgactcaac ttaccgtaca gctgcaacac aacttccaag ccatttctag ttctattgat   4500
gacatttact ctcgactgga cattctttca gccgatgctc aggttgaccg tctcatcacc   4560
ggcagattat cagcacttaa tgcttttgtt gctcaaaccc tcactaagta tactgaggtt   4620
caggctagca ggaagttagc acagcaaaag gttaatgagt gcgttaaatc gcaatctcag   4680
cgttatggtt tttgtggtgg tgatggcgag cacattttct ctctggtaca ggcagcacct   4740
cagggcctgc tgtttttaca tacagtactt gtaccgagtg attttgtaga tgttattgcc   4800
atcgctggct tatgcgttaa cgatgaaatt gccttgactc tacgtgagcc tggcttagtc   4860
ttgtttacgc atgaacttca aaatcatact gcgacggaat attttgtttc atcgcgacgt   4920
atgtttgaac ctagaaaacc taccgttagt gattttgttc aaattgagag ttgtgtggtc   4980
acctatgtca atttgactag agaccaacta ccagatgtaa tcccagatta catcgatgtt   5040
aacaaaacac ttgatgagat tttagcttct ctgcccaata gaactggtcc aagtcttcct   5100
ttagatgttt ttaatgccac ttatcttaat ctcactggtg aaattgcaga tttagagcag   5160
cgttcagagt ctctccgtaa tactacagag gagctccaaa gtcttatata taatatcaac   5220
```

-continued

```
aacacacttg ttgaccttga gtggctcaac cgagttgaga catatatcaa gtggccgtgg   5280
tgggtttggt tgattatttt cattgttctc atctttgttg tgtcattact tgtgttctgc   5340
tgcatttcca cgggttgttg tggatgctgc ggctgctgct gtgcttgttt ctcaggttgt   5400
tgtaggggtc ctagacttca accttacgaa gtttttgaaa aggtccacgt gcagcatcat   5460
caccatcacc actgagtcga cctgcagata tactatatag taataccaat actcaagact   5520
acgaaactga tacaatctct tatcatgtgg gtaatgttct cgatgtcgaa tagccatatg   5580
ccggtagttg cgatatacat aaactgatca ctaattccaa acccacccgc tttttatagt   5640
aagtttttca cccataaata ataaatacaa taattaattt ctcgtaaaag tagaaaatat   5700
attctaattt attgcacggt aaggaagtag aatcataaag aacagtgacg cctcgaggaa   5760
ttcgccacca tggtgagcaa gggcgaggag ctgttcaccg gggtggtgcc catcctggtc   5820
gagctggacg gcgacgtaaa cggccacaag ttcagcgtgt ccggcgaggg cgagggcgat   5880
gccacctacg gcaagctgac cctgaagttc atctgcacca ccggcaagct gcccgtgccc   5940
tggcccaccc tcgtgaccac cctgacctac ggcgtgcagt gcttcagccg ctaccccgac   6000
cacatgaagc agcacgactt cttcaagtcc gccatgcccg aaggctacgt ccaggagcgc   6060
accatcttct tcaaggacga cggcaactac aagacccgcg ccgaggtgaa gttcgagggc   6120
gacaccctgg tgaaccgcat cgagctgaag ggcatcgact tcaaggagga cggcaacatc   6180
ctggggcaca agctggagta caactacaac agccacaacg tctatatcat ggccgacaag   6240
cagaagaacg gcatcaaggt gaacttcaag atccgccaca acatcgagga cggcagcgtg   6300
cagctcgccg accactacca gcagaacacc cccatcggcg acggccccgt gctgctgccc   6360
gacaaccact acctgagcac ccagtccgcc ctgagcaaag accccaacga gaagcgcgat   6420
cacatggtcc tgctggagtt cgtgaccgcc gccgggatca ctctcggcat ggacgagctg   6480
tacaagtaag cggccgcgga gcactgctcg gaggagtgct gcaaagtgga ggaagttctg   6540
tgagaaagtg cgtttttctg taatgtgaaa taagatagcc ttatgtgtgc acagacatgg   6600
cgaacaggct tgtgtttctc gaccccgaga ccctagccga ggccgacggc atccccggct   6660
atggggtgtt cgagcccggc aagaagaaat gcatcttcac aaagatccgc accagcgtcg   6720
cactcgcgtg ccggtacgcc gtctcggacg gcggcctcat cgacgagttc gtcatggcga   6780
catacgggac cagacgcgcg tgccggctcg tccggcacct gacgataagc gcggagggcg   6840
tgatgacccg gcccgccagc aactgcgcgc cgcacatggt gctcatctgc ctcagaggcg   6900
tggccgccgt gtccagcgag gacatgggct tcggtcgctg catcatggag cgcggcacca   6960
tgttcatggt caagtccgcg cacagcgccg tcgtctgcgg caaccccgcc tgcgagctgc   7020
tcgtcctctt ctacgactac ttcacccccca tcccccggcc gctctccgga gacgaggtgc   7080
tgttcacccg cgacctcgcg cacgtggact acgcccccga gtcggcggtc gtcttcaaga   7140
tggattacaa cctcgagacc gacgtggcca cgctgtttgt cggggggtac atattccgcg   7200
ccaagggcct gatgatggag acgcgcgaac aagtgggcga cgagtgcgac tgctgccgcc   7260
acagctcgcc ggtgctcgtc atggatcgcg agaagatgat gtcgtcgctg cgcatgatag   7320
atctgccggt ctccctatag tgagtcgtat taatttcgat aagccaggtt aacctgcatt   7380
aatgaatcgg ccaacgcgcg gggagaggcg gtttgcgtat tgggcgctct tccgcttcct   7440
cgctcactga ctcgctgcgc tcggtcgttc ggctgcggcg agcggtatca gctcactcaa   7500
aggcggtaat acggttatcc acagaatcag gggataacgc aggaaagaac atgtgagcaa   7560
aaggccagca aaaggccagg aaccgtaaaa aggccgcgtt gctggcgttt ttccataggc   7620
```

tccgcccccc tgacgagcat cacaaaaatc gacgctcaag tcagaggtgg cgaaacccga 7680
caggactata aagataccag gcgtttcccc ctggaagctc cctcgtgcgc tctcctgttc 7740
cgaccctgcc gcttaccgga tacctgtccg cctttctccc ttcgggaagc gtggcgcttt 7800
ctcaatgctc acgctgtagg tatctcagtt cggtgtaggt cgttcgctcc aagctgggct 7860
gtgtgcacga accccccgtt cagcccgacc gctgcgcctt atccggtaac tatcgtcttg 7920
agtccaaccc ggtaagacac gacttatcgc cactggcagc agccactggt aacaggatta 7980
gcagagcgag gtatgtaggc ggtgctacag agttcttgaa gtggtggcct aactacggct 8040
acactagaag gacagtattt ggtatctgcg ctctgctgaa gccagttacc ttcggaaaaa 8100
gagttggtag ctcttgatcc ggcaaacaaa ccaccgctgg tagcggtggt ttttttgttt 8160
gcaagcagca gattacgcgc agaaaaaaag gatctcaaga agatcctttg atcttttcta 8220
cggggtctga cgctcagtgg aacgaaaact cacgttaagg gattttggtc atgagattat 8280
caaaaaggat cttcacctag atccttttaa attaaaaatg aagttttaaa tcaatctaaa 8340
gtatatatga gtaaacttgg tctgacagtt accaatgctt aatcagtgag gcacctatct 8400
cagcgatctg tctatttcgt tcatccatag ttgcctgact ccccgtcgtg tagataacta 8460
cgatacggga gggcttacca tctggcccca gtgctgcaat gataccgcga gacccacgct 8520
caccggctcc agatttatca gcaataaacc agccagccgg aagggccgag cgcagaagtg 8580
gtcctgcaac tttatccgcc tccatccagt ctattaattg ttgccgggaa gctagagtaa 8640
gtagttcgcc agttaatagt ttgcgcaacg ttgttgccat tgctacaggc atcgtggtgt 8700
cacgctcgtc gtttggtatg gcttcattca gctccggttc ccaacgatca aggcgagtta 8760
catgatcccc catgttgtgc aaaaaagcgg ttagctcctt cggtcctccg atcgttgtca 8820
gaagtaagtt ggccgcagtg ttatcactca tggttatggc agcactgcat aattctctta 8880
ctgtcatgcc atccgtaaga tgcttttctg tgactggtga gtactcaacc aagtcattct 8940
gagaatagtg tatgcggcga ccgagttgct cttgcccggc gtcaatacgg gataataccg 9000
cgccacatag cagaacttta aaagtgctca tcattggaaa acgttcttcg gggcgaaaac 9060
tctcaaggat cttaccgctg ttgagatcca gttcgatgta acccactcgt gcacccaact 9120
gatcttcagc atcttttact ttcaccagcg tttctgggtg agcaaaaaca ggaaggcaaa 9180
atgccgcaaa aaagggaata agggcgacac ggaaatgttg aatactcata ctcttccttt 9240
ttcaatatta ttgaagcatt tatcagggtt attgtctcat gagcggatac atatttgaat 9300
gtatttagaa aaataaacaa ataggggttc cgcgcacatt tccccgaaaa gtgccacctg 9360
acgtctaaga aaccattatt atcatgacat taacctataa aaataggcgt atcacgaggc 9420
cctttcgtct cgcgcgtttc ggtgatgacg gtgaaaacct ctgacacatg cagctcccgg 9480
agacggtcac agcttgtctg taagcggatg ccgggagcag acaagcccgt cagggcgcgt 9540
cagcgggtgt tggcgggtgt cggggctggc ttaactatgc ggcatcagag cagattgtac 9600
tgagagtgca c 9611

<210> SEQ ID NO 4
<211> LENGTH: 137877
<212> TYPE: DNA
<213> ORGANISM: Artificial Sequence
<220> FEATURE:
<223> OTHER INFORMATION: Recombinant OVRF -024-RabV-G Complete Genome

<400> SEQUENCE: 4

```
cgagaacgcg gaccaggagt tcctgcggga ggagctacgg cagaggctgg aactgctgaa     60
tgctttcgag gacgggcgtc cgcgggaacg cgactccgcg gaggcggcac cccgcagccg    120
cgagacctcg ctctagagtc agggagtccg ggagtcaggg agtcaggagc ccgggagaca    180
gaagtcaagt agtcgggtag acaggagtca ggtggtcggg tgacccgccg tccgagtccc    240
gcaaaaagtt tttataaagt tttcgggaga ggccgaccgc cttccacggt tccgcggaaa    300
agtttttata aaaagttttc gggagaggcc gactccttcc aacgtttcct cctctcgcgt    360
gccgcgggcg gccgctctcc cgcgacggtc ccgccaacgc gtttacaaag ttttaaaagt    420
tttcgagaga ggccgacctg tcttccaacg gttgcgcgaa aaggttctgc ggaggtttgg    480
aagagccgcc cgccctccga catcctccga aaagttttcg caaaagtttt taaaggtttc    540
gcgaggagtt ttcgagggag gcgacctgcc ttcgaggttc cgcgtaaacg tttttacaaa    600
gcgtcggaga ggtgggggcg acctgcccct cctccgaaaa gctcttgaga gtgttcggga    660
gaggcggccg gccttcgcgg tcgcgcgaaa aggttctgcg ggagttcgcg ggagccgccc    720
gccctccgcg cccctccgaa aagtttttgc acgaagtctt ttggcgttct cgagaggacg    780
cctaccccga cggtaacgcg gaacgtctcg ggaggtcggc ctctccgctc ccgcggtcgc    840
gggcggcggc ccgtctccag aggctccgcg aaaaagtttt ataaaagttt tggagaggta    900
cctgacctcc taaagttttc agagagttct cgcaaaagtt ttgggaggtc gacctgacct    960
cctaaagtta tcgaagagtt ctcgcaaaga gtttgagagg ccgacctgcc tccaacggtt   1020
ccgctaaaaa gttttataaa agttttgagg gaggtcgacc tgcctccaac ggttccgcta   1080
aaaagtttta taaaagtttt gagggaggtc gacctactct cgaggttccg cgaaaagttt   1140
tataaaaagt tttacaaag tttttgaggg aggtcgacta cccccggatc ctccgcctcg   1200
cgtgccgcgg gcggccgtcc aagagtttac ggaacgtttt ggagaggaga ggccgacctc   1260
ccaaagattt tgcggaacgt tttggagagg aggactggcc tccgaaaaga tcttacaaag   1320
agtttggagg gaggactggc ctccagaggc tccgcgaaaa agttttgcaa agtttggaga   1380
gaggtcgacc acccccgagg ttccgcgaaa gtgtttgcgg agagtccgag agaggcagac   1440
actgcctgcg aaaagttttc gcggacgggt tgagcgggtc accgacctcc gaacagttta   1500
caaacgtttt acggagagtt gagaggcagg ccgacccgac agtttagttt tggaaggacg   1560
aacctgtcac gggaaaagtt tacgaagagt tttgggagag gccgactgtt agccgagcgc   1620
gcgcgagcga gttcacgttc tctcgctcgt gtgcgggtta actcgctcac tggttctcct   1680
ctctaactcg gaggggcgag cgagtggttg actcgccctc ctctcactct gagtgagtga   1740
taactaaccg ttaactatta actcgtcctc cactctctcg ctctgagtga ggattgactt   1800
gttaactcgt cctcactctc tcgctctctc actctgagtg gtgagagatt aactgttcaa   1860
ctcgttagct cgtcctctgc ctctcactcc aagactgagt gggtgcgttg actgctcttg   1920
ttcccttact ccgaggggcg attgagtgag caacagctac tcgttctctc gttctctcac   1980
accgagtgag cgagtgagta agttaactcg ttctctcgtt ctctcgttct attttccgag   2040
gagtgagcga gtgatgtaac ggttacttgt tacttgttat ctgttccctt acctcggcga   2100
gtggtgcgtc aacttgttct cgtgagcgag tacggtcact tgttttctcg tctctgcctc   2160
gagagtggtc aacttgttct cgtgagtgag ttgacgttaa ctgttgttcc cttacctcgt   2220
gagtgagcgg ttgcttgttc tcgtgggtga gttaaccgcg ttcccttacc ggagtgagcg   2280
ggcggcgata aaaataatta attgactgat tcgctcgttc acgagcgaag ggcggcgcaa   2340
ggggcgcggg atgctggtct aatctactaa ggccgaatac aaaaacggat gggagaccgg   2400
```

-continued

```
ggagagggtc acagctccga gcggtgcatc tgcgccagct ggcggcgcca ctcggccgcg   2460
ggccgcgtgg ccgcccaggc cgcgttgtag ccgcccgcca ccgcgacgca ggtcagctcg   2520
aactccggcg cgagctcgcg cacgtcgtag atgtgcacgg tcgcgacgtt cagcagcagc   2580
gcgcccttgc gcagcgaggc gaaggtcgcg tgcatgccgg cggcgagcgg gtacaccggc   2640
gagagcgtcc cgccgccgtg cgcgaccacc gccatgtgcc gcccgtcgcc gccgacggtc   2700
aggcaggtca ccgaggcgga gccgttcgcg cggacggggc ccgcctccac gagggcggcc   2760
ggcagcggcg gcgccgcggg gcggaagagc ccgccgagga ggaagcccag cgccaccagc   2820
gcgagcgcgc cgagcagcct gcgcggcgag gggtgcatgc ttgctggctg tggtgtggag   2880
ggcgggtgtg ggtgtccgcg gctgtggcgg gagggtctcg actgctaggc ggtccttttt   2940
cactttgcgc cgtggcgcct cctccgcagg cgaagggctg cggcgggccc gggccgggcc   3000
gctaccccgc cgcgcggccc gcggccgcca gcgccgcggc cagccgccgc caccgcgcgc   3060
ccgccgcgag cagcagcccc gccgccgagc gccccgcgcc gccgcgggcg cgcgccgagg   3120
ccgcggcccc gcgccgcgcc agcagcagcg gcagccgcgc gtccagcggg ccgccgcggc   3180
gcagcgccgc gcgcagcagc gccgccagcg gcagccgccc cgccgcgtcc gggcccgccg   3240
cgcgcgcgcc cgccgccagc agcgcgcgca ccagcgccgg cgaggggcgc cgcgcgcgga   3300
ccaggtgctc cacgagcagg gtggtgagca aggattctcg agaagtagga gtcatgtgtg   3360
acgacaagga gagacgttat attaggcgcg tcctacttca ctttgaagat ggtgtaaagt   3420
gttaaaactt gaacaccgtt cactctacca ctgccgttac cgtgtcctgc cccaaaagcg   3480
accacagtgc tttttccacc acctgttcca aatccgttcc aaaagctccc atccattgtt   3540
gttagaactt tcagatgttt ctctaggttg tttagttcca ctgcaagttt tgaccattat   3600
cgttactgga catgctgttg gtaatgagtt taataaccaa tcataaaaat agttataatt   3660
tgttataatt tataatttgt tataaagcta taaagtagca aacactttaa tgttatattt   3720
tgcctaaccc tccgttaaca ccaccattaa caccaccact taagctttta ctaccaccac   3780
taccacctcc aacacacatt cttttctcta aaggtcccca aattccacct cctgaacttg   3840
gacgttttac agcacctccg ggtgtacttg cgtacccttt agaagttcca ctgtgactgt   3900
agatatgata ctgtccttct ccaggcatga ttaaagtgtg ttgtaattag tgttatctac   3960
acaactgtgt gagacgctca aataaaaaga agctacattt tacaattttg attagctgat   4020
gtaccacgct gtatcgcggc caccacaaga acccaatcca gtagaaccaa atccagagtc   4080
gccgcggtcg gtgttgtcca agcagttaac ctcttgaact gctgggcacg atatgcgttc   4140
gcatattagc tgagctatcc tgtctccctt cttaacctca aagtcgctgt ttccgaagtt   4200
aaacagcacc actccgacgt tgcctcggta gtcttcgtcg atcacgccag cgcccacgtc   4260
gataaagtgt ttgactgcaa ggccagaacg tggtgctatg cgtccgtagc aaccagaagg   4320
gggctttatc agaaggtcag taaatactac gcgactgcaa tgcgaaggga tgacacagtc   4380
gtgtgcacta cataggtcta atcctgcggc accaggagat cctctggctg gtatagtggc   4440
gttttggctg aggcgaacaa cctgaagagt ttccgtgtgg cagaactcca tggctagggt   4500
ggcgagcggc cgatcgacta cggggtgtac aatttacact ttctccagaa aaatcagggg   4560
cgggtcagca tggcgcggcg caggtccagc agcgagtcgt acgacaggaa gcacaggatg   4620
gaggtcacga tctccggcgg cagggcgcac gggcacatga ggccggcgat ctgctcggcc   4680
agcgagacgc gcagccgcat catgcagatc ttgccgaaga gcgccgtccc gtagatgggg   4740
```

-continued

```
aactcggccg cgcgctccaa aaaggcgttc tgcacgaaga gcgccttcgc gtcgtccgcc   4800
gcgcgcagca cgtccagcag cgtcgcgtcc gtgtggcagc gcaccgcgcg catgctcgcg   4860
atctcctgct cgcacgcgcg gattacggtc gcgtagtccg ccagcgcgcg ctccgccagc   4920
atgcgcgcgc cctcgccgcg cagcgccagc tcctgcacgc acagcagcgc ggcctccgag   4980
cgtcggaaca cgtggcccca ttgctcggat gtgatcagcg cgcgcgcgag cagctccgtc   5040
ggcgggcggc gcgcgagcac ggccgccgtc gcgcgcacgt tgttgcggcg cagcatctcg   5100
gagaccgcgc ataggcccga ggccgacatg tgctcgagct ccgcgcccat gcgcaccagc   5160
cggcagcagg cgccgtggct gaacaccgcc gcgcggtgca gcgcggtctg caggttgttg   5220
ttgcgcaggt tcaggtccag cccgcgctcg agcacgaagt ccacgacgcc gcctcgcagc   5280
tcccgtaggt cgccatgtag tgcagcatgg tgttcccgca cgcgtctacg gcggccgggt   5340
ccacgcccgt gagcgtgcgc accatgccct cggagatctt ggccgtgcgc gcgaggtggt   5400
gcagcgttgt gcgcccgtac gcgtccacga cgcacgcgtc cgcgcccgcg cgcagcatca   5460
tgtccacgag cgcggcggag acgccgccgg agcacagcag cgccgccagc ggcgtcaagc   5520
cgttgcagtc gcaggcgttt gggttcgcgc cgcgctcgag cagcagccgc agcacgtcct   5580
cgcggatcca ctggttcttg gcgtacacgt gcagcggcgt tacgccgtag gtgttgccct   5640
cgttcacgcg cgcgcccgcg tccagcagca gccgcgcgac ctcgagctcg gcgccgtcgg   5700
ggccgcagaa agccaggaag gaggagagca cgctgtcgca gacgacgacg ctggcgtcgc   5760
agaccacgtc cgcgcccgcc tccagcatga gcgcgaccac ctccggccgc acgccgtcgt   5820
actgcacgta ggcgtgcagc ggcgtgcggc cgcaggagtc cttggctttc acgtccgcac   5880
cggcctccag cagcacgcgc acgatctccg cgcactgctc gtgccgcgcg aagtgcacgc   5940
agaggtgcag cggcgtgcgc ccgtgctcgc cgcggaagtt cacgtccgcg tcggtggcca   6000
cgagcgcgcg gaccgtttcg aggtccacct gcccggactc caggtagcgg aagagcaggt   6060
ccgcgtgcgg gaccacgacg gactcccgcg agagcatggc ggcgtttaca aatattgaaa   6120
tctttttca ctcatcttta tgggcgctgg atgcgcaata agggtgggag taaaaaactt   6180
ctacaaaaag cgtacaaaag gtacaaaagg cggggcgggg acgggctggc agtgggtgct   6240
gcgggccgaa ttggtctcta cacggggacg ccctcgccgg agccggtgag ccggtagccg   6300
gcgccggcga tcatggtcaa gcgctgcacg agctcgttgc gcttgacgcc ggcctctgaa   6360
acgcacacca tgtggtggat gtaccgctcg atgcactcgc agcgcgggag agtggagtca   6420
agatcggatg cgagttgcag aatgtcatcc cagagctcgg agaacttgct gtacagttct   6480
cggaggtctc tctccatgcg agccataaga gagtcaggat gcggcgttcc ttcgggggtc   6540
tgagcgaaca ccgcgaacag gctggttatg ccgtgttcca gaatagagtg gttccgtgtc   6600
aatgccgcag acaagggtcg tcgtccgcgc aacgactggc ggcagagcgc tgtttgtgcc   6660
gcaccgccca ttcctctggc gatcgcgtcc accgacgcag tgatcatctg cgcgccgacg   6720
tcattgtagc gcgcgttaaa ctcagtaatc atgattacga gattgcagat ttcatagtag   6780
cacttttcca agtcgacgcg cagtttcacg atctggttga caatcttgca cgcctttcgc   6840
cgcgtctccg ccacgttggc gactcggact tgcgcttcct ggtcgatgga cggcggaaac   6900
acttcaaacc caaggtcgca cagttcagcg gtggggacta gcgtcacgat gatgtactcc   6960
gcgtcgccac ccacttgcgg caggaagaac accgaccgcg cggcgggaac gaccagaacg   7020
tcgccttcct gcatgttagt ttttagaaac ttagtgttgt tcacggagat gccggccatg   7080
ccctcgtttt ttacacatat tatggtgacg tacgcggcga ccgtgggggc catgtggtgg   7140
```

-continued cgcatgtacc actcgtcgtg cttgagtttc agaccgtgag attcgccgac ctcgaagtgc 7200
atgttggcgt ctctgacgta gcgcgagaac tcgctgcgac agattcgggc gggcgcccgg 7260
tggaacgtcg actcgaagag actgatgtct gtccattcgc ccacatgagt gaccaccgaa 7320
gaagtgtttt cgatccgagt ctcgaacacc gagtccacga gcaccggaca gttggttccg 7380
ggcaccgtca gcaccaaggg ccgcgcctcc acgggggcga cggacgaggc cacggagtcg 7440
gtgtccccgt acccgtagtc gtcgtcggag tcgccgcctc cgtcggcccc gtcgcgcggc 7500
ctccgcagcg gcatgcagcc ggcggtggga acgcactggt ttcggccacg gccgaagcgg 7560
ccaaacagtc tcgccagggc tgacatcctt ggacggccac accaaaacca aaaaaacata 7620
ttttatcagt tatttgtcga ttttcaccgg ctcaccgagg gcaggacctc ctggatcccg 7680
gacacccccg ccaggcagcg ggccgcgcgc tcgcgcaccc agaagcggtc gtagccgtgc 7740
cggagcacga aggccgccgt ggcgtggcag tccacgcgct cgatgaagcc gtggacggcg 7800
cggcgcgcgt agctcgccgc gaaggcgcgg accaccgccg agcagcgccc cgagggcgag 7860
tcgtccgtct ccagcgccag cggcatgctc gcgatgcgcg acatcaggtt ggaggtctgc 7920
gggatgttga gctcgcgcgt ggcggtcatc tgcgcctcga gcccggcctt gagcacctcg 7980
tcgcagcggc cccactccag cgcgcagacc acgcggatct cgtacccctt gagccgcagc 8040
gcggtctcga tgtccacgga ggtgagcacc gcgctgaagc gcaggctctc ctcgtccgcg 8100
gggtcgaaga gcacggggat cttaacctcc gcgctgcgcg tgacctcgca gagcgcgatc 8160
gcgagcagcc cgcgcgtgag cttgctcacc acgcgcggct tgcccacggg gtacactggc 8220
tcgcgacctc gcgcagcggg tacgccagtc tgaagcagcg cgcgtccgcg ggcaccgggc 8280
tcgcgcccca tgttcagcgc ggagaagtgc accgggcagg cggcgcagcc gcgcgcggcg 8340
ttcgcgagca ccatctcgcg cagcccgcgg aaggccgcca tgtcgcagga ggggaagatg 8400
cgcgcgagcg cggcctggtg cgcgagcgcc gcgtccgaga gcgcctgcgc ggccgcggcg 8460
gcggcctcct cggcggcggc cgcgctctcg tccgcggaga ccacgtcttc gggcacgtcc 8520
acgcagacgc cgccccagaa ctcgcagtac tcggagaaga gcgtcgcggg cgcaaagcgc 8580
gcgaggtcca cgaaggcgac gcggttgccg agcctggaga gcagcgtgtt ctccgagatg 8640
cgcgtccagc ccttgccggc gagctccatg acctgccgcg tgtcgaagaa ggagctgtag 8700
aagccgtaca cggtgatgtt ttccttgcac gtcgtcagcc acatgaggaa gtcgcgcacc 8760
accagcttcg cgcagtcgcc ggagaacacg gggccggcgt tcgtcgcgat ggagttcagg 8820
cgcacggtgc cgtcgctgcc gaagcggtac acgaaccagg cggccacgct gttgccggag 8880
ggcgcgtgaa cgtgtggctg cgcccaggag tcggcgctcg cggcggtgcg cacgtcgtgc 8940
gagagcacct cggtgtcggg gcgcgagtag gtgctggggt ctttgatcca gatggcgtag 9000
ctgcccacgc agcacacgtt catgaggtcg agcagcgtct gccggcgcag cggcgtgccg 9060
agccggcgca cggcgtcgtg cgagaccatg cgcaggtcgt agaggcccac gtccgagagc 9120
cactggttga gctcgtccat ggacagggcg tcgcgggggg gcgggctgtc ttcgaaggcg 9180
gcgcggagct cgggctccgt ctccgcgcgc tgccgcagga tgtccaggaa ggggctggag 9240
gagtcgggga tgtagcagtc ggggtcgtgc ctggacacta tagcgaaccg ctgcgtcgcg 9300
ggcgcgggcg gcggggctag cgcgtcggcg cgtgcgtcga tgaaggtgca cgatatacgc 9360
acggacttga gcgaggggag gacgaccgcg gcggcgcgcg cgccctccgc gtcgaagatc 9420
atcgtctttc cgtccctcgc cttcgcgagc gcgtattctc caggcacgag gtccgtcggc 9480

```
ggcggctcgt cccaggcctg ccggtcaggg acgccgccgc acacctttcc ccagaacccc   9540
agcatcctcc aaaataccta ataaggacgg ccaatagcgg ggcttgcggg cgttcggacc   9600
ttccgcgctt taattttaat ttattggctt gcagaactcc gagcgccagt cccgctcgaa   9660
gaccgcggac aggtccttga cgatgtcgcc cttctcggcg ttcacgctca cgaaggcgtg   9720
gtagcggtag tgcgtgccgt cgaggttggc gaccgtgagg tgcgcgaagg tgtcgtccac   9780
gatgagcagc ttagtgttgt tcgcggcgtc gtcccggccg ggtaccacga acttgcgcac   9840
ggacatgtcc acgctgccga cgccaaagtc gtcgaggctg cgcgcggccg agaccgacag   9900
cgggtccgcg ttcttccact cggtaatgat cacgcgcacg cgcacgccgc ggtcgatggc   9960
cgcgcgcagc agcgcgtcta tgatccgcgg ccagtactcc acggcgctgg cgtgcttgat  10020
caccggcacc atagagagca gcgagaggtc gatgctgttc ttggcgttct cgatgcggtg  10080
cagcacgagg tcctcgtcga gcgtgcggta gaagcctagg aagcgctccg gcgagtccga  10140
gaagaatacg ccgcccccgg agtggtcgag gtggaagttc gtggccgtgg gcgtgacgac  10200
ggcgcagcag agccgcgtga acggcacctt cggctccacg atcatggagt agaaggtgtt  10260
gtagcggttc atgaggtccc aggccaggtg cttgttggtg gagtagagcc cgaggttctt  10320
gatggtggac acggacccgc ccgtgagcga ggcgctgccc acgtaccagt gcccggcgtc  10380
cgagagccag aagctgccga gcaggttgcc gacgccttcc cgcgtggaca ccttgacctt  10440
gtagtagttg acgcccgcct cgcgcagctc gtccgcgtcc ttgtccttgc tctgcacgtc  10500
cacgagcagc gtgacgttca cgccctcctt ggcgagcgtg cagagcttgt ccttgacgtc  10560
gacgccctcc ttggtggagc tcaggttgca gcagaagctg cagatgtaca aaaacttctt  10620
cgcggactcg gtgatggcgg tgaagcagtc gagggtgctc atgttgccct gcgccaggga  10680
cgccacctct gcgggcagcg tctccacgac gcggcagtcg gcgcccaggg ggatggagga  10740
gaacggccac atttatttat ctcacaaaaa taatagggct tcagggaaag tcttttagca  10800
ggcgggcgag ttcttcgagt tcccttagga gttcttccat ttcttcggaa gtcagcaact  10860
ggagctcgga ctttagttga atatcttcga ggaaaccgtc tagcatgttc gccatgtctt  10920
ccggggagca ctgcgccaca tcttcgggga caggatcggg tgtgggcatt aggtctccgc  10980
ttacttgaac gtcgtccatc atcctgtcga tgaggtcttc gacttctaga cggggtccgt  11040
agatcagcat atttggtgat ggaggtagtt taaggtgcga gagttagtgt tatacgacgg  11100
ccaacgtgtg tttatcgcgc gtacattttc aataataaca aactcccctt cctgcgcctg  11160
ctcgagaagc agctcgtcca gctcctcctg tcggcgcgcg gccacgcact ccgcacagac  11220
ccaggacgcc gaacaccacc gccgccgaga tcgacagacc cagcagcacc gacatcctca  11280
cgcgggcatc cggctattta atcgttctgg aaacgtatta atatgggcgt cgtcatgtgc  11340
gggtgtctgt ttgtgtgggc gggctggatc gcgcgccgcg tgcgcggctt ctgcgtggcg  11400
ctgcgccaga gggtgtcgcg cgacaagggc tacgtggccg tcatccagac ctgcgacgac  11460
gactacttca cagaggagga gttcgacgac ggcaagcagg tggtcgcgct cctgcgcgac  11520
gtctcgcgcg tggtcgccgc gcccgcgggc gtgacggaat aagttaggat aaggagtcga  11580
ggggagaaaa acagcggtca cactataaac tcgcgcgagg ccgattttga cgtgctcatg  11640
tccggaagct ccgctttctg cagcgcggag cggcacacga agcacacttc cgtgttggtg  11700
ggagttatgc agtggacgtg gtagccgtgc ccgcacacca tgacttggaa cggacacgcg  11760
ccgggacagg ccgcgtttat gcatccttcc ggcgagcgct tgttgcagat gtagcacacg  11820
tctgagcacg ccagcgtgca ggacacggcc agcctccact gcttaacctt aacgggcatg  11880
```

-continued

```
gctagttgaa cacgaccatg ggcgagtcgc gagcctcgag tcgggggttc agggcaaacc  11940
gtttcacgcc gtcaacggtt cttctctttg caattttctc tcggcacagg ctcgtcagcg  12000
tcatctcggc caggcgcgcg tcgttgccta ggtgccgcgc ggcgtcctcg accgtcacgc  12060
ccgtcttgcc ggcctcgtcc atgagcacaa tgcagaccag gtgcgcgcta gagcatatga  12120
cctcctgctc gcgtccgccg gcagcgggga tggttagctc cgcgcgcccg aaggccgcca  12180
gcggcgccac gtcgtaggca gtgtctgctc gggcgagcgc cgactccacg gcaccgcgga  12240
gcgactccgg cggcgtcatc gcggccagcg gcaccggcgt gggcacggtg tacacgttca  12300
cgggcatgag caccatctcc gggtcgtggt ggccgctctc ttcgccgtcg tgctccatgg  12360
gctgcggcgg cggcagcagc gggagcagca gccgtccgga catgagccgg cgcacaaggt  12420
cgttgagcgc ggacgaggcc atcggcgggt acagctccat ggccagcttc agcgataggt  12480
gcttctcgag gttgacgccg gtgtagacgc tcttcacgat tcgcgcgaag gccacgcgcg  12540
cgaaggccgc cagctcctcg cgcggcaggc gctcgatgta ggagagcagc atgtcggtgt  12600
cgcacggcgg cgccgcgacc accgcgccgt agagcgcctt gcccgagagc ctttccagcg  12660
cccttgcgtg caggccgtgg gtcttgagca cgtccacgta gttcacgtac aggcagagcg  12720
cgcgatcgag gttgctctcc gcgacgtgcg tctcgatgca ctccacgatg agcgggccca  12780
tgcggtcctt gatgaggtct atgagcccgc cggaggcgac tcgcgcgctc atgaggcacg  12840
tgcggcagta cgccatcagg ccctcgaggt ccgcggcgat cacgtcctcg accacgttcg  12900
ccacgacgcg cggccagagc cgcaccttgc tcacgttctg gtgccgcacc atgtccacga  12960
gctcgtcgta cgagccgccg ggctcgtgcg cgcgatcgac gatgcacctc gccatggtgc  13020
ggctctggcg catgagctcg ttcgtgaagc gcacgcacgc gtcctcggag aagagcgcgc  13080
tcaggcagga gtagcagcgg tccgcgacga ggtgcgggaa gcggcactcc acgacgccgc  13140
ggccgatccg cagcacgcac tcgccgtaca tctcgtccat ggcctcgcgc agacagtcgt  13200
ccagcacgtc cgcgttgtgc gcccactgga tcacgcagag gtagggctcg atgttctcgc  13260
gcgcgttttc cacctcctgc accatgtact cgagcacggt catgtcctcg tggatgtcgg  13320
tgcccagcat gcgcccgggc ggcagccagc tcttgcgcgc gatcgcctct cgcaggcacg  13380
ccaccgccgt gaaggtgttg acgcggagct tggtcagtag ccgccgcagt cgggagatgt  13440
gtgccacgga gaggtccatc tccatggcct gggcgatgag gcgcgtgagt tcctcctcca  13500
tggcggcggc tccgcgggca gatatacgcg aacaacggta agccgtgcta tttcattttt  13560
ggacaaaaag ctagtcgtcg acgcgcatgt tgtcgaggtt ccggcacagc gagagcacgt  13620
cgtcgcgcgc gcgcctccgg cgcagttgat tgttcgcgcg ccgcgcgtcc gcgagcgcct  13680
gtctgtacat cgcggagtcc gcgtacccgt gcagcggcga gcgccgagtg ccgggcctcg  13740
ggctcgcgcg gcgcgggagc ggcgttggcg cgcgcctcga gcgccgcgcg aagtgcgcct  13800
gcatggccag caggcaaccg aacggcatca tgtatcggtc catgaggcac tggctggccg  13860
cggacggctc gcgcgggtgc agcaagccgc cgcccacgtc ctccatgacg tcgcgcagca  13920
cgcagcgcag catggtctcc atgccgtcca cgggcttgaa cctcattggg gaggcgtcga  13980
cgtagaagcc gtcggccacg aagtagagcg cgtccagccc gccgagtttc tcgccgagac  14040
cgacgaagac tcgtccacgt gccagtccac caccgaggcc ttgaagagca ccacgtgccg  14100
gacgtcgtgc gagcgcgcga gtggcgtcga tgcggcctgt catgcgcacg ctcacgcacg  14160
gcgtcatccc gttcttgtag cagaactggc gcgcgagctc ctcctggcgt acgatgtcga  14220
```

-continued

```
ccatgctctc catgaaggag gtggagagca gcatcgcgcc gcgcgcggcg cgggtcgcgt  14280
tttcgtccac ctccacttcc atcccgccgt cgatcctaat catctatcgt atttaaattt  14340
tcggcggagc agacacgcgg ctgctcgctg cgcgatcgct tcagccgcgg cggcgtcacg  14400
cacgcgttgc ggcggccggc acgcacgaac gaccgccggg gctcttcgct gagcgagcgc  14460
cgcggccgcg tgacgcgaca gtcgcgggtg ggttgccggg agtcgctcgc gcgccttctg  14520
cgcatttcgc cggaacgccg tgtttacgta gggtattata ttttcaacgt aactaaatgg  14580
acgggggcgt gcacaaacgg cctttcatcg tgaacgtgga tggcatgggc aaggtgctcg  14640
tgctccggta cttgcggatg tgcgaggtgc ccgaggctaa gtgcgagggc tcgcgcgcgt  14700
cctgcgtgct caagatggac cctccccgct cacccagttg cgagcgcagg ccgtctctcc  14760
cgccgtcccc cccatgcccc atgcgcacgc cccccgggtc gccgctccag gctcccttga  14820
tgcgcacgca gatgctacag ggctgttcg acgccgccaa aaacaacggc gagcagatgt  14880
gccgccgcca gtaacctagg cgtgcgcagt acgaaagtta gtgcgtgatc acgttttttg  14940
caatgtcgat cacgccgtgc gtgcccgtct tgcgctcgcg ctccaccacg ccagtcacgg  15000
gccgcgcgtc cgagactagc gaccccagca tcgagcgcac ggcgccctcc gcggcggggt  15060
ggcgcgtcag cagcaggaac atcacgatgt gcgcggagac gccgcggcgg ctcagatcgt  15120
gcacggcgtc gccgtccatg agcacggtgt ttgagaagta cgtgaacaga gtgttgtctc  15180
gcaccaggaa ggctgagttc gagacgctct cgaagtccac gatctcgtcg tcctgcacgc  15240
ccatgtccaa cagcgtctgc acgagcgcgg gctcgtccag gaacaccacg gcgcgcgcga  15300
acccgcagtc cagcgcgcgc gcgtccgcct ccaacacgcg cgaggcgccg ccctccggcg  15360
gcaggaaggc gcaaggcagc ggcgtgcgtc cgtccgccgg cgcctccccg agctcctcga  15420
gcgcgaaggc cagcagcgtc tccatgcgcg cgcgcgcctt gtcgaagttg tccgcgaggt  15480
cgcggatgcg gtctgtctgc gagaacatct tcagcatcgc catgagctgc acgaaggggt  15540
gcagcacgta tatgttgtcc acgagcagcg tgggcagcgc gcgcagcgtg gcctgccgca  15600
cgttgaagct gtccaggatg tgcccgccct cctcgtcctg cagcaccacg tagttcttca  15660
ggtagggcac gcgcagcagc acggtctgcc gccccgtgac gaagtagatc aggaaggcga  15720
ggttgatcag gaacgggcgc gcgttcgtct gcaccatgtc gatgtcgccg tactctatct  15780
cggggttcag caggtgcagg gcgtacgagc cgtagcacac gcaccgcttg ttgtgtcggc  15840
gcaggtgctc cttcacgagc cgcttgacca cctccaccag gtccgagtgc ttgtgccgcg  15900
ccatcggcgc ggcctcctcg gacggcggca gcaccgcgta cgagttgagc gcgcggctgg  15960
cgagcgcgcg cgcgcggggc gcgtccacgc gccgcaccgc cgcgttgatt gcaggcgtcg  16020
gcgtcgtgag agagcccagc gtgcgcgtga actcgctcac gatcacgctc tgcagctcca  16080
gcaccgtcag gatctggccc agcttctcca ggcgccgctg cctcgagaag tactcctcga  16140
tgcgcgcggc gatttccttc tcggagccgc ctagcttctt gaagaagcga cgacgactct  16200
ttacaacaag agagagaaaa agcttcctat cgaagttgag gacgcgggtc atgttgcggc  16260
gctgcgcgcg caagagcacg cagcgctcca tggaggggcg cgagccgagg tactcttcga  16320
tcacgggtgg agccatgaca gctctatttt ctgaacccgc gattattgta cagcgcaagc  16380
cgcgcgcaga cctgctggca cagcagcgtc gtgtttcgca tgcacacgcg cgaggactcg  16440
atcgtgcgcg cgtccggtgc ccaggcgcgc agctccatca gttcctgctc gacgaagtcc  16500
acgggctcca cgaagcgctc tgcgcagagt ccgtccgtga acgcgttgac gatctgccgc  16560
acgagcacta ccacgtccac ctgctccacg aggcgcacgc ccatggcgat gtgcacgaag  16620
```

-continued

```
aggcagcgga agagcgcgtc catggccatc tggtggtccg agcagggccc gaccgcggtc  16680
tcgcagccca gcgcgaagcg cccgatgccg cggtactgca ccatctccga gggcgagaag  16740
gagagccgct ccatcttgag cacgggcggc gggcccgccg gcagtccgcg cgcgaggtcc  16800
agcaccggcg tccacccggg cgtgaacatg tccgggatca ggaagagccc gtagctggcc  16860
atgcgcgcga tgtcgaaggc gtggtccacg accttgttca cggcgctgtc cgcgcggttt  16920
acgcgcagcg cctgcaggat cacgtttccg gaggcgtgtc gcgtgatcgc gagtccgcgg  16980
tcgcgtaccc gcgcaggccc ggcaccgcgt acgcggtcag acacacggcc aggcgcgcgc  17040
tgtggcacgt cctcgaccga gcgcagccgc atctctccct ccgacaccag acagccaagc  17100
gactccctca ccgccggcgc gagcacctcc gtggcgcaga gcgcgtcgtg cacgcgcttg  17160
agcgcgttcg gcttcagcgc gtagccgaag agcagccgcg tcatccgcga gcccgagaac  17220
gcgaagcggc gcacgtactc ctccgcgagc tcgggccggt cgttgatcca cgaggtagag  17280
aagacgtggt cggaggcgaa gaggtccgcg ccaaccgcga gcagtgtgga tagagacacg  17340
gtgtcgagga agtccacgac gtcggggaag ttctggcgca cgcaggcctc ggcgacgcgt  17400
ctggtgtgca cgcacatgtc ggtgacgggc acccggtggc cggactccac gacggacacg  17460
cagacgtcct cggtgacggc gtccacgggc atggtacgca gcagcttgcc gagcacgtcg  17520
ccgaacccgc catcgagcgc cttgcgccac acgaaccccg cgtcgaactt gccggggaag  17580
tccgcgatca ccgaaagctc cgcgtgcgag aggttgtcca cgttgaggta ggtggcggcg  17640
tccacgaaga tgggcccgaa ggcgccggtg tcggagacgc ggtctctgag gtagtccctg  17700
gcgtagtgga ggtactcccg cacctggccg gcgcggatgc gctcgagcgc gaaggccttc  17760
atggtttcgg agcagagcac ggagtgccgc agcccgtcca gtgtgcgccg cacgtcgtag  17820
acgccgcgca tctgcgcgag catctcgacg gcgtccgccg gcgtcgccgc cgcgagccct  17880
gagttcactg gaggtatcct gtgttctgcg agcatgcgct tgaggaaaca gaggtccagc  17940
ggccgcgtgg tgtacagcgc ggaggccatc tcggggcgcg cctcgacgat gtcctcgatc  18000
atctcgtccg tgaaggccgc gttgatgttg tgcacgctgc gcgcgttcac gtgcaggagg  18060
atgtcgccca cgttgtcggg gaatcgctcc tcgatgagcc ggacgtcgtc ctccgtgatg  18120
ttcatgtagg gaatgcagcg gcagagcagc gcgtagtccg cgaactgcgc gatgtagggc  18180
gtgtggaact cgatgtgtct ggcgaagagc gcgccgcagc gccgccgcga gagctcttcg  18240
agcaggtcct cgggcgtgac gtgctgcggg cggaagaggt gcaggtgcgt ggggtgatcg  18300
gcggccacgc gcgcgtacag ccgccgcggg aggtgcctgg ggtgcacgcc ggcgagcacg  18360
agctccatgg cctctgaggt agacagtgcg gcgaacgcgc gctcggtgcc gcccgcggcg  18420
acggcggcgc cgacaaatct cttgagcagc tgcagcatcg cgtgtttggg ctttcgcgga  18480
aggcgcttat tttaatgtta ttggcggtgg ccggtgcgag ataaaaatta gaactgatgc  18540
cgcagttgtt gatgatgata ttaattgcgc tggccggcga gagataaaaa ttagaaggtg  18600
atgccgcagt tgttgatgag gatggtgagt gcgctggagc aggcggtgtg gcgcgccagc  18660
ttcttgctgg ccccgtcggc cacggaaacg acctttccgg atatcgtgat ggtgcaggtg  18720
aagcgcggac agtgatcctc tccgccagaa cgcgtctcgc agaactccag agatctgcgc  18780
gtcatcatgc agaactcgtt gaccgcgctg accgggttaa gacttttgag gcgcatcacg  18840
gcagactgag tcatgatgtc gatgtcgccg ccgaagagcg tatcgcaccc agcctcggtc  18900
tccatgggct cggtgtcgga gttttcgtcc tcctcggtgg gcgcggaggg cgcgcactct  18960
```

-continued

```
acgaaccagc ggggcgggtt tccgtcctcg cagcaaacct cgtccgagtc cagcaggcgg  19020
tacagctggc ggttcgcctc gtgtttggat atgccgagtt ccttcgcgat ctgcttggcc  19080
ggcagcttgt cgtcggattt tctgagaagc tcgaggatca gagatgcgca ctcgcaggcc  19140
attgtggcgt atttacgggg cgtgcgtttt tttaggattt tggcttgcct ttcttttcgc  19200
agaacttggg aggattgaaa ctcttttggc aatttttgca ggcgtacttg atcaagggcg  19260
gctcgtccgc cgagcgcgtc tggatcatca tcggcatggt gttcttgctc tggcacgagg  19320
ggcagggcag gttgaacttc tcgtcaagca cgttgaagta cccgctgtag tcgtggtccg  19380
gcacctcctc gatgtcgtag ggcacccgcg cggccgcgca cttgaccgcg aagagcaggt  19440
accgcagcgc gtcgtgctct gcgccgctgg tcgcgcggat ctgcgcgcgc aggtccgcgt  19500
agtcctcgtt cgcgtccacc tccaggctgc gcttgttctt gtacgagagc cggttcttgg  19560
cgtccttcga gtactcgatg ccgatgttgt gcgcggggtc aaagttggtc tcgtcggtgt  19620
tcgaggtctt ggtgttcacg atgttcttca gcgcgaagcg ctgcgcgcag tccagcgccc  19680
atcgcgcgat gcgcgcggcc tctgccgcgt cggtgtgctt cgccgcgagg tcgcgcagcc  19740
ggtcttcgtc catcgcccga ttttaggttg ggtatattat ctcaattccg ctcttccgcg  19800
ggccgcgggc gcgcgcccgc ggcaaattag gcgttacaaa tggacttcgt gcggcggaat  19860
acatgataca cgccatcgac cgcaacctcg acttcatgaa ggccgaggtc cagcagaagg  19920
tctccatctt ccggtcatca ccaaggacgt gctcgcgagc acaaacttct tcgtgttcgt  19980
gcacatgtcg cagcggcacg aggtcttcga cgccgtgctc aaggcggcct tcgacgcgcc  20040
gcagctcttt gtgcgggcgc tctcgcggca cttcgaggcc ttcgttgccg ccatccgggc  20100
ctaccgcgcg acctgcgcgg aactgctggc cgacgcgcgc ttcatggagg tggccgcgcg  20160
cgcggccgag ctcgcggagg tcattggcgt gaaccacgac atcgccgcga acccgctctt  20220
cgcggacggc gagcccgtgc gcgacgcgga gctcatcttc gcaaagacct tccgcaagac  20280
cgagttccgc gccgtcaagc gcctcgccgt gctgcggctg ctggtctggg ccttcctcgt  20340
gaagaaggac cttggcggcg agtacgcgga caacgaccgc caggacctgt ttacgctgct  20400
gcagaaggcc gcggggcccg tgcgccacag cgcgctcacg gagagcatcc gcgagtacct  20460
cttccccgga gacaggccca gccactgggt ctggctgaac gcgcgcgtgg ccgacgacgc  20520
ggaggtgtac cgcgaccggc ccgcgcgcac gctctacgag cgcgtgctca gctacgcgta  20580
ctcagaggtc aagcaggggc gcgtgaacgc caacacgctc aagctcgtgt accggctcga  20640
ggacgacccc gacatcaagg gtctgctgct gcagctcatc tacgacgtgc ccgcggacat  20700
cgtcggcgtc gtggactccg cgaacgagga gtggcggagc tacttcgtga gtctgtaccg  20760
cgagaacttc gtcgacggac gcaccttcac ctcggacgcg cgcttccgcg acgacctctt  20820
ccgcgtggtc gccgccgtcg agcccgactt cttcgagccc gagcgcatcc gcgaggcctt  20880
cagtgcagac gcgcggctgc gagagcgctt cacggacatg gacctcaaca acgccttcat  20940
gtcgcacctc atctacgact ccgtggaccc cgacgtcgcc gccgccgagc gcgggctcgc  21000
gctgcgcgtg cacaacgagg actccgacta cttcatccgg gagtacaaca cctacctctt  21060
cctcagcgag aaggacccgc tggtgctgga ccgcggggcg ctcacgcggc tctctgacgt  21120
ccctaccgag cgcttccgcg acctcttcag cgacagcgtg ctgcgctact tcctggacgc  21180
gaagctgggc acgctcgggc tggtgctcga ggactaccgc gaggacgtgg tcgccgccat  21240
gcttcggcac ctgcgccgcg tcgaggacgt gtcttccttc gtgacgtacg ccgcgcgcaa  21300
gaaccccgcc tgcgttcccg gcgtcgtgcg cgcggtcgtg agcaacttca accccgcggt  21360
```

```
ggtcgcggcc atgcgcccct tcctgcgcga gcacatgacg cgcgtggacg cgctgctgga  21420
cggaatgccg cacctctcgg aggccgaccg tcggtacatc cgccgcgtgg tgctgcaggg  21480
ccgcgcctga ttcgccgtca ataaatcgcg atggtggaca gcggcacgca cgacgtggac  21540
tcagccgcgc aggagcgcac gcccaaccag cagaccttct tcaccaaggg gctcagtccg  21600
ctgatgcgcc acacctacat ctacaacaac tacgcctacg gctggattcc cgagaccgcg  21660
ctctggagca gccgtctggg cgactaccgc gtcacggact tctacccgat atcgctgggc  21720
atgctcaaga agttcgagtt catgttctcg ctgctggcgg accccggcgg cgcctgcccc  21780
gcgtacgagc ccaagctcaa caccgagttc ctgaaccgcg gctccttctc gggccggtac  21840
gtgaacccct tccaccgctt cgcggcgctg cccgagcgcg agtacatctc cttcctgctg  21900
ctgagctcgg tgcccatctt caacatcctc ttctggttta agggcgagac cttcgacact  21960
gccaagcaca gcctgctcgg cgccgtgtac accacgcccg agaggcacat cgagctcgcg  22020
cggtacctgc ggcgcacggg cgactacaag ccgctgttca gccgcctggg caacgacgac  22080
acctactcga agcccttctc ggggttcacg cgcatcagca accccacgcc catcgggcgg  22140
ctgccgccct cggacttcga gacgctggcc aacctgagca ccattctcta ctacacgcgc  22200
tacgacccgg tgctctgttt cctggtcttc tacgtgccgg ggctctccgc gaccacgaag  22260
atcacgcccg gcgtggagtt cctcatggag aagctctcgc tcgcgcccga gaacgtggtg  22320
ctgctgtagc ctcaaacata aaatataggc gcctctgatc gcactgcttc agttcagaca  22380
gagctaaggt cgacatctat atactatata gtaataccaa tactcaagac tacgaaactg  22440
atacaatctc ttatcatgtg ggtaatgttc tcgatgtcga tagccatatg cccggtagtt  22500
gcgatataca taaactgatc actaattcca aacccacccg ctttttatag taagtttttc  22560
acccataaat aataaataca ataattaatt tctcgtaaaa gtagaaaata tattctaatt  22620
tattgcacgg taaggaagta gaatcataaa gaacagtgac gcctcgagga attcatgatc  22680
cttcaggccc ttctgtttgt gcctctccta atctcttcgt tgtgtctcgg gaaattcccc  22740
atctacacaa taccagcaaa cttggtcctt ggagccccat cgatatacat cacctcagct  22800
gtccaaataa tttagttgtg gaggatgaca ggattctctt acatggaact aaaggtggga  22860
tacatctctg ccataaaagt aaatgggttc acttgtaccg gtgttgtgac agaggctgaa  22920
acctatacca actttgttgg ttatgtcacc accacattca agaggaaaca tttccgccct  22980
ataccggatg catgcagggc tgcatacaac tggaagatgg ctggtgatcc tagatatgag  23040
gaatctcttc aaaatcctta tcctgattac cactggctac ggaccgtaaa aaccactaag  23100
gagtctctta tcatcatatc tccgagtgtg gctgatttag acccatacga caaatccctt  23160
cattctaggg tgttccctgg tgggaaatgt ttgggaataa cggtttcttc cacctactgc  23220
tcaaccaacc atgattacac catctggatg cccgaggaac caagactcgg gacatcttgc  23280
gacattttta ccagcagcaa agggaaaaag gcatctaaag gaggcaagac ttgcggattt  23340
gtggatgaaa ggggcttgta caagtctcta aaaggagcgt gtaaactcaa gctgtgcgga  23400
gttctcggac ttagacttat ggatggaacc tgggtttcca ttccaacatc agacgatacc  23460
aaatggtgcc ctccggatca attggtgaat ctacatgact ttcactcaga cgaaatagag  23520
catctcgtcg tggaggagtt ggtcaagaag agggaagagt gtttggacgc attagagtcc  23580
atcatgacca ccaaatctgt aagttttaga cgtctcagct atttgagaaa acttgtccct  23640
gggtttggaa aggcatacac tatattcaac aagactttga tggaggctga cgcccactac  23700
```

-continued

```
aagtcagttc ggacttggaa cgagatcatc ccctccaaag ggtgtttgaa agtcagagag  23760
aggtgtcatc ctcctgtgga cggagtgttc ttcaatggca taattctggg tccagacggg  23820
aatgtcctga taccagagat gcaatcatct ctacttcaac aacatatgga gctgttggaa  23880
tcttctgtaa tccccttaat gcatcccttg gcggacccgt caacagtctt caaggaaggg  23940
gatgaagcgg aggattttgt tgaagttcac ctccctgatg ttcacaaaca aatctcaggg  24000
gttgaccttg gtctcccgag ttgggggaaa tatctcctga tgattgcagg tggtctggcg  24060
actctagttc tgataatctg ctcgatggca tgctgtagaa gaaccaagcg aacagagtca  24120
agaagacgag gctctcgaga gtcagagaaa aaggtaacgg caacccccca gactaggaaa  24180
gtcgtatctt catgggagtt atacaagagt gaaggcgatg ccaggctgga ttacaaggat  24240
gacgacgata agtgagcggc cgcgccggct tcatccgccg cagcataaga aaaacctgca  24300
acttcgcaca cgcgcgcacg cacacggtct acgtgtagtt accctgtaaa gacgggcttg  24360
ctcccgaaca agcgctcgaa gaagagcgtg cacatagcct tattgtccag caagttgact  24420
atctctgtac acagcctctt gaagtacacc tcgtacatga tccgctcgtt tttatccagt  24480
ctgaaggtct tgtcgaccac gcgctcgtag gacttcacgt tcgcgatccg gcgccgccag  24540
gggccctcct cgcacacgta cgcgaagaag tagcgctcgc cgatctcgat ggcctccgcg  24600
ttcgccgcgt tgtaccgcgt caccagcgcc acgttggggt tgtcggggga cttgaagttc  24660
ttgtggtgcg ttcggctcag caggaaccag tccagcggca tgctgcgcgc ctcgaactcg  24720
aaggtgagct cgtcctccag cgagcgcagg atctccacgc ccacgttccc ggagccctcc  24780
tccgccagcg cgcggcagag catgtccttg tacttgcgga tcatgagctt gtggaagggc  24840
gccacgtcgc ggcgcgtctc gctggtgccc ttgctcacgc gctcgctgcc gccgccgtcg  24900
ctcaccgcaa acttgatcgt ggtgtacttc ttcttggact gcatgatcag gttgcagtac  24960
accgcttcga actccacctt gaagttcgcg aagagcacgt gctcgttgat cacgcgctcc  25020
agacagcgcc ccacgcgccg cgagaacgcg atgtcggagg cgcccacctc caggaacacg  25080
gagtcggtgt cgccgtacac gctgcggaag cccacgcgct ccgtgcgctc gccggccacc  25140
gccgcgtcga tctccagctc cgcggcgcgg cccgcgaagg cctcgtcgcg cagcagcggg  25200
ttgtccggcg ccgccgccag cgacagccgc gtgccgcaca ccgacgcgcc gtctagcgtg  25260
cgctccaggt acgcgatcat ggtgcgcccg atggccgtgc agctcttggc cgaggcgtac  25320
gagaagagcg cgctgttgcg gaagcccatg agcccgtaca cggagttggc cgtgatcttg  25380
tacgtgtact gcatcgagtt gtagatctcg cggtccaccg cggtctccgc ggccttcatc  25440
agcttcttgt acttggcgcg cgcgtccagg aaggagcgca gcagcatcgg gatgatgccc  25500
ttggcctcgc ggtcgaagat ggccacctcg gcgacgagct ccggcgagcg cggctcgcag  25560
ggcaccgcga tgtaccgcgg cgccgggaac atccgccgga cgtccacggc cgcgacctcc  25620
gcgtcgagcc ggttgtccga gacgaccacg ccgaccagcg tctccggcga caggttcgcg  25680
tagatgcaac gttcgggtac aggctgttgt agtcgaagat gagcacgtgc ttgttgtgca  25740
tcttctgctt gggcgccatc ttggacttcg tgtccgcgcg caccatcacc gtgcggttct  25800
ccagcagcag cttcatcagc gggcccttga tgcaggtgct cgcgcggtac tcgaagacca  25860
cgctctgcgg cagcaggtac gtggacgcgg cggccgcgat cttggtctcc acgccgtagt  25920
gcgaccagag gtagaggcag aggcaggcgt cgtgcaggca gtaccgcgcc atgtccagac  25980
acacgtccag cgagtagttc gcgtacatgt ccgcgaggct gacgtcgtcc ttgccgaagg  26040
ccagcgtgac gcggtcgccg ggcgcgcgcg ccgcggggtc cgcgaggtcc acggtgaagc  26100
```

```
cgtcctcgcc gacgcgtttg tgcagcacgc ggcacacgcg ctcgtcgacg gtcacgtagt  26160
tgccggtgct gagcacgcgc gcgaacacgg ccgcgttccc gtcggcgtcg gtgctgcggt  26220
cgccgcgaaa gcggaccgcg tccggccgcg cgtcctccac gaccgcggtg cagtggaagg  26280
cgttcttgga tatggcgtcc agcttgtagg agtccagctt ctcggtgcgc tggatgaagg  26340
cgtacaggtc gaagtagatg gtcccgttgt tgttgttgat gtggaaggtg gtgctcgaga  26400
cgccgccgac gcccttgtgg ctggacttcg tgcgctcgta cacgcagaag ttgactgtct  26460
cggtcccgtc cggcagccgg aagcggatgt gctcgcccgt gagcagcgac agccgcgagt  26520
ccaggtaccg caggtcgaag ttgtgcccgt tgaaggtgac cacgaagtcc agcggcatct  26580
cgagcaggcg cttggccacg cgcagcagcg tcacctcggg acacagcgtg acctccgcgt  26640
cgaacttcac gtccgccggg tccaggcaga ccgggatctc gcgccgtgcc gcctcctcga  26700
ggtccgcgtc ggagagcatg tcagagttcg tcagcgtgaa tcgcttctcc gcgccgtcct  26760
tgtccaccac gcagaagctg atgtgcgaga cggcgttctt gaagacggaa ggaaactttt  26820
tctcgaagtg gcactctatg tcgaggaaga gccccgagcg cgtcacgttg aagcgcggga  26880
tcttctccgc gaagcacgcg ccggggtcgt cgcagtggaa gcagttgctc cccaggtcgc  26940
gcagcagcgc ggggtccacg cggtagcacc cgtccgggtc gatgtcgtgc gccacgaaga  27000
accaggacac gttcagaaag tcggacatga agacctctgg cggcgcgagc ttgcgctcgc  27060
tggccaccag acacagctct atctccgagc gctggcgctc cggaatcttc gccgagcgcg  27120
ccacgatctc gtcgatgctg accacggaca tgggcccgag cgcgcgcgtc cacgccagcg  27180
gctgggcgat gtcggccacc gcgtccgcgc gcaccacgta gtaaaagtgc tgcacgaagc  27240
gcaggtacac gacggcgttg tcggcgcggc gcgccttgag gaagaggaac cggctgtcat  27300
tgctgcggtt ctcgaaccag ttcaaacatt tcagctccat ttcaaagagc ataataacat  27360
ttcatttaaa tggagcctcg cttctggggc cgcgccatgt gggcggtgat cttcatcgtg  27420
ctgcggcgct tcgaggagca ccgcgacctc gagcgctgca agcggcagct gtacgtgatc  27480
tgctccacgc tgccctgcat cgcgtgccgg cgacacgcca ccgccgccat cgagaaaaac  27540
aacgtcctct ccagcgagga ccccaactac gtgctcttct tcttcatcaa gctcttcaac  27600
aacctcgcct tcgacgacag atacaagatc gaccccgcga aggtgcgccc gctcgtctag  27660
agcatgccct cgtacgcgcg cgagttgtcc gagtacacgg tcaccgcgat gccctcgcgc  27720
ggcgtcacgt gcacgtgcat ggagtccgtg atcacgaagc ccacgcccgt gaccggctcc  27780
tcgcccgcgt cgtccgtgaa gagcagcccg tggttgaaga ggtagaactc gttctctgcg  27840
agcgaaagcc gcccgcggtc gcagaggtag tagaagatgt cgtcgtcgcg cacggccagc  27900
gtgaacgtgg actcgctcac cacgatgtac ttgtccagct cctccagcac ggacgcggcc  27960
gcgcggcgcg cggtggcgcg gcactgcgtc gggcactcgc acgtgtctgc agagtacagg  28020
atgcgcgttc gccccgaggc ggtctcgaga aaaacgttaa tcgcctccat cgcccagaag  28080
cgactcgagg atcgcgagca ccgtgcgcag cacgagcccg atggtgcaga agggaacctc  28140
tcccgactcc gagcactcgc ggatctccgt ctccacgcgg tcgtgcactt ttatggaggg  28200
agccgtcgtt ccagtggcct ccatcgcgac ggacaccacc ttggccacga actcgcggat  28260
cttgctcatg cgccggagca cggtcacgcg gaagaagacg gccgcgagca ggtactcggc  28320
cacgcagctc gcggcgatga gcgcctgcgc gtgcctggtg ttgagcacgt gcgcgtcggg  28380
cacgaagtcc gagatcttca ggtgcgagag ccgcacgagc gcgttggtgt ccttgacgcc  28440
```

-continued

```
gtcgcaggag atgttcgcga agatgagctt ctcgtagtcg agcgcctcga ccacgcgctg  28500
cgcgtccatg tgccgctcgc ccgagagcgc gcggctcaaa gggccccagc acaccgagcc  28560
cgcgaagcag gggtccacca cgccgtgcat cgccagcagc gtcacgtcgg ccacgccgcg  28620
aggatggccg cgtcgtcgag ctcgttcgcg ggcgtcgcgc ccgtcaggga cgcgctgcgc  28680
agcgccggcg ccgcgtgccg cgcgcagaac tcgcacccgc agcccggcgg cagcggcggc  28740
ttcgagagca gactcatgag cccgcccacg tgcccgtgct cggtgatcag aagcgccagg  28800
atgctgtcgg tgctgccctc tatggcggct gtggccgcgc tcgagggctc tcccgtgacc  28860
tgccatccgc agacaacctt gagcatcttg cgcttgagct cgttgggcgc ctccgaggcc  28920
agcatcgtgc gcgggaacgt cgcgttgagg cggaagtcct gcagcagctt ttcgagcgtc  28980
gcggtcttgg cgtgccgccc tttgcgccac tcctccccca ggtgccacat gagctcctcg  29040
gccgtgtcca gcgtcggcga gacgcgggcc ttgggcacgc gcgccgcgct gcgcatcagc  29100
ggctccgagg cgcggaagct gccgcgcgcg tgcaggcgca tggacgcaga cgaggaccgc  29160
atcgagggtc gctggcagaa gctcgtcatc gtgaagcgcc gcgtgagcgg acctacctcg  29220
tcgcgcgact cgtcgaagtc cgggtcaggg tccgtcgtgt cggtctcggc gctgtgcgtg  29280
ctgggcgcgc tgctgcgggc gctgcgcgtg ctctgcgtgc tgaagctgcg cgtgctgcgc  29340
gtgctctgcg tgctgaagct gcgcgagcag gagtccgccg tgtccgcttc ctcgtagtgg  29400
aagtccacgt gctcctccgg cagccggcgc gagcgcgact tggagatgcc gaccatcccg  29460
tccgcgccga ccgggcgcac gcagagcgcc atcgcgccct cgcgcaccgc ctgcgcgaac  29520
tcgcggctgg caaccatgcg ggggtcgagg aacttgatga tgttgaagta tggccactcg  29580
cagacgagcc gcgcgcaggt cgcgacgtcg tcgacgcttc tgagggccct gttcagcggg  29640
gggatgttgc tgccgtcggc cagtgcgacg aggtcctcgg gggagatctc gagcttggga  29700
atcatctcgt tcacgagcgc ggggtcgatg gcgtggcaga cggtctctac ctcagtgcgc  29760
gagagcttga gctgcgcgca ggccgtccac ggcgcgcacg tgagcgcgaa caccgcggag  29820
actcggccct tgccgaccat cgccacaacc tcgggctcgt agaccaggcc ggccttgagc  29880
agagcctcga gcacctctat gtcgtcggcg gcgagcagcg cgcgcctgtg gaagcacacc  29940
gcgggcatca tcttcttgca gatgccgcgg gtgctcttga gggccgtgat aaggtcgggg  30000
agcctgacgt gctgcggctg gaagaacatg acgttggcgg ggctcgcggc caccgcctcg  30060
tcgtacaccg acatcggcag gtcgccgtgg agcccgcacg gcagcaggct cagcagctgc  30120
gcgcgcgaga gcttctcggc gcagaagttc ttcttggcca gggcggccgc cgcgtcgcgg  30180
gccttcttgg ggtataacaa catggcgggc tttaaacacg aaacaaaaat ccaggttgta  30240
acatttcaat tttgcatgtt ctgggcctcc tcgcagagtt tctccaggcc gccggccacg  30300
atggcgtcga cgaagaggtc ggcctcggtg aagcggtggt tgccgcgcac cgccaccagc  30360
gcgttctcgg tgaccaccac cgacagctgc tgcgcagccg tgcgcaggtc gaagtgtcgg  30420
cacgcgagcc cgtggcccag agtctggtcc agcgccgcga gcacctcctc caggctctcc  30480
tcgcggtggt tgtagaacca catcagtacg aagtaagcca cgtaggtgta gaggtagtgc  30540
gcgaccgcgc gggcgcgcac cagcggctgg ttgcagcgcg cgaaggccat tccgctggcg  30600
atgaggtcgt cgtccagcgt ggcgtagtcg ccccagttga gcgcgctgaa ctgcacgctg  30660
tagaccgcgc gcacgaaccc ggactcgagg atgtcgatct gcgacggcgc gccccaggtc  30720
accagccggt acacgatgcc gcgctgcatc agccgcatga ggtcgccgcc gacctcgcgc  30780
aggcggtgcg tcagcgaggc gaaggccagc ttccgctgcg tgtactgcag gcccacggcc  30840
```

acgcacccgt ccgactccac cagcacgagc ttgtggtccg tgcagccgtc gctgcgcagg 30900
ccgccctcgc gcgccatcat gtcggtgacg aacatgtact tgcgcgcgcg cggcccgacc 30960
aggatgcgcg tcttgccttc catgcgcagc accacgtcct ctagcagccg cgtgctgtcc 31020
acgcgctcca cctgcgggtg gatggtgggc tggtagttgt acagcagccg cggggaccag 31080
ttgtaggcga acgcgaagag gtgcgtgtcc aggagcgaga tggggaagac gccgccttcg 31140
gtggcgcgcc ggaggatggc gagcttggtc tccgcgggca gcaggctccc ggtcaccgcg 31200
ccgaagaaca tggggtggtt gcggaacttg agcgcgtacg cgctcagcac ctcctctcgc 31260
gagaatattg agtccgcggg gttggagctc gcgggcagga gcacgtcctc cacgctcagc 31320
acctcgtcga tgaagggcag caccatgtcc acgttggagg cggtgaacca ctccatgtcc 31380
acggcgttgc gctccacgat cacccggatc gtctcctcgg atatgttctc ggcgaaggcg 31440
ctctgcagct cgatcaggtt ctcggtggcg tcgatgctga gcccgaggcg catgccctgt 31500
tgcagcacgt cgttgatggg gttcacgtac atggccaccg ccatgcaccc ggcggctgca 31560
cgcgccagag gttggagtac gcggacacgt ccgtgatgcg cagcgtctcc agcacgttgt 31620
acatccattt ccagcgtgtc cacgtacacc tccgcgtgct cgaagatgat gtcgagctcg 31680
aacgcggaca gcggcagact cacgtagatc tggcaggcgt cgaagagttc ctgcgcgtac 31740
tcggagaagc acgcgtacgc gatcacgccc gcgcggttga cgatgtagtc ggccttgaac 31800
atcttcgtga ggtaggcgta cagcgaccgg caggccacgt gcggccttag ctcgtcgagc 31860
acggcgtcca gcacctcgcg gtgctgcagc acggaggggt gcaggaactg cgtgaagtcc 31920
accgcggtct cctccatgaa gtcggggatg gtctcgacga ccaagcggtg gttccgcacc 31980
gcgcggaagc cggtgttcat cggcgcgatg ctgtgctggt cgtgaacctc cagcaggatc 32040
tcgtagccga tctctcggca gctcagcgcc gcgcgcgcct ccgtcacgct cgcgttccgg 32100
aagaactgcc gcaggtgctc gtccgtgcgg cagagcgtga cggattgggg gatgcgggaa 32160
aggtcgcaaa gagggctgtg gacggagatg cgccgcagcg cgtggtctac gaactcaaaa 32220
ccgcgcctcg acatcgtgaa gtcgcggagg gcgtacatgt tgtaggaaca gaggcggaag 32280
aggcagtcta tgtctagcat gttggaaacg cagtacgcgt gtctgtggag gtgcgggagc 32340
atggcgggca cgacctcggt cgtgttctgg agcatggtgc atacgaggtc gggcgcggtg 32400
aggtcaggag tgacgatgag gatgcaggag ctggagaact tgctgagctc ggaggccagc 32460
cggtgaaggt tgtagtcgtg gcgctggctg aagttgctgt ttatcgtgcc cgtgaagccc 32520
atgagcgccg ccagcgtcag gtcctcgcgc tcgatggccc agatgtccag gccggaggct 32580
atcatgcagc gcaccagcgc ggcggcgcgg tcgctcgtgg ggtagctcat ggtgctgtcg 32640
gtcgtgcgaa tcagcatggg ataatgcttc atttttacgg tcggggggtg cggactgtgg 32700
ggcgcacagg gcccgcgggc ggctcgtgcc ggtccgcggc gttcgccgaa cgcaggaacg 32760
ggcccatgcg cgcccaggcc atccacagcc ccgccgtcag cgccagcagc cagacgaata 32820
ccacgatcat cttttatgta gcgggaactc gcgctcactc cccgccgcac ggcgacgggg 32880
agagcccaga gccgagctcc atgcgcgtgc tctgcacggt gagcgactcc acgagcttgg 32940
acacgttcat gcgcgtgttg tcgggcacca ggtgcgcgag gcgcgcgtac acgtcctcgt 33000
gcatgcgctt gctgcagcgg tccaggctcg cggagagcgc ggagactagc gcggtgtgct 33060
tcgcgtacac gaagtcgccg agacacacgg tctcgagccc gagcacgtcg gcgctctccg 33120
cgtccttgag cgccacgaat atcttctgct cctcgcgcgt catcgagcgc atgaggtagt 33180
cgtgcagccg cgagcgcgag atgagcccct gagagatctg cgggctgcgc atgaagcgcc 33240
ggcgcatcgc gcacagcagc tcctcgtcga cgacgtacat gctgtccttg atggagctct 33300
tctcgtcgag cacgagcaga ccgtcgttgg cgaccacgtt gatgaaatcg tccacgtgcc 33360
gcgcgtctat gtcgtagcgc gtgccgccgc actcgatgtg cgagggcggc gacttgagcc 33420
ggttcgcgag cgccttcacg tcggagacgt cgatgtacag cgaggactcg cgcgggacgc 33480
agccgaggat gcgcgtctcg agcggcgtga ggatgagcac gcgctcggcg ccgtcgacga 33540
gcttgccgtc gtcgggggaa aagaagttgt tctccacgat gctcgagacg aggctggcga 33600
gcacgccgtc gcggtaggcg ccgagcgcga actcctgcac aaagggcgcg tgcagcaagt 33660
ccacgggaat gcgcatctcc acgcggcgcg cgaccgactt cttcttctgc aggtgccgcc 33720
ggtccaccat ctcgtccacg atgtccgata tgcgggagca gaggtacgcc ttgaggacgt 33780
tggcgtttac cttgttgaag atgagccgtt cgtcctccat ttaagctgct caaacgagct 33840
ttaaatagtg gaaacacagc agcacgccga tcgccgccgc tatcaggccg attagaaaaa 33900
cggtggtcca ggggacgccc ttgggcctat cgcacgccgg cttttcggtc attacggtgc 33960
gcacgatgtt taggaactcc tcgaagtcct cgtccgagtt ggagaggaag gagccgaaga 34020
cgccggtgta cagtttgtcc atttactact agatattaaa cggcgcttcc aactcctcgt 34080
cctcgaagcc cgcgccaggc tcgacgacgc ccaggccgcg cacgtcctgc tcctcggtga 34140
acgtggtctg agtctcgctc atgcgcacac acgtctgctc gccctcgaga ccgagcacgg 34200
tcagcgagca ctcgcgcggc atggtgatct tcttaaccgc gaaggtgact ttgccctcgc 34260
cgcccgagcg gtagaacacc accggcgcta ggatgagcgt cgccatctgc gcgtcgcggg 34320
ttgcgaggtt ttctatctct cgcgtcagcg gacatatctg cggctgggtg tcgtcgtcgc 34380
cggtgaactc caggagagcg ccggtcaggc ggttgagata cagacatccg gacttaaagg 34440
tgttgtcgat ggccgtgtcg gtgttgaagt tgcgcagcga cggcggaacg cgaagccggt 34500
tttgatgttg tcgtatatgt tctccagcag ctggtagagc agcggactgg cgctcacggg 34560
cttgagtacc cgctgtcgtt ctgccgctgc atgtcggtct tcttgctcgg gtagatctta 34620
aactcgccct tcacgacgat gagcggcgag acgagcttgg atgctagact ttcgacgaga 34680
cacacgttga tgttggagca gctcgggtac tgcgacggag ttagagtcac cgcctcgatg 34740
accttggtct ggctcgacga gagcgacttg gcgaagttga tcgcgtcggt gcacgacatc 34800
gcctggttct cgccgaaccg cctggcggac gctgcatcct cctgctgagg agcgcggtta 34860
gacgcgacgg tggttttgga tacagcgcgt ttcattatgc agcgatttta aagtacgtgt 34920
atactttcag ttttgtcgcc gagcgttcag cgcctgcatg cagaggaagt acaggatgat 34980
ggtgcacggg atcgtggtca gcagcgatac gaagtccatc actgtgagga cgcgcagcgc 35040
cccgcgcgag cggatgccca gcgagggcgc gccgcggcgc gcgatggtgg ccccgttcgt 35100
caccactacc agcagcatta ggatggtcgc gcccacggcg acgcccaggt cccgcgactc 35160
catttatagt acagtataga gcgaccgcgt cacgaactct cggctggcca acacgcgtcc 35220
gtcgggcggg tgtccgccgg ccttcccgcg gaactccggg acctcgaagc tggacttcgt 35280
cacgcggtac gtgtacttgc cgcgccagac caggttttcc ttctggaaga cgccgtccat 35340
ggtcacgccc gccatgaagg cgtccttgac gatgaccagc accgcgtcta gcttgcgccc 35400
gttgatgtgc gtgacgaagt ccgtgccgct gcggctcgcg cagcggatgt ccacgcccga 35460
gggcaggtcc accacgaaca cgaagcgctt cggcgcgtag agcaccaggt ccgaggacgg 35520
cgacgccgaa ggcgccgagg ggaactgccg gtggtcaaaa gggtgcacca cgcccacgat 35580

```
ggacgtgacg cggtcgtccg ggaactgcgt cgcggcgccg ccgccgcggt gccgcgtgac   35640
cgtgcttctg cccacgtcgt cgcagaccac gtgcagctcc gacacgatcg gcagcagcgt   35700
ggccagcatg cggtcggtct ctgtgcgcgt cgcgcagcgg tacgcgatcc cgcagtgcgc   35760
gtcctgcgtg cgcccgaaga agagcaccag cacgctcgcg tcctggtcga agggacacac   35820
ggccatcacg cccaccggcg gcggcccgtg gcctgcgtac gcggaggaga actcctgcac   35880
ctcgaccacg gcgtcctcgc gcgcctcgcc gggcaccatc gccgccgccg gccgcagcgc   35940
ccgcacggtc tgcttaaccg cacgcgcggc ggcggccgcg ctcggcgcga ctacgcgcac   36000
ggccgcgtgc gcgcccggcg gcggcgcggt tccggccatc cagcccaccg gcgagaagaa   36060
cacgtcgcag acgtgcacgc ccgcggcctg cagcgcgcgc gcgagcgcgc gcacggcctc   36120
ccactcctcg cgaaaggcgc tcgcgaccgc gagcgccttc agcaccgtgt ccacggagtt   36180
gacgggcttc tggaagaggt tctcgttgtt gtagatgaac tcggggagct ccacgggcac   36240
tgtgaacagc cgaatctcgt gcgcgccgct gggcgtgagc cgcgtcgcgg gcttgcgcac   36300
gccggcgccg atctgcttga agaagtggtt catggcgccg ccggcttctc gggctccggc   36360
gggagcagac tatttattcg ggaggttatc ctttccgaaa gcacctgcac ggacttccgc   36420
gtccagcgct ccatcttcat gtactccttc atgccgtcgc tgagcacctc gacggcctcc   36480
agcttgggcg ctgtcgggtc gaagaggatg ctcttgagca gcgtcatctt cttgtccgcg   36540
aggaagcgga agtaagtgta gatgcagcgc agcgcgcgga agttctccgg gtgcttgatg   36600
gtgcacagga tcatgaagat gcaggtgaac atgccgcact cggactccat gagctggttg   36660
acctcgaggt tgatgcagcc gcgccgcgcc ttgaagttgt ccacgaagaa gcgcatgagc   36720
acgtccacgt cgcagttgcg gttgtccagg tccgcggtct cggcgttcac gttgaagccg   36780
tccgagaagg agtagaagta gaagtacttg caggggtgga actccgaggg gctgttgccg   36840
ccggagtcgt agaaggacac gagccgcgag acggtgtcga agatgcagca cttccagtgg   36900
aacatgtagc agaagccgaa catcacgtag cgccgcccgg cgcgctcgat cttgtccttg   36960
agcgtgaggc tgaccatgtt gcagcggaag cggtccgcct tttcgtggat ggccgcgccg   37020
ttgaggaagt tcaggttgaa ctggcccagg tacgcgacct cggtgccgaa cgcgaagggc   37080
gccaccagac tctggatgct cacgttgctc atccaggcgc cgcggtcggg ctttatggcg   37140
atgggcacca ccttggtgtt cacgcccgtg ctgacgcccg cgcgcgcgag gtcgtccacg   37200
ttcagcggca tctgcgagaa gtccacggcc tcggacacct tctcgcgcaa cgagggcttg   37260
aagaagaagc ccagcgggac cttccactcc agcgcgatcg cctcgcggaa gccgtagcga   37320
cccttgaggc tggccagcaa cgcggtcttc tgcgcgacct cgtccttctc ggtgtccggc   37380
ggcgcggcgt cgatgagccc gcgcttcgcg aagtccagca gcgccgccag cggatgcacg   37440
agacgcgacc ggccgtcgcg gattcgtcga agcgccgcac cacgtacccg ttgcagttgg   37500
tcttgccagg tgcgcgctga gccccaccac cgagtagatg tggcacagaa ggttggtgaa   37560
ccccagctcc gggattttgc tcaccactaa atccgtgtac ttgtccattt atcatggaga   37620
atcatctgcc ggacatgctg atgtttccca actgcgtttc tgtgtttccc tttgagtact   37680
cgctggagga cgtgttccgc ctccccgagg agcgacggcg cgcgttcgcc atggccgtgt   37740
tcccgctctc caagcaccgc tggaggggcg cgcggctcca gcgcgacgag cgaagcgtgt   37800
ggctcagcgt cgaggaggac cgcgggcgcg cgctggacga gcggaactgc tcttggctct   37860
cggacgtggc cgcgcgcatg gtcgacgacg agggccgcgc ggtcacgccc gaggcgtacg   37920
```

ccttcatgcg cgccgcgccc ggcgcgcgcg tcgccgagct cgccgcggac gcgggcgtgc 37980
tagcgggcct cgtcgccggc ggcaacgcgc tgcgcgtctt ctcctcggag tccacgcagg 38040
cgcgcgaggg ctggaaggcg cgcagcgtgg gcgtgctcgg caacgcggcg ccgctggcgc 38100
ccgtgccgct ggcatcgctg cgtccggaag tgcagcgcga gatcttcgcc gcctggatcg 38160
gccgccgccc cgtggtgctc acgggcggca cgggcgtggg gaagacctcg caggttccca 38220
agctgctgat gtggttcaac tacctcttcg gcggcttcga gcgcctggac gccgtccgcg 38280
agttcgcgga gcgcccgctc gtgctctcgc tgccgcgcgt cacgctggtg cgcgcgcaca 38340
ccgcgaccta cctcgcctcg ctgggcttcg gctcggccga cggctccccg gtctcgccgc 38400
ggtacggcgc catcccggac gccgagcgga acacggcccc gcgcgcctac gggctcgtgg 38460
tggccactca ccggctcaca ctgaccgcca tccgccgcta cgacacggtc gtagtggacg 38520
agatccacga gcacgaccag atgggcgaca tcgtggtcgc ggtcgcgcgg aaactgggct 38580
cgaacatgcg atcgctggtg cttatgacgg ccacgctcga ggacgaccgc gcgcgcctgg 38640
aggagttcct agtccggccc gcctttgtgc acatagaggg cgacacgctc ttccccatcc 38700
gcgaggtcta cgtgaagaac acgcaacagc cgccgctctc gcgcaagtac gcggaggcgg 38760
agctgcagaa cgtggcgcag gcgctcggca ccttcgtccc cgagcaggga aagtgcggca 38820
tcctcttcgt agccacggtg gcgcagtgcg cgctcttcgc ggagaccatc gaggccaagc 38880
accccgggct gctggtgcgc gtggtgcacg ggaaggtgcc ctccgtggcc gcggtgctcg 38940
aggaggtcta cgccgcggac cggcccgcgg tgctggtttc cacgccgtac ctggagtcca 39000
gcgtgaccgt gcgcaccgcc acgcacgtct acgacactgg gcgcgtgtac gtgcccgagc 39060
ccttcggcgg ccgcgagacc ttcgtctcca agtccatgta cacgcagcgc aagggccgcg 39120
tgggccgcgt ggcgcccggc acctacgtgc gcttcttcga cacgcggctc gcgctgccgc 39180
tgaagcgcat cgactccgag ttcctgcacc cgtacgtgct ttacgcgcgc atcttcgggc 39240
taacgctgcc cgatgacctg ctcgtgcatc ccagcgacct cgcgctgctg cgccgcaccg 39300
aggagtacgt cgacggcttc ggcatcagcc tctcgcgctg gacgcagctg ctggaccggc 39360
actacatgca catggtcgag tacgcgaagg tgtatgtgcg cggcgggcgc ctcgccgccg 39420
cgctggacgc cttcgagcgc accggcgtga tgacgcacga ggccaccgag gccatccgcg 39480
ccgtggacat gctcgcggcc gtcctaaacg tgcgcaagtc caaggaccgc taccgcgcgg 39540
agtgcaaggt gctcttcggg cccttcgcgg gcaagaagtt cgtggtcgcc gggcggcgtc 39600
cgcccggctc gcacgtgctc atggtcacag accgcgtctt catcgaggcc gagcccccat 39660
tctgaggacc accttcttgg agacgcccga gaagtcgtcg gcgacgccgc ggcgcgccac 39720
cacaaggcag tacgaggtta cgtgcgggca gcgcgcgatg cagcggaagg cttcctcctg 39780
cgacagcgag aaggcgaaca cgtagaaggt gtgcggggac ttcagcggcg tgtggtccat 39840
cgagtagatg acaccgagct tcttcatgcg ccacataagc gcgttgatgt ggtcggcgcg 39900
cagcgcgcgg cccttgagca cgccgcagac gaagctcgag caggccacga cgtcgtagcg 39960
cgtgttcctg ctgaagacca ggtgcggtgc gccgccggcg cgccgcgcgg ccgcgcgatt 40020
ctccacgatg tcctctatgg agcgctcgct cgcaaagaag tccaggaaca tgtactggta 40080
ggccacggcc gggcgcgact tgctgaactt catgaaggcg tccgagtcca tgatggcgtc 40140
catgtcctcg gcggcgagcc ggtgctgcag ccggatgccc tcgaaggtgt ggaagagccg 40200
cgcgtccgcg tgcatggaca gcgcgagagt gacgaagtcg agaaggtccg cgtcgccgaa 40260
gcgcacgagc acgttaccgg gcgtgcgcgt cttgcgcatg agccgcgcgg gcgcgccgtc 40320
gttgtggctg cggcggcgca ttttgtcgcc gggggactcg ggcggcaggc gatcatgacc 40380
agccggtgcc gctgcgcgtc ctcggcgttg aagatcgagg acgtgaagcc cgggtacagc 40440
atcgcgctcc gagatggcgt gcagcacgtc gcgcttgagc ccggccacca gccgctccgc 40500
gttctcaacg aagtagttct cgtagtccag gatgtcgtgc gccatccagg ggaagttcag 40560
gtacgcgttc atggcgtagt cctcggcgtc gaagcagatg cgcgtgtctg gcgtcgccgc 40620
gatcggaagg tccttgatgc cgcggagcag cccgtcgtag tcggactcgt ctacgaagga 40680
aagcaccaca aagaggtcct cgcccacggt ctcgtagtcg aagaggtggt agagctctct 40740
tagcgccagc acggcgagcg cgttgtccag cgaggcgtgc acgcgcgcca ggatgctgta 40800
gaagggcgtg gccatcatca cggccttgcc gccctcgcag gcgacggcgc gcgggaaaat 40860
gacctccggc gtgcgcggca gccgcccgaa cgtcgcgttc agcagcgcga ccgtggccgc 40920
gtcgctctgg cgcaggaaca ctaccaccga ggggcccgag atgctgagca tgcgctcgcg 40980
catgcgcgct ggcaggtccg gcgtggtcac gaggtccgcg aagcggccgc cgttgtagag 41040
gtcgccgccg ccgaggaagg tgagcacgtc gaagcagtgc agcacctcgt tgcggaagta 41100
gtactcgttc tcgagctcct tggcgtacgc gcgtatgtcc acgttctcga agtttgttcg 41160
cagaccgccg ccgtcgaaga accaggacgc aagctcgcgg acggcgtccg cgggcctgtt 41220
gcggcggctc ttgcaccaga agctcatgta gttgcgcgag gtggaggcgt tcgccaggaa 41280
gaagcggtgg tcgaaggaga tgagcacatg ctcgagcagg tgcgcgagcc ccaggaccgc 41340
gcccacgtcg cgcccaaaac cgaagtttga tatccccagg tagacgtccc gtttcataga 41400
cggcctcagg aacaccctga cgccgttttc caacactatc attctccggt atttacttac 41460
ccaaaagtag tattgggaga agtgtttgaa cgtcccctcg ccttttttaaa tcaaaagtag 41520 acttctcgcg cccgtgcgcc accgtcacgc gcgcgcggcg cgagtccata ccggcgatca 41580
ccgcgctgct ctgcggtgcg tccggccgcg ggaagagcac ggactcggag atcccgtcca 41640
gctgcgcgtc ggtgcgctgt cgcccacgcgt gcgcgtccgc gagctcgcgc acggccagct 41700
gcatcttgtt cgtcggcagg aacgtgaaca cgtacgccgc cgccaggaag actgcgaaga 41760
gcacgaactc aaccgcccat gacatttagg gagctgattt tgttccacgc ggcgacgcac 41820
gtcgtgacgg gcgaccccga ggcgccgcgg cgcgcggcct cgctgtgccg cggcttcggc 41880
gtggacttcc gcgcgattca cgcggagttc gcgcggcggt acccgcgcac cgcggccgcc 41940
gtggagcgcg cgcagccgct gcccgaagtc gacgccgcct ttccgccgga cgcgcgccgg 42000
caagtcgtgc ggctgcgcct cgaggctgcg gcgctggtcg tcaaggagtc gcgtgcgctc 42060
tcggcctcca tgcgcggcgt ggcggtggtc gacggctgct gcgtgcgcgt gtgccgcgct 42120
aacgacgagc tgctggggtt cctcgcgcgg cgctacgacc ccgcggtcta ccgctacgcg 42180
gaggtgccct cgccgagcgt gcgcccgggc tcgaaagtct tcgcgtgtgc gggccgcagc 42240
gtcacctttg cggccgcgca ccggagccgc atcacggcca accgcccgct gcgcgtggtc 42300
gtgaccgagg cctgtgtgga cggcgtgctc gcgcgcggcg ccgcggaggt attcgaccgc 42360
ggctccggcg tgctgccccg cgcgctgcgc gagatcttct accgcctcga cgaggacggc 42420
tgtcccacgg gccagacgcc aggcttcgcg gacagtatgg cgtcgcgcag ctgatctatg 42480
tccacctttt tctcgtcgat ctgcgccacg accacgaaac tgcgaatgtc cacagcggcc 42540
atggtcttgg ccaccgggtc gtacttgagg agcagcacgt actcgttgcc gaagtgctcg 42600
gtgacctcgg tgatgagccg gtacacgccc atgccgagca cgttcaccgc accgtccttg 42660

```
gcgaagagcg agaggatgtt cacgcacttc agctccatct cgccctcgag gcgcgcgagc  42720
atgcgccggg tgacctcgca tactgaacaa agaggcttac ctagtaagat aagcgttagc  42780
ttagccgcgg tcggtgacgc gtcggaggcc atttatgggg atcaaaaact taaaggcgtt  42840
gctgctcagc cacggcgcgc tgaccccgca cgagccgggc ggcgacgagc gcttccctgc  42900
cgtgttcgtg gacggcttca gcgtcatgat gaccatggcg tactcgtgcg cggacgaaga  42960
cgagttccgc gcggccgtcg aggagcgcgt gcagcactgg atgagcgtgt ccgagagcgg  43020
gcggatcgtg gtcttcctcg accgcggcga gattccgatc aagcagccgc tgcgcgacca  43080
gcgccgcaaa gccacgcgcg accgcgccgc gcgccaccgc gagttcatcg ccgccgcgga  43140
ggcagaggcg gcggcagagg ccgttggcgc ccgcgaggac aagcaggagg acgagcacgc  43200
ggagttcgcc gaggagatcc gcgccgagaa gcagctaaag ctgcagcgca tccgcttcca  43260
gctcagcatc gccaaccacg aggtcgttaa gtcgctgata gagtccacgc cgcgcgcgct  43320
ggcgatgccg tggagatcgt cttctgcgac ggcgtcgacg cggagatggt catgtgcgcg  43380
cggcgccgag gccgagcgtc gcgggcgctg gccgctgctc gtgaccacgg accaggacgc  43440
gcttttgttc acgtccaccg atcgcgacga gaagatagtg agcaccgtct ccgcctgcta  43500
cgcgttcagg cccaccgaga cgaccgagta cctgtgcaaa cttgcggcgc tggccaacgg  43560
ctgcgacttc ttccccgggc tcggcggcat atgcgtgagt gtggagtcgc tgcgccgcgc  43620
cacgcttttc ccggaattct ccgtgcgcaa cgccgccgtg agtctgtgca cgcggcccat  43680
gcggctgtcc acgcaggacg cgctggagcc agaggccgcc gccgaggtcg tggaattcat  43740
caggcggtac gccgccggcg acgagcgcat ctaccgcgag gtgccgcccg gcgcgtgctg  43800
cggacgcgcg tttgtgcgcg gagcgctcgc ggccgagtgg gccgaagcgc tgccggcggc  43860
cacgggtctg agcgtggtcg cggacatgat cgcgtgtctg cccgcgcggc gggaccccgc  43920
gcccgaggag gtagagcggc tgctggcgct ggaggcgcgc gcgcgaggcg cgcgcgtcac  43980
ggatgcgatg ctcgcgcaga ctgcgcagct gctgggttac ggcgcgagtg cgggcgccga  44040
cggcgcctcc gccttcgcgg tctcgggcgc caagggcctg atgtgtcgcc tgcgcggcac  44100
ggccatgttc ttcaacgcgg agtacgtgga aattgaaagc gaacccagac tgttaaagct  44160
gcggtagcat ggtgttcccg atcgtgtgct caacgtgcgg ccgcgacctg tcgcacgagc  44220
ggtttctgct catcgtgcga cagcggccgc taaaggttgt tttgcggacg gtgcgcaacg  44280
tctgctgccg tataaagttg tctacacaaa tagagccgca ccggaacctg acggtgctgc  44340
ccatgctcga cataagctga tttttctttt ccgctctgta tgcgcgagtt cggactcgcg  44400
gcgcgcatgg cccgcgccat cgaggacgtg tgtccgcgcg gcgcggtgat attcgtatcc  44460
agcgccgcgt ccatgaccga ctgccttaac ccgtcggtgt tcaagcacgc ggcgatatac  44520
gcggggcgcg tggaccgcgc gccgctgccg ccgccctcgc cggtcccggc ggaggccgtg  44580
acggagccct gcgcgataga cgccatagcg ccttacggcg cgcgcgtggt cctgctctcg  44640
gagctgctgc ggagctgcgt ggccgttcag gcctaccgcc tggcagtccc cggcgccctc  44700
gcgctcatga acctcgcggc cgacgcggcc ttcgagctcg tgggcacgcc ctacggcttt  44760
aacagcgacc gaacgtactg cttcaagctc gttgccgact gctttgctag cgtgggcgtg  44820
acaacgaaga ccaggcgcat catgggtcgc gacgtcgtgc tcagccagga cttcctggag  44880
agcggcatgt ggaccaaggt gctggactcc gccgcggagc cgccgtggct ggtctagaac  44940
agcggcggcg cgcgggtccc gagaacgggc cgcgccacct gcagccgctg ctgcagcgcg  45000
cggcactgcg cctcggcgtc ggcagtctcg gcagggtcga cgggcgtcgg agtcgcggag  45060
```

```
gtggtcctga acggctgcgt gttcaccgag acgcggatgc gctccttgca ggagcgctgc  45120
tcgatgcagt tggccagcat cttcatcacg tgcaggtact ccagcaacac gaacttttcg  45180
agggtgatgc cgtcgaaggg cgacgacccc accacgccca gcgggctgga caccgcgccg  45240
tcgagcacct cgccgcggga ctccttgcgc gcgcgctcga gcaggtcctc tgtccgagcc  45300
accacgctgc cgaagtcggc ggccgcgggg gcgggaacag gcgcagcagc tgcgccgtcc  45360
gcgtccgccg gcatctcctc gatcttgaga ccggccgcga actccgaggc cgcgtgcacg  45420
ggcgaggcgc cgcgccgcac catgaagtcg cacagacgcg atagcgcgga ggagcgcacc  45480
ggcatgtcga gcaggcgctc ggcctccatc tcggcgaccg agtcggcgca cgcgtccggc  45540
gcgcccgccc gcacgagctc gtcgcagcac cccgcctcct ccatgagcgc gggcatgagc  45600
ttgtactgcg ccatgttcac cagcccgtac ttgagctcga gcaggtccgc gagctcggag  45660
gccatgggtc ggtttttggt gtagatgacg cgctccacgg cctccgccat gtccacggcc  45720
tgcatgagct cgccgacgag cacgctggcc acgagcgtgg ccagcgtgac gcgcacggtg  45780
ggcacacaga ccgcgaagaa ggaggtggag tgggtgaagc gcatgagcgc gccgtgcaga  45840
cgcgcgaggt ccgcgctgtt gcccgcgtgc acgaagcgcc ggcgcagccg cgccagcgcc  45900
tccacgaggt cctcgcgcgt ggtcacgcgc acgttcgcga tgcacaggtc gtggtcgcgt  45960
tggcgatctg cgcgcggcgc tgcggcgagc tgccgggcag cagccgcgcc ttggcctcga  46020
cgtcgagaca gccgcaggcg gcgccgcgga cgacgaactt caacaacgac tcgaacacgc  46080
gcgcgcccgc gcggggcgct tgcttggacg actccattta ctttaaataa tttacgagat  46140
caaaataaaa tgactctgcg catcaaactc gagaagctca agcagatcgt aacctacttc  46200
tcggagttca gcgaggaggt ctcggtgaac gtggacgtcg gcgatggcct catgtacata  46260
ttcgcggcgc tgggcgggtc cgtgaacatc tggaccatcg tgccgctcag cgcgagcgtg  46320
gtatacgacg gcgatgtcag ccgcgtgttc aacctgcccg tgctcaaggt gaaggcctgt  46380
ctgtgcagct tccaccccga ctcggtggtg agcctggagc ccgacctcga ggacaacgtg  46440
gtgcggctct cgagccacca cgtggtcagc gtggactgcg acaacgagcc cgtggcgcac  46500
cgcacgaaca ccgccatctg cttgggcatt aaccagcgca agtcctacgt gttcaacttc  46560
cggcgctacg aggagaagtg ctgcggccgc accatcgtca acctggacct gctgctgggg  46620
ttcatcaagt gcatccacca gtaccagtac atcacggtct gcttccgcga caagaagatg  46680
gtgctgcaca cgcccgggaa ggtggacaac ttcttccgcg agtactccat gaccgagtgg  46740
gcgcccgacc tcgagcgctt ctcgttcaag atccccatct cctccgtgaa caaactccgc  46800
ggcttcaaga agcgcgtggt catgttcgag tcgcgcgtgg tcatggacgc cgacgacaac  46860
atcatcggca tgctcttcac cgaccgcgtg ggcatgtacc gcgttaacgt gttcatgtcc  46920
tttcaggacc ggtctctttc atgcgactaa ataccctcat gggcgggtcg gtgagcctgc  46980
cctcgcggga cctgccgccg ccggtgcgca cgccggagat gaacatcgtg cccgagcgcg  47040
acctcgcgga cacgatggcg cgcctctcca ccgcagaccc gccgcagccg ctgggcgtcg  47100
gcgacgacgc gcgcatggcc gtgctgaaga cgaccttccc cgagttcgcg atatcgcggc  47160
ccgcgacggg catgctcgcc gcgcagcgaa tcaggtacga cggcgacccg cgcgtctgct  47220
gcggcgggtt cgggatctca cattactggg agaggggggc gcgccgatcg aacgtcgcgt  47280
tcgagggcgc ggcgctgcgc acctgcgacc ccacgcgctt cgacgcgggc gcgtgcgacg  47340
cgctgctctt ccgcgagtgc gccgccggcg gcgtcgacgc ggacttctgc gcgcactgga  47400
```

-continued

```
tcaacgcggc cgtgacgcgg cgcacggacc gacagtcgcg cgcgcggctg aacgacatgt  47460
tcgtgcgcga ttgccaaaac gacgccgccc ggcctcactg cgtggcctgg atccgcgcga  47520
tgcgaagcgc gcgcgcgacg gcggacgacg gtctaataga cgccgtgctc tcggtgcaga  47580
gtcccgagtt caagggcaaa cacatgcgct gcagctaccc ctcgccggcc acactcgcca  47640
tggccgcgaa cgtagacgag ccgcgcgagt gttgggaccc cgagtgcgtg gccgggaacg  47700
tggacttcat gctgagcgat aactacacga acctgggcct gtgtcggctc tcgcgctgct  47760
ccatcggcgt cacacacctg cggatagacg cgcgttcgcg gctgcgcatg cggtgcgccg  47820
gcgcgcttgc cgggctcacg aaggcgcccg tgaaccagac tgtcgtcgtc ggcgacaacc  47880
tcgcgcgcgc cttcgagccg cgcgtggaaa cgctcggcgt gttggcgctg tgcgtggtgt  47940
atctgctaat tgtctggctc taaatggggg ccgccgccag cattcagacc accgtgacca  48000
ccgtcagcga gcgcatccgc aacgagctcg agcagagcgc gagcgctagc gcgaccgccg  48060
actgcgacgt caccatcggg agtctgatta tccgcaagaa cctgggatgc agcgtttccg  48120
tccggaacat gtgctcggcc aacgccggcg cgcagctgga cgccgtcatg aaggccgtga  48180
gcagcacctt caacgacctc tcgtcggacc agaaggccta cgtgcccggg ctgctcacgg  48240
ccgcgctcaa catccagacc acggtgaaca ccgccgtcaa ggacttcgag acgtacatga  48300
agcagacctg cacggcggac gcggtcattc acaacaaaat caagatccaa aacatcgtca  48360
tggaagagtg cgcctctctg ccagggagtc cggccacgca cctggagttc gtgaacaccg  48420
gcacggccgt gggcaactgc ggcgtgaagg ccgtgatgga cgtgctcgcg aaggccagca  48480
ccaccgtgcg caacgaccag gaggccggca agggctacca gaccatcatc atcgcgatcg  48540
tggtcgccat cctggcggcc atcttcgcct ggtacgcgcg gcacatgcta ttcatgtcca  48600
cctccgacaa aatcaagctc gagctcgcca agaagcccgt ggtgcactgg accacctacc  48660
tggacacctt ctttacggaa tttccgccgt ccgtctagat acgcgcaaca ttgaaacatt  48720
atatccacct ctcaaacggc ggtatggtcc gacgcgtcct cctcgagcgc gtggacggca  48780
tcgtcgagca ctcgcgcgca gaccgacgct acttggaggc cattcagcga cacctcgagg  48840
ggtctacgcc cgggctgcgg cagatgtggc gcttcctcta cgacctgctg cgacggtgtt  48900
cgtcgtcatg tacatcgtct tccgcctaat cgtgcgcaac cccggcatct gcgccatcct  48960
cgcgccgcgg tgtactacct gtttttgtgt ctctttagca tggactgatg gcgatcacag  49020
acagaccatc gcccgcgcgc gcgtgaccag ctccggcgcc gcgaagacgt cctgcaccgg  49080
gaagtcgtcg atctcgaaca cggagccgtc cgcggaccag atcacgcgca cgttgtcgct  49140
caccgagacc tcggtcagcg tcacgcccag cacaaccgcg tcgttggtgc tcaccagcac  49200
cagcgcgccg ggctccgcgc gccggtgcag cggcggcccc gagactgagc gccgctgcac  49260
gcggaacatg tccgcgaact gcttcgagag caagtccagg tggttgcgga tgatccactc  49320
gaagaagtac gcgcaacctc cgccgccgca caggaagcgc gaacccgcgg gcatcagcag  49380
ccgcacaacg tccatgtagc aggcctgcgg caggctcgcg cggtacagcc gcgtcttcgg  49440
cgagagcacc accaggctgg aggtgctcat ctggaagacc agctggctaa cggagacggt  49500
gagcgtgcac gcgggcacgg aaaccacgtc caggcagatg tcgtccagaa agatgctccg  49560
ctggtagagg tggtacagga tggccacgat ctgaaaggcc gtggcgtcgc tgatggcgca  49620
ggggcggtcg gcgcagcgca tctgcgcgca ggaccagccc ccgaaggact cgaagcagac  49680
ggtgatcatg cccgtgctcg gacagtgtgg cgagcgccga cacaccggaa agcccacggc  49740
cttgcggcag cgcaccatgg tcgagagctc tatccagcag cctgcctcct cctcgcccat  49800
```

```
gcccatggct accggcgtga aggccgtgac gtcgtcgcag atgcgccgct ccagaaaccc  49860
cacgcccgag gaggggtgcg cggccggtgg cgaggtgatg cgcgccggga cgcggctcgg  49920
agcgggctcg ggaggcgagc tgcgctcgac ccgggcagcc gccgccggcc gcgatgccct  49980
gcgcgcgggc gcgcgttcgc gcgacttgtt tgacttgctg gcctcgtcgc tagcgtcatc  50040
gaagcggtcg ttcctgtcgc cgcggacgtc cgcctcgtcg cccgccggcc gcgcggcggg  50100
cgacgtgccg tcccgcgtac ggcccgcgtt cggcgcgaat gtcacgcgcc ggtgcacgta  50160
cggctccgta gagcccgtgg gggcgccgcg cccgcgccct cggcggaagg cctgccggga  50220
cgcgccgaag cgggcgaact cccccttcgc ccggcccctt ttttcttcca tgatatttat  50280
cacaaaaaaa acttctctaa atgaccaatc tgctttcgtt ggtcgacccg gaggacctgg  50340
ccttctgcgc cgggttcccg tccttcgacg agaccatgct cgtgatcgcg gggcgcgcgag  50400
tgcgcttccc acgctcgctg ctctcgctct tcaacgtggt gccgcgcacc atgacgcgct  50460
acgaaaccga gctcgtgggc accgagatgg tggtgggcgc cgtgttcacc accgcgtaca  50520
acgtccgccg caacctaggc ctcggcgagg agcccgtgac catgcgcgac atcgagaagt  50580
acttcctgga ctccgagaac gaggtgctca cgctcatcgt gcacaacacc gacttttccg  50640
ccatgagcgg cgtgcgccgg cgcggcggcc ggcgcatcgc caaccccgtc atcttccgca  50700
gcgggtccac gccgctgctc atcgtgatgg agtcgcgcaa gaagaccaac atctaccgcg  50760
agcgcaccgc ggagcaggcc aacgcctcct acagggaggt cggctcctcg ctcgcgctgg  50820
tcactcggta cgcgggtctg cagctggtcg acgtgcacac gcccagctcc gtgctaacgg  50880
tctccgccgt ctacggcttc accgaggaca aggggctcaa gaagctgggc tccgacaagg  50940
agctcgcgga ctaccagtcc acgccgctca ccgaccccat ccggctcagc gacttctcca  51000
atatattcga cggcgtcaag aagagcatcc agctcacgaa cgtgcccgtg ccctccgccg  51060
gcgccgaggc cgcgccgtag gctttcatgc gcgataaatc ggatggcggc gccgacgacg  51120
cccgtggtgc acctcacgcc ggtgttcgtg gagcctacga tcgcgcactc gctgctgcgc  51180
gcagagtcct acctcgcgat cgcggtcctt gagctcgtgc tcgcgctcgt gctcgcgctc  51240
gtcttcttcc gcgacgagct gggcgcgcta ttccgccgcg cgccgcgagc gccttcgccg  51300
ctggacgcgt acctgcaggc gagcctcgtc tgcgacggcg acgcgctgct gatcgagctg  51360
cccgaaggcc gggtgccggc gctcgcgctg gacgggcgac ccgtcgcgtt cccggggtgc  51420
gagagccttt tgtaccgcat aaatggacca cgaaaagtac gtcttgtcga tgttcttgga  51480
ggaagataac tccttcttct cgttcgtcgc cgcgctgtcc gatgacgagg cgctcggcgc  51540
cgtgcagtcc gctgccgccc tcctggactt cctgctctcc gtggtggtcc gcggcaagga  51600
gaagctcgcc gccgcggggc accactacga ctccatcgcg gacggacgcg cgcgcgccgc  51660
gttcgagttc cgagacctgc gcgagctggc gcagctcttc gaccggcggc cctgcggcgt  51720
ccaggaccgc gtgcgtgtgc gcgacgggcc cgcgcgcgcc ttcgtggacg cggcactggg  51780
gctcatgcgc gagcgaggct tcgacggcac gcaggccgcg gagcgcgcgc gctcatcgcg  51840
ccgaacgatc tgcccgcgct gggggcaata tcggccacgc tctcgccggg tctataacgt  51900
aaaaagaagg tccgtgtgtt tcgcgggcgg ccaacaaacc agtcgcttaa atggaggggg  51960
tggaaatgga caagccgctc ctctacttcg acgagatcgc gggcgcgcgc gactacgacg  52020
cggccttcgc ggagaagcac gagccgccca agatccccgg ccgcggacag atgaagctgc  52080
tggtctgcga gctcgtgttt ctcaaccggc tgcacctgca cggcatgctc gacggcagcg  52140
```

```
tcatcgtgta cgtgggctcc gcgcccggac ggcacatctg ctgcctgcac tcgcacttcc  52200
aggagctcgg cgtctcgctt aagtgggtgc tcattgacgg gcgcaagcac gacccctgtc  52260
tctcggggct gcggaacgtg accacggtga cgcgattcgc ggacgaggcc tacctccgcg  52320
agctgcgcgg cgagctgcgg cgcgccaaga tcgtgctcat ttcggacatc cgctccaacc  52380
gcgtggacac agagcccacc accgcggacc tgctgcgcga ctacgcgctc cagaacacca  52440
tggtgagcgt gctcaagccc gtggcctcca gcctgaagtg gcgctgcccc ttcccggact  52500
cctgggagaa ggacttctac gtgccctgcg gcaaggagat gctgcagccg ttcgcgccgc  52560
cgttctccgc ggagatgcgg ctgctcaccg tgcactcgga gacgcgcccg aagctgcgtc  52620
tgatcacgct cagcgacgcg gtcaactatg aaaagaggat gttctacctc aatagcgtgg  52680
tccgccagcg cgtaattctg aactttgact atcccaacca ggagtacgac ttctttcaca  52740
tgttctgtct gctctcgtcg gtggtgtgct cgtgcgaatt taaatcgccc aaagagaagg  52800
tgctgagcct gcagaaccgc ttcttccgct tcctgcgcat cccgccctcc atcacgctcg  52860
ggctgcgccg gcacgatgaa ccgccacaac acgcggtacc tggccaagat cctctgccta  52920
aaggccgcgg taagaagcga ccccttcgcg gtggtaagta gggacaccgt gcgcatgtac  52980
gacatcgagg tcgagtacgg cgacctcgtg acggtggtca ccgtcacgca caaactcgag  53040
accagccgca ccgtcttcca ggtcttcaac gagacctcgg tcgcgtactc gccgctgccg  53100
gacgactacg gcgagcccat cgtgctcacc acgtacatgc agcgcgagca caccaagttc  53160
ccgctctcca tgctctacat cgacgtggtc gcctcggaca tgttccccac gttcaagcgc  53220
cccaccgagg aggaggccgc ggtggtcgcg gccatgcagc gcgtgggcgg gcgccgcgat  53280
cccgtgctca agctcccgcg catgctggac accgagctcg tgtgcaagat actgcacctg  53340
cccgagcacc cgctgcgcgt ggtgcgcttc ctgcgccgaa acatgttcac gggcgtggag  53400
gtcgccgacc gctcggtgtc cgtggtcctc gactgacgaa gggcagcacg gccagcgagg  53460
ccgccgccac caagcacagc ggcagccacg cgcgcgggtc cgccacgggc acgaagacgt  53520
gctggttcag gtatttcgcc tggaagcgct ccgcggtgga gtccaccttg gacccgcagg  53580
cgttggtgag gcgcacgacc gcgtccgcga cgcgcacgtc cccgagcgat atcacgcagt  53640
ccgagacgtt gcacccggcg atgtttttct tcagcgcgcg cggtagcagc gcgtccgcgc  53700
gcttgcaggg cgcgtaccag cagtagtagg gcaggcgcgt gtcgcggccg gtgtcgacca  53760
cggcctggct gggcttgagg cacgcgcagc gctcgtcgtc cgggtgcgcg tcgcagaagg  53820
cgtaaatctc ctcgtcgggc gcgtccggcc cgggcgcggt cggcggcgcc gcgcgacggc  53880
ggaagaacat ctctgaaaaa atacttcgac cagaaaacga ccaccgatct tatttcaaag  53940
ataaaaatac tattaatacg cactcggaga atcatgtcgg tggtggcgcg cgtatcgtac  54000
agcctgtact cgcagagcga gataagcgcc acggacgtgg tcatcagcca gttgaagaac  54060
gacgaggacc tgggcacggt gaaggacccg cgcctgggcg cctcggacgg gtccatatgc  54120
cgcacctgcg ggctcacgga gatggagtgt ttcgggcact ggggcaaggt gcgcatctac  54180
gagtcctaca tcgtgcgccc cgagtacatc cccgaggtgg tgcggctgct caaccacctc  54240
tgcgtgcgct gcgggctgct gcgctcgcgc gacccgtaca cgacggacgt ggccgcgctc  54300
agcgtgcacg agatgcgcaa gatgaaggac cgcatgatgt ccaagaagaa ggcctgctgg  54360
aacagcaagt gtctgcagcc gtaccagaag atcgtcttct ccaagaagaa gatctgcttc  54420
gtgaacaagg tggacgagat acccgtcccc aacgcgctca tctaccagaa gctgacctcc  54480
atccaccgca agttctggcc gctgctggag gtgttccagg accccgcgaa cctgttctac  54540
```

aaggagtaca tgcccgtccc gccgctgctc atccggccgg cgatcagctt ctggatagac 54600
aacatcccca aggagaccaa cgagctcacc tacctgctgg gcatgatcgt gaagtactgc 54660
tccatgaacg ccgaggagca ggtcatccag cgcgccgtga tcgagtacga caacatcaag 54720
atcatctcct cgaactcgag cagcatcaac ctctcctaca tcatcggggc aagagcaaca 54780
tgctgcgcag cttcgtggtc gcgcggcgca aggaccagac cgcgcgctcg gtcatcggga 54840
ctccgcgctc tcggtgtgcg aggtcggcat ccccgactac atccggaaca cgctcacgca 54900
gaaggtgttc gtgaactacc tcaccagcaa gcgcgtgcgc gcgctgttcg aggaccgcgc 54960
ggtcaagttc tacttcaaca agcggctgcg ccagctcacg cgcatcaagg agggcaagtt 55020
catcaaggac aagatccacc tgctgcccgg cgactgggtg gagatcccca tgtccgaggg 55080
cacgaacgtg atattcggcc gccagccctc gctgcaccga cacaacgtca tatcctcgac 55140
cgcgcgcgcc tcgcccggct acaccatcaa gatcccgccc gggatcgcga actcgcagaa 55200
cgcggacttc gacggcgacg aggagtgggc cgtgctcgag cagaacccca agtccgtgat 55260
cgagcagagc gtgctcatgt acccggtgac tatcttcaag cacgacgcgc acggcgcgcc 55320
ggtgtacggg tccatccagg acgagatcgt ggccgcgttc tcgctgttcc ggcaccagaa 55380
cctctcgctg gacgaggtgc tgaacctgct cgggcgctac gggcgagact tcgcgccgga 55440
gcctggccag aagaccttct cgggcgccga cgtcttccga ttcatgatag gcgcggacat 55500
aaacttcaag ggcgtgctcg agaacgggcg cgtggtggcg ccgaacgtcg acagcgacct 55560
cgtggtggcc atgcgcgcaa cctcgctagc ggggctgatc gcggactacg ccacgaacgt 55620
ggagggcgtg cgcttcgtgg acatggcctc ctacgtgtac aagcggtacc tggccatcta 55680
cggcttcggc gtgaccttcc gcgacctgcg cccggacccg agtctggttc gccggctgca 55740
cgcgctgaac accgagaaga tagagcagat caaggacgcg tactcgcggt acctgcagga 55800
cgtcgcggac gggaagctgg tgccgatggc gcccgcggac gaagccgacg cgctggactc 55860
gctgctggcc aacctgacca acctcaacgt gcgcgagatc aacgagtaca tgcgcgagac 55920
gctggagcgc aaccccgata acagcctgct caagatggcg cgcgccgggt acaaggtcaa 55980
ccccacagag ctcatgtacc tgctgggcac ctacgggcag cagcgcgtga acggcgccgt 56040
cgccgagacc aagatatacg ggcgcgtgct cccgtacgcg ttccccgact ccgcggaccc 56100
ggaggcgcgc ggctacatca tcaactcgct catgaacggt ctctccggct cgcagttcta 56160
cttcgcgatg ctggtggcgc gctcgcagtc cacggacata gtctgcgaga cctcgcgcac 56220
gggcacgctc gcgcgcaagg tcatcaagaa gatggaggac acggtcgtgg acggtacgg 56280
acagatcgtg agcggctcgg tactgctcaa gtacgcggcc aactacgcga agatcccggg 56340
gtccaccacc aagcccgtgg agctgctctt cccgcacgag agcatgacct ggttcctgga 56400
gatcagcgcg ctctggacga agatccggca cgggttcgtg cgcatgcacc ggcagcgcct 56460
ggccaccaag atcctggcgc cgttcaactt cctggtcttc gtgaaaccgg cgccctcgga 56520
ggcggaggcg ctctccgcgc gggacctgta ccacatgatc cagcgcgtga tgaacgacgt 56580
gcgcgagaag tacttcttct cgctggcgaa cgtggacttc atggagtacg tcttcctcac 56640
gcacctgaac ccctcgcgcg tgcgcatcac gcgcgcgacc gccgagctca tcttccgcaa 56700
gctgtaccag aagctgaacg cgctgctcgg cggcggcacg cccgtgggca tcatgtccgc 56760
gcaggtgctc tgcgagaagt tcacgcagca ggcgctctcg agcttccaca ccaccgagaa 56820
gagcggcgcc gcgaaggtga agctgggctt caacgagttc agcaacctca tcagcatgag 56880
ccgcaaccac accgagatag tggcgctgac cgcgccgagc ccggataagc tgatgccgct 56940
gaaggtaaac ttcgagttcg tgtgtctggg cgagctcgtg cccgagatcg agacccggcc 57000
ctcgggacgg ccctccgtgc accgcgtgga catcacggtg caccgcctgc gcatcaagcg 57060
cgcgcacctg accgaggtcc tggtggacac catcatcgag cgcttcgtgt ccttcaacgt 57120
gctcgtgaag gagtggggca gcgacatgac cgtggagggc gaccgcgtca cgtacacgct 57180
gctgctgcgc ttcgtggagc cggagcagct caacttccac aagttcatgc tggtgctgcc 57240
cggcgccgcg aacaagggca aggtgagcag gttcaagatc ccgatcaccg agaccacggt 57300
ctacgacgac ttcgacgccg cgcgcaaggc ctaccgcatg aacatcgagc tcatgagtct 57360
gaaggagctg gggatattcg acctcgagga cgtgaacgtg gtccccggca tgtggaacac 57420
cttcgacata ttcggcatcg aggccgcgcg cgggcacctc tgcgagagca tgctggacac 57480
ctacggcacg ggcttcgact acctgtttcc ctcctgcgac ctgctcgcga gcctgctctg 57540
ctccgggtac gagcccgagt ccgtgaacaa gttcaagttc tggaacgcga gcgcgctgaa 57600
gaaggccacc ttcggcgacg gccgcgcgct gctgaacgcg gcgctgcaca accgcaccga 57660
cgcggtcgcg gacaacagca gctgccactt cttcagcaag acgccctgcg tggcacgggc 57720
tactacaagt acttcgtgaa cgtggagatg ttcatgcgca tggagcgcga gatccaggcg 57780
cgccgcgcaa gatggaggag atcgaggagg ccgccgagga ggagttctag gcgcgacagc 57840
gccttacttt gcgaccgtgt tacgacgaca cgacacggtt aggacggcga gtcgcagacg 57900
aacattttta tgagctggta gcggaagttg gcgttttcca ggaaggcgcc gcggaggtcc 57960
cggatctcgt agtaggtttt gaggaagtac acgaagcgcg cgggctgcgt catagtcggg 58020
ttctccgcaa gccgcttgtg catcacgtac cccatggcgg cggcgccgct gcggttgacg 58080
ccggccacgc agtgcacgag cgtgggcttc tgctcggcct cgaggcgcgc cagcagcttc 58140
acgagcgcgg gcatgatgga agcgatgttc gtcgtgtcgt cgtctctcag cggaatgtgg 58200
tacgccgtta tccccgcggg cgtcgagtac ttggacatgg tcatgttaac caggcacttg 58260
aagtcgacgc cggagtcccc ccgcagcacg gcgcgcgcgt cctcggcgct gcccaagtac 58320
acgtggtccg tgagccgcgt catgcccgag ggcagggcca gcggcggccc cgcgcgcgtg 58380
caccgcagca ggagcctggc gtaccactcg ctcttatcgc ccatatttat ttatatgata 58440
caaatggcag acgtcacaac actgacggcc aacggtctga ccctggagtt cgcgcgcgag 58500
cgcgctctgc gcagcctgcg cgccgcgcgc acctccacgc tggtgttctt cacgctcacg 58560
ctcgcggcct cgctgttcgt gctctggctg cagctaaccg agtttcccgt cttcgaggag 58620
ctcggcaagt acgcgcgcat caagagcgcg gtgcggtcct ggcgcccgct ggtggaggct 58680
aagaccgaga tcgagtccga cctcggccgg cagaagaccg ccgaccggcc cgagctcttc 58740
gagttcaggt gcgtggactt cggcaagttc tacctgccgg tgaggtacag ccccacgacc 58800
ttcctgccgc aagccgtgcg ccgcggcgcg ggcgatggct ggatggtgca caaggcggcg 58860
gccgtggacc tcgccgcgca gcagttctgc gagtccgtgc tgcggcaccg cgccaacaac 58920
gtcatcacat gcgggtcaga gatgatgcgg ctggtgggct acagcggcta cttcgaggac 58980
gaccactggt gcgccgcgac gtccggcgtg ctgacgtgaa cgatcacacg atggccgtga 59040
ccagcagccc ggcgatgaac cacagcagcc gcgagttcgg cagcagcagc acgagcacca 59100
gcaggtatgc caggatgaag atgtcgacca cgtccacgtc gaagagcccc atgaaggaga 59160
agagcggcgt ggtgaggaag tagatggcgc cgggccagaa gcgcgctagc cacgtggcga 59220
gcagcgacca cagggagggc gcgccgctga gccgcgtctt cacctgtatg tagtactcgg 59280
ggtagaccac ctgctcggcg ccggagagca ccacgcgcgc cagagagagc cgcttctcca 59340
gcgtgaacac ctcggtgagc aggccgctgc gcagccctcc ctccttgatg atcgcgtcgt 59400
agagcttctt catgccgccg acgctgatga tgtaggcgtc tagcgagacg tcgtatccgc 59460
cggggtagac catgagctcg ggtcgccgg tgccggggac gttggtggcc agcgcgccgg 59520
tcatgtaggt ctccttgagc tgcgtcatgt accagccgtt cgccttcatc gcctcgatga 59580
gcggctttac catctcgggc ttgcggaagg tcatgtcgtt gtcgaccacc aggatgaagt 59640
catcgtcgga gtacttggtg gggacagtgc cggccgatat gctctcccag aggttgaggt 59700
ggtgcgccgc gcggcgctgc atctccttcg gacacgtgga cttgcacatg tccgtgaaga 59760
agtgcgggta gtctttggag tccacgtctt tccattccac cgccttgagc acgtggtcgc 59820
ccttggggtg cggcgcggga ggagatggct tgggtgccgg cgcgggggcc ggcgcggggg 59880
caggtgcagg ggccggtgca ggagagggag caggcgcggg ttgaggcttg ggcgggtcgt 59940
cggcgaggcc caccaggtac ggcagcgtgg ggaacacctc cttggtcccg cggccttcgg 60000
caaccccgat tatgtaggcc gtgatttcgg gtggatccat ttagttatta aaattaatca 60060
tatacaactc ttttatggcg gctatggatt cggctatcca gtccttgacc gagcccacga 60120
tgcccgccag gaacaggaag aaggcgaact ccaggtccac gcggttcaga gagtcgctga 60180
agtacacgaa gacgtcgctg tccgggaaga agctgcgccg gaacatgttg tacccgttga 60240
ccttgtgcgc gacgtgctcc gcgctcagca gcgtctcgtc gaaggggtac gggtcgctga 60300
agcggaacac gtacatggcc gggttcgcgt agtagtactt catggtgttt gtgacgaaga 60360
ggctcgccag cgagatgatg atctttttct tctcgatctc gatcttgatg tggtcctcga 60420
agcgcttcat gttgtaggcg ttggtgtcgt gcacgcggat gagcacgcgc gagtccgaca 60480
tgatgtcctg gaactccgcg cgcgcgtcgg ggctctcggc gggcgtctcc gcgggccgcg 60540
ccacctccgc gcacaccgtc ggcctagcgc gcggcggcgt gcgcatgggc cgcgccccca 60600
cgcgctgcga agcgaaaaac tccacggcgc gagcctcgcc cgcgtccgcg tacactccac 60660
caggtagttg cggctgcgcg tggtgcggcc gatggtgttc agccggtgca gctccgcgac 60720
cagcccgggc atgatggagg tgtacacctc ggtgagcagc atcacggtgt cgaagtcctc 60780
cttgccgcag acgcgcgtct tcacgaggaa gtggtgcaca gccgtcgcga tagagagccg 60840
cagcgtggac tcggtgacct caacgctggc gtccttggtc ttcttcgcgc tccgcgaggc 60900
catgaacgag acgaggaagt ccgcgctgct gttgagcacg atgaccagcg cgacgatgaa 60960
gttgaggttc agcgtcttcg cggactggaa cagctcggtg gccgacgcgt gcacgtcgag 61020
caggttcgcg gagagccgca ggaagaacac gccgcgcttg atctcggccg cgaagcgacg 61080
ttcgtactcc tgccggcgcg cgttgatcgc gatgaggaag ttcaggatga gccggttgat 61140
gttgtacttc acggcccagg tctgcgtctt catgatggtg tcgaaggaca tcacgatgtt 61200
gaagatgaag cgctggctgt gcgagaagta gctgtagggc tcgctgagga agatggactt 61260
gttggtcgcg ggcactacca cgcccgcgcg cgcgccggac gcgtcggtgt tcaggtccgg 61320
gatgttcatg ccgcagatgc ggcagtaggc catgccgtcc tcaaagtaca cgaactcctc 61380
cacgaactcg ttgatcttgg caaagtagtc cacgtccacg cgcatcgcga ccgcgagccg 61440
gatctggtgc tcgcagggcg gcgactcgaa gcgcacaccc tcgccccagc ccggcggctc 61500
gcgcacgacc agcgcggtgc gcgaagccgg gcggaacttg gcgtcgcgcg cgttgagcag 61560
cgccgggaag aggtcgcaga ggtgccggct cgagaggaac acgtacttgt acagcagccg 61620
gcgcgcgtcc gcggccatgg cgtccacgaa ggcgcggccc cactccgcga ccgcgggctg 61680
ctcctccgca aagttgttcg ggtagacctt gtccgtggcc gcgaggaaca ccttcttcac 61740
gtcgaggaag tcgcggatca cgatggggac gcgcgcgccg tcgagctcgt acatgaacac 61800
gtagcgcagg ttgagcttgc gccgcgagac cgggatgccg atgtgccgac acaggtacgc 61860
gaactcgagg tacttcttcg agaagcggat gcggtccagg ttcttggaga cgtactgcag 61920
catgttgcgc atgttgaagg ggatctcgcg cacggcgggc tccgcggcgt cgtcgaaggc 61980
ggtgcgcaga tcgctggtgc gctgcacgac cacggcttcg ccggtggcgt cgtcgtgcac 62040
cagcacgtta acgcgccgct gccggatgac catgtcgaag gtgttgaaga acatctcgta 62100
catgctgtgc cgagtgtcgt ccgcgatgcg ctcgcccacc gagaggctcg cggtggcgtc 62160
gtcgcgcacc tgcttctcga acttgtaccc gatgtaggag aatatcgaga tcagcgtggc 62220
gtcgtcggcg tcggggttct gctccatggt cgcgaagagc aggcggatgt cgtcctccgt 62280
gatcgcgtcc acgttgtaca ggttgaccac gaagatggac ttgttctcgg cgatgaagtc 62340
agtgtaggac ttggtggccg tgttcgggtc gcgcatgtac gcgcggatct tcggcacgat 62400
gctcgcgagg atggactccc tggaatccat ttaaggacgg caagggcgcg cgagaccgtc 62460
tcaaaactga aatcgtataa actcttaaaa aattggtatt gaaagtacgc accaccaaat 62520
aaagcgtcga ggtcgggcat gtcttcgtgg cgactcaaaa tgagcaagtg ttcaggttcc 62580
agcagcgtcc agactctcga ggatctgcgt aatcgtcttc gctccgaggc cttgggcaac 62640
gatttccaag agccccgcga cgacctcttc cccagcggcg aggagtgtct ggacatcgac 62700
gggccctgcc cttgcgatga ggcggagcag gagatcgacc aggagcagtt gcctgtgccc 62760
gaaaccgtgc ccgaaccgcc ggccaagact cctaagcgcc gaccagtgaa gaaggataag 62820
gcagataagg cagataaaga caagtcgacc agaggcgcaa agaaaccgtg cccttcggac 62880
gacaaggatg acgagctcaa gagcaacgac gtcgacaaca acgaagagtc cggcgacaca 62940
gatggcggcg cgagcgcccg aagccccagc gacatcgaca acgtggacga gatggacgac 63000
tccgacctca tggtggcgtt ctccaccatc ctcgcagact tcaaggacat cacccaacga 63060
gtgaaagctc tttcgtccgt actcacggac gtacaggcgg ccggcatacg caggtgcttc 63120
tcgacgctcg gcaaggctct gacggaggcg gcccacatcg ccaacaccgg agctaagcca 63180
gtcaccgcgc ctcgcaagaa gaaggccgcc acctgcaaga agtaggcgca ctaaatagcg 63240
aggctcggta tgcgggcgct gcacctgtca gacggcagac tttttttga caaggagctg 63300 acgcagccgg tccccgacga caaccccgcg tacgctgtcc tcgcgaagat ccggatccca 63360
ccgcacctct cggatgtggt cgtgtacgag caggacctcg agtccgcgca gcagggcctc 63420
atcttcgtcg gccgcgacgc caagggccga aagcagtact tctacgggcg cggacacgtg 63480
gagcggcgca cggccgtccg caacgccgtg ttcgtgcgcg tgcaccgcgt catgaacaag 63540
ataaacgcct tcatcgacga ccacctcgcc tccggcagga ggccgaggcg cagatggccg 63600
ccttcctgct catggagacg agcttcttca tccgcgtcgg caagacgcgc agcgcgagag 63660
cggcaccgtg ggcatgctca cgctgcgcaa caagcacctc gccgaggccg agggcggtga 63720
ggagatccgc gtcgccttcg tgggcaagga ccgagtcgcg cacgagtttg ccgtgcgcga 63780
ggggcagcgg ctcttcgcgg cgctgcgtcg gctctgggac ccgggcgcgc ccgacaggct 63840
gctgttcgac cggctgagcg agcgccgcgt gtacaccttc atgcgacgct tcggcatccg 63900
cgtcaaggac ctgcgcacct acggcgtgaa ctacaccttc ctgtacaact tctggtccaa 63960
cgtgcgctcg ctggagccgc gtccctccgt gaagtcgctc atctgcacct ccgtgcggca 64020

```
gaccgccgag acggtggggc acacgccctc gatctcgcgc agcgcctaca tggccaccgc  64080
ggtgctcgag ctcgtcaggg acggcgcgtt cctggacaga gtcgccgcca ccgacacgct  64140
cgacgacttc gtggacatcg tcgtggacta tgtaaataac tctgagcagg taaatggatg  64200
aggcgctgcg cgtggcggcg cgcgtcgtgg acgggctccg gccgctggac gtggccgtgt  64260
gtctcacgca gctgcgcgga gccgcgcccg agcgccgctt cccggcgctc gacgagtgct  64320
ccggcgaggc cttcctggac ttcgagttcg ccggcgggga cgtggcgtcg cggtacctct  64380
ccgcgcacac gcgcgagctc cgtgcggcgg agcggcgcga gcacatggcc gcgatcgcgc  64440
gctgcgtcac cgaggccgac ctggcgctcg cagaccgccc ccggggcaag gcgcgcgcgg  64500
cgctgcgcgt gtgccgcaac cgcgagaaag tcgcgcgctt ggcgaggctg ctgcgcgacg  64560
ccgagagcag cggcgcggac ttcgccttca tacgcgcggc cgtggcgtag caaaacgtaa  64620
aaacaacaca ttccctaaat cgccatggac gcgccaagtc tcgactgcat gctcgccgca  64680
ctcgcggcga aggcgtcttc ggtggaccga ggcgcccccg aggacgaggt gcaccacgaa  64740
gtggagctcg tgctcgtaga cccgccgctg tccaccctgg ccgccacgct gcgcctggcc  64800
tcggagacgg agtccttcat cctcttcacg gtgaccgcgc tcgccaagga ggagggcaag  64860
ctgcgcgcgc gcgtgcccat gtcgcgcgtc gtcggcctgg acgtgaagaa cgtgcagctg  64920
gtaaacgcca tcgacagcat cgtctgggag cgcaaggcgc tcgtggagga gaccgcgctg  64980
caggaaggct gtctgctgcg ccactccacc gagcggcggc acctcttcgt ggactacaag  65040
aagtacctct cggccatccg cgtggagctg gtaaaccgcg tgcgcgtgcg ctccaaagaa  65100
gtcgtcgcgg acttcaagtt caagtacttt ctggggtccg gcgcgcaggc caagagctcg  65160
ctgctgcacg cgctcaacca ccccaaggtg cggccctcgc ccacgctgga gttcgaggtc  65220
gtccccgcgg gcgaggccgt ggacgaggcc gccgtgctcg cggagctgcg cgccgtggcg  65280
aaggcgctct tcatggcgcc caccgacgcc gtcttcctgg cgccgccggc cgagatgccg  65340
gtgcgcacgc tcatgctgca gaagcaggag atccccgcgc tagacctcga cggcctcttc  65400
gcggtctcca agacggacgg cgtctctgcg agcgtgcgcg tggacgagga cggcgtcttc  65460
tgcgcgttct cgcacctcgc gtacaccatc cggtacccgc tcgcgcgcaa agtgcagggc  65520
cggtaccggc tctggtgcga ggccgtgcgg cccgtgggcg agcgcgtgtg gtccatgttc  65580
gtgctggtcg tggaggagcc tgcgggcgat gaccgcgtcg cggccgtggc cggcgccgtg  65640
gaggcgctgc gcggcgtgtg tgcgcgcgtc gagttcaaac ccaagcgcgt ggacgggccc  65700
ttctcggcga cctccgagct ggtggagcac atcaagagcg cgctgcagac ggagccagag  65760
ggcgtggtgc tcttctacgc gcgcggagag aagtccaagc gcgacctcaa ggtcaagcgc  65820
gacaacacgg tggaccagac cacgaacgtg atgttccggt acatgtccag cgagcccatc  65880
gtcttcggcg agggctccac cttcctggag ttcaagcggt acagcaacga ccgcgggttc  65940
cccaaggagt acggcgcggg gcgcatcttc ctgcgcgagg acgtggtcta ccacaacaac  66000
atctactgca tcgagttcac gaagacgcac ctggaggtgg gcctccgcag cgtggtcgtg  66060
cccgtgaagt tcatcggcga gttctcgcag gaggggtacc tgctgcggcc gcggctggcc  66120
aaaacggagt gctacttccg caacccctca ttctacggga accagcactc ggtggtgctc  66180
gagcacactc gcgaccagct gctctcggtg ggggacgtgt tcgacgagag ccgcatggcc  66240
gccgtcgggc agacgctggc caacgacgcc ttccgcctga acccggacac gccctacttc  66300
accaaccgac gcacgcgcgg gccgctgggc gtgctctcca actacgtgaa gacgctcatg  66360
```

```
atatcgctgt actgctcgaa gaccttcctg aacaacgccg agcgacgcaa ggtgctggcc  66420
gtggacttcg gcaacggcgc ggacctggag aagtacttct tcggcgagat cgcgtccatg  66480
gtggccacgg acccggacgc gcgcgcgatc gagcgcgcca tgggcgctac aaccgcctca  66540
acgcggggct gaagtcgcgc tactacaagt ttaactacat ccaggagacc atccggacct  66600
acgtggagag catccgccag gtcatgtact tcgggcgctt caacatcgtg gactggcaga  66660
tggccatcca ctactccttc cacccgcggc acttcgccac ggtgatgcgc aacctgcgcg  66720
agctcaccgc gcccggctgc aaggtgctca tcaccaccat ggacggggac ttcctgtcga  66780
cgctctccga gaagaccagc ttcgtgatca accgcaacct gcaggagagc gaaaacttca  66840
tgtcgatcga gcgcgtggcc gatgaccagg tcatggtcta cgcgccctcg accatggcgc  66900
agcccatgac ggagtacatc gtgcgccgcg cggacatcgt caagctcttc gcggacaacg  66960
gcttcgacct cgtggaccac gcgaacttcg agaccgtgat ccggcgcagc cgccgcttcg  67020
tcgagggcgt ctcgcggctg gagacgcggc cctccaccaa gaacttcttc gagctcaacc  67080
gcaacgcgct cacggagatg gacagcaccg acgtggccgc gctgctaaag atctacgtgc  67140
tgtacgtctt cagcaagcgg taggcagaac cagggcgtcg attccgcgcc cgcgccggcg  67200
cggaaggcgt tgaacagctc cgccagccag gctgcggtct cgcgcgcgtc gatcgggccg  67260
ccgtcgtccg gcggcggctc gcgcgccgcg cgcaacacca gcgtctccgc gggcggcaga  67320
ggctccagag cctcgaagac cgcgcggctc gggaacagcg cgcgcatcat gcgcgagcgg  67380
tggccgaaca ccgccttgac cgcgcgcagt gccgagcggt tgtccagccg cagcgctcgg  67440
tcaaaacgat gcacgcgcgc gggcgcgccg cggtggtcgc gctccacgag cacgtgccgc  67500
cacgccagcg ccgcgccgac gcggtccagg ctgggcgcga gcgccaccag gcttttcagc  67560
tcatgtaaat ctccgcgcat ggccgacggc tccatttact actgcggagg aacgcacgtg  67620
gtcgcggccg cgccgggcgc cgcgcttgtg gtgctggacg cgcccggagc ggtagcggcg  67680
gccgcgcccg cggggcagcg cgtcttcttc gccgagtacg gcctcgaaaa gcgggccaac  67740
ggcccgatca cggcgcggct gcgacgctcc gggttccgcg gcgccgcgaa cgcctgggcc  67800
tccgtggcgg acttcgaggc cggcggccgt ccctccgcgt ggacgctgcg cgcggaggag  67860
gcttcgcgcg taccgctgcc gacggacgcg gcgctggtcc tggcctgggg cgcgcgcgag  67920
gagccgctgc gggcgtgcgt gctggcgcgc gcggcagacg cagaggcgcc ggtgggcgcc  67980
gcgctcaagg aagccgcctt cgacgcgcgg gcgccggcgg ccgcgctgtt cgcggcgctg  68040
ggcgcgcccg cgctcgcgcc cccgctgcgg gcgcggctag tggcgccgcc gggcgcgccg  68100
ccgcggacgc ggctctgcga gaacccggcc atgctgcgcg cgttcgcagt gggctggttc  68160
ggcgcgcagc tgggcgaggc ttccgaaaat gaaaaggtat ttgccgcctt tgataaggcg  68220
aggtcgtgtt tggacgaccg ctgatggcga cgcccgcgaa cgcacccgcg ctgctcgtcg  68280
cggtgctgcg acaccgcccg taccgcgtgg agtaccaccc ggactgggag ccggtcatcg  68340
agacgctggt ggacgagtac gacgcggtcg cgccctggct gctgcgcgac gcgacgagcc  68400
ccgagcccga gcgcttcttc gcgcagctgg cgaagccgct ggcggacaag cgagtgtgcg  68460
tgtgcggcat cgacccgtac ccgcgcggcg gcaccggcgt gcccttccag tccccggact  68520
tcagcaagaa gaccatccgc gcgatcgcga gctcggtcgc gcgcacgacc ggcacgcagg  68580
gctacgcgaa ctacgacctg gacgcggttc cgggcgtgct gccctggaac tactacctct  68640
cctgccgcga gggcgagacc aagagccacg cgatgtactg ggagcgcatc tcgcggctgc  68700
tgctgcagca cgtggccaag cacgtgagcg tgctctactg catggggcgc acggacttcc  68760
```

agaacgtgcg cgcgcgcctg gacgtgccgg tgacgctggt ggtgggcttc caccccgcgg 68820
cgcgcgacgg gcagttcgcg cgcgagcggg ccttcgaggt catcaacgcc ttattggagc 68880
tcaacgggaa gtctcaagtg gactgggcgc gaggattttc tttttatagt gaaaattaat 68940
ccgtggtcct aaatggcggc gcccatatgc gataactctc acgtgttcct cctcaagcgc 69000
ctgggcgtgc cgtcttcctg ccggcgctcg gaggacccgc gcttcgtgga gatcctgact 69060
cccttcgagc tcgcaaacta catcgagcgg cacccgggat gctgcctctt cgagacgctg 69120
cgcgacgagg aggactgctc cgtcgtgcgc gtcttcgcgg acgtggacat ggacagcgtg 69180
ctcgaggagg aggacttcgt cgcggcgctg gaggacctca tcgtagagct cgcggccttc 69240
ttcgaccgct tcgcgagcgg ctcctgcggc accgtgcccg gcgaggtcaa gcgcgccatg 69300
ctcgcgaact tctcggtcac gcgatccacg gccgagcaca agaccagctt ccacctgatc 69360
ttcacggaga cgtacaccac gctggacacg ctggtggcgg cgaagcgccc gctgctggac 69420
ctgtgccggc gctcggacaa cgtgctgctg cgcgcgctgg acacggcgtg taccgccgcg 69480
gcgcgacgct gcgcgtggtg ggcacgcgca agacgccgga gtcgagcgcg gtccactgcg 69540
acgacatcaa ggactacctg ttcacgttcg tggagctctc ggacgcgagc gtgtacttcg 69600
agctcgcgga gcgcgagcag cacacgctga gcaccgtttg ctgggagacc tcctacatcc 69660
ccttcggcga cgcgatgcgg cgcgtgtgcc aggcggtggt caacgacatc gtgaacctcc 69720
gcgacatcac cgaggacaac ttcctcgaca cgccgctggt catcgactac gcgacgcgct 69780
gcgcgctgtg caagaagccc aagcacaagc acgcgcacca catcaccatg ggcaacggct 69840
gtctgcgcct ggtcaagggc gggaacgcgc acagctgcaa ggtcaagatc atccagctcg 69900
agggcaaccg gctcttcacg gccgcgcaga tcatcatcgc gtccgaggtc gtgaagctca 69960
ccgagcgcaa cgactacatc gtgtggctga acaactcctg gcgcttcagc gcggaggagt 70020
cgctcatcac caagctcatc ctggacgtgc ggcactcgct gcccgcggac tacgccaacg 70080
acatgctgtg tccgcgcaag cgcaaggtcg tggaaaccaa catccgcgac atgctcgtgg 70140
acatctccga gacggacacg cagtacgaca agctgccctt cacgaacggc gtgctggacc 70200
tggccacggg cgagttcctc accggcgacc gcgcgaaggc ctgcgtgtgc acggtctcca 70260
ccgggtacgc cttctcgcgc gaggagttcg cggccgcggc ggactcggag gccatgcgcc 70320
ggctggttgg cgtcatcgac gacatccagc cggacacgcc cgagaacgcc gataaccgcg 70380
cgctgtacga gcgcgccatg tccagcgcgc tctgcggcgc cacgaagacg gtcatcgtct 70440
tcttctacgg cgacaccatg accggcaagt ccacgagcaa gcgtctgctc atgtccgcgc 70500
tcggcggact cttcatcgag accgggcaga ccgtgctcac ggacgtgctc gacaagggcc 70560
cgaacccctt cgtggccaac atgcacctgc ggcgcgcggt cttctgcagc gagctcccgg 70620
acttcgcctg caacaacgcg cgcaagctgc gctccgacaa cttcaagaag ctgaccgagc 70680
cctgcatcgt gggccggccc tgcttctcca acaagatcca caaccgcaac cacgccacct 70740
tcatcatcga caccaactac cgcccggtct tcgaccgcgt ggacaacgcg ctcatgcgcc 70800
gcgtggcgct ggtgcgcttc cgcacgcact tctcctcgtc ggccactcgc gcggccgccg 70860
cgcacaacgt cgagtacagc gcggtcaagg agatggacga gagcctggac accaagatcc 70920
agcgcaacta cttccgctac gccttcctgc gcctgctcgt gcagtggttc ggcaagtacc 70980
acgtcccgca ggtctcgctg gcgcccacgc ccgacgcggt acccgacttc gccttccacc 71040
gccgcgtggc cgagctggtg gtggccagca acgacgcgca ccgccgcgcg atggagtcgc 71100

-continued

```
tgtccaagct ggggtacgtg ctcgtgggcg gcaacgtggc catgcccgcg gacgccttcc  71160
ggcagcggct ggccgcgcac ttcaacgcgc gcgtgcacgg cggcgacata gacgccttca  71220
tgttcaagca caagaaggtc gtcaacgtaa cggaggagta cgtggagtac gtattcatcg  71280
aagatgtcga gaataaatag gcgggcatga actcggacgt gatcaagctc ttcgccgggc  71340
acgacgagtc cgtgcccggc atcctgccgc accagctcgc gaccgtggac ttcctgatac  71400
gccgcgttct agacgacaac gtcagcgtgc ttctcttcca catcatgggc tctgggaaga  71460
ccgtcatcgc gctgctgttc gcgatggtgg cctcgcgcac caagaaggtg tacatcctgg  71520
tgcccaacgt gaacgtcatg aacatattca actacagcat ggtcatggtc gctaacctgt  71580
tcaacgcgcc cttcgtggcc gagaacatat tcgtgtactc gacgactagt ttttattcgc  71640
taaactgcaa cgacggcgtc ataaactaca acggcctcgg caagtacgag aactcggtct  71700
tcgtggtcga cgaggcgcac aacatcttcg ggaacaacac cggcgagctc atgatggtga  71760
tcaagaacaa gacgcgcgtg cccttcctgc tgctctcggc ctcgccgatc acgaacacgc  71820
cgctcacgct cagcagcatc atcagcctca tgtccgataa ggacgtggac gtcggcgaca  71880
tcgtggtgca gggcaagaag gtgttccaga tcctgctgaa cgagcacggc gtgcgcgtga  71940
tccgcgaggt gctcaagggg cgcatctcct actacgagat gccggacacg gacatgcccg  72000
aggtgctcta ccacgggcgc cgcttcctgg acacgcgcgt ggtctactgc cgcatgtcgc  72060
gccggcagga ggacgactac ctcactgtgc gccggctttg caacaacgag atgttcgaga  72120
agaacatgaa caacgtgtcc atggcggtgc tgggcccgct gaacctggtg aacaacctgg  72180
acgtgctctt ccaggcgcag gacaaggacc tgtacccgaa cctgcgcatc agcaacggcg  72240
tgctctacgg gaacgagctc accaagctgg acatcagctg caagttcaag ttcttcatct  72300
cgaaggtggg cgccatgcgc gggaagcact tcatctactt ctccaactcg acctacggca  72360
gcctggtcat ccgcaacgtg atgctcagca acgggtactc gagttcggcg gctcgcagag  72420
caacaacccg cacaccacgc ccgacgggcg cgccaagacc ttcgcgatcg tgagcaagat  72480
gaaggcctcg ctggaggagc tgctcgaggt gtacaactcc gcggagaaca acgacggcgg  72540
cgagctcatg ttcctcttct cctcgaacat catgtccgag tcctacacgc tcaaggaggt  72600
gcggcacatc tggttcatga ccatccccga caccttctcg cagttcaacc agatcctggg  72660
ccgcgccgtg cgcaagttct cctacgcgga cgtggccgcg cccgtgaacg tgtacctcat  72720
ggcggcggtg tactcggact tcgacgagga catcgtctcg ctggaggact acagcgtgga  72780
ggacatcaac gcgctgccct tcgacgtgaa gaagctcttc tacctcaagt tcaaggccaa  72840
ggaaaccaac cgcgtgtacg ccatcctgca ggagctctcg gacgcgtact ccgcgcgccc  72900
gcacccgcag ctcgtggacg tggtgctggg ggagatcgtg cgccagttct tcgcgcggca  72960
ctgccgcgtg cccgccgagg acgccgcgct cgtggccgcc gtcgaggccg ttctcggcac  73020
gcgcgaggca gcggccgagt acatccgcgc gatagtggac ggacacttct tcgtgaccaa  73080
caagaccttc gggaagtgcc tgctcttccg gcacgagcgc gacatcgtga ccgtgccctt  73140
cgagctcgag cacgacccct tcgcgtgggc gatcaacttc cgcaaggagg tcagtgtggt  73200
gaatatataa cggcaaacat aaatagaaag accgtcctcg cgcgcgatgt cgaccttccg  73260
gcagacggtg tacctggcgg tgacgctgca gccgcacgag ctcacgctcg acttccgcgg  73320
caacgtcgcg gaggcggtca tgcgcgagta cctctacaag gagaagggcg ggctcatggc  73380
caccgacatc gaggtctgcc tcggaaacga gatgccgctg gggcgcatag tgaacaacgc  73440
ggttgtggtc tcggtgccct gcaacgtgac cttcaagtac taccgcgtcg gcgacaccgt  73500
```

gagcggcacg ctcaacgtcg aggacgagac caacgtcttc gtggactgcg gcgacctcat 73560
ctgccagctc ggcaagagct cgggcggcgt gaccttcaac gagtccaagt actgcctcgt 73620
gcgcaacgga gtcgtctacg agcacggcag ccgggtctcg gctgtgctgc gcgaggcgcg 73680
ctccggacgc gagtccgcgt tcgtgttctc cgcagtgctg ctggacggcg tccccgccga 73740
ggagaaggac gagaagaagg acgagggcga gaagcccgcg gagaaggaga cgcttgcgag 73800
ccccgccgcc aaaaactagc attattgggc cgcgcgaacc ttcgataaat gcgcacgtac 73860
acgtcgctgc tctcgaagct gctcaagagc aaccggcggc tcgggagcac gcgcgtcttc 73920
cgcgacccgc tgcagcacat cagcgcgacc gcctttgtgc accggcgcat cgaccggcac 73980
cggcgcgtct ccatctgcgc cgtgctcacc accaccgacg ggctcgtggt cgcgtgccgg 74040
cgccggtact cctttttgtc ctccgagctc gcggagacgc gctcgcccgc gcggcgcgtg 74100
ctgctcgcaa ccaagcacgc ggacgctctc gcgcgcctcg gcgccgcgcg cccgcgcgac 74160
gacgtcatgt ttccgggcgg cgcgccgctg tccggggagt cgccgctggc gtgcgtgctg 74220
cgcgaggtcg aggaggagac cgggctgcgc ggcgaccagg tcagcgtgga cgagcggctg 74280
ttcgtgcacg ccttcatcga cgacctggtc tcgggccgcg acttcgacgc gatcatcttc 74340
acgggcgcag tcgcgctttc gagcgcggag gtggcgaagc agttccggcc caacgacgag 74400
gtcaaggggc tggttttcct gcaccccgag gacgcggagg gcgtgggcgt gatggcgcgg 74460
ctggcggcgt tcgcgcgctg cgcggcgcgc ctgcgctgct ggggcgcggc cgtcacgcga 74520
tagaggcggg gtccaccacg tacacgaggc gcccgccgct cacgcgcacg gtgggcgggt 74580
cgcccagcgc ggtcaggaag ttcccgtcgt cgtcgaagag gcgcccgccg cgctcgagga 74640
agcccttgcg caccgtgacc agcgccgtgg aggtggagta ccacacgctc tgcccgtccg 74700
cgagccgcgc cgcgcgcgcg ggcccgcgcg cgtccgccgg gcgcgccacc agcgcggacc 74760
agccggagtc gtcctccagc ggcgcgaagt ccgtgaaggc ctcgcgcacc cactccagcg 74820
agcagcgctt gagcacgcgg aagagctgcg tgaactgccg ggacttgtcg cggatgaggg 74880
ccagcaggtc ctcgtccacg gtggcggcgc cggagtcctg gcgcgcgacc acgaagtgca 74940
cgttcacgta gcggcggtcg ggcggcgtca tctcgtggct gttcaggcgc accgcgcggc 75000
ccacgatctg gcgcagcgag gcctcgttcc aggtcatgtc caggatgaag atgtcgttga 75060
tggagaggaa gctgaggccc tcggagccgc tcagcgagaa cacgcagacc ttgatcttct 75120
cgccgtcggt gttgtcgcag gcgttgaagg cgtccacgag cttggcgcgc gtgtcgcgcg 75180
tgcgcgagga gaactccacg ctggagacgc cgaaggcgcg gaagtagagc agcagcatct 75240
cgatgccggt cacgttgacg aagggctcga agaccagaca cttgcccggc gaggccagga 75300
tgcgcaggca gacctcggtg tacttgcagc tgcgctcgcg cagctcgcga gcagcgagac 75360
gtccgcggag gtcatgcggt cgccgctgac gggcgcgccg ctgcggaaga gccgcatgtc 75420
cgagaagacg cggtccttga cggcgcgcgc gaagtccagg aagagcgcgg ccacggcctc 75480
gtcgtactcc tgcttggaga gcacggactt gtcgggcgcg tcctcgaagg cgaaggtggc 75540
cgcgatgcgc cggtacacgc ggaataccgc ggcgccggac ttgcgctcca tggcggccgc 75600
gcggcggtag gcctcggtct gcttcgcggt catgtccacg tacatcatgc gcacgcgctt 75660
gcgcgcgaag gcggcggagc cgtcgacgtc gtcgaagatg gaggcctcgt tggtgactaa 75720
gtacgagcac aggccgccga gcttgtccac gaggtcctcg gggttcgcga gcgcgccgcc 75780
gttgaagagc ggcgtctgcc cgaccacgcc ggggcgcagc aggttcacgg ccatggagaa 75840

```
ctccttgacg ctgttcacca ccggcgtggc cgtgaggcag agcagcttcc cgcggcccat  75900
ggggatgttc ttcgcgaggt agttgtacac cgtgcgcgcg ggccgctggc gcccgtcctc  75960
cttggtcagc gacatcgaga tgaagttgtg gaactcgtcg atgaccacgc agacgcggct  76020
gctcgacgag gcggtcttca tcagcgtgaa gaagcggtgg tggaagcgcg ggtcgtcgta  76080
gttgatgaag gtgcacccgg gcacggcctc gggcgcgaag cgcatcatcg tcgaggtcca  76140
gggctgctcc acgagcgcct tcttcacgag cacgaccacc gtccagtccg tgaagacgtc  76200
gcgcaggtgc ttgagcacgt acaccgcggt cacggtcttg cccacgcccg tctcgtggaa  76260
gagcagcagc gagtgcatgc tgtccaggcc caggaacacg cgcgccacga agagctggta  76320
gtccttgagg cgcacggact cctccacgcc ctgcatctcg gagggcatgt gcgcggtgcg  76380
ccgcagcgcg tagtcgatgt aggccgcgtg cgcgctggtc atggcgacgg tcggcgctcc  76440
ttttacgggg tctgtcgtct atctattgtc ggcgcgggtc tgatttaggg gcagtagtta  76500
caaaaacgtt tccgctgctc ggcgcggcgt ttggaggagc ggttgcggcc gcggcggcgc  76560
agccgcgcgc ggcgcgtctt cgtggtgcgg tggccgaacc agcgccggtg catgaccggg  76620
tgcgcgaccg cggccgcgcg atccgcgctc atgcaggttg cgtaggtgcg gcacatgctg  76680
cgcagcacgc gccgcgtgcg ccgctccacg gcgtcgagcc gcctcgcgac gatgggaaag  76740
agccggcgcc agccgcgcac ggcgaagagc gggcgctcgc agaccgggcg cgcgagcgcg  76800
tggtaggcgc ccagcagccg cgggtccagc gagcgcacgt aggtctccac gaagccgttg  76860
ccgaagacga tggcctgcgc gcagagcggg ttcgtcatct ccctcttgga ggcgatggcg  76920
tcgcccacga aggcgcgcac gccgcagtgc cgcagcacca ggcgccgccg cgggaagtgc  76980
aggtgcgggc cgagcgccgc gcgggcggcg gggatgtgca gccgcggaga aaaacgcgcg  77040
cgtcccgcca tggcatcgaa gcgctccgtc tgttttcagt tatagcgccg cgggcggcta  77100
ctgcagcagc agcttgagct tgcgctgact ctcgttctcg atgctcttgg actcggaggt  77160
catgctctcg tagagcagcg agtgcgtgac gtagagcgcc tcgtacacgc ggctggcgaa  77220
ggccacgaag cggtccacga actcgctctc tacggggtcc ttgagcacgc ggaagggcac  77280
ggccagcgcg tcgcgccagg cggcggcctt ggtgcgctcg cgcacgtgcg ccacgaaggc  77340
ggcgatggcc gcgcgccgcg gctcgctggc gaccatgacg gcgctgtcct tgagccagct  77400
gtcgctcacg cacttgaaga ggcgcacggt gccgaagagg ctgcagtaca cgcgcagcgc  77460
gtgcaccacg tcggtgccga agagcgtggg cagcttgagc accacgaagc gctcctgcgt  77520
gatctcgagc agcgggcgca tcacctcgaa ggtgatcgcg tggtagtcgg ccacgtagag  77580
gttgttctcg gtgaggtggt tgttggagcg gatggcgccg cgctccttgc ggtagagccg  77640
gttgcgcgcg ctgaggtcga gcacgaccgc gtcggccttg ccgcgcgctc tggagcgcac  77700
gctggtgatg ccgtgcgcct cgagcacctt ctcgacgtcg cgctcgtcga tcatgaggtc  77760
gtgcgtgtac agactcagca tctccgtggg catgcggttg atgtcgttca cccgcgagca  77820
ctgcaggaag tagttggtcc cgtaggccag gctgggcagg tgcccgacgc cgagctgcag  77880
gtccagcgcg ggcgtcgagt cgaaggtggg cagcgtcacg ctgagcccct cgcggatgct  77940
gcggcgcacg gcctccaccg cgtccatggc cgatttattg gacgcacagt ctgttttcat  78000
ttcgcggcta ctgcgcagtc accttctcgg ccacgatccc cgcgtcgtag ctgagccggt  78060
acacctcgtt gcacaccacg accatctgcc gcggcacgta catgagcggg ttgtgcgcct  78120
ccatgtgcgc ggtggtcacg cgcaccgcca gcttgtcctt gcccctggag acgttggagt  78180
tcagcgcggt gggcgagaag aaggtgctgg gcgtaaagtt gaactgcagc gtgcgcacgc  78240
```

cgggcgtctt gccgaggatc tcgccgaaga cgcgcgagac tgcgctgttt ccgagtacag 78300
cacctcgttg ccgaagcgca cgtccatgcg cgcgatgacg tcgatcttgt tcttgaagtc 78360
ccccttgagg aaggggtcgg ccacgaagag gtccttggcg cgcgcctccg gcgagcggtt 78420
gtcgccgttg tacacgttgc gctggcaggt ccacacgccc acgggcacgg aggcgtcgcc 78480
gatgttcacg gagtggatgg cggtcgtgaa gcggatgcgg gaggtcgcgc ggctgtaggc 78540
ccccgtgatg gcggagaact tcttggacat gttgtacacg acggagttct tcctggtggc 78600
gaacactagg atgttcgtgt gcaggaacac gcgcatgccc acgggcacgt cgtcgatgcg 78660
cacgaagacg tcggtgtcct ggatggacac gacgcccgac gggggcacct cgactatctc 78720
cgcggtctcg gggaagccct cggggtagca gttcgagacg atcaccatgt cctccagcag 78780
gcgctccacg aaggccatca cgaagtcgcc ctcggactgc tggaagccgg ggtacgatat 78840
gaagcggttg ttggcgtcgc tgagcacggg cttcatgtac acggacaggg aggtgcacgc 78900
gtgcacgtcc gtgatcaccg cggtggtgtg gttgatctgc tccacgcgcc gccgcggcat 78960
ctcgatgaag gccgggcgcg ggcacaggtt cttgaccatg tagccgatga agctcagctc 79020
catggagtag gggaactcct tggcgagctt ggcggcgtcg aaggtctcgt cgtagaccat 79080
gacgcaggcg acggggttca gcgtgaccgt gaccgtgacc ttgctgtcgc tgagcttgag 79140
cgtgctgaag gtcttgtccg cgtcaaaggg cgtcttgatg taggcgtgca cgcaggcggc 79200
ctccttgatg acgtcgttgg gcgagctccc ggtggagagg tcgttgagct cgcgcgagaa 79260
gcccgagagc tccatcacgc gctcgttgtc caggcaggag tcgaacagct cctcgccgga 79320
ggtctcccag atggtgtccg cggcggagtt cacggccacg tggcggatga gcttgtacgc 79380
gatgtagggc acgtagcaca tcttgcccac gccctttatc tcgggcaggt ccacgctcag 79440
cacgaagttg ttcatggccg agatgtactt gtcgcggatc tcgaaggtca cggtgaccgc 79500
gtcgctggtg gtgtccacca cgccctgcgt ggtgatgtac tgcggcatgt acaccgtggg 79560
cgcgcggtgg tccgtggcga acacgctggc gcgccgcacg gcgtcgtcgc cgcccaccag 79620
gctcaccacg gagttattca tttattccct gggaaaacca gttaaataag gctcttcaga 79680
gccatgcgca ccgtccggcc gtcgggctcc aggtagcagc gcccgtagac gccctccgtg 79740
gcgcgcgtct cgttgatgag cgcgcgcacg cggtcggggt ccgcgtacat ctccagcggc 79800
agcagctcga tcttgggctc ctcgcgcagc gcgacgaggt gccggatgga gcccgcgaag 79860
gagtcgcggc acagccgcga gcagaactcg cccacggcgc cgccgtcgag cgtctccacg 79920
gccagcgcgg ccgtgcccac gcgctgacgg cagaaccagc acgtgccgtc cgcggcgcgc 79980
agcgccagcc gctccgcgga caccgtgttg aagtacttcg gcagcacgta ctcgatgcgg 80040
cacgccgccg gcggcgcgca ggccgacgcc cgcggcgcgg atatgtccac ccgcgagagc 80100
gcgatgcgct tcatgggcgg cggtggatgc tatttatgtc gcccgcggct tttcaaaggt 80160
cgagcgagca cgccgcgaag cgcgcgggcg agaacacgta ctcgtggccg aactccggga 80220
tctgcgcggc gcgcttgcgc gcgcgcatgt gcgcgaggaa gttctcccag gtgagctggt 80280
tgctgttgtt cttcgcgtag ttcttcacgg tctgcggacg caggttgcgc gtcacgcccg 80340
tgacctcgaa gatcttgtcc aggaagaagg agtagttgat ggttttggtg ggcgtgatct 80400
cctggcagaa gaagaccagc tgcttgaata tctcgatgac ctcgttgatc ttctcggtgc 80460
tgaggtccag cttctcgttt ttgacctggt tgatgatctc gaagaccagc ttgtagtcct 80520
tcttgttgat catctcgctg tccttgagga agctggagac gtagttggcg tccacgtcct 80580
cgggccggat ctggtgccgg tccatcatcg cgcgcaggtc gcggatgacc tcctccgagc 80640
actgcttgga gagcagccgc cggagcacgt tccgcaggtg gatgagcttg ttcgacacgt 80700
ggaagttgga cctcttctgc acgcggatgc ccatgggaaa cacggtctcg cagaacaggc 80760
agaactcgta gtccgcgtcg gacacgagcc cgttgcggcg gcagccgccg cacatgcgca 80820
ggttcatgct tgctccagcc ccagcacgcg caggatctcg cggtccagca ctttagtgtc 80880
cagcgtgcgg gttctacaga actggaggaa gcccgcgagc gcgcgcgcgc gccctggctg 80940
cgagagcagc agcatgcgcg cgttcccggg gtcctcgttg atgaagcgcg tgaggttcag 81000
cgagcaccgc gtgcagcgcc gcggcgggtc gagctcgacc gagtacgccg cgaaccagac 81060
gttgtcgccc atgtattatt tattaacaca gaacgtcgca catgttgcgc gaggacatgt 81120
acgggtcgta ctcctgcccg tagatgagga tggtgcagta ccgcgagatc atgagcatgg 81180
cctcctccat ggtgagcagg tcgtcctcga acatggcctt gtgctgcatg tgctggctct 81240
gcttggcggc catcgcggcc gcgccgtcgc cgcgcagcca ctcgttcaga cactggccgt 81300
cgccggcgtc ctgcgcgaag gtgttgcgca tggcgcgcat gagcctggct tccctggccg 81360
agcggctgag cacggtcatg ggtcgtaga gccaggggcc tgcgtccgtg aacaggatgg 81420
tgcagtaccc gttggcgaag gcgtccgcgc cgctgcagtt gtcgatgccg tcgccgaccc 81480
tgtagcacac cgcggagacc agccggtaca tgatgccgtt gagcatcatg tcctgcgaca 81540
cctcgatggg aatgtcgctg atcacgggcc gcatgttcgt gaagcagtcg cccgtgctgg 81600
ccatgccccc gcgccggttc accaggaaca ccagcacgcc gttcgtgatc acgggcgcgc 81660
ggtcgcgctc gtagaggtag ccgctcgccg cgcacacggc ggacgccacg tccgtgcgag 81720
agaccgcgcc catgttctgg gcgggcatgt acagcactcg cccggcctcc gcggtgcacg 81780
agaagggctg ctccccgccc acgtggatgg gcgccgtcga tgtcgtgatc atcttgctgg 81840
agtccaccac caggtagggc accgtgtgca tggccatgtc gcccatgccc ccgatccccg 81900
ttccgaacga cggccgcgac acgctcacga gcgtcggctt gaacgagact atggagaaga 81960
tggaggccaa aatctgctcc tcgtcggtca tgatggaggc gcacgagggg tggatgatct 82020
tcattagggc gttgtcgatg gactcgtcgc tctcgcagta gaagacgccc atgcggaggt 82080
tcaggatgca ccgccgcagg ttggtgtgca gcaccgcgcg ctggatctcc atggacacgg 82140
agtcgccgac gccgggcatc acgatgggcg tttcctcggt gagcttgttc accagcagct 82200
ggtagttgtt gggtcgcacg cggctgttgt ggtggagctg cgccaggagc gagaggctgt 82260
ccccgttgac gaacgcggac tcgatggccg gcagctttac gccgaacagc gccatggcga 82320
tggggtgcac gaagcccacg gagtcggacg acttgaacga gaagagcagg tcgcccgagg 82380
agctcatgtc tttgaagtgc acggactgga actgcgtggc ggagagcaag ttctggtagc 82440
tggacatgct ctgcaggtcg tcgatctcct tcatctgctt gtttacgcgg gtcgagttcc 82500
tcccgtagat gatcaccagc gggtgcgtct ggctcacgga tagccccgag tccgtcatgg 82560
cggcgcgcac gctgttcagc agatcgaaca gctccgaccg gtctctgttc tggatcccga 82620
cctttgccat cacagacatg agctcctgga tggtcatgtt cttgtggtct cggcgcgtgg 82680
accgcaggta gtcggcgatc atctcgcctt ccttacggat cttcatctgc cagtcgtgca 82740
tggaggtcat gcggtccaca ggcatgagca cgctgtcgga ggacgactgc gcggcgctgc 82800
cggactggcg cgagccaggg cgcgcggacg acgggcgcgc ggagctgccg cggctggagg 82860
aggacctgga cctccgcgag gatcttcgct gcgaagagct gcgcacgggc cgctgggcgc 82920
gcgccccggc ggaaaccatg tcctcgcggt ttatgcttag gagcgagctg cagaccgcgc 82980

-continued acgacagcga ctgttttgga atgtggatgt ggtcgcactc cagtgacatg cccgcattgt 83040
cgtagcccgg gaccaagtcg aactttgcgt taaaaaaatc tgatgcgcac gcgggcgatt 83100
ccatttatac cgggagtttt tatgaggtgc cggtattatc cacgcgatct cgcagtgtgc 83160
tgggagtatc tcgcgtagcc gcccccgtga gcaaacgacg caagtcgttg atggccgact 83220
gtgttacgga cttcgccgtc tcgatgtcgc gcgtaaggct gagcgactcg gcgttgaggt 83280
cgcgcacgct gtccgcgatg tcggccagct cctttttgat gaaatcctta tcattatcgg 83340
cgttgatgac tttgtccggc actctagact ctagaaccgg tgacgcggcg ggcgccttga 83400
tcgtcgggca gctggacgcc gggtactggg gcggcggcaa tgattgctgt aggaagacgg 83460
gcttagcggc aggcgccggt tttgtcggca agggcggcgc cggcgggcac tgtcgtgtag 83520
acggcgggca cgccggcgcg gggcacgccg ccggtggcgg acatgtcggc gcagttgcgg 83580
gtggacacgc gggcgcgggc gccggcgcgg ggcacggcgc ggcaggcgca gggcacgcgg 83640
gagccggagc tggagccggg cacggcgcgg caggcgcagg gcacgcggga gccgggcacg 83700
ccggcgcggg aggacatgcc ggcgcagcgg caggacagac caccgctgtc gcggagcacg 83760
cggcaaccgg cgtggagcac gcggcgggca ttacgttcag aggcgtcgac tggaccttgg 83820
caccacgggg cagtagcgat ggcgctaggg gcgactgtcc ggtggttgga cgctgcatgc 83880
aagcaatcgc agatttcaga cgggactggt aatacctgcc cgcttccttc accgtgtact 83940
tgtcgacgga gtctacctcc tcatcgggag gacatggctg ctccggtgcg ggaatgactg 84000
cttgaggaca cttggtgaac agactggagc tggtctccgc tagcaccagt ttagacttgg 84060
ccaagtcgga ggcaaacttt cttctgagat ccatttaagc cttcaaaatt gaacgtgtac 84120
gccgaccgct aaatggaaga atcggtggcc gtcgagtacg cggacgagga cgaggatgaa 84180
ttgaggagta cgaggaggag gacgaggacg aggaggaaga gtctgccgag ggcgccgccg 84240
cctcctcggt ccgacgtagc gctctctgcc gccgagaagc tggtggcctc ggaggtcccg 84300
gacgacgcgg ctgccgcgga caccaacgtg cgtcaacgcg tcaccgcgcg cgtggaggag 84360
cttaaggcgc gctacacacg gcggatgagt ctatttgagc tcaccggaat tgtagcagag 84420
agtttcaatc ttctgtgtcg cgggcggctg ccgctcgtgg cggacgccgc agacccggcg 84480
ctcgacaacg agctcaaagt ggtggttcgg gagctcgagg agggcgtctg ccccatcgtc 84540
atcgagaaaa acggcgagtt cctctcgccg ggcgacttcg accccgagtg cctgcgctac 84600
cacctgacgt acatgaccga cctctggaag tcccaggggc gcatgtagcc gcggctactc 84660
cgactcggcg gcctccgcga ttttttcttt tatcatgtcc agcagctcgc gcaccacgat 84720
ggggcggccg cagtacgtga tgccgttttc ggatatcacg ctctgcgcga tgtccaccag 84780
cgagccctcg cgctcccagt actcgcgcgc gagcacctcc ttgtacaacg cgcggtggtt 84840
ggccacgtac cgcaccagcg tctggatgtt cttcacgccc acgctcttga ggtcctgcgg 84900
cgagaacttc tcgcgcagcg acacgaagac gtcccggacg agcttgccga tctccacgtt 84960
ggtcttgaac tcgttgtaca gcaccacgta gagcttgcac acgaccgtgg cgaacttcgc 85020
gggcttgaga tccttgttct ggaagaccag catgctgctc atcaccttct tcatgaaggc 85080
caggtacttc gcgcggtcgc cctcgacgct cacgctcccg acctcgagat cggacacgca 85140
gcggattccg tgctccgcgc tctccgcgga gacgcgcagc agctcctggt actccttgag 85200
cttctgcttg tccgtcatca gcgagttgtc gaataccgcc accagcttga gcacgtagtt 85260
ctcgtccgag aagaccttgt tcagacactt caccaggaag ctgtagtggc tctgcaggat 85320

-continued

```
cttcatgacc gcgttggctc cgctggctcc gcggacgtgc gatatcatct ccatgatctt  85380
cttggagtcg tcgatgatct cctcggtgtc gtttcgcatg ttgcggtaca tcgcgttcag  85440
cgagaccagc gtctgcgcgg ccaggagcac gtcgcggaac acgcgcgcga actcgcgctt  85500
ctcctccgcg tcggcgatgc tgttgtacac ggacttcgcc accgcgttcg acttcaggaa  85560
ccagaaggag agcgcctggt aattgaagtg cttcattagc gccagcacgt ccgcctcgct  85620
catttccggc gcaatggggc acaccgagct ttcgagcacg ggcaccatgc tgacgagcgt  85680
gtccacgtcc gtgtcgaagt ccaggcagtc cacgcagagc ccggtgccgc ggctcaggtg  85740
atcgcggctg atgttgtaga agcgctcgta gcaggtgcgg aggcggtcca tgtcggctgc  85800
gttttaggga gacacacact cttgaattat ggctgcgggt agaactcctg cagcagcgcc  85860
ggcgcacgcg cggagtccgg ctccactccc agcttcagcg cgcagttcac ggaccaggtc  85920
ttcatgaagc ggtcgggcgc gtccgtgacc acgtgccgga agagcttcgc gaagtggcgg  85980
ctcacggcgt tgggcacggt cgcgttgcgc acgaaggccg tgaagcgcga ggtcagcttc  86040
ggcgcgaagc gcttgccgtc cacgaagaag ccagaggtgg tgagcgagag cccgttctcc  86100
tcgcgcacca cgcgtcgcgc ggccttgtgc ggaaacatgc tcgcgaggcg cccgctcgcg  86160
tcctggtcta ggtggatggc gtccgtggcc gcgtccttgc ggatgcgcac cacgtcgtgc  86220
acgatctcct ggatgaggat gcgcgtggct gcggtctccg tcagccgcat ggggaagtag  86280
accatgtccc cggagatgag cacgttcccg ctagcgttta cgtagctcac tatctcggac  86340
acggtgcgca gacgcacgat cgcgccttcg cagcagtgca ccacgtagta cccggcggtg  86400
gcgcgcaggc gcttgttgtc cgcctcgaag tccgcctcca acccctcgtt gaagtacttg  86460
tcgaatatga tgggcaggaa ggatagtttt gactcggtga ccaccttccc gaagttgagg  86520
atgtacgggt tcagcgcgct gcggtcgacc tcttcgtcgt acacgcagga cttgaaggtg  86580
tcggtgtgcg cctggctgcg caggaagcag cacggaatgc agatgcgctg caggcggtgg  86640
aagatggaga ggaagcccac gctgttgtag cgcccgtcgg ggtccatgca cgaaaacatg  86700
acgccgtttc cgttcacgaa gacctcgcgc gtctcggact tgaagaagtt gttgctgacc  86760
ttggccatgt ccgcgtccag cgactgcacg atcacgggct tgcggttctt ggtcttggtg  86820
ttctggcaga tgcgcgacca gtacacggtc tccaccttgg tgaagtccga ggactgcttc  86880
acgttgttga acatcacgct gatggccacg atcaagaacg tgaagtactt ctcgatgttc  86940
gggatgtagt tcttgacctt cacggacacg tgcgacttcg cgaggatgat cgagatgcgc  87000
ttgtccgtgg agagcaggat gttgttggtc gccgtctcca cgaagatgaa gctcgtttcc  87060
atgtccagct tcatcttaga cgtgatggtc gtgttcagcg acaccttgta ggtgatgtcg  87120
cccttgcgcg gtccatcttt acgtccatgc tctcgatgag cttcgtgaac agactcacgt  87180
cgttcaccgt gagcgtctcc gtcgctcgag atgaccaggt cgccttccgg gccccacacc  87240
gagaggttca gcggctcgtc caccagcagg aagcgcgtcc ccgtcatcga cacgaagaag  87300
tcgtccgtct tcgagagcag gatgtcgaag tcgcccacct ccgctcgctt gtccggcgac  87360
tgctgcgcga tcgcgcggag cccggactcg cgcaggttcg tgcggaagat gttgttgaac  87420
ttggtctcca cgttcatgtt taggtcgagg ttcgcgaact cgcggatgag ccgctcctcg  87480
aacttgagga tggagtcgtt gggctcctcg aaggagccga actccggcgc ggaggtgtcc  87540
gccgcgcgcg ccacccagac caccaggaag ttgcacgcgt ccgcgtacgc gttgtagagg  87600
atgccgtccg tgcggatgag cgttttcttt tgcgtgggcg agaacgggtt gaagatggtg  87660
ttgtccacgt agctgtactc caggttgttc ttgtgcgagt acacgatgat ctcgtcctgc  87720
```

```
aggcccagca ggctccccaa gtaccccttg agctgccgca cgcgcatggt cagcaagatg  87780
tgtctgcgca cgtgctcggg gtccttctgg atgtactgct tcgcgaagaa gtagatcggc  87840
gaggcctcgt ccacggagtc gtacagcgac aggtacagca cgcgctcgat ctcctggtgg  87900
cgccccacca gcaccaccag ctgcggcgcg acggtgtaga gcatggtcgc gcgggcgtat  87960
ttatagccgg cgttaaactg aaataaaata cgcgggtcgc gaggcagcgc catgttccag  88020
ccggtgcccg acatggccgc cgaggccgac atcgacctcg gcgacgtcag cgtggacgcg  88080
acgcgcgcgg gcgcgcgcga gaagaccgtc ttcttcgcgc gcaacaagcg catgtacccg  88140
caccgcagca aggacgagga gcgcaagctg tcgctgggct tcttcttgca gcggctggac  88200
ttcctcacgt cgcgcgaggt caacctgcag ttccggtcgc tggacgcgct gcgcaccgag  88260
aacgtcatga agaagaacaa cgtgctcgtg gcgccgtaca tcctcatcgc gacgctcgcg  88320
gggcgcggct tccgcatgac ggagaccatg gtcgagctct acttccccga gctgtaccgc  88380
gagaccagca agcgcttccg cttctgcgcg cagataaagg tcatccagga cttcctgggg  88440
ttcgcccacg acagctacca cacttacgac ttcgagacgt acttcgcgtt cgtggcgctg  88500
gtgctgcgcg gcgcggactc cgcggccgag gccttcgacg tccgcgccga gagcgggctt  88560
gtgcgcagcc tcaccgagat cacgtaccgg ctctacgtga tgcagctgcg ctccgacgcc  88620
gcgcagtgga gcgtgagcac cggcgccgta gtctcgcagg cggtgaacac cgtgctgtcg  88680
gtcgtcggcg accttgccgc gcgcgcggag gccgagcggc tcacgcccgt gtgcgacctc  88740
gcgcgcgaga acccgctctc gctcgaagac ctgcgcaagt acggcccgcg gctgcgctcg  88800
ctgctcacga ccatggcgcg cgcgcgatcc ttcaagacga accggcggga caaggacgcg  88860
ctgtcccggt tctgccgact gacggcgggc cctagcccgt ctgcgtgccg cgcgtcgcca  88920
taggcgtcgg cgcgcgctcg ccgccggaac actcggggtc gctgaacatg tagatgagcg  88980
cgacgcctag cagcaggtac atgatcatgc tgatcacggt tttgaacacg acggcggcga  89040
acgtgttgga ccgcagtcgg tgctcgcaga agtgcatgaa caggtgccgc atgaggtcga  89100
tggccccgtt ggccacctgg aaaagggcga ggccgccgat ggacttgatc accgtcacgt  89160
agcacggccg cattccgacg acgctattta ctcactgtca aaagaaacgg cgccatccga  89220
ccggaggttg aggttgcgct tcatgttgtt ccagtacatc tcgccgatgc tcgagtagta  89280
cgccgtcagc cgcgatattt tttctcggac cagctcgtag gccttctgca tctccgcaac  89340
gccgatctcc gcgtcgccca cgtaccggcc gctgcggcgc acgatcagca gcagcgcctt  89400
caggttctcc agcgcgatca tgtccatgta cagcgacttc gagagctgca cgaagaggtt  89460
gtaccgctcc aggatgctgt tcttcacctc gtccgcgatc gggactccga agatgcgctc  89520
cgtggtgtac acggactgcg tgagctgctt gaagagcgcg gagatgcagc aggtcgcgcg  89580
cttgacggcg tcgagctgct tctcggagcg cgcgctcgcg atgctcagcg cgctgttcac  89640
gacgttgctc gtgtcgcgca cgtagcgcgt cttcagcgcg gcgttgatgg catccgcgat  89700
ctcgttgctg ctcacgctcg agtcgtccga gctgcccgag acctcgtcca gcagccccga  89760
gatcgtgatg tcgggcgagc cgccgacggt caccagacgg tcgagcaggt tgcagggcat  89820
ggacatgagg atgccctcgc tcgagaggca gccctcgtcg atcatgctct gcaggttgcg  89880
cttgaaggcc gtgttttcgg gcatgaaccc gtccacgctc atgagctcgt cgaccgtgct  89940
cgcggaaaag atgcccctca cgttgatgcg gtccagcatg cccatgtcct gcgagcacag  90000
caccaccgac tggtcggccg tctcggcggc gtccttggcg ccgccgtaga tgatgcgcgg  90060
```

-continued aaaccgccag ctcccggaaa ggagaaggag ggaaaccggc actgcgcgct cgggcctcgg 90120
tagccctgcg cgtcgcgcac gttggcgtga ccatgaactg cagcaggtcg tgcgcggacg 90180
ccatgatctt ctccacctcc tccttgctgc agcagacctt gcccaggctg cgcgcgatgt 90240
tcgttttgct caccgagggc gagaccgtga cggcggtgtg ccggcggctg ccgagcgtgt 90300
acgcgctcac gctaacgcgg taccccatgg cgccgaagag cagcttcacg aagtccaggt 90360
agctctcctt attgatgtag tgcggcgcgc ccttgtcttc catcctcagc ccggcgtagg 90420
ccatgagcac ttccttcatc gccgtctcgg ggtccgagtt gcacaccagc cgcagcatct 90480
ggaagaactg cgtgaaggcg cgctgcgaga gcccgatgtg gtggttgggc tgcgtcgacc 90540
ggcgcgggaa ctccctgggc gtcatggcgt tgatgcccga gagcgtctcc atcacgagcg 90600
cgcccacggt cttctggccc atgacgcgcg ggtaaaagca cacgcggagg ggctccttgc 90660
cggccgcgag cgcgtccgag agcagcgagc agtacgtgac gttgtcgtgg tcgaagagcg 90720
cgaaggtgta gcagacggag ctcatgaaga gcgagtcggc ggtgctcatg gacttgaact 90780
ccgtgtacgc gattccgtcc cagaacaggc tctttccggg cgcgatcagc ggggacgcgc 90840
ggtcggcgcg catcagcatg gagagcagcg tcacgtagta acggatgttg gcggaaacgt 90900
ctacgaactg catgccgggc gaggccacgc gcagggtcgc gcccgaggta gtgagcacct 90960
ccaggctgtc catgagcgtc acgctggggt gcagctgcgc aaggcgcgcc agctggctct 91020
ggtagaagat ggacacggcg aggctggcca cgctgccgcg cgccatgcgc aggttttgtc 91080
cgttgaaggt gagctggcgc agcgagaaca cggagtcgaa gtactggaag aaggtgagca 91140
ggtacttgag cggcatggtc gtcagctcgg tatccacctg cggcgtctgc gtgagcacga 91200
ttccgttctt ggccgcggcg tcggggatgt cgtacatggc gtccattctg gcgcgggagg 91260
cgtcggtgag cagcgcgcgc acgttgagca gcatgagcag gtctcgcgcg agcatggtcc 91320
cgtcgaccag ccgggcgcga aagccgatct cggcggggcc ggcgatgttg gggtagatca 91380
ggttcagcag gtacgtgttg tcgaagctca gcgaggggaa ggagatgggc gacttcgccg 91440
ggaggcctgt ggggtagcgc acgtagccgc cgcagatgcg cgcgtgcgcc tcaaagctgg 91500
tcacgcgagt cttcagcagg ttgcgggtga agggcggcac gtccttgaag gactgcgtgc 91560
agatcacggg gttggcggtg tcggtcagct tgaggttggt gggcttgagc tccgcgaagt 91620
tggggcccag cagcacgggg acgaggtgcg agttggcggc gctgtcgagc aggaagttga 91680
tgccgaactg cttcacggcg acctcggttt cctcgtcgct ggcgagcttc tccgcgtcct 91740
cgaggaagag cgcgtccagc gggtgcacgt acgtgcggtt gacgtcgtag ctgggcttga 91800
agtccgaaca cagcgtgggg agcacggtgg agacgagctg gaacatgtat tccgcgccct 91860
ccacatggtg caaggccatg tgcacgtttg gggccgtcat ttatttagta ttaaatgacg 91920
gccgtaccgg taaccgatat tcctggagac tacgggccga cgtccttttc ggaggacaac 91980
tacccgctga acaagcacta cgagctcacc aaaggccagc tctcgatcct gcgcacggtc 92040
aacgacaagc tgctcgcgcg caccgtgcag cactcggacg gggagagcga tgagagcgag 92100
agcgaggagg acgacatctc cagtccgctg ccgccggacg aggaggagcc ggactcgtgc 92160
gtggcccgag tcatgccgcg ggacgcggac ctggcggcgc caaaaaaggc cgacggctac 92220
atcattgccg ccgagcagca gcgccagcag cgcataaaca ttctggtatc cgatcgagag 92280
gccgtcgtgg agcgggagcc ggttcagacg tcgttcgcgc gcgtctcggc tatcccgatc 92340
cacggggacg gcgcgcgccg caccaccgcc tccttctccg cgaccacgcc gtcgctgggc 92400
gccgtgttcg acgacgccaa gcgcgtgcgg ctgctggagg aggaggtcaa ggagctccgc 92460
agaaagtgcg cgacctctca ggataacgga aacctggaga acttcaccaa ggtgctgttc 92520
ggcaaggcgc cgcgcgcgag cgagctgaac aagcgcgtgg tcatcgtgaa ctacgccacg 92580
ctgaacaacg tgacgctgtc catggatgac ctcgagaagt gctccgacga ggaggtggac 92640
cgcatgtact cggtcatccg gcgctacaac gagacgcgga agaagaagat cctggtcacg 92700
aacgtggtca tcatcgggat caccgtgctc gagcacgtgc tggtgaagct tggcttctcg 92760
gaggtgcgcg ggctcagcgc cgacctctcg tcggagctca tcgacgtgga gatcggcgag 92820
gactgcgagc acatcgcgga gcgcctgggg ttcgggaaca gcccggtgct aaacgtggcg 92880
ctcttcgtgg taaagctgtt cgtgcggaag ctgaacctga tctgatcaac acatgccgcc 92940
gtcgaggtcc atggcgttca tgaggttgga ggcgcggcgg cgcgcgccgg tggaagcggt 93000
ggaggcgctc gaggtcgtga gcagggagtg ttgccggagg aggcgcggcg gcgggagcta 93060
gaagcagaac tcgaggttcc gctggtggtg gcggcgactc gtgccgctcg tgccgctcct 93120
gccagtgcca gtgccgctgc ggcgtgaagt accggtgccg gacctgccgc tggagctttt 93180
cttgcggccg ccgttaacgc tgtcgatgcc gagcaggtcc tcgcacacct cgccgacggt 93240
tccctgcacg tccaacttgc cgttcttgac aaccccgtac acgatcttgc cgcagttgga 93300
cacagcctgg atggtggtct cgtcgctgtc aaaggcgttc attccgccgc acgcgccgtc 93360
gttgtttctt cgagaaggcg cgccgctgcg gcgactccgg gtgctggcgc tggaccgagt 93420
tccggaggac ctggagcccg tggaccggct gccggtcgac ctggtgccgg tagtgcgcct 93480
tctggacgaa gaggaggagg cgcttccgcg gcgggtggac gaactagcct ccagcgcgcc 93540
ggcgccgccc acacaatcca cgtcggcggc ggcagcgcct ccgcgaatga cctgctcgtt 93600
gttgagctgc gtcaggagag atcgcagctg cggcgcgatc ttctgcaagg tgctcacgta 93660
gtcgtcgtag ctgctctgcg ggcgctgcgc catttttcg gacgccattt attacgcgga 93720
atatctacga cgacgcagca ctgaatcggt ttctcgcgac gggagattcc gcggtcggcg 93780
ccggtgcggt gttgtcgccg ggcgacgagg taaccagcgc gtggaaggcg cgcacctggt 93840
cgtccgtcat cttgtcctcg aacgaggacg cgcccggggg aagcaggtcc ttgttgcgcg 93900
gaacggcggg cgccgagacg cacgaccggc ggtacatcat gatgacgatg tagcacacga 93960
tcgagatgac gatcacggtc agcagcgcgt cgaggagccc catttattac ctgtatatgc 94020
ccgcgtttac cgggcggtga gctcaatgtc ggtgttgttt agccgggcgt acgggacgct 94080
gccggagcac ttcctgtaca tgctgaacac gaacagcccg agcagcagca cggcgcccac 94140
tatgaagcag gttacgcaca gcgcgcgcca cacgtagtcg gtgacgttgg tgttcttgct 94200
gaaatccacg aaggcgaaga cgcaggcggc cgtcagcagc agcacgccgc atatcagcac 94260
tccggagtag taagagctca aggtctcgaa tatgtccatt tatctgagga gaaatttaaa 94320
ttactgaatg gacgaagtgg aatagaaacc acgagaacac gacggactgc agcacgaaga 94380
tggtgctcag cttcgtcttc atgggcatgc agaagttcgc ggccagcgcc atacagaaga 94440
tgaacacgag caccgccggg tcgtagtcgg acaccattta cactacgcta aaaggcatat 94500
ctcggcgcgc gacgtccacg agcaccagca cgcggacgcc cgcgggcgcg ccggcggcga 94560
ccgcggcgag ctgcccggcc gtggggttca ccagcagcag tgcgcgcgcg gttcgcggga 94620
cagggtcctc gtaggacatg gtcggtgtgg acccgggacg cagcggccgc ccctgtctgt 94680
cgaagaggcc ctcgggaaac gaggtgcccg gaacggccac gacgacggtg tcgctatcta 94740
gaaacattta tggtcttggt ttccacggat cgcctcgagt agaccgccac gaagtagaag 94800

-continued

```
atgacgcccg ccgcgagcgc cgccaccagg aagggcggca cggcgggcag gttcgcggac  94860
gcgttgtcgc gcacgccggg gtccgggtct gcgtagcccg cgcccacggc cttgccgcag  94920
tcggcgatca tgtgcgcgcg cgagttctgc atgaccaggc tgtccacgtc gatgcggcac  94980
cccacgtagc ggcaccgcga gcgctgctcg tcctggctga agaagagcca cttgcggtcg  95040
cgcgactggt ccgtgcactc gtgcgcgcgg cagacgcgcg ggcccaggta cttcccgagc  95100
gtggtgcccg cgacgcacgc gcactccggc gcggcgcggt gcgcgtcgca gtagcgccgc  95160
agcgcggagt cgccgaaggc gaaggaggcg ggccgcgcca cgcgcacgaa ttccgagcag  95220
aagcgcgcgt ccatgtgctt ggcgcagagc gccgcgtagg tgtccagcgc cgcgtagcgg  95280
cccgtgcgca gccaggccat gcactcgggc gcgtcaggct ccaccgcgca gcggctggcc  95340
atgacgccgt cgcagtgcgc ggtcttgtac ccgttcgcga acacggacgg gcacccgggc  95400
cccggatttg tgcagcagcg cgccatggcg gcgtccgtgg gcggcgccga ggcgccgatc  95460
tcgaacgcgc acatggtgcc ctggcgcagg tacggcttcg cgatctcggg aacgtagtct  95520
gcgcgcagca gcgagcccgg gcggaagaag agcgagtcgc agggcgggcc tcgcacgagc  95580
cgcgcgcggc tcgccagctc tggcgagagg aagcgcccgc actgcccggg gtccatggtc  95640
ggcagcagac agaaccgcgg ccgtacggtc ttcagcttcg ggtcggagaa ggtttctgat  95700
tcttccgcga aggcgaaggt gtccgtggcg ctcgtgtggg tgacgcgcag cgcgtactcg  95760
ccgggcgtcg gcgtgtcgag cacctccacc ttggatacgg tgtcccccat ttgaagacgc  95820
tatttacgcc gctgcctact cggcgaagaa taggtcctcc gacttggcgc ccgcgtacac  95880
cgggcaggcg ggcgcggcgg agcgagtgcg cacgataccg cggccagtga ggcggaaggc  95940
gtagatggcg aacagcaggc cgagcacgat gtacatgaag gtggtggcgc ccacggaccc  96000
ggtcacgtgc gtcacgatga tggtgacgat ggacatgatc gtgcacacga tggccatgcc  96060
ggtgttgttg gccgcgtagg ggtgcatgat ctgcatggcc gcgcagtatc cgatgaccag  96120
gcacggcagc gggaggataa gtgaggcaat acctatcatt actagagcga gcacgggggt  96180
ggacgtcaag gccaatacaa aaatcacaat acctgttagt atgcggatat cctcgtactg  96240
gaggacgctg taaggcgcga tattccctcc aggcactggc cggggggtag ccgggactag  96300
gggggagtcg gcagtgccgg ggtctttggg gagaaaggca ttctgctcct ccgggctgaa  96360
gagctcggcg tcctgaacgc cgccggcggt gaactcgtcg ttatagtaac taaagtagct  96420
ttccatttat atgttgaaaa atgtttggag gcgtacaggt ggacgacaaa ctctacgcgt  96480
acctaaaaaa actcgccgga cgcgggcggc cgctgtgtct gttccgcgac aacggcgagt  96540
tcgtcgaagt cttcgcgggg tccgcgttcc gctttgtgct gcccgtgggc ctcttcgcgg  96600
acctgcgcgt gcgcacgcgc ggcgtggcct tcccaaaact gcgcgactcc gcgcgcatgc  96660
gcggcgtgcg ggtggacgcg cacacgctgc cctcgctgta ccccaaccag cgcatcgtgg  96720
tggacgaggt gctcgcggcc cgcgaccagt tgctggccgc gggccgcgcc gtgtacgtga  96780
cgctgcatct ggcttgcggc ttcgggaaga cgctgaccgc gtgccacctc atcgccacgc  96840
acggccgccg cgcggtggtg tgcgtgccca accgcatgct ggtgccgcag tggcgcgcgg  96900
ccgtggcgga gctgcgggtg cccttcgcgg tctcctgcga cggcgcggcc tcgctgctgc  96960
gctcgggcga gctcgaccgc gccatggtgg ccatcgtggt cagccggcac ttcgccaacg  97020
acgacttctg ccgcgcggtg agccggcagt ttgacgtgct cgtgctcgac gagtcgcaca  97080
catacaacct catgaacaac accgcggtct cgcgcttctt aaccaagtac ccgccgccca  97140
tgtgcttctt cctgaccgcg acgccgcgca cggccaaccg catctactgc aaccgcgtgg  97200
```

tgaacgtgtc cgtggtcagc cgcctcacca aggtggtgcg cgtggtggac gccttcttcg 97260
agccgtacac cacgcccaag atccgcacgc tcgagcgcag cctcgatgga cctcagaaca 97320
agtaccacgt cttcaccgag aagatcctcg gcgaggacgt gcaccgcaac aagctcatcg 97380
tggacaccgt ggtcgcggcc atggccgcgg gcgaggcgcg gcgcgtgctc gtgctcacca 97440
agctgcgcga acacatggtc gggctgcacg ccgcgctctg cgagcgcctc ggtgcggaga 97500
cggtctttct cggcgacgcc aagaacagga agacgcccga ggtcacgcgc gcactgcgcg 97560
acaaggaccg cttcgtgctc gtgtccacgg tcttcttctc aggcacgggc ctggacctgc 97620
ccaacctgga cgcgctcgcg gtggccgcgg ccgtgctcaa ccgcatggtc atggagcaga 97680
tgatcggacg cgtgtgtcgc gagtcgcacg ccaacacgcg cacgctgttc gtgttcccgg 97740
actcctccgt gcgcgcgatc cgcgacaccg tgtctgcgtt tgcgcagcgg ctcgtggcgc 97800
tggcggtgga cgggctgggc ttcgtccgcg agcgcgccgc cgccggcgcg aagaacgagc 97860
cggcgctgta cagcgccatc agcgggcgag atctcgcagc ggtgtaagcg cggacccgca 97920
cgccgcgcac gagagcgtgc tggagcaggc gagtcccagc gacagtgtgg acagcctgtc 97980
cacgtccttg atgctcacca gccgcgagtt gcacgacgag cacacggggt cgctactatc 98040
atcgaccact gtggtgacgc ggcggcgtct gcgctttttg tttccagcgg cgacatcgac 98100
cacgcctccc ttagagcccc ccttcgcccc cgccttagct ttcaccgcgc tcatctttta 98160
tttatcataa aaacacgtct gcgtacgcgt tcgcgcacac gtcccgcaaa tccgcgcgcg 98220
cgccgcagcg cgtgaagcgc gcggcgtccg cctccgcgat ccgcgcgcac ggcagcggcg 98280
cgcccttctc gtccgccatc acgcgcgcag agatcccggt ggcccccagc gcgtacgaca 98340
ccaccacgtc gccgacgcag cggtacacgt tgccggagcc ggcgaggcgg tcgaacgcgg 98400
cgccctcctg gcgcagcttg tcgaatatgc gaggaacgag gatgttaaaa atgagaacga 98460
aatagcagat cagcaaaaac agcgagatca tgacctccga gagcgattta tataccttga 98520
aagagctaat acgacttcgg gactcgctgc acctcgccac cggcgccgcc gtcgagcgct 98580
acaacgcgct cgtggagtgg gccgcgcgca cgtactggac ggtcgcggtg ctgccctccg 98640
caccgtgcgc ctccatcgag aagtactact gcgtgtgcaa acccgactgc gcgctcgagc 98700
ccggcgagta ctccgtgagc cggctgcact tcggactcac gcacgcctgg gtgcgcggcg 98760
ccgccttcaa ctcggccagc ggcgccgagg tcgagccgcc agaggaggtg cgtagggcct 98820
gcgaggcgct cgacgccgcc ttcgcggacc tcaccttcgt gcgcttctcg gtcttcggcc 98880
gcgagtggac ggtcgacgac gccgtcacag accaccctcg cgcgacgagg tgttcgccgc 98940
gtgcgccgcc tccggcgtgc gcgtcgcgcg cacgctgcgt gtgcgcggcg ggcgggagag 99000
tccttcgcgc gcgcggactt cgacgcggtg cacgccgcgc tgcgcgcgga gggcgacgtc 99060
gctcgcggca ccgcggtctg tctcgcgctg cgcgggtcat cgcgccgctg gatagcggac 99120
cgagcgcctc gatgcttcat gcgcgtgcgc cgcgtggagc tcgagcccgt ggacgctcgg 99180
caccactgcc cggtgctgat ctcagcgcgc ggcgaccggg tgctctgccg cggcgtgggg 99240
cacctcgcgg acgcgcgcgc gcgcgagggc gtcttcgtgg ccgtgcgcag gtacccggag 99300
tgtctggtgc tctgcgacga ggcggccgcc ggcgcggcgg agtgctcgcg cgaggaggcg 99360
ctgcggctgc tggtgcgccg cttcgggcgc gacttcgccg tcagcgagga gggctacgtc 99420
ttccgcgtgc aggacatgga cctgcgcggc gtgtccgcgc gactggggct cgcgccctgc 99480
gcgagcctgg aggatctgcg ccgagcggtg gagcgcgacc gcgcgctgat gcggcggctg 99540
cgcgcggagg gcgccgtgcg cctcgcgtgc gagtgcgtgg gatacccgcg ccagaacgcg 99600
gtggagctca taaataatat gcgctttcaa ataacggaag aaggcgcggt ggcgaacttt 99660
gagctggcga acgcgagctg tctcggcaac ccgaccgcgg agtccatctt cgcgagcttc 99720
gcgcagttcg tgccgatctt caacgtgcta tcggcgatcg cgcgcgcgca gccatgatcg 99780
tggcggcctt cgacctgggc acgcgcaacc ccgcgcgcac cgtgctggag gtgctcgacg 99840
gcacggtgcg cgtggtggac gtggccaagc tggactggag ccgcgactgg gagaagcgcg 99900
tgcaccgcga cgtgaccgcc ttccccgcta acgtggtgct cgtggagcgc cagtgcaaga 99960
tgtcgccttt ttctaagttc atatacttca tacgcgggct gctctacgac gggcggcgcc 100020
gcacgcgcgt gctcgcggtg ccgccggcca tgaccggcag cacctaccgg cagcgcaagc 100080
gccgctcggt gcgcaccttc ctcgcgctcg cggagagctt cggcatcctg gacgccgtgc 100140
ccgcgcggaa gaagctcgac gacgtcgcgg acagcttcaa catggccatc aattacgtgc 100200
tccgaacaaa ctgaaatacg actgaacgaa taagtcatgc tggcgctgtt cgagttcctg 100260
cggtccgtgg aggactgcta ccggcgcacc atcttcaact tccacatcgc gcacagcgcc 100320
gaggcgggcg atgtctacgg cgtgctgcgc gaccgcattt tggcggccac gcgcttcgag 100380
gaggtagcgc cgccggggct cgcggacgcg ctggccaagg tggtctactg cgacataagc 100440
accaccaagc acctggtcaa ccacgcggcc ttcgcggcgc gcgcgcggcc ggcgcggcgc 100500
ggaggcagcc tcgcgcagtt cttcgacgtg cacgtgggcg aggacgcgga gagccgccgc 100560
accgcagaga tcttcgaccg cgagcgctcc tcgctggtct cgtacgtgaa gaccacggcc 100620
aagcgctgca agatcgacta cggcgagatc aagcgcacca tccacggcgg gcggcagacc 100680
tacttctcgg ggcggcgctc ggacgacttc ttgagcacca ccgtgcgcgc ggacccgagc 100740
aagccctgga tcaagtccat ctccaagcag ctgcgcgtgg acatcctgca ccacgcgatc 100800
tgcacgcgcg gcaagagctc catcctgcag accatcgaga tcgtgctcac gaaccgcacc 100860
tgcgtgaaga tattcaagga ctcgaccatg cacataatcc tctccaagga cgaccgcgag 100920
cgcgggctcg cggacctcgc ggacaagctc ttcgggacct acgcgaccac cttccgcgtc 100980
atcgcggcca tcaccggcaa cgcctgcttc gcggcggtgg cagacgcggc cgcgcgcgtg 101040
gtcgcgctcc cggacgcgga cgcgaagctg gcggcggtgc gcgggctcgc ggagtgctac 101100
ggcgtgcgca acttcaaaat cggcatgttc aacctcacct tcacgggcgc catcgagcac 101160
acggtcttcc cctcgctgat ccccgcggag agcaagatca agttcttcaa gggcaagaag 101220
cttaacatcg tcgcggtgcg ctccaccgag gagggccgcg agtgcgtgga gcaggcgcag 101280
gcgctgctcg cggccatgcg cgagcgctcc gcgcggctcg cggccgcgga cgtggccacc 101340
gcgagcgtgg acttcctcaa ggagctgctg gggccatagt gaaataatac tgatttctta 101400
aatatggagc aggcgctcgg atacaagttt ttgttgcccg accccaagga cgacgtctac 101460
taccgcccgc tccacttcca gtatgagtcc tacgccaact tcatcaagca ccggcttaag 101520
gacatcctca cggtgcggcg cacgctgctc accttcaaga acggcaccga gtccatcgtg 101580
ctcgagatcg acgacgtgaa gatctcggcg ccggagttct cgcccatcgt ggccagcatc 101640
aagggccaca gctacgaggc gctggtcacc ttcacggtga acatctaccg gcacgtgatg 101700
accaaggacg gcctcaccgt gaccaagatc aacagctacg agggcaccga ctcgcacctc 101760
gtcaagctcc cgctgctcat cggctacggg aacaagaacg cgctggaccc ctccaagttc 101820
gtggtcccga acgccatcgg cggcgtcttc atcaacaagc agtcatcgag aagctcggca 101880
tcaacatgat cgagaagatc accacctggc ccaagttccg cgccgtgaag gccaatcctt 101940
cacgctctcc ttctcctcga tctcgcccgt gcacgtgatg cccgcgcggt accgacacta 102000
caagatcctg ctcgacgtga accagcccga caacttcgtg atctcctccg cgaagacctt 102060
catcaccgtg aacgtgatcg tgatggtgca gttcctcgcg gacgtcacgc tcgagttcgt 102120
tgcgcgcaac ctctgcttcg acatgccgcc cgaggccgcg cacctggcca ccgcgctcgt 102180
ggagagcgcg aagaccgtgc ccgcgggcgc ggacgtggcc gagtacgtga acgcgctcat 102240
cgcggccgag cacgcgaagc agaagtcgac gctgtccaag gaggagttcc gctacgagat 102300
gctcagcaac ttcctcccgc acatgcagga cagcgccaac cagctcaagg gcctgtacct 102360
gctctcgctg gtgcgcaaga tggtcttctg cgtgttcttc ccgaaccggt acccggaccg 102420
cgactcgctg gtctgccacc gcgtgtacac ctacgggcgc tacttcgagg cgctggccat 102480
ggacgagctc gagacctaca tcgggaacat ccgcaacgac atcctcgcga accacaagaa 102540
ccgcggcacc tgcaccgtga acatccacgt gctgaccacg cccggcttca accacgcctt 102600
cgcggcgctg ctcagcggca agttccgcaa gtccgacggc agcttccgca cgcacccgca 102660
ctactcctgg atgcagagca tctccatccc gcgcagcgtg ggcttctacc ccgagcaagt 102720
caagatctcg aagatgttca aggtgcgcat gtaccacccc agccagtacg gcttcttctg 102780
cgcctcggac gtgcccgagc gcgggccgca ggtcgggctc atctcgcagc tctccgtgct 102840
cgcctccatc tcgaacatcc gcaccgcgga cttcgtcgag ctcaccaagc gcgtctgcga 102900
ctacgtgcgc tcctaccccg cgcgcgacat cagctacttc gagaccgggt tcgcggtcac 102960
cgtcgagaac gcgctcgtgg cctcgctgaa ccccgcgatc gtggacgcgt tcgtgctcga 103020
cctgcgccgg cgcaagcggc tcggcttctt cgggaaccgc gagatcggcg tcgcgctcgt 103080
gcgcgaccgc atgaacgagg tgcgcatcaa cttcggcgcg ggccggctca tccgcccgct 103140
gctcgtggtc gagaacggcg tgctcgtcat ggacgcggag gcggagcggc tcgagcgcga 103200
cctctccgcg atgaccttct cggacgtgct gcgcgagttc ccgcacgtga tcgagatcgt 103260
ggacgtggag cagttcagct tcagcaacgt ctgcgactcc gtgcagcgct tccgcacgct 103320
gccgcccgag gagcgcgcgc tcttcgactt ctgcgacttc ccggccgagt tccgcgacgg 103380
gtacgtggcc tcctcgctcg tgggcatcaa ccacaactcc gcgccgcgcg ccatcctcgg 103440
ctgcgcgcag gccaagcagg ccatctcctg cctgagcgcg gacctgcgca acaaggtcga 103500
caacggcatc cacctcatgt tcgcggagcg gcccatcgtg gtcagcaagg cgctggagac 103560
ctccaagatc gcggacaact gcttcgggca ccacgtcacc atcgcgctca tgtccttccg 103620
cggcatgaac caggaggacg gcatcatcct gaagcggcag ttcgcggagc gcggcgggct 103680
cgacatcctc acctgcaaga agtaccaggt cgagatcccg ctcgagaact tcaacaaccg 103740
cgagcgcgtg cgctccgcgg cgtactccaa gatcgacgtc aacggcgtgg tgcgcctgaa 103800
cgccttcctc gagcagggcg acgccatcgc gcggaacgtg tcctcgcgca cgctcgacga 103860
cgacttcgtc gctgacaacc agatcagctt cgacatcgcg gagcggtact cggacatcta 103920
cgccgcgcgc gtggagcgcg tgcaggccga cctcaccgac aaggtcaagg tgcgcgcgct 103980
gaccgtgcgc gagcgccgcg ccatcctcgg ggacaagttc accacgcgca ccagccagaa 104040
gggcacggtc gcgtacgtgg ccgacgagac cgagctgccc tacgacgaga acgggatcgc 104100
gccggacgtg atcatcaact cgacctccat cttctcgcgg aagacgctct ccatgctcat 104160
ggaggtcatc ctcaccacgg cctacggaca caagcccttc gccgaggacg gctccaaccg 104220
cccgatctgc ttccccagca ccaacgagac cgacttcgag acctacatcg agttcgcgcg 104280

-continued gcgctgctac gcgctctcgc accccgaggc cgccgcggac gaccccgagt tcgagcaccg 104340
cgtcttctgc gagcgcgtgc tcttcgaccc cgagaccgac gagcccttcg cggcgcgcgt 104400
cttcttcggg ccgctgtact acctgcgtct gcggcacctc acgctggaca aggccacggt 104460
gcgctgccgc gggcgcaaga ccaagctcat ccggcaggcc aacgagggcc gccgccgcgg 104520
cggcggcatc aagatcggcg agatggagcg cgactgcatg atctcgcacg gcgcggcctt 104580
caccgtcgcc gagatcctgc gcgactccga ggaggacgcg caggaggtgc tcgtctgcga 104640
gaactgcggc gacatcgcgg cgcggctcaa cggcacgcac gtctgcatcc gctgctccaa 104700
gatgagcctc tcgccggtgc tcacgcgcat ggactccacg cacgtgagca aggtcttcac 104760
cacgcagatg aacgcgcgcg gcataaagat ccgcgtggag ttcgagaagc aggacccctg 104820
cttctacggg actccgaaac ggttcagcct cgcgcccgac gagtcgctgt tctcgccgga 104880
ggactgaacc cgccgtcgcg accgcgtcgc tacgactagc ttatcgttcg actgatgcga 104940
aacgcgcggc ggcgccgcga cttagcttat atcgactgat gcgaacgcgc gacctctcgc 105000
gactttctag cttctcagac tgatgctacc atatcgcggc gtgctggccc caccaccagg 105060
gcttctcgcc gtggctgacg cggggctggc tgcgacgcgc gccgcagtag ctgcgcgcgc 105120
cccagtcgcc gcgcacgtgc gccgggggca ggctcccgtc cagcgcatgc cgcgtcacct 105180
cggcgccggg ccggcggcac gtgtgcacgt ccgtcttgtt ggagacgagc actgcgtact 105240
gccgcatggt ctctatgtga tgctccaagt gcttgcccgc cttccggttg gactcacagc 105300
acgtttttgc ttcggctaag gttttttcta gaggggctag tagcttatcc acgcgctcgg 105360
gcaggacgca cgcggagccg tcgagcccca cgcggaacgg ggtcaccggg atgttcccgt 105420
cgtagcggtc ccacagcatc ctgaggtagg ttgtgccgtc gtcgtcggcg tgcgtccaca 105480
ctcgacgatg ttcgtggcaa cgaccgtcgt atgtaagtct gtctcgacgc tcgtaatagt 105540
ttctgcttat attgtacgcg tctccgtact cgaagtagta tatatctccg ggtcctggac 105600
ttgctatatt gttttcgtcg tttctacgat gtataccgtc tggataatac gatattctaa 105660
ctgcactgca atccaccgta gaaggtttag gtaacttttc taattctcct tgttggtcat 105720
ggtcaactga cttgtacaca gctccgtcgt gttctgaggg agttataaat atatccatgg 105780
tgaaagaagt tcctcgtttt gagaatttgt cccatgcggt aaaacaaagg ccgtccatca 105840
taaactccgg tacactcata acaaacctgc acttgtgatc atcaaatgat attttaacat 105900
ggtctttgtc ttttacgtcc gtaccgttaa cttctttcat aaactgtata attgcaagaa 105960
ctcctcttgc gtattctata gttctggtat cagacaccaa cttttctgtt ttaatataaa 106020
cgtcgtttac atctacaccg taccaccagt aaataggaag tcctatgtag atggctgtgt 106080
ttctaaaatg ggatgcaagc gtacttatgt cacggaaaaa ggccacacaa aaaaatcctg 106140
tttttgaatc tataattttt ctggtgctgt cctctgtaac tcctaaaatg tccataattc 106200
tttcgttgtg aagagtaagg tgacctgtca ttatgctgta tacgaccatt aagtaaaact 106260
ttccaagcgt gtctacgttt ataatattta tcttagcatg ctcgcatagc atagttacgt 106320
ggaccttcat ccattcgtcg tcaacaaaca tatttttgta catagtgttt tggtttacgt 106380
atttgctaaa atacaggttt acaggtctac gagatacttt cgttccatct acttttggtg 106440
cgcttcgtat gtactcgcgc aaaacgtctc ttataatttt tctatgagta cgtggtatac 106500
atattaccgt cccaagtgga tgatgccact gacgctgaac gatatcttta aattcagata 106560
ccaacgaact gtggttctcc atttataatt aaataattag accatatcta ccacagacct 106620
taccaaatgg cgccgtgtct ttgacgacgc caccaagcat ctaaattata agtattgtat 106680
ggattatgtc tattaaagat ggatgtgcga ggagttcttg tccatgttgg tctgtaagtc 106740
tctctcacta tggggtaatt gctgctcgtt gtattggaag accctagccc gactggaatt 106800
tttgaacagc aaggtttgtc tttaacgtaa ttttctagag gagatataag tttgtctagt 106860
ttatctatgt ccatacacaa aggattatcg ttattatctt catcgtctat gacttctact 106920
tccgatagag gaggcttcac gctcaataat ccaatgaacc tgtctcttaa aattctgtga 106980
tatgatgtct tatcatcatc tatgtctcca tcaaaacgat gttttaaaca cacaacgtta 107040
tcgtatgtta atttatcccg gcgctcaaat tcattgttcg cagagtcttc tgtgtggcta 107100
tagtagtggt agtctaagta gtacccgttg ttttcatagt ttctagtaaa aatggtaggc 107160
gtttggttat tatcaacatc atgttgttta acataagtat cttctttgta gttagggtgt 107220
ctggcagtaa caccatcttt aggtacgtaa gaaatacgcc tgctaaaact aggatgaaat 107280
ttaaatcgta tagcgcctct atttcctacg tcatcttttg ttataccatc aacaacacct 107340
tgtttggaat gatctagtgt tttatacgta aatccgttat atctagttgg attcataaaa 107400
acatctagat aaaatgtagt tccgtattta gttattttat catatactgt ataacaaagg 107460
ccgtctaaaa tgaactctgg tactgacgat ataaagtttg tgctaaaacc accaaatgat 107520
atatttatat gcggtgtgcg agtagaataa tctccgactt tgtcataagt tatatacata 107580
tatctagcaa aagtcactgc accgttagaa ttctttttag gatcctcttt attaaaataa 107640
tcatcgagta acgtatgtac gtttgtacta agcccatcac ctctccacca atacataggt 107700
attccaaaaa ctaatgactt gttattgtaa taaaacgcta cagaacccat ataccacaaa 107760
aagagataac aaaagtaatc catttgtgta tctacatctc tggggtcgtt taaattcata 107820
ttatccataa taaacccatt gtccgtagct cctgtcatta tcctgtatac taccattagc 107880
aaaagcctac ccactgtact cacgtctgta aaagttttta tagccacagc actttcgtac 107940
atccatacat tgtttctaaa aagctcaaca taaacaggat ttttgtcaac atattgtttc 108000
ataatcaaat ttagtggctt tccagttttt ttatgagtgt cgcttaaaga aggagcattc 108060
ttaatgtact ctcgaagcaa atctctcaca agctttctta tctctatagg aatgcatgtt 108120
tggctgttta attctttata ccagttagcg ctaacaaacg ttctaaactc gtccacgagc 108180
ttctccattt ataattaaat aattacagac ggcaacacag cggttatcta atatctaccg 108240
tatcctgtct gtacatctat ttttttgttg agatcaagaa gagctctacg tagactctcc 108300
aagtgtcttt cagtctgtct aaccggttac ctgtttctct gcagcaatca gttatagttt 108360
tgtaactgtc taacaagctt acgcgctctt ccacactttc tttagttgga gctccagccg 108420
cgtacactcc gttggttgaa ttgcctgtat catcatcagg cggagccaat aggttttctc 108480
cgtcaccttc ctccatattg aatccaacga acacaaacgc gtaagtgttc ctctatttaa 108540
agtattgatt ttagaaaaag gcaggcctcg ctgccctgat tcggtggcaa acacgggttg 108600
aacacgcgga agtcgctcgc ggccgtgaag atctcgtccg cgcacgcctc cacgctcgcg 108660
aagcgcgcgg gcgagacgcc gtcgtgcgag cggaacccga actccgaggc cgccaccgcc 108720
gcgcccttga agagcacgca gcgccacttc ttgcggacgt cgaaggcctc gtcgttgggg 108780
tcgaacacgc gccggtccac gcgcgggccg cccgccgtgc gcgcgaactc cagcgccgcg 108840
ttcgccgcgt tgaactcgcg gatgttgtcg tagttctcgt agacggccca gagctgcagc 108900
gccacgaaca tcgcggccgc cgccgcgagg gccacgcaga gcgcggacac cgcgtccatc 108960
ttttatgtgc agaattattc gtcggcgcgg agctcgcgca gctccgcggc gcgcagccgc 109020

-continued

```
gcgaaggccg ccttgagcgc gcgcagcagc tcctcggtgt ccgcgcgcag catgtcgaag 109080
cggtggtagc tgtccaggcg cgcgcggcag ccgaagaagc gcgcgacgca cgcggtgacg 109140
atgtcgttca cgtagagcac gcccgaggcc gtgcagtaca cggagcgcgg ctcgcgcggg 109200
tccggcggca cgtccacggc gaccgcgtgc gcggccacgt cctcgagcac cttgcgctcg 109260
agcacggcga ggaagtcgcg cagctggcgg cggttgtcca gccaggcgta ggtggtcgcg 109320
aagagcgtga gccgcccgcg cggcgcgatc gcggtgtagg gcgcgtaccc gcggaactcc 109380
cgggggtgca cgaccttgac gttctcgtgc tcgcggcgga aggcctcagt gtcgagcagc 109440
gccgcgagcg cgtccacgag cttgtcggag acctccacgc ccgcgccgaa ggcgatgagc 109500
tcgatcttct gctcgctctt ggggcggaag tcgtggaagg tgtgcagcag catctcgcgg 109560
agctgcggcg gcttctcgac ggcctcgagc gcgtcgccgc ggacgaggaa gtagtcgagg 109620
tcgtgcagcg agacgtgctg cccggcggcg ctctgcgcga acttgaggaa gacgcagagg 109680
cccgcgcggc gctcgagcac gtcctcgacg tgcgcgtgga acacgtgccg cgagggcatg 109740
gcctcgatcg cggagagcca ctcctcgttg acgcaggtgg tggtgttctc cagcaccacg 109800
ccctgcgtga gcgagggcca ctgcaggtgg aaggcgaact cgtgcttgat gagcgaggcc 109860
acggccgggt ccaggtccac ggccagcgcg gcctcgccga cgaggggagc gtccgccatc 109920
acgcggagga cgcctggccc atctcctttt tcgccttttt attcaggatc attattcttt 109980
cgttgaccag gtccatgagc atcttgatgg cggcggccgc ggccgccgcg tcgccgccgc 110040
acatctgcgc gatgcgcgtg agcatgtgca gcagcgcggc ctcgttcagg tcctcctcca 110100
tttagaggcc gtaagggcgc gcgtcgtcgc gacgagggga cgcctcccgc tgcagcgtgg 110160
cgcgcacggc gaaggcgagc agcgcgccgg cgcactgcgt gagcacgcac tccgcgagcg 110220
cgacgaggag ctcggagagc acgagcacca tttagaggcg cgcacgggtt taattgccgc 110280
cgtcagagtc ggcatctccc ttgtcgccgc cgtccttgca gtcgcccttg gcgtcgccgg 110340
cgtcgacgat gtcggcgagc cgcgtcttca tgtgcgagaa ctgcgcgagc aggatgccgg 110400
ggtcgagaca gcgcttgacg acgctctcgt cggcgaagtc gtagcagatg cgctcctggt 110460
tctggcagaa caccgagtct tcgatgatca acaccctcct ggtcccggcc gaccgcatga 110520
tggccatggc ccggatgagc ctcttcttcg atccgcgtat ggacatggac cggagcacgt 110580
tctccacgtc ggagtcggag acgttgcagc agcagaggtg cgtgatgctg gcgcgcccgt 110640
tgacggggat gtgcttgtag gtctggcaga gcagcaccag cgacacgttg atgtgccgcc 110700
cgtagttcat gaggcccaag agtgtgggcg accgcgtctg cgtgtcgccc atatcgtcga 110760
gaatgatgag gaacttctgc ttcttcgtct gcgcgtgccg ctcgatcttg cgcttggcaa 110820
ccgagaggtt gtactcgagc tcctcgtgcg tggtgacctt gtggatgtgg tccggccaca 110880
cgaagccgtc gtaggcggcg ttgtagacgg gcgtgaagag caggatgtgc ttgaagcggc 110940
gcacgagcgt gcggaagagc gagagcaggt aggcggtctt gccggagccg gagccgccga 111000
cgagcgccat cctgaagggc gcctcaatga gactctcccg cttgaagcgc acctcctgca 111060
cgacatccat cgtatattta ctgtcactaa attaccggct ccgagaaata tagaaattag 111120
agcctcctag agcacaccga ggctcatcgg caagatggca cataacacgt tcgaaaacga 111180
tagcgagacg gctaacaacc agtacgtggc gtcagtcaag cgccagaaaa tgattcggcg 111240
atacattaag atgttcttcc ggttcgttac ggcgatagct atcattgtcc tggctattct 111300
agttgtgatc ctgtcgctat ctctagacga atgtctgcac agagaacacc ctcatgacta 111360
ttcgcatgta caaaattcaa catgtcccgg aattccattg ggtgataagt gtttaacact 111420
```

taacacaccg tctacatggg aagatgctaa tcaaatgtgt agcaatctag gtttcagttt 111480
accatcaaaa ggactactta aaacgccgtg gctcacagat taccttgatg gaacttgggg 111540
aaataaactg ggaaatgtct ttggaccaac tggcgaactc gagcaggtca tgggacagca 111600
cgaaacccgc aaatattttt gtgtgtctgg ttagatgatt aaatctaata aatgggttgc 111660
tgtaaggtcc ctaaccgcca gtctataagg actttgaaaa aggtgtcctg cccggtcgcc 111720
agcctcgtta ccattctctc cctagctacc agcctctgtg cgatagtcag atacactaat 111780
ttttttctaa aagaggcgtg tgacgaagga tggatgccaa taaaagacat atgcatttta 111840
aacacgcact ttaaagccac caaggacgac gcccacagaa tatgcgaaag cctagacgga 111900
aatccgccgg ccatccccaa tcccactctg ctaaagggtg taatggttct caccggagaa 111960
agacagtttt ggatgactca ccacccggac tacacatctg tatacgagca taatgaaaag 112020
ttgcaaattc caaaaaacac taagtacgac aaagatagac acatttgttt gatgagcgag 112080
gacggattga tacaccataa ctgcatgatg aacgtaaccg tggtatgcat gaaggagatg 112140
cacggataac tgaaaatata ctgtttgaac gcaaagacgc catgtcgcga cttcaaatac 112200
tgacctcatt tggacaaatc tacgcacccg acgaagctcg gctgcgcgag atcgcgcgtg 112260
atttgggaat atgcaccata aaacgcgcat tcggcgacat gctgtacggc tttatagact 112320
tcaacccggt gcccctgacc caagtaaaca tgctcatgtc caactgctac ttcgcggtca 112380
acggcaacct gcttccgtgc acggaggact tccggctcag actcccggca acggagatct 112440
ctgcggccta cctgacgaga acgggacgga cgatcctgtg cggcaaagac ttcaacatag 112500
tggcgccgtc agggttcaag ccgtccatgc ggctgcgcga ccttagtcac gtgtctgcgc 112560
ttgtagagat cctggagctc tacgacgagt ccggggatta ccaattcgtg ctcggcccca 112620
gcgcgcagtt catgctgcgg ctgatggaga aggagaatgt ctgtctgttc ggcaacggtt 112680
ggtgcatagt ggacctgcgc aagctagacg taaccatata attgctgctg ctatgtcgtg 112740
cccgactctg tgcgacaaag acagcggcta accagactct tcgtccctgt tctccaagca 112800
aaaaactgga gtgagttgcc atttccgtct ccaaccatat aattagcatc cttgttttta 112860
tcctgtattt ttatcagttt ttatgctagt taaaacataa atagtaaggc taaaaagaag 112920
agttctagaa tcttgcaaca accaagatga aggcggcggc ggtgttgttg ctagcgctac 112980
tgggagcgtt caccaacgca gcgcccgtca gcaaccagcg tcttggcagt gaggagaaag 113040
aaaaattctg ctcgactcat catgacgaag tgtacgccag gttccggctt cagatgcgcg 113100
tgggtgtacg acacagtccg ctctacgttc ccagcaacat gtgcatgatg gacatagaag 113160
actctacgga tgacatagaa gagtccacgg agaaagaata cacgtctacg gctacgggtg 113220
aggcggccgg agtgaacgtg tccgtggcac tagtgggaga aggcgtgaaa ataccgttta 113280
gttacatagg ccttggattc aacccatcta cagatggcta cctgtacgtc aacgtctcgt 113340
cacgagctcc ttgggttcaa cagactccag acctatccgc gaacagcggc tggggtatta 113400
aacaggttct agaaaaagag ttactggcca tccagatagg gtgcgacaac caaaaatttc 113460
ccgaagaacc cacaactacc ccctcacttg tcacgacaac gctttcccca acaacgactt 113520
taaatccgaa taacgaaaac acagacacta cgccgacgcc caccggcgcc agtgtagacg 113580
gaaagcgcaa tccagatgac attgacttct cgctgatcgt ggacccccga tgcgtgacct 113640
ctgtaaacct gcacttcgag ctcaaggacg cgtgcatgga ctacaaaaaa gagtcgccgt 113700
tgtcgctgaa ggggaaatat ggagacagtg aactagtaaa acaggagatt aaagacgtgg 113760
gaaagaatca caatatgtgc agtcttaacc tcagccctgg ccattgagct gtttttattc 113820
ggcaatataa taaggtgatt attgaacatt aaacaaaact tatcccacaa cgccgcaaca 113880
atggaagtgt tggtgatcgt ctccattatc gtcgccgtaa tatgcttaac cggagcggcg 113940
atgtacatcc ttattgaact cggcttagcc gccgagcgcg ctaacaaacg cgcgcgcgtg 114000
aagaaaaata tgcgcaaatt agccactcaa ttgggaaatg gatctgtcga ctccggcata 114060
ggcataggcc cgtgcataat gtcgcgcacc atggactctg gacccagtcg ctgggacagc 114120
gacagtgagg gtgacggaga cagcctgtcc acgacgtcca ccagcgaagg ggggactctc 114180
acccgagtgt gggttgggag cgggtccggg cccatgtacg aaaacttctg cgggaacggc 114240
acccaccgcc actctcccac caacgaccct ggctaccact cgcgggagac tctctgcagc 114300
ggacctcccc gtcaggcgcc ggcgctaccg cccaccccga agcccgacga ggtaacggtg 114360
gacgtggggc ccagacccaa cgaccaacac ggtccgtacg aggaacctga tcccattccc 114420
ctgcaggaac ccgagccgcc gatgcagatc gaggtaacca tcaacgggcc cggtgaagaa 114480
ggcgaggtgg agggagagtt tttctacgac gagtagccgc caaaactgaa taactatcgg 114540
gcttcgtaaa cgcgcagaca tgccgctgtt ccggaagctc atggtttcgc gctccctggt 114600
caaggaatgt ctgactctgg acttccggca gggcgagcgt ctccccaccc gatgcttcct 114660
cccggtgccc gcggggacga cattccacag agtctgcgac acctcgccgc tgacggacga 114720
agtatcccgg cacgtgcagg agcccgtcat gggcaccgga cgggtccagt actactactt 114780
cgagagcggg cagggcatga tcggcgacaa cgcgggcatg tcgcgcatgc tcgtgtgcac 114840
gcgctcggcg tacaacggcg gcgacgtcgt cgtgcggtcc acgcggagca gagcagacaa 114900
gaccgtggtc gcgccctgcc agggcatggc gctgctgctg agccccttct gcgccttcga 114960
catcacgccg gtggagagcg gctccgcgat attcgcggag gtcatcgtca cttcgcccag 115020
catggaccac gtcgaggcgg tcaccggcac gggcgaggcg gccgtgcgga tattcaactc 115080
gcaccacccg ctctggccgc gacacggctc gaacgtctgc ttcgcgctgc ggttgctgcg 115140
agacgtgcgc acgggcgagc gcgtggtcga gcagatgttc atggacgggc gctggcacac 115200
cgtgctgagg acgtcctgcg gcaacaaggt ctgcgtgccc gccgacctcg tgggccagac 115260
gaacctcgag gaggtgccct tctgcgacgt gacgcccgag atcatgcgcc gcgcactggc 115320
gatcgacccg ccgtacgagg ccgtggcgca cccgcgccgc tgcgtgtacg gcgccatgga 115380
cgtccggtgc gcgaacgagt acctcgtgta ctgcaccttc aagacggagc cggcgcggcg 115440
cagcacgtcc tcgccgggcc cggacggccc cctgtcgccc gcgactccgt cgacctcgcg 115500
ggccgcggct gcgcgcgccc ccacgacgcc gcaggaagtg gcctcgccga ccacgaggct 115560
cgtggagacc tgcctgcgcg acgccctcga cggactctga cccgaaggac ccaccgtcca 115620
ctcacattcc actgccagac aactcaagct ttttctgcat ctacctcgct aataattgaa 115680
ttgttatagt acaaacaggc gcactcgagc acaatggcgt gttttatcga attgttagac 115740
tccatcttca accgacacca ccgtaatttc gggccggagg acatgtacag gccctctgac 115800
gccccgcccc ccaaatctca cacgcctcgc actccccgca ccccgcggac ccagtgtccc 115860
ggacacccgc ggcgacaaag ctcctctccc atctacggtg cttatgtgga ctccctgccg 115920
aggaacagaa agcggttcca gaatcaacac agttgtcccg gagattacga gcggtgtcaa 115980
ctccaggaca ctatcagcct ggaggcgacg ctactcacgg ttacctcgac ttccatctcc 116040
agcatatcca gctctagtag ctcagactct agctcattgg ggcagtgcag actgtccatt 116100
gtgtccgcga catcgacctc cacgaccttc tcctactcgt cctgagcgcc acacttattt 116160
ttgtataata gtttgtattg aaccttagag acatccacaa atagttagga agcatgagta 116220
gttcaagtag cgagaccacc cctaagccca agcccatccc tgctcctccc atgactcagg 116280
aggagtttaa caaagaagtg aagaaacgaa aagaacagaa aaaggaaaaa tctagaaccg 116340
ttgaacgtga gtcagaaacc gtaactgtat cttccgacgg atcagagata aaaaagactt 116400
acgagcgcga gtctgagaga acaaccgaaa cagaaaagaa caacacgtca accgatgatg 116460
ataataagca gaacacccct gtagagaaac cagaggaaac taagcctgct tctactcctg 116520
aaggtgagaa gccagctgaa actcctgccc cgactactga cccccaaccc actacacaac 116580
cacccgcaga atcaggccct ggaagtcaac ccacacctgt tccagaacca acccccgcac 116640
ctgagcctgc accggaaccc actcctgcca ctcagcctgc atcagtaact caacccgctc 116700
caacaccaga gccaagtcca gcccctgaaa ctactccggc ttccgaacca acccctgcac 116760
cagaacccac tcccgctcca aaacctacac cagccacaga accgactcct caaccaaccg 116820
tagaaacaac accatctgct ccagcaccaa ctcccgaggc ccaaccaccc gccaacaatc 116880
ccactactga aactaccact ggtaccagca cctcctaagt gagtacgtaa gcatttcgga 116940
gtaacgtcgt agcaagcgct agtccgccgc gagcggttct tgcaagtttt ttcgggtaaa 117000
aagcgtacac cgtcgccttg tagcggcggt gtacgctttt ttcacgccct ttttgcaaaa 117060
tttaaattgt acccgcgccg gctctaggaa agatggcgtg cctcagggtg ttcttggcgg 117120
tgctcgcgct gtgcgggagc gtgcactcgg cgcaatggat cggcgagcgc gacttctgca 117180
cggcccacgc acaggacgtc ttcgcgcggc tgcaggtgtg gatgcgcatc gaccggaacg 117240
tgaccgccgc ggacaacagc tcggcctgcg cgctggcgat agagacgccg ccgagcaact 117300
tcgacgcgga cgtctacgtc gccgcggccg gcataaacgt cagcgtgtcc gcgatcaact 117360
gcggcttctt caacatgcgc caagtagaga caacgtacaa cacggcacgc cggcagatgt 117420
acgtgtacat ggactcttgg gacccctgga tgctcgacga cccccagccg ctcttcagcc 117480
aggagtacga aaacgaaacg ctgccgtacc tgctggaggt tctggagcta gcgaggctgt 117540
acattcgcgt gggctgcacg gtgcccggag agcagccctt tgaggtgatc ccggggatcg 117600
actaccccca caccggcatg gagtttctcc agcacgttct acggccgaac cgccggttcg 117660
ctccggcgaa gctgcacatg gacctcgagg tggaccaccg gtgcgtgagc gccgtccacg 117720
tgaaggcgtt cctgcaggac gcctgtagcg cccgcaaggc gcggacgcca ctctacttcg 117780
cggggcatgg ctgcaaccat ccagatcgcc ggccaaaaaa cccagtaccg cgccctcagc 117840
acgtgtcgtc accgatctcc aggaagtgca gcatgcagac ggcgcgctga gggcgctcac 117900
cgcgctgacg gcggccgtgg tgtgcgcgat cgccgttgcg ctcgagcgcg gggcggaggc 117960
cgacgccgtg gaccttatcc ttataaaatt ttcaatgata tgctagtttt tatgcgacct 118020
tccttagaaa attcggaatt caaaaatgaa ataaaacggc gtttagcacg catattatta 118080
ataccgacca ccatggcagg cgtccgcagc tgccagaaga aagtcccttc tactgcgggc 118140
tccatgtcat ttcaacgggg caaccggagc atccagcctg cgatgtccga ggcgttgcag 118200
aatgatttca gctacaaccc gcgaccgcct ccgccgagcg cagaagagat tgacttcttc 118260
tgcgtggaca tgcgcaaagt actgatggaa attgaggcca agcccaacag ctccaagtac 118320
cccaatttca tccacccggt tgacagcagc ccgccgtgca cgccggcgcg caagcgcaac 118380
ggcttcggcc gcaaggcact gaacaagacc ccggtgccgc agcaggccaa gcgtgacggc 118440
tactcccgct aatgcagtcc acacacttca cacactacat cagcactcaa gcttataatc 118500

-continued

```
accacacaat gaattagccc agcccacaca cgtgccaagc acacataaaa tcacccacct 118560
gtcctgatcg ttcccaatta ctcccaatca cccgtgcttt acacgcacgt aaatcaccct 118620
ctccttcgtt cctgatcgct cctcctcctt aatcacacat acaccccgta attttgtact 118680
tttgtacttt aatttgtaca ctttacacac tgactttgta ctgcctttgt actttatttt 118740
tgtactgaaa ttggacgata cttatctttg tattcacatc caagttttgc aaattccaca 118800
gccggtcgcg aaaagtgaaa tcgtaccgtt ttaggcttcg atccccctcc cgcgcgaaga 118860
ctcgccagca tggactctcg taggctcgct cttgccgtcg ccttcggagg cgtcctcgcc 118920
agcatgacac agcgccgccg cctggcttct ctcatcgcca gcatcggcca acggctgatg 118980
ggcggcgacg gcatgcgtcg cgtcgccgtt cggttgatcg accagctcat ggccggaccc 119040
ccggacatca acgacgaggc cttccagcgc gagatccgcg tgggcgagct cttccaggcg 119100
ctccaccgcg tggtcgagca ggcacgccga gagaagtact tcgaggtctg cggcgccggc 119160
aacgacgccg acgcgcccgt cgtcgagatg gacaccgcgg ccgcaccccc gcagccccag 119220
cccgcgccct tcgtggtcac gccgcagaac gcgttcatgt tcgtgccgca aggcagccac 119280
gtgcacgtgg acgagagcgt ggacccgttc ttcggcatga gcccctccat cttcgggcgc 119340
gacctccccc ttcagccgcc cgaggagctg ctgagcgacc acgacccgct catgagccag 119400
gccggcgagc cgccgagccc gcggtcgccc tgcgaggccg acctctggtg cttcgagacg 119460
ctcggcgaca gcgacagcga ttgagcccgc accacacccc acctcaccca ccccacactc 119520
cacctcacct caccctaaca ccaacaccct aacacccaac acctcaaccg gacaatgaag 119580
gagtcccaca tttcactgaa ggacgcggat gaagccgcac atccccacat gaaggattgg 119640
caacggtcaa acatttcacc tgcaatgaag gacgatgcgc ggtcgcattg gcctgcgacc 119700
gacatcgcac acatgaagga cacaattggt ttgttaatcc ggacaatgaa ggacaaattg 119760
tttttgttaa tcaggacaat tggacacaat cagattaatt tttgtacgat cataaaatcg 119820
atatttgatg cacatatatt agtaagtata ttagactaaa ttctccgggg aggcaagcag 119880
ttggatacgg cggggcgggg cacgacgtgc acggagaatt cgggcgggtc cccctccccc 119940
ccacccccac gcaccacgat gcgtctaatc ttagcgctcg tggcctgctt gttggcggcg 120000
ccgatgccgt tatcgggtcg ttcgacaagc accccaaaca cacagtccgt actcggctcg 120060
acgagttcgg aaccaagctc ggaagacgct gtggcttcga gcacaacgac aagcacactc 120120
acaagcacta caagcacact cactatgtcc acaagtgtgg acaccactac tacctcgggc 120180
gctacgacgt ccacaaacag cactcctgca gcgagtgtga gttcttccac acccgcagcc 120240
actgaggcat cgacggcacc aacgacgccg tcgacgcaga cgacagtgaa ggtaacgaaa 120300
gacaaagaca cgaaggcgtc tgcctacctc gttttactaa tcacgttcat ggtcatgaca 120360
acgctagtga tggttgtggt cgtggtcgtg atcgtgtaca aacagggact ttgtgactgc 120420
tgctgtaaga tgtttccctg ctgcaaagag ctcaaggact acctcgacga ggaggagagc 120480
gccgggctgt acgacgcctt gacgtggagc cgctcagacc ccggcctccg gctcgtcgtg 120540
cgcgcggacc ccagatgatg aggatcggat aagatcggcg tgtttttccc gcccgtcgcg 120600
aacattatgc ctctaaatgc cgagaattaa ctgaaattca aacacgcttt gggactcaac 120660
tctgtggccc acacaaccat ggctggcttc ctaggcgcgt tcagaggcgt gtgctccgac 120720
ttatggcagt cgctccgtgg acacggacac cactcttcca gctgcccgcg acgacgcgcc 120780
aacagcatgg acgaccgcga ccggcgccgg caccgccacc gcgagatccc caacagctcg 120840
gcgtcgctga acagcgaccc gatgccgcca cgcagtgcgg gtgcgcgccg gcactacgac 120900
```

tgccgcccct cggaaaagag cagacactcc tccgacaggc accactcggc ggaccgacac 120960
caatcggcgg acagggacag acaccgtcgc agtcgcaaga actacgactc gcacccgtcg 121020
cgcaggaacc gcaactacga gcgggcggac taccagagac atccctcaca gacccaccca 121080
gaagcccccg cgcagacctc gacgctcaag gtgacctccc tcagcaccag ctgcagcacc 121140
ctgtcccaac atcactacga gacccccgac cacatctacg acatcccgga agacggtcgc 121200
ggggcgtcgg ctccccctcg cgcggacctc gcgctccccc cgctcgccat gcccaaatcc 121260
aagccgcgcc gcacgcgccc ggcgtccatg aacgactgcc tgatgaagca ctgcggcgcc 121320
ggcagaccca acctccaaga cgacatatgc acactatgta ctgatataga gacacagctg 121380
agcgcactag agaagtctct ggagtcagag ctcaacttct atcgtcgcta catacaagac 121440
actaagacct tgctcgccac gcgagcagca aacatcggca gcaaagctct gatctacacc 121500
gacgactaca acggcagtgg caacgtcggc gaaggggagc actgctcgga ggagtgctgc 121560
aaagtggagg aagttctgtg agaaagtgcg tttttctgta atgtgaaata agatagcctt 121620
atgtgtgcac agacatggcg aacaggcttg tgtttctcga ccccgagacc ctagccgagg 121680
ccgacggcat ccccggctat ggggtgttcg agcccggcaa gaagaaatgc atcttcacaa 121740
agatccgcac cagcgtcgca ctcgcgtgcc ggtacgccgt ctcggacggc ggcctcatcg 121800
acgagttcgt catggcgaca tacgggacca gacgcgcgtg ccggctcgtc cggcacctga 121860
cgataagcgc ggagggcgtg atgacccggc ccgccagcaa ctgcgcgccg cacatggtgc 121920
tcatctgcct cagaggcgtg gccgccgtgt ccagcgagga catgggcttc ggtcgctgca 121980
tcatggagcg cggcaccatg ttcatggtca agtccgcgca cagcgccgtc gtctgcggca 122040
accccgcctg cgagctgctc gtcctcttct acgactactt cacccccatc cccggccgc 122100
tctccggaga cgaggtgctg ttcacccgcg acctcgcgca cgtggactac gcccccgagt 122160
cggcggtcgt cttcaagatg gattacaacc tcgagaccga cgtggccacg ctgtttgtcg 122220
gggggtacat attccgcgcc aagggcctga tgatggagac gcgcgaacaa gtgggcgacg 122280
agtgcgactg ctgccgccac agctcgccgg tgctcgtcat ggatcgcgag aagatgatgt 122340
cgtcgctgcg catgatcccc agcatcgtgc ccggccagcg ggagatctgc cttcgcgagc 122400
gcggctgggc cgtcctcgag acggacgccc gcggacactg cgagcccggc gtcctgaggc 122460
tggcgctcgc cggcctgcgg ctgttcgcag gatgcctgcg ctccgtcgtg gggcggcgcg 122520
agctgtcgct gttctgctac ggcatcgctc ccaagttcgg cggagagttc gaggacgcgc 122580
cgcgccccat ggagatcgac ggttagttgt ttttatccct gtacatacgc cgcaaactga 122640
aactttaggg caccgcgtaa tagtgcacga acgcccagtg gaccgcttcc gcagccatgg 122700
aaaacaacga aggcaacgaa cgcaacaacg aacacccgca cgttcgagaa ttcaaggagg 122760
cgtccctgta cgggtttctg gtgtcggccg cggacgtgac cgtcgaggac gtgcgccggt 122820
accttcagtt cggcgcggac gtgaactaca ggggcgcgta cctgtgcacg ccgctgcacg 122880
cgtacctgca gtccggctgc gaaaagcgcc tagacgtcgt ggacgcgctg ctggacgccg 122940
gcgcagacat caacgccaag gagatctgcg ggctcacgcc cgtgcacctg tacgcgagct 123000
acgcggatgt ggacgtagag ttcatgcgcg ggctcatcga gcgcggcgcg agcgtgtgcg 123060
gcgagagctc ggtcacgggc tgcctgtact cgtacctgta cacacacagc gtggacggcg 123120
gcgcgcgcct ggacgtggtc gagctgctcg tgcaggcggg cgcggacgtg aacgtccgcg 123180
gcgaggcgcg caagacgccg ctgcacgtgc actgcgcggg cttcgaggtg gattcggaca 123240
tcgtggagct gctgctgcgc gcgggcgcgg accccgaggc gctcgacgaa cacgggctca 123300
cgcccgcgga cgtgctcgtg aagtccgtgg gcgccaacgt ggcgacgctg cggctcttcc 123360
tcgacgcggg cgtgagcgtg gccacgtcgc gcgacgcgcg cggacgcacg ccgctgcacc 123420
accacgcgga ctccttccgg gcgagtgcgg tcatcgtgcg cgaactgctc gccgccggct 123480
gcgacgcggc ggccaccgac gacctcggaa acacgcccct gcacagcctc gccaccttct 123540
gctcgtgccg gcgctcggtg ctcgaccagc tcatcgccgg cggcgcggac atcaacgccc 123600
gcaaccacta cggccacacc tgtctgtact acgcgtccat ctacaacccc tccgtctgct 123660
cgaggctcat cgccgcgggt gcggacgtga ccgcgcgcac gccggacgga cgcacgccgc 123720
tctcgggcat gatcatgcgc aagcacacgc gcgccgtgcg cgccgccctg gcgacgcggc 123780
ctcccgcgga cgccgtcgcc gcgtcgctag acgtcgcggt acagcccgag cccacggacg 123840
ccactcgcgc gtgcgtgcgg tacgtggtgc tctgcggcgg cacgctctcg gcgcgcgtgc 123900
ggtcgcgaca cgcggacttc gtgcgagagt gcgaaagcga ggtggtcgtg ctcagaacca 123960
ccgtggtggg gctgcccggc acctcgctgc tggacatcgt gcgtgcggcg cagccgccgc 124020
cggtactgct ctccccgcgc gtgcaccacg tgctgcagaa gctgtgtgtg tacgcggagt 124080
tggtagacgc gcggctgcgc gagatgcggc acaagaccaa cctcgtggac gcggtgtcgc 124140
ggctcgtgtg tccgtgcgcg ctgccgccgg aggtggtgcg cggcatcctc gtgcacgtgc 124200
cgatagacag cctgcggcac acgttgaccc tcggcgtggc gcaggccttg cgtttccttc 124260
cctcgcataa atgaaatatt attttttgtg gtagaccgga tctccccgat ggaccccgcc 124320
ggacaacgac tgcgcgcgcc agggccgtgg cgcctgaacc cgccgaccgc ggccgcgctg 124380
gaaagcgcgc tgctgcggcc cgcggcgtcg gcgggcgccg accgctgcgc gaacgcgcac 124440
gtggacagcc gcaacatggg cgtcggcgag ggccgagagg tgcccgcgga cgtcgagggg 124500
ctcatgaccg agatccacct gcggtacgga atgacgcgcg tccaccggaa cgttcacttc 124560
gtgcagttct ggcacggcga gcacgtgcgc cggcgccccg cgcgacacgt gttcacggtc 124620
tggatctgcc tcagcggcga ggtgcgcatc tacgcagagt gctgccaggc ggggcacggc 124680
ttcgtgctct gccgccagat ggcggccggg tacatgttcg tgaccgagcc cacggactcg 124740
gtcacggtct cggtgccgca ccggctgcgc aactcgcggt cgccggtgtg gctggcggcg 124800
gtcttcgcca cgcggcactt cgagccgctg ccgccgccca tgtacgccgt gcccgggcac 124860
gtggtgctcg cgcgcagcgc ctccatgctc tgcgactgct ggccgtcgga cccgcggcgc 124920
cgcaacgtga tcttctacat gcggctgtcg ggcgcgatgg tgcgcgtggt cgtgccgggc 124980
gcggagcttg agatcgagtg cacctcgggg ttccggccgg accacttctc catcgacgac 125040
gagtgcgtgt gctgcgagcg gccgcacgtc gcgcgaaccg cggtgtggac gctggcggag 125100
atttgccgcg gcgccacggt ggtgctcgcg ccgccactgc cccgcgaccg cgccgcgggg 125160
ctgctcgcgg agatccgcct ggcctcgctg cgatgggtgc gcgtgcgtgc ggtccgcagc 125220
ggcagagaaa gcgtgggccc gttcccctcg gtggtgtggg cggcggtctt ctccgccgtt 125280
cggctcttcc tggacggaac cgtgcctgcc ttcccggcgt gtgtggagaa tggacgcgcg 125340
gcgtacggca tggtgtacgt gccctcggag gagccgcgga tggacgggct ctgtgtgttc 125400
ccgacgcccg ccgagccggc ggcgctcttc gtccgcggag accaggtgct cgaggccggc 125460
gcggccgccg ccataatcgc ggccgctgag aagcgcgtcc aggccgccaa tgggtctcct 125520
gctgccgcgg aggaggacat aggtgcggcg gccgatgccg ccgcagagag cgtggagcag 125580
gaccagcgcg tcgagtttga ccttgggcct gggcctgacc ccagccaaga agcgcccgcg 125640
gacgcgcagc gtgccgattc ggacgacgac accggctccg agactgagac cggcgacgag 125700
agtgtgggcg gcgaggatga cagcgactcc tcctcctctt actcggtgat gtcggacgac 125760
gaaaacgaca gcggcgacga gggctggggc gactctagcg actccggcat cgaggacgac 125820
gacggcggtg tcggccaggc cgccgaggaa gaagaggagg aagagcgcga cgtcctcggc 125880
gcagcggccc agatgctcgg agactgaccg gtggtgaaaa cataaaaata aactgttcaa 125940
cacttgtact ccgggcacca acactactat ccatacccac cctccctcca cacactacaa 126000
tggcaaacag agaagagatt gacgcctccg ccgtcatggc tgcctacctc gcgagagagt 126060
acgcggcggc tgtagaagaa cagctgacgc cgcgcgagcg cgatgcgctc gaagcccttc 126120
gcgtttccgg cgaggaggtc cggtcgccgc tgctgcaaga actctcgaac gcgggcgagc 126180
accgcgccaa ccccgaaaac tcgcacatcc ccgccgccct cgtctccgcg cttctcgaag 126240
cccccacttc ccccggccgc atggtcactg cgattgagct ctgcgcgcag atgggccggg 126300
tatggacgcg cggccgccgg ctcgtcgact tcatgcggct cgtgtacgtg ctcctagacc 126360
gtctgccgcc cacggccgac gaggacctca gcgcctggct gcaggccgtc gcgcgcgtgc 126420
acggcacgcg gcgccgcctg caccgcgttc tcggcgtcgg ggccgtcatg gcaggcgtcg 126480
gtatgctgct gctcggcgtg cgcgtgttgc ggcgcacata actttttatc tcggctcaaa 126540
ctgaaatacg acattggact acgaaaccta taattttgcc cacggccgcg cgagatagga 126600
taataaataa cctctgagca actaacatgg ccgatgagag agaggccgac ggcgcgctgt 126660
tccggtacct ggagagcgag gaccgtccgg acgtggagca catgcgccgg ctgctggacg 126720
agggcgcgga cgtgaactac gcgggcccgc gcgggtacgc gccgctgcac atgctcatgc 126780
gcggcaaccc gctagacccc gacgcggtgc gactgctgct cgccgcgggc gcggacgtga 126840
acgcgacatc gctctgcggg ttcacgccgc tgcactccta catgtgcttc gggaccgtga 126900
cgccagacac gctgcgtgcg ctcatgcgcc acggcgcgag cgtcagcgac ctcgagcgca 126960
acatcaacgc gctgatcgag tacttcaacc gcgacggctg catgggcggc gcggaggcga 127020
ccgtgatcgc actgctggcg gagcacggcg cgcacgtgaa cgccaaagac gaccttggac 127080
gaacgccgct gcacatctac ctgtccggct tcttcgtgtc ggcaccggtg gcgctcgcgc 127140
tgatcgcgct cggcgcgaac ccgaacgcca cggacgcgta cgggcgcacg ccactgcacg 127200
ccttcctgcg ctcccgcgac gtggaccccg ctgtgctgaa gacgctcata gccgcgggcg 127260
cagacccgct cgcgcgcgac atcatccggc gcacggcgct gcactaccac tgcgagtcct 127320
tcaagacgcg cgctagtgtt atcgagacgc tggtggccgc cggctgcgac cccgcgagca 127380
cagacctgct cgacaacacg gcgctgcaca gcatggccat gggcagctcc tgccgcgcct 127440
cgctgatccg cccgctgctg gccgcgggcg tgtccgtgaa cgcgcgcaac gcgcggctgc 127500
agacgccgct gcacctcgcg gccgtgttca acccgccggc ctgcgcgcgg ctgctggccg 127560
cgggcgcgga ccccgcgctc gcggacctag acgagacaac gccgctgctg agcatggtgc 127620
gacacaactg cgcacgcgcg ctgcgcacgg cgctgccctt ggcgccggac gcgctagtgg 127680
ccggcgcggt taaccgcgtg aacgcgcgca cgccgagcgc ggccacgcgc gagtgcgtga 127740
tggcgctggc gctgcgcggc gcgctggacc tgctgagcgc ggagagcgtt gccacccacg 127800
cggccgcgat ccgcgcctgc gaggcggagg tcgcgctgct gcggcgcacg cgcctgggcg 127860
cgccgccgac gacgctcttc gcgctgctga caggacgacc gaacacgctg gtttccgcaa 127920
aggcggcgcg acgcgcgatg gcggacgtgt gtgtctaccg cgcggcgctg gccgcgcgcg 127980

-continued tggagcgcgt gcgccgaaag tcctcgctgg tcgagcgcct caccgccatg gtgtgtccgt 128040
gcgctctgcc gccagagcta gtgacgcgca tcctcgcgct cctgaccgtg gaggaactcg 128100
cttgcgcaat gcgcaaataa taatgaacta taactaggct tattagaggc actatttgtg 128160
cagagtcgtt agttatagtt agtgtactta caattggaat gtcgaagaac aaaattctgg 128220
tgtgtgttgc gattattctt acttatacat tatacacaga tgcgtattgt gttgagtatt 128280
tagaaagtag ggaagatgaa caacagtgca gcggtagtaa tggtgcgtct gcgagtttac 128340
cgcacatgct cagagaactc agggccgcgt tcggaaaggt aaaaactttc ttccagatga 128400
aagaccaact gaacagtatg ctactcacac agtcgctcct cgacgacttc aaaggctacc 128460
tcgggtgtca ggcactttcc gagatgatac agttttactt ggaagaggtg atgccgcagg 128520
cggaaaatca cgggccggac atcaaagagc acgttaactc gctgggagaa aaactcaaaa 128580
cgctgcgtct tcgactgcgt cgctgccacc gcttcctgcc gtgtgagaac aagagtaagg 128640
ccgtggagca agtcaaacgc gtgttcaaca tgctgcagga acgaggtgtt tacaaggcca 128700
tgagcgagtt cgacatattc atcaactaca tagaatcata catgactact aaaatgtaaa 128760
aatgtatata acttttagct atcgttcgga ttctcgtatc gttctgctac aatgtatata 128820
aaaatgtata ttcacatagt tacagttaca gttacagtta cagttacagc tatattttta 128880
tgctcacaag atgctatata attgaaagga aattgttcac tctctgtcag ggcgccatgg 128940
actttctagg cgccgcgctt cacgactacg ttgccgacgc ggaaaatgtc cgcgttgacg 129000
aggtgcggcg gctgctggcc gcaggcgcct ctgtggagta cgcgggcgag ttcgggaaga 129060
ccgcgctgca ccagtacatg ggccgttccg gcgcggaccc cgacgtcgtg cgcgcgctgc 129120
tggacgccgg cgcgcgcgtg gacctcccgg agacctgctg cggctgcacg cccgtgcacc 129180
tctgtctcat ggccgccaat atcgacgtgg aggttctccg catgctcgtc cacgagggcc 129240
gcgtcgagga ctgcggccgc gccgagcttg cctccgcggt gctcaaggag ttcgtggtga 129300
accgcgcctt cgacgagaac gtcaccgagc gagtgatgcg cgttcttgtg gccgcgggcg 129360
cggacgttaa cgccaccagc gtggtcgacc gcacgccgct gcacgtctgc ctcacgggca 129420
tgtccacgca cccgggcacc atcgccgcgc tgctgcgctt cggtgcggac gtgaacgccg 129480
tggacctctg cggcatgtcg ccgctggcgg tgctagtgcg ctcgcgcgcg gcgaccgcag 129540
agctggtgcg catgctgctc gacgcgggcg cagacgcaca cgcggtcgac agtcgcctgg 129600
actcgctgct gcaccagcac tttcagtccg cgcgcccgcg gccggaggtg gtgcgcgagc 129660
tcatccgcca cggctgctcg ccgcgggcgc ggaaccgaat cggcaacacg ccgctgcacg 129720
aggccgcaaa acactcctcc tgcaaacact cgctggtggg gccgctgctg gctgccggcg 129780
cgagcgtgga cgcgcgaaat aacacgggca agacgccgct ccacttggcg gcggcgtcca 129840
acccgcgcgc gtgccgccgg ctgatcgcgc ttggggcgga cgtggtcgcg cgcagttacg 129900
cgggcgtcac gccgctggcg cagctggtcg cggacaataa ctccgcgctg gtgaccgcgg 129960
cgctggacac gcagcccgag ccgcgggccg tggcagagtc gctgcgagct accacgcccg 130020
tcggcgaaac agcgtgctcg cggctctgtg tggcgtacgt ggtggcgcgc gtgccgagcg 130080
aggtcctcgg cgagcccgag cgcgccctgc acgcggcctt cgtggcggag tgcttagcgg 130140
aggtagcggc gatacgccgt gcgctgcggc acacctccag tctcgctgct ggagatcctg 130200
gtggccgcgc gcccgccgcg gagcctgctc tcgcgccgcg cgcggcggct ggccgagagc 130260
cggacgacgg tctaccgcgc gccgctccgt gcacgcatcg cggccatgcg ccatcgctcg 130320
cgactggtgg agcgcgcgct gcgcacgctg cgcggctgcg tgctcccgcg cgaggtgctg 130380

```
gagcgcgtgc tgcggtgtct gtccacacag gacctgcgga catccggact ggccgagtag 130440
ctttttctga gataagtgaa taaacatggt gggattcgat cgcgccgcca acgccacgcc 130500
atggacgccg ccgagatgga ggagctcgac atcaacgcgg agtcggcgct gtacgactac 130560
ttcatcctga acgcggacag agcccgcgtg ggcgaggtgg tcatgcttct cgcacagggc 130620
gcggaaataa actacgcgga cagcttcgac aagacgccgc tgcacctgta cttgcacacg 130680
cgacacccgc gctcggacgt gattctggcg ctgatggagg caggcgcggt cgtggacacg 130740
ccggagcgct gctgcggcgc gaccgcggcg cacctgtaca tcctcaacgc ggccgaggtc 130800
gacctgtcgg tgctggaggc catgctgacc tggggcgtgc gccagaacga ccagcactcg 130860
gagcggctgc tctcgagctt gttgcgcgag tacgtggtga cccgcgccta ctcggatcag 130920
accgagccga tcatggactt gctcatcggc atgggcgccg acgtggacat gccggtcggc 130980
gtgagtcgca cggcgctgca cgcctgcctt acgggcctga acacgaaccc gtgcatgatt 131040
cgcgcgctgc ttcggcgcgg cgccagcgtg accgcaaaag acacctacga gatgacgccg 131100
ctggcggtgc tgctgaagtc tgcgagcgcg acgccggagc tcgtgcgcat cctcgtggaa 131160
gcaggctccg acgtgagcgc caccgacttc cgcctcaacg gcatgctgca ccagcacgcg 131220
cagtccacgc gcccgcgcgc gagcgtcatg cgcgagctca tccggctggg gtgcagccca 131280
gcggccaaaa acatgtttgg taacacgccg atgcacatgc tggccatgga aagctcctgc 131340
cgccgctcgc tgatcctccc gctgctggag gcagggcttt ccgtgaacga ggagaacccg 131400
cactacggca ccgtgcctct gcacgtggcc tcggggtacg acaacacgca gggctgcctc 131460
aagctcctcc ggcagggagg agaccccgcc gtcgtgtcgg ccgccggacg cacgccgatc 131520
tcgaacatgc tcgtcaaacg caaccacgtg gcggtcgccg gcgcgctgtc gacacacccg 131580
agcgcggtag tggtcgtgca ggctctcgag caggctctcg agcacgtgct gaacgccggg 131640
cccagcgagg cctcgcggct cgccgtggcc tttgtggtgg cgcgcgctgg cgcatccgcg 131700
ctaccggagg ccgtgcgccg tctgcacgag ggctttgtcg ccgactgcga gcgcgaagtc 131760
gcgctgcttt ctcaaaccat gctcggcaca ccggccgtga gcgcgctggc cgtgctggtc 131820
agcaaggagg tctttggcac tgttatctcc tcgcgtgcgc tgcgtgtcgc gcgggaggtc 131880
cgcgtgtacg caaggccgct ccgcgaggcg ctcataaatc tgcgccacaa atgccgctta 131940
gtttccagcc ttaaaaggca ggtgggacct tgctcgctgc ccggcgaact ggtggagcgc 132000
gtgctcgcga ccgtgccact gaccgacttg cgccgctcgt gcggccgccg cgcgcccgag 132060
tgactgccca tcccgttgct acgcgactcg gtgactgccc gctgtttttc tttccccgtt 132120
tcttcttatt aggagttgtt gcccgcctcc atgatcctcg cgcgcgccgg cgggcgacct 132180
cgcacgcccg cggcggccgc ggccgccgcc gaggacggag agcacagtga tcgccggaag 132240
cgcaagcgca agacgcccaa ctgcgaagac gccgacaact ccgacgacga gctagcgcag 132300
acgccgtgtg accgcgagtg gccggactgt cgcgcgagct cgatcacgag ctccgactcg 132360
gtctctctcg gcgacgagat ctacctgcga tacgtggcct cgcaggtgga cttcgcgcag 132420
acctgggccc cgccggtgcg gctgctgcgc ttcttcggga acttctcgaa ggaaacgctc 132480
aaccgcatgt cgcggcgcgg gtacgtgaac cgctcctact tccagatggc gcacgcgcgc 132540
ttctcgccca ccaacgacga catgtaccac atggccacgg gcgggtacgg catcgtgttc 132600
cgcttcgacc gctacgtggt caagtacgtc ttcgagcacc gcaacggcat gtccgagatg 132660
gacgcctcta cggagtacac agtgccgcgg ttcctgcgca ataacctcaa gggcgacgag 132720
```

cgcgagttcg tggtctgcgc gctggccatg gggctgaact accggctggg cttcctgcac 132780
tcgctgtacc ggcgcgtgct gcacacgctg ctgctgctca tgcgcgtgga ggaaggccag 132840
cggccctcgg tggagatgtc caagaagccg ctgctgcgct ggttcgaggc gcgcaaggac 132900
agcgagtcct tcgtgcgcct gatctcgtac ttctacccct cggccgtgca gagcaacgtg 132960
aacctgatca acaacttcca ccacctggtg cacttcttcg agcacgagaa gcgcgcgcgg 133020
tacgtgttcg accgcggggc cgtgatcgtg ttccctctgg cgcgcgggtc cgcggactcg 133080
atctcgccgg aggcggcggc ggcgctgggc ttcgcgccgc actcggagtt cctcaagttc 133140
gtgttcctgc agatcgcgct gctgtacctg aagatctacg agctcccggt ctgcacgaac 133200
ttcctgcacg tggacctgaa gcccgacaac gtgctcatct tcgacagcgc gcgcgcgctc 133260
agcgtgaccg cggccggcgc gactttccgc ttcgaggagc ccgtgcgcgc ggcgctgaac 133320
gacttcgact tcgcgcgcgt ggccaccatc gagaaccgca agatctcggg cagcgtccgc 133380
gtgccgcaga actggtacta cgacttccac ttcttcgcgc acacgctgct gcgcgcgtac 133440
ccgcacatcg ccgcggagga cccgggcttc cacgcgctgc tctcggagct cacggtctcg 133500
tgctcgcgcg ggacctgcga ccgcttccgg ctgcgcgtgt cctcgccgca ccccatcgag 133560
cacctcgcgc ggctggtgcg ccgcgacgtg ttctcccgct ggataaatgc cgctgcagac 133620
gcccccgacg ccgccgcact ctcctgagcc cacgcccgcg gcgccgggct cgctgtacga 133680
cgtcttcctc gcgcgcttcc tgcgccggct ggccgctcgc gcggcgccgg cctcggccgc 133740
ctgcgccgtg cgcgtgggtg cggtgcgcgg ccgcctgcgg aactgcgagc tggtggtgct 133800
gaaccgctgc cacgcggacg cggccggcgc gctcgcgctg gcctccgcgg cgctcgccga 133860
tacgctggcg gagctgccgc gcgcggacaa gctcgccgtc gcgcgcgagc tgggcgtgga 133920
ccccgagcac ccggagctga tgccggaccc cgcctgcgcg ggcgagagcg cgctcgcgca 133980
gaacatcgac atccagacgc tggacctggg cgactgcgga gaccccaaag gccgccgact 134040
gcgcgtggcg ctggtgaaca gcggccacgc ggccgcgaac tgcgcgctcg cgcgcgtggc 134100
gaccgcgctg acgcgccgcg tgcccgcgag ccggcacggc ctcgcggagg gcggcgtgcc 134160
gccgtggacg ctgctgctgg cggtggccgc ggtgacagtg ctcggcgtgg tggcaatctc 134220
gctgctgcgg cgcgcgctgc gggtgcgcta ccgcttcgcg agaccggccg cgctgcgcgc 134280
gtagccgcgc aaaatgtaaa ttataacgcc caacttttaa gggtgaggag ccatgaagtt 134340
gctcgtcggc atactggtag ccgtgtgctt gcaccagtat ctgctgaacg cggacagcag 134400
cacgaaaaga tggtccgaag tgctgaaagg tagcgagtgc aggcctaggc cgattgttgt 134460
tcctgtaagc gagacgcacc cagagctgac ttctcagcgg ttcaacccgc cgtgtgttac 134520
gttgatgcga tgcggcgggt gctgcaacga cgagagcttg gaatgcgtcc ccacggaaga 134580
ggcaaacgtg acgatggaat tcatgggtgt aggtgtgtcc agcactggat ctagtgtgag 134640
cactcaacat ctggaattcg tggagcatac aaagtgcgac tgtcagccgc gcggcggaca 134700
gcagacgaca ccgacgccac ctagacggcg ccgaagggct tattagcagc agtttttgta 134760
gcgggacgtt tctgggtttc cttgcgcgct cggcggcggg gctgctgctc gcggcgggcg 134820
cgcggtggcg gcggctggcc gcggcgctgg cggccgcggg ccgcgcggcg gggtagcggc 134880
ccggcccggg cccgccgcag cccttcgcct gcggaggagg cgccacggcg caaagtgaaa 134940
aaggaccgcc tagcagtcga gaccctcccg ccacagccgc ggacacccac acccgccctc 135000
cacaccacag ccagcaagca tgcacccctc gccgcgcagg ctgctcggcg cgctcgcgct 135060
ggtggcgctg ggcttcctcc tcggcgggct cttccgcccc gcggcgccgc cgctgccggc 135120

```
cgccctcgtg gaggcgggcc ccgtccgcgc gaacggctcc gcctcggtga cctgcctgac 135180
cgtcggcggc gacgggcggc acatggcggt ggtcgcgcac ggcggcggga cgctctcgcc 135240
ggtgtacccg ctcgccgccg gcatgcacgc gaccttcgcc tcgctgcgca agggcgcgct 135300
gctgctgaac gtcgcgaccg tgcacatcta cgacgtgcgc gagctcgcgc cggagttcga 135360
gctgacctgc gtcgcggtgg cgggcggcta caacgcggcc tgggcggcca cgcggcccgc 135420
ggccgagtgg cgccgccagc tggcgcagat gcaccgctcg gagctgtgac cctctccccg 135480
gtctcccatc cgtttttgta ttcggcctta gtagattaga ccagcatccc gcgccccttg 135540
cgccgccctt cgctcgtgaa cgagcgaatc agtcaattaa ttatttttat cgccgcccgc 135600
tcactccggt aagggaacgc ggttaactca cccacgagaa caagcaaccg ctcactcacg 135660
aggtaaggga acaacagtta acgtcaactc actcacgaga acaagttgac cactctcgag 135720
gcagagacga gaaaacaagt gaccgtactc gctcacgaga acaagttgac gcaccactcg 135780
ccgaggtaag ggaacagata acaagtaaca agtaaccgtt acatcactcg ctcactcctc 135840
ggaaaataga acgagagaac gagagaacga gttaacttac tcactcgctc actcggtgtg 135900
agagaacgag agaacgagta gctgttgctc actcaatcgc ccctcggagt aagggaacaa 135960
gagcagtcaa cgcacccact cagtcttgga gtgagaggca gaggacgagc taacgagttg 136020
aacagttaat ctctcaccac tcagagtgag agagcgagag agtgaggacg agttaacaag 136080
tcaatcctca ctcagagcga gagagtggag gacgagttaa tagttaacgg ttagttatca 136140
ctcactcaga gtgagaggag ggcgagtcaa ccactcgctc gcccctccga gttagagagg 136200
agaaccagtg agcgagttaa cccgcacacg agcgagagaa cgtgaactcg ctcgcgcgcg 136260
ctcggctaac agtcggcctc tcccaaaact cttcgtaaac ttttcccgtg acaggttcgt 136320
ccttccaaaa ctaaactgtc gggtcggcct gcctctcaac tctccgtaaa acgtttgtaa 136380
actgttcgga ggtcggtgac ccgctcaacc cgtccgcgaa aacttttcgc aggcagtgtc 136440
tgcctctctc ggactctccg caaacacttt cgcggaacct cgggggtggt cgacctctct 136500
ccaaactttg caaaactttt tcgcggagcc tctggaggcc agtcctccct ccaaactctt 136560
tgtaagatct tttcggaggc cagtcctcct ctccaaaacg ttccgcaaaa tctttgggag 136620
gtcggcctct cctctccaaa acgttccgta aactcttgga cggccgcccg cggcacgcga 136680
ggcggaggat ccgggggtag tcgacctccc tcaaaaactt tgtaaaaact ttttataaaa 136740
cttttcgcgg aacctcgaga gtaggtcgac ctccctcaaa acttttataa aactttttag 136800
cggaaccgtt ggaggcaggt cgacctccct caaaactttt ataaaacttt ttagcggaac 136860
cgttggaggc aggtcggcct ctcaaactct ttgcgagaac tcttcgataa ctttaggagg 136920
tcaggtcgac ctcccaaaac ttttgcgaga actctctgaa aactttagga ggtcaggtac 136980
ctctccaaaa cttttataaa actttttcgc ggagcctctg gagacgggcc gccgcccgcg 137040
accgcgggag cggagaggcc gacctcccga gacgttccgc gttaccgtcg gggtaggcgt 137100
cctctcgaga acgccaaaag acttcgtgca aaaacttttc ggaggggcgc ggagggcggg 137160
cggctcccgc gaactcccgc agaacctttt cgcgcgaccg cgaaggccgg ccgcctctcc 137220
cgaacactct caagagcttt tcggaggagg ggcaggtcgc ccccacctct ccgacgcttt 137280
gtaaaaacgt ttacgcggaa cctcgaaggc aggtcgcctc cctcgaaaac tcctcgcgaa 137340
acctttaaaa acttttgcga aaacttttcg gaggatgtcg gagggcgggc ggctcttcca 137400
aacctccgca gaacctttc gcgcaaccgt tggaagacag gtcggcctct ctcgaaaact 137460
```

-continued tttaaaactt tgtaaacgcg ttggcgggac cgtcgcggga gagcggccgc ccgcggcacg 137520
cgagaggagg aaacgttgga aggagtcggc ctctcccgaa aactttttat aaaaactttt 137580
ccgcggaacc gtggaaggcg gtcggcctct cccgaaaact ttataaaaac tttttgcggg 137640
actcggacgg cgggtcaccc gaccacctga ctcctgtcta cccgactact tgacttctgt 137700
ctcccgggct cctgactccc tgactcccgg actccctgac tctagagcga ggtctcgcgg 137760
ctgcggggtg ccgcctccgc ggagtcgcgt tcccgcggac gcccgtcctc gaaagcattc 137820
agcagttcca gcctctgccg tagctcctcc cgcaggaact cctggtccgc gttctcg 137877

<210> SEQ ID NO 5
<211> LENGTH: 138004
<212> TYPE: DNA
<213> ORGANISM: Artificial Sequence
<220> FEATURE:
<223> OTHER INFORMATION: Recombinant OVRF-121 RabV -G Complete Genome

<400> SEQUENCE: 5
cgagaacgcg gaccaggagt tcctgcggga ggagctacgg cagaggctgg aactgctgaa 60
tgctttcgag gacgggcgtc cgcgggaacg cgactccgcg gaggcggcac cccgcagccg 120
cgagacctcg ctctagagtc agggagtccg ggagtcaggg agtcaggagc ccgggagaca 180
gaagtcaagt agtcgggtag acaggagtca ggtggtcggg tgacccgccg tccgagtccc 240
gcaaaaagtt tttataaagt tttcgggaga ggccgaccgc cttccacggt tccgcggaaa 300
agtttttata aaaagttttc gggagaggcc gactccttcc aacgtttcct cctctcgcgt 360
gccgcgggcg gccgctctcc cgcgacggtc ccgccaacgc gtttacaaag ttttaaaagt 420
tttcgagaga ggccgacctg tcttccaacg gttgcgcgaa aggttctgc ggaggtttgg 480 aagagccgcc cgccctccga catcctccga aaagttttcg caaaagtttt taaaggtttc 540
gcgaggagtt ttcgagggag gcgacctgcc ttcgaggttc cgcgtaaacg tttttacaaa 600
gcgtcggaga ggtgggggcg acctgcccct cctccgaaaa gctcttgaga gtgttcggga 660
gaggcggccg gccttcgcgg tcgcgcgaaa aggttctgcg ggagttcgcg ggagccgccc 720
gccctccgcg cccctccgaa aagtttttgc acgaagtctt ttggcgttct cgagaggacg 780
cctaccccga cggtaacgcg gaacgtctcg ggaggtcggc ctctccgctc ccgcggtcgc 840
gggcggcggc ccgtctccag aggctccgcg aaaaagtttt ataaaagttt tggagaggta 900
cctgacctcc taaagttttc agagagttct cgcaaaagtt ttgggaggtc gacctgacct 960
cctaaagtta tcgaagagtt ctcgcaaaga gtttgagagg ccgacctgcc tccaacggtt 1020
ccgctaaaaa gttttataaa agttttgagg gaggtcgacc tgcctccaac ggttccgcta 1080
aaaagtttta taaaagtttt gagggaggtc gacctactct cgaggttccg cgaaaagttt 1140
tataaaaagt ttttacaaag tttttgaggg aggtcgacta cccccggatc ctccgcctcg 1200
cgtgccgcgg gcggccgtcc aagagtttac ggaacgtttt ggagaggaga ggccgacctc 1260
ccaaagattt tgcggaacgt tttggagagg aggactggcc tccgaaaaga tcttacaaag 1320
agtttggagg gaggactggc ctccagaggc tccgcgaaaa agttttgcaa agtttggaga 1380
gaggtcgacc acccccgagg ttccgcgaaa gtgtttgcgg agagtccgag agaggcagac 1440
actgcctgcg aaaagttttc gcggacgggt tgagcgggtc accgacctcc gaacagttta 1500
caaacgtttt acggagagtt gagaggcagg ccgacccgac agtttagttt tggaaggacg 1560
aacctgtcac gggaaaagtt tacgaagagt tttgggagag gccgactgtt agccgagcgc 1620
gcgcgagcga gttcacgttc tctcgctcgt gtgcgggtta actcgctcac tggttctcct 1680

```
ctctaactcg gaggggcgag cgagtggttg actcgccctc ctctcactct gagtgagtga   1740
taactaaccg ttaactatta actcgtcctc cactctctcg ctctgagtga ggattgactt   1800
gttaactcgt cctcactctc tcgctctctc actctgagtg gtgagagatt aactgttcaa   1860
ctcgttagct cgtcctctgc ctctcactcc aagactgagt gggtgcgttg actgctcttg   1920
ttcccttact ccgaggggcg attgagtgag caacagctac tcgttctctc gttctctcac   1980
accgagtgag cgagtgagta agttaactcg ttctctcgtt ctctcgttct attttccgag   2040
gagtgagcga gtgatgtaac ggttacttgt tacttgttat ctgttccctt acctcggcga   2100
gtggtgcgtc aacttgttct cgtgagcgag tacggtcact tgttttctcg tctctgcctc   2160
gagagtggtc aacttgttct cgtgagtgag ttgacgttaa ctgttgttcc cttacctcgt   2220
gagtgagcgg ttgcttgttc tcgtgggtga gttaaccgcg ttcccttacc ggagtgagcg   2280
ggcggcgata aaaataatta attgactgat tcgctcgttc acgagcgaag ggcggcgcaa   2340
ggggcgcggg atgctggtct aatctactaa ggccgaatac aaaaacggat gggagaccgg   2400
ggagagggtc acagctccga gcggtgcatc tgcgccagct ggcggcgcca ctcggccgcg   2460
ggccgcgtgg ccgcccaggc cgcgttgtag ccgcccgcca ccgcgacgca ggtcagctcg   2520
aactccggcg cgagctcgcg cacgtcgtag atgtgcacgg tcgcgacgtt cagcagcagc   2580
gcgcccttgc gcagcgaggc gaaggtcgcg tgcatgccgg cggcgagcgg gtacaccggc   2640
gagagcgtcc cgccgccgtg cgcgaccacc gccatgtgcc gcccgtcgcc gccgacggtc   2700
aggcaggtca ccgaggcgga gccgttcgcg cggacggggc ccgcctccac gagggcggcc   2760
ggcagcggcg gcgccgcggg gcggaagagc ccgccgagga ggaagcccag cgccaccagc   2820
gcgagcgcgc cgagcagcct gcgcggcgag gggtgcatgc ttgctggctg tggtgtggag   2880
ggcgggtgtg ggtgtccgcg gctgtggcgg gagggtctcg actgctaggc ggtccttttt   2940
cactttgcgc cgtggcgcct cctccgcagg cgaagggctg cggcgggccc gggccgggcc   3000
gctaccccgc cgcgcggccc gcggccgcca gcgccgcggc cagccgccgc caccgcgcgc   3060
ccgccgcgag cagcagcccc gccgccgagc gccccgcgcc gccgcgggcg cgcgccgagg   3120
ccgcggcccc gcgccgcgcc agcagcagcg gcagccgcgc gtccagcggg ccgccgcggc   3180
gcagcgccgc gcgcagcagc gccgccagcg gcagccgccc cgccgcgtcc gggcccgccg   3240
cgcgcgcgcc cgccgccagc agcgcgcgca ccagcgccgg cgaggggcgc cgcgcgcgga   3300
ccaggtgctc cacgagcagg gtggtgagca aggattctcg agaagtagga gtcatgtgtg   3360
acgacaagga gagacgttat attaggcgcg tcctacttca ctttgaagat ggtgtaaagt   3420
gttaaaactt gaacaccgtt cactctacca ctgccgttac cgtgtcctgc cccaaaagcg   3480
accacagtgc tttttccacc acctgttcca aatccgttcc aaaagctccc atccattgtt   3540
gttagaactt tcagatgttt ctctaggttg tttagttcca ctgcaagttt tgaccattat   3600
cgttactgga catgctgttg gtaatgagtt taataaccaa tcataaaaat agttataatt   3660
tgttataatt tataatttgt tataaagcta taaagtagca aacactttaa tgttatattt   3720
tgcctaaccc tccgttaaca ccaccattaa caccaccact taagctttta ctaccaccac   3780
taccacctcc aacacacatt cttttctcta aaggtcccca aattccacct cctgaacttg   3840
gacgttttac agcacctccg ggtgtacttg cgtacccttt agaagttcca ctgtgactgt   3900
agatatgata ctgtccttct ccaggcatga ttaaagtgtg ttgtaattag tgttatctac   3960
acaactgtgt gagacgctca aataaaaaga agctacattt tacaattttg attagctgat   4020
```

-continued

```
gtaccacgct gtatcgcggc caccacaaga acccaatcca gtagaaccaa atccagagtc   4080
gccgcggtcg gtgttgtcca agcagttaac ctcttgaact gctgggcacg atatgcgttc   4140
gcatattagc tgagctatcc tgtctccctt cttaacctca aagtcgctgt ttccgaagtt   4200
aaacagcacc actccgacgt tgcctcggta gtcttcgtcg atcacgccag cgcccacgtc   4260
gataaagtgt ttgactgcaa ggccagaacg tggtgctatg cgtccgtagc aaccagaagg   4320
gggctttatc agaaggtcag taaatactac gcgactgcaa tgcgaaggga tgacacagtc   4380
gtgtgcacta cataggtcta atcctgcggc accaggagat cctctggctg gtatagtggc   4440
gttttggctg aggcgaacaa cctgaagagt ttccgtgtgg cagaactcca tggctagggt   4500
ggcgagcggc cgatcgacta cggggtgtac aatttacact ttctccagaa aaatcagggg   4560
cgggtcagca tggcgcggcg caggtccagc agcgagtcgt acgacaggaa gcacaggatg   4620
gaggtcacga tctccggcgg cagggcgcac gggcacatga ggccggcgat ctgctcggcc   4680
agcgagacgc gcagccgcat catgcagatc ttgccgaaga gcgccgtccc gtagatgggg   4740
aactcggccg cgcgctccaa aaaggcgttc tgcacgaaga gcgccttcgc gtcgtccgcc   4800
gcgcgcagca cgtccagcag cgtcgcgtcc gtgtggcagc gcaccgcgcg catgctcgcg   4860
atctcctgct cgcacgcgcg gattacggtc gcgtagtccg ccagcgcgcg ctccgccagc   4920
atgcgcgcgc cctcgccgcg cagcgccagc tcctgcacgc acagcagcgc ggcctccgag   4980
cgtcggaaca cgtggcccca ttgctcggat gtgatcagcg cgcgcgcgag cagctccgtc   5040
ggcgggcggc gcgcgagcac ggccgccgtc gcgcgcacgt tgttgcggcg cagcatctcg   5100
gagaccgcgc ataggcccga ggccgacatg tgctcgagct ccgcgcccat gcgcaccagc   5160
cggcagcagg cgccgtggct gaacaccgcc gcgcggtgca gcgcggtctg caggttgttg   5220
ttgcgcaggt tcaggtccag cccgcgctcg agcacgaagt ccacgacgcc gcgctcgcag   5280
ctcccgtagg tcgccatgta gtgcagcatg gtgttcccgc acgcgtctac ggcggccggg   5340
tccacgccca ggcccgtgag cgtgcgcacc atgccctcgg agatcttggc cgtgcgcgcg   5400
aggtggtgca gcgttgtgcg cccgtacgcg tccacgacgc acgcgtccgc gcccgcgcgc   5460
agcatcatgt ccacgagcgc ggcggagacg ccgccggagc acagcagcgc cgccagcggc   5520
gtcaagccgt tgcagtcgca ggcgtttggg ttcgcgccgc gctcgagcag cagccgcagc   5580
acgtcctcgc ggatccactg gttcttggcg tacacgtgca gcggcgttac gccgtaggtg   5640
ttgccctcgt tcacgcgcgc gcccgcgtcc agcagcagcc gcgcgacctc gagctcggcg   5700
ccgtcggggc cgcagaaagc caggaaggag gagagcacgc tgtcgcagac gacgacgctg   5760
gcgtcgcaga ccacgtccgc gcccgcctcc agcatgagcg cgaccacctc cggccgcacg   5820
ccgtcgtact gcacgtaggc gtgcagcggc gtgcggccgc aggagtcctt ggctttcacg   5880
tccgcaccgg cctccagcag cacgcgcacg atctccgcgc acgctcgtgc cgcgcgaagt   5940
gcacgcagag gtgcagcggc gtgcgcccgt gctcgccgcg gaagttcacg tccgacgagc   6000
gcgcggaccg tttcgaggtc cacctgcccg gactccaggt agcggaagag caggtccgcg   6060
tgcgggacca cgacggactc ccgcgagagc atggcggcgt ttacaaatat tgaaatcttt   6120
tttcactcat ctttatgggc gctggatgcg caataagggt gggagtaaaa aacttctaca   6180
aaaagcgtac aaaaggtaca aaaggcgggg cggggacggg ctggcagtgg gtgctgcggg   6240
ccgaattggt ctctacacgg ggacgccctc gccggagccg gtgagccggt agccggcgcc   6300
ggcgatcatg gtcaagcgct gcacgagctc gttgcgcttg acgccggcct ctgaaacgca   6360
caccatgtgg tggatgtacc gctcgatgca ctcgcagcgc gggagagtgg agtcaagatc   6420
```

```
ggatgcgagt tgcagaatgt catcccagag ctcggagaac ttgctgtaca gttctcggag   6480
gtctctctcc atgcgagcca taagagagtc aggatgcggc gttccttcgg gggtctgagc   6540
gaacaccgcg aacaggctgg ttatgccgtg ttccagaata gagtggttcc gtgtcaatgc   6600
cgcagacaag ggtcgtcgtc cgcgcaacga ctggcggcag agcgctgttt gtgccgcacc   6660
gcccattcct ctggcgatcg cgtccaccga cgcagtgatc atctgcgcgc cgacgtcatt   6720
gtagcgcgcg ttaaactcag taatcatgat tacgagattg cagatttcat agtagcactt   6780
ttccaagtcg acgcgcagtt tcacgatctg gttgacaatc ttgcacgcct ttcgccgcgt   6840
ctccgccacg ttggcgactc ggacttgcgc ttcctggtcg atggacggcg gaaacacttc   6900
aaacccaagg tcgcacagtt cagcggtggg gactagcgtc acgatgatgt actccgcgtc   6960
gccacccact tgcggcagga agaacaccga ccgcgcggcg ggaacgacca gaacgtcgcc   7020
ttcctgcatg ttagttttta gaaacttagt gttgttcacg gagatgccgg ccatgccctc   7080
gtttttttaca catattatgg tgacgtacgc ggcgaccgtg ggggccatgt ggtggcgcat   7140
gtaccactcg tcgtgcttga gtttcagacc gtgagattcg ccgacctcga agtgcatgtt   7200
ggcgtctctg acgtagcgcg agaactcgct gcgacagatt cgggcgggcg cccggtggaa   7260
cgtcgactcg aagagactga tgtctgtcca ttcgcccaca tgagtgacca ccgaagaagt   7320
gttttcgatc cgagtctcga acaccgagtc cacgagcacc ggacagttgg ttccgggcac   7380
cgtcagcacc aagggccgcg cctccacggg ggcgacggac gaggccacgg agtcggtgtc   7440
cccgtacccg tagtcgtcgt cggagtcgcc gcctccgtcg gccccgtcgc gcggcctccg   7500
cagcggcatg cagccggcgg tgggaacgca ctggtttcgg ccacggccga agcggccaaa   7560
cagtctcgcc agggctgaca tccttggacg gccacaccaa aaccaaaaaa acatatttta   7620
tcagttattt gtcgattttc accggctcac cgagggcagg acctcctgga tcccggacac   7680
ccccgccagg cagcgggccg cgcgctcgcg cacccagaag cggtcgtagc cgtgccggag   7740
cacgaaggcc gccgtggcgt ggcagtccac gcgctcgatg aagccgtgga cggcgcggcg   7800
cgcgtagctc gccgcgaagg cgcggaccac cgccgagcag cgccccgagg gcgagtcgtc   7860
cgtctccagc gccagcggca tgctcgcgat gcgcgacatc aggttggagg tctgcgggat   7920
gttgagctcg cgcgtggcgg tcatctgcgc ctcgagcccg gccttgagca cctcgtcgca   7980
gcggccccac tccagcgcgc agaccacgcg gatctcgtac cccttgagcc gcagcgcggt   8040
ctcgatgtcc acggaggtga gcaccgcgct gaagcgcagg ctctcctcgt ccgcggggtc   8100
gaagagcacg gggatcttaa cctccgcgct gcgcgtgacc tcgcagagcg cgatcgcgag   8160
cagcccgcgc gtgagcttgc tcaccacgcg cggcttgccc acggggtaca gctggctcgc   8220
gacctcgcgc agcgggtacg ccagtctgaa gcagcgcgcg tccgcgggca ccgggctcgc   8280
gcccgtctcc tcgaggaaga gcgcggcctc aaccatgttc agcgcggaga agtgcaccgg   8340
gcaggcggcg cagccgcgcg cggcgttcgc gagcaccatc tcgcgcagcc cgcggaaggc   8400
cgccatgtcg caggagggga agatgcgcgc gagcgcggcc tggtgcgcga gcgccgcgtc   8460
cgagagcgcc tgcgcggccg cggcggcggc ctcctcggcg gcggccgcgc tctcgtccgc   8520
ggagaccacg tcttcgggca cgtccacgca gacgccgccc cagaactcgc agtactcgga   8580
gaagagcgtc gcgggcgcaa agcgcgcgag gtccacgaag gcgacgcggt tgccgagcct   8640
ggagagcagc gtgttctccg agatgcgcgt ccagcccttg ccggcgagct ccatgacctg   8700
ccgcgtgtcg aagaaggagc tgtagaagcc gtacacggtg atgttttcct tgcacgtcgt   8760
```

-continued

```
cagccacatg aggaagtcgc gcaccaccag cttcgcgcag tcgccggaga acacggggcc   8820
ggcgttcgtc gcgatggagt tcaggcgcac ggtgccgtcg tgccgaagcg gtacacgaac   8880
caggcggcca cgctgttgcc ggagggcgcg tgaacgtgtg gctgcgccca ggcgtagctg   8940
cccacgcagc acacgttcat gaggtcgagc agcgtctgcc ggcgcagcgg cgtgccgagc   9000
cggcgcacgg cgtcgtgcga gaccatgcgc aggtcgtaga ggcccacgtc cgagagccac   9060
tggttgagct cgtccatgga cagggcgtcg cggggggggcg ggctgtcttc gaaggcggcg   9120
cggagctcgg gctccgtctc cgcgcgctgc cgcaggatgt ccaggaaggg gctggaggag   9180
tcggggatgt agcagtcggg gtcgtgcctg gacactatag cgaaccgctg cgtcgcgggc   9240
gcgggcggcg gggctagcgc gtcggcgcgt gcgtcgatga aggtgcacga tatacgcacg   9300
gacttgagcg aggggaggac gaccgcggcg gcgcgcgcgc cctccgcgtc gaagatcatc   9360
gtctttccgt ccctcgcctt cgcgagcgcg tattctccag gcacgaggtc cgtcggcggc   9420
ggctcgtccc aggcctgccg gtcagggacg ccgccgcaca cctttcccca gaaccccagc   9480
atcctccaaa atacctaata aggacggcca atagcggggc ttgcgggcgt tcggaccttc   9540
cgcgctttaa ttttaattta ttggcttgca gaactccgag cgccagtccc gctcgaagac   9600
cgcggacagg tccttgacga tgtcgccctt ctcggcgttc acgctcacga aggcgtggta   9660
gcggtagtgc gtgccgtcga ggttggcgac cgtgaggtgc gcgaaggtgt cgtccacgat   9720
gagcagctta gtgttgttcg cggcgtcgtc ccggccgggt accacgaact tgcgcacgga   9780
catgtccacg ctgccgacgc caaagtcgtc gaggctgcgc gcggccgaga ccgacagcgg   9840
gtccgcgttc ttccactcgg taatgatcac gcgcacgcgc acgccgcggt cgatggccgc   9900
gcgcagcagc gcgtctatga tccgcggcca gtactccacg gcgctggcgt gcttgatcac   9960
cggcaccata gagagcagcg agaggtcgat gctgttcttg gcgttctcga tgcggtgcag  10020
cacgaggtcc tcgtcgagcg tgcggtagaa gcctaggaag cgctccggcg agtccgagaa  10080
gaatacgccg cccccggagt ggtcgaggtg gaagttcgtg gccgtgggcg tgacgacggc  10140
gcagcagagc cgcgtgaacg gcaccttcgg ctccacgatc atggagtaga aggtgttgta  10200
gcggttcatg aggtcccagg ccaggtgctt gttggtggag tagagcccga ggttcttgat  10260
ggtggacacg gacccgcccg tgagcgaggc gctgcccacg taccagtgcc cggcgtccga  10320
gagccagaag ctgccgagca ggttgccgac gccttcccgc gtggacacct tgaccttgta  10380
gtagttgacg cccgcctcgc gcagctcgtc cgcgtccttg tccttgctct gcacgtccac  10440
gagcagcgtg acgttcacgc cctccttggc gagcgtgcag agcttgtcct tgacgtcgac  10500
gccctccttg gtggagctca ggttgcagca gaagctgcag atgtacaaaa acttcttcgc  10560
ggactcggtg atggcggtga agcagtcgag ggtgctcatg ttgccctgcg ccagggacgc  10620
cacctctgcg ggcagcgtct ccacgacgcg gcagtcggcg cccaggggga tggaggagaa  10680
cggccacatt tatttatctc acaaaaataa tagggcttca gggaaagtct tttagcaggc  10740
gggcgagttc ttcgagttcc cttaggagtt cttccatttc ttcggaagtc agcaactgga  10800
gctcggactt tagttgaata tcttcgagga aaccgtctag catgttcgcc atgtcttccg  10860
gggagcactg cgccacatct tcggggacag gatcgggtgt gggcattagg tctccgctta  10920
cttgaacgtc gtccatcatc ctgtcgatga ggtcttcgac ttctagacgg ggtccgtaga  10980
tcagcatatt tggtgatgga ggtagtttaa ggtgcgagag ttagtgttat acgacggcca  11040
acgtgtgttt atcgcgcgta cattttcaat aattaacaaa ctccccttcc tgcgcctgct  11100
cgagaagcag ctcgtccagc tcctcctgtc ggcgcgcggc cacgcgtctt tccgcgaaga  11160
```

```
gtaccatcag ctccagcccc actccgcaca gacccaggac gccgaacacc accgccgccg   11220

agatcgacag acccagcagc accgacatcc tcacgcgggc atccggctat ttaatcgttc   11280

tggaaacgta ttaatatggg cgtcgtcatg tgcgggtgtc tgtttgtgtg ggcgggctgg   11340

atcgcgcgcc gcgtgcgcgg cttctgcgtg gcgctgcgcc agagggtgtc gcgcgacaag   11400

ggctacgtgg ccgtcatcca gacctgcgac gacgactact tcacagagga ggagttcgac   11460

gacggcaagc aggtggtcgc gctcctgcgc gacgtctcgc gcgtggtcgc cgcgcccgcg   11520

ggcgtgacgg aataagttag gataaggagt cgaggggaga aaaacagcgg tcacactata   11580

aactcgcgcg aggccgattt tgacgtgctc atgtccggaa gctccgcttt ctgcagcgcg   11640

gagcggcaca cgaagcacac ttccgtgttg gtgggagtta tgcagtggac gtggtagccg   11700

tgcccgcaca ccatgacttg gacggacacg cgccgggaca ggccgcgttt atgcatcctt   11760

ccggcgagcg cttgttgcag atgtagcaca cgtcccactg cttaacctta acgggcatgg   11820

ctagttgaac acgaccatgg gcgagtcgcg agcctcgagt cggggttcag ggcaaaccgt   11880

ttcacgccgt caacggttct tctctttgca attttctctc ggcacaggct cgtcagcgtc   11940

atctcggcca ggcgcgcgtc gttgcctagg tgccgcgcgg cgtcctcgac cgtcacgccc   12000

gtcttgccgg cctcgtccat gagcacaatg cagaccaggt gcgcgctaga gcatatgacc   12060

tcctgctcgc gtccgccggc agcggggatg gttagctccg cgcgcccgaa ggccgccagc   12120

ggcgccacgt cgtaggcagt gtctgctcgg gcgagcgccg actccacggc accgcggagc   12180

gactccggcg gcgtcatcgc ggccagcggc accggcgtgg gcacggtgta cacgttcacg   12240

ggcatgagca ccatctccgg gtcgtggtgg ccgctctctt cgccgtcgtg ctccatgggc   12300

tgcggcggcg gcagcagcgg gagcagcagc cgtccggaca tgagccggcg cacaaggtcg   12360

ttgagcgcgg acgaggccat cggcgggtac agctccatgg ccagcttcag cgataggtgc   12420

ttctcgaggt tgacgccggt gtagacgctc ttcacgattc gcgcgaaggc cacgcgcgcg   12480

aaggccgcca gctcctcgcg cggcaggcgc tcgatgtagg agagcagcat gtcggtgtcg   12540

cacggcggcg ccgcgaccac cgcgccgtag agcgccttgc ccgagagcct ttccagcgcc   12600

cttgcgtgca ggccgtgggt cttgagcacg tccacgtagt tcacgtacag gcagagcgcg   12660

cgatcgaggt tgctctccgc gacgtgcgtc tcgatgcact ccacgatgag cgggcccatg   12720

cggtccttga tgaggtctat gagcccgccg gaggcgactc gcgcgctcat gaggcacgtg   12780

cggcagtacg ccatcaggcc ctcgaggtcc gcggcgatca cgtcctcgac cacgttcgcc   12840

acgacgcgcg gccagagccg caccttgctc acgttctggt gccgcaccat gtccacgagc   12900

tcgtcgtacg agccgccggg ctcgtgcgcg cgatcgacga tgcacctcgc catggtgcgg   12960

ctctggcgca tgagctcgtt cgtgaagcgc acgcacgcgt cctcggagaa gagcgcgctc   13020

aggcaggagt agcagcggtc cgcgacgagg tgcgggaagc ggcactccac gacgccgcgg   13080

ccgatccgca gcacgcactc gccgtacatc tcgtccatgg cctcgcgcag acagtcgtcc   13140

agcacgtccg cgttgtgcgc ccactggatc acgcagaggt agggctcgat gttctcgcgc   13200

gcgttttcca cctcctgcac catgtactcg agcacggtca tgtcctcgtg gatgtcggtg   13260

cccagcatgc gcccgggcgg cagccagctc ttgcgcgcga tcgcctctcg caggcacgcc   13320

accgccgtga aggtgttgac gcggagcttg gtcagtagcc gccgcagtcg ggagatgtgt   13380

gccacggaga ggtccatctc catggcctgg gcgatgaggc gcgtgagttc ctcctccatg   13440

gcggcggctc cgcgggcaga tatacgcgaa caacggtaag ccgtgctatt tcattttgg    13500
```

-continued acaaaaagct agtcgtcgac gcgcatgttg tcgaggttcc ggcacagcga gagcacgtcg 13560
tcgcgcgcgc gcctccggcg cagttgattg ttcgcgcgcc gcgcgtccgc gagcgcctgt 13620
ctgtacatcg cggagtccgc gtacccgtgc agcggcgagc gccgagtgcc gggcctcggg 13680
ctcgcgcggc gcgggagcgg cgttggcgcg cgcctcgagc gccgcgcgaa gtgcgcctgc 13740
atggccagca ggcaaccgaa cggcatcatg tatcggtcca tgaggcactg gctggccgcg 13800
gacggctcgc gcgggtgcag caagccgccg cccacgtcct ccatgacgtc gcgcagcacg 13860
cagcgcagca tggtctccat gccgtccacg ggcttgaacc tcattgggga ggcgtcgacg 13920
tagaagccgt cggccacgaa gtagagcgcg tccagcccgc cgagtttctc gccgagaccg 13980
acgaagagct cgtccacgtg ccagtccacc accgaggcct tgaagagcac cacgtgccgg 14040
acgtcgtgcg agcgcgcgag ctcccaggtg tcctcgccga tgttgctggc gtcgatgcgg 14100
cctgtcatgc gcacgctcac gcacggcgtc atcccgttct tgtagcagaa ctggcgcgcg 14160
agctcctcct ggcgtacgat gtcgaccatg ctctccatga aggaggtgga gagcagcatc 14220
gcgccgcgcg cggcgcgggt cgcgttttcg tccacctcca cttccatccc gccgtcgatc 14280
ctaatcatct atcgtattta aattttcggc ggagcagaca cgcggctgct cgctgcgcga 14340
tcgcttcagc cgcggcggcg tcacgcacgc gttgcggcgg ccggcacgca cgaacgaccg 14400
ccggggctct tcgctgagcg agcgccgcgg ccgcgtgacg cgacagtcgc gggtgggttg 14460
ccgggagtcg ctcgcgcgcc ttctgcgcat ttcgccggaa cgccgtgttt acgtagggta 14520
ttatattttc aacgtaacta aatggacggg ggcgtgcaca aacggccttt catcgtgaac 14580
gtggatggca tgggcaaggt gctcgtgctc cggtacttgc ggatgtgcga ggtgcccagg 14640
ctaagtgcga gggctcgcgc gcgtcctgcg tgctcaagat ggaccctccc cgctcaccca 14700
gttgcgagtc ccccccatgc cccatgcgca cgccccccgg gtcgccgctc caggctccct 14760
taggagaagc aaggttcagc aaaaacaacg gcgagcagat gtgccgccgc cagtaaccta 14820
ggcgtgcgca gtacgaaagt tagtgcgtga tcacgttttt tgcaatgtcg atcacgccgt 14880
gcgtgcccgt cttgcgctcg cgctccacca cgccagtcac gggccgcgcg tccgagacta 14940
gcgaccccag catcgagcgc acggcgccct ccgcggcggg gtggcgcgtc agcagcagga 15000
acatcacgat gtgcgcggag acgccgcggc ggctcagatc gtgcacggcg tcgccgtcca 15060
tgagcacggt gtttgagaag tacgtgaaca gagtgttgtc tcgcaccagg aaggctgagt 15120
tcgagacgct ctcgaagtcc acgatctcgt cgtcctgcac gcccatgtcc aacagcgtct 15180
gcacgagcgc gggctcgtcc aggaacacca cggcgcgcgc gaacccgcag tccagcgcgc 15240
gcgcgtccgc ctccaacacg cgcgaggcgc cgccctccgg cggcaggaag gcgcaaggca 15300
gcggcgtgcg tccgtccgcc ggcgcctccc cgagctcctc gagcgcgaag gccagcagcg 15360
tctccatgcg cgcgcgcgcc ttgtcgaagt tgtccgcgag gtcgcggatg cggtctgtct 15420
gcgagaacat cttcagcatc gccatgagct gcacgaaggg gtgcagcacg tatatgttgt 15480
ccacgagcag cgtgggcagc gcgcgcagcg tggcctgccg cacgttgaag ctgtccagga 15540
tgtgcccgcc ctcctcgtcc tgcagcacca cgtagttctt caggtagggc acgcgcagca 15600
gcacggtctg ccgccccgtg acgaagtaga tcaggaaggc gaggttgatc aggaacgggc 15660
gcgcgttcgt ctgcaccatg tcgatgtcgc cgtactctat ctcggggttc agcaggtgca 15720
gggcgtacga gccgtagcac acgcaccgct tgttgtgtcg gcgcaggtgc tccttcacga 15780
gccgcttgac cacctccacc aggtccgagt gcttgtgccg cgccatcggc gcggcctcct 15840
cggacggcgg cagcaccgcg tacgagttga gcgcgcggct ggcgagcgcg cgcgcgcggg 15900

```
gcgcgtccac gcgccgcacc gccgcgttga ttgcaggcgt cggcgtcgtg agagagccca  15960
gcgtgcgcgt gaactcgctc acgatcacgc tctgcagctc cagcaccgtc aggatctggc  16020
ccagcttctc caggcgccgc tgcctcgaga agtactcctc gatgcgcgcg gcgatttcct  16080
tctcggagcc gcctagcttc ttgaagaagc gacgacgact ctttacaaca agagagagaa  16140
aaagcttcct atcgaagttg aggacgcggg tcatgttgcg gcgctgcgcg cgcaagagca  16200
cgcagcgctc catggagggg cgcgagccga ggtactcttc gatcacgggt ggagccatga  16260
cagctctatt ttctgaaccc gcgattattg tacagcgcaa gccgcgcgca gacctgctgg  16320
cacagcagcg tcgtgtttcg catgcacacg cgcgaggact cgatcgtgcg cgcgtccggt  16380
gcccaggcgc gcagctccat cagttcctgc tcgacgaagt ccacgggctc cacgaagcgc  16440
tctgcgcaga gtccgtccgt gaacgcgttg acgatctgcc gcacgagcac taccacgtcc  16500
acctgctcca cgaggcgcac gcccatggcg atgtgcacga agaggcagcg gaagagcgcg  16560
tccatggcca tctggtggtc cgagcagggc ccgaccgcgg tctcgcagcc cagcgcgaag  16620
cgcccgatgc cgcggtactg caccatctcc gagggcgaga aggagagccg ctccatcttg  16680
agcacgggcg gcgggcccgc cggcagtccg cgcgcgaggt ccagcaccgg cgtccacccg  16740
ggcgtgaaca tgtccgggat caggaagagc ccgtagctgg ccatgcgcgc gatgtcgaag  16800
gcgtggtcca cgaccttgtt cacggcgctg tccgcgcggt ttacgcgcag cgcctgcagg  16860
atcacgtttc cggaggcgtg tcgcgtgatc gcgaggtccg cggtcgcgta cccgcgcagg  16920
cccggcaccg cgtacgcggt cagacacacg gccaggcgcg cgctgtgctc cgaggagaag  16980
atctcctgct cgtagccctc ctcgggctcc tcgcactcgc gagggcgccg cacgtcctcg  17040
accgagcgca gccgcatctc tccctccgac accagacagc caagcgactc cctcaccgcc  17100
ggcgcgagca cctccgtggc gcagagcgcg tcgtgcacgc gcttgagcgc gttcggcttc  17160
agcgcgtagc cgaagagcag ccgcgtcatc cgcgagcccg agaacgcgaa gcggcgcacg  17220
tactcctccg cgagctcggg ccggtcgttg atccacgagg tagagaagac gtggtcggag  17280
gcgaagaggt ccgcgccaac cgcgagcagt gtggatagag acacggtgtc gaggaagtcc  17340
acgacgtcgg ggaagttctg gcgcacgcag gcctcggcga cgcgtctggt gtgcacgcac  17400
atgtcggtga cgggcacccg gtggccggac tccacgacgg acacgcagac gtcctcggtg  17460
acggcgtcca cgggcatggt acgcagcagc ttgccgagca cgtcgccgaa cccgccatcg  17520
agcgccttgc gccacacgaa cccccgtcga acttgccggg gaagtccgcg atcaccgaaa  17580
gctccgcgtg cgagaggttg tccacgttga ggtaggcgta gtggaggtac tcccgcacct  17640
ggccggcgcg gatgcgctcg agcgcgaagg ccttcatggt ttcggagcag agcacggagt  17700
gccgcagccc gtccagtgtg cgccgcacgt cgtagacgcc gcgcatctgc gcgagcatct  17760
cgacggcgtc cgccggcgtc gccgccgcga gccctgagtt cactggaggt atcctgtgtt  17820
ctgcgagcat gcgcttgagg aaacagaggt ccagcggccg cgtggtgtac agcgcggagg  17880
ccatctcggg gcgcgcctcg acgatgtcct cgatcatctc gtccgtgaag gccgcgttga  17940
tgttgtgcac gctgcgcgcg ttcacgtgca ggaggatgtc gcccacgttg tcggggaatc  18000
gctcctcgat gagccggacg tcgtcctccg tgatgttcat gtagggaatg cagcggcaga  18060
gcagcgcgta gtccgcgaac tgcgcgatgt agggcgtgtg gaactcgatg tgtctggcga  18120
agagcgcgcc gcagcgccgc cgcgagagct cttcgagcag gtcctcgggc gtgacgtgct  18180
gcgggcggaa gaggtgcagg tgcgtggggt gatcggcggc cacgcgcgcg tacagccgcc  18240
```

gcgggaggtg cctggggtgc acgccggcga gcacgagctc catggcctct gaggtagaca 18300
gtgcggcgaa cgcgcgctcg gtgccgcccg cggcgacggc ggcgccgaca aatctcttga 18360
gcagctgcag catcgcgtgt ttgggctttc gcggaaggcg cttattttaa tgttattggc 18420
ggtggccggt gcgagataaa aattagaact gatgccgcag ttgttgatga tgatattaat 18480
tgcgctggcc ggcgagagat aaaaattaga aggtgatgcc gcagttgttg atgaggatgg 18540
tgagtgcgct ggagcaggcg gtgtggcgcg ccagcttctt gctggccccg tcggccacgg 18600
aaacgacctt tccggatatc gtgatggtgc aggtgaagcg cggacagtga tcctctccgc 18660
cagaacgcgt ctcgcagaac tccagagatc tgcgcgtcat catgcagaac tcgttgaccg 18720
cgctgaccgg gttaagactt ttgaggcgca tcacggcaga ctgagtcatg atgtcgatgt 18780
cgccgccgaa gagcgtatcg cacccagcct cggtctccat gggctcggtg tcggagtttt 18840
cgtcctcctc ggtgggcgcg gagggcgcgc actctacgaa ccagcggggc gggtttccgt 18900
cctcgcagca aacctcgtcc gagtccagca ggcggtacag ctggcggttc gcctcgtgtt 18960
tggatatgcc gagttccttc gcgatctgct tggccggcag cttgtcgtcg gatttctgga 19020
gaagctcgag gatcagagat gcgcactcgc aggccattgt ggcgtattta cggggcgtgc 19080
gtttttttag gattttggct tgcctttctt ttcgcagaac ttgggaggat tgaaactctt 19140
ttggcaattt ttgcaggcgt acttgatcaa gggcggctcg tccgccgagc gcgtctggat 19200
catcatcggc atggtgttct tgctctggca cgaggggcag ggcaggttga acttctcgtc 19260
aagcacgttg aagtacccgc tgtagtcgtg gtccggcacc tcctcgatgt cgtagggcac 19320
ccgcgcggcc gcgcacttga ccgcgaagag caggtaccgc agcgcgtcgt gctctgcgcc 19380
gctggtcgcg cggatctgcg cgcgcaggtc cgcgtagtcc tcgttcgcgt ccacctccag 19440
gctgcgcttg ttcttgtacg agagccggtt cttggcgtcc ttcgagtact cgatgccgat 19500
gttgtgcgcg gggtcaaagt tggtctcgtc ggtgttcgag gtcttggtgt tcacgatgtt 19560
cttcagcgcg aagcgctgcg cgcagtccag cgcccatcgc gcgatgcgcg cggcctctgc 19620
cgcgtcggtg tgcttcgccg cgaggtcgcg cagccggtct tcgtccatcg cccgatttta 19680
ggttgggtat attatctcaa ttccgctctt ccgcgggccg cgggcgcgcg cccgcggcaa 19740
attaggcgtt acaaatggac ttcgtgcggc ggaagtacat gatacacgcc atcgaccgca 19800
acctcgactt catgaaggcc gaggtccagc agaaggtctc catcttctcc ccgggcacgt 19860
gctcgcgctc cactacctgg tcaccgcctt tccgcaggcg gtcatcacca aggacgtgct 19920
cgcgagcaca aacttcttcg tgttcgtgca catgtcgcag cggcacgagg tcttcgacgc 19980
cgtgctcaag gcggccttcg acgcgccgca gctctttgtg cgggcgctct cgcggcactt 20040
cgaggccttc gttgccgcca tccgggccta ccgcgcgacc tgcgcggaac tgctggccga 20100
cgcgcgcttc atggaggtgg ccgcgcgcgc ggccgagctc gcggaggtca ttggcgtgaa 20160
ccacgacatc gccgcgaacc cgctcttcgc ggacggcgag cccgtgcgcg acgcggagct 20220
catcttcgca aagaccttcc gcaagaccga gttccgcgcc gtcaagcgcc tcgccgtgct 20280
gcggctgctg gtctgggcct tcctcgtgaa gaaggacctt ggcggcgagt acgcggacaa 20340
cgaccgccag gacctgttta cgctgctgca gaaggccgcg gggcccgtgc gccacagcgc 20400
gctcacggag agcatccgcg agtacctctt ccccggagac aggcccagcc actgggtctg 20460
gctgaacgcg cgcgtggccg acgacgcgga ggtgtaccgc gaccggcccg cgcgcacgct 20520
ctacgagcgc gtgctcagct acgcgtactc agaggtcaag caggggcgcg tgaacgccaa 20580
cacgctcaag ctcgtgtacc ggctcgagga cgaccccgac atcaagggtc tgctgctgca 20640
gctcatctac gacgtgcccg cggacatcgt cggcgtcgtg gactccgcga acgaggagtg 20700
gcggagctac ttcgtgagtc tgtaccgcga gaacttcgtc gacggacgca ccttcacctc 20760
ggacgcgcgc ttccgcgacg acctcttccg cgtggtcgcc gccgtcgagc ccgacttctt 20820
cgagcccgag cgcatccgcg aggccttcag tgcagacgcg cggctgcgag agcgcttcac 20880
ggacatggac ctcaacaacg ccttcatgtc gcacctcatc tacgactccg tggaccccga 20940
cgtcgccgcc gccgagcgcg ggctcgcgct gcgcgtgcac aacgaggact ccgactactt 21000
atccgggagt acaacaccta cctcttcctc agcgagaagg acccgctggt gctggaccgc 21060
ggggcgctca cgcggctctc tgacgtccct accgagcgct tccgcgacct cttcagcgac 21120
agcgtgctgc gctacttcct ggacgcgaag ctgggcacgc tcgggctggt gctcgaggac 21180
taccgcgagg acgtggtcgc cgccatgctt cggcacctgc gccgcgtcga ggacgtgtct 21240
tccttcgtga cgtacgccgc gcgcaagaac cccgcctgcg ttcccggcgt cgtgcgcgcg 21300
gtcgtgagca acttcaaccc cgcggtggtc gcggccatgc gccccttcct gcgcgagcac 21360
atgacgcgcg tggacgcgct gctggacgga atgccgcacc tctcggaggc cgaccgtcgg 21420
tacatccgcc gcgtggtgct gcagggccgc gcctgattcg ccgtcaataa atcgcgatgg 21480
tggacagcgg cacgcacgac gtggactcag ccgcgcagga gcgcacgccc aaccagcaga 21540
ccttcttcac caaggggctc agtccgctga tgcgccacac ctacatctac aacaactacg 21600
cctacggctg gattcccgag accgcgctct ggagcagccg tctgggcgac taccgcgtca 21660
cggacttcta cccgatatcg ctgggcatgc tcaagaagtt cgagttcatg ttctcgctgc 21720
tggcggaccc cggcggcgcc tgccccgcgt acgagcccaa gctcaacacc gagttcctga 21780
accgcggctc cttctcgggc cggtacgtga accccttcca ccgcttcgcg gcgctgcccg 21840
agcgcgagta catctccttc ctgctgctga gctcggtgcc catcttcaac atcctcttct 21900
ggtttaaggg cgagaccttc gacactgcca agcacagcct gctcggcgcc gtgtacacca 21960
cgcccgagag gcacatcgag ctcgcgcggt acctgcggcg cacgggcgac tacaagccgc 22020
tgttcagccg cctgggcaac gacgacacct actcgaagcc cttctcgggg ttcacgcgca 22080
tcagcaaccc cacgcccatg ggcggctgcc gccctcggac ttcgagacgc tggccaacct 22140
gagcaccatt ctctactaca cgcgctacga cccggtgctc tgtttcctgg tcttctacgt 22200
gccggggctc tccgcgacca cgaagatcac gcccggcgtg gagttcctca tggagaagct 22260
ctcgctcgcg cccgagaacg tggtgctgct gtagcctcaa acataaaata taggcgcctc 22320
tgatcgcact gcttcagttc agacagagct aagatggcct cctacgtcag cggcgctagc 22380
gccagcgcga acaccgccca gggcggcgat tctcagtacc cacattacta ttcccacaca 22440
cgcacctcca aggcgacatc cgcgacgaaa gcgaaggttg cttccacacc acggacgacg 22500
agcacttgga tctgtccgac gactacctcg gcgatggcgc accacactgc ggacacagcc 22560
acaaccacag tcgcagagat ggagatcggc accgccagcg cgcaccgcgg ctctacgagg 22620
acccggtgcc cgcgaacatc atggtgccca cgctcagtct agagcagctg ctggaggaaa 22680
cctcggtcgc ggggggcctt ctcggcggca ggacggagag ggacgtggaa cagctcctgg 22740
aggagttctc cgcgctctgt cccggggacc agatcaccgc gctgcgctgc atggcggcct 22800
ccttctaccg cgacgcgctg ttcgcgccgt acgcctgcat gcacctcatc gccagtcgga 22860
tgcgcgtgca ctacgcgcgc gaggtcgtgc acgtggccga ggacctcgcg gacgcgatgt 22920
cggcgaacag cggcgtctgc ttccggcggt accgaaagcg cgtgctagag gacatgctcg 22980

-continued

```
cggaggagat gagcgtgtac aattacctcg cgcgcgccaa cgcggacatc tgcgaggaca  23040
acctgctctc ggccgtggag acgctgctgc ggcgcttccg tcggatgggc tgctaccgct  23100
ctctgtgcat gctcaagatc ctcgcgctgc agcacgagga cctggccggc ttcatccgcc  23160
gcagcataag aaaaacctgc aacttcgcac acgcgcgcac gcacacggtc tacgtgtagt  23220
taccctgtaa agacgggctt gctcccgaac aagcgctcga agaagagcgt gcacatagcc  23280
ttattgtcca gcaagttgac tatctctgta cacagcctct tgaagtacac ctcgtacatg  23340
atccgctcgt ttttatccag tctgaaggtc ttgtcgacca cgcgctcgta ggacttcacg  23400
ttcgcgatcc ggcgccgcca ggggccctcc tcgcacacgt acgcgaagaa gtagcgctcg  23460
ccgatctcga tggcctccgc gttcgccgcg ttgtaccgcg tcaccagcgc cacgttgggg  23520
ttgtcggggg acttgaagtt cttgtggtgc gttcggctca gcaggaacca gtccagcggc  23580
atgctgcgcg cctcgaactc gaaggtgagc tcgtcctcca gcgagcgcag gatctccacg  23640
cccacgttcc cggagccctc ctccgccagc gcgcggcaga gcatgtcctt gtacttgcgg  23700
atcatgagct tgtggaaggg cgccacgtcg cggcgcgtct cgctggtgcc cttgctcacg  23760
cgctcgctgc cgccgccgtc gctcaccgca aacttgatcg tggtgtactt cttcttggac  23820
tgcatgatca ggttgcagta caccgcttcg aactccacct tgaagttcgc gaagagcacg  23880
tgctcgttga tcacgcgctc cagacagcgc cccacgcgcc gcgagaacgc gatgtcggag  23940
gcgcccacct ccaggaacac ggagtcggtg tcgccgtaca cgctgcggaa gcccacgcgc  24000
tccgtgcgct cgccggccac cgccgcgtcg atctccagct ccgcggcgcg gcccgcgaag  24060
gcctcgtcgc gcagcagcgg gttgtccggc gccgccgcca gcgacagccg cgtgccgcac  24120
accgacgcgc cgtctagcgt gcgctccagg tacgcgatca tggtgcgccc gatggccgtg  24180
cagctcttgg ccgaggcgta cgagaagagc gcgctgttgc ggaagcccat gagcccgtac  24240
acggagttgg ccgtgatctt gtacgtgtac tgcatcgagt tgtagatctc gcggtccacc  24300
gcggtctccg cggccttcat cagcttcttg tacttggcgc gcgcgtccag gaaggagcgc  24360
agcagcatcg ggatgatgcc cttggcctcg cggtcgaaga tggccacctc ggcgacgagc  24420
tccggcgagc gcggctcgca gggcaccgcg atgtaccgcg gcgccgggaa catccgccgg  24480
acgtccacgg ccgcgactcc gcgtcgagcc ggttgtccga gacgaccacg ccgaccagcg  24540
tctccggcga caggttcgcg tagatgcaca cgttcgggta caggctgttg tagtcgaaga  24600
tgagcacgtg cttgttgtgc atcttctgct tgggcgccat cacgcggccg ccctcgtaga  24660
agaacttgga cttcgtgtcc gcgcgcacca tcaccgtgcg gttctccagc agcagcttca  24720
tcagcgggcc cttgatgcag gtgctcgcgc ggtactcgaa gaccacgctc tgcggcagca  24780
ggtacgtgga cgcggcggcc gcgatcttgg tctccacgcc gtagtgcgac cagaggtaga  24840
ggcagaggca ggcgtcgtgc aggcagtacc gcgccatgtc cagacacacg tccagcgagt  24900
agttcgcgta catgtccgcg aggctgacgt cgtccttgcc gaaggccagc gtgacgcggt  24960
cgccgggcgc gcgcgccgcg gggtccgcga ggtccacggt gaagccgtcc tcgccgacgc  25020
gtttgtgcag cacgcggcac acgcgctcgt cgacggtcac gtagttgccg gtgctgagca  25080
cgcgcgcgaa cacggccgcg ttcccgtcgg cgtcggtgct gcggtcgccg cgaaagcgga  25140
ccgcgtccgg ccgcgcgtcc tccacgaccg cggtgcagtg gaaggcgttc ttggatatgg  25200
cgtccagctt gtaggagtcc agcttctcgg tgcgctggat gaaggcgtac aggtcgaagt  25260
agatggtccc gttgttgttg ttgatgtgga aggtggtgct cgagacgccg ccgacgccct  25320
tgtggctgga cttcgtgcgc tcgtacacgc agaagttgac tgtctcggtc ccgtccggca  25380
```

gccggaagcg gatgtgctcg cccgtgagca gcgacagccg cgagtccagg taccgcaggt 25440
cgaagttgtg cccgttgaag gtgaccacga agtccagcgg catctcgagc aggcgcttgg 25500
ccacgcgcag cagcgtcacc tcgggacaca gcgtgacctc cgcgtcgaac ttcacgtccg 25560
ccgggtccag gcagaccggg atctcgcgcc gtgccgcctc ctcgaggtcc gcgtcggaga 25620
gcatgtcaga gttcgtcagc gtgaatcgct tctccgcgcc gtccttgtcc accacgcaga 25680
agctgatgtg cgagacggcg ttcttgaaga cggaaggaaa ctttttctcg aagtggcact 25740
ctatgtcgag gaagagcccc gagcgcgtca cgttgaagcg cgggatcttc tccgcgaagc 25800
acgcgccggg gtcgtcgcag tggaagcagt tgctccccag gtcgcgcagc agcgcggggt 25860
ccacgcggta gcacccgtcc gggtcgatgt cgtgcgccac gaagaaccag gacacgttca 25920
gaaagtcgga catgaagacc tctggcggcg cgagcttgcg ctcgctggcc accagacaca 25980
gctctatctc cgagcgctgg cgctccggaa tcttcgccga gcgcgccacg atctcgtcga 26040
tgctgaccac ggacatgggc ccgagcgcgc gcgtccacgc cagcggctgg gcgatgtcgg 26100
ccaccgcgtc cgcgcgcacc acgtagtaaa agtgctgcac gaagcgcagg tacacgacgg 26160
cgttgtcggc gcggcgcgcc ttgaggaaga ggaaccggct gtcattgctg cggttctcga 26220
accagttcaa acatttcagc tccatttcaa agagcataat aacatttcat ttaaatggag 26280
cctcgcttct ggggccgcgc catgtgggcg gtgatcttct cgtgctgcgg cgcttcgagg 26340
agcaccgcga cctcgagcgc tgcaagcggc agctgtacgt gatctgctcc gctgccctgc 26400
atcgcgtgcc ggcgacacgc caccgccgcc atcgagaaaa acaacgtcct ctccagcgag 26460
gaccccaact acgtgctctt cttcttcatc aagctcttca acaacctcgc cttcgacgac 26520
agatacaaga tcgaccccgc gaaggtgcgc ccgctcgtct agagcatgcc ctcgtacgcg 26580
cgcgagttgt ccgagtacac ggtcaccgcg atgccctcgc gcggcgtcac gtgcacgtgc 26640
atggagtccg tgatcacgaa gcccacgccc gtgaccggct cctcgcccgc gtcgtccgtg 26700
aagagcagcc cgtggttgaa gaggtagaac tcgttctctg cgagcgaaag ccgcccgcgg 26760
tcgcagaggt agtagaagat gtcgtcgtcg cgcacggcca gcgtgaacgt ggactcgctc 26820
accacgatgt acttgtccag ctcctccagc acggacgcgg ccgcgcggcg cgcggtggcg 26880
cggcactgcg tcgggcactc gcacgtgtct gcagagtaca ggatgcgcgt tcgccccgag 26940
gcggtctcga gaaaaacgtt aatcgcctcc atcgcccaga agcgactcga ggatcgcgag 27000
caccgtgcgc agcacgagcc cgatggtgca gaagggaacc tctcccgact ccgagcactc 27060
gcggatctcc gtctccacgc ggtcgtgcac ttttatggag ggagccgtcg ttccagtggc 27120
ctccatcgcg acggacacca ccttggccac gaactcgcgg atcttgctca tgcgccggag 27180
cacggtcacg cggaagaaga cggccgcgag caggtactcg gccacgcagc tcgcggcgat 27240
gagcgcctgc gcgtgcctgg tgttgagcac gtgcgcgtcg ggcacgaagt ccgagatctt 27300
caggtgcgag agccgcacga gcgcgttggt gtccttgacg ccgtcgcagg agatgttcgc 27360
gaagatgagc ttctcgtagt cgagcgcctc gaccacgcgc tgcgcgtcca tgtgccgctc 27420
gcccgagagc gcgcggctca aagggcccca gcacaccgag cccgcgaagc aggggtccac 27480
cacgccgtgc atcgccagca gcgtcacgtc ggccaccgcc gcgaggatgg ccgcgtcgtc 27540
gagctcgttc gcgggcgtcg cgcccgtcag ggacgcgctg cgcagcgcgg acccgcccgg 27600
cgccgcgtgc cgcgcgcaga actcgcaccc gcagcccggc ggcagcggcg gcttcgagag 27660
cagactcatg agcccgccca cgtgcccgtg ctcggtgatc agaagcgcca ggatgctgtc 27720

-continued

```
ggtgctgccc tctatggcgg ctgtggccgc gctcgagggc tctcccgtga cctgccatcc  27780
gcagacaacc ttgagcatct tgcgcttgag ctcgttgggc gcctccgagg ccagcatcgt  27840
gcgcgggaac gtcgcgttga ggcggaagtc ctgcagcagc ttttcgagcg tcgcggtctt  27900
ggcgtgccgc cctttgcgcc actcctcccc caggtgccac atgagctcct cggccgtgtc  27960
cagcgtcggc gagacgcggg ccttgggcac gcgcgccgcg ctgcgcatca gcggctccga  28020
ggcgcggaag ctgccgcgcg cgtgcaggcg catggacgca gacgaggacc gcatcgaggg  28080
tcgctggcag aagctcgtca tcgtgaagcg ccgcgtgagc ggacctacct cgtcgcgcga  28140
ctcgtcgaag tccgggtcag ggtccgtcgt gtcggtctcg gcgctgtgcg tgctgggcgc  28200
gctgctgcgg gcgctgcgcg tgctctgcgt gctgaagctg cgcgtgctgc gcgtgctctg  28260
cgtgctgaag ctgcgcgagc aggagtccgc cgtgtccgct tcctcgtagt ggaagtccac  28320
gtgctcctcc ggcagccggc gcgagcgcga cttggagatg ccgaccatcc cgtccgcgcc  28380
gaccgggcgc acgcagagcg ccatcgcgcc ctcgcgcacc gcctgcgcga actcgcggct  28440
ggcaaccatg cgggggtcga ggaacttgat gatgttgaag tatggccact cgcagacgag  28500
ccgcgcgcag gtcgcgacgt cgtcgacgct tctgagggcc ctgttcagcg gggggatgtt  28560
gctgccgtcg gccagtgcga cgaggtcctc gggggagatc tcgagcttgg gaatcatctc  28620
gttcacgagc gcggggtcga tggcgtggca gacggtctct acctcagtgc gcgagagctt  28680
gagctgcgcg caggccgtcc acggcgcgca cgtgagcgcg aacaccgcgg agactcggcc  28740
cttgccgacc atcgccacaa cctcgggctc gtagaccagg ccggccttga gcagagcctc  28800
gagcacctct atgtcgtcgg cggcgagcag cgcgcgcctg tggaagcaca ccgcgggcat  28860
catcttcttg cagatgccgc gggtgctctt gagggccgtg ataaggtcgg ggagcctgac  28920
gtgctgcggc tggaagaaca tgacgttggc ggggctcgcg gccaccgcct cgtcgtacac  28980
cgacatcggc aggtcgccgt ggagcccgca cggcagcagg ctcagcagct gcgcgcgcga  29040
gagcttctcg gcgcagaagt tcttcttggc cagggcggcc gccgcgtcgc gggccttctt  29100
ggggtataac aacatggcgg gctttaaaca cgaaacaaaa atccaggttg taacatttca  29160
attttgcatg ttctgggcct cctcgcagag tttctccagg ccgccggcca cgatggcgtc  29220
gacgaagagg tcggcctcgg tgaagcggtg gttgccgcgc accgccacca gcgcgttctc  29280
ggtgaccacc accgacagct gctgcgcagc cgtgcgcagg tcgaagtgtc ggcacgcgag  29340
cccgtggccc agagtctggt ccagcgccgc gagcacctcc tccaggctct cctcgcggtg  29400
gttgtagaac cacatcagta cgaagtaagc cacgtaggtg tagaggtagt gcgcgaccgc  29460
gcgggcgcgc accagcggct ggttgcagcg cgcgaaggcc attccgctgg cgatgaggtc  29520
gtcgtccagc gtggcgtagt cgccccagtt gagcgcgctg aactgcacgc tgtagaccgc  29580
gcgcacgaac ccggactcga ggatgtcgat ctgcgacggc gcgccccagg tcaccagccg  29640
gtacacgatg ccgcgctgca tcagccgcat gaggtcgccg ccgacctcgc gcaggcggtg  29700
cgtcagcgag gcgaaggcca gcttccgctg cgtgtactgc aggcccacgg ccacgcaccc  29760
gtccgactcc accagcacga gcttgtggtc cgtgcagccg tcgctgcgca ggccgccctc  29820
gcgcgccatc atgtcggtga cgaacatgta cttgcgcgcg cgcggcccga ccaggatgcg  29880
cgtcttgcct tccatgcgca gcaccacgtc ctctagcagc cgcgtgctgt ccacgcgctc  29940
cacctgcggg tggatggtgg gctggtagtt gtacagcagc cgcggggacc agttgtaggc  30000
gaacgcgaag aggtgcgtgt ccaggagcga gatggggaag acgccgcctt cggtggcgcg  30060
ccggaggatg gcgagcttgg tctccgcggg cagcaggctc ccggtcaccg cgccgaagaa  30120
```

catggggtgg ttgcggaact tgagcgcgta cgcgctcagc acctcctctc gcgagaatat 30180
tgagtccgcg gggttggagc tcgcgggcag gagcacgtcc tccacgctca gcacctcgtc 30240
gatgaagggc agcaccatgt ccacgttgga ggcggtgaac cactccatgt ccacggcgtt 30300
gcgctccacg atcacccgga tcgtctcctc ggatatgttc tcggcgaagg cgctctgcag 30360
ctcgatcagg ttctcggtgg cgtcgatgct gagcccgagg cgcatgccct gttgcagcac 30420
gtcgttgatg gggttcacgt acatggccac cgccatgcac ccggccggct gcacgcgcca 30480
gaggttggag tacgcggaca cgtccgtgat gcgcagcgtc tccagcacgt tgtacatcgc 30540
cgcgcgcatt tccagcgtgt ccacgtacac ctccgcgtgc tcgaagatga tgtcgagctc 30600
gaacgcggac agcggcagac tcacgtagat ctggcaggcg tcgaagagtt cctgcgcgta 30660
ctcggagaag cacgcgtacg cgatcacgcc cgcgcggttg acgatgtagt cggccttgaa 30720
catcttcgtg aggtaggcgt acagcgaccg gcaggccacg tgcggcctta gctcgtcgag 30780
cacggcgtcc agcacctcgc ggtgctgcag cacggagggg tgcaggaact gcgtgaagtc 30840
caccgcggtc tcctccatga agtcggggat ggtctcgacg accaagcggt ggttccgcac 30900
cgcgcggaag ccggtgttca tcggcgcgat gctgtgctgg tcgtgaacct ccagcaggat 30960
ctcgtagccg atctctcggc agctcagcgc cgcgcgcgcc tccgtcacgc tcgcgttccg 31020
gaagaactgc cgcaggtgct cgtccgtgcg gcagagcgtg acggattggg ggatgcggga 31080
aaggtcgcaa agagggctgt ggacggagat gcgccgcagc gcgtggtcta cgaactcaaa 31140
accgcgcctc gacatcgtga agtcgcggag ggcgtacatg ttgtaggaac agaggcggaa 31200
gaggcagtct atgtctagca tgttggaaac gcagtacgcg tgtctgtgga ggtgcgggag 31260
catggcgggc acgacctcgg tcgtgttctg gagcatggtg catacgaggt cgggcgcggt 31320
gaggtcagga gtgacgatga ggatgcagga gctggagaac ttgctgagct cggaggccag 31380
ccggtgaagg ttgtagtcgt ggcgctggct gaagttgctg tttatcgtgc ccgtgaagcc 31440
catgagcgcc gccagcgtca ggtcctcgcg ctcgatggcc cagatgtcca ggccggaggc 31500
tatcatgcag cgcaccagcg cggcggcgcg gtcgctcgtg gggtagctca tggtgctgtc 31560
ggtcgtgcga atcagcatgg gataatgctt catttttacg gtcgggggt gcggactgtg 31620 gggcgcacag ggcccgcggg cggctcgtgc cggtccgcgg cgttcgccga acgcaggaac 31680
gggcccatgc gcgcccaggc catccacagc cccgccgtca gcgccagcag ccagacgaat 31740
accacgatca tcttttatgt agcgggaact cgcgctcact ccccgccgca cggcgacggg 31800
gagagcccag agccgagctc catgcgcgtg ctctgcacgg tgagcgactc cacgagcttg 31860
gacacgttca tgcgcgtgtt gtcgggcacc aggtgcgcga ggcgcgcgta cacgtcctcg 31920
tgcatgcgct tgctgcagcg gtccaggctc gcggagagcg cggagactag cgcggtgtgc 31980
ttcgcgtaca cgaagtcgcc gagacacacg gtctcgagcc cgagcacgtc ggcgctctcc 32040
gcgtccttga gcgccacgaa tatcttctgc tcctcgcgcg tcatcgagcg catgaggtag 32100
tcgtgcagcc gcgagcgcga gatgagcccc tgagagatct gcgggctgcg catgaagcgc 32160
cggcgcatcg cgcacagcag ctcctcgtcg acgacgtaca tgctgtcctt gatggagctc 32220
ttctcgtcga gcacgagcag accgtcgttg gcgaccacgt tgatgaaatc gtccacgtgc 32280
cgcgcgtcta tgtcgtagcg cgtgccgccg cactcgatgt gcgagggcgg cgacttgagc 32340
cggttcgcga gcgccttcac gtcggagacg tcgatgtaca gcgaggactc gcgcgggacg 32400
cagccgagga tgcgcgtctc gagcggcgtg aggatgagca cgcgctcggc gccgtcgacg 32460

-continued

```
agcttgccgt cgtcggggga aaagaagttg ttctccacga tgctcgagac gaggctggcg  32520
agcacgccgt cgcggtaggc gccgagcgcg aactcctgca caaagggcgc gtgcagcaag  32580
tccacgggaa tgcgcatctc cacgcggcgc gcgaccgact tcttcttctg caggtgccgc  32640
cggtccacca tctcgtccac gatgtccgat atgcgggagc agaggtacgc cttgaggacg  32700
ttggcgttta ccttgttgaa gatgagccgt tcgtcctcca tttaagctgc tcaaacgagc  32760
tttaaatagt ggaaacacag cagcacgccg atcgccgccg ctatcaggcc gattagaaaa  32820
acggtggtcc aggggacgcc cttgggccta tcgcacgccg gcttttcggt cattacggtg  32880
cgcacgatgt ttaggaactc ctcgaagtcc tcgtccgagt tggagaggaa ggagccgaag  32940
acgccggtgt acagtttgtc catttactac tagatattaa acggcgcttc caactcctcg  33000
tcctcgaagc ccgcgccagg ctcgacgacg cccaggccgc gcacgtcctg ctcctcggtg  33060
aacgtggtct gagtctcgct catgcgcaca cacgtctgct cgccctcgag accgagcacg  33120
gtcagcgagc actcgcgcgg catggtgatc ttcttaaccg cgaaggtgac tttgccctcg  33180
ccgcccgagc ggtagaacac caccggcgct aggatgagcg tcgccatctg cgcgtcgcgg  33240
gttgcgaggt tttctatctc tcgcgtcagc ggacatatct gcggctgggt gtcgtcgtcg  33300
ccggtgaact ccaggagagc gccggtcagg cggttgagat acagacatcc ggacttaaag  33360
gtgttgtcga tggccgtgtc ggtgttgaag ttgcgcagcg acggcggaac gcgaacgccg  33420
gttttgatgt tgtcgtatat gttctccagc agctggtaga gcagcggact ggcgctcacg  33480
ggcttgaggc gaccgaagta cccgctgtcg ttctgccgct gcatgtcggt cttcttgctc  33540
gggtagatct taaactcgcc cttcacgacg atgagcggcg agacgagctt ggatgctaga  33600
ctttcgacga gacacacgtt gatgttggag cagctcgggt actgcgacgg agttagagtc  33660
accgcctcga tgaccttggt ctggctcgac gagagcgact tggcgaagtt gatcgcgtcg  33720
gtgcacgaca tcgcctggtt ctcgccgaac cgcctggcgg acgctgcatc ctcctgctga  33780
ggagcgcggt tagacgcgac ggtggttttg gatacagcgc gtttcattat gcagcgattt  33840
taaagtacgt gtatactttc agttttgtcg ccgagcgttc agcgcctgca tgcagaggaa  33900
gtacaggatg atggtgcacg ggatcgtggt cagcagcgat acgaagtcca tcactgtgag  33960
gacgcgcagc gccccgcgcg agcggatgcc cagcgagggc gcgccgcggc gcgcgatggt  34020
ggccccgttc gtcaccacta ccagcagcat taggatggtc gcgcccacgg cgacgcccag  34080
gtcccgcgac tccatttata gtacagtata gagcgaccgc gtcacgaact ctcggctggc  34140
caacacgcgt ccgtcgggcg ggtgtccgcc ggccttcccg cggaactccg ggacctcgaa  34200
gctggacttc gtcacgcggt acgtgtactt gccgcgccag accaggtttt ccttctggaa  34260
gacgccgtcc atggtcacgc ccgccatgaa ggcgtccttg acgatgacca gcaccgcgtc  34320
tagcttgcgc ccgttgatgt gcgtgacgaa gtccgtgccg ctgcggctcg cgcagcggat  34380
gtccacgccc gagggcaggt ccaccacgaa cacgaagcgc ttcggcgcgt agagcaccag  34440
gtccgaggac ggcgacgccg aaggcgccga ggggaactgc cggtggtcaa aagggtgcac  34500
cacgcccacg atggacgtga cgcggtcgtc cgggaactgc gtcgcggcgc cgccgccgcg  34560
gtgccgcgtg accgtgcttc tgcccacgtc gtcgcagacc acgtgcagct ccgacacgat  34620
cggcagcagc gtggccagca tgcggtcggt ctctgtgcgc gtcgcgcagc ggtacgcgat  34680
cccgcagtgc gcgtcctgcg tgcgcccgaa gaagagcacc agcacgctcg cgtcctggtc  34740
gaagggacac acggccatca cgcccaccgg cggcggcccg tggcctgcgt acgcggagga  34800
gaactcctgc acctcgacca cggcgtcctc gcgcgcctcg ccgggcacca tcgccgccgc  34860
```

cggccgcagc gcccgcacgg tctgcttaac cgcacgcgcg gcggcggccg cgctcggcgc 34920
gactacgcgc acggccgcgt gcgcgcccgg cggcggcgcg gttccggcca tccagcccac 34980
cggcgagaag aacacgtcgc agacgtgcac gcccgcggcc tgcagcgcgc gcgcgagcgc 35040
gcgcacggcc tcccactcct cgcgaaaggc gctcgcgacc gcgagcgcct tcagcaccgt 35100
gtccacggag ttgacgggct tctggaagag gttctcgttg ttgtagatga actcggggag 35160
ctccacggca ctgtgaacag ccgaatctcg tgcgcgccgc tgggcgtgag ccgcgtcgcg 35220
ggcttgcgca cgccggcgcg atctgcttga agaagtggtt catggcgccg ccggcttctc 35280
gggctccggc gggagcagac tatttattcg ggaggttatc ctttccgaaa gcacctgcac 35340
ggacttccgc gtccagcgct ccatcttcat gtactccttc atgccgtcgc tgagcacctc 35400
gacggcctcc agcttgggcg ctgtcgggtc gaagaggatg ctcttgagca gcgtcatctt 35460
cttgtccgcg aggaagcgga agtaagtgta gatgcagcgc agcgcgcgga agttctccgg 35520
gtgcttgatg gtgcacagga tcatgaagat gcaggtgaac atgccgcact cggactccat 35580
gagctggttg acctcgaggt tgatgcagcc gcgccgcgcc ttgaagttgt ccacgaagaa 35640
gcgcatgagc acgtccacgt cgcagttgcg gttgtccagg tccgcggtct cggcgttcac 35700
gttgaagccg tccgagaagg agtagaagta gaagtacttg caggggtgga actccgaggg 35760
gctgttgccg ccggagtcgt agaaggacac gagccgcgag acggtgtcga agatgcagca 35820
cttccagtgg aacatgtagc agaagccgaa catcacgtag cgccgcccgg cgcgctcgat 35880
cttgtccttg agcgtgaggc tgaccatgtt gcagcggaag cggtccgcct tttcgtggat 35940
ggccgcgccg ttgaggaagt tcaggttgaa ctggcccagg tacgcgacct cggtgccgaa 36000
cgcgaagggc gccaccagac tctggatgct cacgttgctc atccaggcgc cgcggtcggg 36060
ctttatggcg atgggcacca ccttggtgtt cacgcccgtg ctgacgcccg cgcgcgcgag 36120
gtcgtccacg ttcagcggca tctgcgagaa gtccacggcc tcggacacct tctcgcgcaa 36180
cgagggcttg aagaagaagc ccagcgggac cttccactcc agcgcgatcg cctcgcggaa 36240
gccgtagcga cccttgaggc tggccagcaa cgcggtcttc tgcgcgacct cgtccttctc 36300
ggtgtccggc ggcgcggcgt cgatgagccc gcgcttcgcg aagtccagca gcgccgccag 36360
cgggatgcac gagacgcgac cggccgtcgc ggattcgtcg aagcgccgca ccacgtaccc 36420
gttgcagttg gtcttgaagt tggacacgtc caggtgcgcg ctgagcccca ccaccgagta 36480
gatgtggcac agaaggttgg tgaaccccag ctccgggatt ttgctcacca ctaaatccgt 36540
gtacttgtcc atttatcatg gagaatcatc tgccggacat gctgatgttt cccaactgcg 36600
tttctgtgtt tccctttgag tactcgctgg aggacgtgtt ccgcctcccc gaggagcgac 36660
ggcgcgcgtt cgccatggcc gtgttcccgc tctccaagca ccgctggagg ggcgcgcggc 36720
tccagcgcga cgagcgaagc gtgtggctca gcgtcgagga ggaccgcggg cgcgcgctgg 36780
acgagcggaa ctgctcttgg ctctcggacg tggccgcgcg catggtcgac gacgagggcc 36840
gcgcggtcac gcccgaggcg tacgccttca tgcgcgccgc gcccggcgcg cgcgtcgccg 36900
agctcgccgc ggacgcgggc gtgctagcgg gcctcgtcgc cggcggcaac gcgctgcgcg 36960
tcttctcctc ggagtccacg caggcgcgcg agggctggaa ggcgcgcagc gtgggcgtgc 37020
tcggcaacgc ggcgccgctg gcgcccgtgc cgctggcatc gctgcgtccg gaagtgcagc 37080
gcgagatctt cgccgcctgg atcggccgcc gccccgtggt gctcacgggc ggcacgggcg 37140
tggggaagac ctcgcaggtt cccaagctgc tgatgtggtt caactacctc ttcggcggct 37200

-continued

```
tcgagcgcct ggacgccgtc cgcgagttcg cggagcgccc gctcgtgctc tcgctgccgc  37260
gcgtcacgct ggtgcgcgcg cacaccgcga cctacctcgc ctcgctgggc ttcggctcgg  37320
ccgacggctc cccggtctcg ccgcggtacg gcgccatccc ggacgccgag cggaacacgg  37380
ccccgcgcgc ctacgggctc gtggtggcca ctcaccggct cacactgacc gccatccgcc  37440
gctacgacac ggtcgtagtg gacgagatcc acgagcacga ccagatgggc gacatcgtgg  37500
tcgcggtcgc gcggaaactg ggctcgaaca tgcgatcgct ggtgcttatg acggccacgc  37560
tcgaggacga ccgcgcgcgc ctggaggagt tcctagtccg gcccgccttt gtgcacatag  37620
agggcgacac gctcttcccc atccgcgagg tctacgtgaa gaacacgcaa cagccgccgc  37680
tctcgcgcaa gtacgcggag gcggagctgc agaacgtggc gcaggcgctc ggcaccttcg  37740
tccccgagca gggaaagtgc ggcatcctct tcgtagccac ggtggcgcag tgcgcgctct  37800
tcgcggagac catcgaggcc aagcaccccg ggctgctggt gcgcgtggtg cacgggaagg  37860
tgccctccgt ggccgcggtg ctcgaggagg tctacgccgc ggaccggccc gcggtgctgg  37920
tttccacgcc gtacctggag tccagcgtga ccgtgcgcac cgccacgcac gtctacgaca  37980
ctgggcgcgt gtacgtgccc gagcccttcg gcggccgcga gaccttcgtc tccaagtcca  38040
tgtacacgca gcgcaagggc cgcgtgggcc gcgtggcgcc cggcacctac gtgcgcttct  38100
tcgacacgcg gctccgctgc cgctgaagcg catcgactcc gagttcctgc acccgtacgt  38160
gctttacgcg cgcatcttcg ggctaagctg cccgatgacc tgctcgtgca tcccagcgac  38220
ctcgcgctgc tgcgccgcac cgaggagtac gtcgacggct tcggcatcag cctctcgcgc  38280
tggacgcagc tgctggaccg gcactacatg cacatggtcg agtacgcgaa ggtgtatgtg  38340
cgcggcgggc gcctcgccgc cgcgctggac gccttcgagc gcaccggcgt gatgacgcac  38400
gaggccaccg aggccatccg cgccgtggac atgctcgcgg ccgtcctaaa cgtgcgcaag  38460
tccaaggacc gctaccgcgc ggagtgcaag gtgctcttcg ggcccttcgc gggcaagaag  38520
ttcgtggtcg ccgggcggcg tccgcccggc tcgcacgtgc tcatggtcac agaccgcgtc  38580
ttcatcgagg ccgagccccc attctgagga ccaccttctt ggagacgccc gagaagtcgt  38640
cggcgacgcc gcggcgcgcc accacaaggc agtacgaggt tacgtgcggg cagcgcgcga  38700
tgcagcggaa ggcttcctcc tgcgacagcg agaaggcgaa cacgtagaag gtgtgcgggg  38760
acttcagcgg cgtgtggtcc atcgagtaga tgacaccgag cttcttcatg cgccacataa  38820
gcgcgttgat gtggtcggcg cgcagcgcgc ggcccttgag cacgccgcag acgaagctcg  38880
agcaggccac gacgtcgtag cgcgtgttcc tgctgaagac caggtgcggt gcgccgccgg  38940
cgcgccgcgc ggccgcgcga ttctccacga tgtcctctat ggagcgctcg ctcgcaaaga  39000
agtccaggaa catgtactgg taggccacgg ccgggcgcga cttgctgaac ttcatgaagg  39060
cgtccgagtc catgatggcg tccatgtcct cggcggcgag ccggtgctgc agccggatgc  39120
cctcgaaggt gtggaagagc cgcgcgtccg cgtgcatgga cagcgcgaga gtgacgaagt  39180
cgagaaggtc cgcgtcgccg aagcgcacga gcacgttacc gggcgtgcgc gtcttgcgca  39240
tgagccgcgc gggcgcgccg tcgttgtggc tgcggcggcg cattttgtcg ccgggggact  39300
cgggcggcag gtcgatcatg accagccggt gccgctgcgc gtcctcggcg ttgaagatcg  39360
aggacgtgaa gcccgggtac agcaccacgc agtcgcgctc cgagatggcg tgcagcacgt  39420
cgcgcttgag cccggccacc agccgctccg cgttctcaac gaagtagttc tcgtagtcca  39480
ggatgtcgtg cgccatccag gggaagttca ggtacgcgtt catggcgtag tcctcggcgt  39540
cgaagcagat gcgcgtgtct ggcgtcgccg cgatcggaag gtccttgatg ccgcggagca  39600
```

```
gcccgtcgta gtcggactcg tctacgaagg aaagcaccac aaagaggtcc tcgcccacgg  39660
tctcgtagtc gaagaggtgg tagagctctc ttagcgccag cacggcgagc gcgttgtcca  39720
gcgaggcgtg cacgcgcgcc aggatgctgt agaagggcgt ggccatcatc acggccttgc  39780
cgccctcgca ggcgacggcg cgcgggaaaa tgacctccgg cgtgcgcggc agccgcccga  39840
acgtcgcgtt cagcagcgcg accgtggccg cgtcgctctg gcgcaggaac actaccaccg  39900
aggggcccga gatgctgagc atgcgctcgc gcatgcgcgc tggcaggtcc ggcgtggtca  39960
cgaggtccgc gaagcggccg ccgttgtaga ggtcgccgcc gccgaggaag gtgagcacgt  40020
cgaagcagtg cagcacctcg ttgcggaagt agtactcgtt ctcgagctcc ttggcgtacg  40080
cgcgtatgtc cacgttctcg aagtttgttc gcagaccgcc gccgtcgaag aaccaggacg  40140
caagctcgcg gacggcgtcc gcgggcctgt tgcggcggct cttgcaccag aagctcatgt  40200
agttgcgcga ggtggaggcg ttcgccagga agaagcggtg gtcgaaggag atgagcacat  40260
gctcgagcag gtgcgcgagc cccaggaccg cgcccacgtc gcgcccaaaa ccgaagtttg  40320
atatccccag gtagacgtcc cgtttcatag acggcctcag gaacaccctg acgccgtttt  40380
ccaacactat cattctccgg tatttactta cccaaaagta gtattgggag aagtgtttga  40440
acgtcccctc gcctttttaa atcaaaagta gacttctcgc gcccgtgcgc caccgtcacg  40500
cgcgcgcggc gcgagtccat accggcgatc accgcgctgc tctgcggtgc gtccggccgc  40560
gggaagagca cggactcgga gatcccgtcc agctgcgcgt cggtgcgctg tcgccacgcg  40620
tgcgcgtccg cgagctcgcg cacggccagc tgcatcttgt tcgtcggcag gaacgtgaac  40680
acgtacgccg ccgccaggaa gactgcgaag agcacgaact caaccgccca tgacatttag  40740
ggagctgatt ttgttccacg cggcgacgca cgtcgtgacg ggcgaccccg aggcgccgcg  40800
gcgcgcggcc tcgctgtgcc gcggcttcgg cgtggacttc cgcgcgattc acgcggagtt  40860
cgcgcggcgg tacccgcgca ccgcggccgc cgtggagcgc gcgcagccgc tgcccgaagt  40920
cgacgccgcc tttccgccgg acgcgcgccg gcaagtcgtg cggctgcgcc tcgaggctgc  40980
ggcgctggtc gtcaaggagt cgcgtgcgct ctcggcctcc atgcgcggcg tggcggtggt  41040
cgacggctgc tgcgtgcgcg tgtgccgcgc taacgacgag ctgctggggt tcctcgcgcg  41100
gcgctacgac cccgcggtct accgctacgc ggaggtgccc tcgccgagcg tgcgcccggg  41160
ctcgaaagtc ttcgcgtgtg cgggccgcag cgtcaccttt gcggccgcgc accggagccg  41220
catcacggcc aaccgcccgc tgcgcgtggt cgtgaccgag gcctgtgtgg acggcgtgct  41280
cgcgcgcggc gccgcggagg tattcgaccg cggctccggc gtgctgcccc gcgcgctgcg  41340
cgagatcttc taccgcctcg acgaggacgg ctgtcccacg ggccagacgc caggcttcgc  41400
ggacagtatg gcgtcgcgca gctgatctat gtccaccttt ttctcgtcga tctgcgccac  41460
gaccacgaaa ctgcgaatgt ccacagcggc catggtcttg gccaccgggt cgtacttgag  41520
gagcagcacg tactcgttgc cgaagtgctc ggtgacctcg gtgatgagcc ggtacacgcc  41580
catgccgagc acgttcaccg caccgtcctt ggcgaagagc gagaggatgt tcacgcactt  41640
cagctccatc tcgccctcga ggcgcgcgag catgcgccgg gtgacctcgc atactgaaca  41700
aagaggctta cctagtaaga taagcgttag cttagccgcg gtcggtgacg cgtcggaggc  41760
catttatggg gatcaaaaac ttaaaggcgt tgctgctcag ccacggcgcg ctgaccccgc  41820
acgagccggg cggcgacgag cgcttccctg ccgtgttcgt ggacggcttc agcgtcatga  41880
tgaccatggc gtactcgtgc gcggacgaag acgagttccg cgcggccgtc gaggagcgcg  41940
```

tgcagcactg gatgagcgtg tccgagagcg ggcggatcgt ggtcttcctc gaccgcggcg 42000
agattccgat caagcagccg ctgcgcgacc agcgccgcaa agccacgcgc gaccgcgccg 42060
cgcgccaccg cgagttcatc gccgccgcgg aggcagaggc ggcggcagag gccgttggcg 42120
cccgcgagga caagcaggag gacgagcacg cggagttcgc cgaggagatc cgcgccgaga 42180
agcagctaaa gctgcagcgc atccgcttcc agctcagcat cgccaaccac gaggtcgtta 42240
agtcgctgat agagtccacg ctcgcgcgcg ctggcgatgc cgtggagatc gtcttctgcg 42300
acggcgtcga cgcggagatg gtcatgtgcg cgcgcggacg cgccgaggcc gagcgtcgcg 42360
ggcgctggcc gctgctcgtg accacggacc aggacgcgct tttgttcacg tccaccgatc 42420
gcgacgagaa gatagtgagc accgtctccg cctgctacgc gttcaggccc accgagacga 42480
ccgagtacct gtgcaaactt gcggcgctgg ccaacggctg cgacttcttc cccgggctcg 42540
gcggcatatg cgtgagtgtg gagtcgctgc gccgcgccac gcttttcccg gaattctccg 42600
tgcgcaacgc cgccgtgagt ctgtgcacgc ggcccatgcg gctgtccacg caggacgcgc 42660
tggagccaga ggccgccgcc gaggtcgtgg aattcatcag gcggtacgcc gccggcgacg 42720
agcgcatcta ccgcgaggtg ccgcccggcg cgtgctgcgg acgcgcgttt gtgcgcggag 42780
cgctcgcggc cgagtgggcc gaagcgctgc cggcggccac gggtctgagc gtggtcgcgg 42840
acatgatcgc gtgtctgccc gcgcggcggg accccgcgcc cgaggaggta gagcggctgc 42900
tggcgctgga ggcgcgcgcg cgaggcgcgc gcgtcacgga tgcgatgctc gcgcagactg 42960
cgcagctgct gggttacggc gcgagtgcgg gcgccgacgg cgcctccgcc ttcgcggtct 43020
cgggcgccaa gggcctgatg tgtcgcctgc gcggcacggc catgttcttc aacgcggagt 43080
acgtggaaat tgaaagcgaa cccagactgt taaagctgcg gtagcatggt gttcccgatc 43140
gtgtgctcaa cgtgcggccg cgacctgtcg cacgagcggt ttctgctcat cgtgcgacag 43200
cggccgctaa aggttgtttt gcggacggtg cgcaacgtct gctgccgtat aaagttgtct 43260
acacaaatag agccgcaccg gaacctgacg gtgctgccca tgctcgacat aagctgattt 43320
ttcttttccg ctctgtatgc gcgagttcgg actcgcggcg cgcatggccc gcgccatcga 43380
ggacgtgtgt ccgcgcggcg cggtgatatt cgtatccagc gccgcgtcca tgaccgactg 43440
ccttaacccg tcggtgttca agcacgcggc gatatacgcg gggcgcgtgg accgcgcgcc 43500
gctgccgccg ccctcgccgg tcccggcgga ggccgtgacg gagccctgcg cgatagacgc 43560
catagcgcct tacggcgcgc gcgtggtcct gctctcggag ctgctgcgga gctgcgtggc 43620
cgttcaggcc taccgcctgg cagtccccgg cgccctcgcg ctcatgaacc tcgcggccga 43680
cgcggccttc gagctcgtgg gcacgcccta cggctttaac agcgaccgaa cgtactgctt 43740
caagctcgtt gccgactgct ttgctagcgt gggcgtgaca acgaagacca ggcgcatcat 43800
gggtcgcgac gtcgtgctca gccaggactt cctggagagc ggcatgtgga ccaaggtgct 43860
ggactccgcc gcggagccgc cgtggctggt ctagaacagc ggcggcgcgc gggtcccgag 43920
aacgggccgc gccacctgca gccgctgctg cagcgcgcgg cactgcgcct cggcgtcggc 43980
agtctcggca gggtcgacgg gcgtcggagt cgggaggtgg tcctgaacgg ctgcgtgttc 44040
accgagacgc ggatgcgctc cttgcaggag cgctgctcga tgcattggcc agcatcttca 44100
tcacgtgcag gtactccagc aacacgaact tttcgagggt gatgccgtcg aagggcgacg 44160
accccaccac gcccagcggg ctggacaccg cgccgtcgag cacctcgccg cgggactcct 44220
tgcgcgcgcg ctcgagcagg tcctctgtcc gagccaccac gctgccgaag tcggcggccg 44280
cgggggcggg aacaggcgca gcagctgcgc cgtccgcgtc cgccggcatc tcctcgatct 44340

```
tgagaccggc cgcgaactcc gaggccgcgt gcacgggcga ggcgccgcgc cgcaccatga  44400
agtcgcacag acgcgatagc gcggaggagc gcaccggcat gtcgagcagg cgctcggcct  44460
ccatctcggc gaccgagtcg gcgcacgcgt ccggcgcgcc cgcccgcacg agctcgtcgc  44520
agcaccccgc ctcctccatg agcgcgggca tgagcttgta ctgcgccatg ttcaccagcc  44580
cgtacttgag ctcgagcagg tccgcgagct cggaggccat gggtcggttt ttggtgtaga  44640
tgacgcgctc cacggcctcc gccatgtcca cggcctgcat gagctcgccg acgagcacgc  44700
tggccacgag cgtggccagc gtgacgcgca cggtgggcac acagaccgcg aagaaggagg  44760
tggagtgggt gaagcgcatg agcgcgccgt gcagacgcgc gaggtccgcg ctgttgcccg  44820
cgtgcacgaa gcgccggcgc agccgcgcca gcgcctccac gaggtcctcg cgcgtggtca  44880
cgcgcacgtt cgcgatgcac aggtcgtgga tcgcgttggc gatctgcgcg cggcgctgcg  44940
gcgagctgcc gggcagcagc cgcgccttgg cctcgacgtc gacggtgctc gaaagacagc  45000
cgcaggcggc gccgcggacg acgaacttca acaacgactc gaacacgcgc gcgcccgcgc  45060
ggggcgcttg cttggacgac tccatttact ttaaataatt tacgagatca aaataaaatg  45120
actctgcgca tcaaactcga gaagctcaag cagatcgtaa cctacttctc ggagttcagc  45180
gaggaggtct cggtgaacgt ggacgtcggc gatggcctca tgtacatatt cgcggcgctg  45240
ggcgggtccg tgaacatctg gaccatcgtg ccgctcagcg cgagcgtggt atacgacggc  45300
gatgtcagcc gcgtgttcaa cctgcccgtg ctcaaggtga aggcctgtct gtgcagcttc  45360
caccccgact cggtggtgag cctggagccc gacctcgagg acaacgtggt gcggctctcg  45420
agccaccacg tggtcagcgt ggactgcgac aacgagcccg tggcgcaccg cacgaacacc  45480
gccatctgct tgggcattaa ccagcgcaag tcctacgtgt tcaacttccg gcgctacgag  45540
gagaagtgct gcggccgcac catcgtcaac ctggacctgc tgctggggtt catcaagtgc  45600
atccaccagt accagtacat cacggtctgc ttccgcgaca agaagatggt gctgcacacg  45660
cccgggaagg tggacaactt cttccgcgag tactccatga ccgagtgggc gcccgacctc  45720
gagcgcttct cgttcaagat ccccatctcc tccgtgaaca aactccgcgg cttcaagaag  45780
cgcgtggtca tgttcgagtc gcgcgtggtc atggacgccg acgacaacat catcggcatg  45840
ctcttcaccg accgcgtggg catgtaccgc gttaacgtgt tcatgtcttt caggaccggt  45900
ctctttcatg cgactaaata ccctcatggg cgggtcggtg agcctgccct cgcgggacct  45960
gccgccgccg gtgcgcacgc cggagatgaa catcgtgccc gagcgcgacc tcgcggacac  46020
gatggcgcgc ctctccaccg cagacccgcc gcagccgctg ggcgtcggcg acgacgcgcg  46080
catggccgtg ctgaagacga ccttccccga gttcgcgata tcgcggcccg cgacgggcat  46140
gctcgccgcg cagcgaatca ggtacgacgg cgacccgcgc gtctgctgcg gcgggttcgg  46200
gatctcacat tactgggaga ggggggcgcg ccgatcgaac gtcgcgttcg agggcgcggc  46260
gctgcgcacc tgcgacccca cgcgcttcga cgcgggcgcg tgcgacgcgc tgctcttccg  46320
cgagtgcgcc gccggcggcg tcgacgcgga cttctgcgcg cactggatca acgcggccgt  46380
gacgcggcgc acggaccgac agtcgcgcgc gcggctgaac gacatgttcg tgcgcgattg  46440
ccaaaacgac gccgcccggc ctcactgcgt ggcctggatc cgcgcgatgc gaagcgcgcg  46500
cgcgacggcg gacgacggtc taatagacgc cgtgctctcg gtgcagagtc ccgagttcaa  46560
gggcaaacac atgcgctgca gctacccctc gccggccaca ctcgccatgg ccgcgaacgt  46620
agacgagccg cgcgagtgtt gggaccccga gtgcgtggcc gggaacgtgg acttcatgct  46680
```

-continued

```
gagcgataac tacacgaacc tgggcctgtg tcggctctcg cgctgctcca tcggcgtcac  46740
acacctgcgg atagacgcgc gttcgcggct gcgcatgcgg tgcgccggcg cgcttgccgg  46800
gctcacgaag gcgcccgtga accagactgt cgtcgtcggc gacaacctcg cgcgcgcctt  46860
cgagccgcgc gtggaaacgc tcggcgtgtt ggcgctgtgc gtggtgtatc tgctaattgt  46920
ctggctctaa atgggggccg ccgccagcat tcagaccacg tgaccaccgt cagcgagcgc  46980
atccgcaacg agctcgagca gagcgcgagc gctagcgcga ccgccgactg ccgtcaccat  47040
cgggagtctg attatccgca agaacctggg atgcagcgtt tccgtccgga acatgtgctc  47100
ggccaacgcc ggcgcgcagc tggacgccgt catgaaggcc gtgagcagca ccttcaacga  47160
cctctcgtcg gaccagaagg cctacgtgcc cgggctgctc acggccgcgc tcaacatcca  47220
gaccacggtg aacaccgccg tcaaggactt cgagacgtac atgaagcaga cctgcacggc  47280
ggacgcggtc attcacaaca aaatcaagat ccaaaacatc gtcatggaag agtgcgcctc  47340
tctgccaggg agtccggcca cgcacctgga gttcgtgaac accggcacgg ccgtgggcaa  47400
ctgcggcgtg aaggccgtga tggacgtgct cgcgaaggcc agcaccaccg tgcgcaacga  47460
ccaggaggcc ggcaagggct accagaccat catcatcgcg atcgtggtcg ccatcctggc  47520
ggccatcttc gcctggtacg cgcggcacat gctattcatg tccacctccg acaaaatcaa  47580
gctcgagctc gccaagaagc ccgtggtgca ctggaccacc tacctggaca ccttctttac  47640
ggaatttccg ccgtccgtct agatacgcgc aacattgaaa cattatatcc acctctcaaa  47700
cggcggtatg gtccgacgcg tcctcctcga gcgcgtggac ggcatcgtcg agcactcgcg  47760
cgcagaccga cgctacttgg aggccattca gcgacacctc gaggggtcta cgcccgggct  47820
gcggcagatg tggcgcttcc tctacgacct gctgctgacg gtgttcgtcg tcatgtacat  47880
cgtcttccgc ctaatcgtgc gcaaccccgg catctgcgcc atcctcgcgc tcgcggccgc  47940
ggtgtactac ctgtttttgt gtctctttag catggactga tggcgatcac agacagacca  48000
tcgcccgcgc gcgcgtgacc agctccggcg ccgcgaagac gtcctgcacc gggaagtcgt  48060
cgatctcgaa cacggagccg tccgcggacc agatcacgcg cacgttgtcg ctcaccgaga  48120
cctcggtcag cgtcacgccc agcacaaccg cgtcgttggt gctcaccagc accagcgcgc  48180
cgggctccgc gcgccggtgc agcggcggcc ccgagactga gcgccgctgc acgcggaaca  48240
tgtccgcgaa ctgcttcgag agcaagtcca ggtggttgcg gatgatccac tcgaagaagt  48300
acgcgcaacc tccgccgccg cacaggaagc gcgaacccgc gggcatcagc agccgcacaa  48360
cgtccatgta gcaggcctgc ggcaggctcg cgcggtacag ccgcgtcttc ggcgagagca  48420
ccaccaggct ggaggtgctc atctggaaga ccagctggct aacggagacg gtgagcgtgc  48480
acgcgggcac ggaaaccacg tccaggcaga tgtcgtccag aaagatgctc cgctggtaga  48540
ggtggtacag gatggccacg atctgaaagg ccgtggcgtc gctgatggcg caggggcggt  48600
cggcgcagcg catctgcgcg caggaccagc ccccgaagga ctcgaagcag acggtgatca  48660
tgcccgtgct cggacagtgt ggcgagcgcc gacacaccgg aaagcccacg gccttgcggc  48720
agcgcaccat ggtcgagagc tctatccagc agcctgcctc ctcctcgccc atgcccatgg  48780
ctaccggcgt gaaggccgtg acgtcgtcgc agatgcgccg ctccagaaac ccccacgcccg  48840
aggaggggtg cgcggccggt ggcgaggtga tgcgcgccgg gaccggctcg gagcgggctc  48900
gggaggcgag ctgcgctcga cccgggcagc cgccgccggc cgcgatgccc tgcgcgcggg  48960
cgcgcgttcg cgcgacttgt ttgacttgct ggcctcgtcg ctagcgtcat cgaagcggtc  49020
gttcctgtcg ccgcggacgt ccgcctcgtc gcccgccggc cgcgcggcgg gcgacgtgcc  49080
```

```
gtccgcgtac ggcccgcgtt cggcgcgaat gtcacgcgcc ggtgcacgta cggctccgta  49140
gagcccgtgg gggcgccgcg cccgcgccct cggcggaagg cctgccggga cgcgccgaag  49200
cgggcgaact ccccttcgc ccggcccctt ttttcttcca tgatatttat cacaaaaaaa  49260
acttctctaa atgaccaatc tgctttcgtt ggtcgacccg gaggacctgg ccttctgcgc  49320
cgggttcccg tccttcgacg agaccatgct cgtgatcgcg ggggcgcgag tgcgcttccc  49380
acgctcgctg ctctcgctct tcaacgtggt gccgcgcacc atgacgcgct acgaaaccga  49440
gctcgtgggc accgagatgg tggtgggcgc cgtgttcacc accgcgtaca acgtccgccg  49500
caacctaggc ctcggcgagg agcccgtgac catgcgcgac atcgagaagt acttcctgga  49560
ctccgagaac gaggtgctca cgctcatcgt gcacaacacc gacttttccg ccatgagcgg  49620
cgtgcgccgg cgcggcggcc ggcgcatcgc caaccccgtc atcttccgca gcgggtccac  49680
gccgctgctc atcgtgatgg agtcgcgcaa gaagaccaac atctaccgcg agcgcaccgc  49740
ggagcaggcc aacgcctcct acagggaggt cggctcctcg ctcgcgctgg tcactcggta  49800
cgcgggtctg cagctggtcg acgtgcacac gcccagctcc gtgctaacgg tctccgccgt  49860
ctacggcttc accgaggaca aggggctcaa gaagctgggc tccgcaagga gctcgcggac  49920
taccagtcca cgccgctcac cgaccccatc cggctcagcg acttctccaa tatattgacg  49980
gcgtcaagaa gagcatccag ctcacgaacg tgcccgtgcc ctccgccggc gccgaggccg  50040
cgccgtaggc tttcatgcgc gataaatcgg atggcggcgc cgacgacgcc cgtggtgcac  50100
ctcacgccgg tgttcgtgga gcctacgatc gcgcactcgc tgctgcgcgc agagtcctac  50160
ctcgcgatcg cggtccttga gctcgtgctc gcgctcgtgc tcgcgctcgt cttcttccgc  50220
gacgagctgg gcgcgctatt ccgccgcgcg ccgcgagcgc cttcgccgct ggacgcgtac  50280
ctgcaggcga gcctcgtctg cgacggcgac gcgctgctga tcgagctgcc cgaaggccgg  50340
gtgccggcgc tcgcgctgga cgggcgaccc gtcgcgttcc cggggtgcga gagccttttg  50400
taccgcataa atggaccacg aaaagtacgt cttgtcgatg ttcttggagg aagataactc  50460
cttcttctcg ttcgtcgccg cgctgtccga tgacgaggcg ctcggcgccg tgcagtccgc  50520
tgccgccctc ctggacttcc tgctctccgt ggtggtccgc ggcaaggaga agctcgccgc  50580
cgcggggcac cactacgact ccatcgcgga cggacgcgcg cgcgccgcgt tcgagttccg  50640
agacctgcgc gagctggcgc agctcttcga ccggcggccc tgcggcgtcc aggaccgcgt  50700
gcgtgtgcgc gacgggcccg cgcgcgcctt cgtggacgcg gcactggggc tcatgcgcga  50760
gcgaggcttc gacggcacgc aggccgcgga gcgcgcgcgc tacatcgcgc cgaacgatct  50820
gcccgcgctg gggggcaatat cggccacgct ctcgccgggt ctataacgta aaaaatatta  50880
gtaaaattct gaaggtccgt gtgtttcgcg ggcggccaac aaaccagtcg cttaaatgga  50940
gggggtggaa atggacaagc cgctcctcta cttcgacgag atcgcgggcg cgcgcgacta  51000
cgacgcggcc ttcgcggaga agcacgagcc gcccaagatc cccggccgcg gacagatgaa  51060
gctgctggtc tgcgagctcg tgtttctcaa ccggctgcac ctgcacggca tgctcgacgg  51120
cagcgtcatc gtgtacgtgg gctccgcgcc cggacggcac atctgctgcc tgcactcgca  51180
cttccaggag ctcggcgtct cgcttaagtg ggtgctcatt gacgggcgca agcacgaccc  51240
ctgtctctcg gggctgcgga acgtgaccac ggtgacgcga ttcgcggacg aggcctacct  51300
ccgcgagctg cgcggcgagc tgcggcgcgc caagatcgtg ctcatttcgg acatccgctc  51360
caaccgcgtg gacacagagc ccaccaccgc ggacctgctg cgcgactacg cgctccagaa  51420
```

-continued

```
caccatggtg agcgtgctca agcccgtggc ctccagcctg aagtggcgct gccccttccc  51480
ggactcctgg gagaaggact tctacgtgcc ctgcggcaag gagatgctgc agccgttcgc  51540
gccgccgttc tccgcggaga tgcggctgct caccgtgcac tcggagacgc gcccgaagct  51600
gcgtctgatc acgctcagcg acgcggtcaa ctatgaaaag aggatgttct acctcaatag  51660
cgtggtccgc cagcgcgtaa ttctgaactt tgactatccc aaccaggagt acgacttctt  51720
tcacatgttc tgtctgctct cgtcggtggt gtgctcgtgc gaatttaaat cgcccaaaga  51780
gaaggtgctg agcctgcaga accgcttctt ccgcttcctg cgcatcccgc cctccatcac  51840
gctcgggctg cgccggcacg atgaaccgcc acaacacgcg gtacctggcc aagatcctct  51900
gcctaaaggc cgcggtaaga agcgacccct tcgcggtggt aagtagggac accgtgcgca  51960
tgtacgacat cgaggtcgag tacggcgacc tcgtgacggt ggtcaccgtc acgcacaaac  52020
tcgagaccag ccgcaccgtc ttccaggtct tcaacgagac ctcggtcgcg tactcgccgc  52080
tgccggacga ctacggcgag cccatcgtgc tcaccacgta catgcagcgc gagcacacca  52140
agttcccgct ctccatgctc tacatcgacg tggtcgcctc ggacatgttc cccacgttca  52200
agcgccccac cgaggaggag gccgcggtgg tcgcggccat gcagcgcgtg ggcgggcgcc  52260
gcgatcccgt gctcaagctc ccgcgcatgc tggacaccga gctcgtgtgc aagatactgc  52320
acctgcccga gcacccgctg cgcgtggtgc gcttcctgcg ccgaaacatg ttcacgggcg  52380
tggaggtcgc cgaccgctcg gtgtccgtgg tcctcgactg acgaagggca gcacggccag  52440
cgaggccgcc gccaccaagc acagcggcag ccacgcgcgc gggtccgcca cgggcacgaa  52500
gacgtgctgg ttcaggtatt tcgcctggaa gcgctccgcg gtggagtcca ccttggaccc  52560
gcaggcgttg gtgaggcgca cgaccgcgtc cgcgacgcgc acgtccccga gcgatatcac  52620
gcagtccgag acgttgcacc cggcgatgtt tttcttcagc gcgcgcggta gcagcgcgtc  52680
cgcgcgcttg cagggcgcgt accagcagta gtagggcagg cgcgtgtcgc ggccggtgtc  52740
gaccacggcc tggctgggct tgaggcacgc gcagcgctcg tcgtccgggt gcgcgtcgca  52800
gaaggcgtaa atctcctcgt cgggcgcgtc cggcccgggc gcggtcggcg gcccgcgcga  52860
cggcggaaga acatctctga aaaaatactt cgaccagaaa acgaccaccg atcttatttc  52920
aaagtaaaaa tactattaat acgcactcgg agaatcatgt cggtggtggc gcgcgtatcg  52980
tacagcctgt actcgcagag cgagataagc gccacggacg tggtcatcag ccagttgaag  53040
aacgacgagg acctgggcac ggtgaaggac ccgcgcctgg gcgcctcgga cgggtccata  53100
tgccgcacct gcgggctcac ggagatggag tgtttcgggc actggggcaa ggtgcgcatc  53160
tacgagtcct acatcgtgcg ccccgagtac atccccgagg tggtgcggct gctcaaccac  53220
ctctgcgtgc gctgcgggct gctgcgctcg cgcgacccgt acacgacgga cgtggccgcg  53280
ctcagcgtgc acgagatgcg caagatgaag gaccgcatga tgtccaagaa gaaggcctgc  53340
tggaacagca agtgtctgca gccgtaccag aagatcgtct tctccaagaa gaagatctgc  53400
ttcgtgaaca aggtggacga gatacccgtc cccaacgcgc tcatctacca gaagctgacc  53460
tccatccacc gcaagttctg gccgctgctg gaggtgttcc aggaccccgc gaacctgttc  53520
tacaaggagt acatgcccgt cccgccgctg ctcatccggc cggcgatcag cttctggata  53580
gacaacatcc ccaaggagac caacgagctc acctacctgc tgggcatgat cgtgaagtac  53640
tgctccatga acgccgagga gcaggtcatc cagcgcgccg tgatcgagta cgacaacatc  53700
aagatcatct cctcgaactc gagcagcatc aacctctcct acatcatcgc gggcaagagc  53760
aacatgctgc gcagcttcgt ggtcgcgcgg cgcaaggacc agaccgcgcg ctcggtcatc  53820
```

gggcccgact ccgcgctctc ggtgtgcgag gtcggcatcc ccgactacat ccggaacacg 53880
ctcacgcaga aggtgttcgt gaactacctc accagcaagc gcgtgcgcgc gctgttcgag 53940
gaccgcgcgg tcaagttcta cttcaacaag cggctgcgcc agctcacgcg catcaaggag 54000
ggcaagttca tcaaggacaa gatccacctg ctgcccggcg actgggtgga gatccccatg 54060
tccgagggca cgaacgtgat attcggccgc cagccctcgc tgcaccgaca caacgtcata 54120
tcctcgaccg cgcgcgcctc gcccggctac accatcaaga tcccgcccgg gatcgcgaac 54180
tcgcagaacg cggacttcga cggcgacgag gagtgggccg tgctcgagca gaaccccaag 54240
tccgtgatcg agcagagcgt gctcatgtac ccggtgacta tcttcaagca cgacgcgcac 54300
ggcgcgccgg tgtacgggtc catccaggac gagatcgtgg ccgcgttctc gctgttccgg 54360
caccagaacc tctcgctgga cgaggtgctg aacctgctcg ggcgctacgg gcgagacttc 54420
gcgccggagc ctggccagaa gaccttctcg ggcgccgacg tcttccgatt catgataggc 54480
gcggacataa acttcaaggg cgtgctcgag aacgggcgcg tggtggcgcc gaacgtcgac 54540
agcgacctcg tggtggccat gcgcgcaacc tcgctagcgg ggctgatcgc ggactacgcc 54600
acgaacgtgg agggcgtgcg cttcgtggac atggcctcct acgtgtacaa gcggtacctg 54660
gccatctacg gcttcggcgt gaccttccgc gacctgcgcc cggacccgag tctggttcgc 54720
cggctgcacg cgctgaacac cgagaagata gagcagatca aggacgcgta ctcgcggtac 54780
ctgcaggacg tcgcggacgg gaagctggtg ccgatggcgc ccgcggacga agccgacgcg 54840
ctggactcgc tgctggccaa cctgaccaac ctcaacgtgc gcgagatcaa cgagtacatg 54900
cgcgagacgc tggagcgcaa ccccgataac agcctgctca agatggcgcg cgccgggtac 54960
aaggtcaacc ccacagagct catgtacctg ctgggcacct acgggcagca gcgcgtgaac 55020
ggcgccgtcg ccgagaccaa gatatacggg cgcgtgctcc cgtacgcgtt ccccgactcc 55080
gcggacccgg aggcgcgcgg ctacatcatc aactcgctca tgaacggtct ctccggctcg 55140
cagttctact tcgcgatgct ggtggcgcgc tcgcagtcca cggacatagt ctgcgagacc 55200
tcgcgcacgg gcacgctcgc gcgcaaggtc atcaagaaga tggaggacac ggtcgtggac 55260
gggtacggac agatcgtgag cggctcggta ctgctcaagt acgcggccaa ctacgcgaag 55320
atcccggggt ccaccaccaa gcccgtggag ctgctcttcc cgcacgagag catgacctgg 55380
ttcctggaga tcagcgcgct ctggacgaag atccggcacg ggttcgtgcg catgcaccgg 55440
cagcgcctgg ccaccaagat cctggcgccg ttcaacttcc tggtcttcgt gaaaccggcg 55500
ccctcggagg cggaggcgct ctccgcgcgg gacctgtacc acatgatcca gcgcgtgatg 55560
aacgacgtgc gcgagaagta cttcttctcg ctggcgaacg tggacttcat ggagtacgtc 55620
ttcctcacgc acctgaaccc ctcgcgcgtg cgcatcacgc gcgcgaccgc cgagctcatc 55680
ttccgcaagc tgtaccagaa gctgaacgcg ctgctcggcg gcggcacgcc cgtgggcatc 55740
atgtccgcgc aggtgctctg cgagaagttc acgcagcagg cgctctcgag cttccacacc 55800
ccgagaagag cggcgccgcg aaggtgaagc tgggcttcaa cgagttcagc aacctcatca 55860
gcatgagccg cacacaccga gatagtggcg ctgaccgcgc cgagcccgga taagctgatg 55920
ccgctgaagg taaacttcga gttcgtgtgt ctgggcgagc tcgtgcccga gatcgagacc 55980
cggccctcgg gacggccctc cgtgcaccgc gtggacatca cggtgcaccg cctgcgcatc 56040
aagcgcgcgc acctgaccga ggtcctggtg gacaccatca tcgagcgctt cgtgtccttc 56100
aacgtgctcg tgaaggagtg gggcagcgac atgaccgtgg agggcgaccg cgtcacgtac 56160
acgctgctgc tgcgcttcgt ggagccggag cagctcaact tccacaagtt catgctggtg 56220
ctgcccggcg ccgcgaacaa gggcaaggtg agcaggttca agatcccgat caccgagacc 56280
acggtctacg acgacttcga cgccgcgcgc aaggcctacc gcatgaacat cgagctcatg 56340
agtctgaagg agctggggat attcgacctc gaggacgtga acgtggtccc cggcatgtgg 56400
aacaccttcg acatattcgg catcgaggcc gcgcgcgggc acctctgcga gagcatgctg 56460
gacacctacg gcacgggctt cgactacctg tttccctcct gcgacctgct cgcgagcctg 56520
ctctgctccg ggtacgagcc cgagtccgtg aacaagttca agttctggaa cgcgagcgcg 56580
ctgaagaagg ccaccttcgg cgacggccgc gcgctgctga acgcggcgct gcacaaccgc 56640
accgacgcgg tcgcggacaa cagcagctgc cacttcttca gcaagacgcc ctgcgtgggc 56700
acgggctact acaagtactt cgtgaacgtg gagatgttca tgcgcatgga gcgcgagatc 56760
caggcgcgcg tggcggcgcg caagatggag gagatcgagg aggccgccga ggaggagttc 56820
taggcgcgac agcgccttac tttgcgaccg tgttacgacg acacgacacg gttaggacgg 56880
cgagtcgcag acgaacattt ttatgagctg gtagcggaag ttggcgtttt ccaggaaggc 56940
gccgcggagg tcccggatct cgtagtaggt tttgaggaag tacacgaagc gcgcgggctg 57000
cgtcatagtc gggttctccg caagccgctt gtgcatcacg taccccatgg cggcggcgcc 57060
gctgcggttg acgccggcca cgcagtgcac gagcgtgggc ttctgctcgg cctcgaggcg 57120
cgccagcagc ttcacgagcg cggcatgat ggaagcgatg ttcgtcgtgt cgtcgtctct 57180
cagcggaatg tggtacgccg ttatccccgc gggcgtcgag tacttggaca tggtcatgtt 57240
aaccaggcac ttgaagtcga cgccggagtc cccccgcagc acggcgcgcg cgtcctcggc 57300
gctgcccaag tacacgtggt ccgtgagccg cgtcatgccc gagggcaggg ccagcggcgg 57360
ccccgcgcgc gtgcaccgca gcaggagcct ggcgtaccac tcgctcttat cgcccatatt 57420
tatttatatg atacaaatgg cagacgtcac aacactgacg gccaacggtc tgaccctgga 57480
gttcgcgcgc gagcgcgctc tgcgcagcct gcgcgccgcg cgcacctcca cgctggtgtt 57540
cttcacgctc acgctcgcgg cctcgctgtt cgtgctctgg ctgcagctaa ccgagtttcc 57600
cgtcttcgag gagctcggca agtacgcgcg catcaagagc gcggtgcggt cctggcgccc 57660
gctggtggag gctaagaccg agatcgagtc cgacctcggc cggcagaaga ccgccgaccg 57720
gcccgagctc ttcgagttca ggtgcgtgga cttcggcaag ttctacctgc cggtgaggta 57780
cagccccacg accttcctgc cgcaagccgt gcgccgcggc gcgggcgatg gctggatggt 57840
gcacaaggcg gcggccgtgg acctcgccgc gcagcagttc tgcgagtccg tgctgcggca 57900
ccgcgccaac aacgtcatca catgcgggtc agagatgatg cggctggtgg gctacagcgg 57960
ctacttcgag gacgaccact ggtgcgccgc gacgtccggc gtgctgacgt gaacgatcac 58020
acgatggccg tgaccagcag cccggcgatg aaccacagca gccgcgagtt cggcagcagc 58080
agcacgagca ccagcaggta tgccaggatg aagatgtcga ccacgtccac gtcgaagagc 58140
cccatgaagg agaagagcgg cgtggtgagg aagtagatgg cgccgggcca gaagcgcgct 58200
agccacgtgg cgagcagcga ccacagggag ggcgcgccgc tgagccgcgt cttcacctgt 58260
atgtagtact cggggtagac cacctgctcg gcgccggaga gcaccacgcg cgccagagag 58320
agccgcttct ccagcgtgaa cacctcggtg agcaggccgc tgcgcagccc tccctccttg 58380
atgatcgcgt cgtagagctt cttcatgccg ccgacgctga tgatgtaggc gtctagcgag 58440
acgtcgtatc cgccggggta gaccatgagc tcggggtcgc cggtgccggg gacgttggtg 58500
gccagcgcgc cggtcatgta ggtctccttg agctgcgtca tgtaccagcc gttcgccttc 58560

-continued

```
atcgcctcga tgagcggctt taccatctcg ggcttgcgga aggtcatgtc gttgtcgacc  58620
accaggatga agtcatcgtc ggagtacttg gtggggacag tgccggccga tatgctctcc  58680
cagaggttga ggtggtgcgc cgcgcggcgc tgcatctcct tcggacacgt ggacttgcac  58740
atgtccgtga agaagtgcgg gtagtctttg gagtccacgt ctttccattc caccgccttg  58800
agcacgtggt cgcccttggg gtgcggcgcg ggaggagatg gcttgggtgc cggcgcgggg  58860
gccggcgcgg gggcaggtgc aggggccggt gcaggagagg gagcaggcgc gggttgaggc  58920
ttgggcgggt cgtcggcgag gcccaccagg tacggcagcg tggggaacac ctccttggtc  58980
ccgcggcctt cggcaacccc gattatgtag gccgtgattt cgggtggatc catttagtta  59040
ttaaaattaa tcatatacaa ctcttttatg gcggctatgg attcggctat ccagtccttg  59100
accgagccca cgatgcccgc caggaacagg aagaaggcga actccaggtc cacgcggttc  59160
agagagtcgc tgaagtacac gaagacgtcg ctgtccggga agaagctgcg ccggaacatg  59220
ttgtacccgt tgaccttgtg cgcgacgtgc tccgcgctca gcagcgtctc gtcgaagggg  59280
tacgggtcgc tgaagcggaa cacgtacatg gccgggttcg cgtagtagta cttcatggtg  59340
tttgtgacga agaggctcgc cagcgagatg atgatctttt tcttctcgat ctcgatcttg  59400
atgtggtcct cgaagcgctt catgttgtag gcgttggtgt cgtgcacgcg gatgagcacg  59460
cgcgagtccg acatgatgtc ctggaactcc gcgcgcgcgt cggggctctc ggcgggcgtc  59520
tccgcgggcc gcgccacctc cgcgcacacc gtcggcctag cgcgcggcgg cgtgcgcatg  59580
ggccgcgccc ccacgcgctg cgaagcgaaa aactccacgg cgcgagcctc gcccgcgtcc  59640
gcgtacgact ccaccaggta gttgcggctg cgcgtggtgc ggccgatggt gttcagccgg  59700
tgcagctccg cgaccagccg gcggtagtgc gcctccagct cctcgggcat gatggaggtg  59760
tacacctcgg tgagcagcat cacggtgtcg aagtcctcct tgccgcagac gcgcgtcttc  59820
acgaggaagt ggtgcacagc cgtcgcgata gagagccgca gcgtggactc ggtgacctca  59880
acgctggcgt ccttggtctt cttcgcgctc cgcgaggcca tgaacgagac gaggaagtcc  59940
gcgctgctgt tgagcacgat gaccagcgcg acgatgaagt tgaggttcag cgtcttcgcg  60000
gactggaaca gctcggtggc cgacgcgtgc acgtcgagca ggttcgcgga gagccgcagg  60060
aagaacacgc cgcgcttgat ctcggccgcg aagcgacgtt cgtactcctg ccggcgcgcg  60120
ttgatcgcga tgaggaagtt caggatgagc cggttgatgt tgtacttcac ggcccaggtc  60180
tgcgtcttca tgatggtgtc gaaggacatc acgatgttga agatgaagcg ctggctgtgc  60240
gagaagtagc tgtagggctc gctgaggaag atggacttgt tggtcgcggg cactaccacg  60300
cccgcgcgcg cgccggacgc gtcggtgttc aggtccggga tgttcatgcc gcagatgcgg  60360
cagtaggcca tgccgtcctc aaagtacacg aactcctcca cgaactcgtt gatcttggca  60420
aagtagtcca cgtccacgcg catcgcgacc gcgagccgga tctggtgctc gcagggcggc  60480
gactcgaagc gcacaccctc gccccagccc ggcggctcgc gcacgaccag cgcggtgcgc  60540
gaagccgggc ggaacttggc gtcgcgcgcg ttgagcagcg ccgggaagag gtcgcagagg  60600
tgccggctcg agaggaacac gtacttgtac agcagccggc gcgcgtccgc ggccatggcg  60660
tccacgaagg cgcggcccca ctccgcgacc gcgggctgct cctccgcaaa gttgttcggg  60720
tagaccttgt ccgtggccgc gaggaacacc ttcttcacgt cgaggaagtc gcggatcacg  60780
atggggacgc gcgcgccgtc gagctcgtac atgaacacgt agcgcaggtt gagcttgcgc  60840
cgcgagaccg ggatgccgat gtgccgacac aggtacgcga actcgaggta cttcttcgag  60900
```

aagcggatgc ggtccaggtt cttggagacg tactgcagca tgttgcgcat gttgaagggg 60960
atctcgcgca cggcgggctc cgcggcgtcg tcgaaggcgg tgcgcagatc gctggtgcgc 61020
tgcacgacca cggcttcgcc ggtggcgtcg tcgtgcacca gcacgttaac gcgccgctgc 61080
cggatgacca tgtcgaaggt gttgaagaac atctcgtaca tgctgtgccg agtgtcgtcc 61140
gcgatgcgct cgcccaccga gaggctcgcg gtggcgtcgt cgcgcacctg cttctcgaac 61200
ttgtacccga tgtaggagaa tatcgagatc agcgtggcgt cgtcggcgtc ggggttctgc 61260
tccatggtcg cgaagagcag gcggatgtcg tcctccgtga tcgcgtccac gttgtacagg 61320
ttgaccacga agatggactt gttctcggcg atgaagtcag tgtaggactt ggtggccgtg 61380
ttcgggtcgc gcatgtacgc gcggatcttc ggcacgatgc tcgcgaggat ggactccctg 61440
gaatccattt aaggacggca agggcgcgcg agaccgtctc aaaactgaaa tcgtataaac 61500
tcttaaaaaa ttggtattga aagtacgcac caccaaataa agcgtcgagg tcgggcatgt 61560
cttcgtggcg actcaaaatg agcaagtgtt caggttccag cagcgtccag actctcgagg 61620
atctgcgtaa tcgtcttcgc tccgaggcct tgggcaacga tttccaagag ccccgcgacg 61680
acctcttccc cagcggcgag gagtgtctgg acatcgacgg gccctgccct tgcgatgagg 61740
cggagcagga gatcgaccag gagcagttgc ctgtgcccga aaccgtgccc gaaccgccgg 61800
ccaagactcc taagcgccga ccagtgaaga aggataaggc agataaggca gataaagaca 61860
agtcgaccag aggcgcaaag aaaccgtgcc cttcggacga caaggatgac gagctcaaga 61920
gcaacgacgt cgacaacaac gaagagtccg gcgacacaga tggcggcgcg agcgcccgaa 61980
gccccagcga catcgacaac gtggacgaga tggacgactc cgacctcatg gtggcgttct 62040
ccaccatcct cgcagacttc aaggacatca cccaacgagt gaaagctctt tcgtccgtac 62100
tcacggacgt acaggcggcc ggcatacgca ggtgcttctc gacgctcggc aaggctctga 62160
cggaggcggc ccacatcgcc aacaccggag ctaagccagt caccgcgcct cgcaagaaga 62220
aggccgccac ctgcaagaag taggcgcact aaatagcgag gctcggtatg cgggcgctgc 62280
acctgtcaga cggcagactt ttttttgaca aggagctgac gcagccggtc cccgacgaca 62340
accccgcgta cgctgtcctc gcgaagatcc ggatcccacc gcacctctcg gatgtggtcg 62400
tgtacgagca ggacctcgag tccgcgcagc agggcctcat cttcgtcggc cgcgacgcca 62460
agggccgaaa gcagtacttc tacgggcgcg gacacgtgga gcggcgcacg gccgtccgca 62520
acgccgtgtt cgtgcgcgtg caccgcgtca tgaacaagat aaacgccttc atcgacgacc 62580
acctcgcctc cggcagcgag gccgaggcgc agatggccgc cttcctgctc atggagacga 62640
gcttcttcat ccgcgtcggc aagacgcgct acgacgcgag agcggcaccg tgggcatgct 62700
cacgctgcgc aacaagcacc tcgccgaggc cgagggcggt gaggagatcc gcgtcgcctt 62760
cgtgggcaag gaccgagtcg cgcacgagtt tgccgtgcgc gaggggcagc ggctcttcgc 62820
ggcgctgcgt cggctctggg acccgggcgc gcccgacagg ctgctgttcg accggctgag 62880
cgagcgccgc gtgtacacct tcatgcgacg cttcggcatc cgcgtcaagg acctgcgcac 62940
ctacggcgtg aactacacct tcctgtacaa cttctggtcc aacgtgcgct cgctggagcc 63000
gcgtccctcc gtgaagtcgc tcatctgcac ctccgtgcgg cagaccgccg agacggtggg 63060
gcacacgccc tcgatctcgc gcagcgccta catggccacc gcggtgctcg agctcgtcag 63120
ggacggcgcg ttcctggaca gagtcgccgc caccgacacg ctcgacgact tcgtggacat 63180
cgtcgtggac tatgtaaata actctgagca ggtaaatgga tgaggcgctg cgcgtggcgg 63240
cgcgcgtcgt ggacgggctc cggccgctgg acgtggccgt gtgtctcacg cagctgcgcg 63300
gagccgcgcc cgagcgccgc ttcccggcgc tcgacgagtg ctccggcgag gccttcctgg 63360
acttcgagtt cgccggcggg gacgtggcgt cgcggtacct ctccgcgcac acgcgcgagc 63420
tccgtgcggc ggagcggcgc gagcacatgg ccgcgatcgc gcgctgcgtc accgaggccg 63480
acctggcgct cgcagaccgc ccccggggca aggcgcgcgc ggcgctgcgc gtgtgccgca 63540
accgcgagaa agtcgcgcgc ttggcgaggc tgctgcgcga cgccgagagc agcggcgcgg 63600
acttcgcctt catacgcgcg gccgtggcgt agcaaaacgt aaaaacaaca cattccctaa 63660
atcgccatgg acgcgccaag tctcgactgc atgctcgccg cactcgcggc gaaggcgtct 63720
tcggtggacc gaggcgcccc cgaggacgag gtgcaccacg aagtggagct cgtgctcgta 63780
gacccgccgc tgtccaccct ggccgccacg ctgcgcctgg cctcggagac ggagtccttc 63840
atcctcttca cggtgaccgc gctcgccaag gaggagggca agctgcgcgc gcgcgtgccc 63900
atgtcgcgcg tcgtcggcct ggacgtgaag aacgtgcagc tggtaaacgc catcgacagc 63960
atcgtctggg agcgcaaggc gctcgtggag gagaccgcgc tgcaggaagg ctgtctgctg 64020
cgccactcca ccgagcggcg gcacctcttc gtggactaca agaagtacct ctcggccatc 64080
cgcgtggagc tggtaaaccg cgtgcgcgtg cgctccaaag aagtcgtcgc ggacttcaag 64140
ttcaagtact ttctggggtc cggcgcgcag gccaagagct cgctgctgca cgcgctcaac 64200
caccccaagg tgcggccctc gcccacgctg gagttcgagg tcgtccccgc gggcgaggcc 64260
gtggacgagg ccgccgtgct cgcggagctg cgcgccgtgg cgaaggcgct cttcatggcg 64320
cccaccgacg ccgtcttcct ggcgccgccg gccgagatgc cggtgcgcac gctcatgctg 64380
cagaagcagg agatccccgc gctagacctc gacggcctct tcgcggtctc caagacggac 64440
ggcgtctctg cgagcgtgcg cgtggacgag gacggcgtct tctgcgcgtt ctcgcacctc 64500
gcgtacacca tccggtaccc gctcgcgcgc aaagtgcagg gccggtaccg gctctggtgc 64560
gaggccgtgc ggcccgtggg cgagcgcgtg tggtccatgt tcgtgctggt cgtggaggag 64620
cctgcgggcg atgaccgcgt cgcggccgtg gccggcgccg tggaggcgct gcgcggcgtg 64680
tgtgcgcgcg tcgagttcaa acccaagcgc gtggacgggc ccttctcggc gacctccgag 64740
ctggtggagc acatcaagag cgcgctgcag acggagccag agggcgtggt gctcttctac 64800
gcgcgcggag agaagtccaa gcgcgacctc aaggtcaagc gcgacaacac ggtggaccag 64860
accacgaacg tgatgttccg gtacatgtcc agcgagccca tcgtcttcgg cgagggctcc 64920
accttcctgg agttcaagcg gtacagcaac gaccgcgggt tccccaagga gtacggcgcg 64980
gggcgcatct tcctgcgcga ggacgtggtc taccacaaca acatctactg catcgagttc 65040
acgaagacgc acctggaggt gggcctccgc agcgtggtcg tgcccgtgaa gttcatcggc 65100
gagttctcgc aggaggggta cctgctgcgg ccgcggctgg ccaaaacgga gtgctacttc 65160
cgcaacccct cattctacgg gaaccagcac tcggtggtgc tcgagcacac tcgcgaccag 65220
ctgctctcgg tgggggacgt gttcgacgag agccgcatgg ccgccgtcgg gcagacgctg 65280
gccaacgacg ccttccgcct gaacccggac acgccctact tcaccaaccg acgcacgcgc 65340
gggccgctgg gcgtgctctc caactacgtg aagacgctca tgatatcgct gtactgctcg 65400
aagaccttcc tgaacaacgc cgagcgacgc aaggtgctgg ccgtggactt cggcaacggc 65460
gcggacctgg agaagtactt cttcggcgag atcgcgtcca tggtggccac ggacccggac 65520
gcgcgcgcga tcgagcgcgc catggagcgc tacaaccgcc tcaacgcggg gctgaagtcg 65580
cgctactaca agtttaacta catccaggag accatccgat ccgagaccta cgtggagagc 65640

-continued

```
atccgccagg tcatgtactt cgggcgcttc aacatcgtgg actggcagat ggccatccac  65700
tactccttcc acccgcggca cttcgccacg gtgatgcgca acctgcgcga gctcaccgcg  65760
cccggctgca aggtgctcat caccaccatg gacggggact tcctgtcgac gctctccgag  65820
aagaccagct tcgtgatcaa ccgcaacctg caggagagcg aaaacttcat gtcgatcgag  65880
cgcgtggccg atgaccaggt catggtctac gcgccctcga ccatggcgca gcccatgacg  65940
gagtacatcg tgcgccgcgc ggacatcgtc aagctcttcg cggacaacgg cttcgacctc  66000
gtggaccacg cgaacttcga gaccgtgatc cggcgcagcc gccgcttcgt cgagggcgtc  66060
tcgcggctgg agacgcggcc ctccaccaag aacttcttcg agctcaaccg caacgcgctc  66120
acggagatgg acagcaccga cgtggccgcg ctgctaaaga tctacgtgct gtacgtcttc  66180
agcaagcggt aggcagaacc agggcgtcga ttccgcgccc gcgccggcgc ggaaggcgtt  66240
gaacagctcc gccagccagg ctgcggtctc gcgcgcgtcg atcgggccgc cgtcgtccgg  66300
cggcggctcg cgcgccgcgc gcaacaccag cgtctccgcg ggcggcagag gctccagagc  66360
ctcgaagacc gcgcggctcg ggaacagcgc gcgcatcatg cgcgagcggt ggccgaacac  66420
cgccttgacc gcgcgcagtg ccgagcggtt gtccagccgc agcgctcggt caaaacgatg  66480
cacgcgcgcg ggcgcgccgc ggtggtcgcg ctccacgagc acgtgccgcc acgccagcgc  66540
cgcgccgacg cggtccaggc tgggcgcgag cgccaccagg cttttcagct catgtaaatc  66600
tccgcgcatg gccgacggct ccatttacta ctgcggagga acgcacgtgg tcgcggccgc  66660
gccgggcgcc gcgcttgtgg tgctggacgc gcccggagcg gtagcggcgg ccgcgcccgc  66720
ggggcagcgc gtcttcttcg ccgagtacgg cctcgaaaag cgggccaacg gcccgatcac  66780
ggcgcggctg cgacgctccg ggttccgcgg cgccgcgaac gcctgggcct ccgtggcgga  66840
cttcgaggcc ggcggccgtc cctccgcgtg gacgctgcgc gcggaggagg cttcgcgcgt  66900
accgctgccg acggacgcgg cgctggtcct ggcctggggc gcgcgcgagg agccgctgcg  66960
ggcgtgcgtg ctggcgcgcg cggcagacgc agaggcgccg gtgggcgccg cgctcaagga  67020
agccgccttc gacgcgcggg cgccggcggc cgcgctgttc gcggcgctgg gcgcgcccgc  67080
gctcgcgccc ccgctgcggg cgcggctagt ggcgccgccg ggcgcgccgc cgcggacgcg  67140
gctctgcgag aacccggcca tgctgcgcgc gttcgcagtg ggctggttcg gcgcgcagct  67200
gggcgaggct tccgaaaatg aaaaggtatt tgccgccttt gataaggcga ggtcgtgttt  67260
ggacgaccgc tgatggcgac gcccgcgaac gcacccgcgc tgctcgtcgc ggtgctgcga  67320
caccgcccgt accgcgtgga gtaccacccg gactgggagc cggtcatcga gacgctggtg  67380
gacgagtacg acgcggtcgc gccctggctg ctgcgcgacg cgacgagccc cgagcccgag  67440
cgcttcttcg cgcagctggc gaagccgctg gcggacaagc gagtgtgcgt gtgcggcatc  67500
gacccgtacc cgcgcggcgg caccggcgtg cccttccagt ccccggactt cagcaagaag  67560
accatccgcg cgatcgcgag ctcggtcgcg cgcacgaccg gcacgcaggg ctacgcgaac  67620
tacgacctgg acgcggttcc gggcgtgctg ccctggaact actacctctc ctgccgcgag  67680
ggcgagacca agagccacgc gatgtactgg gagcgcatct cgcggctgct gctgcagcac  67740
gtggccaagc acgtgagcgt gctctactgc atggggcgca cggacttcca gaacgtgcgc  67800
gcgcgcctgg acgtgccggt gacgctggtg gtgggcttcc accccgcggc gcgcgacggg  67860
cagttcgcgc gcgagcgggc cttcgaggtc atcaacgcct tattggagct caacgggaag  67920
tctcaagtgg actgggcgcg aggattttct ttttatagtg aaaattaatc cgtggtccta  67980
aatggcggcg cccatatgcg ataactctca cgtgttcctc ctcaagcgcc tgggcgtgcc  68040
```

gtcttcctgc cggcgctcgg aggacccgcg cttcgtggag atcctgactc ccttcgagct 68100
cgcaaactac atcgagcggc acccgggatg ctgcctcttc gagacgctgc gcgacgagga 68160
ggactgctcc gtcgtgcgcg tcttcgcgga cgtggacatg gacagcgtgc tcgaggagga 68220
ggacttcgtc gcggcgctgg aggacctcat cgtagagctc gcggccttct tcgaccgctt 68280
cgcgagcggc tcctgcggca ccgtgcccgg cgaggtcaag cgcgccatgc tcgcgaactt 68340
ctcggtcacg cgatccacgg ccgagcacaa gaccagcttc cacctgatct tcacggagac 68400
gtacaccacg ctggacacgc tggtggcggc gaagcgcccg ctgctggacc tgtgccggcg 68460
ctcggacaac gtgctgctgc gcgcgctgga cacggccgtg taccgccgcg gcgcgacgct 68520
gcgcgtggtg ggcacgcgca agacgccgga gtcgagcgcg gtccactgca tgcagtcgcc 68580
cgacgacgac atcaaggact acctgttcac gttcgtggag ctctcggacg cgagcgtgta 68640
cttcgagctc gcggagcgcg agcagcacac gctgagcacc gtttgctggg agacctccta 68700 catcccctc ggcgacgcga tgcggcgcgt gtgccaggcg gtggtcaacg acatcgtgaa 68760
cctccgcgac atcaccgagg acaacttcct cgacacgccg ctggtcatcg actacgcgac 68820
gcgctgcgcg ctgtgcaaga agcccaagca caagcacgcg caccacatca ccatgggcaa 68880
cggctgtctg cgcctggtca agggcgggaa cgcgcacagc tgcaaggtca agatcatcca 68940
gctcgagggc aaccggctct tcacggccgc gcagatcatc atcgcgtccg aggtcgtgaa 69000
gctcaccgag cgcaacgact acatcgtgtg gctgaacaac tcctggcgct tcagcgcgga 69060
ggagtcgctc atcaccaagc tcatcctgga cgtgcggcac tcgctgcccg cggactacgc 69120
caacgacatg ctgtgtccgc gcaagcgcaa ggtcgtggaa accaacatcc gcgacatgct 69180
cgtggacatc tccgagacgg acacgcagta cgacaagctg cccttcacga acggcgtgct 69240
ggacctggcc acgggcgagt tcctcaccgg cgaccgcgcg aaggcctgcg tgtgcacggt 69300
ctccaccggg tacgccttct cgcgcgagga gttcgcggcc gcggcggact cggaggccat 69360
gcgccggctg gttggcgtca tcgacgacat ccagccggac acgcccgaga acgccgataa 69420
ccgcgcgctg tacgagcgcg ccatgtccag cgcgctctgc ggcgccacga agacggtcat 69480
cgtcttcttc tacggcgaca ccatgaccgg caagtccacg agcaagcgtc tgctcatgtc 69540
cgcgctcggc ggactcttca tcgagaccgg gcagaccgtg ctcacggacg tgctcgacaa 69600
gggcccgaac cccttcgtgg ccaacatgca cctgcggcgc gcggtcttct gcagcgagct 69660
cccggacttc gcctgcaaca acgcgcgcaa gctgcgctcc gacaacttca agaagctgac 69720
cgagccctgc atcgtgggcc ggccctgctt ctccaacaag atccacaacc gcaaccacgc 69780
caccttcatc atcgacacca actaccgccc ggtcttcgac cgcgtggaca acgcgctcat 69840
gcgccgcgtg gcgctggtgc gcttccgcac gcacttctcc tcgtcggcca ctcgcgcggc 69900
cgccgcgcac aacgtcgagt acagcgcggt caaggagatg gacgagagcc tggacaccaa 69960
gatccagcgc aactacttcc gctacgcctt cctgcgcctg ctcgtgcagt ggttcggcaa 70020
gtaccacgtc ccgcaggtct cgctggcgcc cacgcccgac gcggtacccg acttcgcctt 70080
ccaccgccgc gtggccgagc tggtggtggc cagcaacgac gcgcaccgcc gcgcgatgga 70140
gtcgctgtcc aagctggggt acgtgctcgt gggcggcaac gtggccatgc ccgcggacgc 70200
cttccggcag cggctggccg cgcacttcaa cgcgcgcgtg cacggcggcg acatagacgc 70260
cttcatgttc aagcacaaga aggtcgtcaa cgtaacggag gagtacgtgg agtacgtatt 70320
catcgaagat gtcgagaata aataggcggg catgaactcg gacgtgatca agctcttcgc 70380

-continued cgggcacgac gagtccgtgc ccggcatcct gccgcaccag ctcgcgaccg tggacttcct 70440
gatacgccgc gttctagacg acaacgtcag cgtgcttctc ttccacatca tgggctctgg 70500
gaagaccgtc atcgcgctgc tgttcgcgat ggtggcctcg cgcaccaaga aggtgtacat 70560
cctggtgccc aacgtgaacg tcatgaacat attcaactac agcatggtca tggtcgctaa 70620
cctgttcaac gcgcccttcg tggccgagaa catattcgtg tactcgacga ctagtttta 70680
ttcgctaaac tgcaacgacg gcgtcataaa ctacaacggc ctcggcaagt acgagaactc 70740
ggtcttcgtg gtcgacgagg cgcacaacat cttcgggaac aacaccggcg agctcatgat 70800
ggtgatcaag aacaagacgc gcgtgccctt cctgctgctc tcggcctcgc cgatcacgaa 70860
cacgccgctc acgctcagca gcatcatcag cctcatgtcc gataaggacg tggacgtcgg 70920
cgacatcgtg gtgcagggca agaaggtgtt ccagatcctg ctgaacgagc acggcgtgcg 70980
cgtgatccgc gaggtgctca aggggcgcat ctcctactac gagatgccgg acacggacat 71040
gcccgaggtg ctctaccacg ggcgccgctt cctggacacg cgcgtggtct actgccgcat 71100
gtcgcgccgg caggaggacg actacctcac tgtgcgccgg ctttgcaaca acgagatgtt 71160
cgagaagaac atgaacaacg tgtccatggc ggtgctgggc ccgctgaacc tggtgaacaa 71220
cctggacgtg ctcttccagg cgcaggacaa ggacctgtac ccgaacctgc gcatcagcaa 71280
cggcgtgctc tacgggaacg agctcaccaa gctggacatc agctgcaagt tcaagttctt 71340
catctcgaag gtgggcgcca tgcgcgggaa gcacttcatc tacttctcca actcgaccta 71400
cggcagcctg gtcatccgca acgtgatgct cagcaacggg tactcggagt tcggcggctc 71460
gcagagcaac aacccgcaca ccacgcccga cgggcgcgcc aagaccttcg cgatcgtgac 71520
cagcaagatg aaggcctcgc tggaggagct gctcgaggtg tacaactccg cggagaacaa 71580
cgacggcggc gagctcatgt tcctcttctc ctcgaacatc atgtccgagt cctacacgct 71640
caaggaggtg cggcacatct ggttcatgac catccccgac accttctcgc agttcaacca 71700
gatcctgggc cgcgccgtgc gcaagttctc ctacgcggac gtggccgcgc ccgtgaacgt 71760
gtacctcatg gcggcggtgt actcggactt cgacgaggac atcgtctcgc tggaggacta 71820
cagcgtggag gacatcaacg cgctgccctt cgacgtgaag aagctcttct acctcaagtt 71880
caaggccaag gaaaccaacc gcgtgtacgc catcctgcag gagctctcgg acgcgtactc 71940
cgcgcgcccg cacccgcagc tcgtggacgt ggtgctgggg gagatcgtgc gccagttctt 72000
cgcgcggcac tgccgcgtgc ccgccgagga cgccgcgctc gtggccgccg tcgaggccgt 72060
tctcggcacg cgcgaggcag cggccgagta catccgcgcg atagtggacg gacacttctt 72120
cgtgaccaac aagaccttcg ggaagtgcct gctcttccgg cacgagcgcg acatcgtgac 72180
cgtgcccttc gagctcgagc acgacccctt cgcgtgggcg atcaacttcc gcaaggaggt 72240
cagtgtggtg aatatataac ggcaaacata aatagaaaga ccgtcctcgc gcgcgatgtc 72300
gaccttccgg cagacggtgt acctggcggt gacgctgcag ccgcacgagc tcacgctcga 72360
cttccgcggc aacgtcgcgg aggcggtcat gcgcgagtac ctctacaagg agaagggcgg 72420
gctcatggcc accgacatcg aggtctgcct cggaaacgag atgccgctgg ggcgcatagt 72480
gaacaacgcg gttgtggtct cggtgccctg caacgtgacc ttcaagtact accgcgtcgg 72540
cgacaccgtg agcggcacgc tcaacgtcga ggacgagacc aacgtcttcg tggactgcgg 72600
cgacctcatc tgccagctcg gcaagagctc gggcggcgtg accttcaacg agtccaagta 72660
ctgcctcgtg cgcaacggag tcgtctacga gcacggcagc cgggtctcgg ctgtgctgcg 72720
cgaggcgcgc tccggacgcg agtccgcgtt cgtgttctcc gcagtgctgc tggacggcgt 72780 cccgccgag gagaaggacg agaagaagga cgagggcgag aagcccgcgg agaaggagac 72840
gcttgcgagc cccgccgcca aaaactagca ttattgggcc gcgcgaacct tcgataaatg 72900
cgcacgtaca cgtcgctgct ctcgaagctg ctcaagagca accggcggct cgggagcacg 72960
cgcgtcttcc gcgacccgct gcagcacatc agcgcgaccg cctttgtgca ccggcgcatc 73020
gaccggcacc ggcgcgtctc catctgcgcc gtgctcacca ccaccgacgg gctcgtggtc 73080
gcgtgccggc gccggtactc ctttttgtcc tccgagctcg cggagacgcg ctcgcccgcg 73140
cggcgcgtgc tgctcgcaac caagcacgcg gacgctctcg cgcgcctcgg cgccgcgcgc 73200
ccgcgcgacg acgtcatgtt tccgggcggc gcgccgctgt ccggggagtc gccgctggcg 73260
tgcgtgctgc gcgaggtcga ggaggagacc gggctgcgcg gcgaccaggt cagcgtggac 73320
gagcggctgt tcgtgcacgc cttcatcgac gacctggtct cgggccgcga cttcgacgcg 73380
atcatcttca cgggcgcagt cgcgctttcg agcgcggagg tggcgaagca gttccggccc 73440
aacgacgagg tcaaggggct ggttttcctg caccccgagg acgcggaggg cgtggggtga 73500
tggcgcggct ggcggcgttc gcgcgctgcg cggcgcgcct gcgctgctgg ggcgcggccg 73560
tcacgcgaga ggcggggtcc accacgtaca cgaggcgccc gccgctcacg cgcacggtgg 73620
gcgggtcgcc cagcgcggtc aggaagttcc cgtcgtcgtc gaagaggcgc ccgccgcgct 73680
cgaggaagcc cttgcgcacc gtgaccagcg ccgtggaggt ggagtaccac acgctctgcc 73740
cgtccgcgag ccgcgccgcg cgcgcgggcc cgcgcgcgtc cgccgggcgc gccaccagcg 73800
cggaccagcc ggagtcgtcc tccagcggcg cgaagtccgt gaaggcctcg cgcacccact 73860
ccagcgagca gcgcttgagc acgcggaaga gctgcgtgaa ctgccgggac ttgtcgcgga 73920
tgagggccag caggtcctcg tccacggtgg cggcgccgga gtcctggcgc gcgaccacga 73980
agtgcacgtt cacgtagcgg cggtcgggcg gcgtcatctc gtggctgttc aggcgcaccg 74040
cgcggcccac gatctggcgc agcgaggcct cgttccaggt catgtccagg atgaagatgt 74100
cgttgatgga gaggaagctg aggccctcgg agccgctcag cgagaacacg cagaccttga 74160
tcttctcgcc gtcggtgttg tcgcaggcgt tgaaggcgtc cacgagcttg gcgcgcgtgt 74220
cgcgcgtgcg cgaggagaac tccacgctgg agacgccgaa ggcgcggaag tagagcagca 74280
gcatctcgat gccggtcacg ttgacgaagg gctcgaagac cagacacttg cccggcgagg 74340
ccaggatgcg caggcagacc tcggtgtact tgcagctgcg ctcgcgcagc tccgcgagca 74400
gcgagacgtc cgcggaggtc atgcggtcgc cgctgacggg cgcgccgctg cggaagagcc 74460
gcatggccgc ctccgagaag acgcggtcct tgacggcgcg cgcgaagtcc aggaagagcg 74520
cggccacggc ctcgtcgtac tcctgcttgg agagcacgga cttgtcgggc gcgtcctcga 74580
aggcgaaggt ggccgcgatg cgccggtaca cgcggaatac cgcggcgccg gacttgcgct 74640
ccatggcggc cgcgcggcgg taggcctcgg tctgcttcgc ggtcatgtcc acgtacatca 74700
tgcgcacgcg cttgcgcgcg aaggcggcgg agccgtcgac gtcgtcgaag atggaggcct 74760
cgttggtgac taagtacgag cacaggccgc cgagcttgtc cacgaggtcc tcggggttcg 74820
cgagcgcgcc gccgttgaag agcggcgtct gcccgaccac gccggggcgc agcaggttca 74880
cggccatgga gaactccttg acgctgttca ccaccggcgt ggccgtgagg cagagcagct 74940
tcccgcggcc catggggatg ttcttcgcga ggtagttgta caccgtgcgc gcgggccgct 75000
ggcgcccgtc ctccttggtc agcgacatcg agatgaagtt gtggaactcg tcgatgacca 75060
cgcagacgcg gctgctcgac gaggcggtct tcatcagcgt gaagaagcgg tggtggaagc 75120

-continued

```
gcgggtcgtc gtagttgatg aaggtgcacc cgggcacggc ctcgggcgcg aagcgcatca  75180
tcgtcgaggt ccagggctgc tccacgagcg ccttcttcac gagcacgacc accgtccagt  75240
ccgtgaagac gtcgcgcagg tgcttgagca cgtacaccgc ggtcacggtc ttgcccacgc  75300
ccgtctcgtg gaagagcagc agcgagtgca tgctgtccag gcccaggaac acgcgcgcca  75360
cgaagagctg gtagtccttg aggcgcacgg actcctccac gccctgcatc tcggagggca  75420
tgtgcgcggt gcgccgcagc gcgtagtcga tgtaggccgc gtgcgcgctg gtcatggcga  75480
cggtcggcgc tccttttacg ggtctgtcg tctatctatt gtcggcgcgg gtctgattta  75540
ggggcagtag ttacaaaaac gtttccgctg ctcggcgcgg cgtttggagg agcggttgcg  75600
gccgcggcgg cgcagccgcg cgcggcgcgt cttcgtggtg cggtggccga accagcgccg  75660
gtgcatgacc gggtgcgcga ccgcggccgc gcgatccgcg ctcatgcagg ttgcgtaggt  75720
gcggcacatg ctgcgcagca cgcgccgcgt gcgccgctcc acggcgtcga gccgcctcgc  75780
gacgatggga aagagccggc gccagccgcg cacggcgaag agcgggcgct cgcagaccgg  75840
gcgcgcgagc gcgtggtagg cgcccagcag ccgcgggtcc agcgagcgca cgtaggtctc  75900
cacgaagccg ttgccgaaga cgatggcctg cgcgcagagc gggttcgtca tctccctctt  75960
ggaggcgatg gcgtcgccca cgaaggcgcg cacgccgcag tgccgcagca ccaggcgccg  76020
ccgcgggaag tgcaggtgcg ggccgagcgc cgcgcgggcg gcggggatgt gcagccgcgg  76080
agaaaaacgc gcgcgtcccg ccatggcatc gaagcgctcc gtctgttttc agttatagcg  76140
ccgcgggcgg ctactgcagc agcagcttga gcttgcgctg actctcgttc tcgatgctct  76200
tggactcgga ggtcatgctc tcgtagagca gcgagtgcgt gacgtagagc gcctcgtaca  76260
cgcggctggc gaaggccacg aagcggtcca cgaactcgct ctctacgggg tccttgagca  76320
cgcggaaggg cacggccagc gcgtcgcgcc aggcggcggc cttggtgcgc tcgcgcacgt  76380
gcgccacgaa ggcggcgatg gccgcgcgcc gcggctcgct ggcgaccatg acggcgctgt  76440
cctgagccag ctgtcgctca cgcacttgaa gaggcgcacg gtgccgaaga ggctgcagta  76500
cacgcgcagc gcgtgccacg tcggtgccga agagcgtggg cagcttgagc accacgaagc  76560
gctcctgcgt gatctcgagc agcgggcgca tcacctcgaa ggtgatcgcg tggtagtcgg  76620
ccacgtagag gttgttctcg gtgaggtggt tgttggagcg gatggcgccg cgctccttgc  76680
ggtagagccg gttgcgcgcg ctgaggtcga gcacgaccgc gtcggccttg ccgcgcgctc  76740
tggagcgcac gctggtgatg ccgtgcgcct cgagcacctt ctcgacgtcg cgctcgtcga  76800
tcatgaggtc gtgcgtgtac agactcagca tctccgtggg catgcggttg atgtcgttca  76860
cccgcgagca ctgcaggaag tagttggtcc cgtaggccag gctgggcagg tgcccgacgc  76920
cgagctgcag gtccagcgcg ggcgtcgagt cgaaggtggg cagcgtcacg ctgagcccct  76980
cgcggatgct gcggcgcacg gcctccaccg cgtccatggc cgatttattg gacgcacagt  77040
ctgttttcat ttcgcggcta ctgcgcagtc accttctcgg ccacgatccc cgcgtcgtag  77100
ctgagccggt acacctcgtt gcacaccacg accatctgcc gcggcacgta catgagcggg  77160
ttgtgcgcct ccatgtgcgc ggtggtcacg cgcaccgcca gcttgtcctt gcccctggag  77220
acgttggagt tcagcgcggt gggcgagaag aaggtgctgg gcgtaaagtt gaactgcagc  77280
gtgcgcacgc cgggcgtctt gccgaggatc tcgccgaaga cgcgcgagac tgcgctgttc  77340
tccgagtaca gcacctcgtt gccgaagcgc acgtccatgc gcgcgatgac gtcgatcttg  77400
ttcttgaagt ccacgcccctt gaggaagggg tcggccacga agaggtcctt ggcgcgcgcc  77460
tccggcgagc ggttgtcgcc gttgtacacg ttgcgctggc aggtccacac gcccacgggc  77520
```

```
acggaggcgt cgccgatgtt cacggagtgg atggcggtcg tgaagcggat gcgggaggtc  77580
gcgcggctgt aggcccccgt gatggcggag aacttcttgg acatgttgta cacgacggag  77640
ttcttcctgg tggcgaacac taggatgttc gtgtgcagga acacgcgcat gcccacgggc  77700
acgtcgtcga tgcgcacgaa gacgtcggtg tcctggatgg acacgacgcc cgacgggggc  77760
acctcgacta tctccgcggt ctcggggaag ccctcggggt agcagttcga gacgatcacc  77820
atgtcctcca gcaggcgctc cacgaaggcc atcacgaagt cgccctcgga ctgctggaag  77880
ccggggtacg atatgaagcg gttgttggcg tcgctgagca cgggcttcat gtacacggac  77940
agggaggtgc acgcgtgcac gtccgtgatc accgcggtgg tgtggttgat ctgctccacg  78000
cgccgccgcg gcatctcgat gaaggccggg cgcgggcaca ggttcttgac catgtagccg  78060
atgaagctca gctccatgga gtaggggaac tccttggcga gcttggcggc gtcgaaggtc  78120
tcgtcgtaga ccatgacgca ggcgacgggg ttcagcgtga ccgtgaccgt gaccttgctg  78180
tcgctgagct tgagcgtgct gaaggtcttg tccgcgtcaa agggcgtctt gatgtaggcg  78240
tgcacgcagg cggcctcctt gatgacgtcg ttgggcgagc tcccggtgga gaggtcgttg  78300
agctcgcgcg agaagcccga gagctccatc acgcgctcgt tgtccaggca ggagtcgaac  78360
agctcctcgc cggaggtctc ccagatggtg tccgcggcgg agttcacggc cacgtggcgg  78420
atgagcttgt acgcgatgta gggcacgtag cacatcttgc ccacgccctt tatctcgggc  78480
aggtccacgc tcagcacgaa gttgttcatg gccgagatgt acttgtcgcg gatctcgaag  78540
gtcacggtga ccgcgtcgct ggtggtgtcc accacgccct gcgtggtgat gtactgcggc  78600
atgtacaccg tgggcgcgcg gtggtccgtg gcgaacacgc tggcgcgccg cacggcgtcg  78660
tcgccgccca ccaggctcac cacggagtta ttcatttatt ccctgggaaa accagttaaa  78720
taaggctctt cagagccatg cgcaccgtcc ggccgtcggg ctccaggtag cagcgcccgt  78780
agacgccctc cgtggcgcgc gtctcgttga tgagcgcgcg cacgcggtcg gggtccgcgt  78840
acatctccag cggcagcagc tcgatcttgg gctcctcgcg cagcgcgacg aggtgccgga  78900
tggagcccgc gaaggagtcg cggcacagcc gcgagcagaa ctcgcccacg gcgccgccgt  78960
cgagcgtctc cacggccagc gcggccgtgc ccacgcgctg acggcagaac cagcacgtgc  79020
cgtccgcggc gcgcagcgcc agccgctccg cggacaccgt gttgaagtac ttcggcagca  79080
cgtactcgat gcggcacgcc gccggcggcg cgcaggccga cgcccgcggc gcggatatgt  79140
ccacccgcga gagcgcgatg cgcttcatgg gcggcggtgg atgctattta tgtcgcccgc  79200
ggcttttcaa aggtcgagcg agcacgccgc gaagcgcgcg ggcgagaaca cgtactcgtg  79260
gccgaactcc gggatctgcg cggcgcgctt gcgcgcgcgc atgtgcgcga ggaagttctc  79320
ccaggtgagc tggttgctgt tgttcttcgc gtagttcttc acggtctgcg gacgcaggtt  79380
gcgcgtcacg cccgtgacct cgaagatctt gtccaggaag aaggagtagt tgatggtttt  79440
ggtgggcgtg atctcctggc agaagaagac cagctgcttg aatatctcga tgacctcgtt  79500
gatcttctcg gtgctgaggt ccagcttctc gtttttgacc tggttgatga tctcgaagac  79560
cagcttgtag tccttcttgt tgatcatctc gctgtccttg aggaagctgg agacgtagtt  79620
ggcgtccacg tcctcgggcc ggatctggtg ccggtccatc atcgcgcgca ggtcgcggat  79680
gacctcctcc gagcactgct tggagagcag ccgccggagc acgttccgca ggtggatgag  79740
cttgttcgac acgtggaagt tggacctctt ctgcacgcgg atgcccatgg gaaacacggt  79800
ctcgcagaac aggcagaact cgtagtccgc gtcggacacg agcccgttgc ggcggcagcc  79860
```

-continued gccgcacatg cgcaggttca tgcttgctcc agccccagca cgcgcaggat ctcgcggtcc 79920
agcactttag tgtccagcgt gcgggttcta cagaactgga ggaagcccgc gagcgcgcgc 79980
gcgcgccctg gctgcgagag cagcagcatg cgcgcgttcc cggggtcctc gttgatgaag 80040
cgcgtgaggt tcagcgagca ccgcgtgcag cgccgcggcg ggtcgagctc gaccgagtac 80100
gccgcgaacc agacgttgtc gcccatgtat tatttattaa cacagaacgt cgcacatgtt 80160
gcgcgaggac atgtacgggt cgtactcctg cccgtagatg aggatggtgc agtaccgcga 80220
gatcatgagc atggcctcct ccatggtgag caggtcgtcc tcgaacatgg ccttgtgctg 80280
catgtgctgg ctctgcttgg cggccatcgc ggccgcgccg tcgccgcgca gccactcgtt 80340
cagacactgg ccgtcgccgg cgccgctctc ctgcgcgaag gtgttgcgca tggcgcgcat 80400
gagcctggct tccctggccg agcggctgag cacggtcatg gggtcgtaga gccaggggcc 80460
tgcgtccgtg aacaggatgg tgcagtaccc gttggcgaag gcgtccgcgc cgctgcagtt 80520
gtcgatgccg tcgccgaccc tgtagcacac cgcggagacc agccggtaca tgatgccgtt 80580
gagcatcatg tcctgcgaca cctcgatggg aatgtcgctg atcacgggcc gcatgttcgt 80640
gaagcagtcg cccgtgctgg ccatgccccc gcgccggttc accaggaaca ccagcacgcc 80700
gttcgtgatc acgggcgcgc ggtcgcgctc gtagaggtag ccgctcgccg cgcacacggc 80760
ggacgccacg tccgtgcgag agaccgcgcc catgttctgg gcgggcatgt acagcactcg 80820
cccggcctcc gcggtgcacg agaagggctg ctccccgccc acgtggatgg gcgccgtcga 80880
tgtcgtgatc atcttgctgg agtccaccac caggtagggc accgtgtgca tggccatgtc 80940
gcccatgccc ccgatccccg ttccgaacga cggccgcgac acgctcacga gcgtcggctt 81000
gaacgagact atggagaaga tggaggccaa aatctgctcc tcgtcggtca tgatggaggc 81060
gcacgagggg tggatgatct tcattagggc gttgtcgatg gactcgtcgc tctcgcagta 81120
gaagacgccc atgcggaggt tcaggatgca ccgccgcagg ttggtgtgca gcaccgcgcg 81180
ctggatctcc atggacacgg agtcgccgac gccgggcatc acgatgggcg tttcctcggt 81240
gagcttgttc accagcagct ggtagttgtt gggtcgcacg cggctgttgt ggtggagctg 81300
cgccaggagc gagaggctgt ccccgttgac gaacgcggac tcgatggccg gcagctttac 81360
gccgaacagc gccatggcga tggggtgcac gaagcccacg gagtcggacg acttgaacga 81420
gaagagcagg tcgcccgagg agctcatgtc tttgaagtgc acggactgga actgcgtggc 81480
ggagagcaag ttctggtagc tggacatgct ctgcaggtcg tcgatctcct tcatctgctt 81540
gtttacgcgg gtcgagttcc tcccgtagat gatcaccagc gggtgcgtct ggctcacgga 81600
tagccccgag tccgtcatgg cggcgcgcac gctgttcagc agatcgaaca gctccgaccg 81660
gtctctgttc tggatcccga cctttgccat cacagacatg agctcctgga tggtcatgtt 81720
cttgtggtct cggcgcgtgg accgcaggta gtcggcgatc atctcgcctt ccttacggat 81780
cttcatctgc cagtcgtgca tggaggtcat gcggtccaca ggcatgagca cgctgtcgga 81840
ggacgactgc gcggcgctgc cggactggcg cgagccaggg cgcgcggacg acgggcgcgc 81900
ggagctgccg cggctggagg aggacctgga cctccgcgag gatcttcgct gcgaagagct 81960
gcgcacgggc cgctgggcgc gcgccccggc ggaaaccatg tcctcgcggt ttatgcttag 82020
gagcgagctg cagaccgcgc acgacagcga ctgttttgga atgtggatgt ggtcgcactc 82080
cagtgacatg cccgcattgt cgtagcccgg gaccaagtcg aactttgcgt taaaaaaatc 82140
tgatgcgcac gcgggcgatt ccatttatac cgggagtttt tatgaggtgc cggtattatc 82200
cacgcgatct cgcagtgtgc tgggagtatc tcgcgtagcc gcccccgtga gcaaacgacg 82260

```
caagtcgttg atggccgact gtgttacgga cttcgccgtc tcgatgtcgc gcgtaaggct  82320
gagcgactcg gcgttgaggt cgcgcacgct gtccgcgatg tcggccagct ccttttttgat  82380
gaaatcctta tcattatcgg cgttgatgac tttgtccggc actctagact ctagaaccgg  82440
tgacgcggcg ggcgccttga tcgtcgggca gctggacgcc gggtactggg gcggcggcaa  82500
tgattgctgt aggaagacgg gcttagcggc aggcgccggt tttgtcggca agggcggcgc  82560
cggcgggcac tgtcgtgtag acggcgggca cgccggcgcg gggcacgccg ccggtggcgg  82620
acatgtcggc gcagttgcgg gtggacacgc gggcgcgggc gccggcgcgg ggcacggcgc  82680
ggcaggcgca gggcacgcgg gagccggagc tggagccggg cacggcgcgg caggcgcagg  82740
gcacgcggga gccgggcacg ccggcgcggg aggacatgcc ggcgcagcgg caggacagac  82800
caccgctgtc gcggagcacg cggcaaccgg cgtggagcac gcggcgggca ttacgttcag  82860
aggcgtcgac tggaccttgg caccacgggg cagtagcgat ggcgctaggg gcgactgtcc  82920
ggtggttgga cgctgcatgc aagcaatcgc agatttcaga cgggactggt aatacctgcc  82980
cgcttccttc accgtgtact tgtcgacgga gtctacctcc tcatcgggag gacatggctg  83040
ctccggtgcg ggaatgactg cttgaggaca cttggtgaac agactggagc tggtctccgc  83100
tagcaccagt ttagacttgg ccaagtcgga ggcaaacttt cttctgagat ccatttaagc  83160
cttcaaaatt gaacgtgtac gccgaccgct aaatggaaga atcggtggcc gtcgagtacg  83220
cggacgagga cgaggatgag attgaggagt acgaggagga ggacgaggac gaggaggaag  83280
agtctgccga gggcgccgcc gcctcctcgg tcagcgacgt agcgctctct gccgccgaga  83340
agctggtggc ctcggaggtc ccggacgacg cggctgccgc ggacaccaac gtgcgtcaac  83400
gcgtcaccgc gcgcgtggag gagcttaagg cgcgctacac acggcggatg agtctatttg  83460
agctcaccgg aattgtagca gagagtttca atcttctgtg tcgcgggcgg ctgccgctcg  83520
tggcggacgc cgcagacccg gcgctcgaca acgagctcaa agtggtggtt cgggagctcg  83580
aggagggcgt ctgccccatc gtcatcgaga aaaacggcga gttcctctcg ccgggcgact  83640
tcgaccccga gtgcctgcgc taccacctga cgtacatgac cgacctctgg aagtcccagg  83700
ggcgcatgta gccgcggcta ctccgactcg gcggcctccg cgattttttc ttttatcatg  83760
tccagcagct cgcgcaccac gatggggcgg ccgcagtacg tgatgccgtt ttcggatatc  83820
acgctctgcg cgatgtccac cagcgagccc tcgcgctccc agtactcgcg cgcgagcacc  83880
tccttgtaca acgcgcggtg gttggccacg taccgcacca gcgtctggat gttcttcacg  83940
cccacgctct tgaggtcctg cggcgagaac ttctcgcgca gcgacacgaa gacgtcccgg  84000
acgagcttgc cgatctccac gttggtcttg aactcgttgt acagcaccac gtagagcttg  84060
cacacgaccg tggcgaactt cgcgggcttg agatccttgt tctggaagac cagcatgctg  84120
ctcatcacct tcttcatgaa ggccaggtac ttcgcgcggt cgccctcgac gctcacgctc  84180
ccgacctcga gatcggacac gcagcggatt ccgtgctccg cgctctccgc ggagacgcgc  84240
agcagctcct ggtactcctt gagcttctgc ttgtccgtca tcagcgagtt gtcgaatacc  84300
gccaccagct tgagcacgta gttctcgtcc gagaagacct tgttcagaca cttcaccagg  84360
aagctgtagt ggctctgcag gatcttcatg accgcgttgg ctccgctggc tccgcggacg  84420
tgcgatatca tctccatgat cttcttggag tcgtcgatga tctcctcggt gtcgtttcgc  84480
atgttgcggt acatcgcgtt cagcgagacc agcgtctgcg cggccaggag cacgtcgcgg  84540
aacacgcgcg cgaactcgcg cttctcctcc gcgtcggcga tgctgttgta cacggacttc  84600
```

gccaccgcgt tcgacttcag gaaccagaag gagagcgcct ggtaattgaa gtgcttcatt 84660
agcgccagca cgtccgcctc gctcatttcc ggcgcaatgg ggcacaccga gctttcgagc 84720
acgggcacca tgctgacgag cgtgtccacg tccgtgtcga agtccaggca gtccacgcag 84780
agcccggtgc cgcggctcag gtgatcgcgg ctgatgttgt agaagcgctc gtagcaggtg 84840
cggaggcggt ccatgtcggc tgcgttttag ggagacacac actcttgaat tatggctgcg 84900
ggtagaactc ctgcagcagc gccggcgcac gcgcggagtc cggctccact cccagcttca 84960
gcgcgcagtt cacggaccag gtcttcatga agcggtcggg cgcgtccgtg accacgtgcc 85020
ggaagagctt cgcgaagtgg cggctcacgg cgttgggcac ggtcgcgttg cgcacgaagg 85080
ccgtgaagcg cgaggtcagc ttcggcgcga agcgcttgcc gtccacgaag aagccagagg 85140
tggtgagcga gagcccgttc tcctcgcgca ccacgcgtcg cgcggccttg tgcggaaaca 85200
tgctcgcgag gcgcccgctc gcgtcctggt ctaggtggat ggcgtccgtg gccgcgtcct 85260
tgcggatgcg caccacgtcg tgcacgatct cctggatgag gatgcgcgtg gctgcggtct 85320
ccgtcagccg catggggaag tagaccatgt ccccggagat gagcacgttc ccgctagcgt 85380
ttacgtagct cactatctcg gacacggtgc gcagacgcac gatcgcgcct tcgcagcagt 85440
gcaccacgta gtacccggcg gtggcgcgca ggcgcttgtt gtccgcctcg aagtccgcct 85500
ccaacccctc gttgaagtac ttgtcgaata tgatgggcag gaaggatagt tttgactcgg 85560
tgaccacctt cccgaagttg aggatgtacg ggttcagcgc gctgcggtcg acctcttcgt 85620
cgtacacgca ggacttgaag gtgtcggtgt gcgcctggct gcgcaggaag cagcacggaa 85680
tgcagatgcg ctgcaggcgg tggaagatgg agaggaagcc cacgctgttg tagcgcccgt 85740
cggggtccat gcacgaaaac atgacgccgt ttccgttcac gaagacctcg cgcgtctcgg 85800
acttgaagaa gttgttgctg accttggcca tgtccgcgtc cagcgactgc acgatcacgg 85860
gcttgcggtt cttggtcttg gtgttctggc agatgcgcga ccagtacacg gtctccacct 85920
tggtgaagtc cgaggactgc ttcacgttgt tgaacatcac gctgatggcc acgatcaaga 85980
acgtgaagta cttctcgatg ttcgggatgt agttcttgac cttcacggac acgtgcgact 86040
tcgcgaggat gatcgagatg cgcttgtccg tggagagcag gatgttgttg gtcgccgtct 86100
ccacgaagat gaagctcgtt tccatgtcca gcttcatctt agacgtgatg gtcgtgttca 86160
gcgacacctt gtaggtgatg tcgcccttga cgcggtccat ctttacgtcc atgctctcga 86220
tgagcttcgt gaacagactc acgtcgttca ccgtgagcgt cttcccgtcg ctcgagatga 86280
ccaggtcgcc ttccgggccc cacaccgaga ggttcagcgg ctcgtccacc agcaggaagc 86340
gcgtccccgt catcgacacg aagaagtcgt ccgtcttcga gagcaggatg tcgaagtcgc 86400
ccacctccgc tcgcttgtcc ggcgactgct gcgcgatcgc gcggagcccg gactcgcgca 86460
ggttcgtgcg gaagatgttg ttgaacttgg tctccacgtt catgtttagg tcgaggttcg 86520
cgaactcgcg gatgagccgc tcctcgaact tgaggatgga gtcgttgggc tcctcgaagg 86580
agccgaactc cggcgcggag gtgtccgccg cgcgcgccac ccagaccacc aggaagttgc 86640
acgcgtccgc gtacgcgttg tagaggatgc cgtccgtgcg gatgagcgtt ttcttttgcg 86700
tgggcgagaa cgggttgaag atggtgttgt ccacgtagct gtactccagg ttgttcttgt 86760
gcgagtacac gatgatctcg tcctgcaggc ccagcaggct ccccaagtac cccttgagct 86820
gccgcacgcg catggtcagc aagatgtgtc tgcgcacgtg ctcggggtcc ttctggatgt 86880
actgcttcgc gaagaagtag atcggcgagg cctcgtccac ggagtcgtac agcgacaggt 86940
acagcacgcg ctcgatctcc tggtggcgcc ccaccagcac caccagctgc ggcgcgacgg 87000
tgtagagcat ggtcgcgcgg gcgtatttat agccggcgtt aaactgaaat aaaatacgcg 87060
ggtcgcgagg cagcgccatg ttccagccgg tgcccgacat ggccgccgag gccgacatcg 87120
acctcggcga cgtcagcgtg gacgcgacgc gcgcgggcgc gcgcgagaag accgtcttct 87180
tcgcgcgcaa caagcgcatg tacccgcacc gcagcaagga cgaggagcgc aagctgtcgc 87240
tgggcttctt cttgcagcgg ctggacttcc tcacgtcgcg cgaggtcaac ctgcagttcc 87300
ggtcgctgga cgcgctgcgc accgagaacg tcatgaagaa gaacaacgtg ctcgtggcgc 87360
cgtacatcct catcgcgacg ctcgcggggc gcggcttccg catgacggag accatggtcg 87420
agctctactt ccccgagctg taccgcgaga ccagcaagcg cttccgcttc tgcgcgcaga 87480
taaaggtcat ccaggacttc ctggggttcg cccacgacag ctaccacact tacgacttcg 87540
agacgtactt cgcgttcgtg gcgctggtgc tgcgcggcgc ggactccgcg gccgaggcct 87600
tcgacgtccg cgccgagagc gggcttgtgc gcagcctcac cgagatcacg taccggctct 87660
acgtgatgca gctgcgctcc gacgccgcgc agtggagcgt gagcaccggc gccgtagtct 87720
cgcaggcggt gaacaccgtg ctgtcggtcg tcggcgacct tgccgcgcgc gcggaggccg 87780
agcggctcac gcccgtgtgc gacctcgcgc gcgagaaccc gctctcgctc gaagacctgc 87840
gcaagtacgg cccgcggctg cgctcgctgc tcacgaccat ggcgcgcgcg cgatccttca 87900
agacgaaccg gcgggacaag gacgcgctgt cccggttctg ccgactgacg gcgggcccta 87960
gcccgtctgc gtgccgcgcg tcgccatagg cgtcggcgcg cgctcgccgc cggaacactc 88020
ggggtcgctg aacatgtaga tgagcgcgac gcctagcagc aggtacatga tcatgctgat 88080
cacggttttg aacacgacgg cggcgaacgt gttggaccgc agtcggtgct cgcagaagtg 88140
catgaacagg tgccgcatga ggtcgatggc cccgttggcc acctggaaaa gggcgaggcc 88200
gccgatggac ttgatcaccg tcacgtagca cggccgcatt cgacgacgct atttactcac 88260
tgtcaaaaga aacggcgcca tccgaccgga ggttgaggtt gcgcttcatg ttccagtaca 88320
tctcgccgat gctcgagtag tacgccgtca gccgcgatat tttttctcgg accagctcgt 88380
aggccttctg catctccgca acgccgatct ccgcgtcgcc cacgtaccgg ccgctgcggc 88440
gcacgatcag cagcagcgcc ttcaggttct ccagcgcgat catgtccatg tacagcgact 88500
tcgagagctg cacgaagagg ttgtaccgct ccaggatgct gttcttcacc tcgtccgcga 88560
tcgggactcc gaagatgcgc tccgtggtgt acacggactg cgtgagctgc ttgaagagcg 88620
cggagatgca gcaggtcgcg cgcttgacgg cgtcgagctg cttctcggag cgcgcgctcg 88680
cgatgctcag cgcgctgttc acgacgttgc tcgtgtcgcg cacgtagcgc gtcttcagcg 88740
cggcgttgat ggcatccgcg atctcgttgc tgctcacgct cgagtcgtcc gagctgcccg 88800
agacctcgtc cagcagcccc gagatcgtga tgtcgggcga gccgccgacg gtcaccagac 88860
ggtcgagcag gttgcagggc atggacatga ggatgccctc gctcgagagg cagccctcgt 88920
cgatcatgct ctgcaggttg cgcttgaagg ccgtgttttc gggcatgaac ccgtccacgc 88980
tcatgagctc gtcgaccgtg ctcgcggaaa agatgcccct cacgttgatg cggtccagca 89040
tgcccatgtc ctgcgagcac agcaccaccg actggtcggc cgtctcggcg gcgtccttgg 89100
cgccgccgta gatgatgcgc ggaaaccgcc agctcgccgg aaaggagaag gagggaaacc 89160
ggcactgcgc gctcgggcct cggtagccct gcgcgtcgcg cacgttggtg gccgtgacca 89220
tgaactgcag caggtcgtgc gcggacgcca tgatcttctc cacctcctcc ttgctgcagc 89280
agaccttgcc caggctgcgc gcgatgttcg ttttgctcac cgagggcgag accgtgacgg 89340
cggtgtgccg gcggctgccg agcgtgtacg cgctcacgct aacgcggtac cccatggcgc 89400
cgaagagcag cttcacgaag tccaggtagc tctccttatt gatgtagtgc ggcgcgccct 89460
tgtcttccat cctcagcccg gcgtaggcca tgagcacttc cttcatcgcc gtctcggggt 89520
ccgagttgca caccagccgc agcatctgga agaactgcgt gaaggcgcgc tgcgagagcc 89580
cgatgtggtg gttgggctgc gtcgaccggc gcgggaactc cctgggcgtc atggcgttga 89640
tgcccgagag cgtctccatc acgagcgcgc ccacggtctt ctggcccatg acgcgcgggt 89700
aaaagcacac gcggaggggc tccttgccgg ccgcgagcgc gtccgagagc agcgagcagt 89760
acgtgacgtt gtcgtggtcg aagagcgcga aggtgtagca gacggagctc atgaagagcg 89820
agtcggcggt gctcatggac ttgaactccg tgtacgcgat tccgtcccag aacaggctct 89880
ttccgggcgc gatcagcggg gacgcgcggt cggcgcgcat cagcatggag agcagcgtca 89940
cgtagtaacg gatgttggcg gaaacgtcta cgaactgcat gccgggcgag gccacgcgca 90000
gggtcgcgcc cgaggtagtg agcacctcca ggctgtccat gagcgtcacg ctggggtgca 90060
gctgcgcaag gcgcgccagc tggctctggt agaagatgga cacggcgagg ctggccacgc 90120
tgccgcgcgc catgcgcagg ttttgtccgt tgaaggtgag ctggcgcagc gagaacacgg 90180
agtcgaagta ctggaagaag gtgagcaggt acttgagcgg catggtcgtc agctcggtat 90240
ccacctgcgg cgtctgcgtg agcacgattc cgttcttggc cgcggcgtcg gggatgtcgt 90300
acatggcgtc cattctggcg cgggaggcgt cggtgagcag cgcgcgcacg ttgagcagca 90360
tgagcaggtc tcgcgcgagc atggtcccgt cgaccagccg ggcgcgaaag ccgatctcgg 90420
cggggccggc gatgttgggg tagatcaggt tcagcaggta cgtgttgtcg aagctcagcg 90480
aggggaagga gatgggcgac ttcgccggga ggcctgtggg gtagcgcacg tagccgccgc 90540
agatgcgcgc gtgcgcctca aagctggtca cgcgagtctt cagcaggttg cgggtgaagg 90600
gcggcacgtc cttgaaggac tgcgtgcaga tcacggggtt ggcggtgtcg gtcagcttga 90660
ggttggtggg cttgagctcc gcgaagttgg ggcccagcag cacggggacg aggtgcgagt 90720
tggcggcgct gtcgagcagg aagttgatgc cgaactgctt cacggcgacc tcggtttcct 90780
cgtcgctggc gagcttctcc gcgtcctcga ggaagagcgc gtccagcggg tgcacgtacg 90840
tgcggttgac gtcgtagctg ggcttgaagt ccgaacacag cgtggggagc acggtggaga 90900
cgagctggaa catgtattcc gcgccctcca catggtgcaa ggccatgtgc acgtttgggg 90960
ccgtcattta tttagtatta aatgacggcc gtaccggtaa ccgatattcc tggagactac 91020
gggccgacgt ccttttcgga ggacaactac ccgctgaaca agcactacga gctcaccaaa 91080
ggccagctct cgatcctgcg cacggtcaac gacaagctgc tcgcgcgcac cgtgcagcac 91140
tcggacgggg agagcgatga gagcgagagc gaggaggacg acatctcagt ccgctgccgc 91200
cggacgagga ggagccggac tcgtgcgtgg cccgagtcat gccgcgggac gcggacctgc 91260
ggcgccaaaa aaggccgacg gctacatcat tgccgccgag cagcagcgcc agcagcgcat 91320
aaacattctg gtatccgatc gagaggccgt cgtggagcgg gagccggttc agacgtcgtt 91380
cgcgcgcgtc tcggctatcc cgatccacgg ggacggcgcg cgccgcacca ccgcctcctt 91440
ctccgcgacc acgccgtcgc tgggcgccgt gttcgacgac gccaagcgcg tgcggctgct 91500
ggaggaggag gtcaaggagc tccgcagaaa gtgcgcgacc tctcaggata acggaaacct 91560
ggagaacttc accaaggtgc tgttcggcaa ggcgccgcgc gcgagcgagc tgaacaagcg 91620
cgtggtcatc gtgaactacg ccacgctgaa caacgtgacg ctgtccatgg atgacctcga 91680
gaagtgctcc gacgaggagg tggaccgcat gtactcggtc atccggcgct acaacgagac 91740

-continued

```
gcggaagaag aagatcctgg tcacgaacgt ggtcatcatc gggatcaccg tgctcgagca  91800
cgtgctggtg aagcttggct tctcggaggt gcgcgggctc agcgccgacc tctcgtcgga  91860
gctcatcgac gtggagatcg gcgaggactg cgagcacatc gcggagcgcc tggggttcgg  91920
gaacagcccg gtgctaaacg tggcgctctt cgtggtaaag ctgttcgtgc ggaagctgaa  91980
cctgatctga tcaacacatg ccgccgtcga ggtccatggc gttcatgagg ttggaggcgc  92040
ggcggcgcgc gccggtggaa gcggtggagg cgctcgaggt cgtggagcag ggagtgttgc  92100
cggaggaggc gcggcggcgg gagctagaag cagaactcga ggttccgctg gtggtgctgc  92160
ggcgactcgt gccgctcgtg ccgctcctgc cagtgccagt gccgctgcgg cgtgaagtac  92220
cggtgccgga cctgccgctg gagcttttct tgcggccgcc gttaacgctg tcgatgccga  92280
gcaggtcctc gcacacctcg ccgacggttc cctgcacgtc caacttgccg ttcttgacaa  92340
ccccgtacac gatcttgccg cagttggaca cagcctggat ggtggtctcg tcgctgtcaa  92400
aggcgttcat tccgccgcac gcgccgtcgt tgtttcttcg agaaggcgcg ccgctgcggc  92460
gactccgggt gctggcgctg gaccgagttc cggaggacct ggagcccgtg gaccggctgc  92520
cggtcgacct ggtgccggta gtgcgccttc tggacgaaga ggaggaggcg cttccgcggc  92580
gggtggacga actagcctcc agcgcgccgg cgccgcccac acaatccacg tcggcggcgg  92640
cagcgcctcc gcgaatgacc tgctcgttgt tgagctgcgt caggagagat cgcagctgcg  92700
gcgcgatctt ctgcaaggtg ctcacgtagt cgtcgtagct gctctgcggg cgctgcgcca  92760
tttttcgga cgccatttat tacgcggaat atctacgacg acgcagcact gaatcggttt  92820
ctcgcgacgg gagattccgc ggtcggcgcc ggtgcggtgt tgtcgccggg cgacgaggta  92880
accagcgcgt ggaaggcgcg cacctggtcg tccgtcatct tgtcctcgaa cgaggacgcg  92940
cccgggggaa gcaggtcctt gttgcgcgga acggcgggcg ccgagacgca cgaccggcgg  93000
tacatcatga tgacgatgta gcacacgatc gagatgacga tcacggtcag cagcgcgtcg  93060
aggagcccca tttattacct gtatatgccc gcgtttaccg ggcggtgagc tcaatgtcgg  93120
tgttgtttag ccgggcgtac gggacgctgc cggagcactt cctgtacatg ctgaacacga  93180
acagcccgag cagcagcacg gcgcccacta tgaagcaggt tacgcacagc gcgcgccaca  93240
cgtagtcggt gacgttggtg ttcttgctga aatccacgaa ggcgaagacg caggcggccg  93300
tcagcagcag cacgccgcat atcagcactc cggagtagta agagctcaag gtctcgaata  93360
tgtccattta tctgaggaga aatttaaatt actgaatgga cgaagtggaa tagaaaccac  93420
gagaacacga cggactgcag cacgaagatg gtgctcagct tcgtcttcat gggcatgcag  93480
aagttcgcgg ccagcgccat acagaagatg aacacgagca ccgccgggtc gtagtcggac  93540
accatttaca ctacgctaaa aggcatatct cggcgcgcga cgtccacgag caccagcacg  93600
cggacgcccg cgggcgcgcc ggcggcgacc gcggcgagct gcccggccgt ggggttcacc  93660
agcagcagtg cgcgcgcggt tcgcgggaca gggtcctcgt aggacatggt cggtgtggac  93720
ccgggacgca gcggccgccc ctgtctgtcg aagaggccct cgggaaacga ggtgcccgga  93780
acggccacga cgacggtgtc gctatctaga aacatttatg gtcttggttt ccacggatcg  93840
cctcgagtag accgccacga agtagaagat gacgcccgcc gcgagcgccg ccaccaggaa  93900
gggcggcacg gcgggcaggt tcgcggacgc gttgtcgcgc acgccggggt ccgggtctgc  93960
gtagcccgcg cccacggcct tgccgcagtc ggcgatcatg tgcgcgcgcg agttctgcat  94020
gaccaggctg tccacgtcga tgcggcaccc cacgtagcgg caccgcgagc gctgctcgtc  94080
```

-continued

```
ctggctgaag aagagccact tgcggtcgcg cgactggtcc gtgcactcgt gcgcgcggca  94140
gacgcgcggg cccaggtact tcccgagcgt ggtgcccgcg acgcacgcgc actccggcgc  94200
ggcgcggtgc gcgtcgcagt agcgccgcag cgcggagtcg ccgaaggcga aggaggcggg  94260
ccgcgccacg cgcacgaatt ccgagcagaa gcgcgcgtcc atgtgcttgg cgcagagcgc  94320
cgcgtaggtg tccagcgccg cgtagcggcc cgtgcgcagc caggccatgc actcgggcgc  94380
gtcaggctcc accgcgcagc ggctggccat gacgccgtcg cagtgcgcgg tcttgtaccc  94440
gttcgcgaac acggacgggc acccgggccc cggatttgtg cagcagcgcg ccatggcggc  94500
gtccgtgggc ggcgccgagg cgccgatctc gaacgcgcac atggtgccct ggcgcaggta  94560
cggcttcgcg atctcgggaa cgtagtctgc gcgcagcagc gagcccgggc ggaagaagag  94620
cgagtcgcag ggcgggcctc gcacgagccg cgcgcggctc gccagctctg gcgagaggaa  94680
gcgcccgcac tgcccggggt ccatggtcgg cagcagacag aaccgcggcc gtacggtctt  94740
cagcttcggg tcggagaagg tttctgattc ttccgcgaag gcgaaggtgt ccgtggcgct  94800
cgtgtgggtg acgcgcagcg cgtactcgcc gggcgtcggc gtgtcgagca cctccacctt  94860
ggatacggtg tcccccattt gaagacgcta tttacgccgc tgcctactcg gcgaagaata  94920
ggtcctccga cttggcgccc gcgtacaccg ggcaggcggg cgcggcggag cgagtgcgca  94980
cgataccgcg gccagtgagg cggaaggcgt agatggcgaa cagcaggccg agcacgatgt  95040
acatgaaggt ggtggcgccc acggacccgg tcacgtgcgt cacgatgatg gtgacgatgg  95100
acatgatcgt gcacacgatg gccatgccgg tgttgttggc cgcgtagggg tgcatgatct  95160
gcatggccgc gcagtatccg atgaccaggc acggcagcgg gaggataagt gaggcaatac  95220
ctatcattac tagagcgagc acgggggtgg acgtcaaggc caatacaaaa atcacaatac  95280
ctgttagtat gcggatatcc tcgtactgga ggacgctgta aggcgcgata ttccctccag  95340
gcactggccg gggggtagcc gggactaggg gggagtcggc agtgccgggg tctttgggga  95400
gaaaggcatt ctgctcctcc gggctgaaga gctcggcgtc ctgaacgccg ccggcggtga  95460
actcgtcgtt atagtaacta aagtagcttt ccatttatat gttgaaaaat gtttggaggc  95520
gtacaggtgg acgacaaact ctacgcgtac ctaaaaaaac tcgccggacg cgggcggccg  95580
ctgtgtctgt tccgcgacaa cggcgagttc gtcgaagtct tcgcggggtc cgcgttccgc  95640
tttgtgctgc ccgtgggcct cttcgcggac ctgcgcgtgc gcacgcgcgg cgtggccttc  95700
ccaaaactgc gcgactccgc gcgcatgcgc ggcgtgcggg tggacgcgca cacgctgccc  95760
tcgctgtacc ccaaccagcg catcgtggtg gacgaggtgc tcgcggcccg cgaccagttg  95820
ctggccgcgg gccgcgccgt gtacgtgacg ctgcatctgg cttgcggctt cgggaagacg  95880
ctgaccgcgt gccacctcat cgccacgcac ggccgccgcg cggtggtgtg cgtgcccaac  95940
cgcatgctgg tgccgcagtg gcgcgcggcc gtggcggagc tgcgggtgcc cttcgcggtc  96000
tcctgcgacg gcgcggcctc gctgctgcgc tcgggcgagc tcgaccgcgc catggtggcc  96060
atcgtggtca gccggcactt cgccaacgac gacttctgcc gcgcggtgag ccggcagttt  96120
gacgtgctcg tgctcgacga gtcgcacaca tacaacctca tgaacaacac cgcggtctcg  96180
cgcttcttaa ccaagtaccc gccgcccatg tgcttcttcc tgaccgcgac gccgcgcacg  96240
gccaaccgca tctactgcaa ccgcgtggtg aacgtgtccg tggtcagccg cctcaccaag  96300
gtggtgcgcg tggtggacgc cttcttcgag ccgtacacca cgcccaagat ccgcacgctc  96360
gagcgcagcc tcgatggacc tcagaacaag taccacgtct tcaccgagaa gatcctcggc  96420
gaggacgtgc accgcaacaa gctcatcgtg gacaccgtgg tcgcggccat ggccgcgggc  96480
```

-continued

```
gaggcgcggc gcgtgctcgt gctcaccaag ctgcgcgaac acatggtcgg gctgcacgcc  96540
gcgctctgcg agcgcctcgg tgcggagacg gtctttctcg gcgacgccaa gaacaggaag  96600
acgcccgagg tcacgcgcgc actgcgcgac aaggaccgct tcgtgctcgt gtccacggtc  96660
ttcttctcag gcacgggcct ggacctgccc aacctggacg cgctcgcggt ggccgcggcc  96720
gtgctcaacc gcatggtcat ggagcagatg atcggacgcg tgtgtcgcga gtcgcacgcc  96780
aacacgcgca cgctgttcgt gttcccggac tcctccgtgc gcgcgatccg cgacaccgtg  96840
tctgcgtttg cgcagcggct cgtggcgctg gcggtggacg ggctgggctt cgtccgcgag  96900
cgcgccgccg ccggcgcgaa gaacgagccg gcgctgtaca gcgccatcag cgggcgagat  96960
ctcgcagcgg tgtaagcgcg gacccgcacg ccgcgcacga gagcgtgctg gagcaggcga  97020
gtcccagcga cagtgtggac agcctgtcca cgtccttgat gctcaccagc cgcgagttgc  97080
acgagagcac acggggtcgc tactatcatc gaccactgtg gtgacgcggc ggcgtctgcg  97140
ctttttgttt ccagcgcgac atcgaccacg cctcccttag agccccccctt cgcccccgcc  97200
ttagctttca ccgcgctcat cttttattta tcataaaaac acgtctgcgt acgcgttcgc  97260
gcacacgtcc cgcaaatccg cgcgcgcgcc gcagcgcgtg aagcgcgcgg cgtccgcctc  97320
cgcgatccgc gcgcacggca gcggcgcgcc cttctcgtcc gccatcacgc gcgcagagat  97380
cccggtggcc cccagcgcgt acgacaccac cacgtcgccg acgcagcggt acacgttgcc  97440
ggagccggcg aggcggtcga acgcggcgcc ctcctggcgc agcttgtcga atatgcgagg  97500
aacgaggatg ttaaaaatga gaacgaaata gcagatcagc aaaaacagcg agatcatgac  97560
ctccgagagc gatttatata ccttgaaaga gctaatacga cttcgggact cgctgcacct  97620
cgccaccggc gccgccgtcg agcgctacaa cgcgctcgtg gagtgggccg cgcgcacgta  97680
ctggacggtc gcggtgctgc cctccgcacc gtgcgcctcc atcgagaagt actactgcgt  97740
gtgcaaaccc gactgcgcgc tcgagcccgg cgagtactcc gtgagccggc tgcacttcgg  97800
actcacgcac gcctgggtgc gcggcgccgc cttcaactcg gccagcggcg ccgaggtcga  97860
gccgccagag gaggtgcgta gggcctgcga ggcgctcgac gccgccttcg cggacctcac  97920
cttcgtgcgc ttctcggtct tcggccgcga gtggacggtc gacgacgccg tcacagacca  97980
ctcctcgcgc gacgaggtgt tcgccgcgtg cgccgcctcc ggcgtgcgcg tcgcgcgcac  98040
gctgcgtgtg cgcgtgcggg cgggagagtc cttcgcgcgc gcggacttcg acgcggtgca  98100
cgccgcgctg cgcgcggagg gcgacgtcgc tcgcggcacc gcggtctgtc tcgcgctgcg  98160
cgggtcatcg cgccgctgga tagcggaccg agcgcctcga tgcttcatgc gcgtgcgccg  98220
cgtggagctc gagcccgtgg acgctcggca ccactgcccg gtgctgatct cagcgcgcgg  98280
cgaccgggtg ctctgccgcg gcgtggggca cctcgcggac gcgcgcgcgc gcgagggcgt  98340
cttcgtggcc gtgcgcaggt acccggagtg tctggtgctc tgcgacgagg cggccgccgg  98400
cgcggcggag tgctcgcgcg aggaggcgct gcggctgctg gtgcgccgct tcgggcgcga  98460
cttcgccgtc agcgaggagg gctacgtctt ccgcgtgcag gacatggacc tgcgcggcgt  98520
gtccgcgcga ctggggctcg cgccctgcgc gagcctggag gatctgcgcc gagcggtgga  98580
gcgcgaccgc gcgctgatgc ggcggctgcg cgcggagggc gccgtgcgcc tcgcgtgcga  98640
gtgcgtggga tacccgcgcc agaacgcggt ggagctcata aataatatgc gctttcaaat  98700
aacggaagaa ggcgcggtgg cgaactttga gctggcgaac gcgagctgtc tcggcaaccc  98760
gaccgcggag tccatcttcg cgagcttcgc gcagttcgtg ccgatcttca acgtgctatc  98820
```

-continued

```
ggcgatcgcg cgcgcgcagc catgatcgtg gcggccttcg acctgggcac gcgcaacccc  98880
gcgcgcaccg tgctggaggt gctcgacggc acggtgcgcg tggtggacgt ggccaagctg  98940
gactggagcc gcgactggga gaagcgcgtg caccgcgacg tgaccgcctt ccccgctaac  99000
gtggtgctcg tggagcgcca gtgcaagatg tcgccttttt ctaagttcat atacttcata  99060
cgcgggctgc tctacgacgg gcggcgccgc acgcgcgtgc tcgcggtgcc gccggccatg  99120
accggcagca cctaccggca gcgcaagcgc cgctcggtgc gcaccttcct cgcgctcgcg  99180
gagagcttcg gcatcctgga cgccgtgccc gcgcggaaga agctcgacga cgtcgcggac  99240
agcttcaaca tggccatcaa ttacgtgctc cgaacaaact gaaatacgac tgaacgaata  99300
agtcatgctg gcgctgttcg agttcctgcg gtccgtggag gactgctacc ggcgcaccat  99360
cttcaacttc cacatcgcgc acagcgccga ggcgggcgat gtctacggcg tgctgcgcga  99420
ccgcattttg gcggccacgc gcttcgagga ggtagcgccg ccggggctcg cggacgcgct  99480
ggccaaggtg gtctactgcg acataagcac caccaagcac ctggtcaacc acgcggcctt  99540
cgcggcgcgc gcgcggccgg cgcggcgcgg aggcagcctc gcgcagttct tcgacgtgca  99600
cgtgggcgag gacgcggaga gccgccgcac cgcagagatc ttcgaccgcg agcgctcctc  99660
gctggtctcg tacgtgaaga ccacggccaa gcgctgcaag atcgactacg gcgagatcaa  99720
gcgcaccatc cacggcgggc ggcagaccta cttctcgggg cggcgctcgg acgacttctt  99780
gagcaccacc gtgcgcgcgg acccgagcaa gccctggatc aagtccatct ccaagcagct  99840
gcgcgtggac atcctgcacc acgcgatctg cacgcgcggc aagagctcca tcctgcagac  99900
catcgagatc gtgctcacga accgcacctg cgtgaagata ttcaaggact cgaccatgca  99960
cataatcctc tccaaggacg accgcgagcg cgggctcgcg gacctcgcgg acaagctctt 100020
cgggacctac gcgaccacct tccgcgtcat cgcggccatc accggcaacg cctgcttcgc 100080
ggcggtggca gacgcggccg cgcgcgtggt cgcgctcccg gacgcggacg cgaagctggc 100140
ggcggtgcgc gggctcgcgg agtgctacgg cgtgcgcaac ttcaaaatcg gcatgttcaa 100200
cctcaccttc acgggcgcca tcgagcacac ggtcttcccc tcgctgatcc ccgcggagag 100260
caagatcaag ttcttcaagg gcaagaagct taacatcgtc gcggtgcgct ccaccgagga 100320
gggccgcgag tgcgtggagc aggcgcaggc gctgctcgcg gccatgcgcg agcgctccgc 100380
gcggctcgcg gccgcggacg tggccaccgc gagcgtggac ttcctcaagg agctgctggg 100440
gccatagtga aataatactg atttcttaaa tatggagcag gcgctcggat acaagttttt 100500
gttgcccgac cccaaggacg acgtctacta ccgcccgctc cacttccagt atgagtccta 100560
cgccaacttc atcaagcacc ggcttaagga catcctcacg gtgcggcgca cgctgctcac 100620
cttcaagaac ggcaccgagt ccatcgtgct cgagatcgac gacgtgaaga tctcggcgcc 100680
ggagttctcg cccatcgtgg ccagcatcaa gggccacagc tacgaggcgc tggtcacctt 100740
cacggtgaac atctaccggc acgtgatgac caaggacggc ctcaccgtga ccaagatcaa 100800
cagctacgag ggcaccgact cgcacctcgt caagctcccg ctgctcatcg gctacgggaa 100860
caagaacgcg ctggacccct ccaagttcgt ggtcccgaac gccatcggcg gcgtcttcat 100920
caacaagcag tccatcgaga agctcggcat caacatgatc gagaagatca ccacctggcc 100980
caagttccgc gccgtgaagg ccaactcctt cacgctctcc ttctcctcga tctcgcccgt 101040
gcacgtgatg cccgcgcggt accgacacta caagatcctg ctcgacgtga accagcccga 101100
caacttcgtg atctcctccg cgaagacctt catcaccgtg aacgtgatcg tgatggtgca 101160
gttcctcgcg gacgtcacgc tcgagttcgt tgcgcgcaac ctctgcttcg acatgccgcc 101220
```

cgaggccgcg cacctggcca ccgcgctcgt ggagagcgcg aagaccgtgc ccgcgggcgc 101280
ggacgtggcc gagtacgtga acgcgctcat cgcggccgag cacgcgaagc agaagtcgac 101340
gctgtccaag gaggagttcc gctacgagat gctcagcaac ttcctcccgc acatgcagga 101400
cagcgccaac cagctcaagg gcctgtacct gctctcgctg gtgcgcaaga tggtcttctg 101460
cgtgttcttc ccgaaccggt acccggaccg cgactcgctg gtctgccacc gcgtgtacac 101520
ctacgggcgc tacttcgagg cgctggccat ggacgagctc gagacctaca tcgggaacat 101580
ccgcaacgac atcctcgcga accacaagaa ccgcggcacc tgcaccgtga acatccacgt 101640
gctgaccacg cccggcttca accacgcctt cgcggcgctg ctcagcggca agttccgcaa 101700
gtccgacggc agcttccgca cgcacccgca ctactcctgg atgcagagca tctccatccc 101760
gcgcagcgtg ggcttctacc ccgagcaagt caagatctcg aagatgttca aggtgcgcat 101820
gtaccacccc agccagtacg gcttcttctg cgcctcggac gtgcccgagc gcgggccgca 101880
ggtcgggctc atctcgcagc tctccgtgct cgcctccatc tcgaacatcc gcaccgcgga 101940
cttcgtcgag ctcaccaagc gcgtctgcga ctacgtgcgc tcctaccccg cgcgcgacat 102000
cagctacttc gagaccgggt tcgcggtcac cgtcgagaac gcgctcgtgg cctcgctgaa 102060
ccccgcgatc gtggacgcgt tcgtgctcga cctgcgccgg cgcaagcggc tcggcttctt 102120
cgggaaccgc gagatcggcg tcgcgctcgt gcgcgaccgc atgaacgagg tgcgcatcaa 102180
cttcggcgcg ggccggctca tccgcccgct gctcgtggtc gagaacggcg tgctcgtcat 102240
ggacgcggag gcggagcggc tcgagcgcga cctctccgcg atgaccttct cggacgtgct 102300
gcgcgagttc ccgcacgtga tcgagatcgt ggacgtggag cagttcagct tcagcaacgt 102360
ctgcgactcc gtgcagcgct tccgcacgct gccgcccgag gagcgcgcgc tcttcgactt 102420
ctgcgacttc ccggccgagt tccgcgacgg gtacgtggcc tcctcgctcg tgggcatcaa 102480
ccacaactcc gcgccgcgcg ccatcctcgg ctgcgcgcag gccaagcagg ccatctcctg 102540
cctgagcgcg gacctgcgca acaaggtcga caacggcatc cacctcatgt tcgcggagcg 102600
gcccatcgtg gtcagcaagg cgctggagac ctccaagatc gcggacaact gcttcgggca 102660
ccacgtcacc atcgcgctca tgtccttccg cggcatgaac caggaggacg gcatcatcct 102720
gaagcggcag ttcgcggagc gcggcgggct cgacatcctc acctgcaaga agtaccaggt 102780
cgagatcccg ctcgagaact tcaacaaccg cgagcgcgtg cgctccgcgg cgtactccaa 102840
gatcgacgtc aacggcgtgg tgcgcctgaa cgccttcctc gagcagggcg acgccatcgc 102900
gcggaacgtg tcctcgcgca cgctcgacga cgacttcgtc gctgacaacc agatcagctt 102960
cgacatcgcg gagcggtact cggacatcta cgccgcgcgc gtggagcgcg tgcaggccga 103020
cctcaccgac aaggtcaagg tgcgcgcgct gaccgtgcgc gagcgccgcg ccatcctcgg 103080
ggacaagttc accacgcgca ccagccagaa gggcacggtc gcgtacgtgg ccgacgagac 103140
cgagctgccc tacgacgaga acgggatcgc gccggacgtg atcatcaact cgacctccat 103200
cttctcgcgg aagacgctct ccatgctcat ggaggtcatc ctcaccacgg cctacggaca 103260
caagcccttc gccgaggacg gctccaaccg cccgatctgc ttccccagca ccaacgagac 103320
cgacttcgag acctacatcg agttcgcgcg gcgctgctac gcgctctcgc accccgaggc 103380
cgccgcggac gaccccgagt tcgagcaccg cgtcttctgc gagcgcgtgc tcttcgaccc 103440
cgagaccgac gagcccttcg cggcgcgcgt cttcttcggg ccgctgtact acctgcgtct 103500
gcggcacctc acgctggaca aggccacggt gcgctgccgc gggcgcaaga ccaagctcat 103560
ccggcaggcc aacgagggcc gccgccgcgg cggcggcatc aagatcggcg agatggagcg 103620
cgactgcatg atctcgcacg gcgcggcctt caccgtcgcc gagatcctgc gcgactccga 103680
ggaggacgcg caggaggtgc tcgtctgcga gaactgcggc gacatcgcgg cgcggctcaa 103740
cggcacgcac gtctgcatcc gctgctccaa gatgagcctc tcgccggtgc tcacgcgcat 103800
ggactccacg cacgtgagca aggtcttcac cacgcagatg aacgcgcgcg gcataaagat 103860
ccgcgtggag ttcgagaagc aggacccctg cttctacggg actccgaaac ggttcagcct 103920
cgcgcccgac gagtcgctgt tctcgccgga ggactgaacc cgccgtcgcg accgcgtcgc 103980
tacgactagc ttatcgttcg actgatgcga aacgcgcggc ggcgccgcga cttagcttat 104040
atcgactgat gcgaacgcgc gacctctcgc gactttctag cttctcagac tgatgctacc 104100
atatcgcggc gtgctggccc caccaccagg gcttctcgcc gtggctgacg cggggctggc 104160
tgcgacgcgc gccgcagtag ctgcgcgcgc cccagtcgcc gcgcacgtgc gccgggggca 104220
ggctcccgtc cagcgcatgc cgcgtcacct cggcgccggg ccggcggcac gtgtgcacgt 104280
ccgtcttgtt ggagacgagc actgcgtact gccgcatggt ctctatgtga tgctccaagt 104340
gcttgcccgc cttccggttg gactcacagc acgtttttgc ttcggctaag gtttttttcta 104400 gaggggctag tagcttatcc acgcgctcgg gcaggacgca cgcggagccg tcgagcccca 104460
cgcggaacgg ggtcaccggg atgttcccgt cgtagcggtc ccacagcatc ctgaggtagg 104520
ttgtgccgtc gtcgtcggcg tgcgtccaca ctcgacgatg ttcgtggcaa cgaccgtcgt 104580
atgtaagtct gtctcgacgc tcgtaatagt ttctgcttat attgtacgcg tctccgtact 104640
cgaagtagta tatatctccg ggtcctggac ttgctatatt gttttcgtcg tttctacgat 104700
gtataccgtc tggataatac gatattctaa ctgcactgca atccaccgta gaaggtttag 104760
gtaacttttc taattctcct tgttggtcat ggtcaactga cttgtacaca gctccgtcgt 104820
gttctgaggg agttataaat atatccatgg tgaaagaagt tcctcgtttt gagaatttgt 104880
cccatgcggt aaaacaaagg ccgtccatca taaactccgg tacactcata acaaacctgc 104940
acttgtgatc atcaaatgat attttaacat ggtctttgtc ttttacgtcc gtaccgttaa 105000
cttctttcat aaactgtata attgcaagaa ctcctcttgc gtattctata gttctggtat 105060
cagacaccaa cttttctgtt ttaatataaa cgtcgtttac atctacaccg taccaccagt 105120
aaataggaag tcctatgtag atggctgtgt ttctaaaatg ggatgcaagc gtacttatgt 105180
cacggaaaaa ggccacacaa aaaaatcctg tttttgaatc tataattttt ctggtgctgt 105240
cctctgtaac tcctaaaatg tccataattc tttcgttgtg aagagtaagg tgacctgtca 105300
ttatgctgta tacgaccatt aagtaaaact ttccaagcgt gtctacgttt ataatattta 105360
tcttagcatg ctcgcatagc atagttacgt ggaccttcat ccattcgtcg tcaacaaaca 105420
tatttttgta catagtgttt tggtttacgt atttgctaaa atacaggttt acaggtctac 105480
gagatacttt cgttccatct acttttggtg cgcttcgtat gtactcgcgc aaaacgtctc 105540
ttataatttt tctatgagta cgtggtatac atattaccgt cccaagtgga tgatgccact 105600
gacgctgaac gatatcttta aattcagata ccaacgaact gtggttctcc atttataatt 105660
aaataattag accatatcta ccacagacct taccaaatgg cgccgtgtct ttgacgacgc 105720
caccaagcat ctaaattata agtattgtat ggattatgtc tattaaagat ggatgtgcga 105780
ggagttcttg tccatgttgg tctgtaagtc tctctcacta tggggtaatt gctgctcgtt 105840
gtattggaag accctagccc gactggaatt tttgaacagc aaggtttgtc tttaacgtaa 105900
ttttctagag gagatataag tttgtctagt ttatctatgt ccatacacaa aggattatcg 105960
ttattatctt catcgtctat gacttctact tccgatagag gaggcttcac gctcaataat 106020
ccaatgaacc tgtctcttaa aattctgtga tatgatgtct tatcatcatc tatgtctcca 106080
tcaaaacgat gttttaaaca cacaacgtta tcgtatgtta atttatcccg gcgctcaaat 106140
tcattgttcg cagagtcttc tgtgtggcta tagtagtggt agtctaagta gtacccgttg 106200
ttttcatagt ttctagtaaa aatggtaggc gtttggttat tatcaacatc atgttgttta 106260
acataagtat cttctttgta gttagggtgt ctggcagtaa caccatcttt aggtacgtaa 106320
gaaatacgcc tgctaaaact aggatgaaat ttaaatcgta tagcgcctct atttcctacg 106380
tcatcttttg ttataccatc aacaacacct tgtttggaat gatctagtgt tttatacgta 106440
aatccgttat atctagttgg attcataaaa acatctagat aaaatgtagt tccgtattta 106500
gttattttat catatactgt ataacaaagg ccgtctaaaa tgaactctgg tactgacgat 106560
ataaagtttg tgctaaaacc accaaatgat atatttatat gcggtgtgcg agtagaataa 106620
tctccgactt tgtcataagt tatatacata tatctagcaa aagtcactgc accgttagaa 106680
ttctttttag gatcctcttt attaaaataa tcatcgagta acgtatgtac gtttgtacta 106740
agcccatcac ctctccacca atacataggt attccaaaaa ctaatgactt gttattgtaa 106800
taaaacgcta cagaacccat ataccacaaa aagagataac aaaagtaatc catttgtgta 106860
tctacatctc tggggtcgtt taaattcata ttatccataa taaacccatt gtccgtagct 106920
cctgtcatta tcctgtatac taccattagc aaaagcctac ccactgtact cacgtctgta 106980
aaagttttta tagccacagc actttcgtac atccatacat tgtttctaaa aagctcaaca 107040
taaacaggat ttttgtcaac atattgtttc ataatcaaat ttagtggctt tccagttttt 107100
ttatgagtgt cgcttaaaga aggagcattc ttaatgtact ctcgaagcaa atctctcaca 107160
agctttctta tctctatagg aatgcatgtt tggctgttta attctttata ccagttagcg 107220
ctaacaaacg ttctaaactc gtccacgagc ttctccattt ataattaaat aattacagac 107280
ggcaacacag cggttatcta atatctaccg tatcctgtct gtacatctat tttttgttg 107340
agatcaagaa gagctctacg tagactctcc aagtgtcttt ctagtctgtc taaccggtta 107400
cctgtttctc tgcagcaatc agttatagtt ttgtaactgt ctaacaagct tacgaggcgc 107460
tcttccacac tttctttagt tggagctcca gccgcgtaca ctccgttggt tgaattgcct 107520
gtatcatcat caggcggagc caataggttt tctccgtcac cttcctccat attgaatcca 107580
acgaacacaa acgcgtaagt gttcctctat ttaaagtatt gattttagaa aaaggcaggc 107640
ctcgctgccc tgattcggtg gcaaacacgg gttgaacacg cggaagtcgc tcgcggccgt 107700
gaagatctcg tccgcgcacg cctccacgct cgcgaagcgc gcgggcgaga cgccgtcgtg 107760
cgagcggaac ccgaactccg aggccgccac cgccgcgccc ttgaagagca cgcagcgcca 107820
cttcttgcgg acgtcgaagg cctcgtcgtt ggggtcgaac acgcgccggt ccacgcgcgg 107880
gccgcccgcc gtgcgcgcga actccagcgc cgcgttcgcc gcgttgaact cgcggatgtt 107940
gtcgtagttc tcgtagacgg cccagagctg cagcgccacg aacatcgcgg ccgccgccgc 108000
gagggccacg cagagcgcgg acaccgcgtc catcttttat gtgcagaatt attcgtcggc 108060
gcggagctcg cgcagctccg cggcgcgcag ccgcgcgaag gccgccttga gcgcgcgcag 108120
cagctcctcg gtgtccgcgc gcagcatgtc gaagcggtgg tagctgtcca ggcgcgcgcg 108180
gcagccgaag aagcgcgcga cgcacgcggt gacgatgtcg ttcacgtaga gcacgcccga 108240
ggccgtgcag tacacggagc gcggctcgcg cgggtccggc ggcacgtcca cggcgaccgc 108300
gtgcgcggcc acgtcctcga gcaccttgcg ctcgagcacg gcgaggaagt cgcgcagctg 108360
gcggcggttg tccagccagg cgtaggtggt cgcgaagagc gtgagccgcc cgcgcggcgc 108420
gatcgcggtg tagggcgcgt acccgcggaa ctcccggggg tgcacgacct tgacgttctc 108480
gtgctcgcgg cggaaggcct cagtgtcgag cagcgccgcg agcgcgtcca cgagcttgtc 108540
ggagacctcc acgcccgcgc cgaaggcgat gagctcgatc ttctgctcgc tcttggggcg 108600
gaagtcgtgg aaggtgtgca gcagcatctc gcggagctgc ggcggcttct cgacggcctc 108660
gagcgcgtcg ccgcggacga ggaagtagtc gaggtcgtgc agcgagacgt gctgcccggc 108720
ggcgctctgc gcgaacttga ggaagacgca gaggcccgcg cggcgctcga gcacgtcctc 108780
gacgtgcgcg tggaacacgt gccgcgaggg catggcctcg atcgcggaga gccactcctc 108840
gttgacgcag gtggtggtgt tctccagcac cacgccctgc gtgagcgagg gccactgcag 108900
gtggaaggcg aactcgtgct tgatgagcga ggccacggcc gggtccaggt ccacggccag 108960
cgcggcctcg ccgacgaggg gagcgtccgc catcacgcgg aggacgcctg gcccatctcc 109020
tttttcgcct ttttattcag gatcattatt ctttcgttga ccaggtccat gagcatcttg 109080
atggcggcgg ccgcggccgc cgcgtcgccg ccgcacatct gcgcgatgcg cgtgagcatg 109140
tgcagcagcg cggcctcgtt caggtcctcc tccatttaga ggccgtaagg gcgcgcgtcg 109200
tcgcgacgag gggacgcctc ccgctgcagc gtggcgcgca cggcgaaggc gagcagcgcg 109260
ccggcgcact gcgtgagcac gcactccgcg agcgcgacga ggagctcgga gagcacgagc 109320
accatttaga ggcgcgcacg ggtttaattg ccgccgtcag agtcggcatc tcccttgtcg 109380
ccgccgtcct tgcagtcgcc cttggcgtcg ccggcgtcga cgatgtcggc gagccgcgtc 109440
ttcatgtgcg agaactgcgc gagcaggatg ccggggtcga gacagcgctt gacgacgctc 109500
tcgtcggcga agtcgtagca gatgcgctcc tggttctggc agaacaccga gtcttcgatg 109560
atcaacaccc tcctggtccc ggccgaccgc atgatggcca tggcccggat gagcctcttc 109620
ttcgatccgc gtatggacat ggaccggagc acgttctcca cgtcggagtc ggagacgttg 109680
cagcagcaga ggtgcgtgat gctggcgcgc ccgttgacgg ggatgtgctt gtaggtctgg 109740
cagagcagca ccagcgacac gttgatgtgc cgcccgtagt tcatgaggcc caagagtgtg 109800
ggcgaccgcg tctgcgtgtc gcccatatcg tcgagaatga tgaggaactt ctgcttcttc 109860
gtctgcgcgt gccgctcgat cttgcgcttg gcaaccgaga ggttgtactc gagctcctcg 109920
tgcgtggtga ccttgtggat gtggtccggc cacacgaagc cgtcgtaggc ggcgttgtag 109980
acgggcgtga agagcaggat gtgcttgaag cggcgcacga gcgtgcggaa gagcgagagc 110040
aggtaggcgg tcttgccgga gccggagccg ccgacgagcg ccatcctgaa gggcgcctca 110100
atgagactct cccgcttgaa gcgcacctcc tgcacgacat ccatcgtata tttactgtca 110160
ctaaattacc ggctccgaga aatatagaaa ttagagcctc ctagagcaca ccgaggctca 110220
tcggcaagat ggcacataac acgttcgaaa acgatagcga gacggctaac aaccagtacg 110280
tggcgtcagt caagcgccag aaaatgattc ggcgatacat taagatgttc ttccggttcg 110340
ttacggcgat agctatcatt gtcctggcta ttctagttgt gatcctgtcg ctatctctag 110400
acgaatgtct gcacagagaa caccctcatg actattcgca tgtacaaaat tcaacatgtc 110460
ccggaattcc attgggtgat aagtgtttaa cacttaacac accgtctaca tgggaagatg 110520
ctaatcaaat gtgtagcaat ctaggtttca gtttaccatc aaaaggacta cttaaaacgc 110580
cgtggctcac agattacctt gatggaactt ggggaaataa actgggaaat gtctttggac 110640
caactggcga actcgagcag gtcatgggac agcacgaaac ccgcaaatat ttttgtgtgt 110700
ctggttagat gattaaatct aataaatggg ttgctgtaag gtccctaacc gccagtctat 110760
aaggactttg aaaaaggtgt cctgcccggt cgccagcctc gttaccattc tctccctagc 110820
taccagcctc tgtgcgatag tcagatacac taattttttt ctaaaagagg cgtgtgacga 110880
aggatggatg ccaataaaag acatatgcat tttaaacacg cactttaaag ccaccaagga 110940
cgacgcccac agaatatgcg aaagcctaga cggaaatccg ccggccatcc ccaatcccac 111000
tctgctaaag ggtgtaatgg ttctcaccgg agaaagacag ttttggatga ctcaccaccc 111060
ggactacaca tctgtatacg agcataatga aaagttgcaa attccaaaaa acactaagta 111120
cgacaaagat agacacattt gtttgatgag cgaggacgga ttgatacacc ataactgcat 111180
gatgaacgta accgtggtat gcatgaagga gatgcacgga taactgaaaa tatactgttt 111240
gaacgcaaag acgccatgtc gcgacttcaa atactgacct catttggaca aatctacgca 111300
cccgacgaag ctcggctgcg cgagatcgcg cgtgatttgg gaatatgcac cataaaacgc 111360
gcattcggcg acatgctgta cggctttata gacttcaacc cggtgcccct gacccaagta 111420
aacatgctca tgtccaactg ctacttcgcg gtcaacggca acctgcttcc gtgcacggag 111480
gacttccggc tcagactccc ggcaacggag atctctgcgg cctacctgac gagaacggga 111540
cggacgatcc tgtgcggcaa agacttcaac atagtggcgc cgtcagggtt caagccgtcc 111600
atgcggctgc gcgaccttag tcacgtgtct gcgcttgtag agatcctgga gctctacgac 111660
gagtccgggg attaccaatt cgtgctcggc cccagcgcgc agttcatgct gcggctgatg 111720
gagaaggaga atgtctgtct gttcggcaac ggttggtgca tagtggacct gcgcaagcta 111780
gacgtaacca tataattgct gctgctatgt cgtgcccgac tctgtgcgac aaagacagcg 111840
gctaaccaga ctcttcgtcc ctgttctcca agcaaaaaac tggagtgagt tgccatttcc 111900
gtctccaacc atataattag catccttgtt tttatcctgt atttttatca gtttttatgc 111960
tagttaaaac ataaatagta aggctaaaaa gaagagttct agaatcttgc aacaaccaag 112020
atgaaggcgg cggcggtgtt gttgctagcg ctactgggag cgttcaccaa cgcagcgccc 112080
gtcagcaacc agcgtcttgg cagtgaggag aaagaaaaat tctgctcgac tcatcatgac 112140
gaagtgtacg ccaggttccg gcttcagatg cgcgtgggtg tacgacacag tccgctctac 112200
gttcccagca acatgtgcat gatggacata gaagactcta cggatgacat agaagagtcc 112260
acggagaaag aatacacgtc tacggctacg ggtgaggcgg ccggagtgaa cgtgtccgtg 112320
gcactagtgg gagaaggcgt gaaaataccg tttagttaca taggccttgg attcaaccca 112380
tctacagatg gctacctgta cgtcaacgtc tcgtcacgag ctccttgggt tcaacagact 112440
ccagacctat ccgcgaacag cggctggggt attaaacagg ttctagaaaa agagttactg 112500
gccatccaga tagggtgcga caaccaaaaa tttcccgaag aacccacaac tacccccctca 112560 cttgtcacga caacgctttc cccaacaacg actttaaatc cgaataacga aaacacagac 112620
actacgccga cgcccaccgg cgccagtgta gacggaaagc gcaatccaga tgacattgac 112680
ttctcgctga tcgtggaccc ccgatgcgtg acctctgtaa acctgcactt cgagctcaag 112740
gacgcgtgca tggactacaa aaaagagtcg ccgttgtcgc tgaaggggaa atatggagac 112800
agtgaactag taaaacagga gattaaagac gtgggaaaga atcacaatat gtgcagtctt 112860
aacctcagcc ctggccattg agctgttttt attcggcaat ataataaggt gattattgaa 112920
cattaaacaa aacttatccc acaacgccgc aacaatggaa gtgttggtga tcgtctccat 112980
tatcgtcgcc gtaatatgct taaccggagc ggcgatgtac atccttattg aactcggctt 113040
agccgccgag cgcgctaaca aacgcgcgcg cgtgaagaaa aatatgcgca aattagccac 113100
tcaattggga aatggatctg tcgactccgg cataggcata ggcccgtgca taatgtcgcg 113160
caccatggac tctggaccca gtcgctggga cagcgacagt gagggtgacg gagacagcct 113220
gtccacgacg tccaccagcg aagggggac tctcacccga gtgtgggttg ggagcgggtc 113280
cgggcccatg tacgaaaact tctgcgggaa cggcacccac cgccactctc ccaccaacga 113340
ccctggctac cactcgcggg agactctctg cagcggacct ccccgtcagg cgccggcgct 113400
accgcccacc ccgaagcccg acgaggtaac ggtggacgtg gggcccagac ccaacgacca 113460
acacggtccg tacgaggaac ctgatcccat tcccctgcag gaacccgagc cgccgatgca 113520
gatcgaggta accatcaacg ggcccggtga agaaggcgag gtggagggag agtttttcta 113580
cgacgagtag ccgccaaaac tgaataacta tcgggcttcg taaacgcgca gacatgccgc 113640
tgttccggaa gctcatggtt tcgcgctccc tggtcaagga atgtctgact ctggacttcc 113700
ggcagggcga gcgtctcccc acccgatgct tcctcccggt gcccgcgggg acgacattcc 113760
acagagtctg cgacacctcg ccgctgacgg acgaagtatc ccggcacgtg caggagcccg 113820
tcatgggcac cggacgggtc cagtactact acttcgagag cgggcagggc atgatcggcg 113880
acaacgcggg catgtcgcgc atgctcgtgt gcacgcgctc ggcgtacaac ggcggcgacg 113940
tcgtcgtgcg gtccacgcgg agcagagcag acaagaccgt ggtcgcgccc tgccagggca 114000
tggcgctgct gctgagcccc ttctgcgcct tcgacatcac gccggtggag agcggctccg 114060
cgatattcgc ggaggtcatc gtcacttcgc ccagcatgga ccacgtcgag gcggtcaccg 114120
gcacgggcga ggcggccgtg cggatattca actcgcacca cccgctctgg ccgcgacacg 114180
gctcgaacgt ctgcttcgcg ctgcggttgc tgcgagacgt gcgcacgggc gagcgcgtgg 114240
tcgagcagat gttcatggac gggcgctggc acaccgtgct gaggacgtcc tgcggcaaca 114300
aggtctgcgt gcccgccgac ctcgtgggcc agacgaacct cgaggaggtg cccttctgcg 114360
acgtgacgcc cgagatcatg cgccgcgcac tggcgatcga cccgccgtac gaggccgtgg 114420
cgcacccgcg ccgctgcgtg tacggcgcca tggacgtccg gtgcgcgaac gagtacctcg 114480
tgtactgcac cttcaagacg gagccggcgc ggcgcagcac gtcctcgccg ggcccggacg 114540
gccccctgtc gcccgcgact ccgtcgacct cgcgggccgc ggctgcgcgc gcccccacga 114600
cgccgcagga agtggcctcg ccgaccacga ggctcgtgga gacctgcctg cgcgacgccc 114660
tcgacggact ctgacccgaa ggacccaccg tccactcaca ttccactgcc agacaactca 114720
agctttttct gcatctacct cgctaataat tgaattgtta tagtacaaac aggcgcactc 114780
gagcacaatg gcgtgtttta tcgaattgtt agactccatc ttcaaccgac accaccgtaa 114840
tttcgggccg gaggacatgt acaggccctc tgacgccccg ccccccaaat ctcacacgcc 114900
tcgcactccc cgcaccccgc ggacccagtg tcccggacac ccgcggcgac aaagctcctc 114960
tcccatctac ggtgcttatg tggactccct gccgaggaac agaaagcggt tccagaatca 115020
acacagttgt cccggagatt acgagcggtg tcaactccag gacactatca gcctggaggc 115080
gacgctactc acggttacct cgacttccat ctccagcata tccagctcta gtagctcaga 115140
ctctagctca ttggggcagt gcagactgtc cattgtgtcc gcgacatcga cctccacgac 115200
cttctcctac tcgtcctgag cgccacactt atttttgtat aatagtttgt attgaacctt 115260
agagacatcc acaaatagtt aggaagcatg agtagttcaa gtagcgagac cacccctaag 115320
cccaagccca tccctgctcc tcccatgact caggaggagt ttaacaaaga agtgaagaaa 115380
cgaaaagaac agaaaaagga aaaatctaga accgttgaac gtgagtcaga aaccgtaact 115440
gtatcttccg acggatcaga gataaaaaag acttacgagc gcgagtctga gagaacaacc 115500
gaaacagaaa agaacaacac gtcaaccgat gatgataata agcagaacac ccctgtagag 115560
aaaccagagg aaactaagcc tgcttctact cctgaaggtg agaagccagc tgaaactcct 115620
gccccgacta ctgaccccca acccactaca caaccacccg cagaatcagg ccctggaagt 115680
caacccacac ctgttccaga accaaccccc gcacctgagc ctgcaccgga acccactcct 115740
gccactcagc ctgcatcagt aactcaaccc gctccaacac cagagccaag tccagcccct 115800
gaaactactc cggcttccga accaacccct gcaccagaac ccactcccgc tccaaaacct 115860
acaccagcca cagaaccgac tcctcaacca accgtagaaa caacaccatc tgctccagca 115920
ccaactcccg aggcccaacc acccgccaac aatcccacta ctgaaactac cactggtacc 115980
agcacctcct aagtgagtac gtaagcattt cggagtaacg tcgtagcaag cgctagtccg 116040
ccgcgagcgg ttcttgcaag ttttttcggg taaaaagcgt acaccgtcgc cttgtagcgg 116100
cggtgtacgc tttttttcacg ccctttttgc aaaatttaaa ttgtacccgc gccggctcta 116160
ggaaagatgg cgtgcctcag ggtgttcttg gcggtgctcg cgctgtgcgg gagcgtgcac 116220
tcggcgcaat ggatcggcga gcgcgacttc tgcacggccc acgcacagga cgtcttcgcg 116280
cggctgcagg tgtggatgcg catcgaccgg aacgtgaccg ccgcggacaa cagctcggcc 116340
tgcgcgctgg cgatagagac gccgccgagc aacttcgacg cggacgtcta cgtcgccgcg 116400
gccggcataa acgtcagcgt gtccgcgatc aactgcggct tcttcaacat gcgccaagta 116460
gagacaacgt acaacacggc acgccggcag atgtacgtgt acatggactc ttgggacccc 116520
tggatgctcg acgaccccca gccgctcttc agccaggagt acgaaaacga aacgctgccg 116580
tacctgctgg aggttctgga gctagcgagg ctgtacattc gcgtgggctg cacggtgccc 116640
ggagagcagc cctttgaggt gatcccgggg atcgactacc cccacaccgg catggagttt 116700
ctccagcacg ttctacggcc gaaccgccgg ttcgctccgg cgaagctgca catggacctc 116760
gaggtggacc accggtgcgt gagcgccgtc cacgtgaagg cgttcctgca ggacgcctgt 116820
agcgcccgca aggcgcggac gccactctac ttcgcggggc atggctgcaa ccatccagat 116880
cgccggccaa aaaacccagt accgcgccct cagcacgtgt cgtcaccgat ctccaggaag 116940
tgcagcatgc agacggcgcg ctgagggcgc tcaccgcgct gacggcggcc gtggtgtgcg 117000
cgatcgccgt tgcgctcgag cgcggggcgg aggccgacgc cgtggacctt atccttataa 117060
aattttcaat gatatgctag tttttatgcg accttcctta gaaaattcgg aattcaaaaa 117120
tgaaataaaa cggcgtttag cacgcatatt attaataccg accaccatgg caggcgtccg 117180
cagctgccag aagaaagtcc cttctactgc gggctccatg tcatttcaac ggggcaaccg 117240
gagcatccag cctgcgatgt ccgaggcgtt gcagaatgat ttcagctaca acccgcgacc 117300
gcctccgccg agcgcagaag agattgactt cttctgcgtg gacatgcgca aagtactgat 117360
ggaaattgag gccaagccca acagctccaa gtaccccaat ttcatccacc cggttgacag 117420
cagcccgccg tgcacgccgg cgcgcaagcg caacggcttc ggccgcaagg cactgaacaa 117480
gaccccggtg ccgcagcagg ccaagcgtga cggctactcc cgctaatgca gtccacacac 117540
ttcacacact acatcagcac tcaagcttat aatcaccaca caatgaatta gcccagccca 117600
cacacgtgcc aagcacacat aaaatcaccc acctgtcctg atcgttccca attactccca 117660
atcacccgtg ctttacacgc acgtaaatca ccctctcctt cgttcctgat cgctcctcct 117720
ccttaatcac acatacaccc cgtaattttg tacttttgta ctttaatttg tacactttac 117780
acactgactt tgtactgcct ttgtacttta tttttgtact gaaattggac gatacttatc 117840
tttgtattca catccaagtt ttgcaaattc cacagccggt cgcgaaaagt gaaatcgtac 117900
cgttttaggc ttcgatcccc ctcccgcgcg aagactcgcc agcatggact ctcgtaggct 117960
cgctcttgcc gtcgccttcg gaggcgtcct cgccagcatg acacagcgcc gccgcctggc 118020
ttctctcatc gccagcatcg gccaacggct gatgggcggc gacggcatgc gtcgcgtcgc 118080
cgttcggttg atcgaccagc tcatggccgg acccccggac atcaacgacg aggccttcca 118140
gcgcgagatc cgcgtgggcg agctcttcca ggcgctccac cgcgtggtcg agcaggcacg 118200
ccgagagaag tacttcgagg tctgcggcgc cggcaacgac gccgacgcgc ccgtcgtcga 118260
gatggacacc gcggccgcac ccccgcagcc ccagcccgcg cccttcgtgg tcacgccgca 118320
gaacgcgttc atgttcgtgc cgcaaggcag ccacgtgcac gtggacgaga gcgtggaccc 118380
gttcttcggc atgagcccct ccatcttcgg gcgcgacctc cccccttcagc cgcccgagga 118440 gctgctgagc gaccacgacc cgctcatgag ccaggccggc gagccgccga gcccgcggtc 118500
gccctgcgag gccgacctct ggtgcttcga gacgctcggc gacagcgaca gcgattgagc 118560
ccgcaccaca ccccacctca cccaccccac actccacctc acctcaccct aacaccaaca 118620
ccctaacacc caacacctca accggacaat gaaggagtcc cacatttcac tgaaggacgc 118680
ggatgaagcc gcacatcccc acatgaagga ttggcaacgg tcaaacattt cacctgcaat 118740
gaaggacgat gcgcggtcgc attggcctgc gaccgacatc gcacacatga aggacacaat 118800
tggtttgtta atccggacaa tgaaggacaa attgtttttg ttaatcagga caattggaca 118860
caatcagatt aatttttgta cgatcataaa atcgatattt gatgcacata tattagtaag 118920
tatattagac taaattctcc ggggaggcaa gcagttggat acggcggggc ggggcacgac 118980
gtgcacggag aattcgggcg ggtccccctt ccccccaccc ccacgcacca cgatgcgtct 119040
aatcttagcg ctcgtggcct gcttgttggc ggcgccgatg ccgttatcgg gtcgttcgac 119100
aagcacccca aacacacagt ccgtactcgg ctcgacgagt tcggaaccaa gctcggaaga 119160
cgctgtggct tcgagcacaa cgacaagcac actcacaagc actacaagca cactcactat 119220
gtccacaagt gtggacacca ctactacctc gggcgctacg acgtccacaa acagcactcc 119280
tgcagcgagt gtgagttctt ccacacccgc agccactgag gcatcgacgg caccaacgac 119340
gccgtcgacg cagacgacag tgaaggtaac gaaagacaaa gacacgaagg cgtctgccta 119400
cctcgtttta ctaatcacgt tcatggtcat gacaacgcta gtgatggttg tggtcgtggt 119460
cgtgatcgtg tacaaacagg gactttgtga ctgctgctgt aagatgtttc cctgctgcaa 119520
agagctcaag gactacctcg acgaggagga gagcgccggg ctgtacgacg ccttgacgtg 119580
gagccgctca gaccccggcc tccggctcgt cgtgcgcgcg gaccccagat gatgaggatc 119640
ggataagatc ggcgtgtttt tcccgcccgt cgcgaacatt atgcctctaa atgccgagaa 119700
ttaactgaaa ttcaaacacg ctttgggact caactctgtg gcccacacaa ccaagcttgc 119760
atgcctgcag gtcgacatct atatactata tagtaatacc aatactcaag actacgaaac 119820
tgatacaatc tcttatcatg tgggtaatgt tctcgatgtc gatagccata tgcccggtag 119880
ttgcgatata cataaactga tcactaattc caaacccacc cgctttttat agtaagtttt 119940
tcacccataa ataataaata caataattaa tttctcgtaa aagtagaaaa tatattctaa 120000
tttattgcac ggtaaggaag tagaatcata aagaacagtg acgcctcgag gaattcatga 120060
tccttcaggc ccttctgttt gtgcctctcc taatctcttc gttgtgtctc gggaaattcc 120120
ccatctacac aataccagac aaacttggtc cttggagccc catcgatata catcacctca 120180
gctgtccaaa taatttagtt gtggaggatg aagggtgcac caatctatca ggattctctt 120240
acatggaact aaaggtggga tacatctctg ccataaaagt aaatgggttc acttgtaccg 120300
gtgttgtgac agaggctgaa acctatacca actttgttgg ttatgtcacc accacattca 120360
agaggaaaca tttccgccct ataccggatg catgcagggc tgcatacaac tggaagatgg 120420
ctggtgatcc tagatatgag gaatctcttc aaaatcctta tcctgattac cactggctac 120480
ggaccgtaaa aaccactaag gagtctctta tcatcatatc tccgagtgtg gctgatttag 120540
acccatacga caaatccctt cattctaggg tgttccctgg tgggaaatgt ttgggaataa 120600
cggtttcttc cacctactgc tcaaccaacc atgattacac catctggatg cccgaggaac 120660
caagactcgg gacatcttgc gacattttta ccagcagcaa agggaaaaag gcatctaaag 120720
gaggcaagac ttgcggattt gtggatgaaa ggggcttgta caagtctcta aaaggagcgt 120780
gtaaactcaa gctgtgcgga gttctcggac ttagacttat ggatggaacc tgggtttcca 120840
ttccaacatc agacgatacc aaatggtgcc ctccggatca attggtgaat ctacatgact 120900
ttcactcaga cgaaatagag catctcgtcg tggaggagtt ggtcaagaag agggaagagt 120960
gtttggacgc attagagtcc atcatgacca ccaaatctgt aagttttaga cgtctcagct 121020
atttgagaaa acttgtccct gggtttggaa aggcatacac tatattcaac aagactttga 121080
tggaggctga cgcccactac aagtcagttc ggacttggaa cgagatcatc ccctccaaag 121140
ggtgtttgaa agtcagagag aggtgtcatc ctcctgtgga cggagtgttc ttcaatggca 121200
taattctggg tccagacggg aatgtcctga taccagagat gcaatcatct ctacttcaac 121260
aacatatgga gctgttggaa tcttctgtaa tccccttaat gcatcccttg gcggacccgt 121320
caacagtctt caaggaaggg gatgaagcgg aggattttgt tgaagttcac ctccctgatg 121380
ttcacaaaca aatctcaggg gttgaccttg gtctcccgag ttgggggaaa tatctcctga 121440
tgattgcagg tggtctggcg actctagttc tgataatctg ctcgatggca tgctgtagaa 121500
gaaccaagcg aacagagtca agaagacgag gctctcgaga gtcagagaaa aaggtaacgg 121560 caaccccccca gactaggaaa gtcgtatctt catgggagtt atacaagagt gaaggcgatg 121620
ccaggctgga ttacaaggat gacgacgata agtgagcggc cgcgcagcac tgctcggagg 121680
agtgctgcaa agtggaggaa gttctgtgag aaagtgcgtt tttctgtaat gtgaaataag 121740
atagccttat gtgtgcacag acatggcgaa caggcttgtg tttctcgacc ccgagaccct 121800
agccgaggcc gacggcatcc ccggctatgg ggtgttcgag cccggcaaga agaaatgcat 121860
cttcacaaag atccgcacca gcgtcgcact cgcgtgccgg tacgccgtct cggacggcgg 121920
cctcatcgac gagttcgtca tggcgacata cgggaccaga cgcgcgtgcc ggctcgtccg 121980
gcacctgacg ataagcgcgg agggcgtgat gacccggccc gccagcaact gcgcgccgca 122040
catggtgctc atctgcctca gaggcgtggc cgccgtgtcc agcgaggaca tgggcttcgg 122100
tcgctgcatc atggagcgcg gcaccatgtt catggtcaag tccgcgcaca gcgccgtcgt 122160
ctgcggcaac cccgcctgcg agctgctcgt cctcttctac gactacttca cccccatccc 122220
ccggccgctc tccggagacg aggtgctgtt cacccgcgac ctcgcgcacg tggactacgc 122280
ccccgagtcg gcggtcgtct tcaagatgga ttacaacctc gagaccgacg tggccacgct 122340
gtttgtcggg gggtacatat tccgcgccaa gggcctgatg atggagacgc gcgaacaagt 122400
gggcgacgag tgcgactgct gccgccacag ctcgccggtg ctcgtcatgg atcgcgagaa 122460
gatgatgtcg tcgctgcgca tgatccccag catcgtgccc ggccagcggg agatctgcct 122520
tcgcgagcgc ggctgggccg tcctcgagac ggacgcccgc ggacactgcg agcccggcgt 122580
cctgaggctg gcgctcgccg gcctgcggct gttcgcagga tgcctgcgct ccgtcgtggg 122640
gcggcgcgag ctgtcgctgt tctgctacgg catcgctccc aagttcggcg gagagttcga 122700
ggacgcgccg cgccccatgg agatcgacgg ttagttgttt ttatccctgt acatacgccg 122760
caaactgaaa ctttagggca ccgcgtaata gtgcacgaac gcccagtgga ccgcttccgc 122820
agccatggaa aacaacgaag gcaacgaacg caacaacgaa cacccgcacg ttcgagaatt 122880
caaggaggcg tccctgtacg ggtttctggt gtcggccgcg gacgtgaccg tcgaggacgt 122940
gcgccggtac cttcagttcg gcgcggacgt gaactacagg ggcgcgtacc tgtgcacgcc 123000
gctgcacgcg tacctgcagt ccggctgcga aaagcgccta gacgtcgtgg acgcgctgct 123060
ggacgccggc gcagacatca acgccaagga gatctgcggg ctcacgcccg tgcacctgta 123120
cgcgagctac gcggatgtgg acgtagagtt catgcgcggg ctcatcgagc gcggcgcgag 123180
cgtgtgcggc gagagctcgg tcacgggctg cctgtactcg tacctgtaca cacacagcgt 123240
ggacggcggc gcgcgcctgg acgtggtcga gctgctcgtg caggcgggcg cggacgtgaa 123300
cgtccgcggc gaggcgcgca agacgccgct gcacgtgcac tgcgcgggct tcgaggtgga 123360
ttcggacatc gtggagctgc tgctgcgcgc gggcgcggac cccgaggcgc tcgacgaaca 123420
cgggctcacg cccgcggacg tgctcgtgaa gtccgtgggc gccaacgtgg cgacgctgcg 123480
gctcttcctc gacgcgggcg tgagcgtggc cacgtcgcgc gacgcgcgcg gacgcacgcc 123540
gctgcaccac cacgcggact ccttccgggc gagtgcggtc atcgtgcgcg aactgctcgc 123600
cgccggctgc gacgcggcgg ccaccgacga cctcggaaac acgcccctgc acagcctcgc 123660
caccttctgc tcgtgccggc gctcggtgct cgaccagctc atcgccggcg gcgcggacat 123720
caacgcccgc aaccactacg gccacacctg tctgtactac gcgtccatct acaacccctc 123780
cgtctgctcg aggctcatcg ccgcgggtgc ggacgtgacc gcgcgcacgc cggacggacg 123840
cacgccgctc tcgggcatga tcatgcgcaa gcacacgcgc gccgtgcgcg ccgccctggc 123900
gacgcggcct cccgcggacg ccgtcgccgc gtcgctagac gtcgcggtac agcccgagcc 123960
cacggacgcc actcgcgcgt gcgtgcggta cgtggtgctc tgcggcggca cgctctcggc 124020
gcgcgtgcgg tcgcgacacg cggacttcgt gcgagagtgc gaaagcgagg tggtcgtgct 124080
cagaaccacc gtggtggggc tgcccggcac ctcgctgctg gacatcgtgc gtgcggcgca 124140
gccgccgccg gtactgctct ccccgcgcgt gcaccacgtg ctgcagaagc tgtgtgtgta 124200
cgcggagttg gtagacgcgc ggctgcgcga gatgcggcac aagaccaacc tcgtggacgc 124260
ggtgtcgcgg ctcgtgtgtc cgtgcgcgct gccgccggag gtggtgcgcg gcatcctcgt 124320
gcacgtgccg atagacagcc tgcggcacac gttgaccctc ggcgtggcgc aggccttgcg 124380
tttccttccc tcgcataaat gaaatattat tttttgtggt agaccggatc tccccgatgg 124440
accccgccgg acaacgactg cgcgcgccag ggccgtggcg cctgaacccg ccgaccgcgg 124500
ccgcgctgga aagcgcgctg ctgcggcccg cggcgtcggc gggcgccgac cgctgcgcga 124560
acgcgcacgt ggacagccgc aacatgggcg tcggcgaggg ccgagaggtg cccgcggacg 124620
tcgaggggct catgaccgag atccacctgc ggtacggaat gacgcgcgtc caccggaacg 124680
ttcacttcgt gcagttctgg cacggcgagc acgtgcgccg gcgccccgcg cgacacgtgt 124740
tcacggtctg gatctgcctc agcggcgagg tgcgcatcta cgcagagtgc tgccaggcgg 124800
ggcacggctt cgtgctctgc cgccagatgg cggccgggta catgttcgtg accgagccca 124860
cggactcggt cacggtctcg gtgccgcacc ggctgcgcaa ctcgcggtcg ccggtgtggc 124920
tggcggcggt cttcgccacg cggcacttcg agccgctgcc gccgcccatg tacgccgtgc 124980
ccgggcacgt ggtgctcgcg cgcagcgcct ccatgctctg cgactgctgg ccgtcggacc 125040
cgcggcgccg caacgtgatc ttctacatgc ggctgtcggg cgcgatggtg cgcgtggtcg 125100
tgccgggcgc ggagcttgag atcgagtgca cctcggggtt ccggccggac cacttctcca 125160
tcgacgacga gtgcgtgtgc tgcgagcggc cgcacgtcgc gcgaaccgcg gtgtggacgc 125220
tggcggagat ttgccgcggc gccacggtgg tgctcgcgcc gccactgccc cgcgaccgcg 125280
ccgcggggct gctcgcggag atccgcctgg cctcgctgcg atgggtgcgc gtgcgtgcgg 125340
tccgcagcgg cagagaaagc gtgggcccgt tcccctcggt ggtgtgggcg gcggtcttct 125400
ccgccgttcg gctcttcctg gacggaaccg tgcctgcctt cccggcgtgt gtggagaatg 125460
gacgcgcggc gtacggcatg gtgtacgtgc cctcggagga gccgcggatg gacgggctct 125520
gtgtgttccc gacgcccgcc gagccggcgg cgctcttcgt ccgcggagac caggtgctcg 125580
aggccggcgc ggccgccgcc ataatcgcgg ccgctgagaa gcgcgtccag gccgccaatg 125640
ggtctcctgc tgccgcggag gaggacatag gtgcggcggc cgatgccgcc gcagagagcg 125700
tggagcagga ccagcgcgtc gagtttgacc ttgggcctgg gcctgacccc agccaagaag 125760 cgccccgcgga cgcgcagcgt gccgattcgg acgacgacac cggctccgag actgagaccg 125820
gcgacgagag tgtgggcggc gaggatgaca gcgactcctc ctcctcttac tcggtgatgt 125880
cggacgacga aaacgacagc ggcgacgagg gctggggcga ctctagcgac tccggcatcg 125940
aggacgacga cggcggtgtc ggccaggccg ccgaggaaga agaggaggaa gagcgcgacg 126000
tcctcggcgc agcggcccag atgctcggag actgaccggt ggtgaaaaca taaaaataaa 126060
ctgttcaaca cttgtactcc gggcaccaac actactatcc atacccaccc tccctccaca 126120
cactacaatg gcaaacagag aagagattga cgcctccgcc gtcatggctg cctacctcgc 126180
gagagagtac gcggcggctg tagaagaaca gctgacgccg cgcgagcgcg atgcgctcga 126240
agcccttcgc gtttccggcg aggaggtccg gtcgccgctg ctgcaagaac tctcgaacgc 126300
gggcgagcac cgcgccaacc ccgaaaactc gcacatcccc gccgccctcg tctccgcgct 126360
tctcgaagcc cccacttccc ccggccgcat ggtcactgcg attgagctct gcgcgcagat 126420
gggccgggta tggacgcgcg gccgccggct cgtcgacttc atgcggctcg tgtacgtgct 126480
cctagaccgt ctgccgccca cggccgacga ggacctcagc gcctggctgc aggccgtcgc 126540
gcgcgtgcac ggcacgcggc gccgcctgca ccgcgttctc ggcgtcgggg ccgtcatggc 126600
aggcgtcggt atgctgctgc tcggcgtgcg cgtgttgcgg cgcacataac tttttatctc 126660
ggctcaaact gaaatacgac attggactac gaaacctata attttgccca cggccgcgcg 126720
agataggata ataaataacc tctgagcaac taacatggcc gatgagagag aggccgacgg 126780
cgcgctgttc cggtacctgg agagcgagga ccgtccggac gtggagcaca tgcgccggct 126840
gctggacgag ggcgcggacg tgaactacgc gggcccgcgc gggtacgcgc cgctgcacat 126900
gctcatgcgc ggcaacccgc tagaccccga cgcggtgcga ctgctgctcg ccgcgggcgc 126960
ggacgtgaac gcgacatcgc tctgcgggtt cacgccgctg cactcctaca tgtgcttcgg 127020
gaccgtgacg ccagacacgc tgcgtgcgct catgcgccac ggcgcgagcg tcagcgacct 127080
cgagcgcaac atcaacgcgc tgatcgagta cttcaaccgc gacggctgca tgggcggcgc 127140
ggaggcgacc gtgatcgcac tgctggcgga gcacggcgcg cacgtgaacg ccaaagacga 127200
ccttggacga acgccgctgc acatctacct gtccggcttc ttcgtgtcgg caccggtggc 127260

-continued gctcgcgctg atcgcgctcg gcgcgaaccc gaacgccacg gacgcgtacg ggcgcacgcc 127320
actgcacgcc ttcctgcgct cccgcgacgt ggaccccgct gtgctgaaga cgctcatagc 127380
cgcgggcgca gacccgctcg cgcgcgacat catccggcgc acggcgctgc actaccactg 127440
cgagtccttc aagacgcgcg ctagtgttat cgagacgctg gtggccgccg gctgcgaccc 127500
cgcgagcaca gacctgctcg acaacacggc gctgcacagc atggccatgg gcagctcctg 127560
ccgcgcctcg ctgatccgcc cgctgctggc cgcgggcgtg tccgtgaacg cgcgcaacgc 127620
gcggctgcag acgccgctgc acctcgcggc cgtgttcaac ccgccggcct gcgcgcggct 127680
gctggccgcg ggcgcggacc ccgcgctcgc ggacctagac gagacaacgc cgctgctgag 127740
catggtgcga cacaactgcg cacgcgcgct gcgcacggcg ctgcccttgg cgccggacgc 127800
gctagtggcc ggcgcggtta accgcgtgaa cgcgcgcacg ccgagcgcgg ccacgcgcga 127860
gtgcgtgatg gcgctggcgc tgcgcggcgc gctggacctg ctgagcgcgg agagcgttgc 127920
cacccacgcg gccgcgatcc gcgcctgcga ggcggaggtc gcgctgctgc ggcgcacgcg 127980
cctgggcgcg ccgccgacga cgctcttcgc gctgctgaca ggacgaccga acacgctggt 128040
ttccgcaaag gcggcgcgac gcgcgatggc ggacgtgtgt gtctaccgcg cggcgctggc 128100
cgcgcgcgtg gagcgcgtgc gccgaaagtc ctcgctggtc gagcgcctca ccgccatggt 128160
gtgtccgtgc gctctgccgc cagagctagt gacgcgcatc ctcgcgctcc tgaccgtgga 128220
ggaactcgct tgcgcaatgc gcaaataata atgaactata actaggctta ttagaggcac 128280
tatttgtgca gagtcgttag ttatagttag tgtacttaca attggaatgt cgaagaacaa 128340
aattctggtg tgtgttgcga ttattcttac ttatacatta tacacagatg cgtattgtgt 128400
tgagtattta gaaagtaggg aagatgaaca acagtgcagc ggtagtaatg gtgcgtctgc 128460
gagtttaccg cacatgctca gagaactcag ggccgcgttc ggaaaggtaa aaactttctt 128520
ccagatgaaa gaccaactga acagtatgct actcacacag tcgctcctcg acgacttcaa 128580
aggctacctc gggtgtcagg cactttccga gatgatacag ttttacttgg aagaggtgat 128640
gccgcaggcg gaaaatcacg ggccggacat caaagagcac gttaactcgc tgggagaaaa 128700
actcaaaacg ctgcgtcttc gactgcgtcg ctgccaccgc ttcctgccgt gtgagaacaa 128760
gagtaaggcc gtggagcaag tcaaacgcgt gttcaacatg ctgcaggaac gaggtgttta 128820
caaggccatg agcgagttcg acatattcat caactacata gaatcataca tgactactaa 128880
aatgtaaaaa tgtatataac ttttagctat cgttcggatt ctcgtatcgt tctgctacaa 128940
tgtatataaa aatgtatatt cacatagtta cagttacagt tacagttaca gttacagcta 129000
tatttttatg ctcacaagat gctatataat tgaaaggaaa ttgttcactc tctgtcaggg 129060
cgccatggac tttctaggcg ccgcgcttca cgactacgtt gccgacgcgg aaaatgtccg 129120
cgttgacgag gtgcggcggc tgctggccgc aggcgcctct gtggagtacg cgggcgagtt 129180
cgggaagacc gcgctgcacc agtacatggg ccgttccggc gcggaccccg acgtcgtgcg 129240
cgcgctgctg gacgccggcg cgcgcgtgga cctcccggag acctgctgcg gctgcacgcc 129300
cgtgcacctc tgtctcatgg ccgccaatat cgacgtggag gttctccgca tgctcgtcca 129360
cgagggccgc gtcgaggact gcggccgcgc cgagcttgcc tccgcggtgc tcaaggagtt 129420
cgtggtgaac cgcgccttcg acgagaacgt caccgagcga gtgatgcgcg ttcttgtggc 129480
cgcgggcgcg gacgttaacg ccaccagcgt ggtcgaccgc acgccgctgc acgtctgcct 129540
cacgggcatg tccacgcacc cgggcaccat cgccgcgctg ctgcgcttcg gtgcggacgt 129600
gaacgccgtg gacctctgcg gcatgtcgcc gctggcggtg ctagtgcgct cgcgcgcggc 129660
gaccgcagag ctggtgcgca tgctgctcga cgcgggcgca gacgcacacg cggtcgacag 129720
tcgcctggac tcgctgctgc accagcactt tcagtccgcg cgcccgcggc cggaggtggt 129780
gcgcgagctc atccgccacg gctgctcgcg cgggcgcgga accgaatcgg caacacgccg 129840
ctgcacgagg ccgcaaaaca ctcctcctgc aaacactcgc tggtggggcc gctgctggct 129900
gccggcgcga gcgtggacgc gcgaaataac acgggcaaga cgccgctcca cttggcggcg 129960
gcgtccaacc cgcgcgcgtg ccgccggctg atcgcgcttg gggcggacgt ggtcgcgcgc 130020
agttacgcgg gcgtcacgcc gctggcgcag ctggtcgcgg acaataactc cgcgctggtg 130080
accgcggcgc tggacacgca gcccgagccg cgggccgtgg cagagtcgct gcgagctacc 130140
acgcccgtcg gcgaaacagc gtgctcgcgg ctctgtgtgg cgtacgtggt ggcgcgcgtg 130200
ccgagcgagg tcctcggcga gcccgagcgc gccctgcacg cggccttcgt ggcggagtgc 130260
ttagcggagg tagcggcgat acgccgtgcg ctgcggcaca cctccagtct cgctgctgga 130320
gatcctggtg gccgcgcgcc cgccgcggag cctgctctcg cgccgcgcgc ggcggctggc 130380
cgagagccgg acgacggtct accgcgcgcc gctccgtgca cgcatcgcgg ccatgcgcca 130440
tcgctcgcga ctggtggagc gcgcgctgcg cacgctgcgc ggctgcgtgc tcccgcgcga 130500
ggtgctggag cgcgtgctgc ggtgtctgtc cacacaggac ctgcggacat ccggactggc 130560
cgagtagctt tttctgagat aagtgaataa acatggtggg attcgatcgc gccgccaacg 130620
ccacgccatg gacgccgccg agatggagga gctcgacatc aacgcggagt cggcgctgta 130680
cgactacttc atcctgaacg cggacagagc ccgcgtgggc gaggtggtca tgcttctcgc 130740
acagggcgcg gaaataaact acgcggacag cttcgacaag acgccgctgc acctgtactt 130800
gcacacgcga cacccgcgct cggacgtgat tctggcgctg atggaggcag gcgcggtcgt 130860
ggacacgccg gagcgctgct gcggcgcgac cgcggcgcac ctgtacatcc tcaacgcggc 130920
cgaggtcgac ctgtcggtgc tggaggccat gctgacctgg ggcgtgcgcc agaacgacca 130980
gcactcggag cggctgctct cgagcttgtt gcgcgagtac gtggtgaccc gcgcctactc 131040
ggatcagacc gagccgatca tggacttgct catcggcatg ggcgccgacg tggacatgcc 131100
ggtcggcgtg agtcgcacgg cgctgcacgc ctgccttacg ggcctgaaca cgaacccgtg 131160
catgattcgc gcgctgcttc ggcgcggcgc cagcgtgacc gcaaaagaca cctacgagat 131220
gacgccgctg gcggtgctgc tgaagtctgc gagcgcgacg ccggagctcg tgcgcatcct 131280
cgtggaagca ggctccgacg tgagcgccac cgacttccgc ctcaacggca tgctgcacca 131340
gcacgcgcag tccacgcgcc cgcgcgcgag cgtcatgcgc gagctcatcc ggctggggtg 131400
cagcccagcg gccaaaaaca tgtttggtaa cacgccgatg cacatgctgg ccatggaaag 131460
ctcctgccgc cgctcgctga tcctcccgct gctggaggca gggctttccg tgaacgagga 131520
gaacccgcac tacggcaccg tgcctctgca cgtggcctcg gggtacgaca acacgcaggg 131580
ctgcctcaag ctcctccggc agggaggaga ccccgccgtc gtgtcggccg ccggacgcac 131640
gccgatctcg aacatgctcg tcaaacgcaa ccacgtggcg gtcgccggcg cgctgtcgac 131700
acacccgagc gcggtagtgg tcgtgcaggc tctcgagcag gctctcgagc acgtgctgaa 131760
cgccgggccc agcgaggcct cgcggctcgc cgtggccttt gtggtggcgc gcgctggcgc 131820
atccgcgcta ccggaggccg tgcgccgtct gcacgagggc tttgtcgccg actgcgagcg 131880
cgaagtcgcg ctgctttctc aaaccatgct cggcacaccg gccgtgagcg cgctggccgt 131940
gctggtcagc aaggaggtct ttggcactgt tatctcctcg cgtgcgctgc gtgtcgcgcg 132000
ggaggtccgc gtgtacgcaa ggccgctccg cgaggcgctc ataaatctgc gccacaaatg 132060
ccgcttagtt tccagcctta aaaggcaggt gggaccttgc tcgctgcccg gcgaactggt 132120
ggagcgcgtg ctcgcgaccg tgccactgac cgacttgcgc cgctcgtgcg gccgccgcgc 132180
gcccgagtga ctgcccatcc cgttgctacg cgactcggtg actgcccgct gtttttcttt 132240
ccccgtttct tcttattagg agttgttgcc cgcctccatg atcctcgcgc gcgccggcgg 132300
gcgacctcgc acgcccgcgg cggccgcggc cgccgccgag gacggagagc acagtgatcg 132360
ccggaagcgc aagcgcaaga cgcccaactg cgaagacgcc gacaactccg acgacgagct 132420
agcgcagacg ccgtgtgacc gcgagtggcc ggactgtcgc gcgagctcga tcacgagctc 132480
cgactcggtc tctctcggcg acgagatcta cctgcgatac gtggcctcgc aggtggactt 132540
cgcgcagacc tgggccccgc cggtgcggct gctgcgcttc ttcgggaact tctcgaagga 132600
aacgctcaac cgcatgtcgc ggcgcgggta cgtgaaccgc tcctacttcc agatggcgca 132660
cgcgcgcttc tcgcccacca acgacgacat gtaccacatg gccacgggcg ggtacggcat 132720
cgtgttccgc ttcgaccgct acgtggtcaa gtacgtcttc gagcaccgca acggcatgtc 132780
cgagatggac gcctctacgg agtacacagt gccgcggttc ctgcgcaata acctcaaggg 132840
cgacgagcgc gagttcgtgg tctgcgcgct ggccatgggg ctgaactacc ggctgggctt 132900
cctgcactcg ctgtaccggc gcgtgctgca cacgctgctg ctgctcatgc gcgtggagga 132960
aggccagcgg ccctcggtgg agatgtccaa gaagccgctg ctgcgctggt tcgaggcgcg 133020
caaggacagc gagtccttcg tgcgcctgat ctcgtacttc taccccctcgg ccgtgcagag 133080
caacgtgaac ctgatcaaca acttccacca cctggtgcac ttcttcgagc acgagaagcg 133140
cgcgcggtac gtgttcgacc gcggggccgt gatcgtgttc cctctggcgc gcgggtccgc 133200
ggactcgatc tcgccggagg cggcggcggc gctgggcttc gcgccgcact cggagttcct 133260
caagttcgtg ttcctgcaga tcgcgctgct gtacctgaag atctacgagc tcccggtctg 133320
cacgaacttc ctgcacgtgg acctgaagcc cgacaacgtg ctcatcttcg acagcgcgcg 133380
cgcgctcagc gtgaccgcgg ccggcgcgac tttccgcttc gaggagcccg tgcgcgcggc 133440
gctgaacgac ttcgacttcg cgcgcgtggc caccatcgag aaccgcaaga tctcgggcag 133500
cgtccgcgtg ccgcagaact ggtactacga cttccacttc ttcgcgcaca cgctgctgcg 133560
cgcgtacccg cacatcgccg cggaggaccc gggcttccac gcgctgctct cggagctcac 133620
ggtctcgtgc tcgcgcggga cctgcgaccg cttccggctg cgcgtgtcct cgccgcaccc 133680
catcgagcac ctcgcgcggc tggtgcgccg cgacgtgttc tcccgctgga taaatgccgc 133740
tgcagacgcc cccgacgccg ccgcactctc ctgagcccac gcccgcggcg ccgggctcgc 133800
tgtacgacgt cttcctcgcg cgcttcctgc gccggctggc cgctcgcgcg gcgccggcct 133860
cggccgcctg cgccgtgcgc gtgggtgcgg tgcgcggccg cctgcggaac tgcgagctgg 133920
tggtgctgaa ccgctgccac gcggacgcgg ccggcgcgct cgcgctggcc tccgcggcgc 133980
tcgccgatac gctggcggag ctgccgcgcg cggacaagct cgccgtcgcg cgcgagctgg 134040
gcgtggaccc cgagcacccg gagctgatgc cggaccccgc ctgcgcgggc gagagcgcgc 134100
tcgcgcagaa catcgacatc cagacgctgg acctgggcga ctgcggagac cccaaaggcc 134160
gccgactgcg cgtggcgctg gtgaacagcg gccacgcggc cgcgaactgc gcgctcgcgc 134220
gcgtggcgac cgcgctgacg cgccgcgtgc ccgcgagccg gcacggcctc gcggagggcg 134280
gcgtgccgcc gtggacgctg ctgctggcgg tggccgcggt gacagtgctc ggcgtggtgg 134340
caatctcgct gctgcggcgc gcgctgcggg tgcgctaccg cttcgcgaga ccggccgcgc 134400
tgcgcgcgta gccgcgcaaa atgtaaatta taacgcccaa cttttaaggg tgaggagcca 134460
tgaagttgct cgtcggcata ctggtagccg tgtgcttgca ccagtatctg ctgaacgcgg 134520
acagcagcac gaaaagatgg tccgaagtgc tgaaaggtag cgagtgcagg cctaggccga 134580
ttgttgttcc tgtaagcgag acgcacccag agctgacttc tcagcggttc aacccgccgt 134640
gtgttacgtt gatgcgatgc ggcgggtgct gcaacgacga gagcttggaa tgcgtcccca 134700
cggaagaggc aaacgtgacg atggaattca tgggtgtagg tgtgtccagc actggatcta 134760
gtgtgagcac tcaacatctg gaattcgtgg agcatacaaa gtgcgactgt cagccgcgcg 134820
gcggacagca gacgacaccg acgccaccta gacggcgccg aagggcttat tagcagcagt 134880
ttttgtagcg ggacgtttct gggtttcctt gcgcgctcgg cggcggggct gctgctcgcg 134940
gcgggcgcgc ggtggcggcg gctggccgcg gcgctggcgg ccgcgggccg cgcggcgggg 135000
tagcggcccg gcccgggccc gccgcagccc ttcgcctgcg gaggaggcgc cacggcgcaa 135060
agtgaaaaag gaccgcctag cagtcgagac cctcccgcca cagccgcgga cacccacacc 135120
cgccctccac accacagcca gcaagcatgc acccctcgcc gcgcaggctg ctcggcgcgc 135180
tcgcgctggt ggcgctgggc ttcctcctcg gcgggctctt ccgccccgcg gcgccgccgc 135240
tgccggccgc cctcgtggag gcgggccccg tccgcgcgaa cggctccgcc tcggtgacct 135300
gcctgaccgt cggcggcgac gggcggcaca tggcggtggt cgcgcacggc ggcgggacgc 135360
tctcgccggt gtacccgctc gccgccggca tgcacgcgac cttcgcctcg ctgcgcaagg 135420
gcgcgctgct gctgaacgtc gcgaccgtgc acatctacga cgtgcgcgag ctcgcgccgg 135480
agttcgagct gacctgcgtc gcggtggcgg gcggctacaa cgcggcctgg gcggccacgc 135540
ggcccgcggc cgagtggcgc cgccagctgg cgcagatgca ccgctcggag ctgtgaccct 135600
ctccccggtc tcccatccgt ttttgtattc ggccttagta gattagacca gcatcccgcg 135660
ccccttgcgc cgcccttcgc tcgtgaacga gcgaatcagt caattaatta tttttatcgc 135720
cgcccgctca ctccggtaag ggaacgcggt taactcaccc acgagaacaa gcaaccgctc 135780
actcacgagg taagggaaca acagttaacg tcaactcact cacgagaaca agttgaccac 135840
tctcgaggca gagacgagaa aacaagtgac cgtactcgct cacgagaaca agttgacgca 135900
ccactcgccg aggtaaggga acagataaca agtaacaagt aaccgttaca tcactcgctc 135960
actcctcgga aaatagaacg agagaacgag agaacgagtt aacttactca ctcgctcact 136020
cggtgtgaga gaacgagaga acgagtagct gttgctcact caatcgcccc tcggagtaag 136080
ggaacaagag cagtcaacgc acccactcag tcttggagtg agaggcagag gacgagctaa 136140
cgagttgaac agttaatctc tcaccactca gagtgagaga gcgagagagt gaggacgagt 136200
taacaagtca atcctcactc agagcgagag agtggaggac gagttaatag ttaacggtta 136260
gttatcactc actcagagtg agaggagggc gagtcaacca ctcgctcgcc cctccgagtt 136320
agagaggaga accagtgagc gagttaaccc gcacacgagc gagagaacgt gaactcgctc 136380
gcgcgcgctc ggctaacagt cggcctctcc caaaactctt cgtaaacttt tcccgtgaca 136440
ggttcgtcct tccaaaacta aactgtcggg tcggcctgcc tctcaactct ccgtaaaacg 136500
tttgtaaact gttcggaggt cggtgacccg ctcaacccgt ccgcgaaaac ttttcgcagg 136560
cagtgtctgc ctctctcgga ctctccgcaa acactttcgc ggaacctcgg gggtggtcga 136620
cctctctcca aactttgcaa aactttttcg cggagcctct ggaggccagt cctccctcca 136680
aactctttgt aagatctttt cggaggccag tcctcctctc caaaacgttc cgcaaaatct 136740
ttgggaggtc ggcctctcct ctccaaaacg ttccgtaaac tcttggacgg ccgcccgcgg 136800
cacgcgaggc ggaggatccg ggggtagtcg acctccctca aaaactttgt aaaaactttt 136860
tataaaactt ttcgcggaac ctcgagagta ggtcgacctc cctcaaaact tttataaaac 136920
tttttagcgg aaccgttgga ggcaggtcga cctccctcaa aacttttata aaacttttta 136980
gcggaaccgt tggaggcagg tcggcctctc aaactctttg cgagaactct tcgataactt 137040
taggaggtca ggtcgacctc ccaaaacttt tgcgagaact ctctgaaaac tttaggaggt 137100
caggtacctc tccaaaactt ttataaaact ttttcgcgga gcctctggag acgggccgcc 137160
gcccgcgacc gcgggagcgg agaggccgac ctcccgagac gttccgcgtt accgtcgggg 137220
taggcgtcct ctcgagaacg ccaaaagact tcgtgcaaaa acttttcgga ggggcgcgga 137280
gggcgggcgg ctcccgcgaa ctcccgcaga accttttcgc gcgaccgcga aggccggccg 137340
cctctcccga acactctcaa gagcttttcg gaggaggggc aggtcgcccc cacctctccg 137400
acgctttgta aaaacgttta cgcggaacct cgaaggcagg tcgcctccct cgaaaactcc 137460
tcgcgaaacc tttaaaaact tttgcgaaaa cttttcggag gatgtcggag ggcgggcggc 137520
tcttccaaac ctccgcagaa ccttttcgcg caaccgttgg aagacaggtc ggcctctctc 137580
gaaaactttt aaaactttgt aaacgcgttg gcgggaccgt cgcgggagag cggccgcccg 137640
cggcacgcga gaggaggaaa cgttggaagg agtcggcctc tcccgaaaac tttttataaa 137700
aacttttccg cggaaccgtg gaaggcggtc ggcctctccc gaaaacttta taaaaacttt 137760
ttgcgggact cggacggcgg gtcacccgac cacctgactc ctgtctaccc gactacttga 137820
cttctgtctc ccgggctcct gactccctga ctcccggact ccctgactct agagcgaggt 137880
ctcgcggctg cggggtgccg cctccgcgga gtcgcgttcc cgcggacgcc cgtcctcgaa 137940
agcattcagc agttccagcc tctgccgtag ctcctcccgc aggaactcct ggtccgcgtt 138000
ctcg 138004

<210> SEQ ID NO 6
<211> LENGTH: 39
<212> TYPE: DNA
<213> ORGANISM: Artificial Sequence
<220> FEATURE:
<223> OTHER INFORMATION: primers 024LF-Fw(HindIII)

<400> SEQUENCE: 6
taaggcctct aagcttaacc agcagacctt cttcaccaa 39

<210> SEQ ID NO 7
<211> LENGTH: 40
<212> TYPE: DNA
<213> ORGANISM: Artificial Sequence
<220> FEATURE:
<223> OTHER INFORMATION: primers 024LF-Rv(SalI)

<400> SEQUENCE: 7
cagaattcgc gtcgacctta gctctgtctg aactgaagca 40

<210> SEQ ID NO 8
<211> LENGTH: 40
<212> TYPE: DNA
<213> ORGANISM: Artificial Sequence
<220> FEATURE:
<223> OTHER INFORMATION: primer 024RF-Fw(NotI)

<400> SEQUENCE: 8
attcttatgc ggccgcgccg gcttcatccg ccgcagcata 40

<210> SEQ ID NO 9
<211> LENGTH: 40
<212> TYPE: DNA
<213> ORGANISM: Artificial Sequence
<220> FEATURE:
<223> OTHER INFORMATION: primer 024RF-Rv(BglII

<400> SEQUENCE: 9
cagaattcgc agatcttacg gcgacaccga ctccgtgttc 40

<210> SEQ ID NO 10
<211> LENGTH: 40
<212> TYPE: DNA
<213> ORGANISM: Artificial Sequence
<220> FEATURE:
<223> OTHER INFORMATION: primer 121LF-Fw(SpeI)

<400> SEQUENCE: 10
attcttatgc ggccgcgcag cactgctcgg aggagtgctc 40

<210> SEQ ID NO 11
<211> LENGTH: 40
<212> TYPE: DNA
<213> ORGANISM: Artificial Sequence
<220> FEATURE:
<223> OTHER INFORMATION: primer 121LF-Rv(HindIII)

<400> SEQUENCE: 11
cagaattcgc aagcttggtt gtgtgggcca cagagttgag 40

<210> SEQ ID NO 12
<211> LENGTH: 39
<212> TYPE: DNA
<213> ORGANISM: Artificial Sequence
<220> FEATURE:
<223> OTHER INFORMATION: primer 121RF-Fw(NotI)

<400> SEQUENCE: 12
attcttatgc ggccgcggag cactgctcgg aggagtgct 39

<210> SEQ ID NO 13
<211> LENGTH: 40
<212> TYPE: DNA
<213> ORGANISM: Artificial Sequence
<220> FEATURE:
<223> OTHER INFORMATION: 121RF-Rv(BglII)

<400> SEQUENCE: 13
cagaattcgc agatctatca tgcgcagcga cgacatcatc 40

<210> SEQ ID NO 14
<211> LENGTH: 40
<212> TYPE: DNA
<213> ORGANISM: Artificial Sequence
<220> FEATURE:
<223> OTHER INFORMATION: primer 121LF-Fw(SpeI)

<400> SEQUENCE: 14
attcttatgc ggccgcgcag cactgctcgg aggagtgctc 40

<210> SEQ ID NO 15
<211> LENGTH: 40
<212> TYPE: DNA
<213> ORGANISM: Artificial Sequence
<220> FEATURE:

<223> OTHER INFORMATION: primer 121LF-Rv(HindIII)

<400> SEQUENCE: 15
cagaattcgc aagcttggtt gtgtgggcca cagagttgag 40

<210> SEQ ID NO 16
<211> LENGTH: 39
<212> TYPE: DNA
<213> ORGANISM: Artificial Sequence
<220> FEATURE:
<223> OTHER INFORMATION: primer 21RF-Fw(NotI)

<400> SEQUENCE: 16
attcttatgc ggccgcggag cactgctcgg aggagtgct 39

<210> SEQ ID NO 17
<211> LENGTH: 40
<212> TYPE: DNA
<213> ORGANISM: Artificial Sequence
<220> FEATURE:
<223> OTHER INFORMATION: primer 121RF-Rv(BglII)

<400> SEQUENCE: 17
cagaattcgc agatctatca tgcgcagcga cgacatcatc 40

<210> SEQ ID NO 18
<211> LENGTH: 20
<212> TYPE: DNA
<213> ORGANISM: Artificial Sequence
<220> FEATURE:
<223> OTHER INFORMATION: primer PEDV-intS-Fw

<400> SEQUENCE: 18
cgtggtgggt ttggttgatt 20

<210> SEQ ID NO 19
<211> LENGTH: 20
<212> TYPE: DNA
<213> ORGANISM: Artificial Sequence
<220> FEATURE:
<223> OTHER INFORMATION: primer PEDV-intS-Rv

<400> SEQUENCE: 19
ctgcacgtgg accttttcaa 20

<210> SEQ ID NO 20
<211> LENGTH: 20
<212> TYPE: DNA
<213> ORGANISM: Artificial Sequence
<220> FEATURE:
<223> OTHER INFORMATION: primer 121int-Fw

<400> SEQUENCE: 20
ggcggactac cagagacatc 20

<210> SEQ ID NO 21
<211> LENGTH: 20
<212> TYPE: DNA
<213> ORGANISM: Artificial Sequence
<220> FEATURE:
<223> OTHER INFORMATION: primer 121int-Rv

<400> SEQUENCE: 21
gtcttccggg atgtcgtaga 20